(12) United States Patent
Miyata et al.

(10) Patent No.: US 11,358,951 B2
(45) Date of Patent: Jun. 14, 2022

(54) Π(PI)-CONJUGATED COMPOUND, ORGANIC ELECTROLUMINESCENCE ELEMENT MATERIAL, LIGHT-EMITTING MATERIAL, LIGHT-EMITTING THIN FILM, ORGANIC ELECTROLUMINESCENCE ELEMENT, DISPLAY DEVICE, AND ILLUMINATION DEVICE

(71) Applicant: Konica Minolta, Inc., Tokyo (JP)

(72) Inventors: Yasuo Miyata, Kanagawa (JP); Taketo Namikawa, Tokyo (JP); Takayuki Iijima, Shizuoka (JP); Ryutaro Sugawara, Tokyo (JP); Tetsuya Yamada, Kanagawa (JP); Takatugu Suzuki, Tokyo (JP)

(73) Assignee: MERCK PATENT GMBH, Darmstadt (DE)

( * ) Notice: Subject to any disclaimer, the term of this patent is extended or adjusted under 35 U.S.C. 154(b) by 827 days.

(21) Appl. No.: 15/572,412

(22) PCT Filed: Apr. 27, 2016

(86) PCT No.: PCT/JP2016/063242
§ 371 (c)(1),
(2) Date: Nov. 7, 2017

(87) PCT Pub. No.: WO2016/181846
PCT Pub. Date: Nov. 17, 2016

(65) Prior Publication Data
US 2018/0170914 A1    Jun. 21, 2018

(30) Foreign Application Priority Data

May 8, 2015  (JP) .................................. 2015-095804
Oct. 15, 2015  (JP) .................................. 2015-203878
Oct. 15, 2015  (JP) ............................. JP2015-203876

(51) Int. Cl.
*C07D 403/14*   (2006.01)
*C07D 401/14*   (2006.01)
(Continued)

(52) U.S. Cl.
CPC .......... *C07D 403/14* (2013.01); *C07C 255/51* (2013.01); *C07D 209/86* (2013.01);
(Continued)

(58) Field of Classification Search
None
See application file for complete search history.

(56) References Cited

U.S. PATENT DOCUMENTS

2016/0072076 A1    3/2016  Stoessel et al.
2016/0197286 A1    7/2016  Kawamura et al.
2018/0053901 A1*   2/2018  Yoshida ............... C07D 403/14

FOREIGN PATENT DOCUMENTS

CN    101087776 A    12/2007
CN    104693185 A    6/2015
(Continued)

OTHER PUBLICATIONS

Machine English translation of Yabe et al. (JP 2006-199679 A). Nov. 18, 2020.*
(Continued)

*Primary Examiner* — Jay Yang
(74) *Attorney, Agent, or Firm* — Lucas & Mercanti, LLP

(57) ABSTRACT

In order to provide a novel π-conjugated compound capable of increasing the light-emission efficiency of an organic electroluminescence element, for example, this π-conjugated compound has a structure indicated by general formula (1).

[Formula 1]

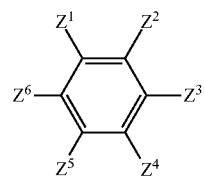

(1)

(In general formula (1): $Z^1$-$Z^6$ each independently indicate a hydrogen atom, a deuterium atom, an electron-donating group D, or an electron-withdrawing group A; at least out of two among $Z^1$-$Z^6$ is an electron-donating group D and the other is an electron-withdrawing group A; and at least one ortho position combination $Z^1$ and $Z^2$, $Z^2$ and $Z^3$, $Z^3$ and $Z^4$, $Z^4$ and $Z^5$, $Z^5$ and $Z^6$, or $Z^6$ and $Z^1$ among $Z^1$-$Z^6$ is one (Continued)

combination out of an electron-donating group D and an electron-donating group D, an electron-withdrawing group A and an electron-withdrawing group A, or an electron-donating group D and an electron-withdrawing group A.)

8 Claims, 16 Drawing Sheets

(51) Int. Cl.
| | |
|---|---|
| *C07D 251/24* | (2006.01) |
| *C09K 11/06* | (2006.01) |
| *H01L 51/00* | (2006.01) |
| *H01L 51/50* | (2006.01) |
| *C07D 265/38* | (2006.01) |
| *C07D 519/00* | (2006.01) |
| *C07D 471/14* | (2006.01) |
| *C07D 491/048* | (2006.01) |
| *C07D 417/10* | (2006.01) |
| *C07D 209/86* | (2006.01) |
| *C07D 241/24* | (2006.01) |
| *C07C 255/51* | (2006.01) |
| *C07D 413/14* | (2006.01) |
| *C07D 409/14* | (2006.01) |
| *C07D 417/14* | (2006.01) |
| *C07D 405/14* | (2006.01) |
| *C07D 495/04* | (2006.01) |
| *C07D 219/02* | (2006.01) |
| *C07D 487/04* | (2006.01) |

(52) U.S. Cl.
CPC ......... *C07D 219/02* (2013.01); *C07D 241/24* (2013.01); *C07D 251/24* (2013.01); *C07D 265/38* (2013.01); *C07D 401/14* (2013.01); *C07D 405/14* (2013.01); *C07D 409/14* (2013.01); *C07D 413/14* (2013.01); *C07D 417/10* (2013.01); *C07D 417/14* (2013.01); *C07D 471/14* (2013.01); *C07D 487/04* (2013.01); *C07D 491/048* (2013.01); *C07D 495/04* (2013.01); *C07D 519/00* (2013.01); *C09K 11/06* (2013.01); *H01L 51/0067* (2013.01); *H01L 51/0071* (2013.01); *H01L 51/0072* (2013.01); *C09K 2211/1029* (2013.01); *C09K 2211/1059* (2013.01); *H01L 51/5012* (2013.01); *H01L 51/5016* (2013.01)

(56) References Cited

FOREIGN PATENT DOCUMENTS

| | | | |
|---|---|---|---|
| EP | 1829871 | A1 | 9/2007 |
| JP | 2006199679 | A | 8/2006 |
| JP | 2009182088 | A * | 8/2009 |
| JP | 2013116975 | A | 6/2013 |
| JP | 2016115940 | A | 6/2016 |
| JP | 6627508 | B2 * | 12/2019 |
| WO | 2010134350 | A1 | 11/2010 |
| WO | 2013154064 | A1 | 10/2013 |
| WO | 14092083 | A1 † | 6/2014 |
| WO | 2014092083 | A1 | 6/2014 |
| WO | 2014146752 | A1 | 9/2014 |
| WO | 15022835 | A1 † | 2/2015 |
| WO | 2015022835 | A1 | 2/2015 |
| WO | WO-2015/022835 | A1 * | 2/2015 |
| WO | 2015029964 | A1 | 3/2015 |
| WO | 2015129714 | A1 | 9/2015 |
| WO | 2016158540 | A1 | 10/2016 |

OTHER PUBLICATIONS

Machine English Translation of Oshiyama et al. (JP-6627508 B2). Mar. 8, 2021.*
Kimura et al. (Inorg. Chem. 2003, 42, p. 2821).*
Machine English Translation of Oshiyama et al. (JP 2009-182088 A). Nov. 9, 2021.*
Written Opinion dated Aug. 2, 2016 from corresponding International Application No. PCT/JP2016/063242.
CNIPA, English translation of Office Action for the corresponding Chinese Patent Application No. 201680026463.2, dated Aug. 26, 2020.
D.R. Lee, et al; Design strategy for 25% external quantum efficiency in green and blue thermally activated . . . ; Advanced Materials; vol. 27; 2015; pp. 5861-5867.
H. Nakanotani, et al; High-efficiency organic light-emitting diodes with fluorescent emitters; Nature Communications; vol. 5; 2014, pp. 4016-4022.
H. Uoyama, et al; Highly efficient organic light-emitting diodes from delayed fluorescence; Nature; Letter; vol. 492; 2012; pp. 234-240.
Q. Zhang, et al; Nearly 100% internal quantum efficiency in undoped electroluminescent devices employing pure organic emitters; Advanced Materials; 2015; pp. 1-5.
Q. Zhang, et al; Efficient blue organic light-emitting diodes employing thermally activated delayed fluorescence; Nature Photonics; pp. 1-7.
International Search Report dated Aug. 2, 2016 for PCT/JP2016/063242 and English translation.
CNIPA, Office Action for the corresponding Chinese Patent Application No. 201680026463.2, dated Dec. 6, 2019, with English translation.
JPO, Notice of the Reasons for Rejection for the corresponding Japanese Patent Application No. 2017-517881, dated Jan. 21, 2020, with English translation.
KIPO, Notice of the Reasons for Rejection for the corresponding Korean Patent Application No. 10-2017-7029655, dated Aug. 12, 2019, with machine English translation (25 pages).

* cited by examiner
† cited by third party

Π(PI)-CONJUGATED COMPOUND, ORGANIC ELECTROLUMINESCENCE ELEMENT MATERIAL, LIGHT-EMITTING MATERIAL, LIGHT-EMITTING THIN FILM, ORGANIC ELECTROLUMINESCENCE ELEMENT, DISPLAY DEVICE, AND ILLUMINATION DEVICE

CROSS REFERENCE TO RELATED APPLICATION

This Application is a 371 of PCT/JP2016/063242 filed on Nov. 8, 2017, which, in turn, claimed the priority of Japanese Patent Application No. JP 2015-095804 filed May 8, 2015, Japanese Patent Application No. JP 2015-203876 filed Oct. 15, 2015 and Japanese Patent Application No. JP 2015-203878 filed Oct. 15, 2015, all applications are incorporated herein by reference.

TECHNICAL FIELD

The present invention relates to a π-conjugated compound, an organic electroluminescent element material, a light-emitting material, a light-emitting thin film, an organic electroluminescent element, a display apparatus, and a lighting apparatus.

BACKGROUND ART

Organic electroluminescent (hereinafter referred to as "EL") elements (also referred to as "organic electroluminescence light emitting elements" or "organic EL elements"), which employ electroluminescence of organic materials, have already been put into practice as novel light-emitting systems capable of planar light emission. Organic EL elements have recently been applied to electronic displays and also to lighting apparatuses, and further development of organic EL elements is anticipated.

Organic EL elements emit light based on either the following two emission modes: "phosphorescence," which occurs during transfer from the triplet excited state to the ground state, and "fluorescence," which occurs during transfer from the singlet excited state to the ground state.

When an electric field is applied to such an organic EL element, holes and electrons are respectively injected from an anode and a cathode into a light-emitting layer, and the injected holes and electrons are recombined in the light-emitting layer to generate excitons. In this case, singlet excitons and triplet excitons are generated at a ratio of 25%:75%, and thus, phosphorescence, which employs triplet excitons, theoretically provides internal quantum efficiency higher than that of fluorescence. Unfortunately, achievement of high quantum efficiency in a phosphorescent mode requires use of a complex of a rare metal, such as iridium or platinum as a central metal, which may cause future significant problems in the industry in terms of the reserves and price of rare metals.

Meanwhile, various fluorescent elements also have been developed for improving the emission efficiency, and a new movement has occurred in recent years. For example, PTL 1 discloses a technique focused on a triplet-triplet annihilation (TTA) phenomenon (hereinafter also called "triplet-triplet fusion (TTF)") wherein singlet excitons are generated by collision of two triplet excitons. This technique allows the TTA phenomenon to occur efficiently and thus improves the emission efficiency of a fluorescent element. This technique can increase the emission efficiency of the fluorescent material to two to three times that of a conventional fluorescent material. However, a problem of improving the emission efficiency remains, unlike a phosphorescent material, because singlet excitons are theoretically generated at efficiency of only about 40% by the TTA phenomenon.

In more recent years, fluorescent materials based on a thermally activated delayed fluorescence (hereinafter abbreviated as "TADF" as appropriate) phenomenon, which employs a phenomenon in which reverse intersystem crossing (hereinafter, abbreviated as "RISC" as appropriate) from the triplet excitons to the singlet excitons is caused, and applicability of the materials to organic EL elements has been reported (see, for example, PTL 2 and NPLs 1 and 2). Use of delayed fluorescence by means of this TADF mechanism can theoretically achieve 100% internal quantum efficiency, equivalent to phosphorescence, even in fluorescence caused by electric-field excitation.

To develop the TADF phenomenon, it is necessary to cause reverse intersystem crossing from 75% of triplet excitons to singlet excitons generated by electric-field excitation at room temperature or the light-emitting layer temperature in the light-emitting element. Additionally, singlet excitons generated by reverse intersystem crossing emit fluorescence similarly to 25% of singlet excitons generated by direct excitation to enable theoretically 100% internal quantum efficiency to be achieved. In order to cause this reverse intersystem crossing, the absolute value of the difference between the lowest singlet excited energy level ($S_1$) and the lowest triplet excited energy level ($T_1$) ($\Delta E_{ST}$) is required to be small.

For example, to develop the TADF phenomenon, reducing $\Delta E_{ST}$ of an organic compound is effective. To reduce $\Delta E_{ST}$, it is effective to localize (distinctly separate) the highest occupied molecular orbital (HOMO) and the lowest unoccupied molecular orbital (LUMO) in a molecule without mixing the orbitals.

Additionally, it is known that incorporation of a material exhibiting the TADF property as a third component (assist dopant material) into a light-emitting layer constituted by a host material and a light-emitting material is effective for achieving high emission efficiency (see NPL 3). Generation of 25% of singlet excitons and 75% of triplet excitons on the assist dopant material by electric-field excitation enables production of singlet excitons through reverse intersystem crossing (RISC). The energy of the singlet excitons is transferred to the light-emitting material by fluorescence resonance energy transfer (hereinafter, abbreviated as FRET, as appropriate), and the light-emitting material can emit light by means of the transferred energy. Thus, use of the theoretically 100% exciton energy enables the light-emitting material to emit light, and high emission efficiency is developed.

FIG. 1 and FIG. 2 are schematic illustrations of an energy diagram of a compound that develops a TADF phenomenon (TADF compound) (FIG. 1) and of a common fluorescent material (FIG. 2). For example, in 2CzPN having a structure shown in FIG. 1, the HOMO is localized on the carbazolyl group at position 1 and position 2 on the benzene ring, and the LUMO is localized on the cyano group at position 4 and position 5. Thus, the HOMO and LUMO of 2CzPN can be separated. This separation significantly reduces $\Delta E_{ST}$ to develop the TADF phenomenon. Meanwhile, in 2CzXy (FIG. 2), in which the cyano groups at position 4 and position 5 of 2CzPN are substituted by a methyl group, the structure is similar to that of 2CzPN, but the HOMO cannot be distinctly separated from the LUMO. Thus, $\Delta E_{ST}$ cannot be reduced and the TADF phenomenon cannot be developed.

In the conventional art, approaches including use of a strong electron-donating group or electron-withdrawing group are known to distinctly separate the HOMO and LUMO. Use of a strong electron-donating group or electron-withdrawing group, however, generates a strong intramolecular charge-transfer (CT)-type excited state, and is responsible to lengthening of wavelengths in an absorption spectrum or emission spectrum, leading to a problem of difficult control of the emission wavelength. Conversely, weakening the electron-donating property or electron-withdrawing property to control the emission wavelength may compromise the development of the TADF phenomenon. Accordingly, there has been a desire for a novel approach to develop the TADF phenomenon while the emission wavelength is controlled.

Incidentally, improvement in the production stability and quality stability (reliability) of organic EL elements also has been required in recent years.

An organic EL element usually includes a cathode, an anode, and a plurality of organic layers disposed therebetween. Specifically, an organic EL element includes a cathode/an electron injection layer/an electron transport layer/a light-emitting layer/a hole transport layer/a hole injection layer/an anode in the order mentioned. The more the number of organic layers, the more the number of manufacturing steps accordingly. Thus, the production stability tends to be compromised. From the viewpoint of improving the production stability of organic EL elements, it is required that the number of organic layers between the cathode and the anode be reduced and that preferably only the light-emitting layer be disposed.

The light-emitting layer usually includes two or more of luminescent compounds and host compounds. When the light-emitting layer includes many components, simultaneous deposition has to be conducted while the concentration of these components are adjusted, and thus the production stability and quality stability tend to be compromised. From the viewpoint of improving the production stability and quality stability (reliability) of organic EL devices, it is required that the types of components of the light-emitting layer be reduced as much as possible and also that preferably the light-emitting layer be constituted only by luminescent compounds with no host compound included.

In other words, from the viewpoint of improving the production stability and quality stability (reliability) of organic EL elements, it is required that 1) the number of the organic layers between the cathode and the anode be reduced and that 2) the types of the components of the light-emitting layer be reduced to simplify the configuration of the organic EL elements as much as possible.

In contrast, a method that includes allowing the light-emitting layer to contain a fluorescence-emitting compound or phosphorescence-emitting compound at a high concentration has been contemplated. Allowing a light-emitting layer to contain a fluorescence-emitting compound or phosphorescence-emitting compound at a high concentration, however, leads to a problem of reduction in the emission efficiency of the element. For this reason, it was not possible to constitute the light-emitting layer only by these compounds, and it has been required to allow the light-emitting layer to further contain a host compound.

A method that includes allowing the light-emitting layer to contain a luminescent TADF compound at a high concentration without incorporation of a host compound has been proposed (see, e.g., NPL 4).

CITATION LIST

Patent Literature

PTL 1
International Publication No. WO2010/134350
PTL 2
Japanese Patent Application Laid-Open No. 2013-116975

Non-Patent Literature

NPL 1
H. Uoyama, et al., Nature, 2012, 492, 234-238
NPL 2
Q. Zhang, et al., Nature, Photonics, 2014, 8, 326-332
NPL 3
H. Nakanotani, et al., Nature Communication, 2014, 5, 4016-4022
NPL 4
Advanced MaterialsDOI:10.1002/adma.20140574

SUMMARY OF INVENTION

Technical Problem

Unfortunately, any of the organic EL elements including a light-emitting layer constituted singly by a luminescent TADF compound described in NPL 4 exhibited low durability in continuous operation and had a practically insufficient function. The reason for their rapid deterioration is presumed to be degradation of the diphenylsulfonyl group in the TADF compound (see Journal of Physical chemistry C 2014, 118, 7569-7578).

In contrast, light-emitting layers constituted singly by a TADF compound such as 4CzIPN and 2CzPN described in NPLs 1 and 3 were not able to emit light, and further incorporation of a host compound was required. Thus, it was not possible to sufficiently simplify the configuration of organic EL elements.

The present invention has prepared in the view of the above problems and situations, and an object of the present invention is to provide a novel π-conjugated compound that may improve the emission efficiency of organic electroluminescent elements, for example. Another object of the present invention is to provide an organic electroluminescent element material, a light-emitting material, a light-emitting thin film and the like each containing the π-conjugated compound. Still another object of the present invention is to provide an organic electroluminescent element that can simplify the configuration of the organic electroluminescent element without compromising its emission efficiency and durability and has high production stability and reliability, and a display apparatus and a lighting apparatus including the organic electroluminescent element.

Solution to Problem

The present inventors, who have conducted studies to solve the problems described above, have newly conceived an organic electroluminescent element containing a π-conjugated compound obtained by substituting at least one combination in the ortho position of the benzene ring by a combination of any of a combination of electron-donating moieties, a combination of electron-withdrawing moieties, or a combination of an electron-donating moiety and an electron-withdrawing moiety and has found that this element can improve the emission efficiency, having achieved the present invention The problems according to the present invention described above are solved by the following aspects:

[1] A π-conjugated compound comprising a structure represented by the following general formula 1:

[Formula 1]

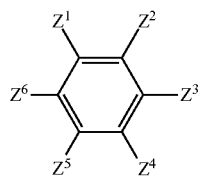

(1)

wherein $Z^1$ to $Z^6$ each represent a hydrogen atom, deuterium atom, electron-donating group D, or electron-withdrawing group A, one of at least two of $Z^1$ to $Z^6$ is the electron-donating group D, and the other is the electron-withdrawing group A, at least one of ortho-position combinations: $Z^1$ and $Z^2$, $Z^2$ and $Z^3$, $Z^3$ and $Z^4$, $Z^4$ and $Z^5$, $Z^5$ and $Z^6$, and $Z^6$ and $Z^1$ among $Z^1$ to $Z^6$ is preferably any of a combination of the electron-donating group D and the electron-donating group D, a combination of the electron-withdrawing group A and the electron-withdrawing group A, or a combination of the electron-donating group D and the electron-withdrawing group A, the electron-donating group D is a group selected from the group consisting of an aryl group substituted by an electron-donating group, an optionally substituted electron-donating heterocyclic group, an optionally substituted amino group, and an alkyl group, and the electron-withdrawing group A is a group selected from the group consisting of a fluorine atom, an alkyl group substituted by a fluorine atom, an optionally substituted carbonyl group, an optionally substituted sulfonyl group, an optionally substituted phosphine oxide group, an optionally substituted boryl group, an aryl group optionally substituted by an electron-withdrawing group, and an optionally substituted electron-withdrawing heterocyclic group.

[2] The π-conjugated compound according to [1], wherein the compound is represented by any of the following general formulas 2 to 10 or 101:

[Formula 2]

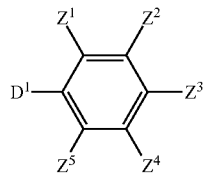

(2)

-continued

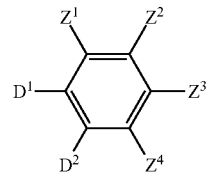

(3)

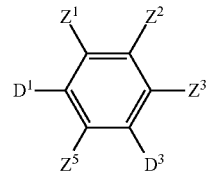

(4)

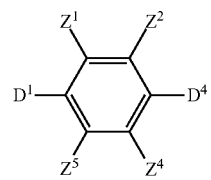

(5)

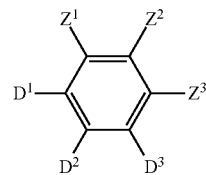

(6)

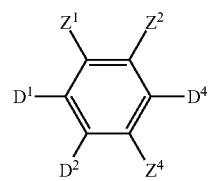

(7)

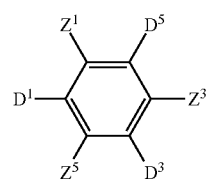

(8)

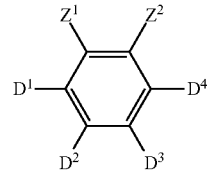

(9)

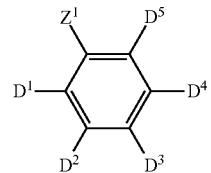

(10)

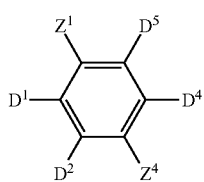
(101)
wherein
D¹ to D⁵ each independently represent the electron-donating group D, and
Z¹ to Z⁵ each independently represent a hydrogen atom, a deuterium atom, or the electron-withdrawing group A.
[3] The π-conjugated compound according to [1] or [2], wherein the compound is represented by any of the following general formulas 11 to 42:
[Formula 3]
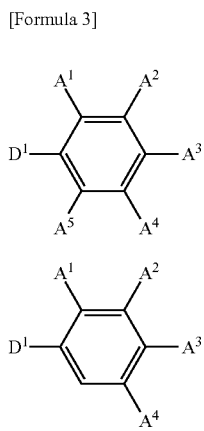
(11)
(12)
(13)
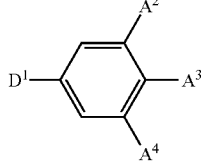
(14)
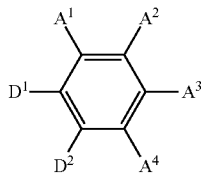
(15)
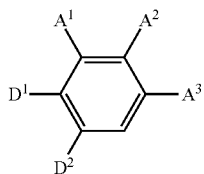
(16)
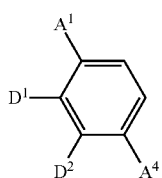
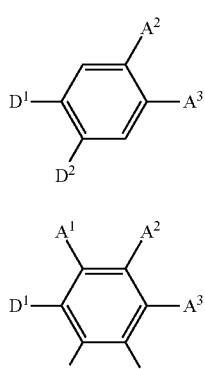
(17)
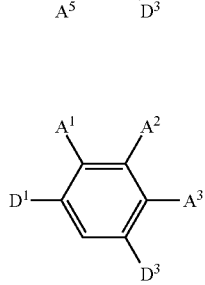
(18)
(19)
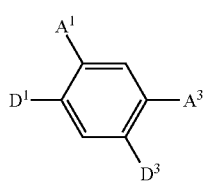
(20)
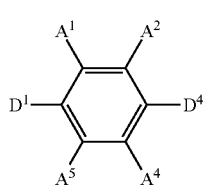
(21)
(22)
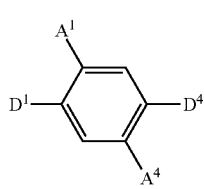
(23)
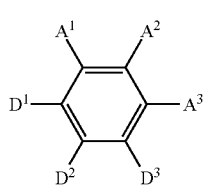
(24)
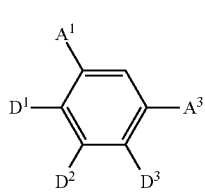

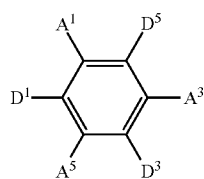
(25)
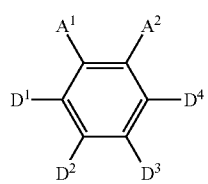
(26)
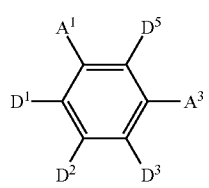
(27)
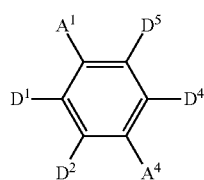
(28)
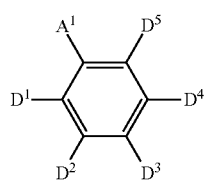
(29)
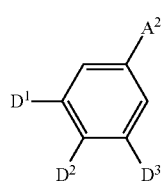
(30)
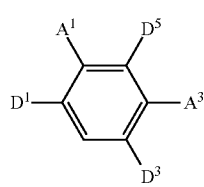
(31)
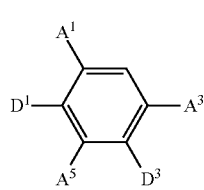
(32)
(33)
(34)
(35)
(36)
(37)
(38)
(39)
(40)
(41)

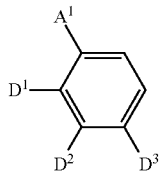

(42)

wherein $D^1$ to $D^5$ each independently represent the electron-donating group D, and $A^1$ to $A^5$ each independently represent the electron-withdrawing group A.

[4] The π-conjugated compound according to [3], wherein, in general formulas 11 to 42, $D^1$ to $D^5$ each independently comprise a group selected from a phenyl group substituted by an electron-donating group, an optionally substituted carbazolyl group, an optionally substituted azacarbazolyl group, an optionally substituted diazacarbazolyl group, an optionally substituted 9,10-dihydroacridyl group, an optionally substituted phenoxazyl group, an optionally substituted phenothiazyl group, an optionally substituted 5,10-dihydrophenazyl group, an optionally substituted diphenylamino group, and an optionally substituted dialkylamino group, and $A^1$ to $A^5$ each independently comprise a group selected from an aryl group substituted by a cyano group, an unsubstituted nitrogen-containing aromatic six-membered ring group, a nitrogen-containing aromatic six-membered ring group substituted by a fluorine atom, a nitrogen-containing aromatic six-membered ring group substituted by a cyano group, a nitrogen-containing aromatic six-membered ring group substituted by a fluorine-substituted alkyl group, and a nitrogen-containing aromatic six-membered ring group substituted by an optionally substituted aryl group.

[5] The π-conjugated compound according to [3] or [4], wherein the compound is represented by the following general formulas 11 to 15, 18, 19, 23, 24, 26, 27, 29, 30, 39, 40, or 42.

[6] The π-conjugated compound according to any of [3] to [5], wherein the compound is represented by the following general formulas 13, 15, 18, 19, 23, 24, 27, 30, 40, or 42.

[7] The π-conjugated compound according to any of [3] to [6], wherein, in general formulas 11 to 42, at least one of $D^1=D^2=D^3=D^4=D^5$ and $A^1=A^2=A^3=A^4=A^5$ is satisfied.

[8] The π-conjugated compound according to any of [1] to [7], wherein the absolute value of the energy difference between the lowest singlet excited level and the lowest triplet excited level $\Delta E_{ST}$ is 0.50 eV or less.

[9] An organic electroluminescent element material comprising the π-conjugated compound according to any of [1] to [8].

[10] A light-emitting material comprising the π-conjugated compound according to any of [1] to [8], wherein the π-conjugated compound emits fluorescence.

[11] The light-emitting material according to [10], wherein the π-conjugated compound emits delayed fluorescence.

[12] A light-emitting thin film comprising the π-conjugated compound according to any of [1] to [8].

[13] The light-emitting thin film according to [12], wherein the π-conjugated compound emits delayed fluorescence.

[14] An organic electroluminescent element comprising an anode, a cathode, and a light-emitting layer provided between the anode and the cathode, wherein at least one layer of the light-emitting layer comprises the π-conjugated compound according to any of [1] to [8].

[15] The organic electroluminescent element according to [14], wherein the π-conjugated compound generates excitons.

[16] The organic electroluminescent element according to [14] or [15], wherein the π-conjugated compound emits fluorescence.

[17] The organic electroluminescent element according to [16], wherein the π-conjugated compound emits delayed fluorescence.

[18] The organic electroluminescent element according to any of [14] to [17], wherein the light-emitting layer comprises the π-conjugated compound and a host compound.

[19] The organic electroluminescent element according to any of [14] to [17], wherein the light-emitting layer comprises the π-conjugated compound and at least one of a fluorescence-emitting compound and a phosphorescence-emitting compound.

[20] The organic electroluminescent element according to any of [14] to [17], wherein the light-emitting layer comprises the π-conjugated compound, at least one of a fluorescence-emitting compound and a phosphorescence-emitting compound, and a host compound.

[21] The organic electroluminescent element according to [18] or [20], wherein the host compound has a structure represented by the following general formula I:

[Formula 4]

General formula I

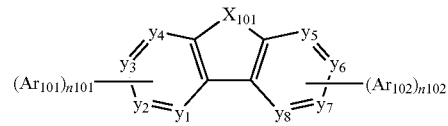

wherein $X_{101}$ represents $NR_{101}$, an oxygen atom, sulfur atom, sulfinyl group, sulfonyl group, $CR_{102}R_{103}$, or $SiR_{104}R_{105}$.

$y_1$ to $y_8$ each independently represent $CR_{106}$ or a nitrogen atom, $R_{101}$ to $R_{106}$ each independently represent a hydrogen atom or a substituent, and may be bonded with each other to form a ring, $Ar_{101}$ and $Ar_{102}$ each independently represent an optionally substituted aryl group or optionally substituted heteroaryl group, n101 and n102 each represent an integer of 0 to 4, provided that n101 represents an integer of 1 to 4 when $R_{101}$ is a hydrogen atom.

[22] The organic electroluminescent element according to [21], wherein the host compound having a structure represented by the following general formula I has a structure represented by the following general formula II:

[Formula 5]

General formula II

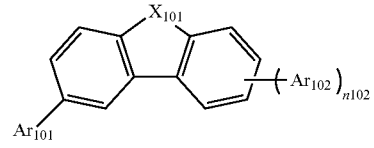

wherein $X_{101}$ represents $NR_{101}$, an oxygen atom, sulfur atom, sulfinyl group, sulfonyl group, $CR_{102}R_{103}$, or $SiR_{104}R_{105}$, $R_{101}$ to $R_{105}$ each represent a hydrogen atom or substituent, and may be bonded with each other to form a ring, $Ar_{101}$ and $Ar_{102}$ each independently represent an optionally substituted aryl group or optionally substituted heteroaryl group, and n102 represents an integer of 0 to 4.

[23] A display apparatus comprising the organic electroluminescent element according to any of [14] to [22]

[24] A lighting apparatus comprising the organic electroluminescent element according to any of [14] to [22].

[25] An organic electroluminescent element comprising an anode, a cathode, and an organic layer disposed between the anode and the cathode, wherein the organic layer substantially comprises a π-conjugated compound represented by general formula 201:

[Formula 6]

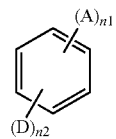

General formula 201 wherein

A is an electron-withdrawing group and represents an optionally substituted nitrogen-containing aromatic six-membered ring group, n1 represents an integer of 1 to 3, and when n1 is 2 or more, the two or more A's each may be the same or different, D is an electron-donating group and represents an aryl group substituted by an electron-donating group, optionally substituted amino group, or alkyl group, n2 represents 2 or 3, the two or more D's each may be the same or different, and the two or more D's are each located in the ortho position.

[26] The organic electroluminescent element according to [25], wherein the organic layer is a light-emitting layer.

[27] The organic electroluminescent element according to [26], further comprising at least one of a hole transport layer disposed between the light-emitting layer and the anode and an electron transport layer disposed between the light-emitting layer and the cathode.

[28] The organic electroluminescent element according to [26] or [27], further comprising at least one of a hole injection layer disposed between the light-emitting layer and the anode and an electron injection layer disposed between the light-emitting layer and the cathode.

[29] The organic electroluminescent element according to [25] or [26], wherein one surface of the organic layer is in contact with the anode and the other surface of the organic layer is in contact with the cathode.

[30] An organic electroluminescent element comprising an anode, a cathode, and an organic layer of which one surface is in contact with the anode and of which the other surface is in contact with the cathode, and wherein the organic layer substantially comprises the π-conjugated compound represented by general formula 201 and a guest compound:

[Formula 7]

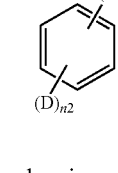

General formula 201 wherein

A is an electron-withdrawing group and represents an optionally substituted nitrogen-containing aromatic six-membered ring group, n1 represents an integer of 1 to 3, and when n1 is 2 or more, the two or more A's each may be the same or different, D is an electron-donating group and represents an aryl group substituted by an electron-donating group, optionally substituted amino group, or alkyl group, n2 represents 2 or 3, the two or more D's each may be the same or different, and the two or more D's are each located in the ortho position.

[31] The organic electroluminescent element according to [30], wherein the guest compound is a fluorescence-emitting compound (excluding the π-conjugated compound represented by general formula 201) or a phosphorescence-emitting compound.

[32] The organic electroluminescent element according to [30] or [31], wherein the guest compound is a fluorescence-emitting compound, and the content of the fluorescence-emitting compound is 20 vol % or less based on the organic layer.

[33] The organic electroluminescent element according to any of [25] to [32], wherein the π-conjugated compound represented by the general formula 201 is represented by any of the following general formulas 202 to 205:

[Formula 8]

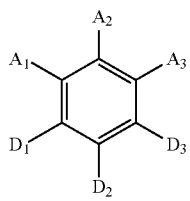

General formula 202

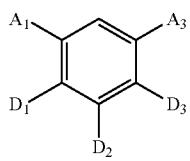

General formula 203

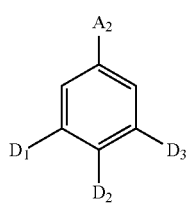

General formula 204

-continued

General formula 205

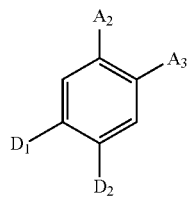

wherein $A^1$ to $A^3$ each have the same definition as A in the general formula 201, and $D^1$ to $D^3$ each have the same definition as D in the general formula 201.

[34] The organic electroluminescent element according to any of [25] to [33], wherein D in the general formula 201 is a group represented by the following general formula D-1:

[Formula 9]

General formula D-1

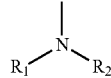

wherein $R_1$ and $R_2$ each represent an optionally substituted aryl group or optionally substituted heteroaryl group, and $R_1$ and $R_2$ may be bonded with each other to form a ring.

[35] The organic electroluminescent element according to any of [25] to [34], wherein the A in the general formula 201 is a group represented by the following general formulas A-1 or A-2:

[Formula 10]

General formula A-1

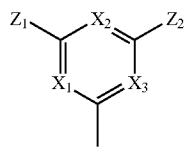

General formula A-2

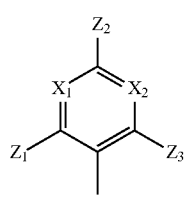

wherein $X_1$ to $X_3$ are each —CH or a nitrogen atom, and at least one of $X_1$ to $X_3$ represents a nitrogen atom, and $Z_1$ to $Z_3$ are each a hydrogen atom, cyano group, optionally substituted aryl group, or optionally substituted heteroaryl group.

[36] The organic electroluminescent element according to any of [25] to [35], wherein the π-conjugated compound represented by the general formula 201 is represented by the following general formulas 206 or 207:

[Formula 11]

General formula 206

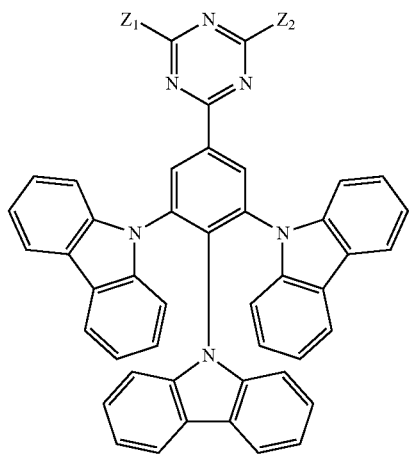

General formula 207

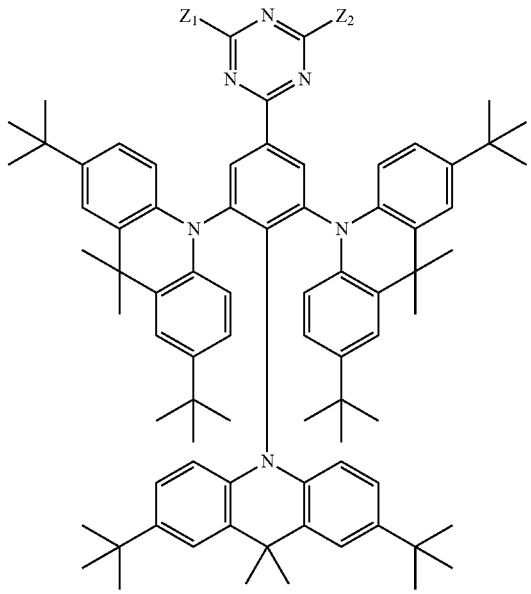

wherein $Z^1$ and $Z^2$ are each an optionally substituted aryl group.

[37] The organic electroluminescent element according to [25] to [35], wherein the π-conjugated compound represented by the general formula 201 is represented by the following general formula 208:

[Formula 12]

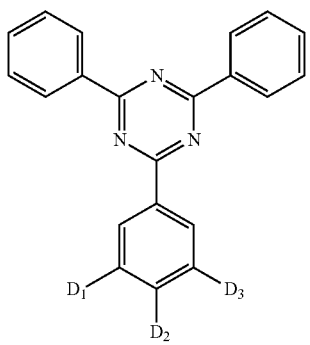

General formula 208 wherein $D^1$ to $D^3$ are each an optionally substituted amino group.

[38] The π-conjugated compound according to any of [25] to [37], wherein the absolute value of the energy difference between the lowest singlet excited energy level and the lowest triplet excited energy level of the π-conjugated compound ΔEst is 0.50 eV or less.

[39] A display apparatus comprising the organic electroluminescent element according to any of [25] to [38].

[40] A lighting apparatus comprising the organic electroluminescent element according to any of [25] to [38].

Advantageous Effects of Invention

According to the aspects of the present invention described above, a novel π-conjugated compound that may improve the emission efficiency of organic electroluminescent elements, for example, can be provided. According to the aspects of the present invention described above, a novel organic electroluminescent element having improved emission efficiency can be also provided. Additionally, an organic electroluminescent element material, a light-emitting thin film, and a light-emitting material containing the π-conjugated compound, and a display apparatus and a lighting apparatus including the organic electroluminescent element can be provided.

Further, according to the present invention, an organic EL element that can simplify the configuration of the organic EL element without compromising its emission efficiency and durability and has high production stability and reliability, and a display apparatus and a lighting apparatus including the organic EL element can be provided.

DESCRIPTION OF EMBODIMENTS

Figure 1A:
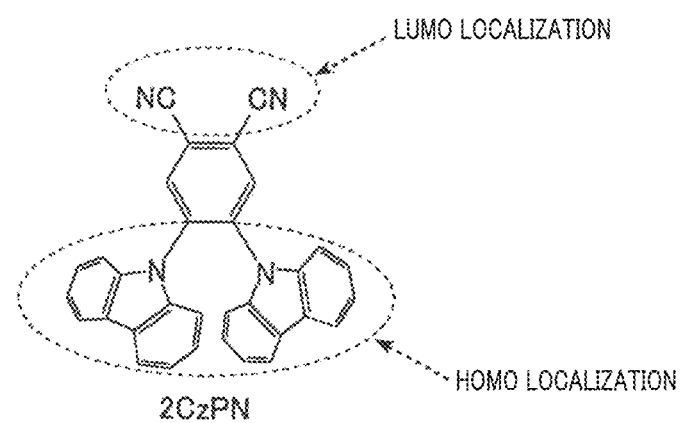
FIG. 1 is a schematic illustration of an energy diagram of a TADF compound.
Figure 1B:
Figure 1B:
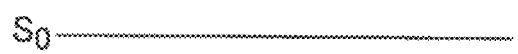
Figure 2A:
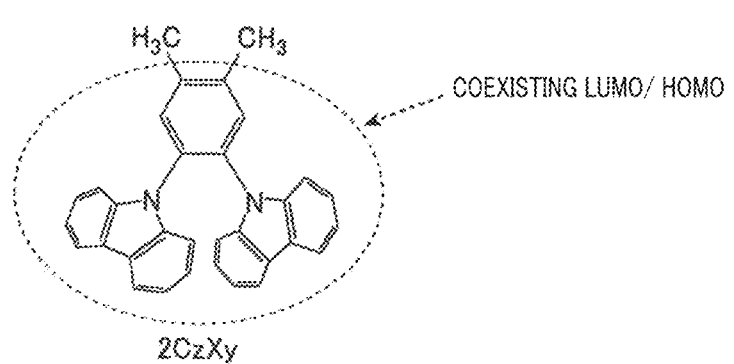
FIG. 2 is a schematic illustration of an energy diagram of a common fluorescence-emitting compound.
Figure 2B:
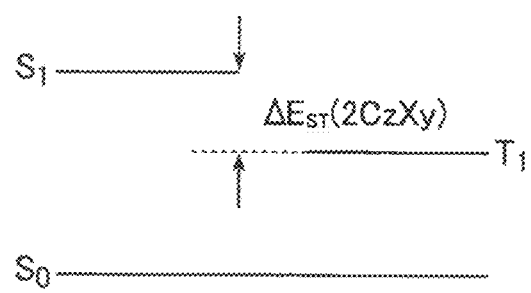

Hereinafter, the present invention and components thereof, and embodiments and aspects for carrying out the present invention will be explained in detail. Herein, "to" between numerical values is used to mean to include the numerical values described before and after "to" as the lower limit and the upper limit.

The present inventors have found that the emission efficiency of an organic electroluminescent element, for example, can be improved by using, in a π-conjugated compound including a benzene ring and an electron-withdrawing group A and an electron-donating group D substituting the benzene ring, any of "an electron-donating group D and an electron-donating group D", "an electron-withdrawing group A and an electron-withdrawing group A", "an electron-withdrawing group A and an electron-donating group D" as at least one combination in the ortho position substituting the benzene ring. The reason for the findings is not necessarily clear, but it is presumed as follows.

(Combination of Homogeneous Groups)

Two or more electron-donating groups D's (or electron-donating groups A's) substituting the benzene ring are likely to provide a higher electron-donating property or a higher electron-withdrawing property than one electron-donating group D (or electron-withdrawing group A) substituting the benzene ring.

Additionally, two or more electron-donating groups (or two or more electron-withdrawing groups A's) substitute at the ortho position of the benzene ring, that is, are "adjacent to each other in space". Then, a plurality of electron-donating groups (or electron-withdrawing groups) can spatially resonate to stabilize the positive charge carried by the electron-donating moiety (or a negative charge carried by the electron-withdrawing moiety) in an excited state. Thus, it is conceived that the excited state is stabilized and non-radiative deactivation is inhibited to thereby enable the emission efficiency to be improved.

(Combination of Heterogeneous Groups)

When an electron-withdrawing group A and an electron-donating group D are located in the ortho position of the benzene ring, the electron-donating group D and the electron-withdrawing group A are "spatially adjacent to each other". Accordingly, it is conceived that the emission efficiency is improved not because a CT-type excited state is formed via bonding from the electron-donating group D to the electron-withdrawing group A but because a CT-type excited state can be formed between the electron-donating group D and the electron-withdrawing group A extremely vicinally located to thereby stabilize the CT-type excited state.

In any aspects, since the electron-withdrawing group A and the electron-donating group D interact with each other not via through-bond coupling but via through-space coupling, it is conceived that lengthening of wavelengths in absorption spectrum or emission spectrum can be inhibited.

(Specific π-Conjugated Compound)

As aforementioned, conventionally-known fluorescence-emitting compounds or phosphorescence-emitting compounds, when allowed to exist in the light-emitting layer of an organic EL element at a high concentration, promote non-radiative deactivation to thereby reduce the emission efficiency. For this reason, when a fluorescence-emitting compound or phosphorescence-emitting compound is singly used to constitute a light-emitting layer, only low emission efficiency is provided. This is conceivably because that existence of the fluorescence-emitting compound and phosphorescence-emitting compound at a high concentration leads to a stable structure among a plurality of molecules via intermolecular interaction in an excited state to thereby promote non-radiative deactivation. Accordingly, a host compound has been further required to improve the emission efficiency.

Conventionally-known TADF compounds such as 4CzIPN and 2CzPN, even when singly included in the light-emitting layer, promote non-radiative deactivation at a high concentration to thereby fail to achieve high emission efficiency, as in the case of the fluorescence-emitting compound and phosphorescence-emitting compound aforementioned.

In contrast to this, a specific π-conjugated compound (a π-conjugated compound represented by general formula 201), even when exists in the light-emitting layer at a high concentration, may have high emission efficiency. The reason is assumed as follows.

That is, in a specific π-conjugated compound including a benzene ring, an electron-withdrawing group (A of general formula 201) and a plurality of electron-donating groups (D of general formula 201) substituting the benzene ring, the plurality of electron-donating groups D's are allowed to substitute the benzene ring at the ortho position. Then, as aforementioned, the electron-donating groups D's are located spatially adjacent in the molecule, and the plurality of electron-donating groups D's can spatially resonate to stabilize the positive charge carried by the electron-donating groups D's in an excited state. As a result, the intermolecular interaction is unlikely to occur, the non-radiative deactivation is inhibited, and the emission efficiency can be improved. In this manner, the specific π-conjugated compound has high emission efficiency even when existing singly in the light-emitting layer, and thus a host compound conventionally required is no longer required.

As the electron-withdrawing group A substituting the benzene ring of the specific π-conjugatable compound, a "nitrogen-containing aromatic six-membered ring" is employed to enable high electron transportability to be achieved.

In this manner, in the specific π-conjugated compound, the plurality of electron-donating groups D's substituting the benzene group in the ortho position can transport holes among molecules, and the electron-withdrawing group A constituted by the nitrogen-containing aromatic six-membered ring and substituting the benzene ring can transport electrons among molecules. Accordingly, if the specific π-conjugated compound is substantially singly used to constitute an organic layer to be disposed between the anode and the cathode, holes and electrons can be transported sufficiently in the organic layer and thus recombined to thereby emit light.

DMAC-DPS, a conventionally-known TADF compound, may emit light even when singly contained in the light-emitting layer, but its sulfonyl group is easily decomposed. Thus elements have low durability.

In contrast to this, elements including the specific π-conjugated compound represented by general formula 201 also have excellent durability. The "nitrogen-containing aromatic six-membered ring group", which is the electron-withdrawing group A contained in the π-conjugated compound represented by general formula 201, has a stable structure which is difficult to decompose, and the plurality of electron-donating groups D's in the molecule resonate in an excited state to form a stable structure. Thus, it is conceived that such elements are difficult to decompose.

Use of the specific π-conjugated compound represented by general formula 201 in the light-emitting layer in this manner can simplify the configuration of organic electroluminescent elements and may improve the durability of such elements. Accordingly, the production stability and reliability of the organic EL elements can be improved.

In addition, in the specific π-conjugated compound represented by general formula 201, the plurality of electron-donating groups D's are adjacent to each other. Thus, not interaction via molecule chains, but interaction via space is likely to occur. It is conceived that this interaction also can inhibit lengthening of wavelengths in the absorption spectrum or emission spectrum.

1. π-Conjugated Compound

The π-conjugated compound of the present invention preferably has a structure represented by the following general formula 1.

[Formula 13]

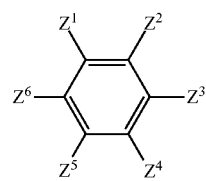

(1)

$Z^1$ to $Z^6$ in general formula 1 each represent a hydrogen atom, deuterium atom, electron-donating group D, or electron-withdrawing group A, provided that $Z^1$ to $Z^6$ are not bonded to one another to form a ring.

From the viewpoint of achieving high emission efficiency, one of at least two of $Z^1$ to $Z^6$ is preferably an electron-donating group D, and the other is preferably an electron-withdrawing group A.

At least one of ortho-position combinations: $Z^1$ and $Z^2$, $Z^2$ and $Z^3$, $Z^3$ and $Z^4$, $Z^4$ and $Z^5$, $Z^5$ and $Z^6$, and $Z^6$ and $Z^1$ among $Z^1$ to $Z^6$ is preferably any of a combination of an electron-donating group D and an electron-donating group D, combination of an electron-withdrawing group A and an electron-withdrawing group A, or combination of an electron-donating group D and an electron-withdrawing group A. From the viewpoint of enhancing the electron-donating property or electron-withdrawing property or the viewpoint of easily generating a CT-type excited state between the electron-donating group and the electron-withdrawing group, two or more, preferably three or more in the ortho position of $Z^1$ to $Z^6$ are preferably electron-donating groups D's or electron-withdrawing groups A's.

More preferably, three or more electron-donating groups D's are sequentially located in the ortho position (adjacent positions) or three or more electron-withdrawing groups A's are sequentially located in the ortho position. When three or more electron-donating groups D's (or three or more electron-withdrawing groups A's) are sequentially located in the ortho position, rotational movement of an electron-donating group D (or an electron-withdrawing group A) sandwiched between two electron-donating groups D's (or two electron-withdrawing groups A's) is inhibited to thereby stabilize the excited state.

Additionally, from the viewpoint that the balance between the electron-donating group D and the electron-withdrawing group A becomes satisfactory and a CT-type excited state is easily generated, particularly preferably, three electron-donating groups D's are sequentially located in the ortho position and/or three electron-withdrawing groups A's are sequentially located in the ortho position.

(Electron-Donating Group D)

The electron-donating group D may be an "aryl group substituted by an electron-donating group", "optionally substituted electron-donating heterocyclic group", "optionally substituted amino group", or "alkyl group".

The aryl group in the "aryl group substituted by an electron-donating group" represented by D is preferably a group derived from a $C_{6-24}$ aromatic hydrocarbon ring. Examples of the aromatic hydrocarbon ring include benzene ring, indene ring, naphthalene ring, azulene ring, fluorene ring, phenanthrene ring, anthracene ring, acenaphthylene ring, biphenylene ring, naphthacene ring, pyrene ring, pentalene ring, aceanthrylene ring, heptalene ring, triphenylene ring, as-indacene ring, chrysene ring, s-indacene ring, pleiadene ring, phenalene ring, fluoranthene ring, perylene ring, acephenanthrylene ring, biphenyl ring, terphenyl ring, and tetraphenyl ring. Of these, benzene ring, naphthalene ring, fluorene ring, phenanthrene ring, anthracene ring, biphenylene ring, chrysene ring, pyrene ring, triphenylene ring, chrysene ring, fluoranthene ring, perylene ring, biphenyl ring, and terphenyl ring are preferred.

Examples of the electron-donating group carried by the aryl group include alkyl groups, alkoxy groups, optionally substituted amino groups, and optionally substituted electron-donating heterocyclic groups. Of these, optionally substituted amino groups and optionally substituted electron-donating heterocyclic groups are preferred.

The alkyl group may be any of straight-chain, branched or cyclic groups, and, for example, may be $C_{1-20}$ straight-chain or branched alkyl group or $C_{5-20}$ cyclic alkyl group. Examples of the alkyl group include methyl group, ethyl group, n-propyl group, isopropyl group, n-butyl group, s-butyl group, t-butyl group, n-pentyl group, neopentyl group, n-hexyl group, cyclohexyl group, 2-ethylhexyl group, n-heptyl group, n-octyl group, 2-hexyloctyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-icosyl group; and the alkyl group is preferably methyl group, ethyl group, isopropyl group, t-butyl group, cyclohexyl group, 2-ethylhexyl group, and 2-hexyloctyl group.

The alkoxy group may be any of straight-chain, branched or cyclic groups, and, for example, may be $C_{1-20}$ straight-chain or branched alkoxy group or $C_{6-20}$ cyclic alkoxy group. Examples of the alkoxy group include methoxy group, ethoxy group, n-propoxy group, isopropoxy group, n-butoxy group, isobutoxy group, t-butoxy group, n-pentyloxy group, neopentyloxy group, n-hexyloxy group, cyclohexyloxy group, n-heptyloxy group, n-octyloxy group, 2-ethylhexyloxy group, nonyloxy group, decyloxy group, 3,7-dimethyloctyloxy group, n-undecyloxy group, n-dodecyloxy group, n-tridecyloxy group, n-tetradecyloxy group, 2-n-hexyl-n-octyloxy group, n-pentadecyloxy group, n-hexadecyloxy group, n-heptadecyloxy group, n-octadecyloxy group, n-nonadecyloxy group, and n-icosyloxy group, and the alkoxy group is preferably methoxy group, ethoxy group, isopropoxy group, t-butoxy group, cyclohexyloxy group, 2-ethylhexyloxy group, and 2-hexyloctyloxy group.

Examples of the substituents in optionally substituted amino groups include alkyl groups and aryl groups optionally substituted by an alkyl group. The alkyl group and aryl group have the same definition as the aforementioned alkyl group and aryl group (in an aryl group substituted by an electron-donating group), respectively.

Examples of the optionally substituted electron-donating heterocyclic group include those similar to electron-donating heterocyclic groups described below.

The "electron-donating heterocyclic group", represented by D, in an "optionally substituted electron-donating heterocyclic group" is preferably a group derived from a $C_{4-24}$ electron-donating heterocycle. Examples of the heterocycle include pyrrole ring, indole ring, carbazole ring, indoloindole ring, 9,10-dihydroacridine ring, 5,10-dihydrophenazine ring, 5,10-dihydrodibenzoazasiline ring, phenoxazine ring, phenothiazine ring, dibenzothiophene ring, benzofurylindole ring, benzothienoindole ring, indolocarbazole ring, benzofurylcarbazole ring, benzothienocarbazole ring, benzothienobenzothiophene ring, benzocarbazole ring, dibenzocarbazole ring, azacarbazole ring, and diazacarbazole ring. Of these, carbazole ring, azacarbazole ring, diazacarbazole ring, indoloindole ring, 9,10-dihydroacridine ring, 5,10-dihydrophenazine ring, phenoxazine ring, phenothiazine ring, dibenzothiophene ring, and benzofurylindole ring are preferred. Further preferable examples thereof include optionally substituted carbazole ring, optionally substituted azacarbazole ring, optionally substituted diazacarbazole ring, optionally substituted 9,10-dihydroacridine ring, optionally substituted phenoxazine ring, optionally substituted phenothiazine ring, and optionally substituted 5,10-dihydrophenazine ring. The electron-donating heterocyclic group may be two or more same or different heterocycles connected via a single bond.

Examples of the substituents that may be carried on the heterocyclic group include alkyl groups and aryl groups optionally substituted by an alkyl group. The alkyl group and aryl group have the same definition as the aforementioned alkyl group and aryl group, respectively.

Examples of the substituent in the "optionally substituted amino group" represented by D include alkyl groups, aryl groups optionally substituted by an alkyl group. The alkyl group and aryl group may be similar to the aforementioned alkyl group and aryl group, respectively.

The "alkyl group" represented by D has the same definition as the aforementioned alkyl group.

Of these, examples of the preferable electron-donating group D having a high electron-donating property include "aryl groups substituted by an electron-donating group", "optionally substituted electron-donating heterocyclic groups", and "optionally substituted amino groups". The electron-donating group D is specifically preferably a phenyl group substituted by an electron-donating group, optionally substituted carbazolyl group, optionally substituted azacarbazolyl group, optionally substituted diazacarbazolyl group, optionally substituted 9,10-dihydroacridyl group, optionally substituted phenoxazyl group, optionally substituted phenothiazyl group, optionally substituted 5,10-dihydrophenazyl group, optionally substituted diphenylamino group, or optionally substituted dialkylamino group. Further preferably, the electron-donating group D is an optionally substituted carbazolyl group, optionally substituted azacarbazolyl group, optionally substituted diazacarbazolyl group, optionally substituted 9,10-dihydroacridyl group, or optionally substituted diphenylamino group.

(Electron-Withdrawing Group A)

The electron-withdrawing group A may be a "fluorine atom", "alkyl group substituted by a fluorine atom", "optionally substituted carbonyl group", "optionally substituted sulfonyl group", "optionally substituted phosphine oxide group", "optionally substituted boryl group", "optionally substituted aryl group (preferably, aryl group optionally substituted by an electron-withdrawing group)", or "optionally substituted electron-withdrawing heterocyclic group".

The alkyl group in the "alkyl group substituted by a fluorine atom" represented by A has the same definition as the aforementioned alkyl group. Examples of the alkyl group substituted by a fluorine atom include —$CF_3$, —$CF_2H$, —$CH_2F$, and —$CF_2CF_3$.

Examples of the substituent in the "optionally substituted carbonyl group", "optionally substituted sulfonyl group", "optionally substituted phosphine oxide group", and "optionally substituted boryl group" represented by A include deuterium atom, fluorine atom, cyano group, alkyl groups optionally substituted by a fluorine atom, optionally substituted aryl groups, and optionally substituted electron-withdrawing heterocyclic groups.

The aryl group in the "optionally substituted aryl group" represented by A has the same definition as the aforementioned aryl group.

Examples of the substituent that may be carried on the aryl group include deuterium atom, fluorine atom, cyano group, alkyl groups optionally substituted by fluorine, optionally substituted carbonyl group, optionally substituted sulfonyl groups, optionally substituted phosphine oxide groups, optionally substituted boryl groups, optionally substituted electron-withdrawing heterocyclic groups, and optionally substituted amino groups.

Of these, the substituent that may be carried on the aryl group is preferably an electron-withdrawing group, preferably fluorine atom, cyano group, alkyl group optionally substituted by fluorine, optionally substituted carbonyl group, optionally substituted sulfonyl group, optionally substituted phosphine oxide group, optionally substituted boryl group, and optionally substituted electron-withdrawing heterocyclic group; more preferably a fluorine atom, cyano group, alkyl group optionally substituted by fluorine, and optionally substituted electron-withdrawing heterocyclic group.

The "optionally substituted electron-withdrawing heterocyclic group" represented by A is preferably a group derived from a $C_{3-24}$ electron-withdrawing heterocycle. Examples of the heterocyclic group include dibenzothiophene oxide ring, dibenzothiophene dioxide ring, pyridine ring, pyridazine ring, pyrimidine ring, pyradine ring, triazine ring, quinoline ring, isoquinoline ring, quinazoline ring, cinnoline ring, quinoxaline ring, phthalazine ring, pteridin ring, phenanthridine ring, phenanthroline ring, dibenzofuran ring, dibenzosilole ring, dibenzoborole ring, and dibenzophosphole oxide ring. Of these, the heterocyclic group is preferably pyridine ring, pyrimidine ring, pyrazine ring, triazine ring, quinoline ring, isoquinoline ring, quinazoline ring, quinoxaline ring, phenanthridine ring, phenanthroline ring, dibenzofuran ring, dibenzoborole ring, or dibenzophosphole oxide ring, particularly preferably a nitrogen-containing aromatic six-membered ring. The electron-withdrawing heterocyclic group may be the above two or more same or different heterocycles connected.

Examples of the substituent that may be carried on the electron-withdrawing heterocyclic group include deuterium atom, fluorine atom, cyano group, alkyl groups optionally substituted by fluorine, aryl groups optionally substituted by an alkyl group optionally substituted by fluorine, and aryl groups optionally substituted by fluorine, and are preferably fluorine atom, cyano group, alkyl groups optionally substituted by fluorine, and aryl groups optionally substituted by fluorine.

Examples of the electron-withdrawing group having a high electron-withdrawing property A particularly preferably include aryl groups substituted by a cyano group, unsubstituted nitrogen-containing aromatic six-membered ring groups, nitrogen-containing aromatic six-membered ring groups substituted by a fluorine atom, nitrogen-containing aromatic six-membered ring groups substituted by a cyano group, nitrogen-containing aromatic six-membered ring groups substituted by a fluorine-substituted alkyl group, and nitrogen-containing aromatic six-membered ring groups substituted by an optionally substituted aryl group. Examples of the nitrogen-containing aromatic six-membered ring include pyridine ring, pyridazine ring, pyrimidine ring, pyrazine ring, triazine ring, quinoline ring, isoquinoline ring, quinazoline ring, cinnoline ring, quinoxaline ring, phthalazine ring, pteridin ring, phenanthridine ring, and phenanthroline ring. Of these, a pyridine ring, pyrimidine ring, pyrazine ring, and triazine ring are preferred. The nitrogen-containing aromatic six-membered ring may be the above two or more same or different nitrogen-containing aromatic six-membered rings connected.

Examples of a more preferable electron-withdrawing group A include phenyl groups substituted by a cyano group, pyridyl groups substituted by a cyano group, optionally substituted pyrazyl groups, optionally substituted pyrimidyl groups, and optionally substituted triazyl groups and include more preferably a p-cyanophenyl group, m-cyanophenyl group, o-cyanophenyl group, m-dicyanophenyl group, 2-cyanopyridyl group, 3-cyanopyridyl group, 2,6-dicyanopyridyl group, 2-cyanopyrazyl group, 2-cyanopyrimidyl group, 5-cyanopyrimidyl group, optionally substituted 2,4-diphenylpyrimidyl groups, and optionally substituted diphenyltriazyl groups.

The π-conjugated compound is preferably represented by any of the following general formulas 2 to 10 or 101.

[Formula 14]

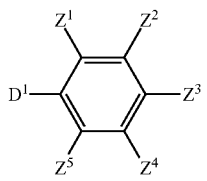

(2)

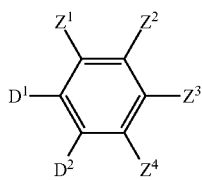

(3)

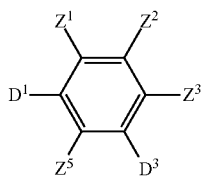

(4)

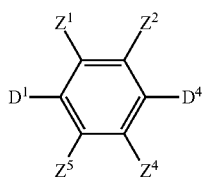

(5)

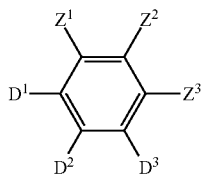

(6)

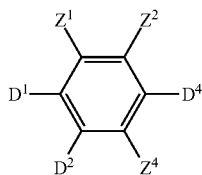

(7)


(8)

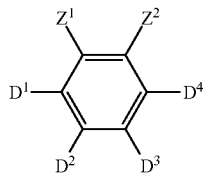

(9)

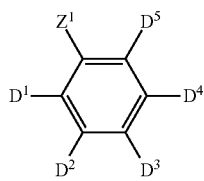

(10)

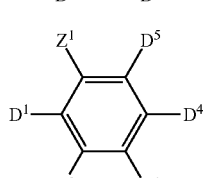

(101)

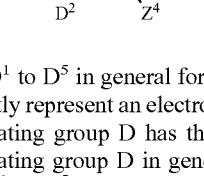

$D^1$ to $D^5$ in general formula 2 to 10 or 101 each independently represent an electron-donating group D. The electron-donating group D has the same definition as the electron-donating group D in general formula 1.

$Z^1$ to $Z^5$ in general formulas 2 to 10 or 101 each independently represent a hydrogen atom, deuterium atom, or electron-withdrawing group A. The electron-withdrawing group A has the same definition as the electron-withdrawing group A in general formula 1.

In general formulas 2 to 10 or 101, at least one of $D^1=D^2=D^3=D^4=D^5$ and $Z^1=Z^2=Z^3=Z^4=Z^5$ is preferably satisfied. This is because not only the synthesis is relatively facile but also satisfactory emission efficiency is easily achieved.

The π-conjugated compound is more preferably represented by any of the following general formula 11 to 42.

[Formula 15]

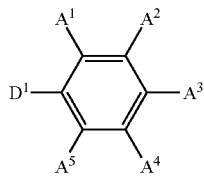

(11)

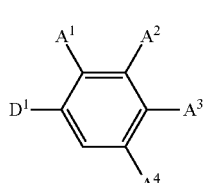

(12)

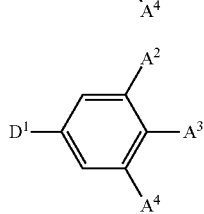

(13)

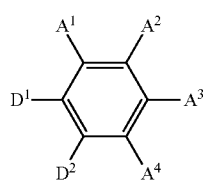
(14)
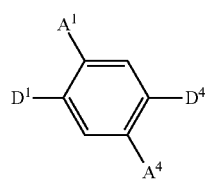
(22)
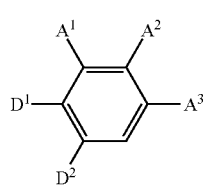
(15)
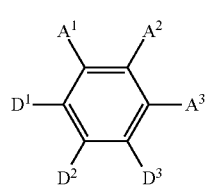
(23)
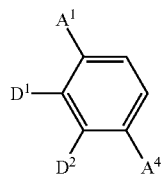
(16)
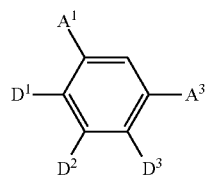
(24)
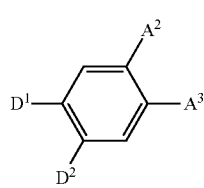
(17)
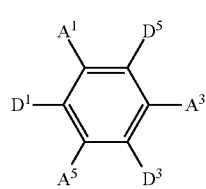
(25)
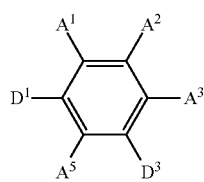
(18)
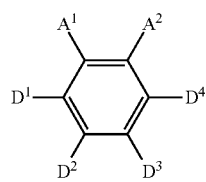
(26)
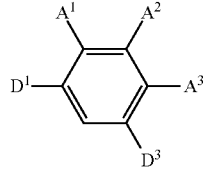
(19)
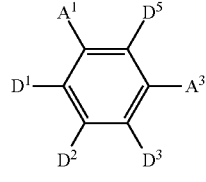
(27)
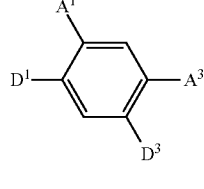
(20)
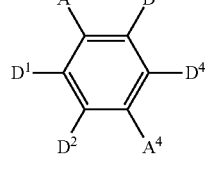
(28)
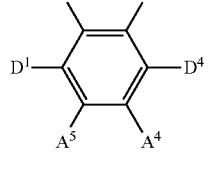
(21)
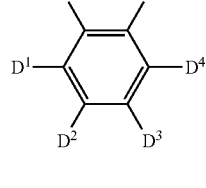
(29)

(29) 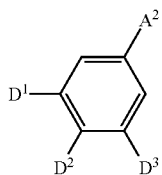 (30) 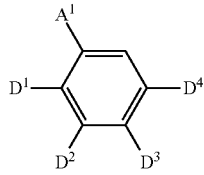

(31) 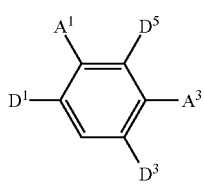 (39) 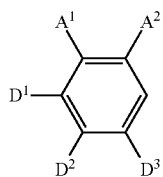

(32) 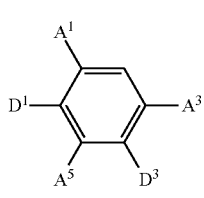 (40) 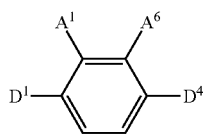

(33) 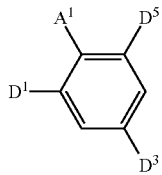 (41) 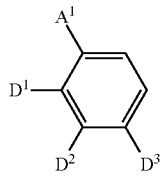

(34) 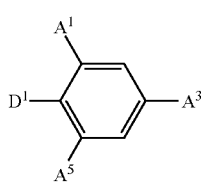 (42)

(35) 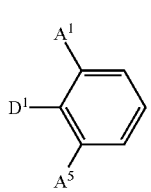

(36) 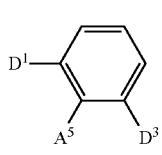

(37) 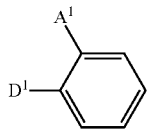

(38) 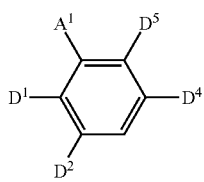

$D^1$ to $D^5$ in general formula 11 to 42 each independently represent an electron-donating group D. The electron-donating group D has the same definition as the electron-donating group D in general formula 1.

$A^1$ to $A^5$ in general formula 11 to 42 each independently represent electron-withdrawing group A. The electron-withdrawing group A has the same definition as the electron-withdrawing group A in general formula 1.

In general formulas 11 to 42, at least one of $D^1=D^2=D^3=D^4=D^5$ and $A^1=A^2=A^3=A^4=A^5$ is preferably satisfied.

Also of compounds represented by general formula 11 to 42, compounds in which three or more electron-donating groups D's are sequentially located in the ortho position or three or more electron-withdrawing groups A's are sequentially located in the ortho position are preferred from the viewpoint of the stability of the excited state. Specifically, compounds 11 to 15, 18, 19, 23, 24, 26, 27, 29, 30, 39, 40, or 42 are more preferred.

Particularly preferably, three electron-donating groups D's are sequentially located in the ortho position and/or three electron-withdrawing groups A's are sequentially located in the ortho position, and compounds represented by general formula 13, 15, 18, 19, 23, 24, 27, 30, 40, or 42 are particularly preferred.

The π-conjugated compound having a structure represented by general formula 1 aforementioned can be used as an organic electroluminescent element material containing the π-conjugated compound, a light-emitting thin film containing the π-conjugated compound, and an organic electroluminescent element containing the π-conjugated compound.

The π-conjugated compound having a structure represented by the general formula 1 aforementioned is brought into an excited state by electric-field excitation to thereby enable excitons to be formed. Accordingly, the π-conjugated compound having a structure represented by general formula 1 aforementioned is preferably contained in the light-emitting layer of organic electroluminescent elements. That is, from the viewpoint of a high light-emitting property, the light-emitting layer preferably singly contains the π-conjugated compound having a structure represented by general formula 1 aforementioned; contains the π-conjugated compound having a structure represented by general formula 1 aforementioned and a host compound described below; contains the π-conjugated compound having a structure represented by general formula 1 aforementioned and at least one of a fluorescence-emitting compound and a phosphorescence-emitting compound described below; or contains the π-conjugated compound having a structure represented by general formula 1 aforementioned, at least one of a fluorescence-emitting compound and a phosphorescence-emitting compound described below, and a host compound described below.

In the π-conjugated compound having a structure represented by general formula 1 aforementioned, the absolute value of the energy difference between the lowest singlet excited level and the lowest triplet excited level of the π-conjugated compound ($\Delta E_{ST}$) is preferably 0.50 eV or less, and the compound is preferably contained in the organic electroluminescent element, element material, or light-emitting thin film.

The organic electroluminescent element of the present invention may be suitably included in lighting apparatuses and display apparatuses.

Preferred specific example of the π-conjugated compound according to the present invention are listed below. In some cases, these compounds may further have a substituent, or structural isomers or the like may exist, and thus, the compound is not limited to this description.

[Formula 16]

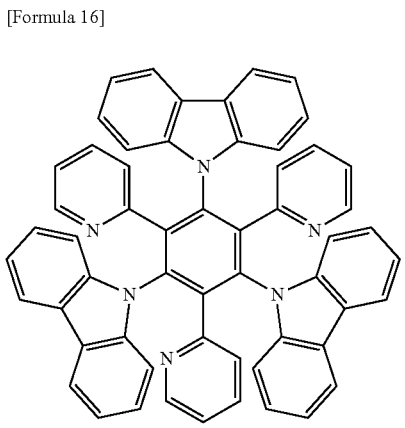
T-1

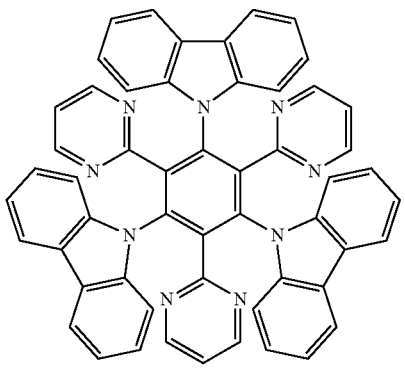
T-2

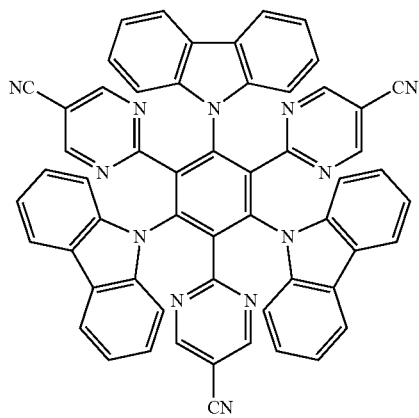
T-3

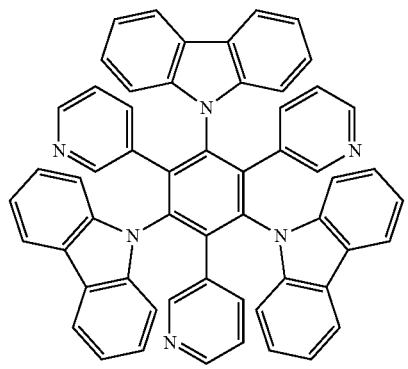
T-4

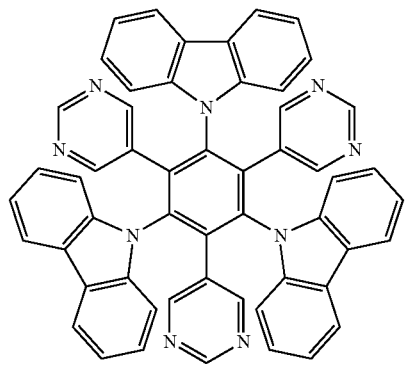
T-5

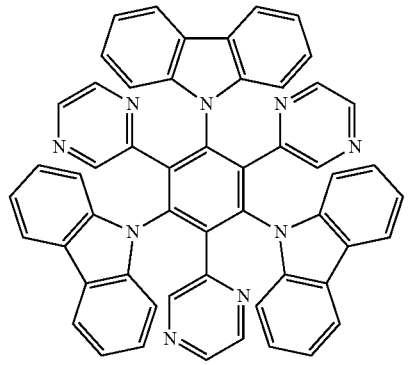
T-6

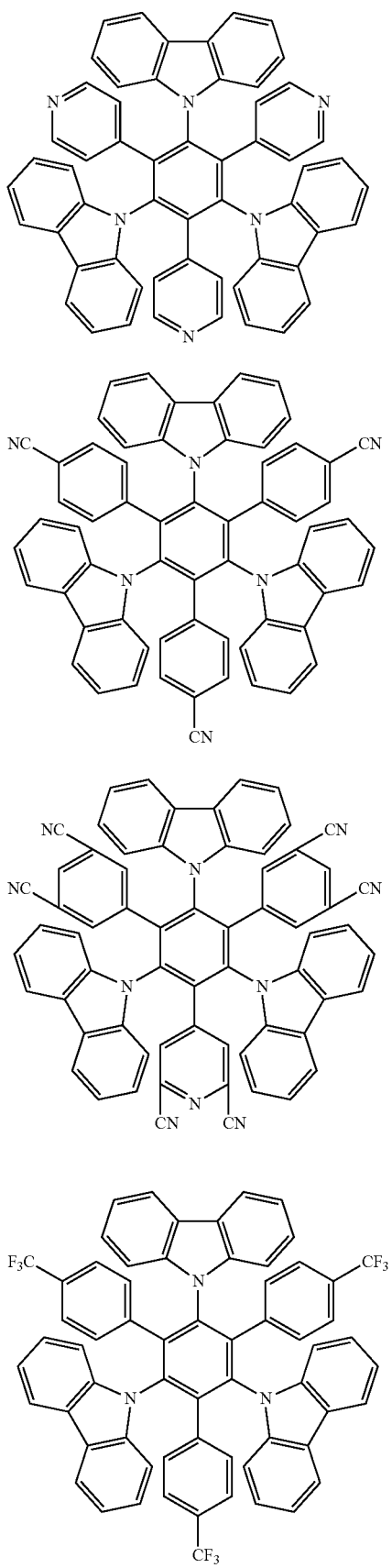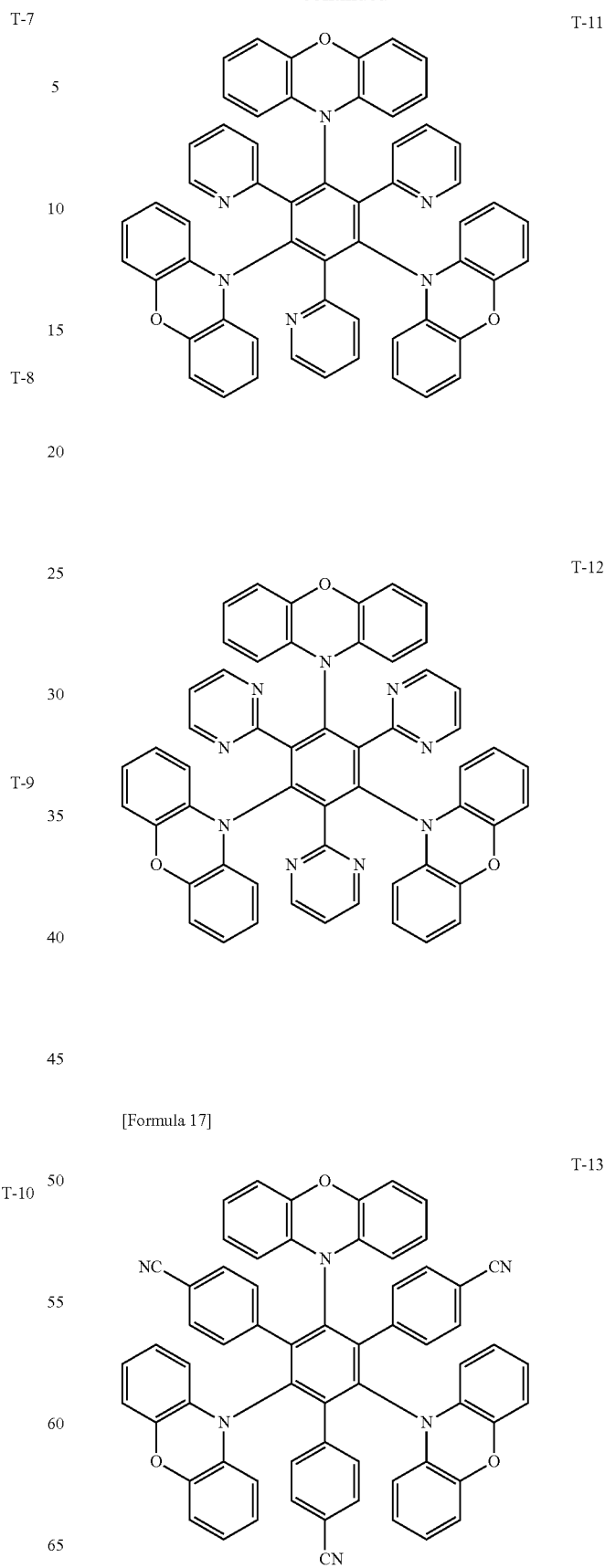

T-14
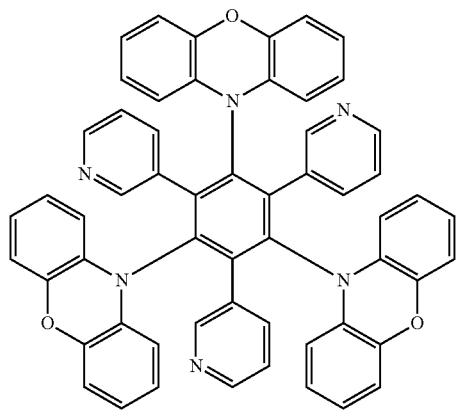
T-15
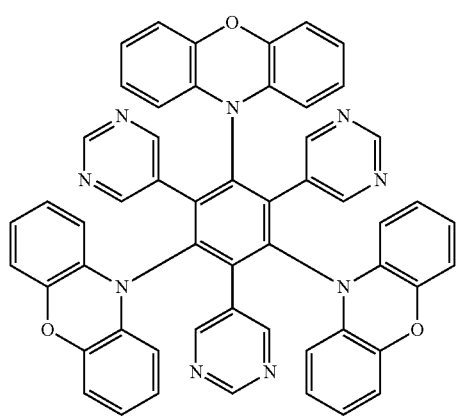
T-16
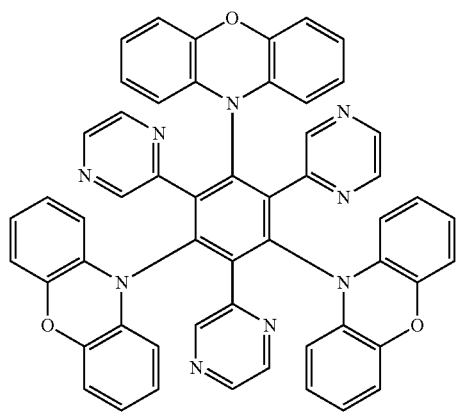
T-17
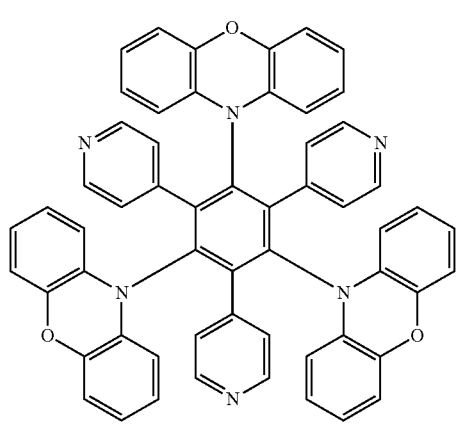
T-18
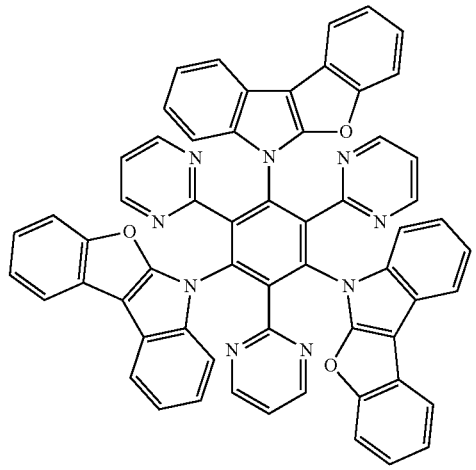
T-19
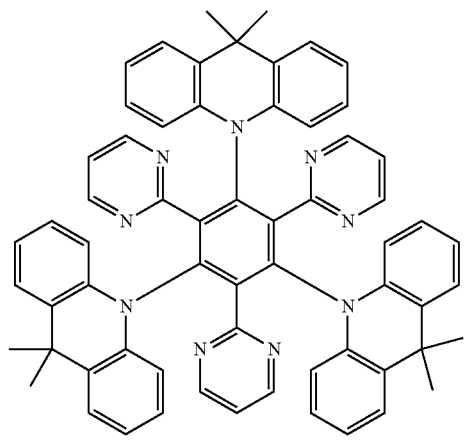
T-20
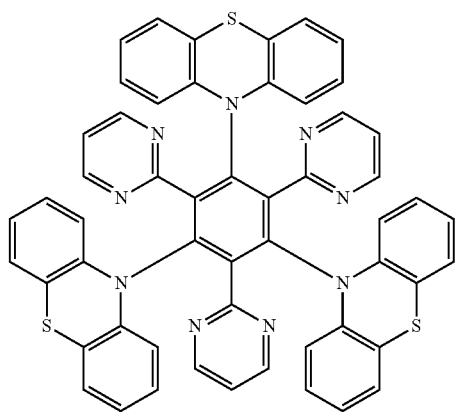

-continued
T-21
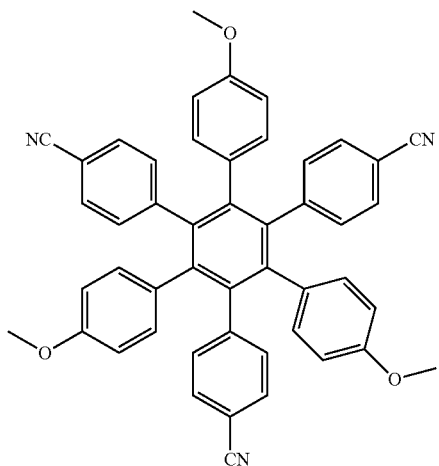
T-22
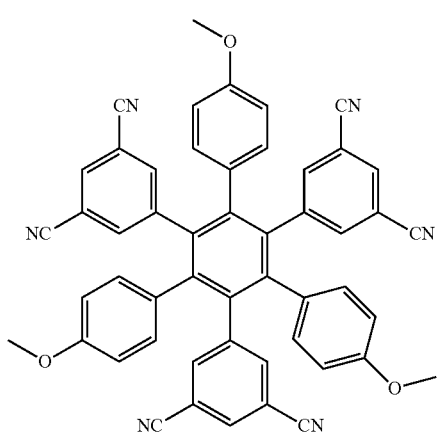
T-23
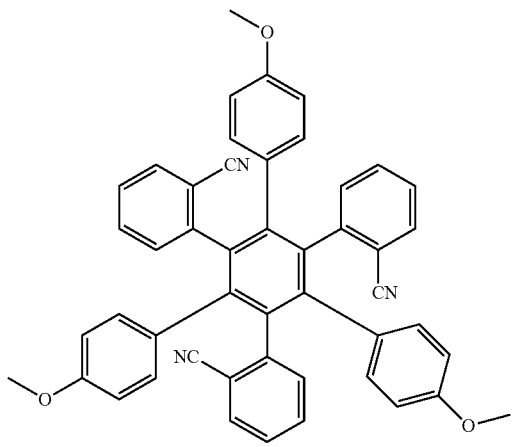
-continued
T-24
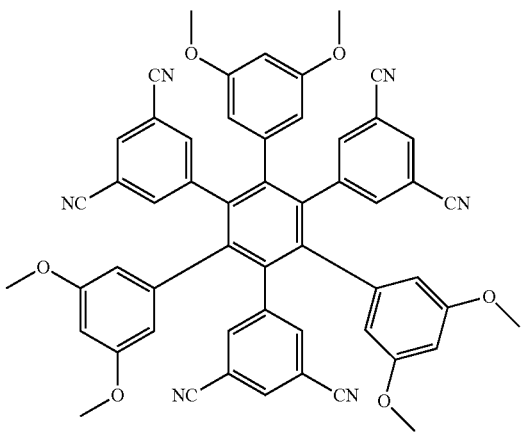
Formula 18]
T-25
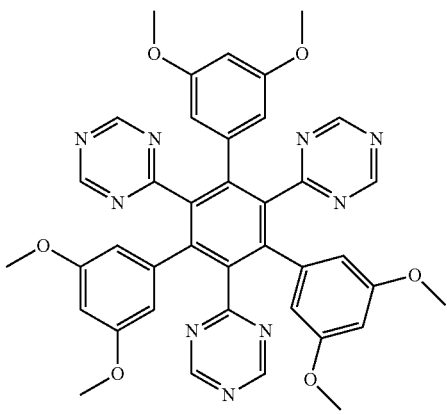
T-26
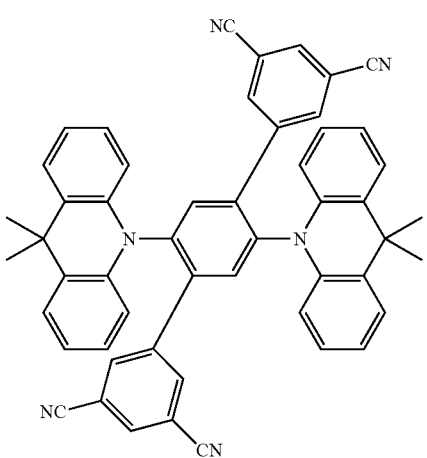

T-27
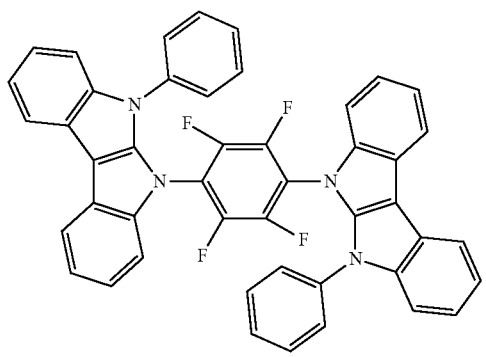
T-28
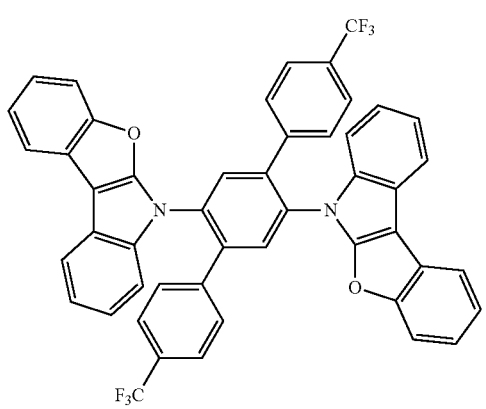
T-29
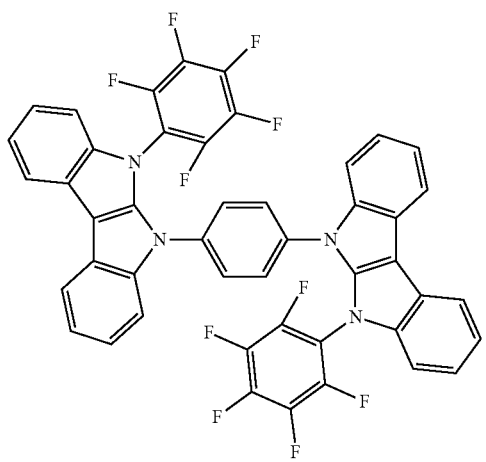
T-30
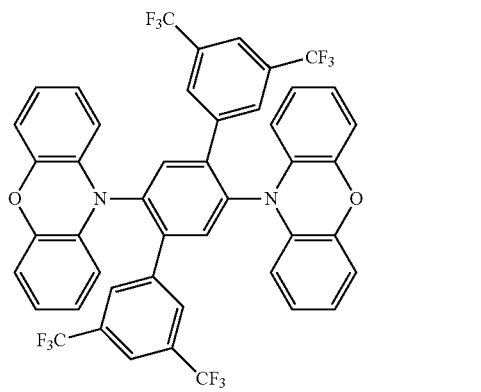
T-31
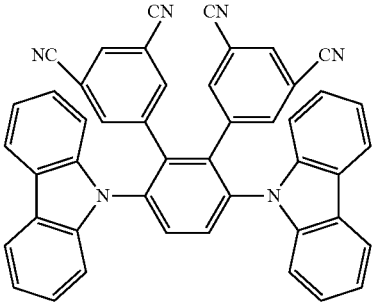
T-32
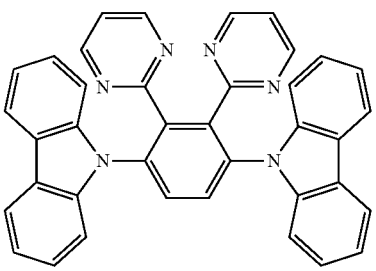
T-33
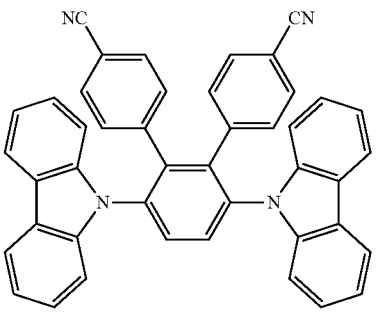
T-34
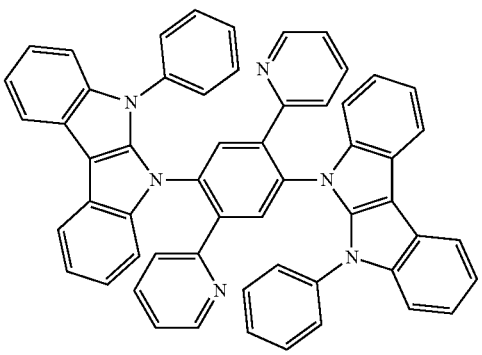

T-35
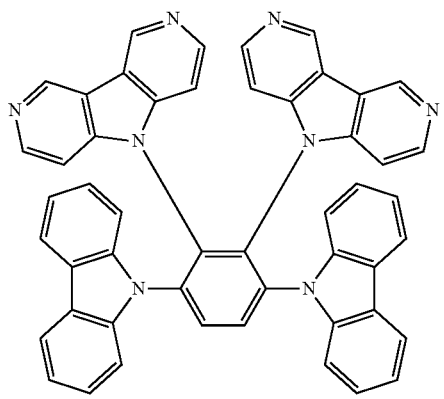
T-36
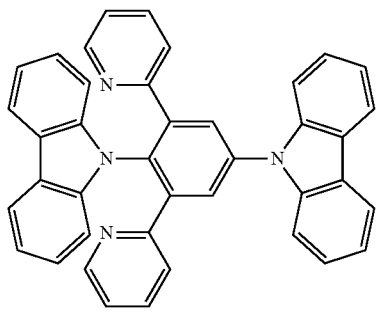
[Formula 19]
T-37
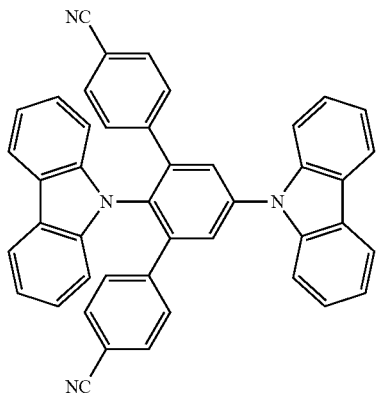
T-38
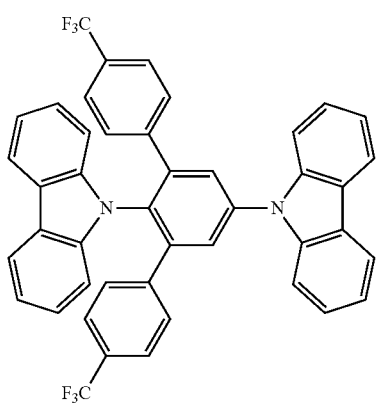
T-39
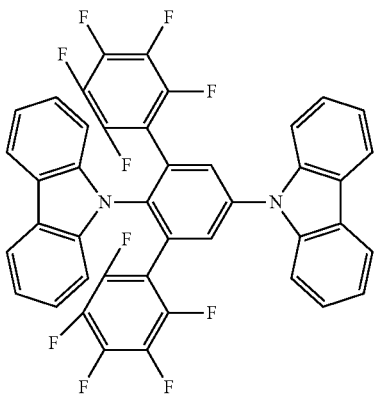
T-40
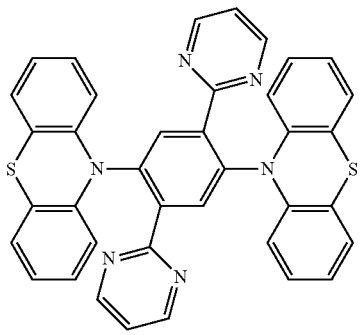
T-41
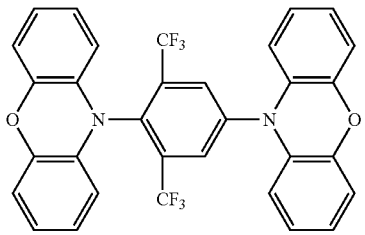
T-42
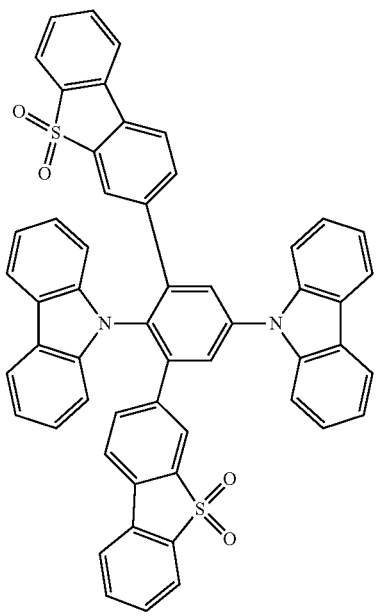

T-43
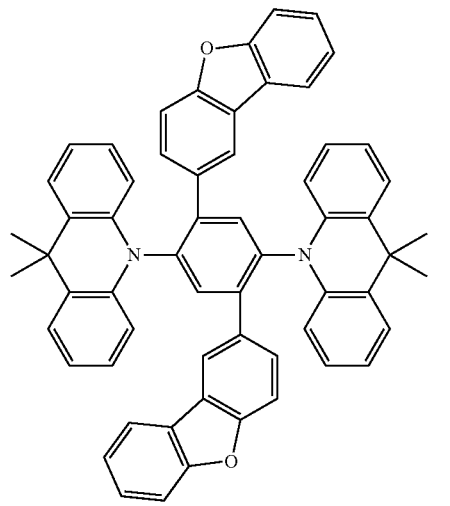
T-44
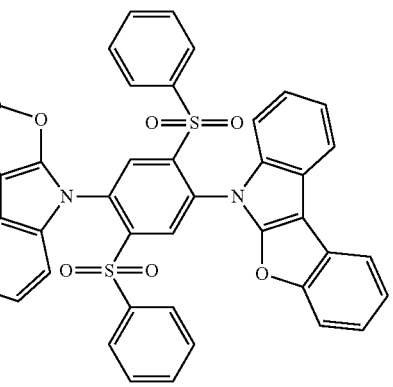
T-45
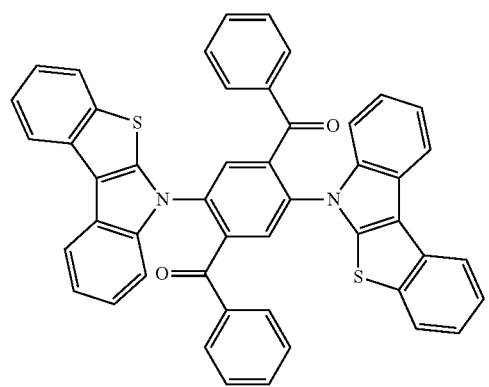
T-46
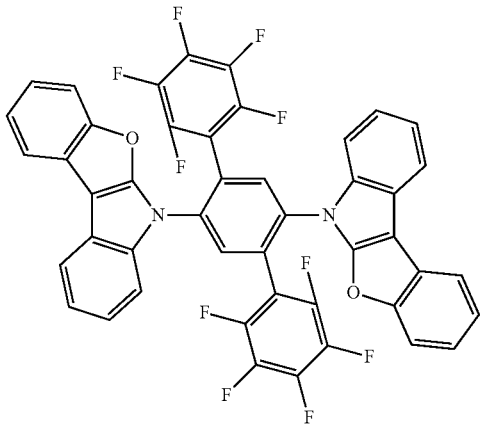
T-47
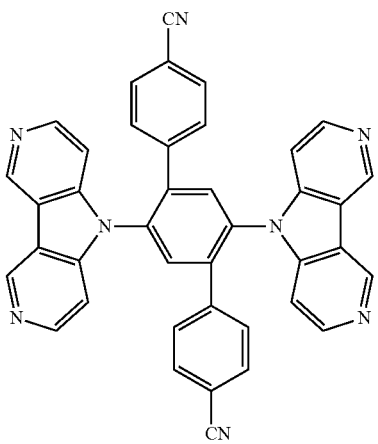
T-48
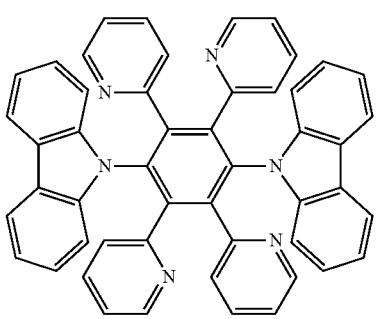
[Formula 20]
T-49
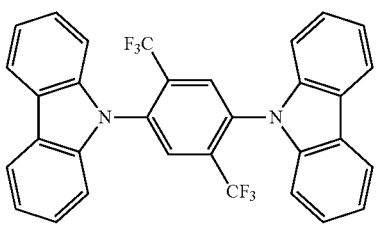

T-50
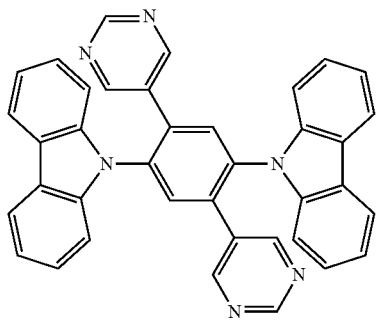
T-51
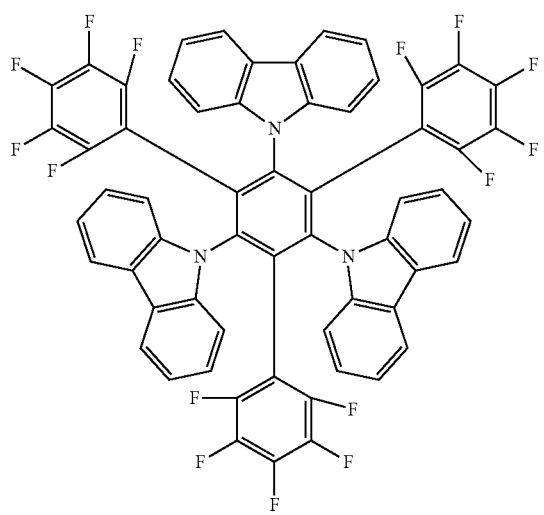
T-52
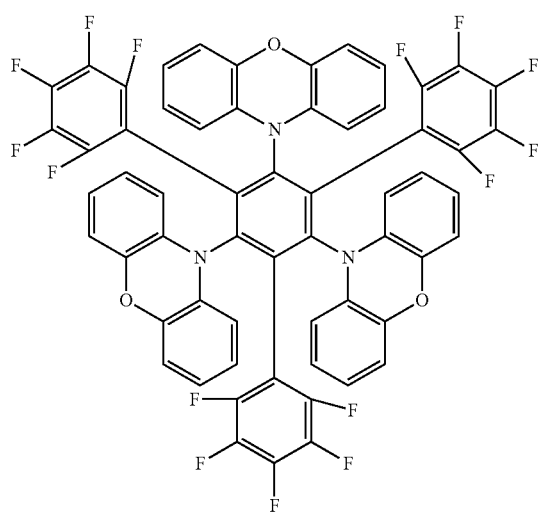
T-53
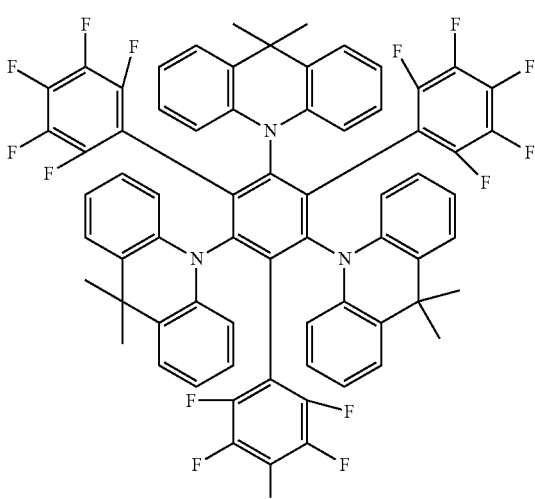
T-54
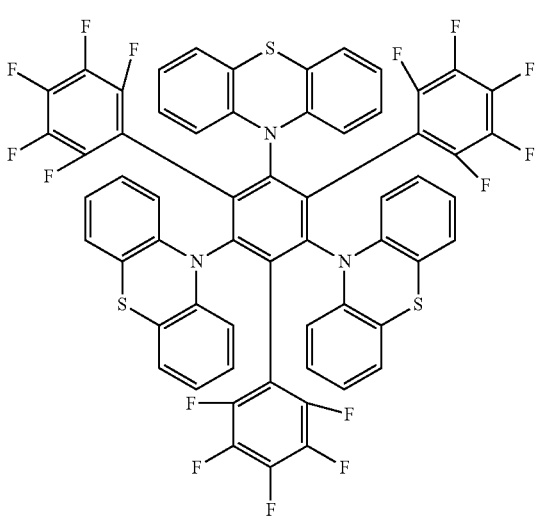
T-55
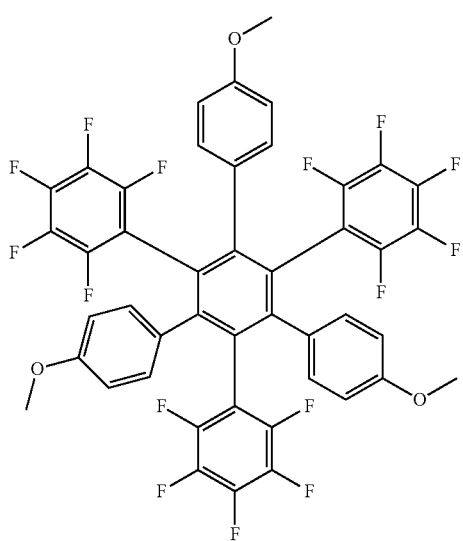

[Formula 21]
T-56
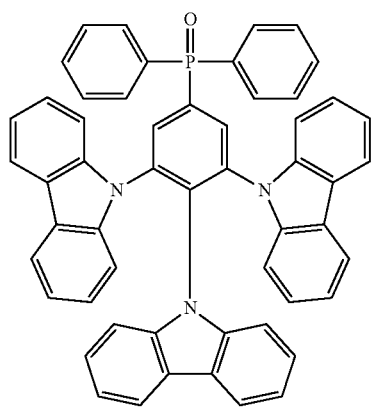
T-57
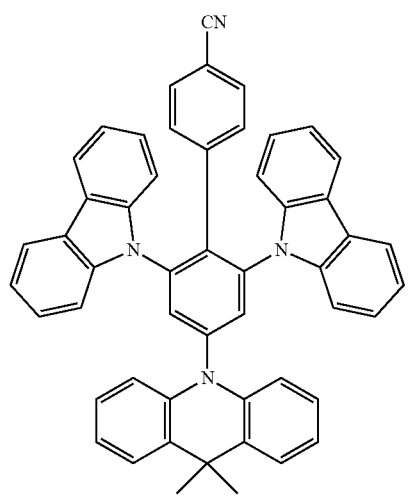
T-58
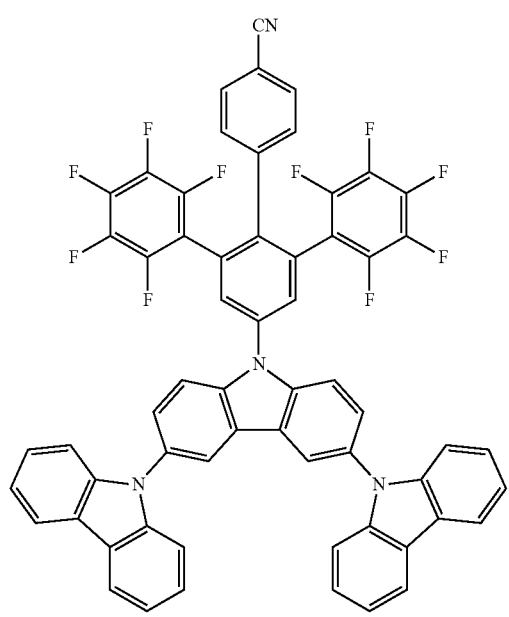
T-59
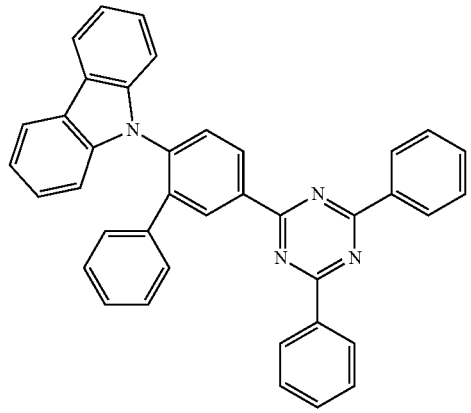
T-60
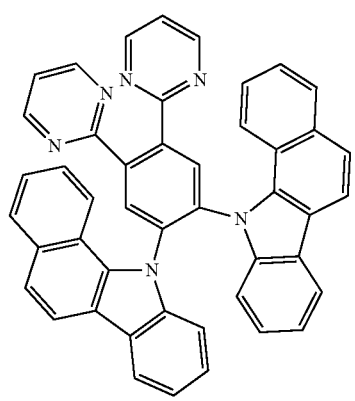
T-61
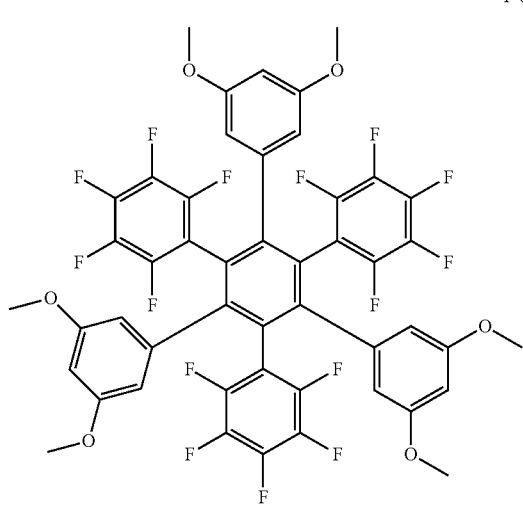

T-62
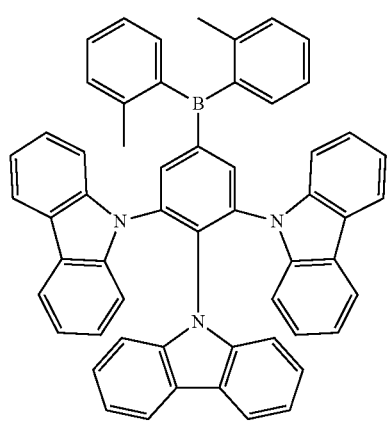
[Formula 22]
T-63
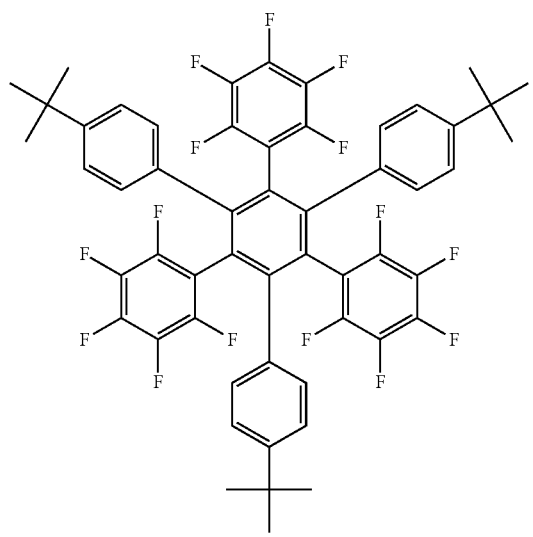
T-64
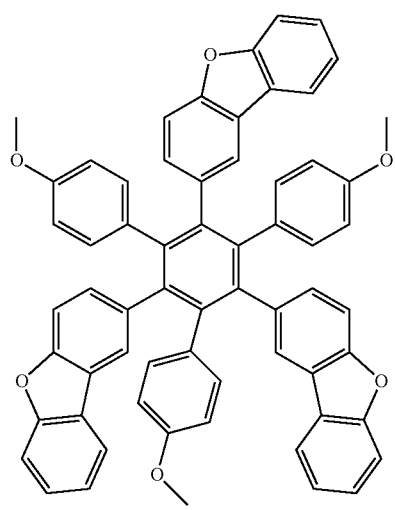
T-65
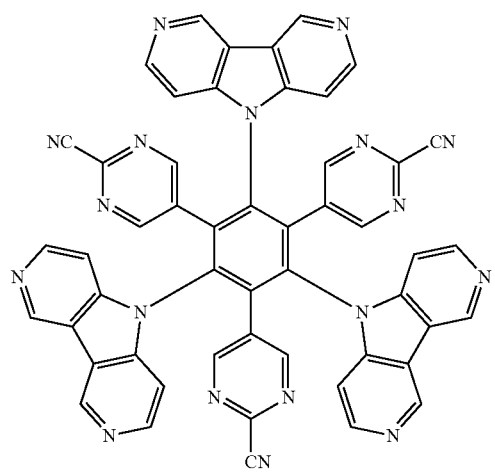
T-66
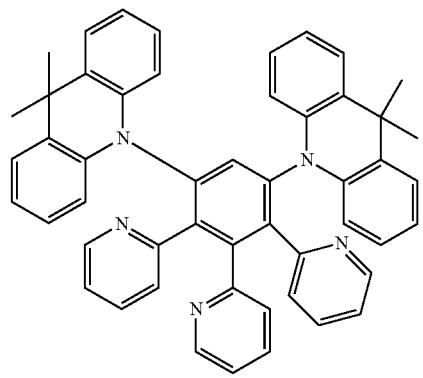
T-67
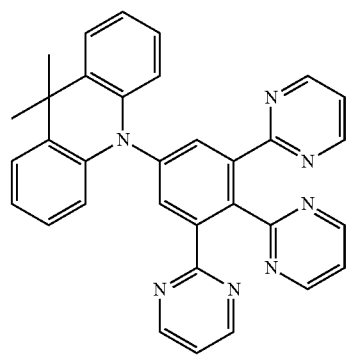
T-68
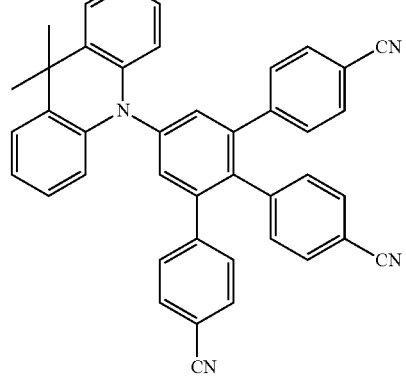

-continued
T-69
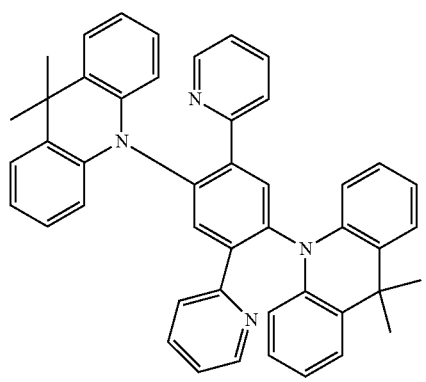
[Formula 23]
T-70
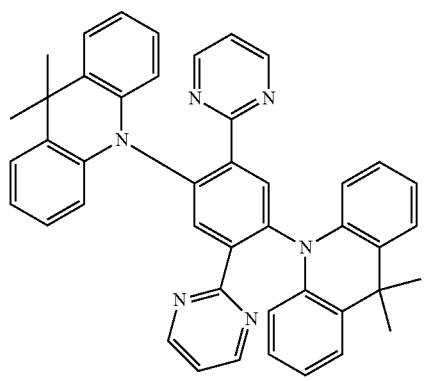
T-71
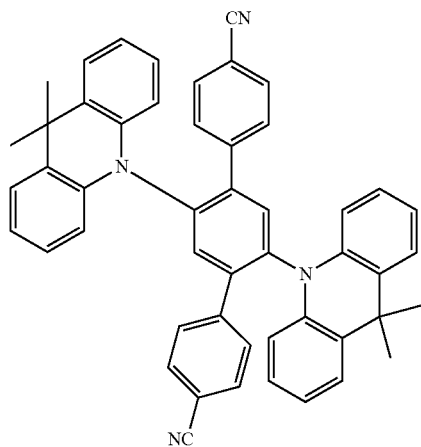
T-72
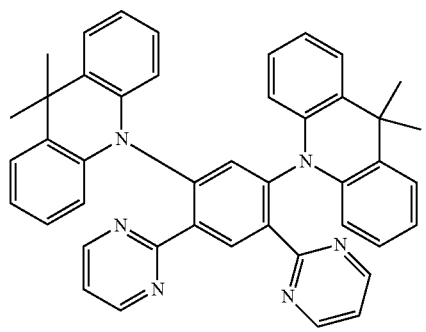
-continued
T-73
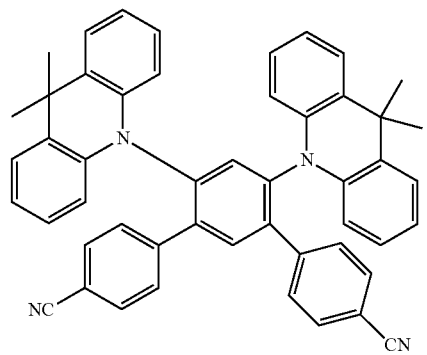
T-74
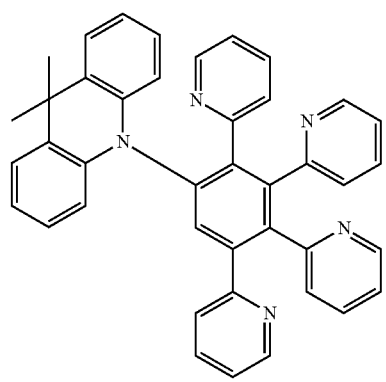
T-75
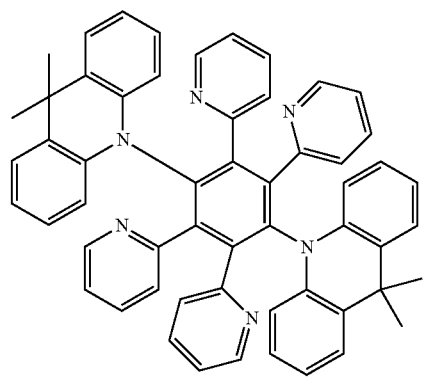
T-76
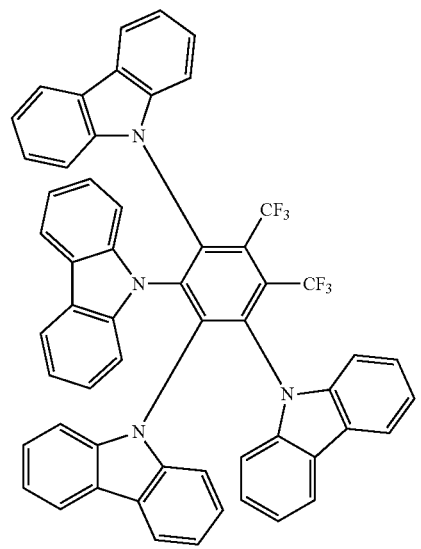

T-77
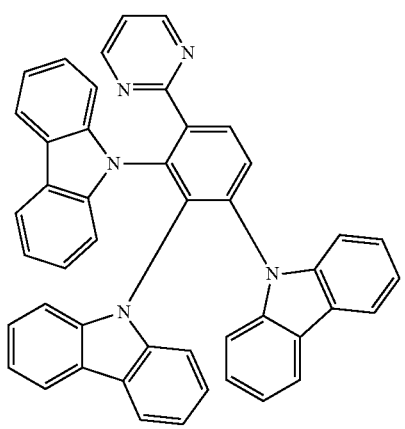
T-78
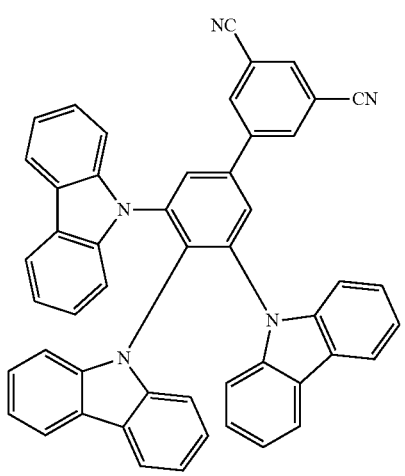
T-79
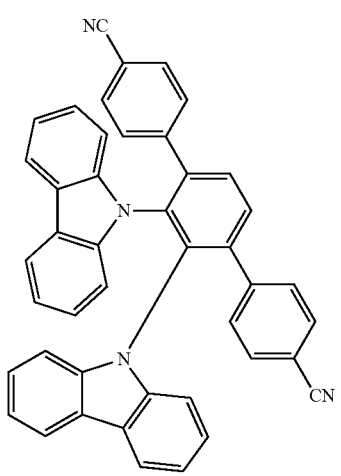
T-80
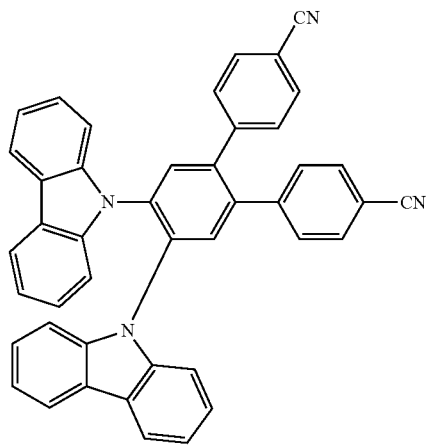
T-81
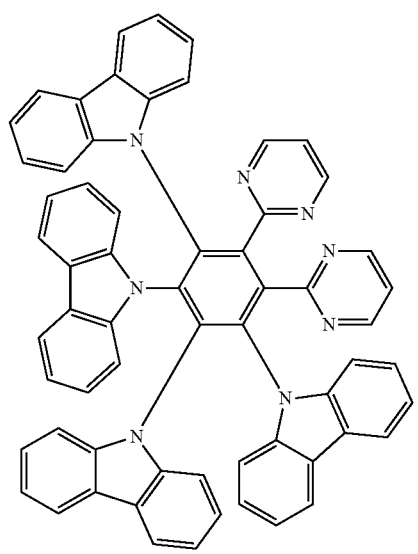
[Formula 24]
T-82
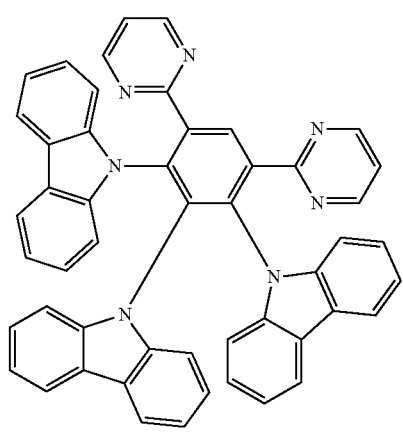

T-83
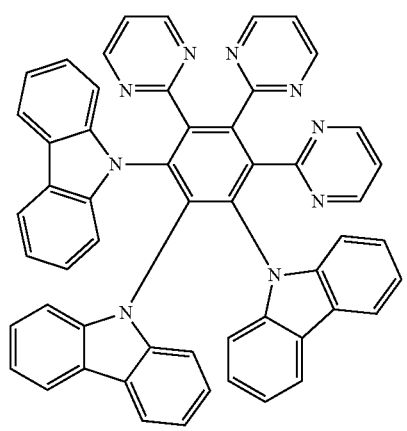
T-84
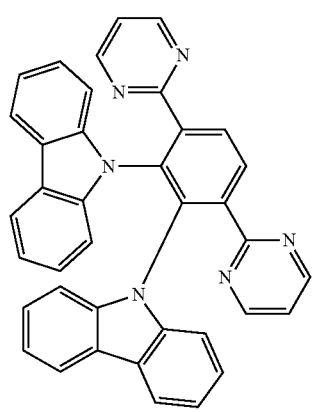
T-85
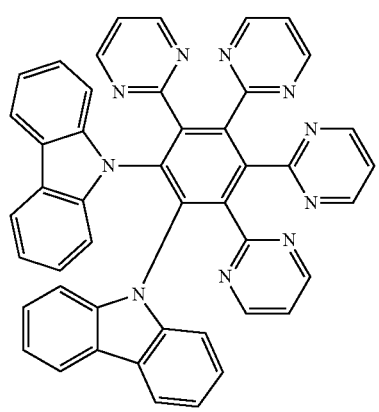
T-86
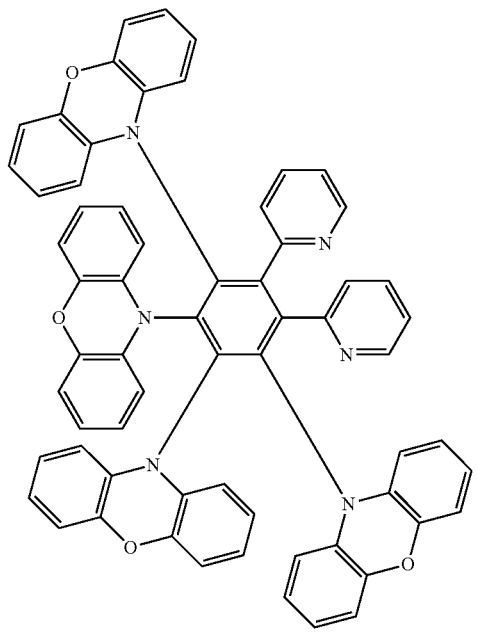
T-87
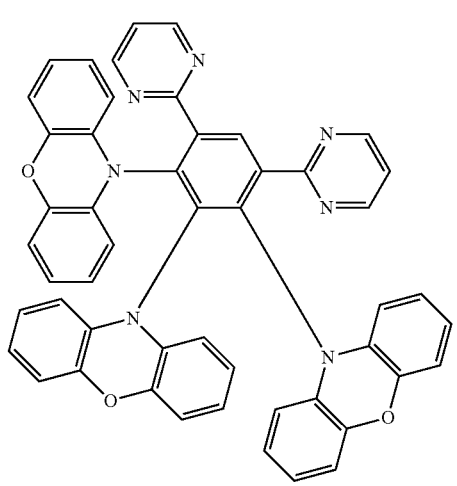
T-88
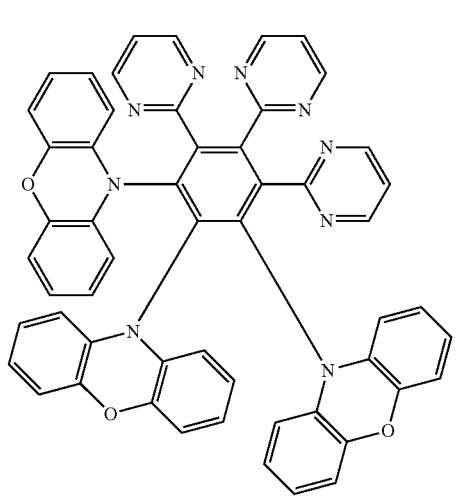

T-89
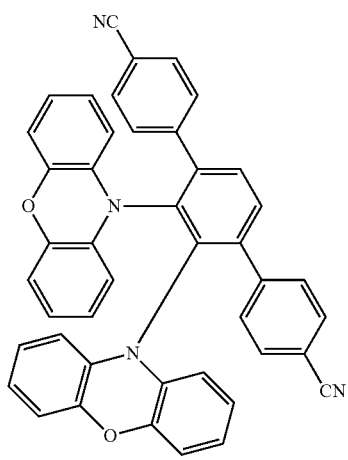
T-90
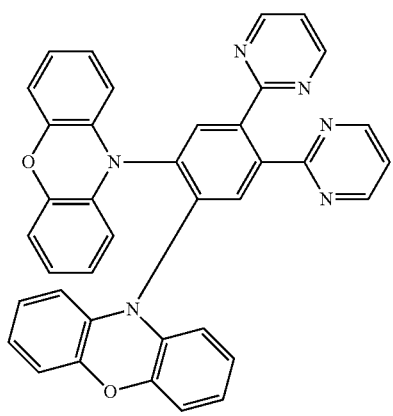
[Formula 25]
T-91
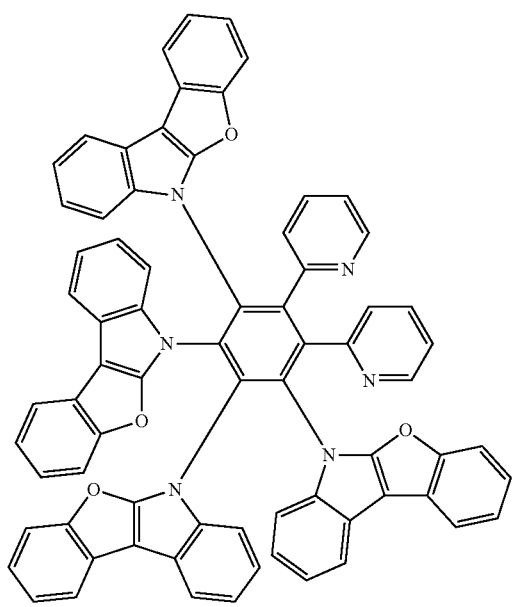
T-92
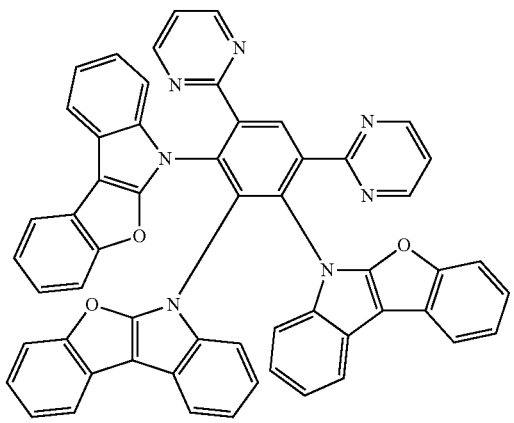
T-93
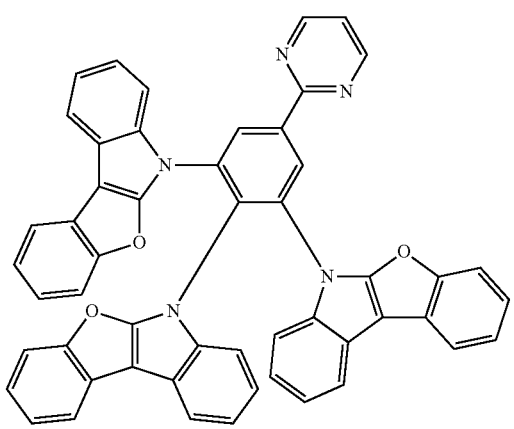
T-94
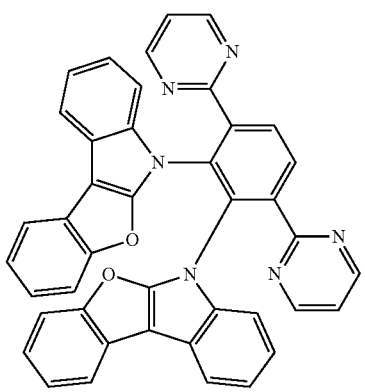
T-95
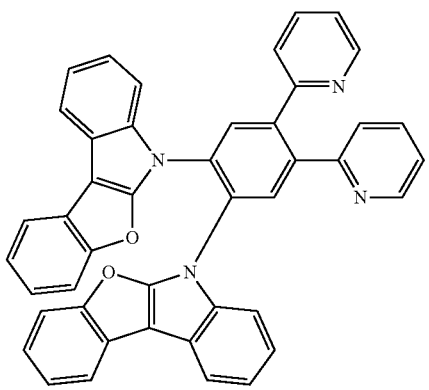

T-96
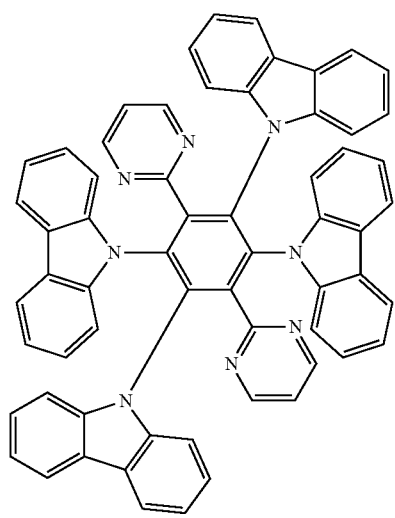
T-97
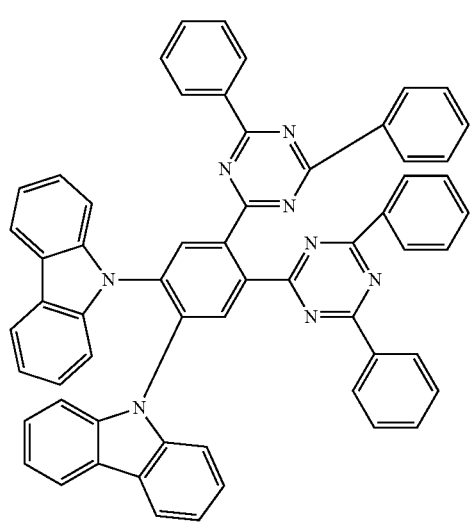
T-98
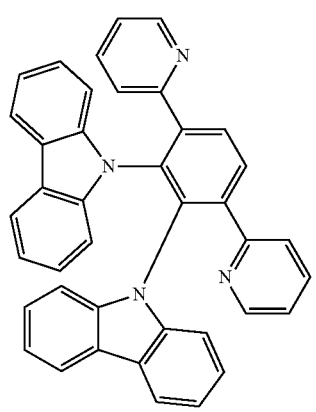
T-99
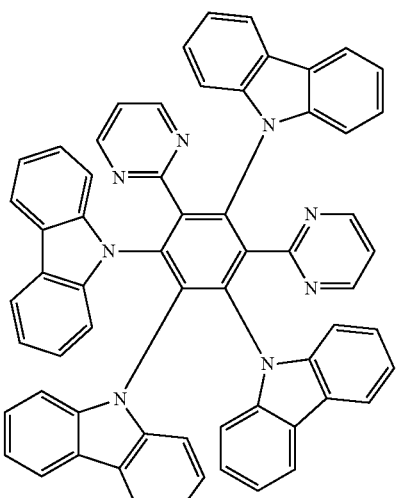
T-100
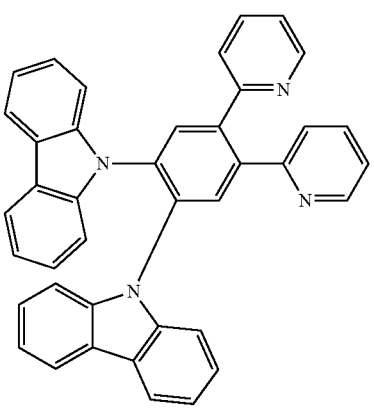
T-101
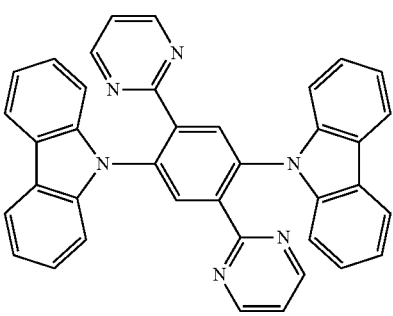
[Formula 26]
T-102
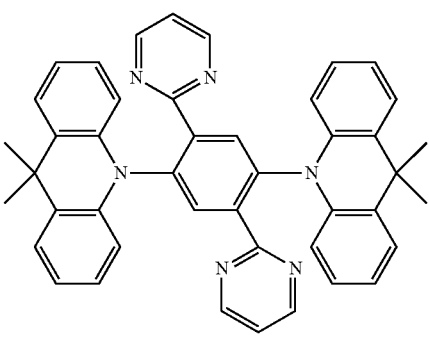

T-103
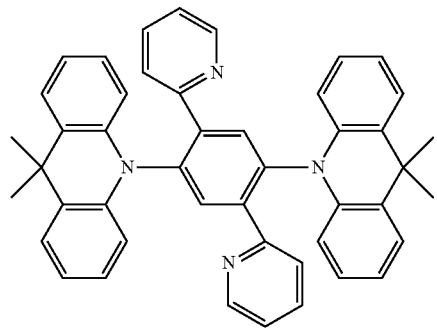
T-107
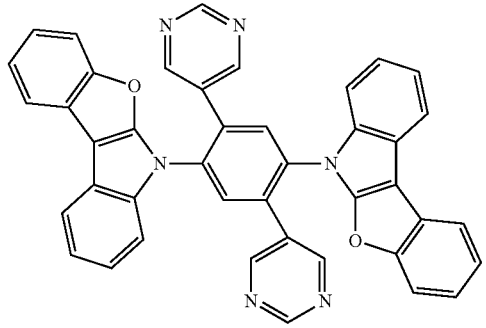
T-104
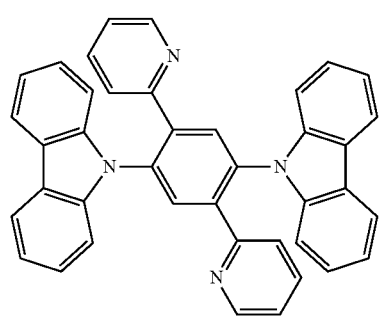
T-108
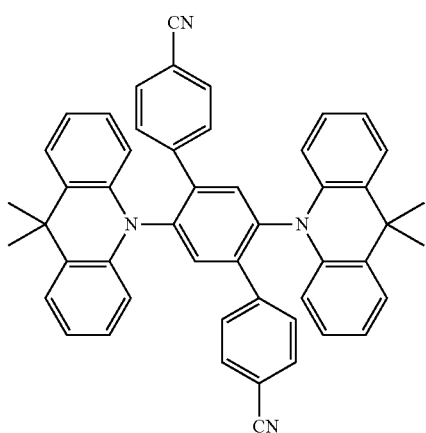
T-105
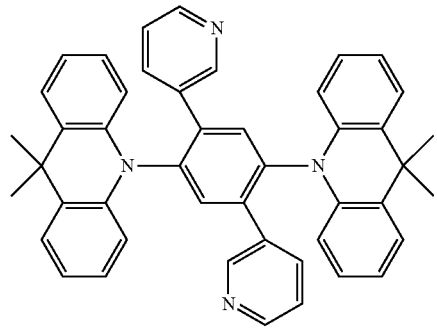
T-109
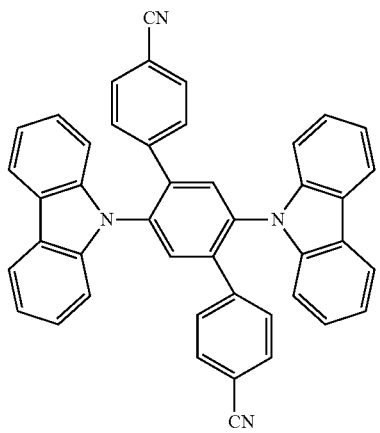
T-106
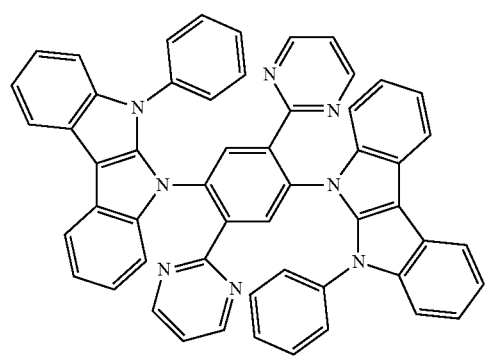
T-110
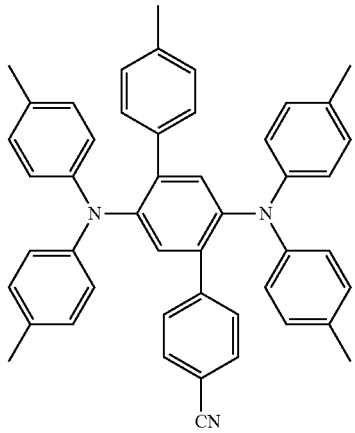

T-111 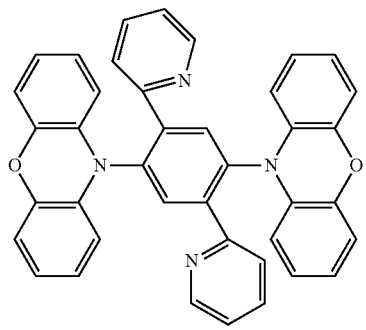
T-115 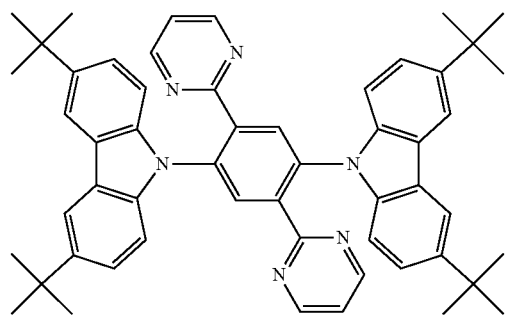
T-112 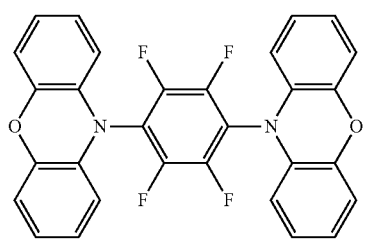
T-116 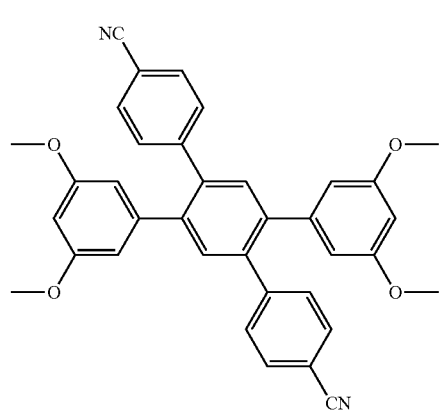
T-113 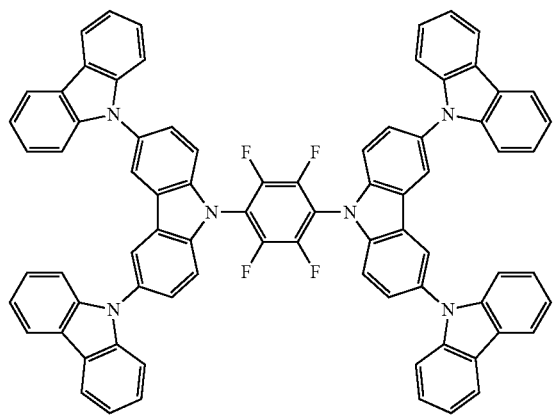
[Formula 27]
T-117 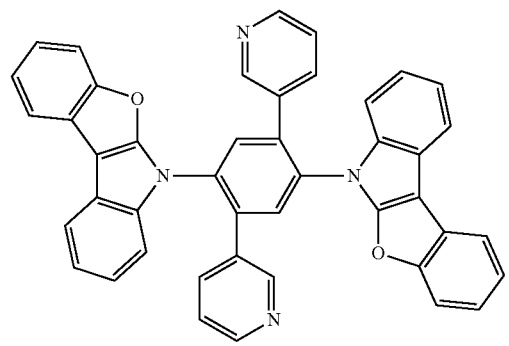
T-114 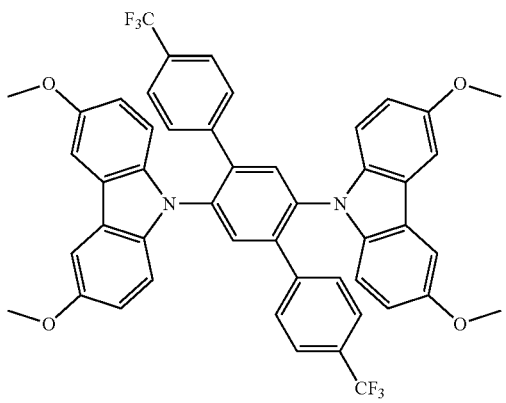
T-118 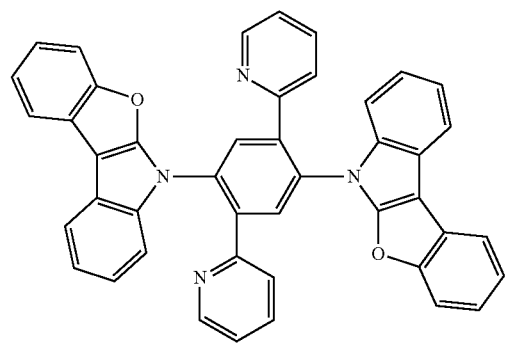

T-119
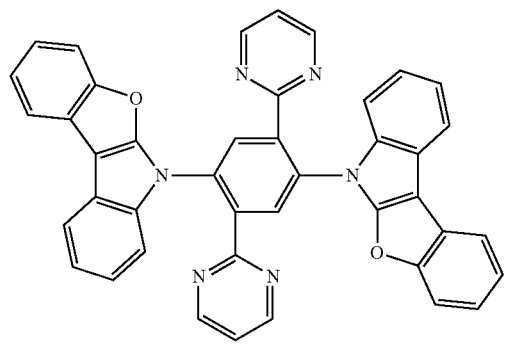
T-120
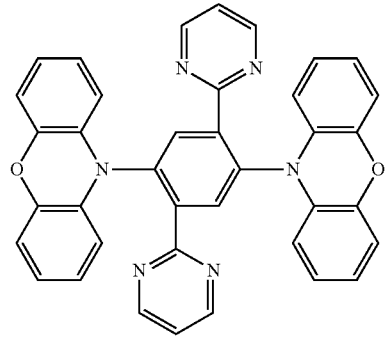
T-121
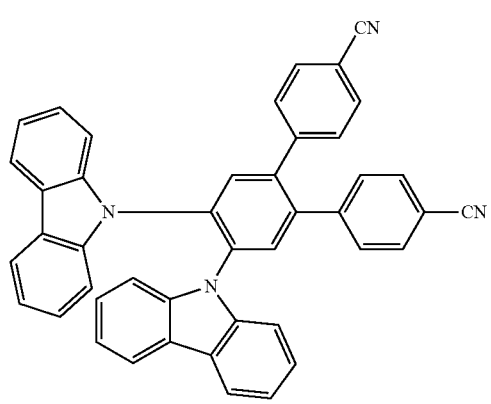
T-122
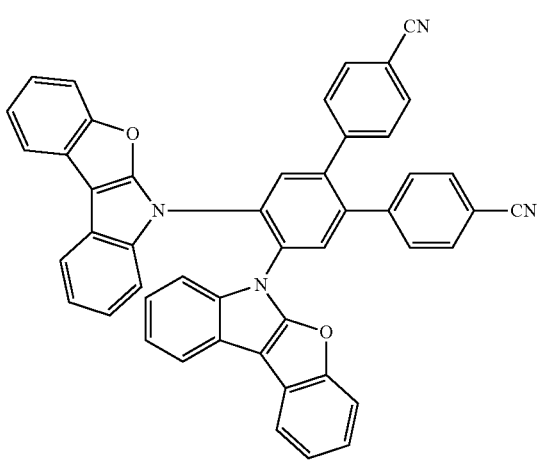
T-123
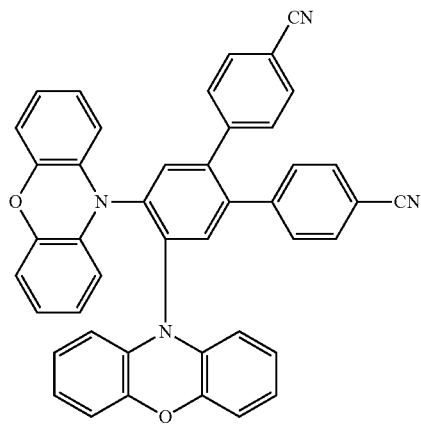
T-124
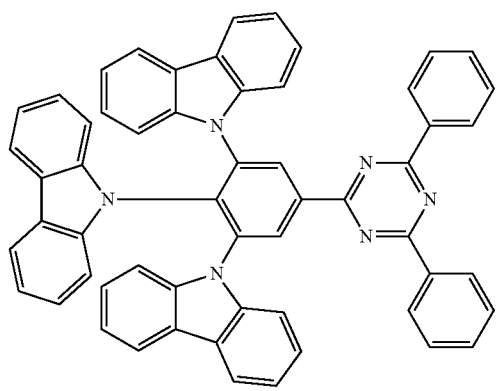
T-125
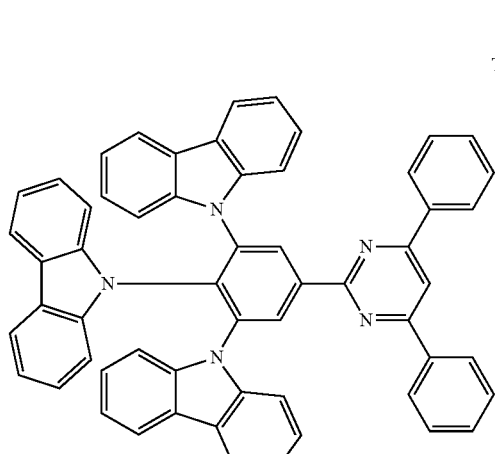

[Formula 28]

T-126

T-127

T-128

T-129

T-130

T-131

T-132
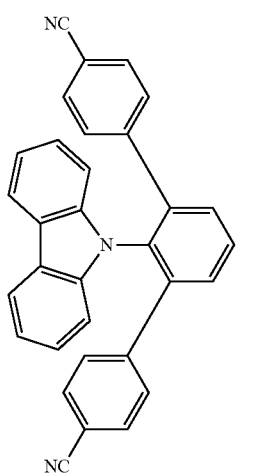
T-133
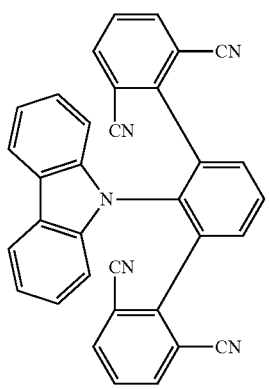
T-134
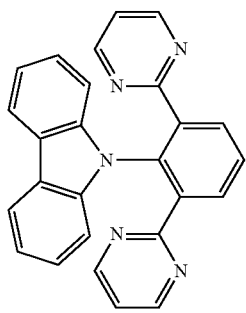
[Formula 29]
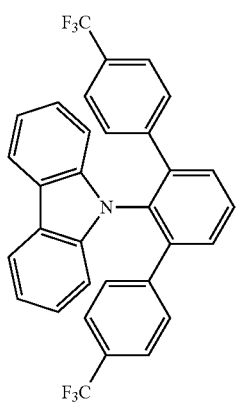
T-136
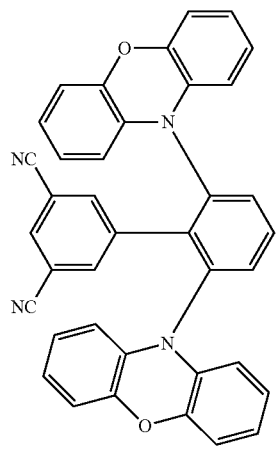
T-137
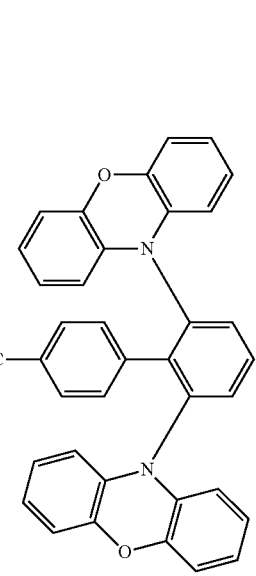
T-138
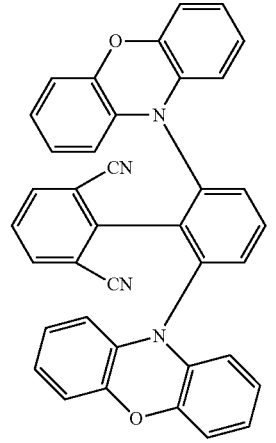

T-139
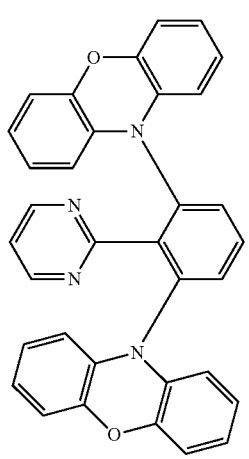
T-140
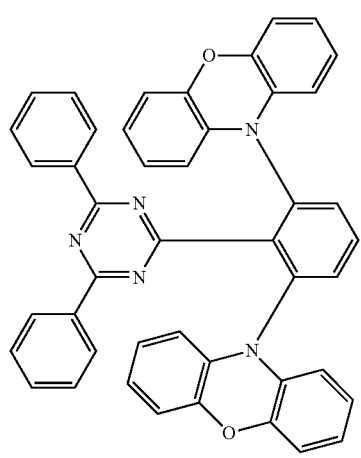
T-141
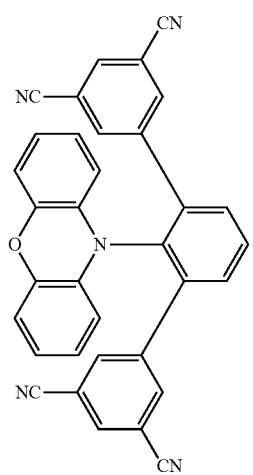
T-142
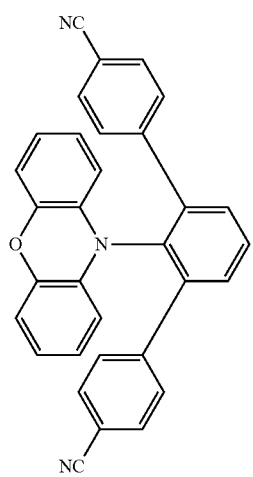
T-143
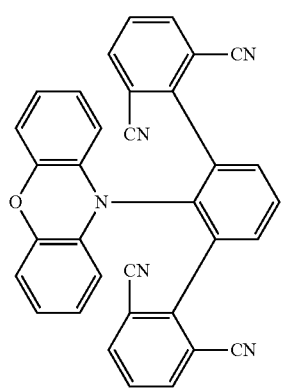
[Formula 30]
T-144
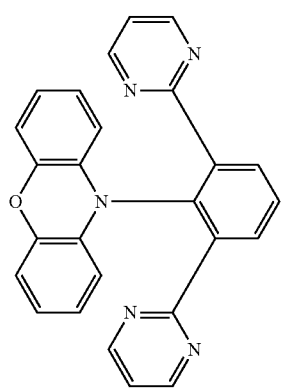

-continued
T-145
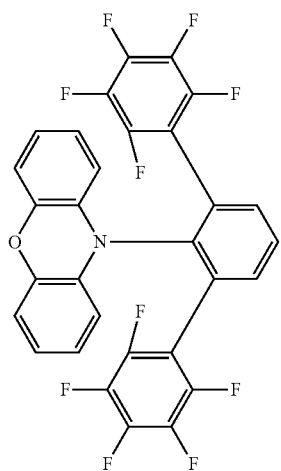
T-146
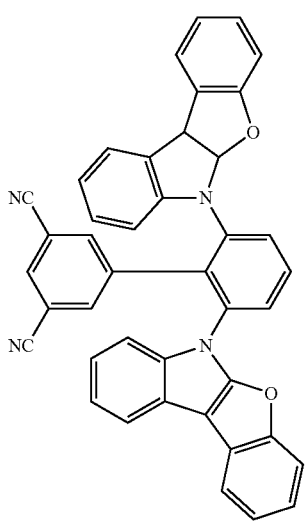
T-147
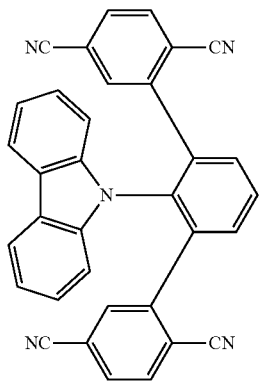
-continued
T-148
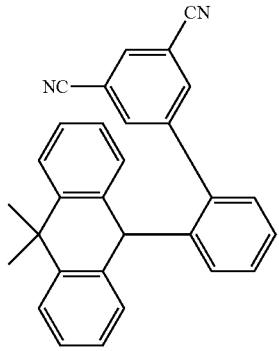
T-149
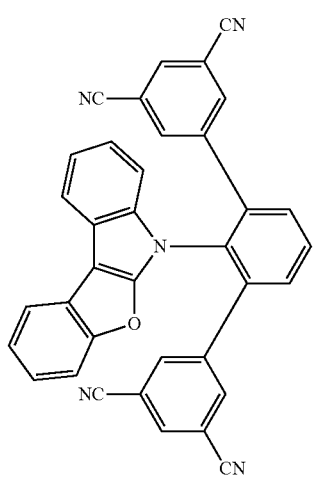
T-150
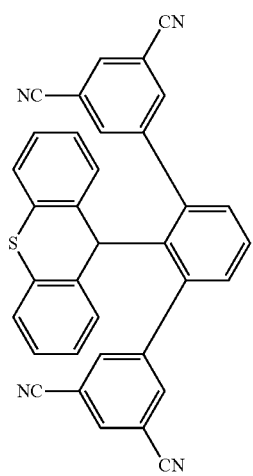

T-151
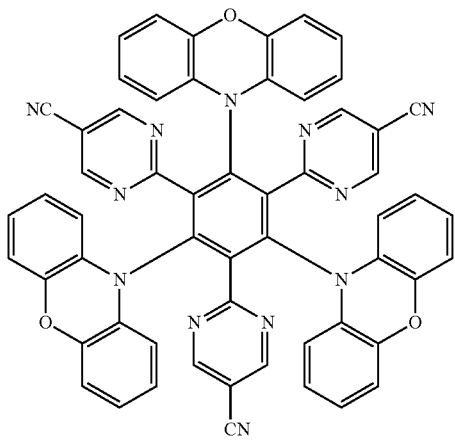
T-152
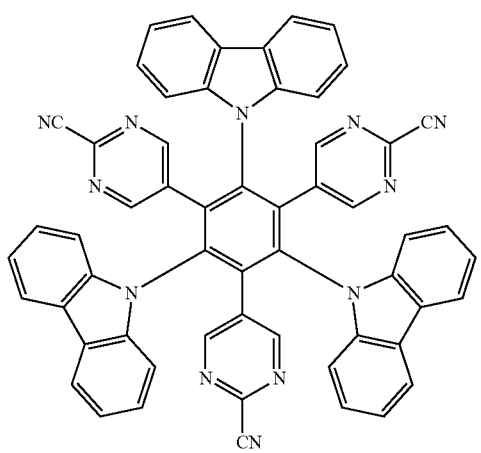
[Formula 31]
T-153
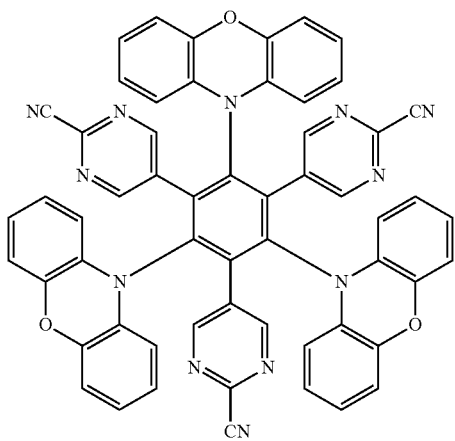
T-154
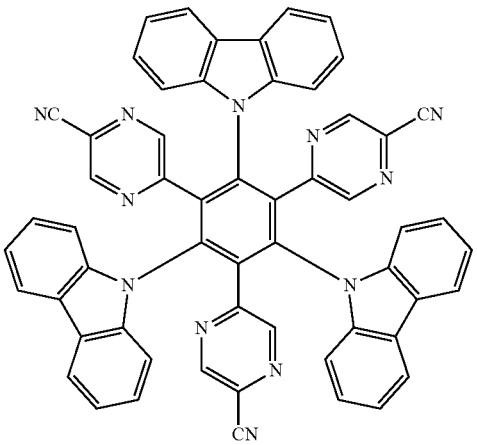
T-155
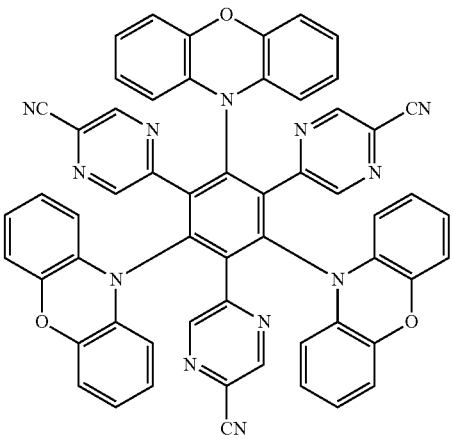
T-156
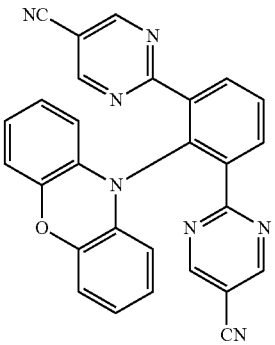
T-157
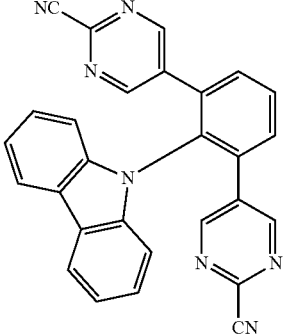

T-158
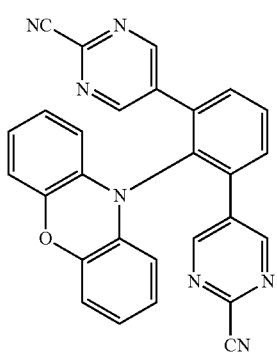
T-159
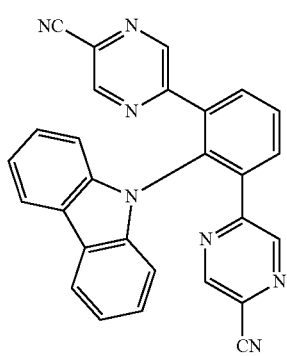
T-160
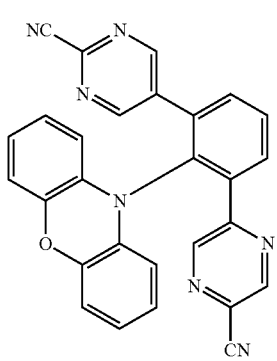
T-161
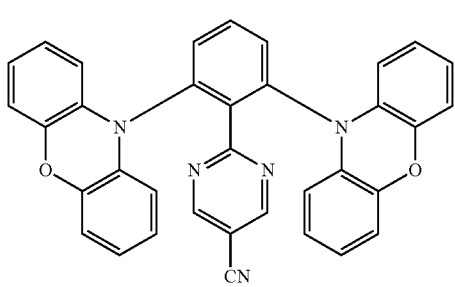
T-162
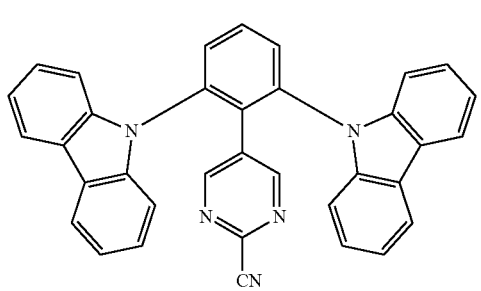
T-163
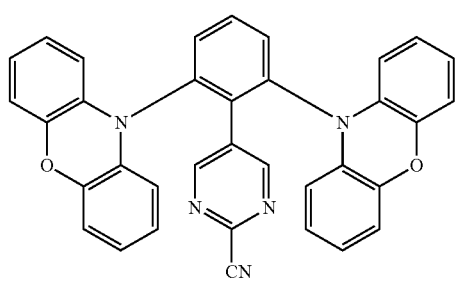
T-164
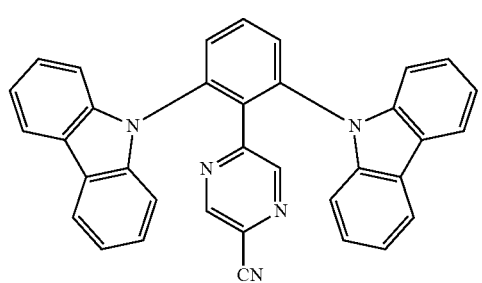
[Formula 32]
T-165
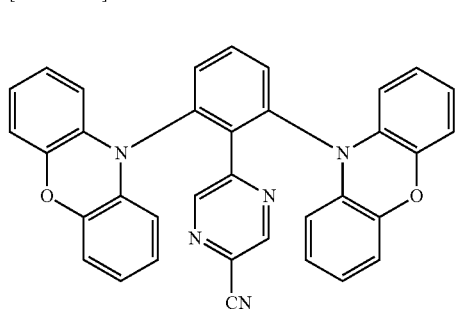
T-166
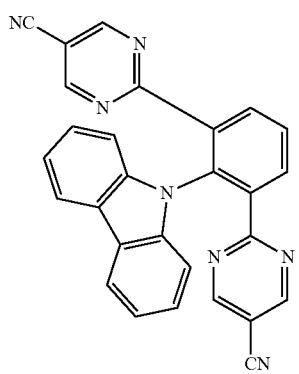

-continued
T-167
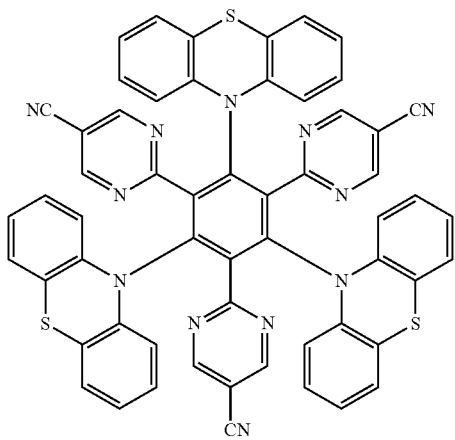
T-168
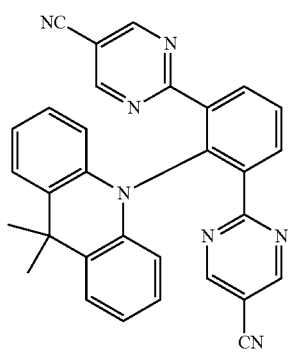
T-169
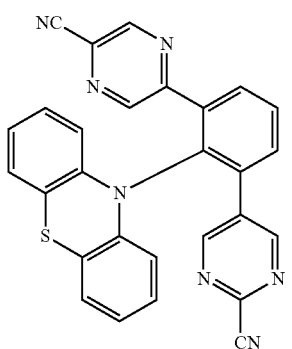
T-170
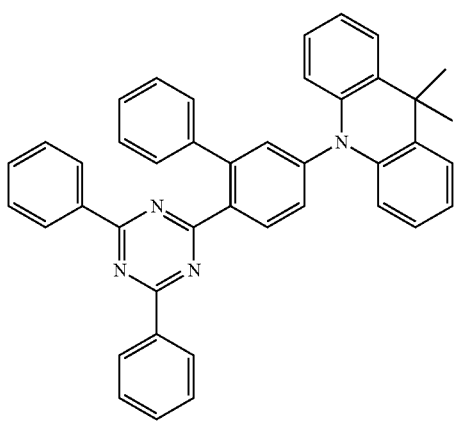
-continued
T-171
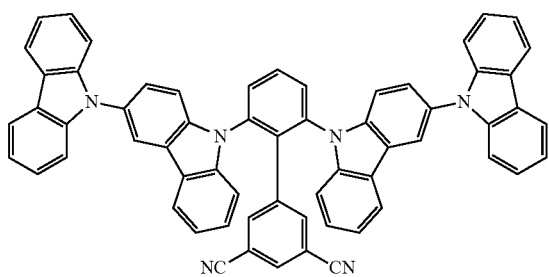
T-172
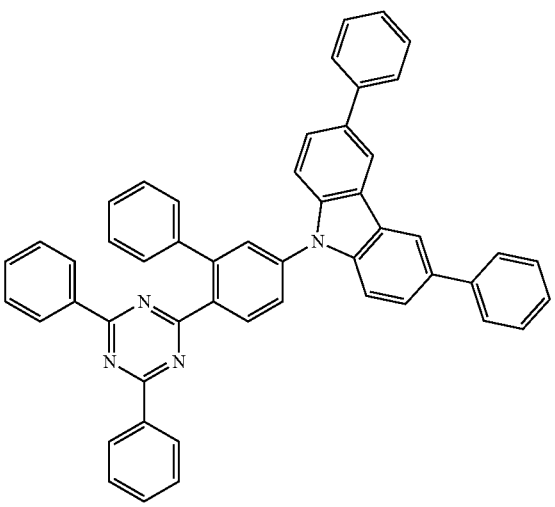
T-173
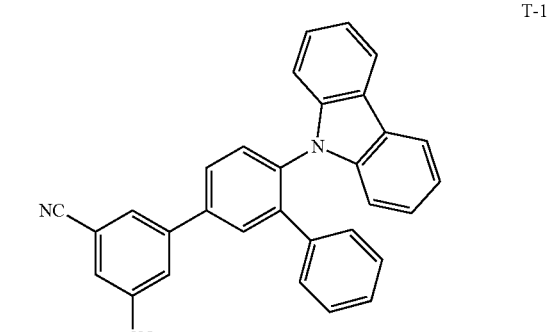
T-174
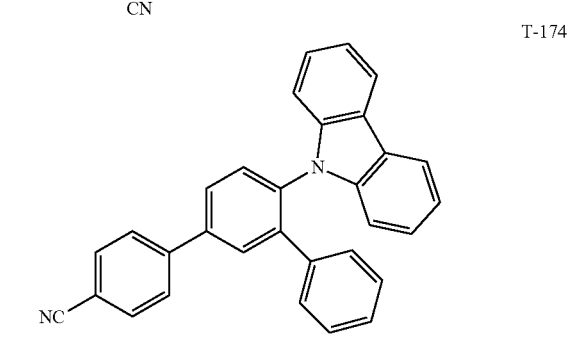

T-175
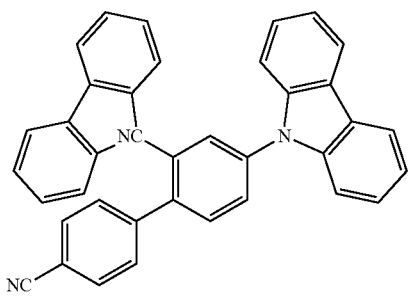
[Formula 33]
T-176
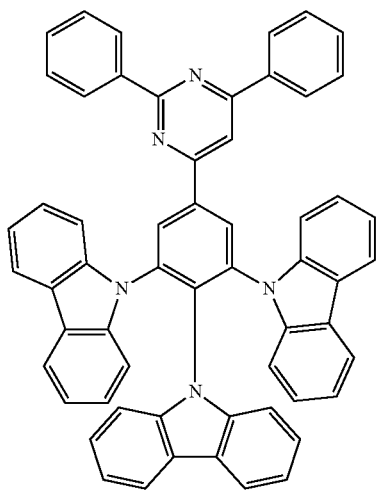
T-177
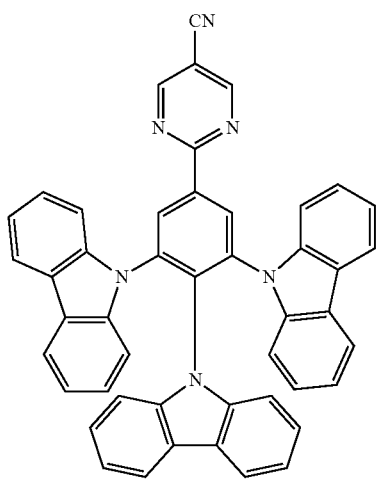
T-178
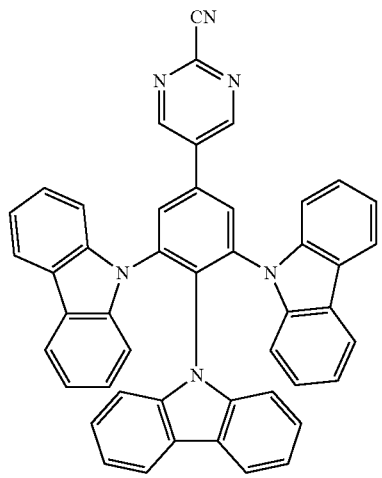
T-179
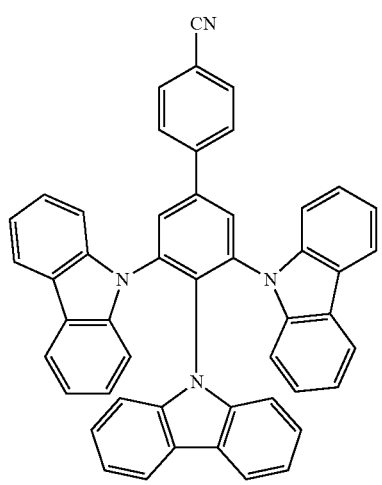
T-180
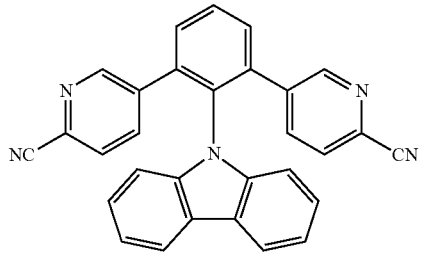

T-181
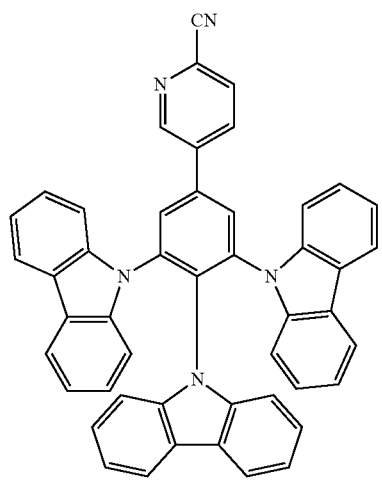
[Formula 34]
T-182
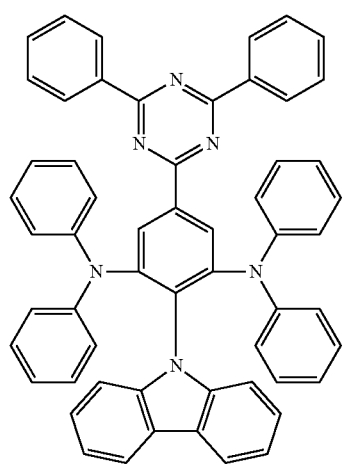
T-183
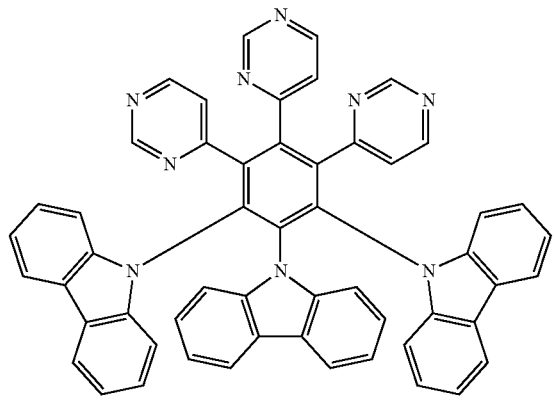
T-184
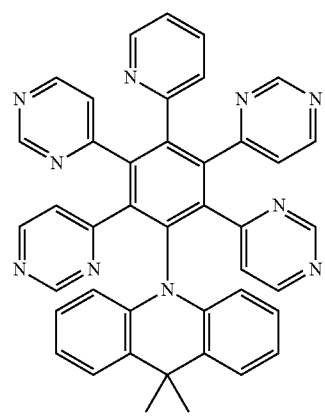
T-185
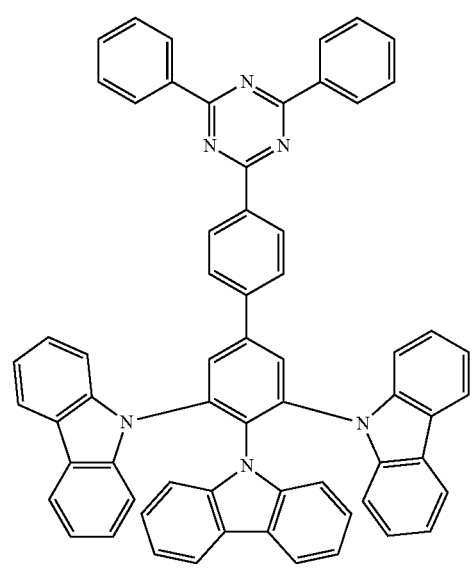
T-186
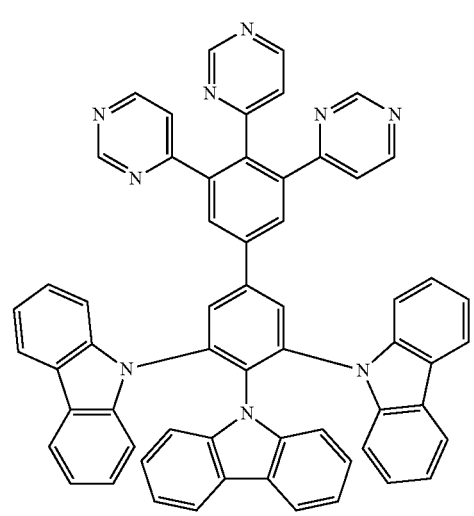

T-187 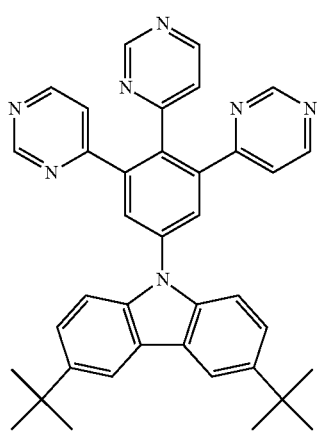
T-188 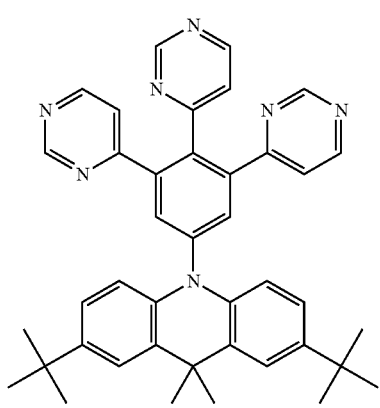
T-189 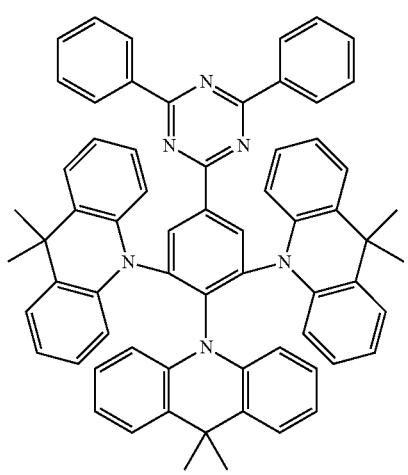
T-190 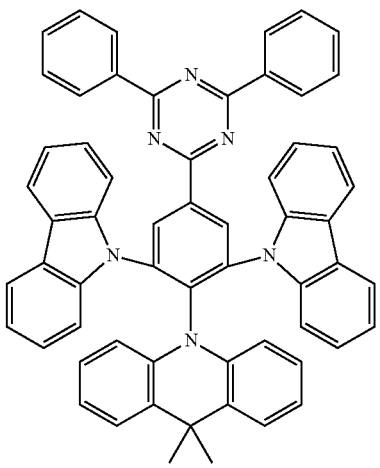
[Formula 35]
T-191 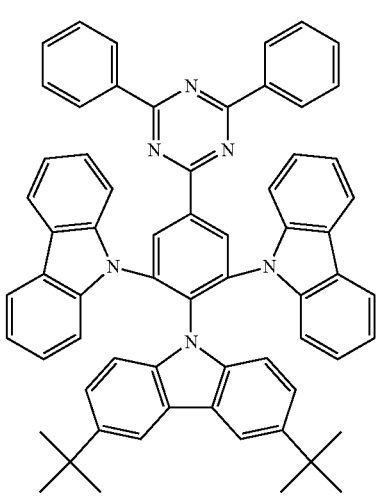
T-192 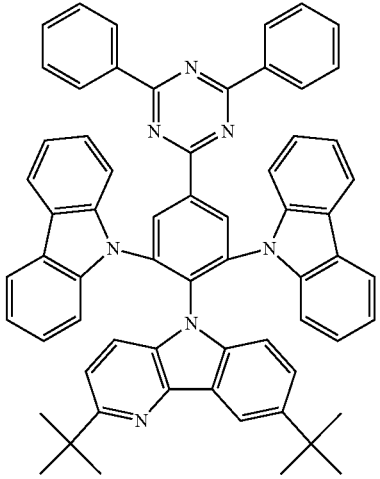

T-193
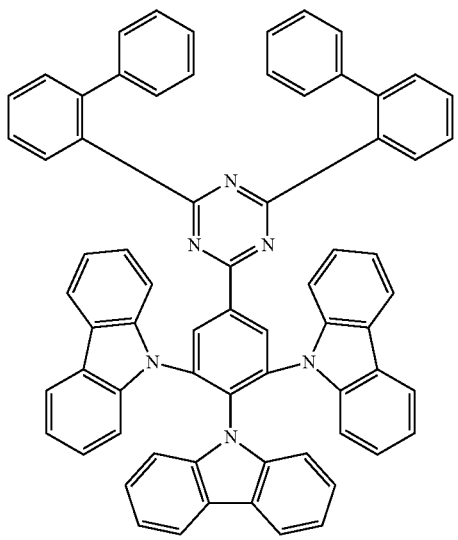
T-194
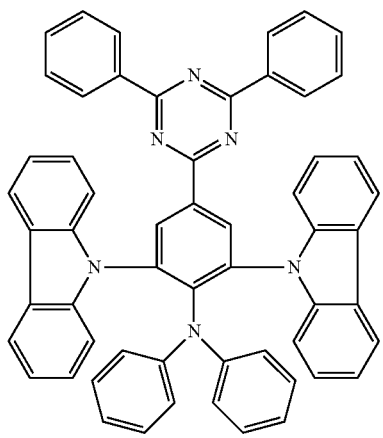
T-195
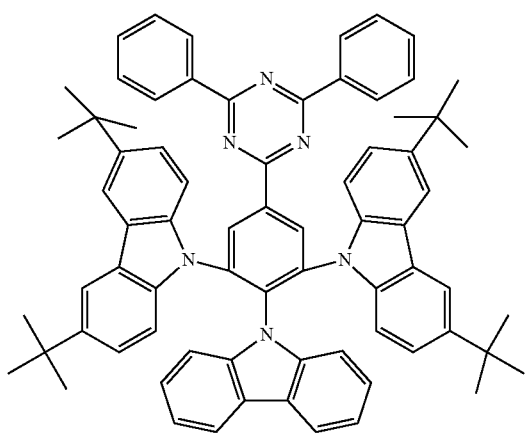
T-196
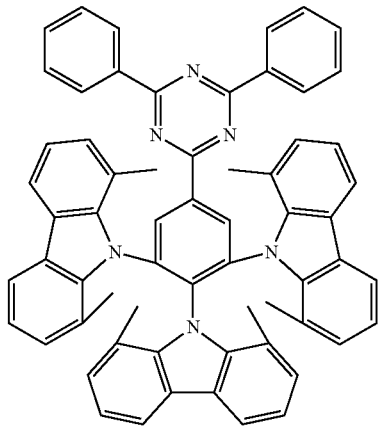
T-197
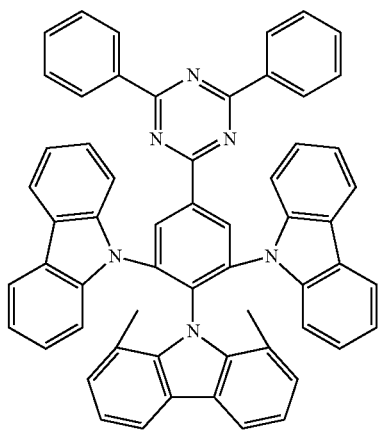
T-198
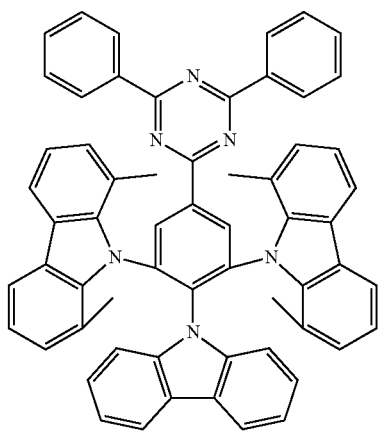

T-199
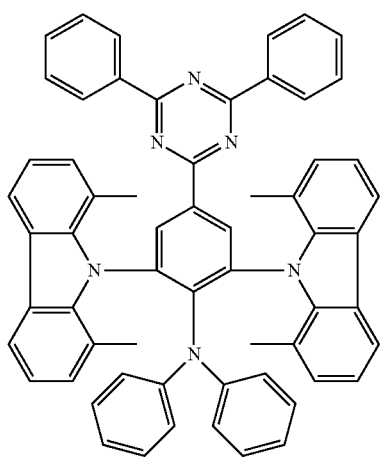
[Formula 36]
T-200
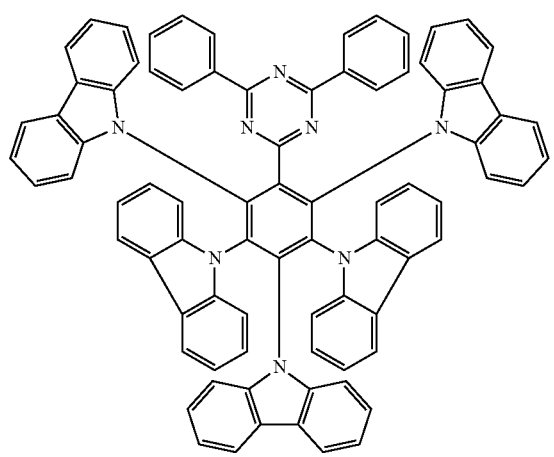
T-201
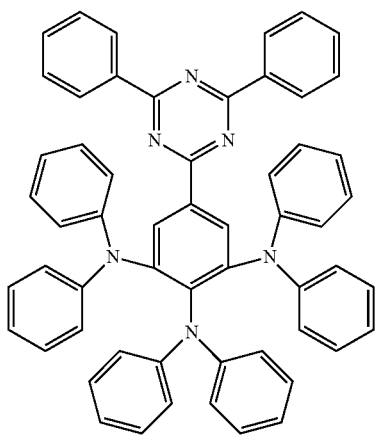
T-202
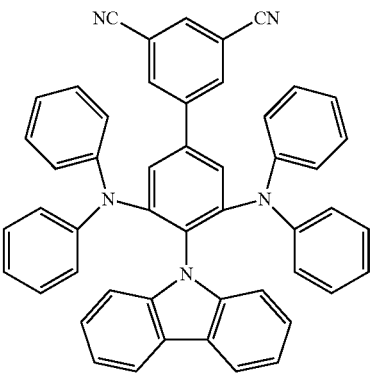
T-203
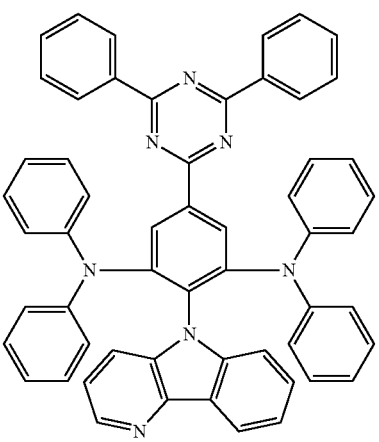
T-204
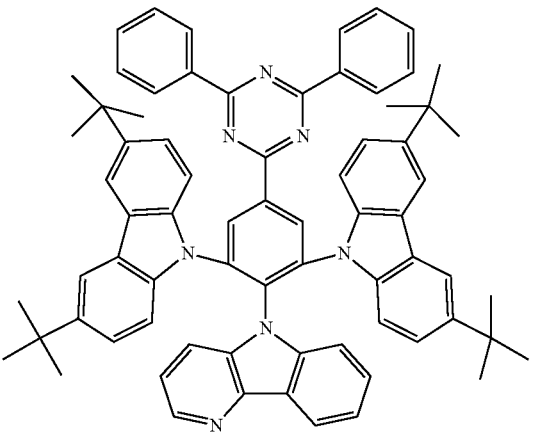

T-205
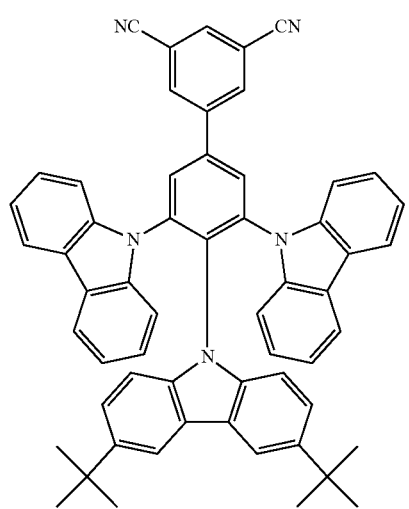
T-208
[Formula 37]
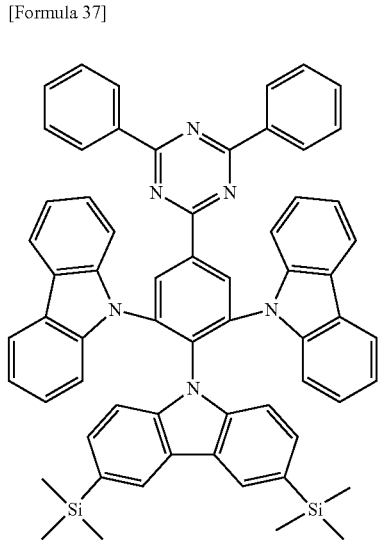
T-206
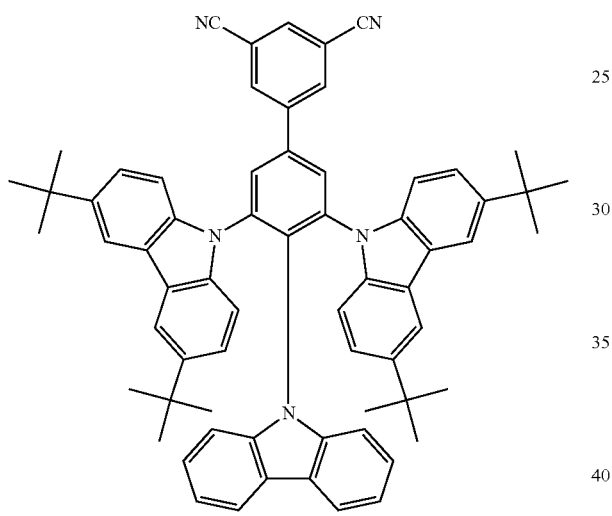
T-209
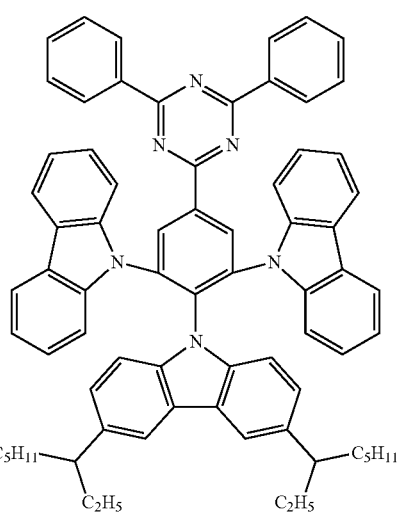
T-207
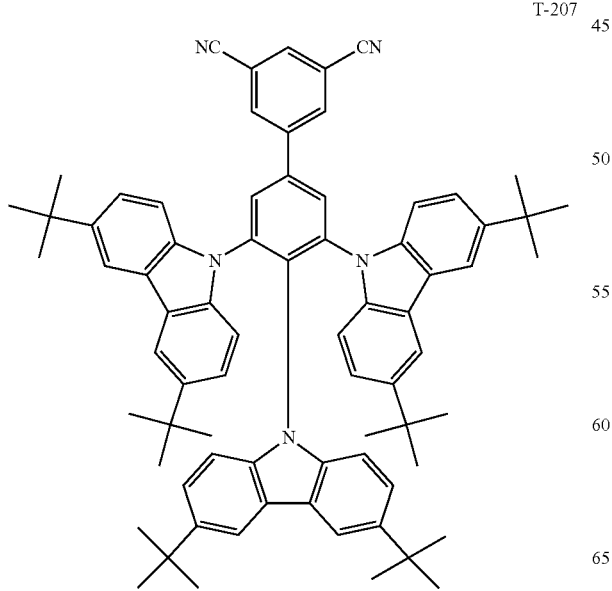
T-210
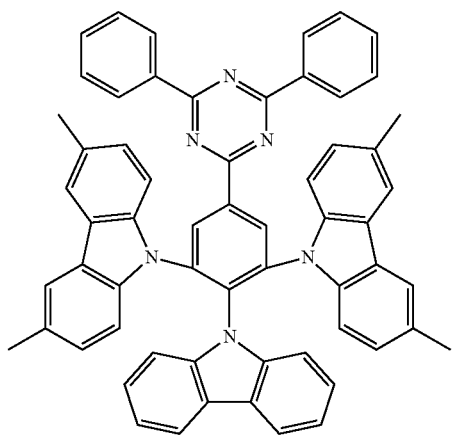

T-211
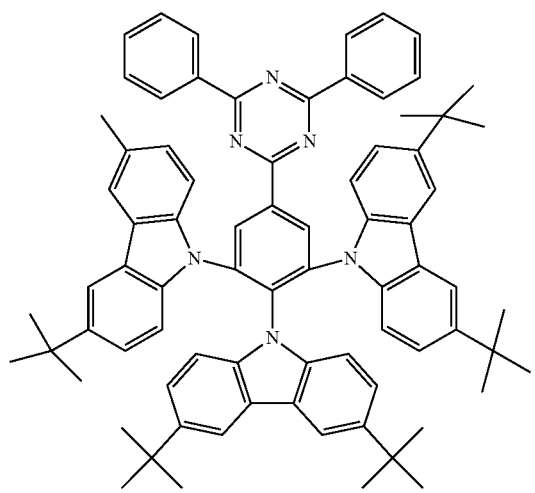
T-214
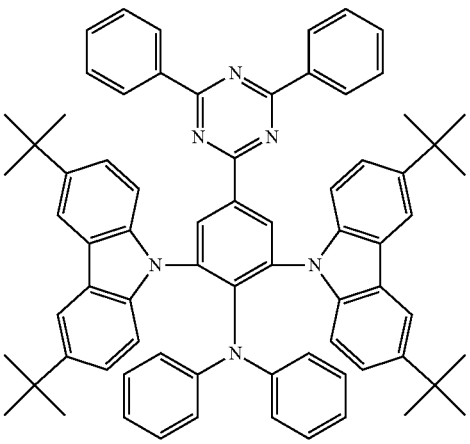
T-212
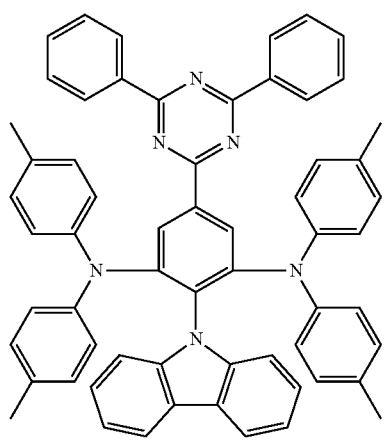
T-215
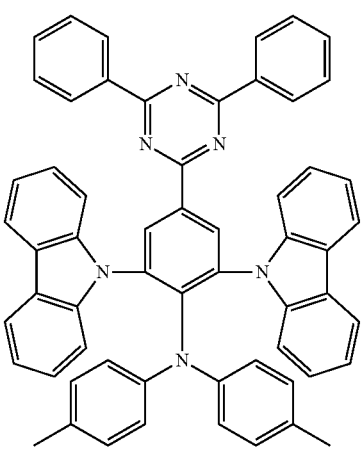
T-213
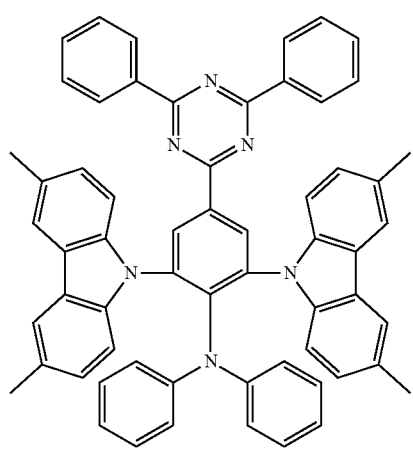
T-216
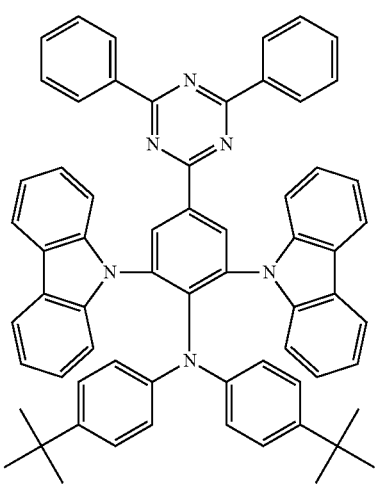

[Formula 38]
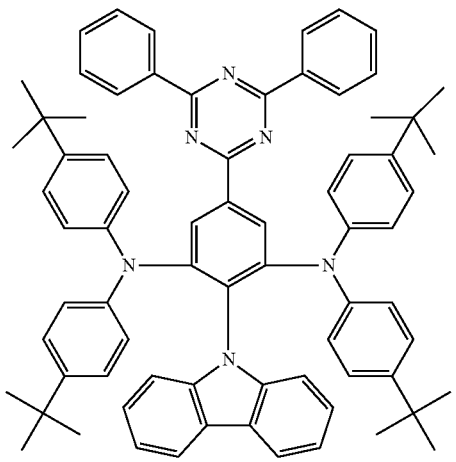
T-217
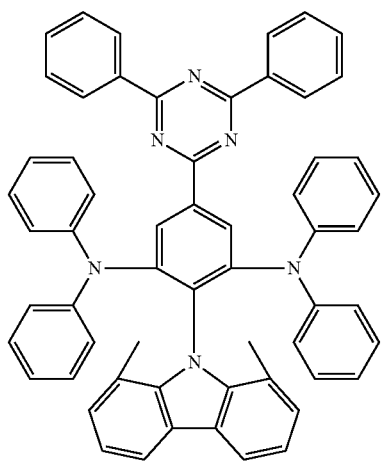
T-220
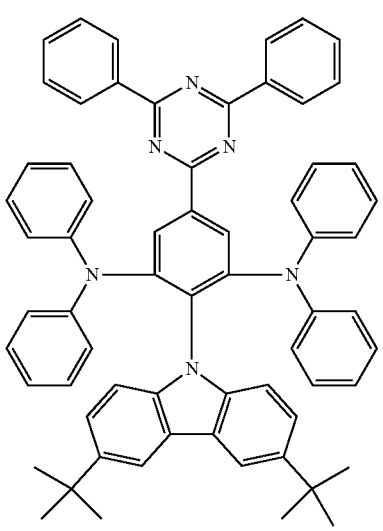
T-218
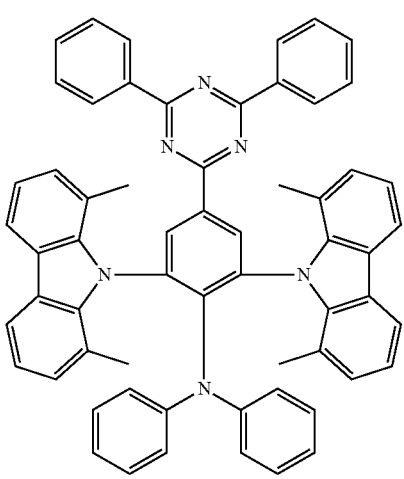
T-219
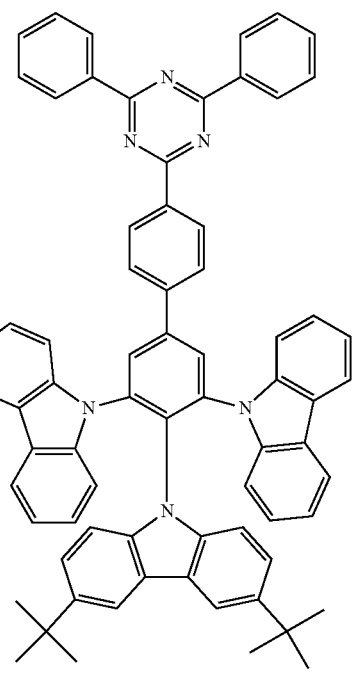
T-221

T-222
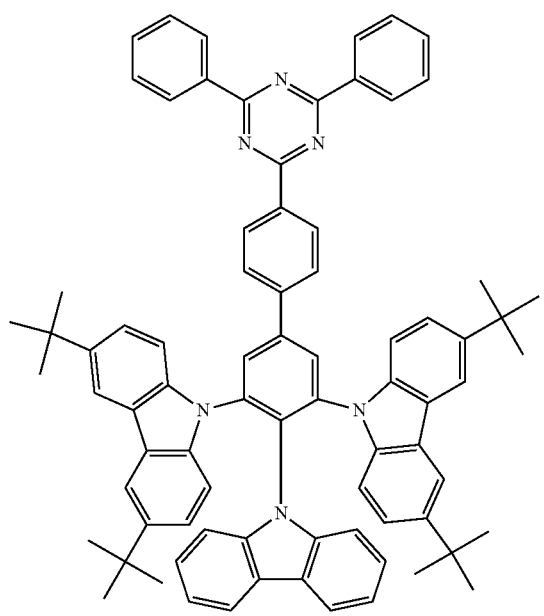
T-223
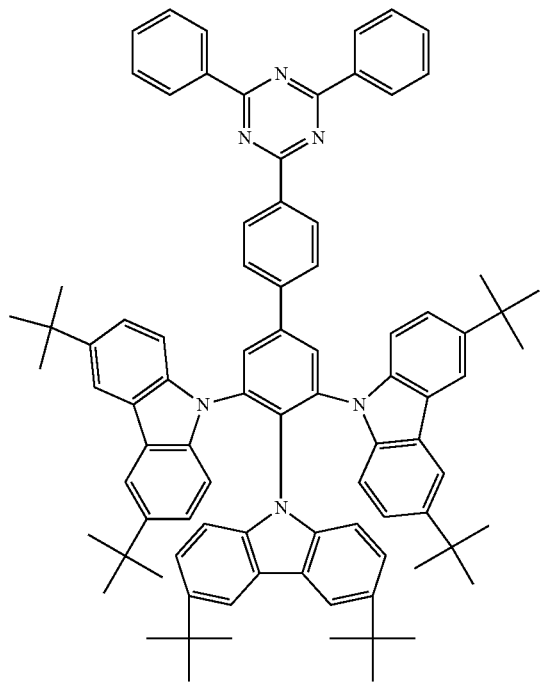
T-224
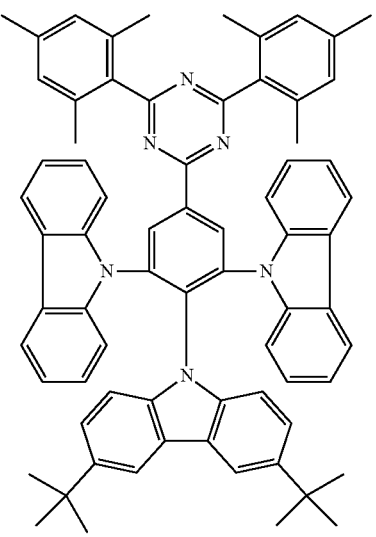
T-225
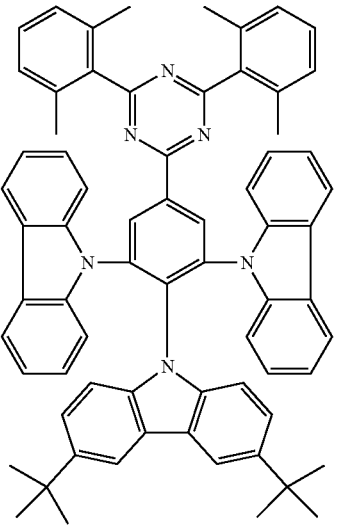
[Formula 39]
T-226
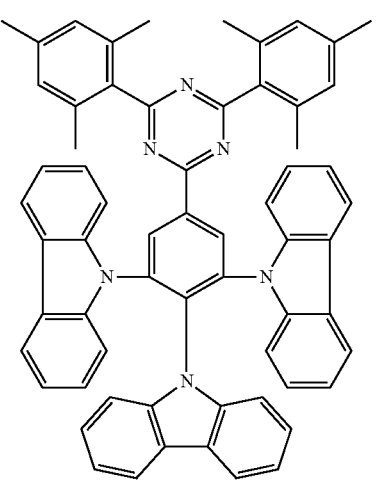

T-227
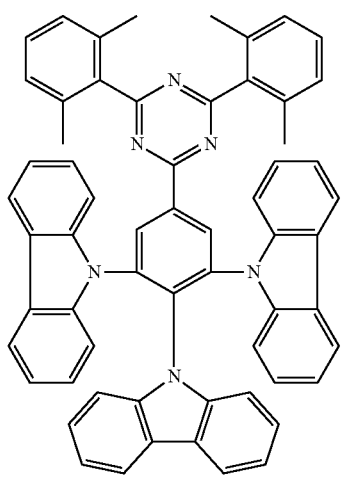
T-228
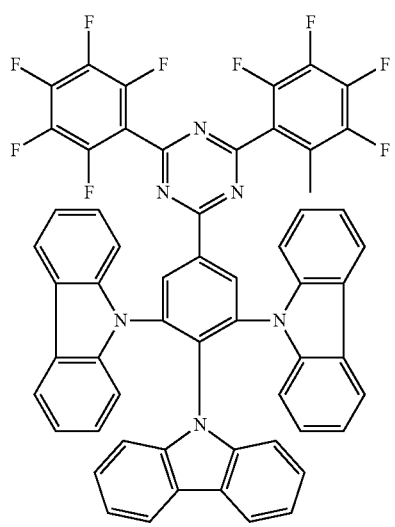
T-229
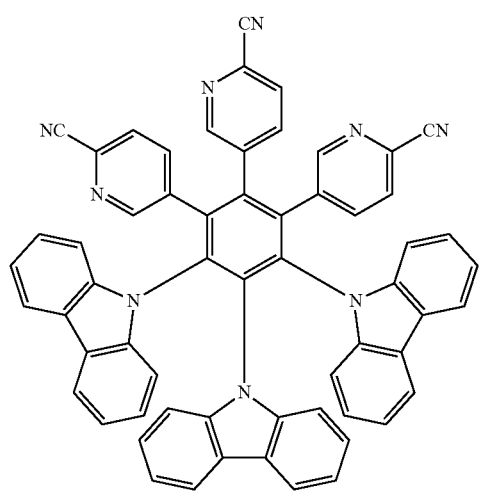
T-230
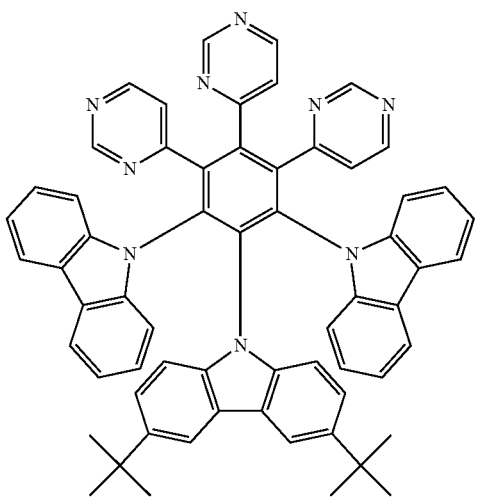
T-231
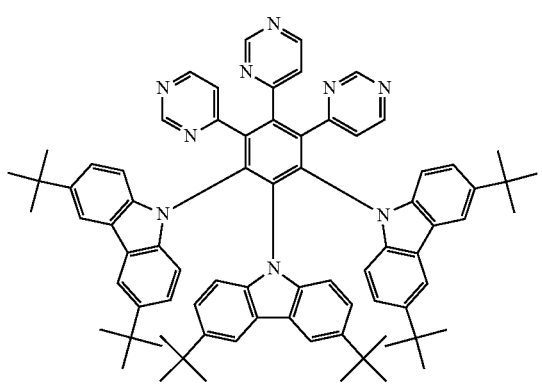
T-232
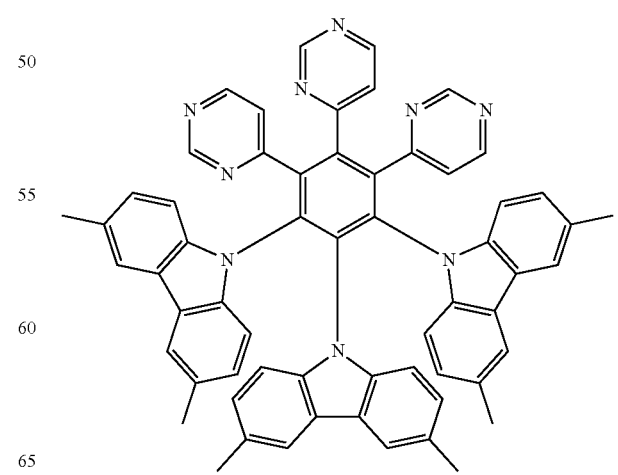

[Formula 40]
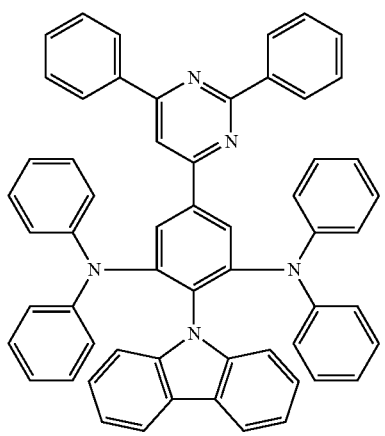
T-233
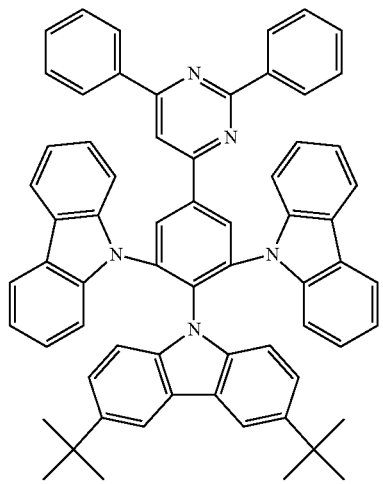
T-236
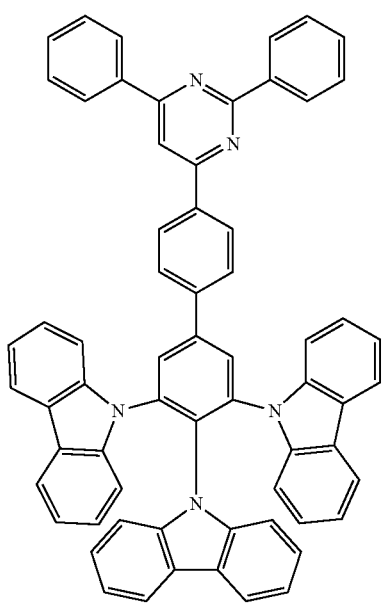
T-234
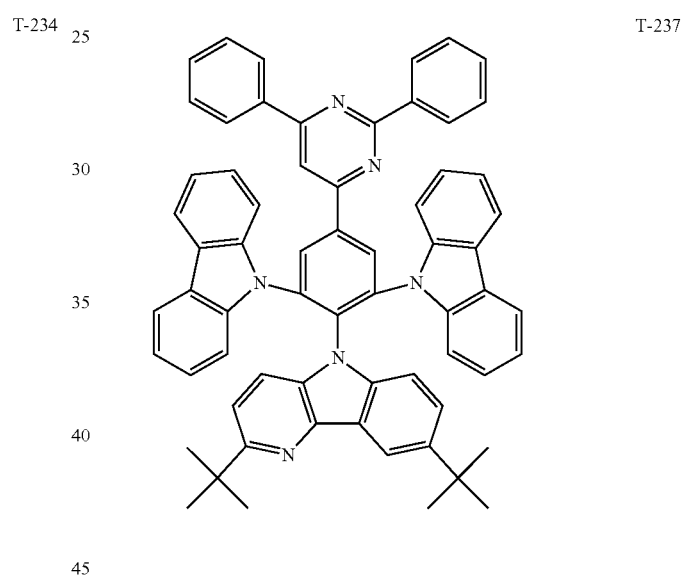
T-237
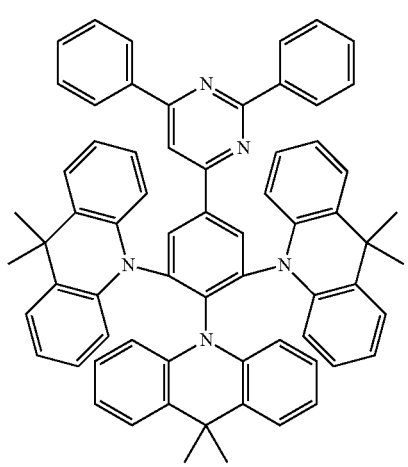
T-235
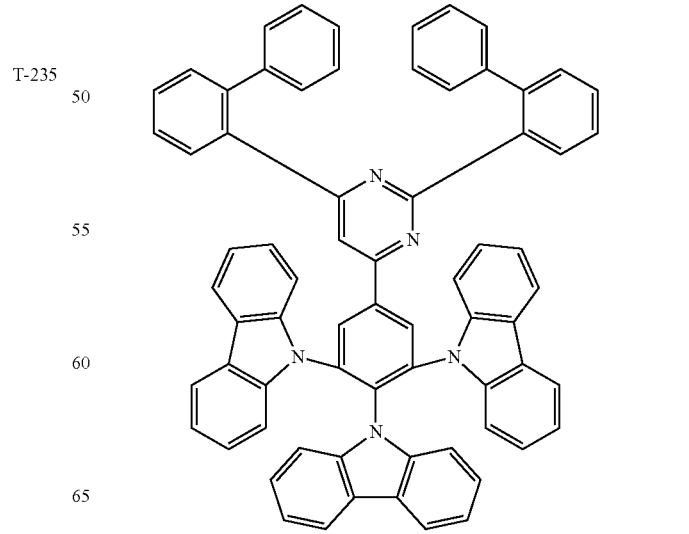
T-238

T-239
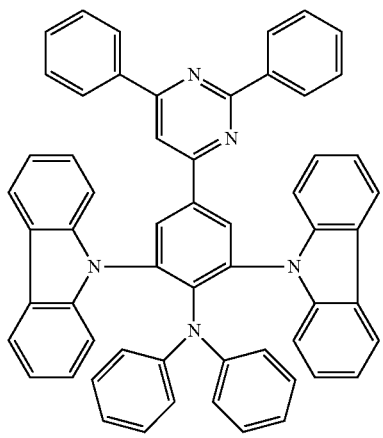
T-240
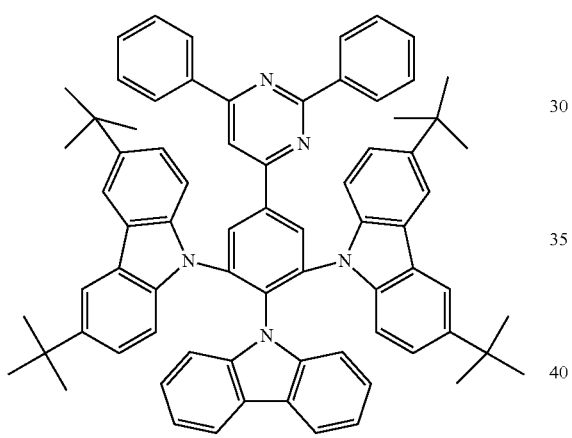
T-241
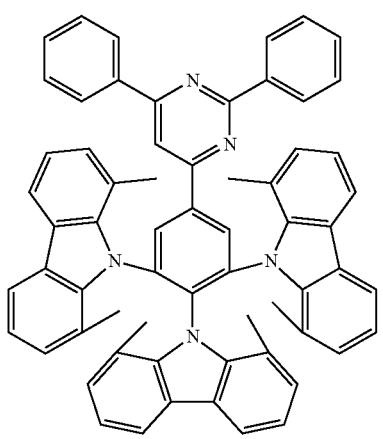
[Formula 41]
T-242
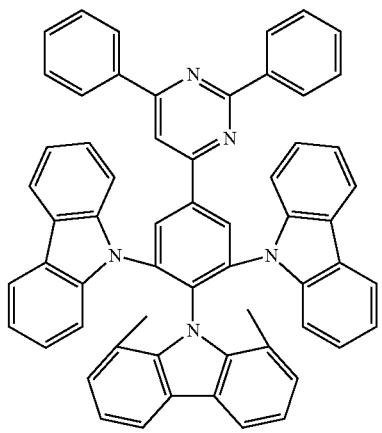
T-243
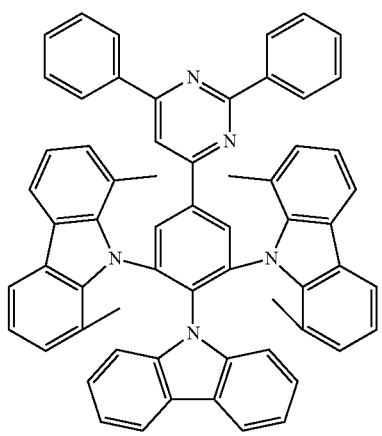
T-244
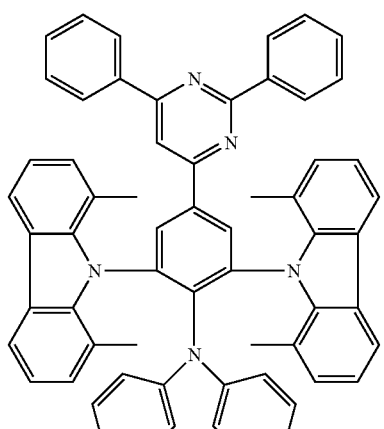

-continued
T-245
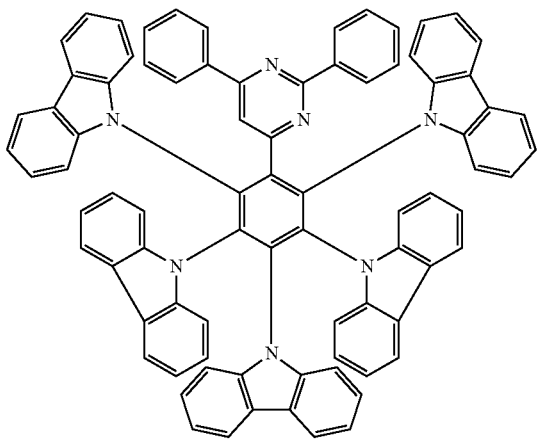
T-246
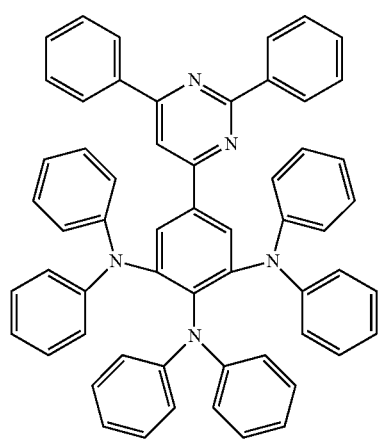
T-247
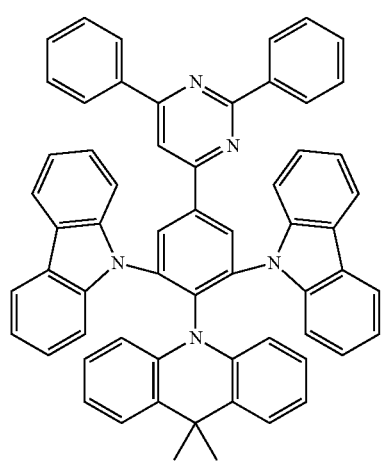
-continued
T-248
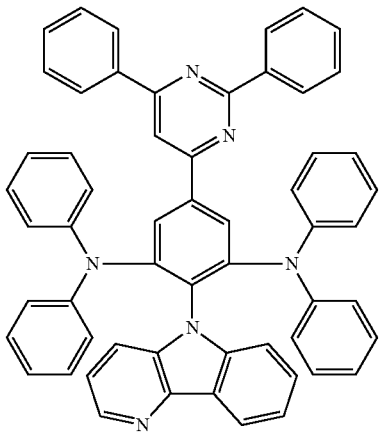
T-249
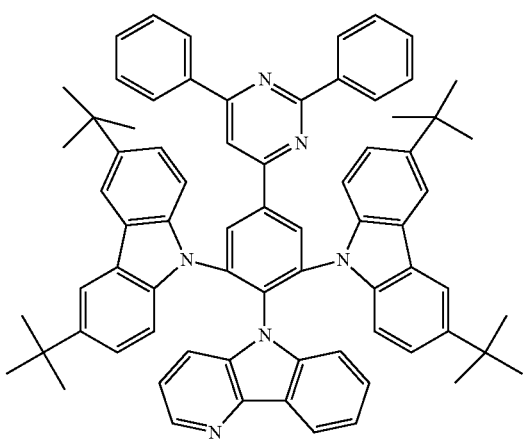
T-250
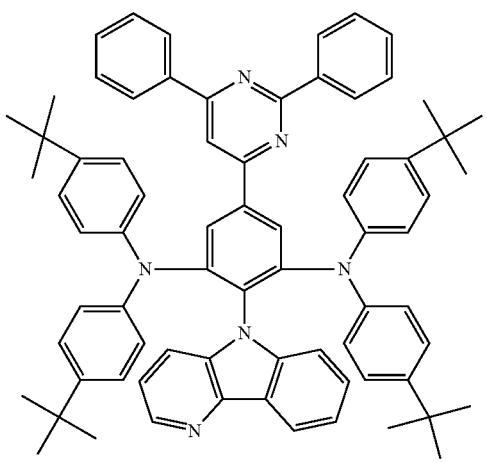

[Formula 42]
T-251
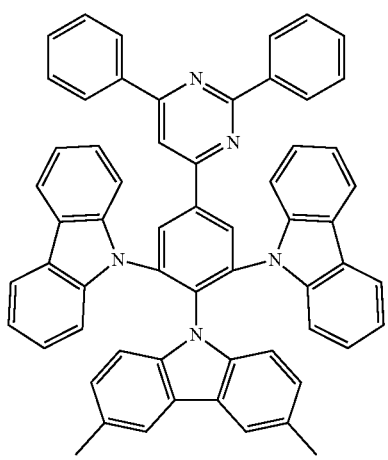
T-252
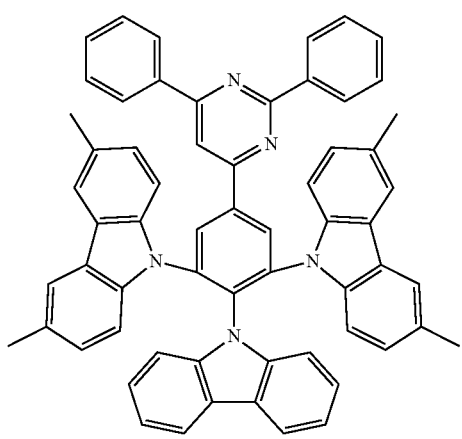
T-254
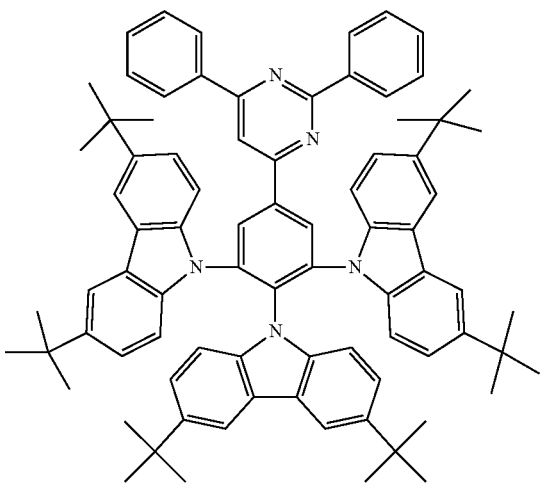
T-255
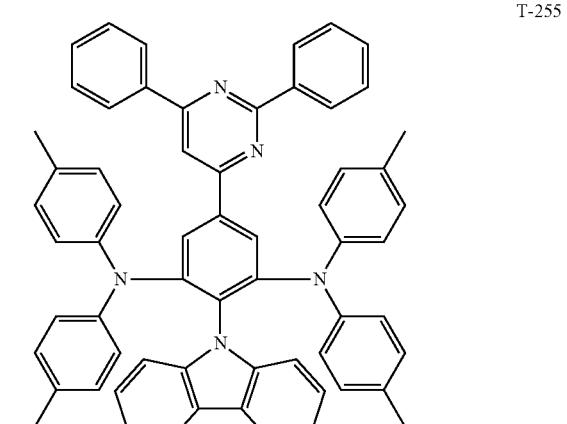
T-253
T-256
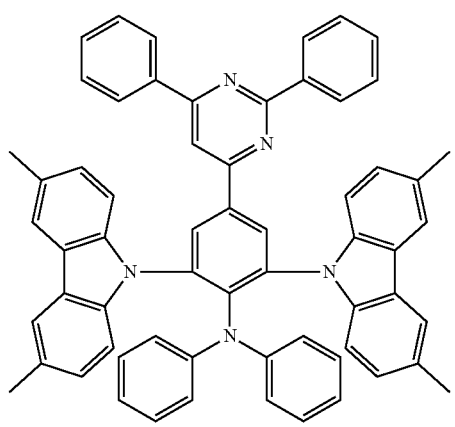

T-257
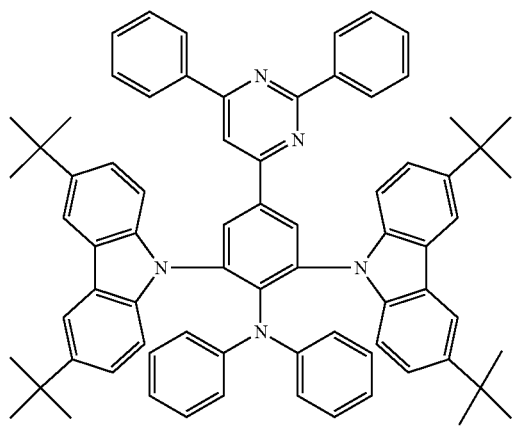
T-258
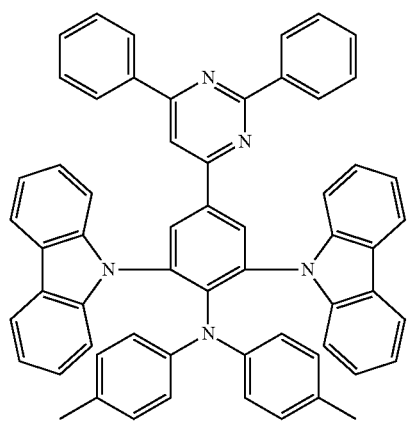
T-259
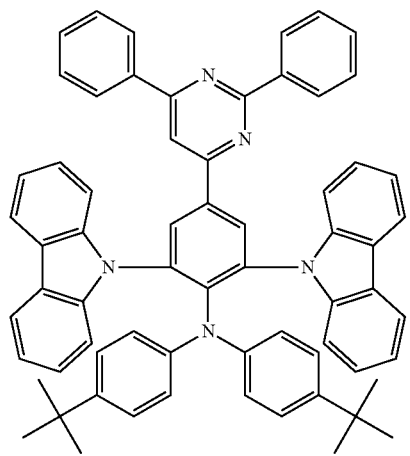
[Formula 43]
T-260
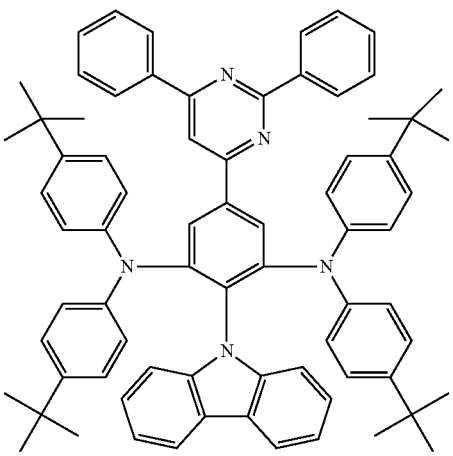
T-261
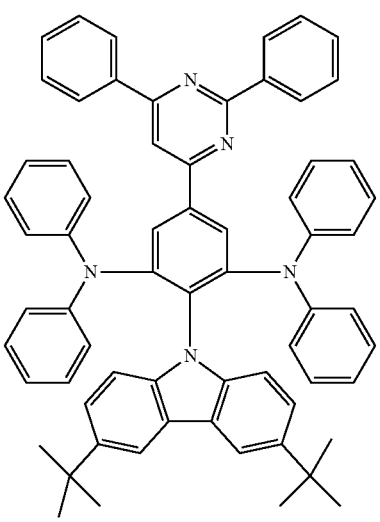
T-262
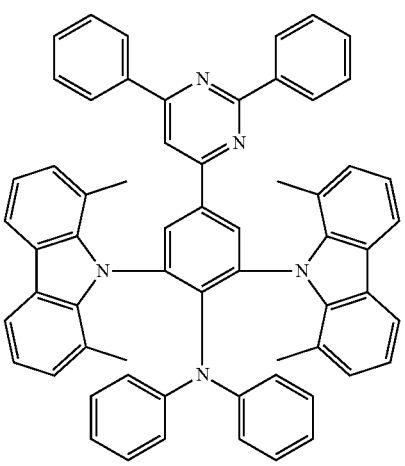

T-263
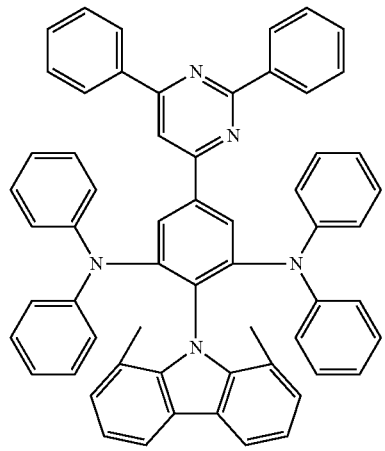
T-265
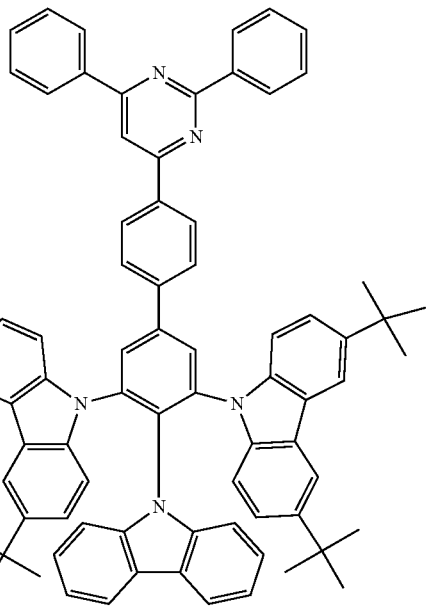
T-264
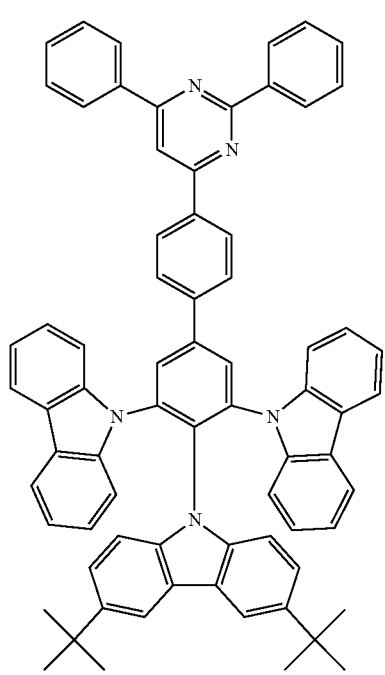
T-266
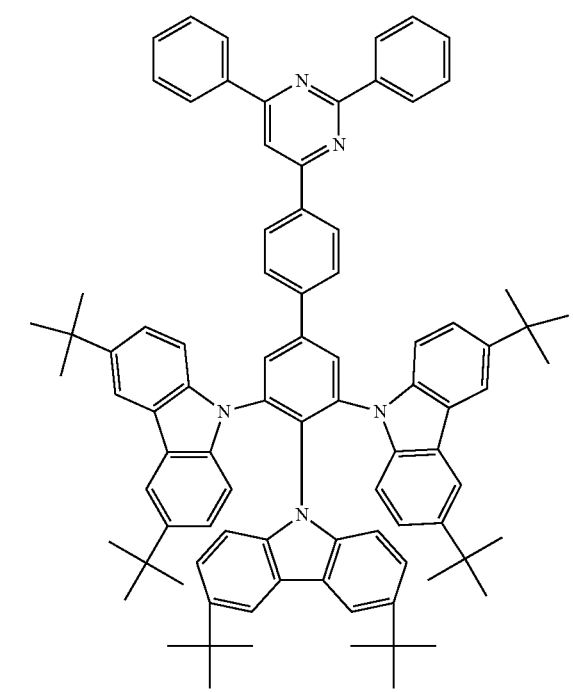

T-267
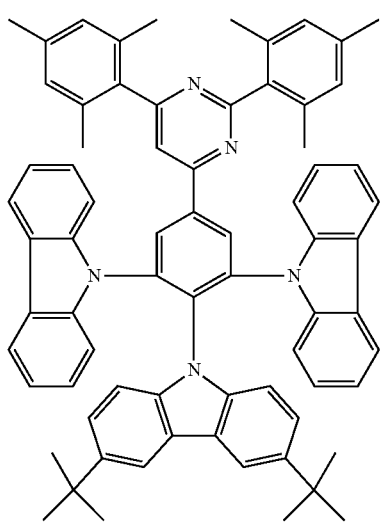
T-268
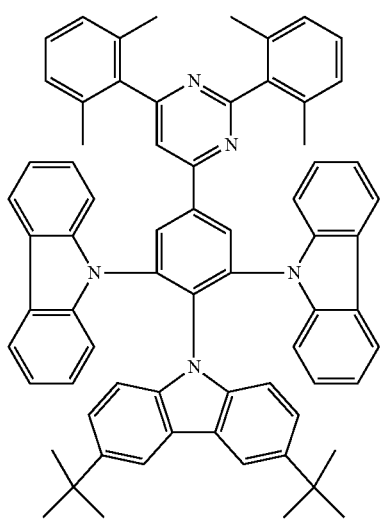
[Formula 44]
T-269
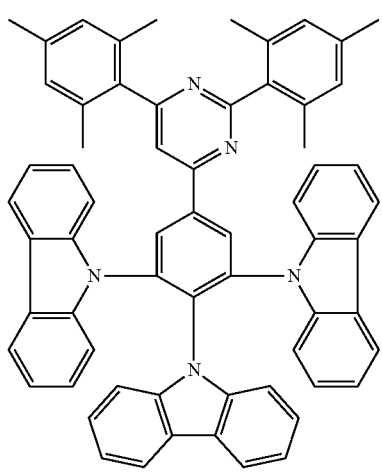
T-270
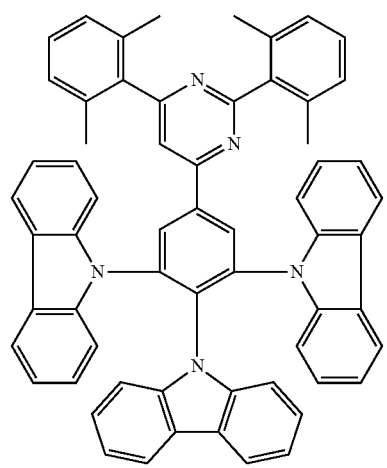
T-271
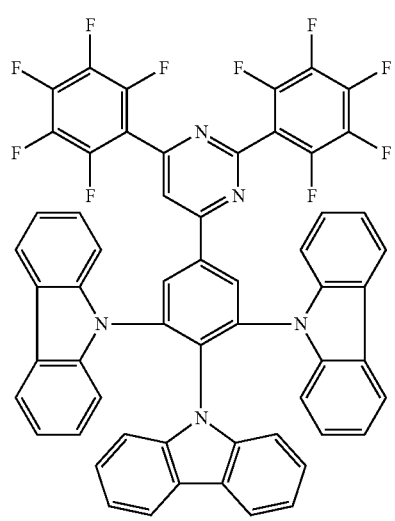
T-272
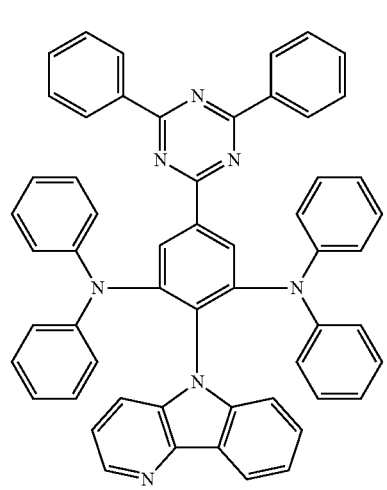

T-273
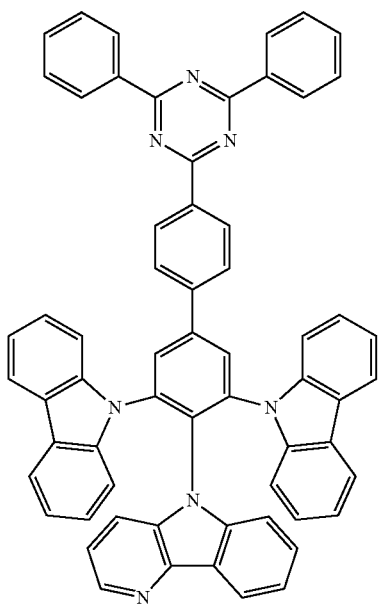
T-274
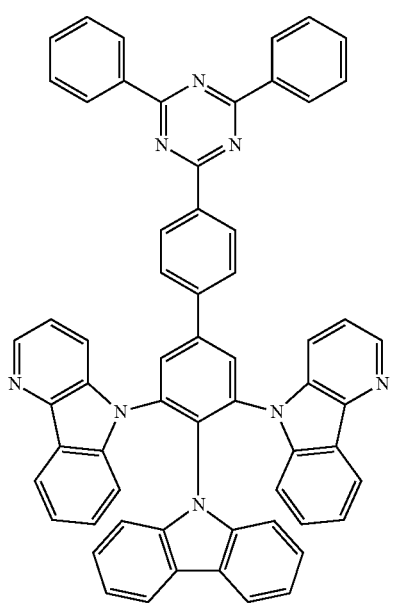
T-275
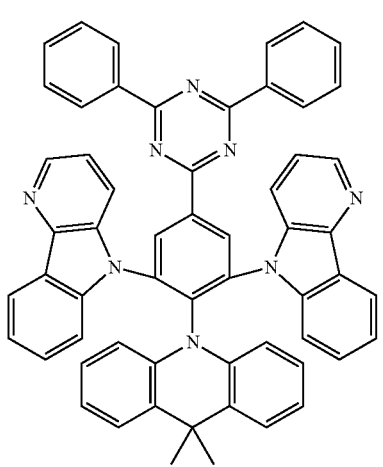
T-276

T-277
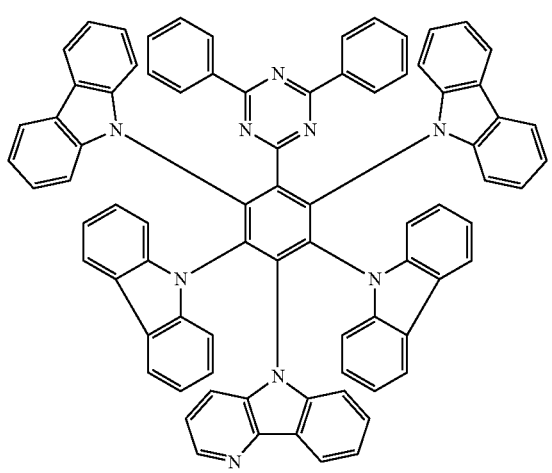
[Formula 45]
T-278
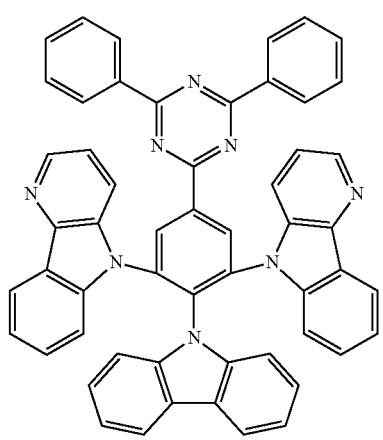

-continued
T-279
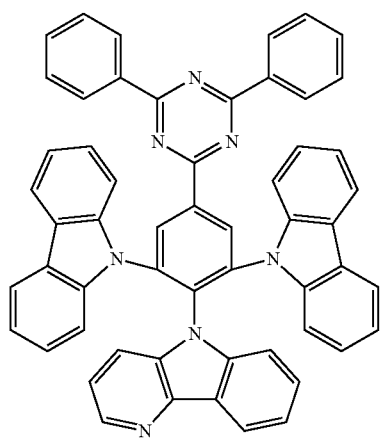
T-280
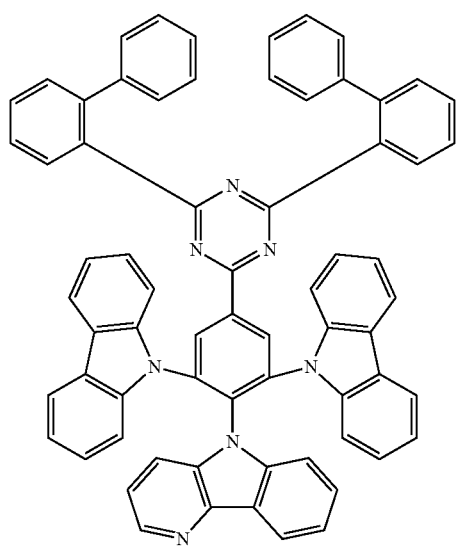
T-281
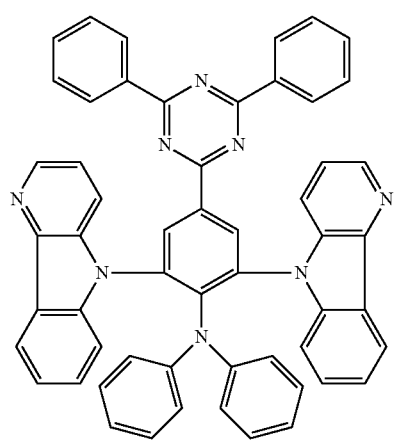
-continued
T-282
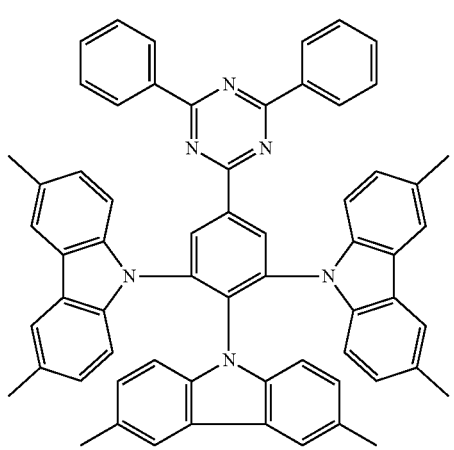
T-283
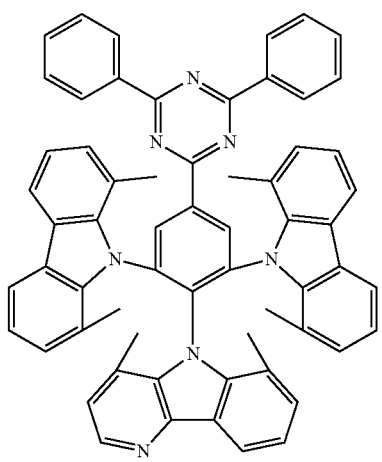
T-284
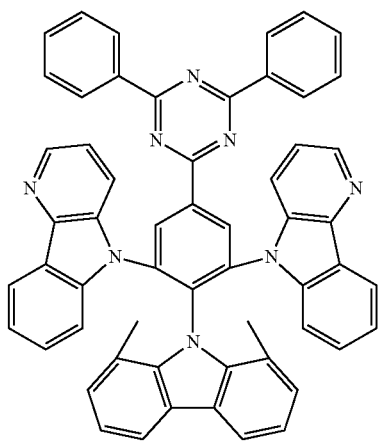

T-285
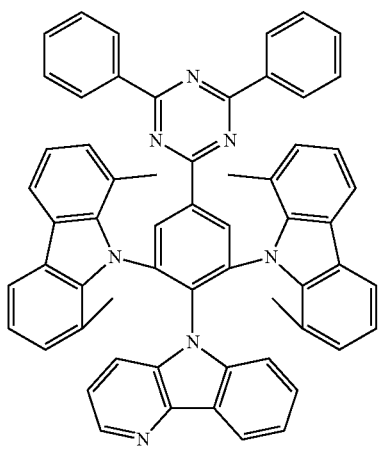
T-286
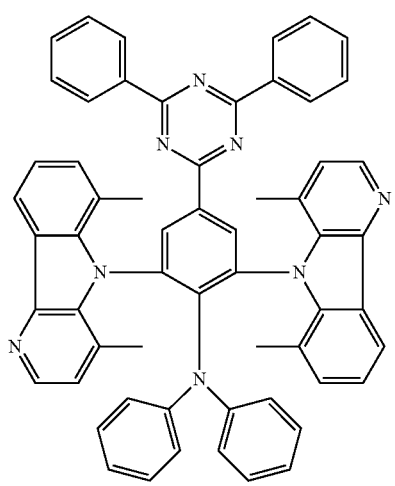
[Formula 46]
T-287
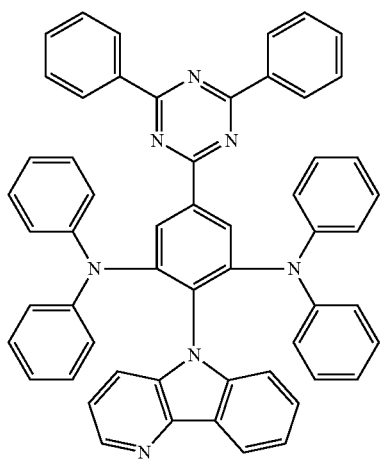
T-288
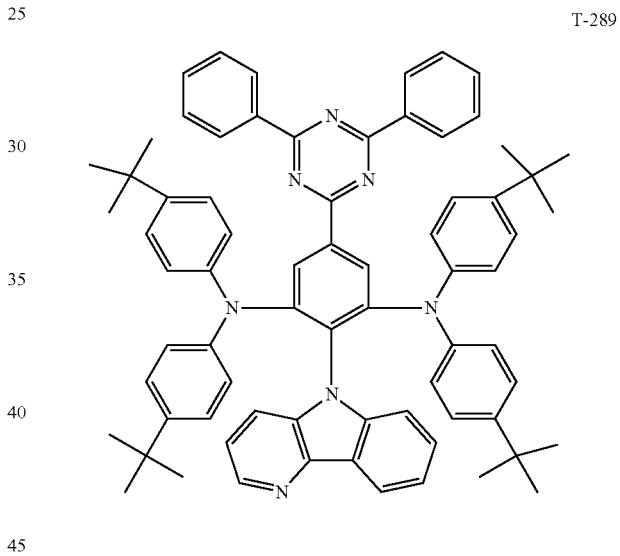
T-289
T-290
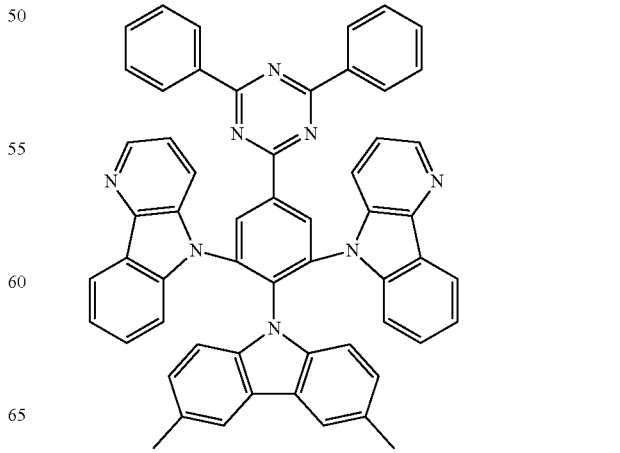

T-291
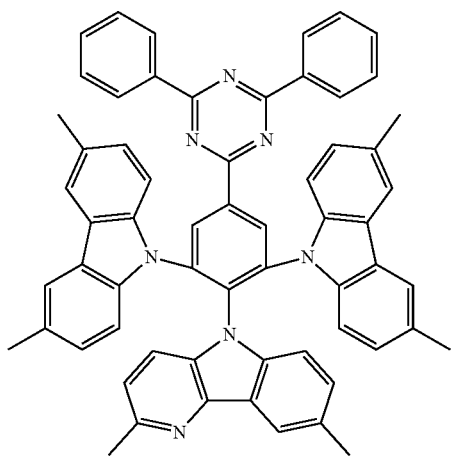
T-294
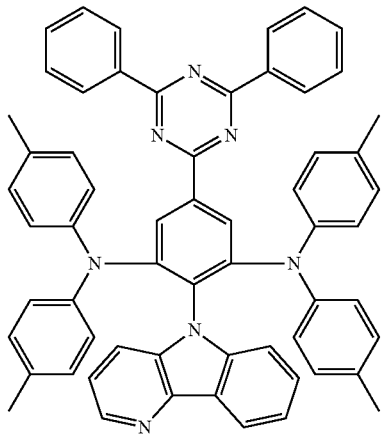
T-292
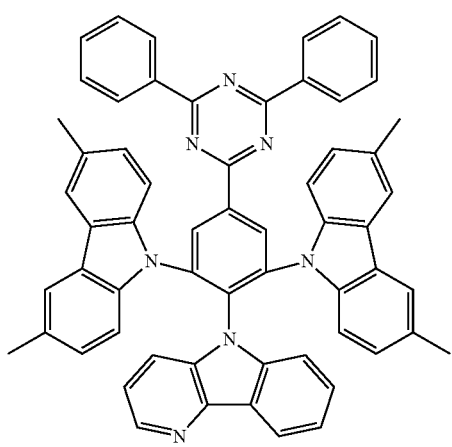
T-295
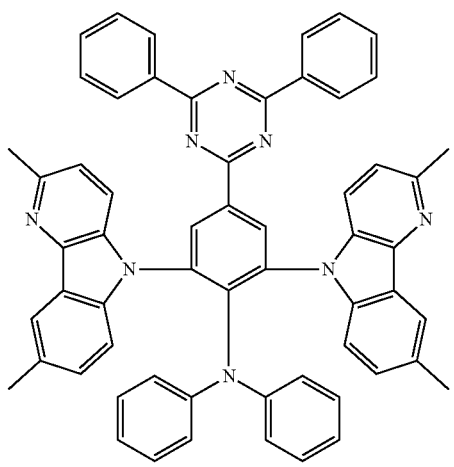
T-293
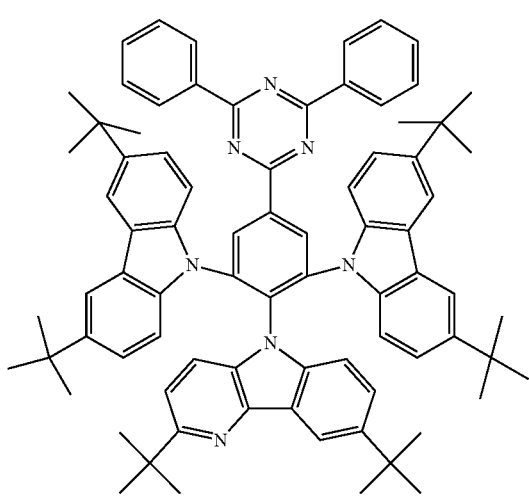
[Formula 47]
T-296
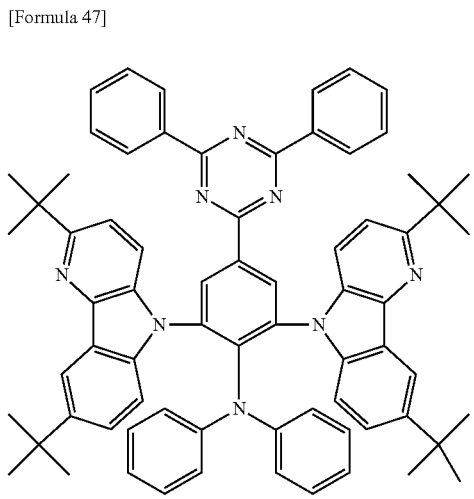

-continued
T-297
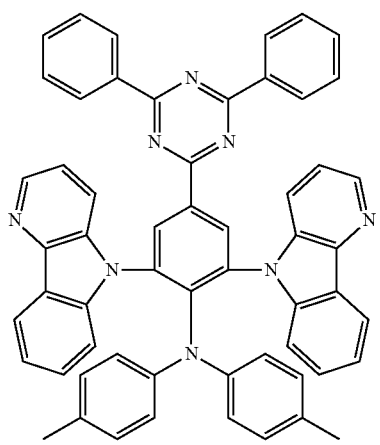
T-298
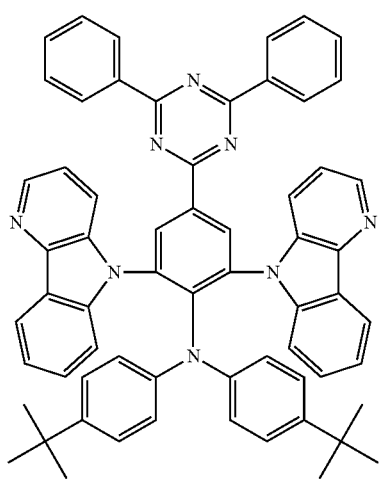
T-299
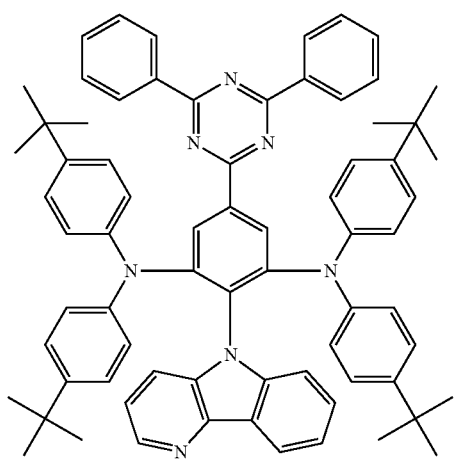
-continued
T-300
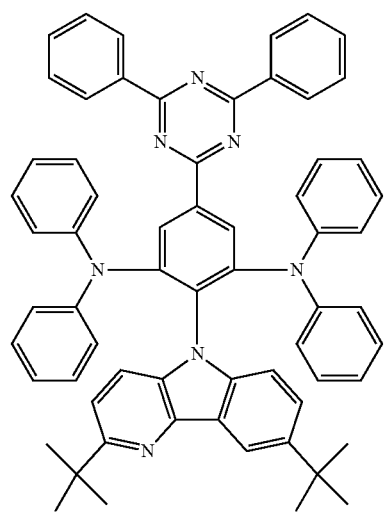
T-301
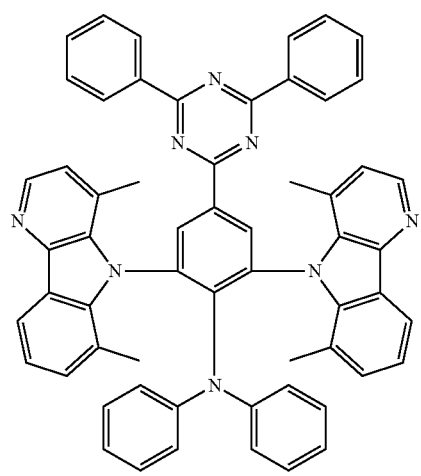
T-302
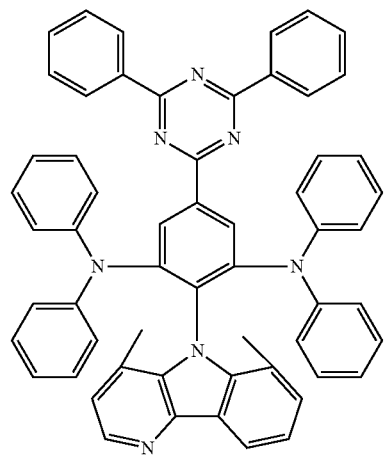

T-303
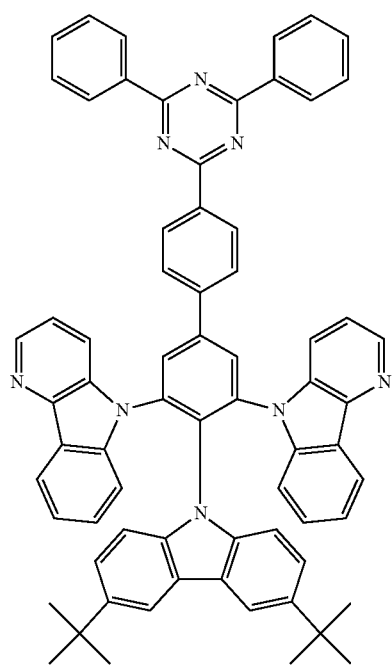
T-304
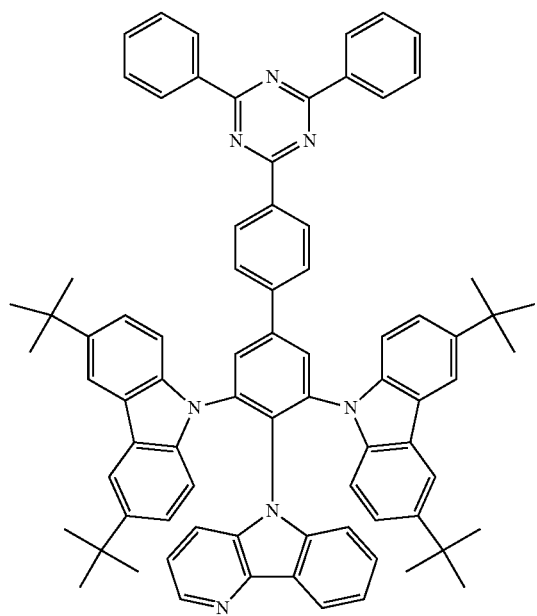
[Formula 48]
T-305
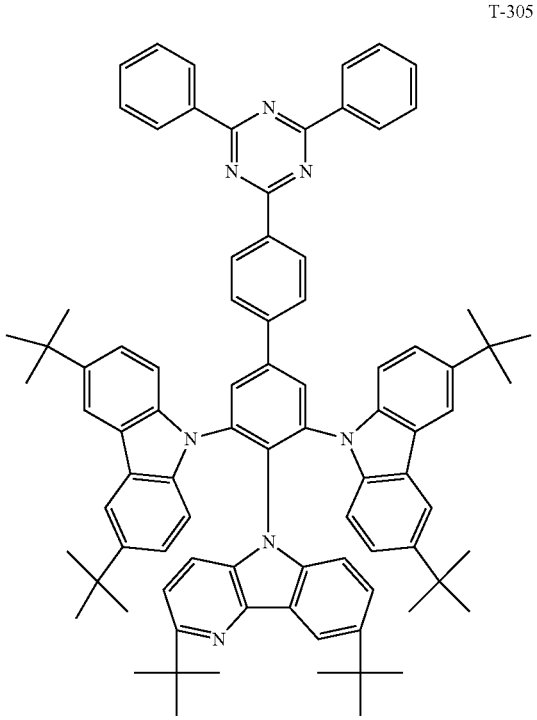
T-306
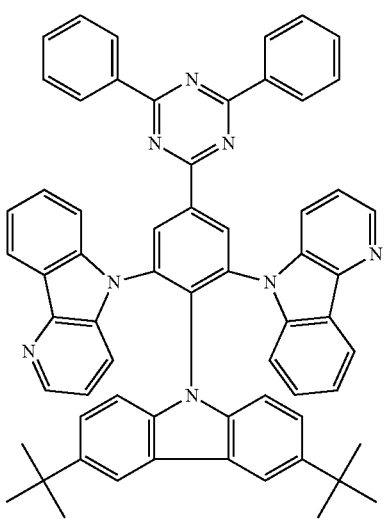

T-307
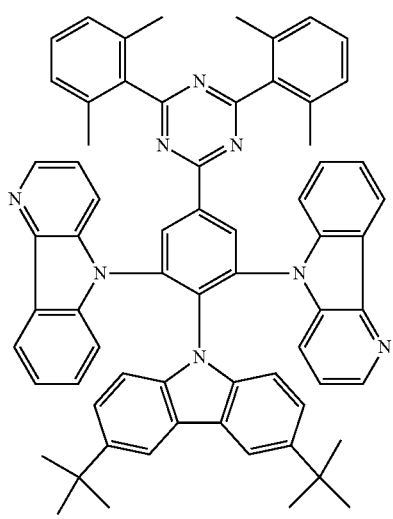
T-308
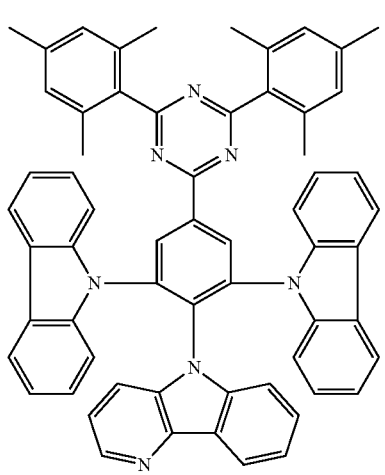
T-309
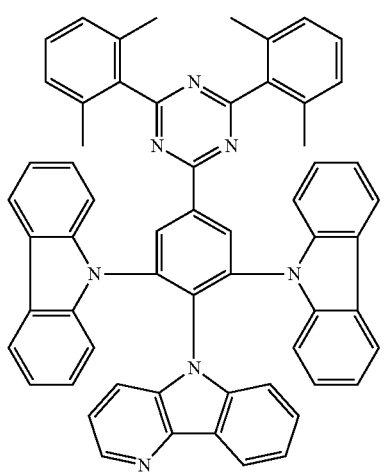
T-310
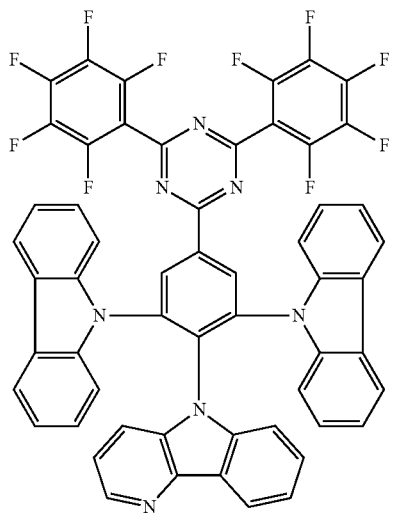
T-311
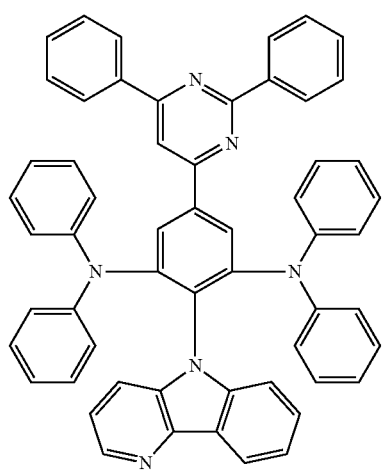
T-312
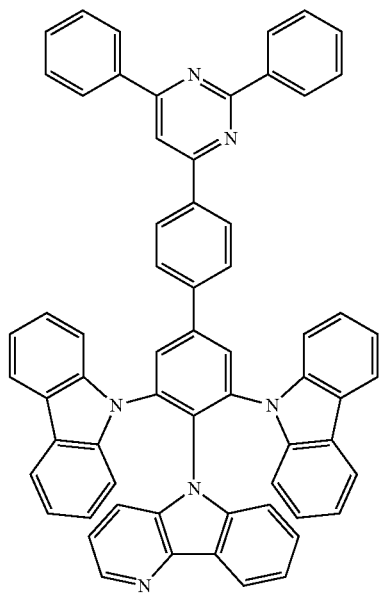

T-313
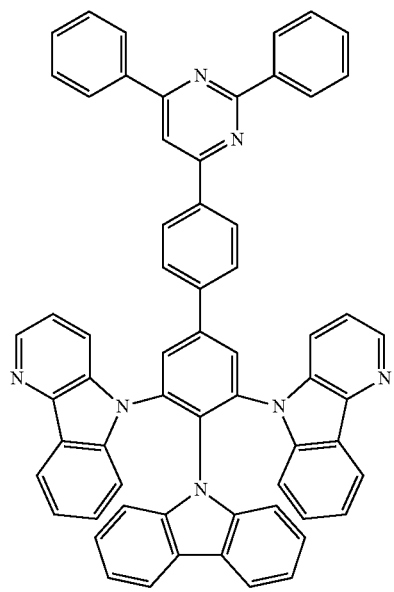
[Formula 49]
T-314
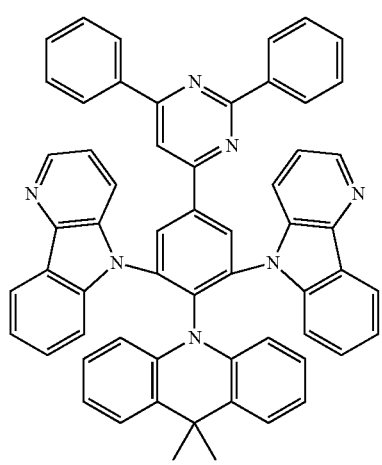
T-315
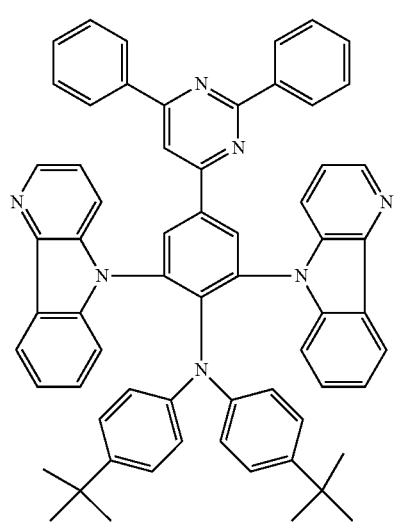
T-316
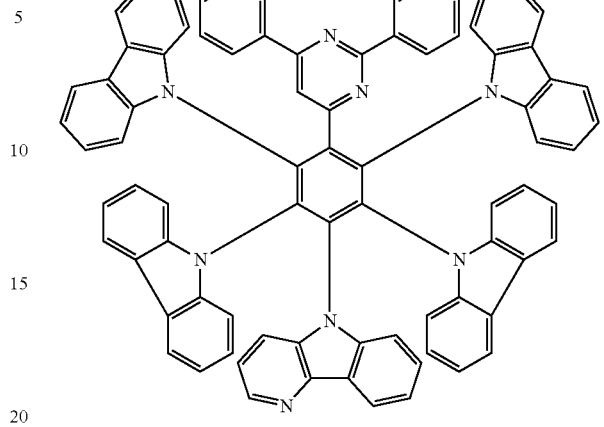
T-317
T-318
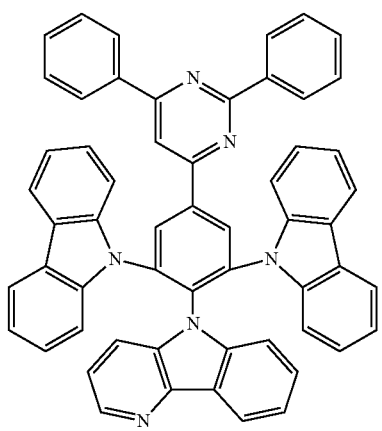

T-319
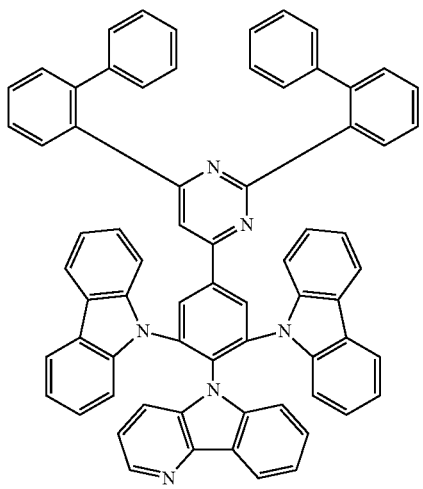
T-322
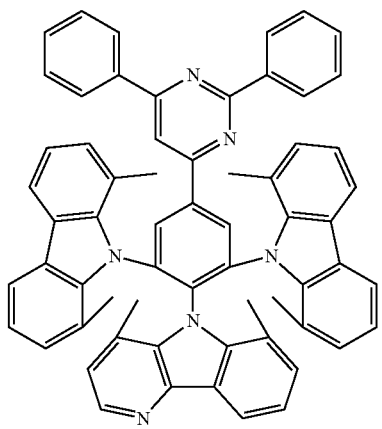
[Formula 50]
T-320
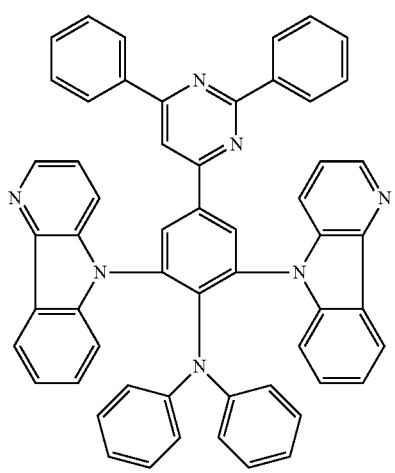
T-323
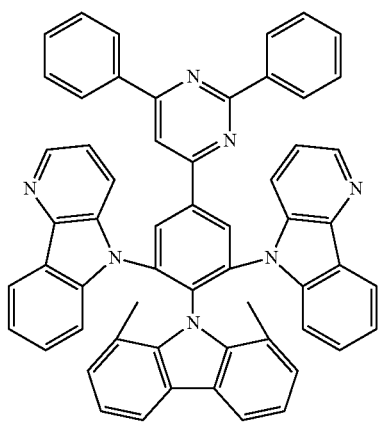
T-321
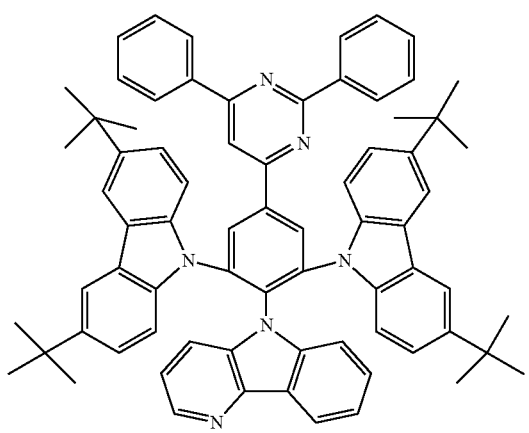
T-324
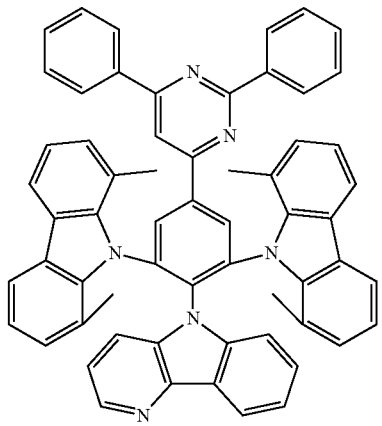

T-325
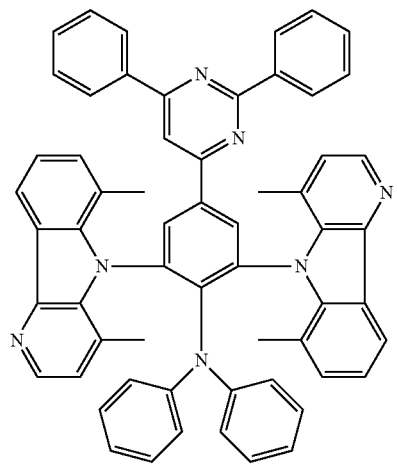
T-328
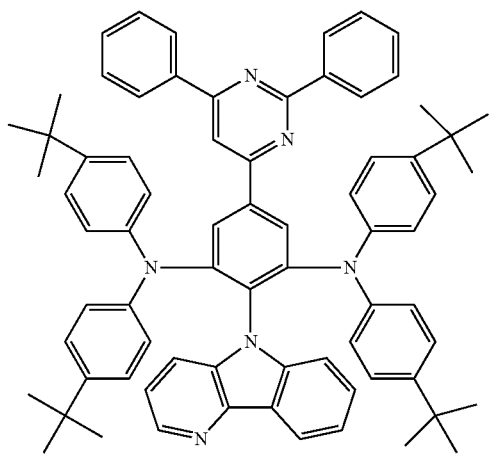
T-326
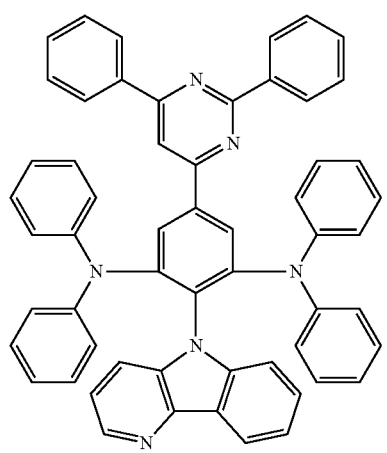
T-329
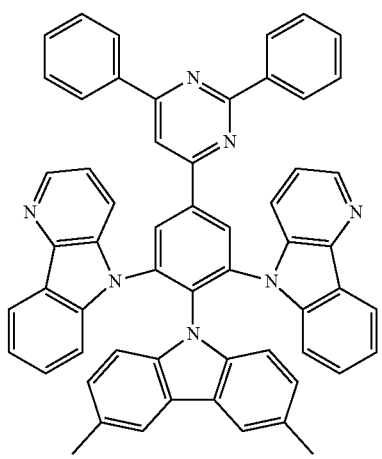
T-327
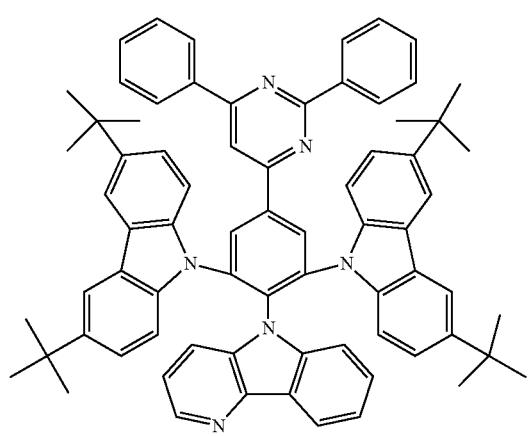
T-330
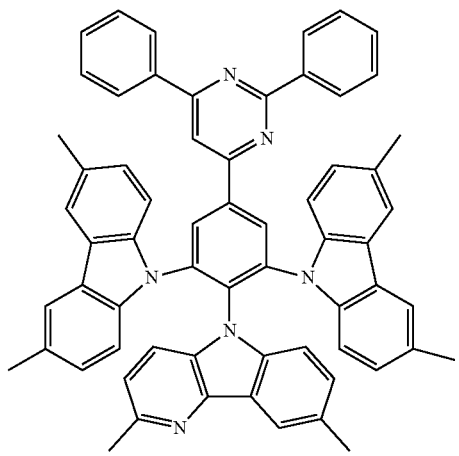

T-331
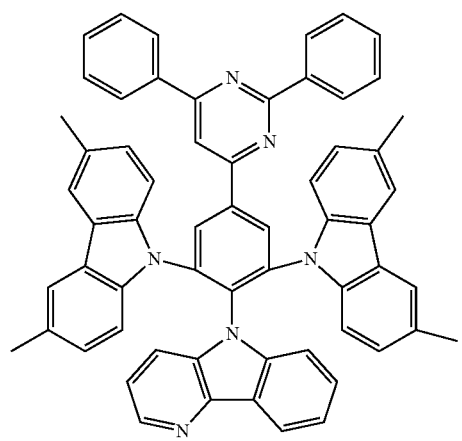
[Formula 51]
T-332
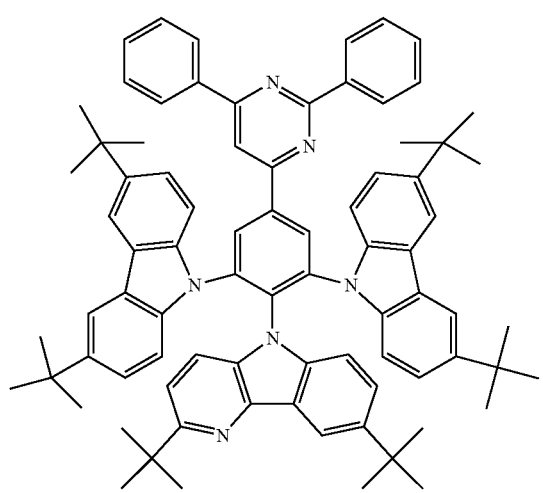
T-333
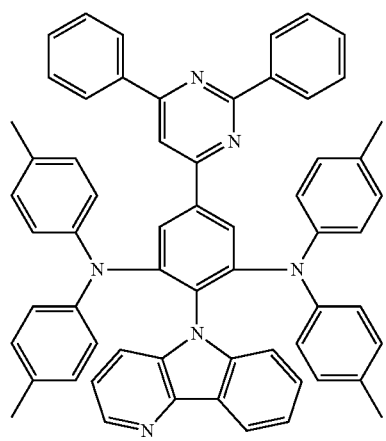
T-334
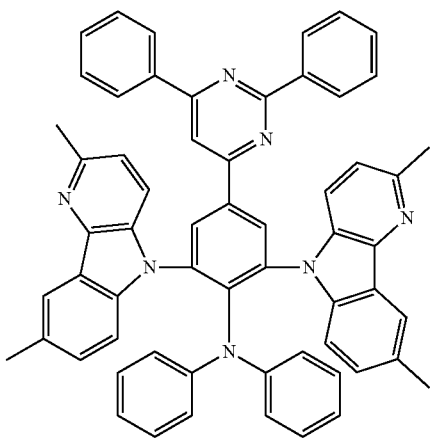
T-335
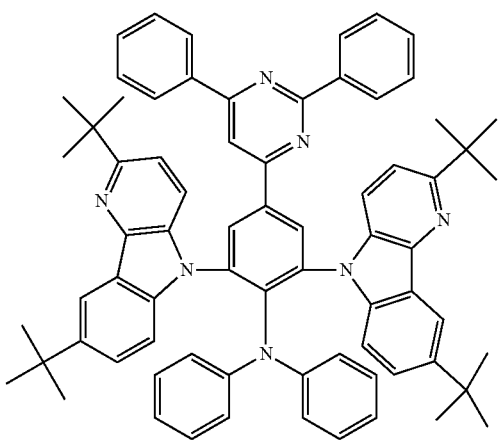
T-336
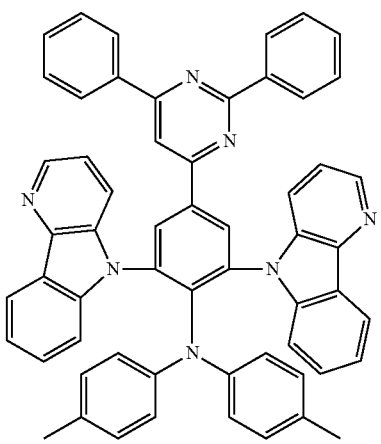

T-337
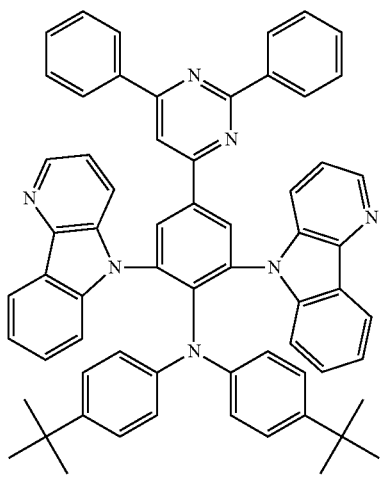
T-338
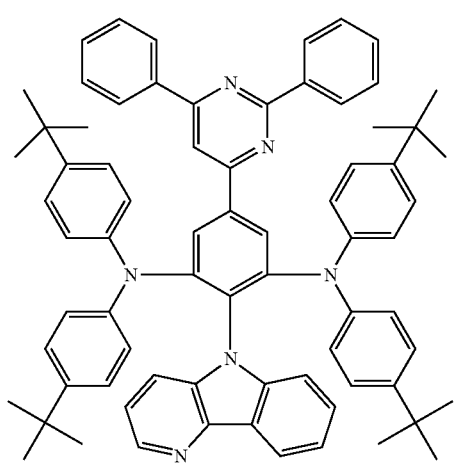
T-339
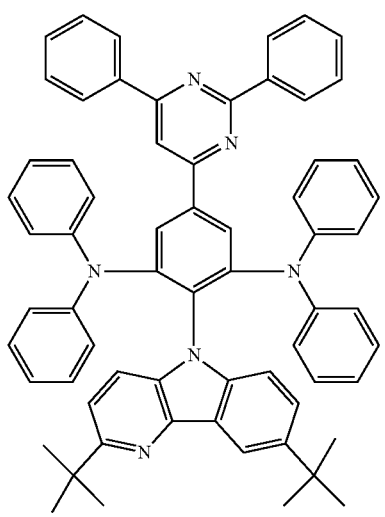
T-340
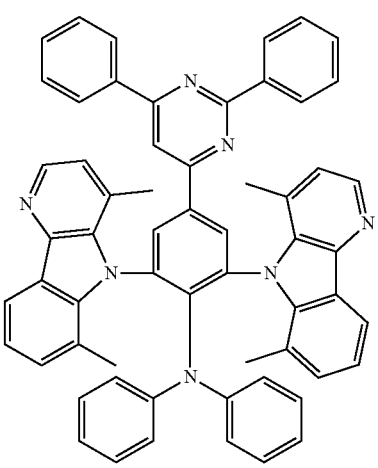
[Formula 52]
T-341
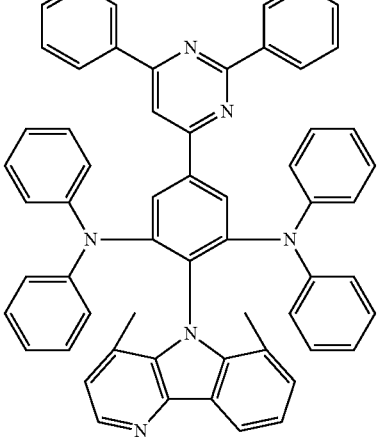
T-342
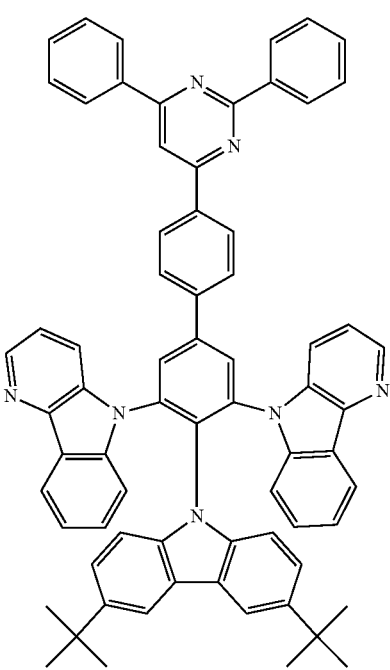

T-343
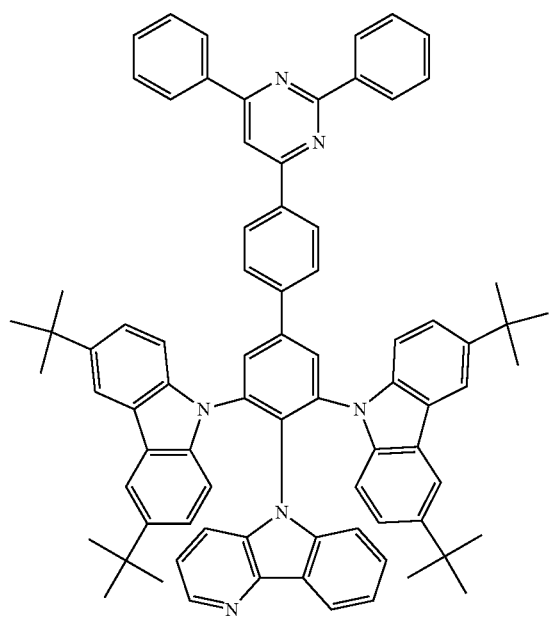
T-344
T-345
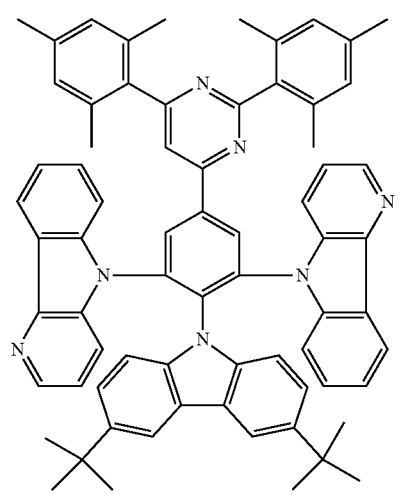
T-346
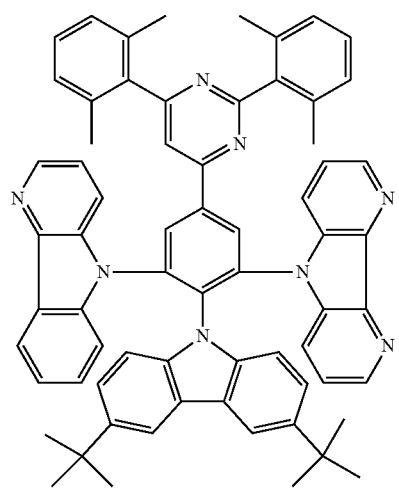
T-347
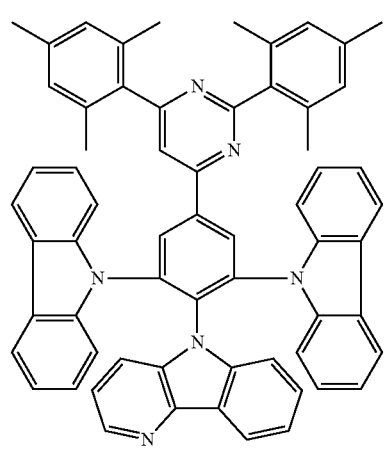

T-348
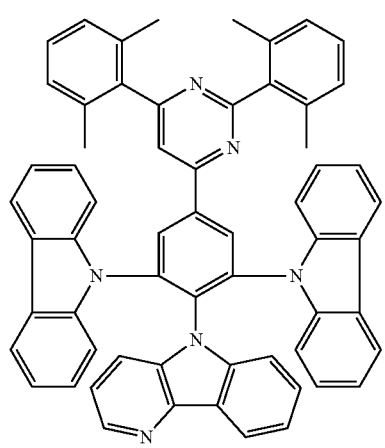
T-349
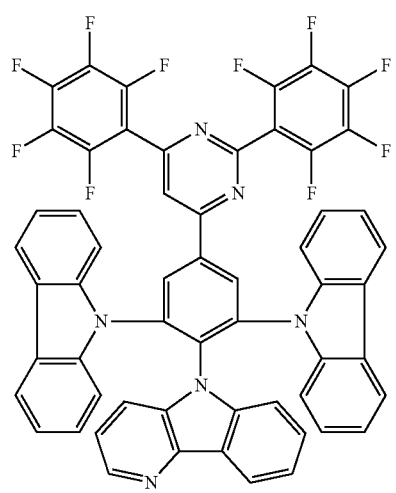
[Formula 53]
T-350
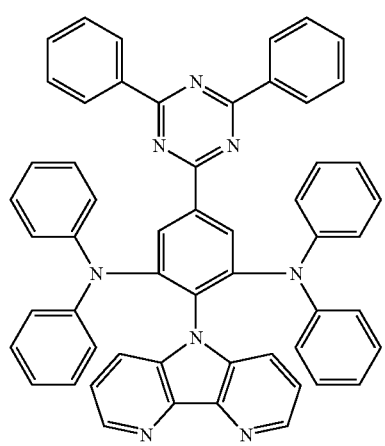
T-351
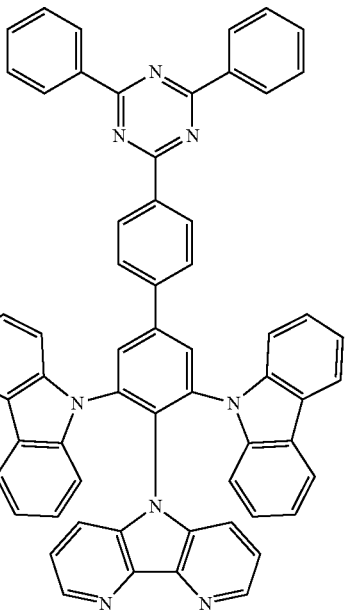
T-352
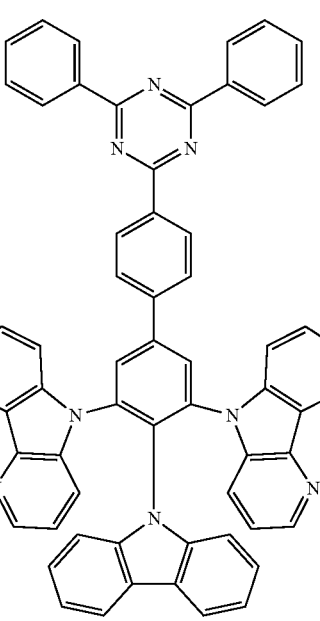

T-353
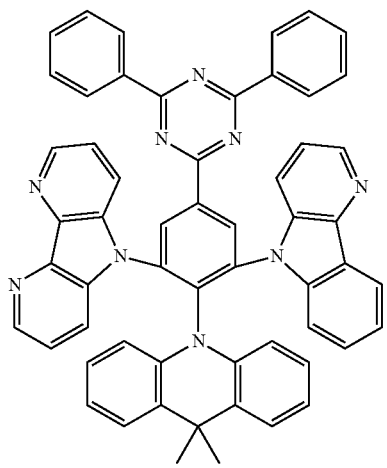
T-354
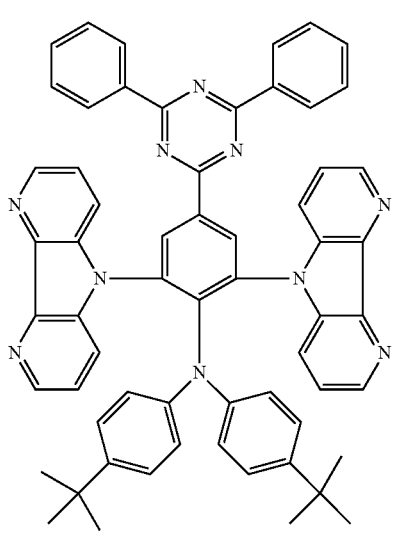
T-355
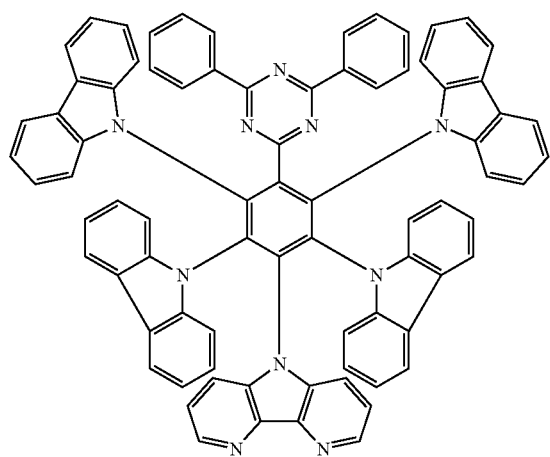
T-356
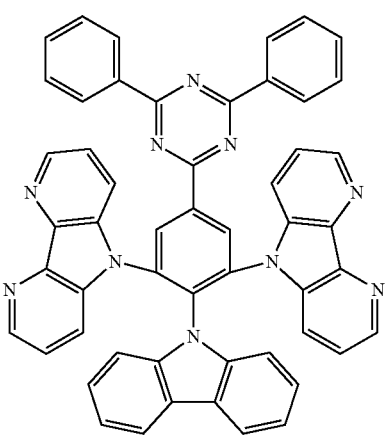
T-357
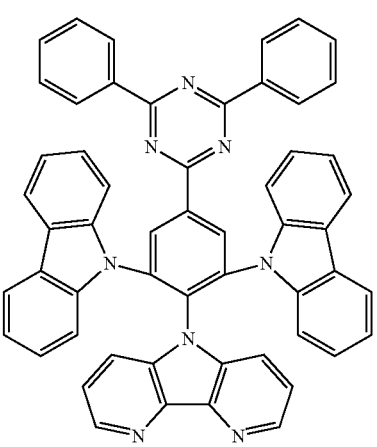
T-358
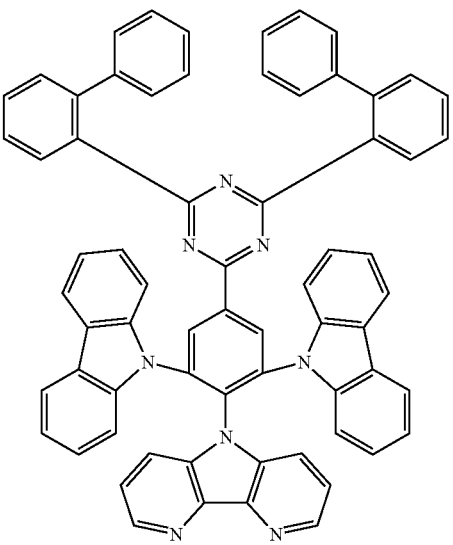

[Formula 54]
T-359
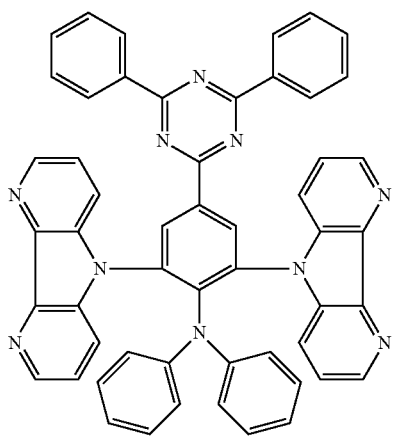
T-360
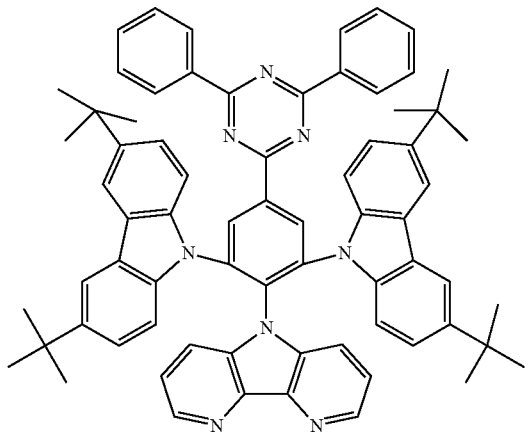
T-361
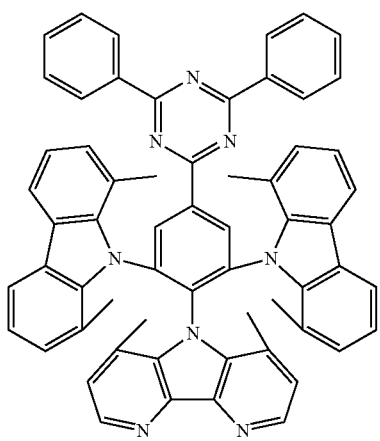
T-362
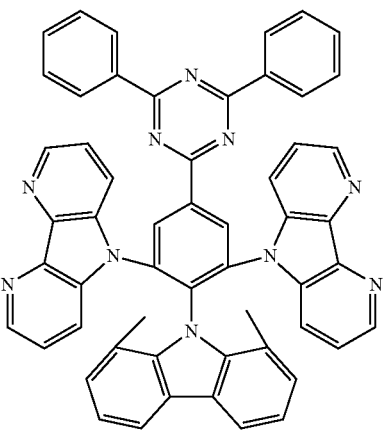
T-363
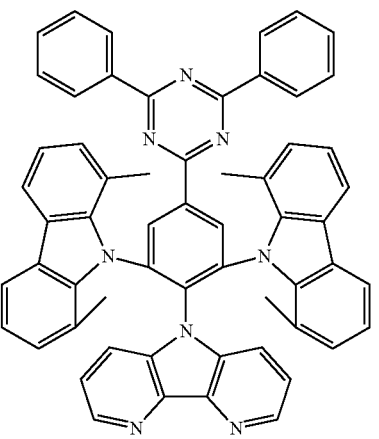
T-364
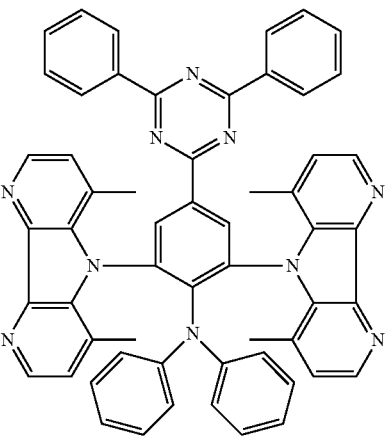

T-365
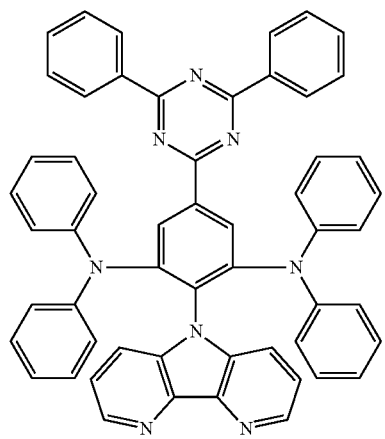
T-368
[Formula 55]
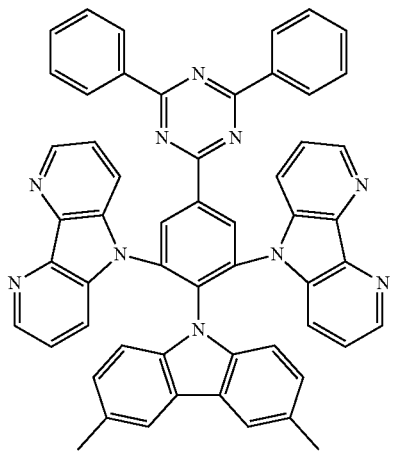
T-366
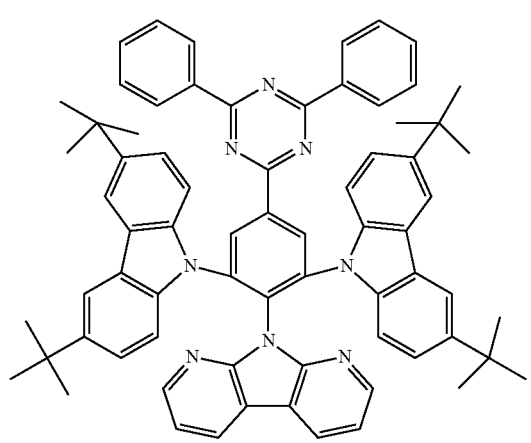
T-369
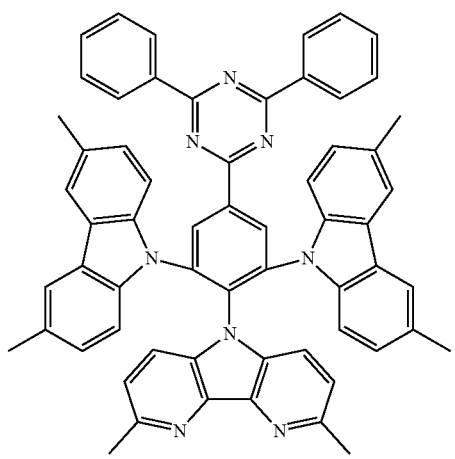
T-367
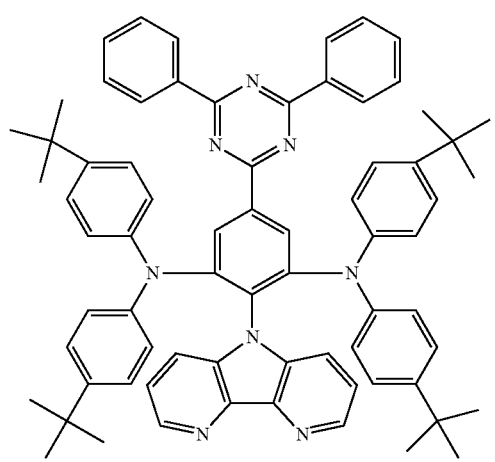
T-370
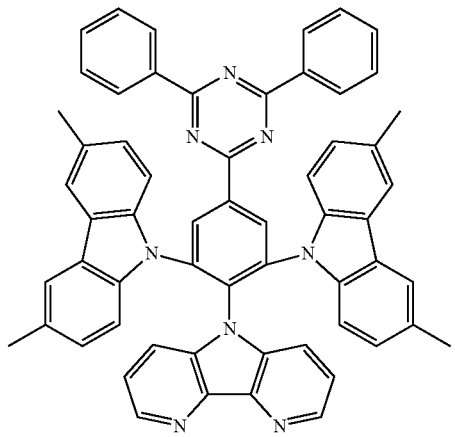

T-371 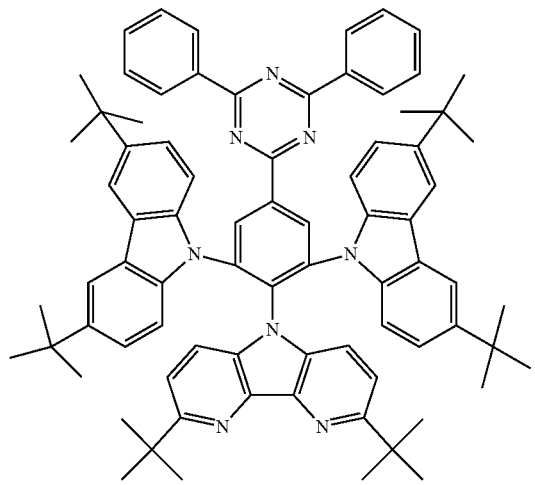
T-374 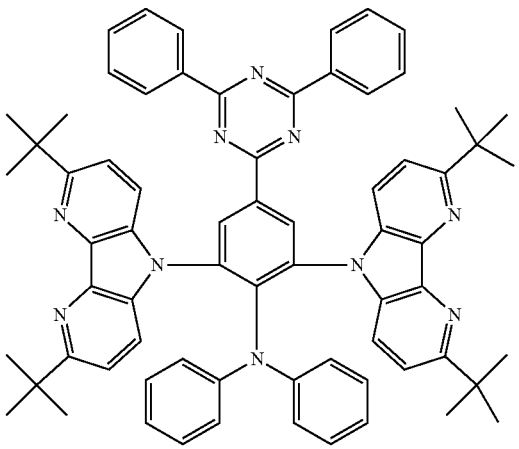
T-372 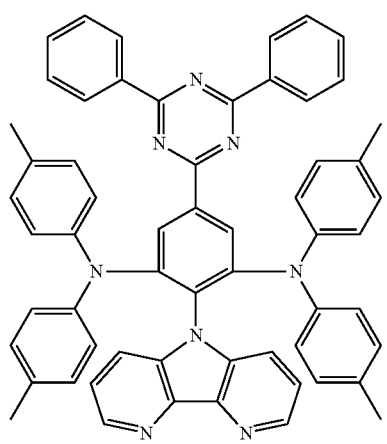
T-375 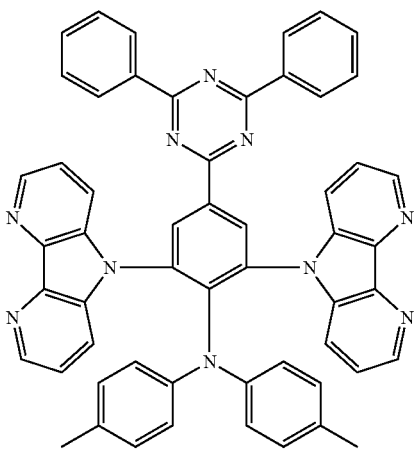
T-373 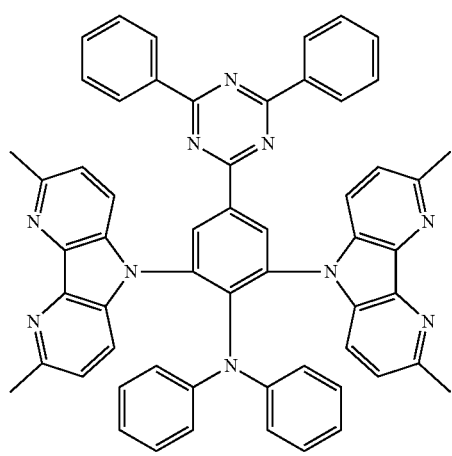
T-376 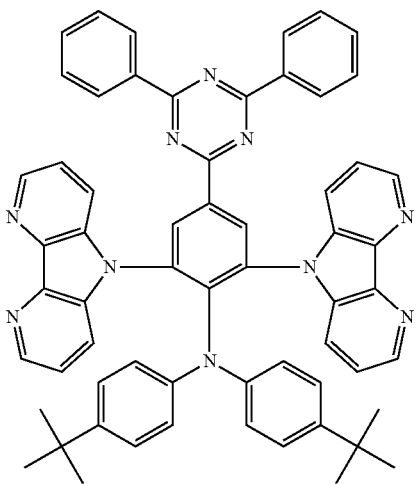

[Formula 56]
T-377
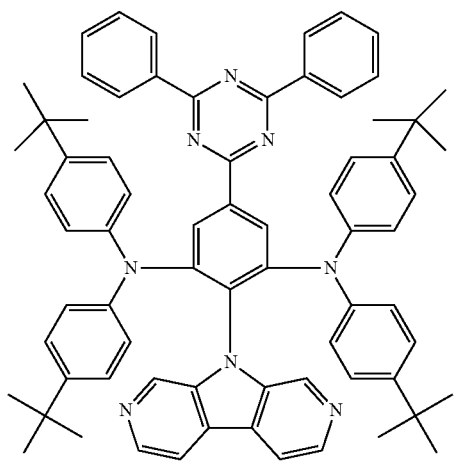
T-378
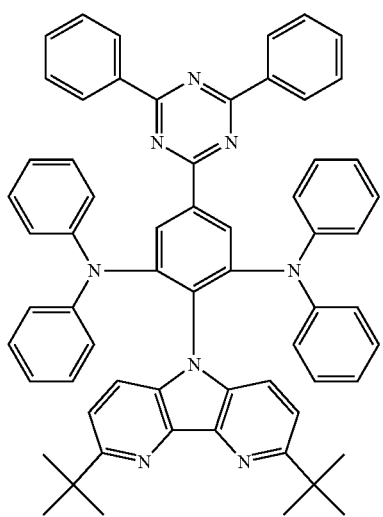
T-379
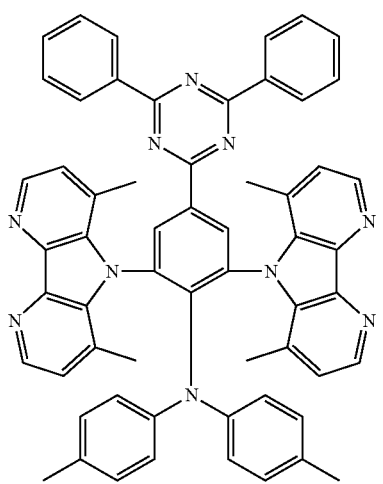
T-380
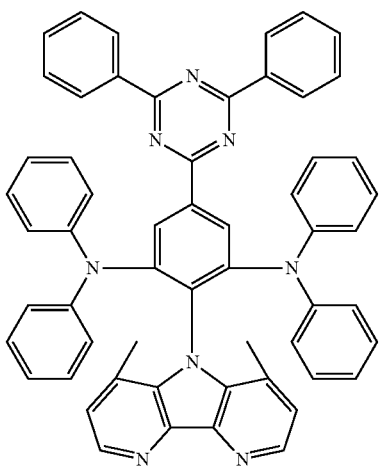
T-381
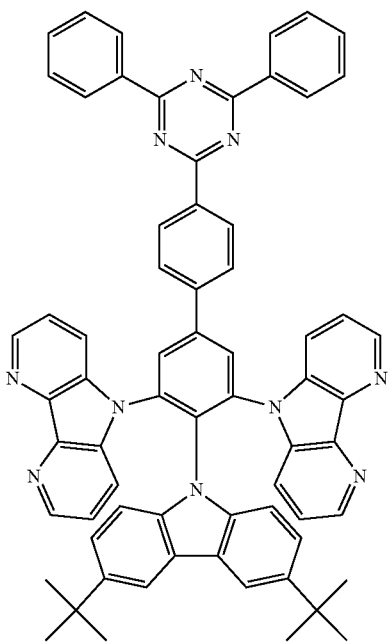

-continued
T-382
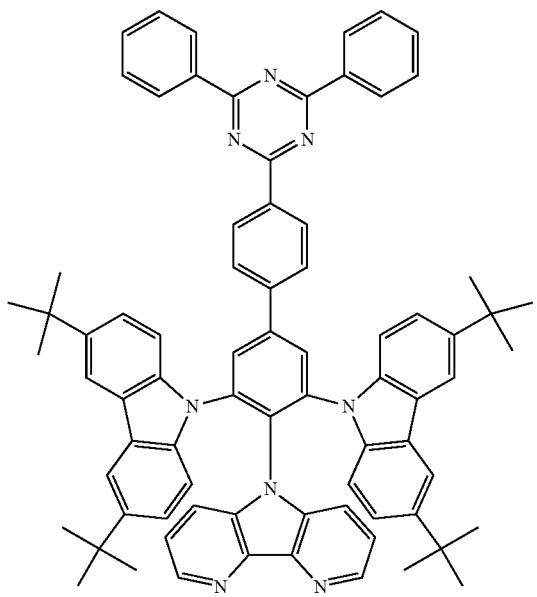
T-384
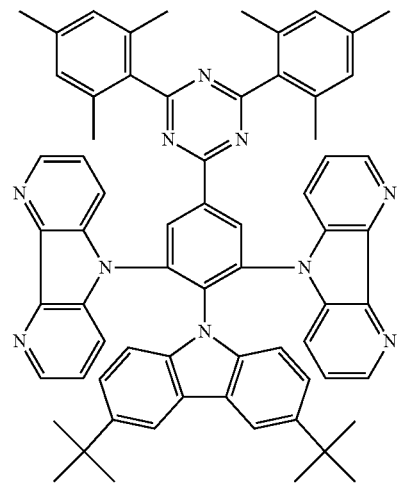
T-385
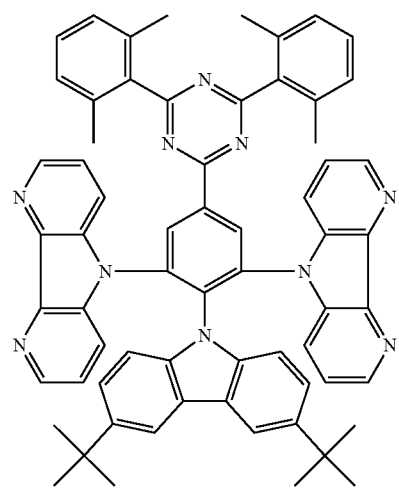
T-383
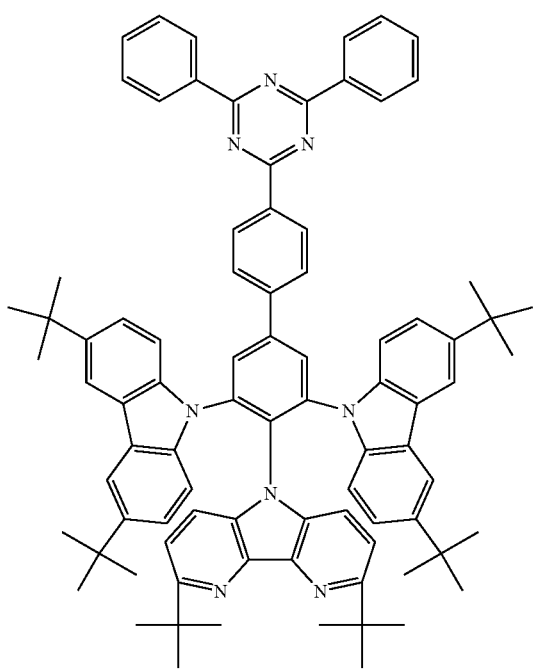
[Formula 57]
T-386
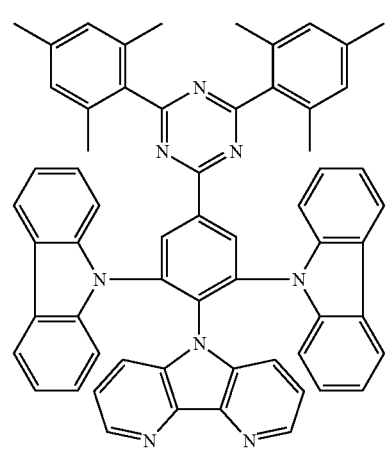

T-387
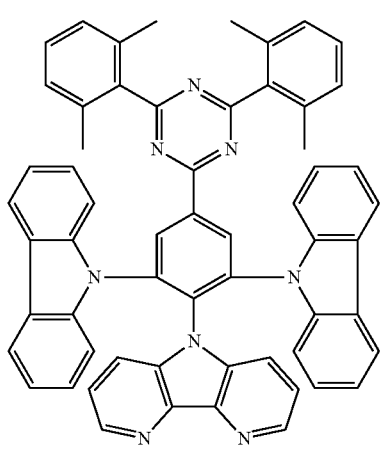
T-388
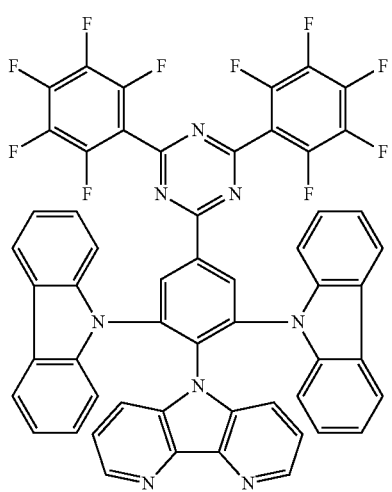
T-389
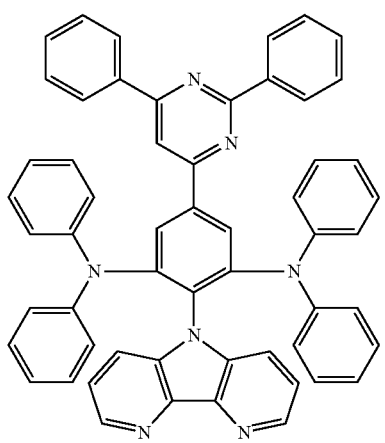
T-390
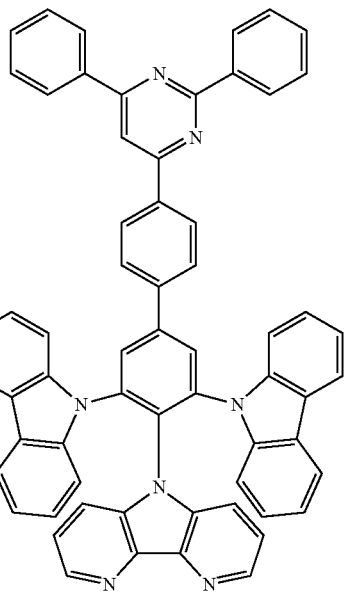
T-391
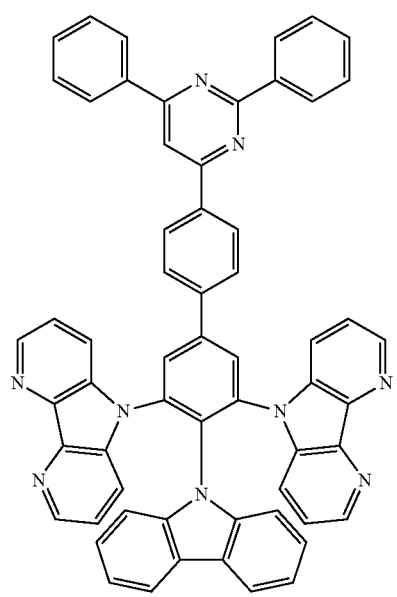
T-392
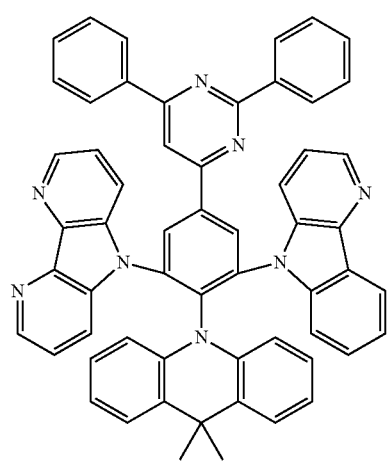

-continued
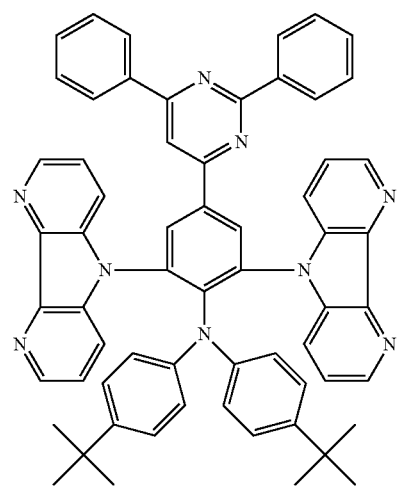
T-393
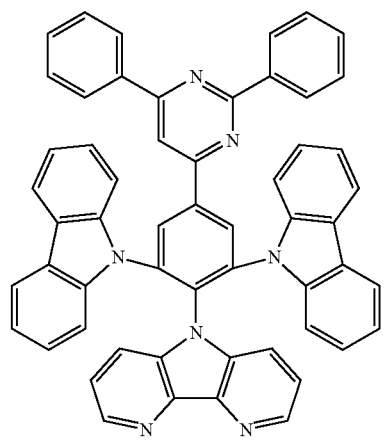
T-396
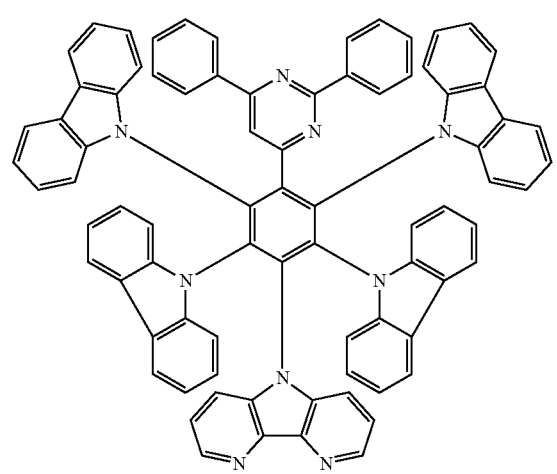
T-394
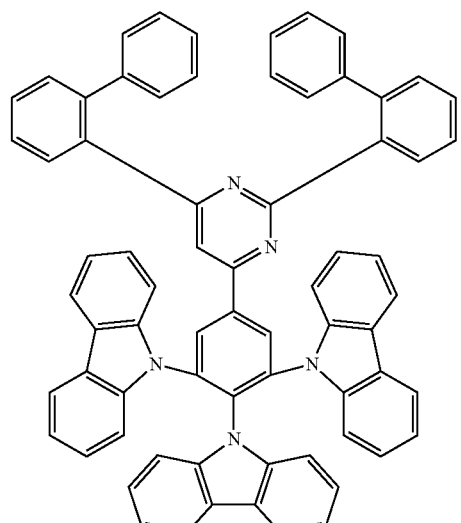
T-397
[Formula 58]
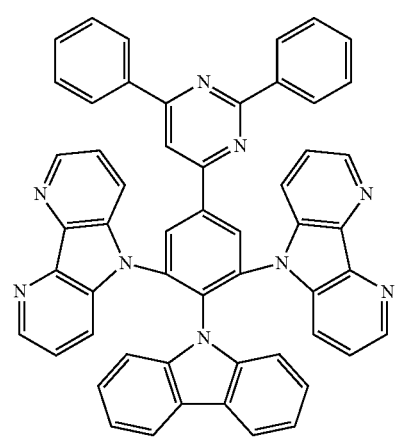
T-395
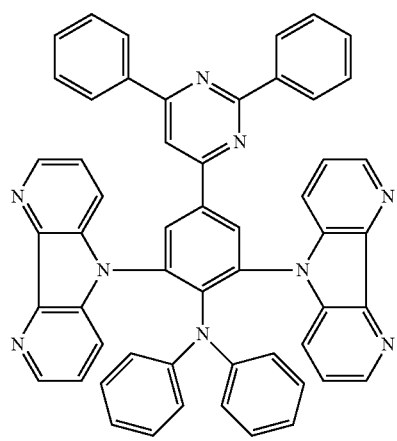
T-398

-continued
T-399
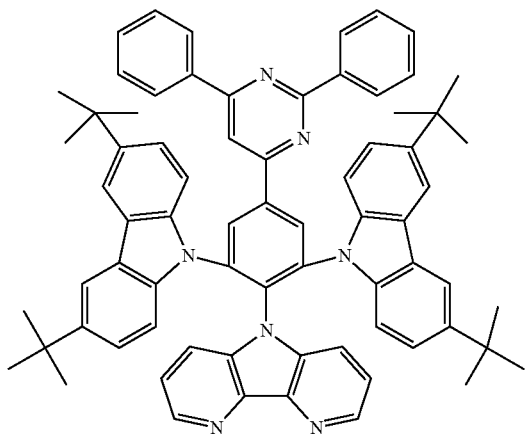
T-400
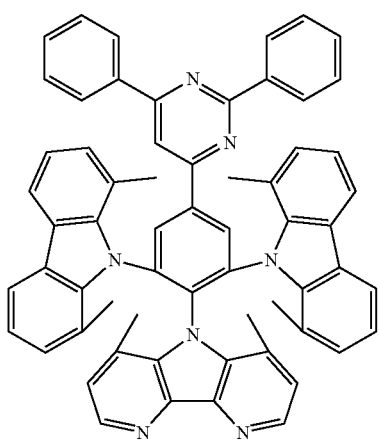
T-401
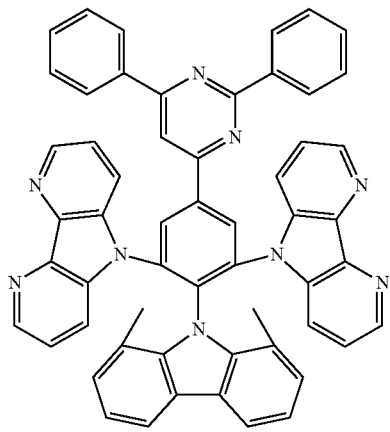
-continued
T-402
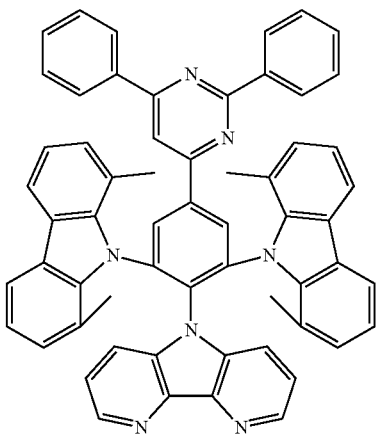
T-403
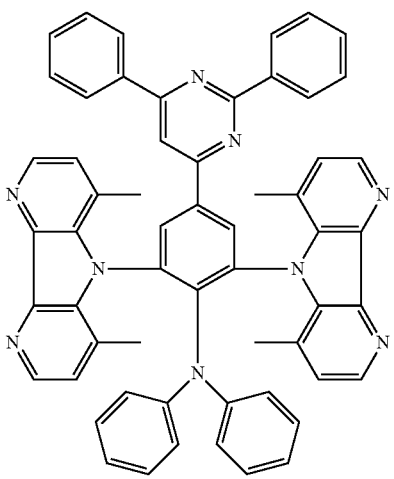
[Formula 59]
T-404
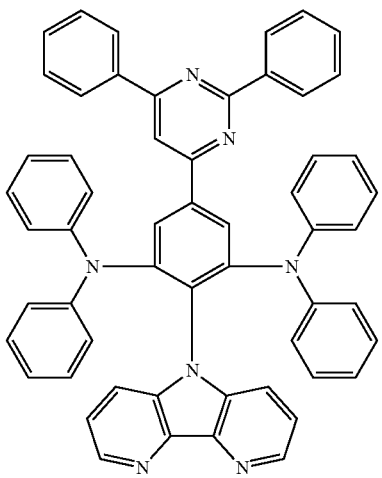

-continued
T-405
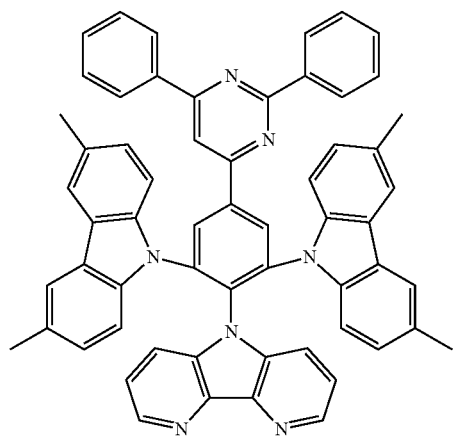
T-408
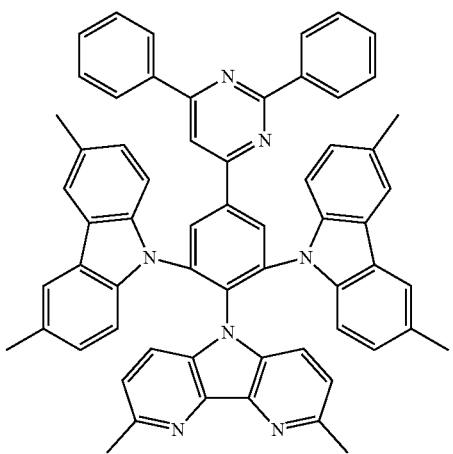
T-406
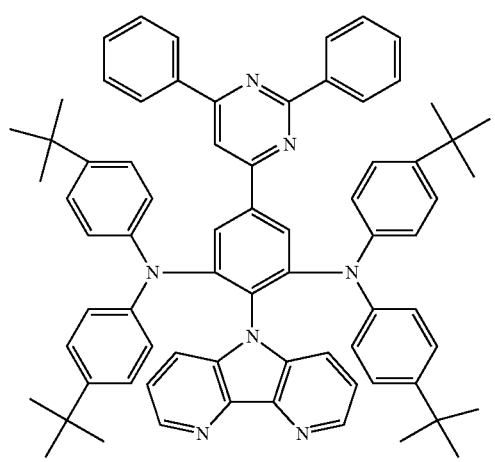
T-409
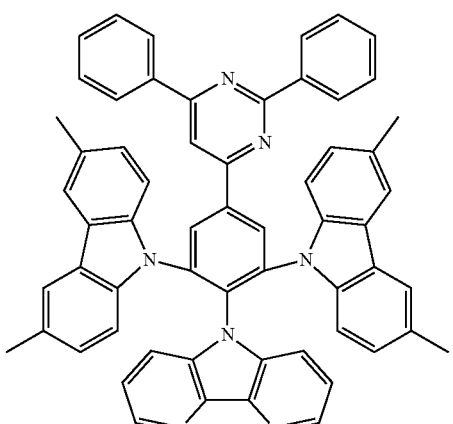
T-407
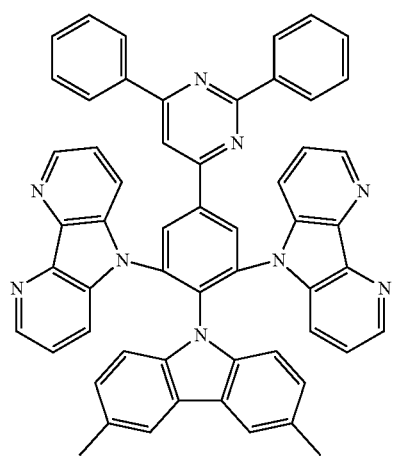
T-410
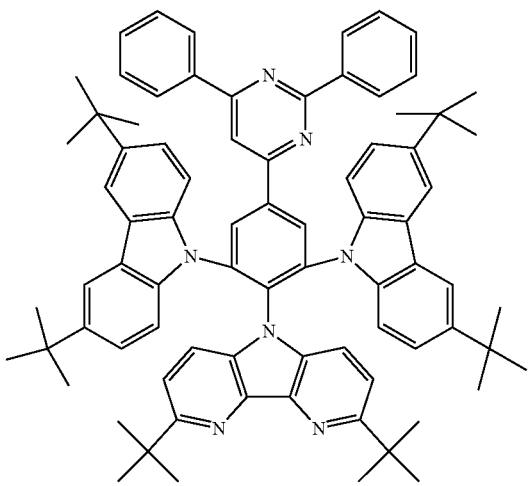

T-411
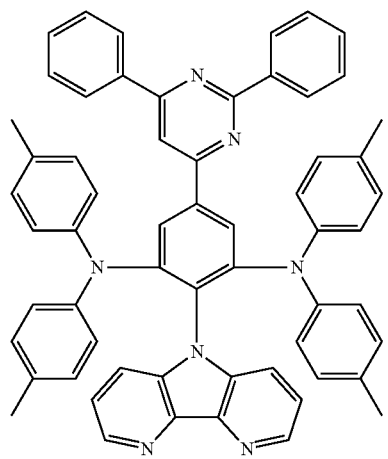
T-414
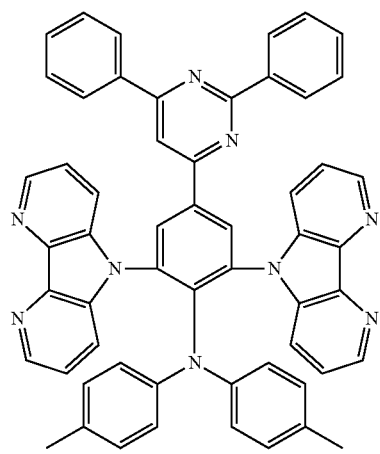
T-412
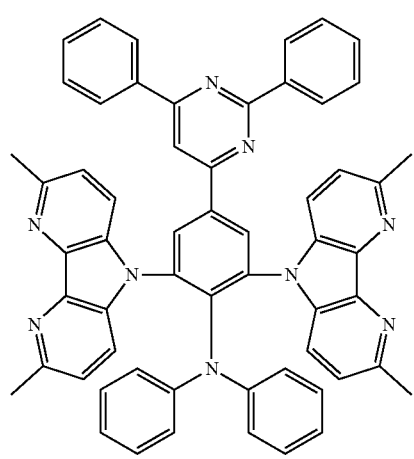
T-415
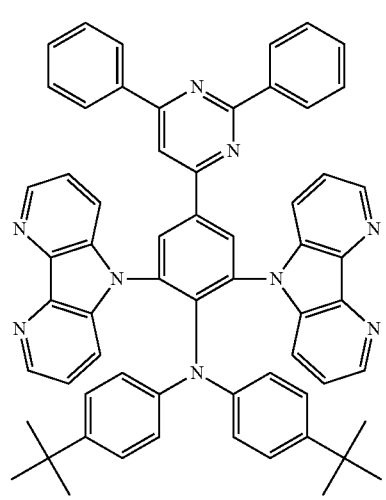
[Formula 60]
T-413
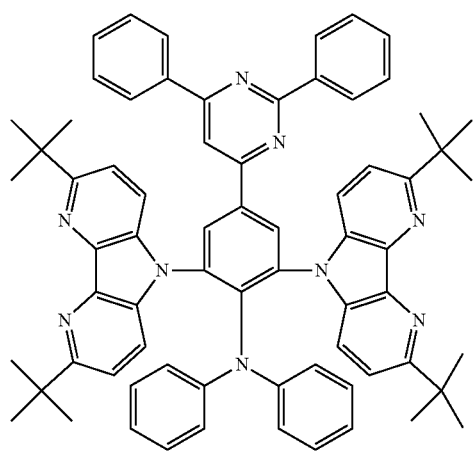
T-416
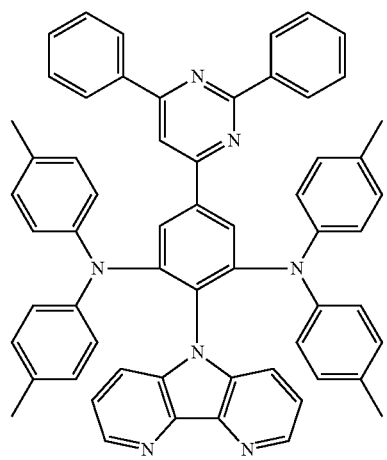

-continued
T-417
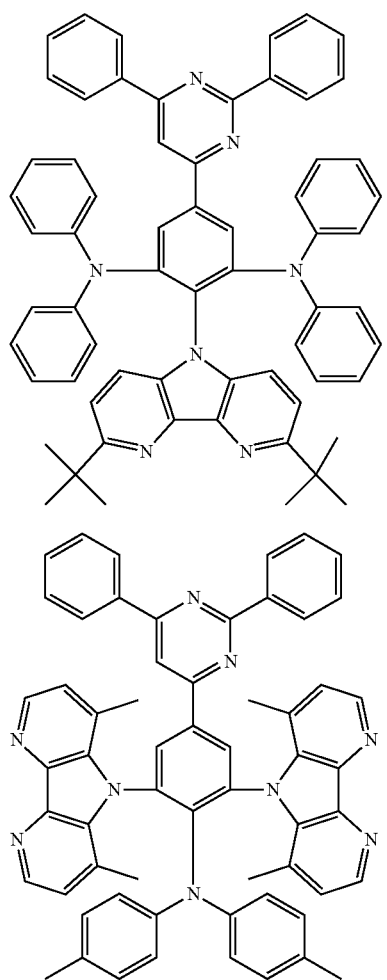
T-418
T-419
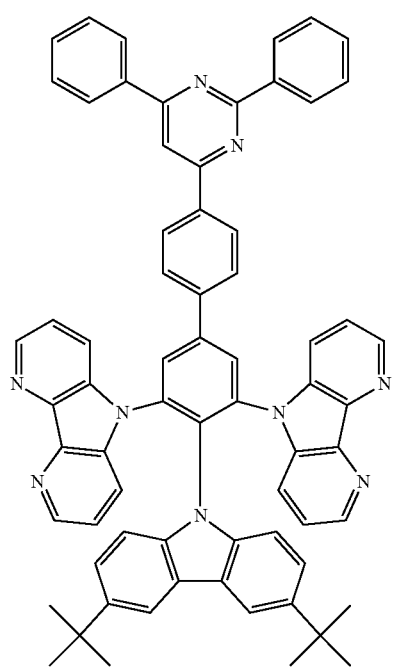
-continued
T-420
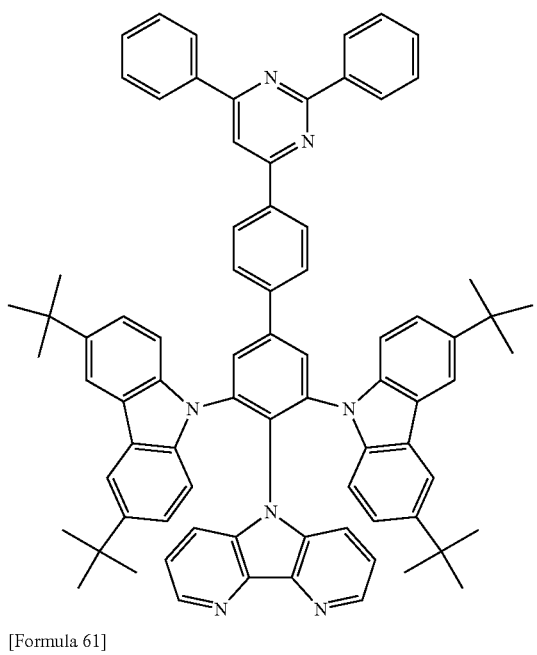
[Formula 61]
T-421
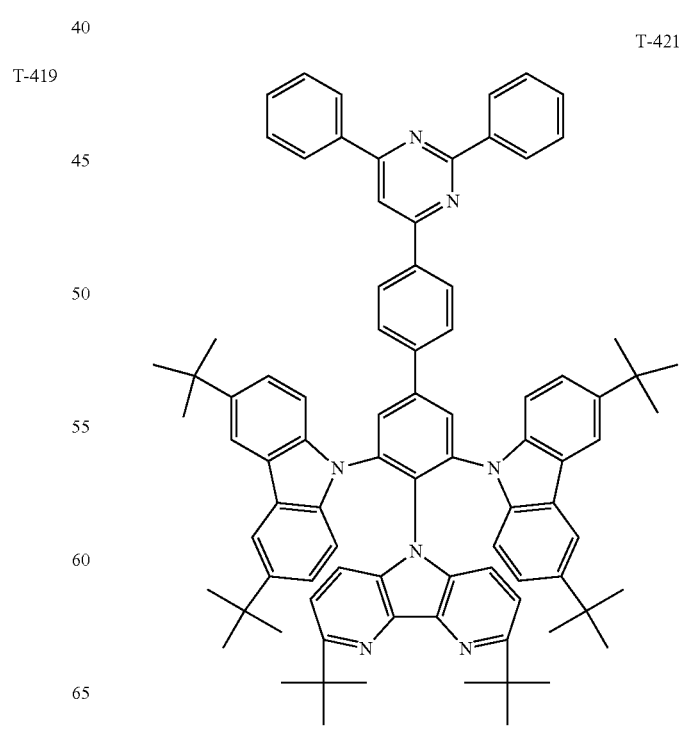

-continued
T-422
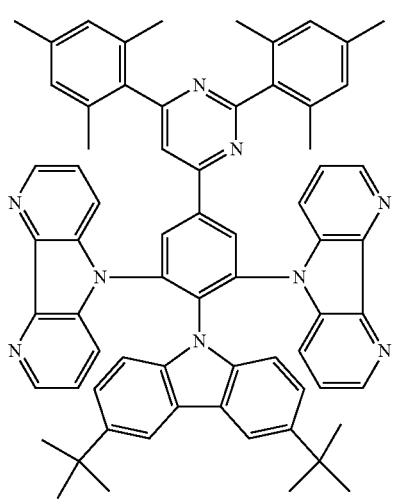
T-423
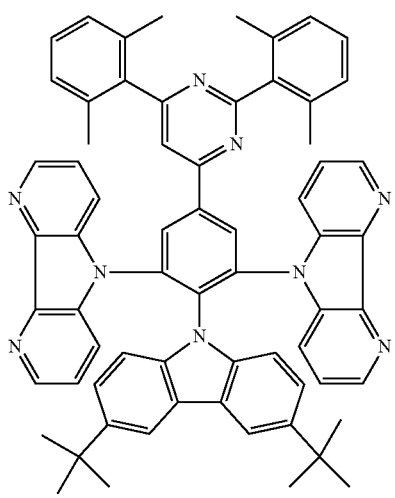
T-424
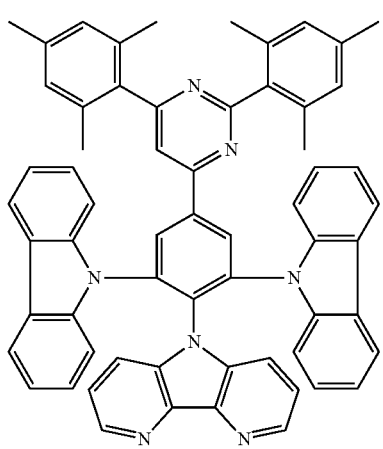
-continued
T-425
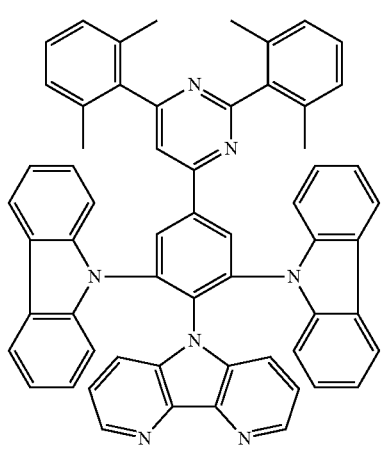
T-426
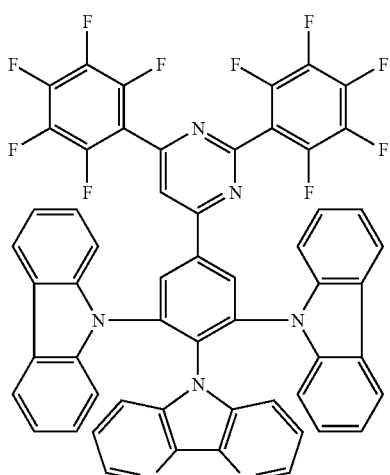
T-427
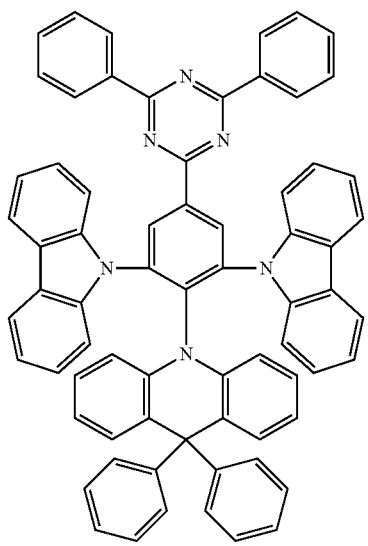

T-428
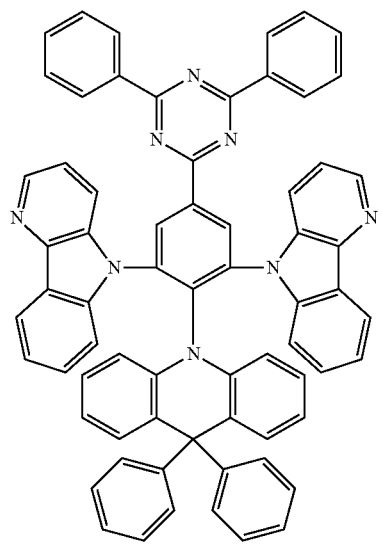
T-429
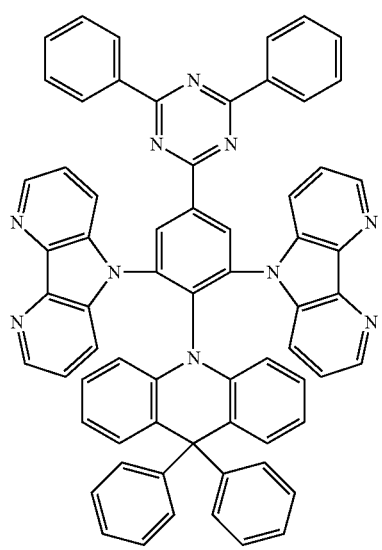
[Formula 62]
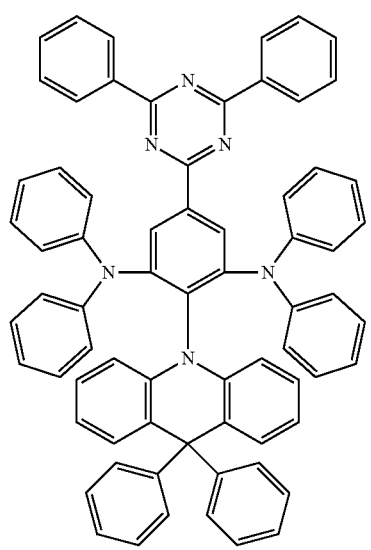
T-431

T-432
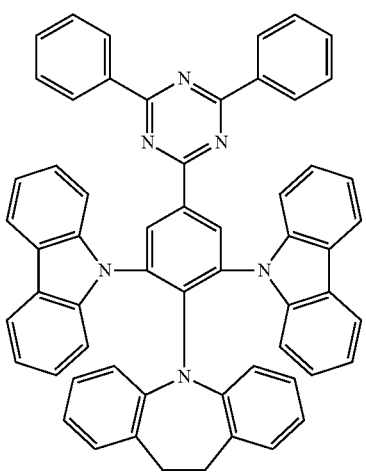
T-430
T-433
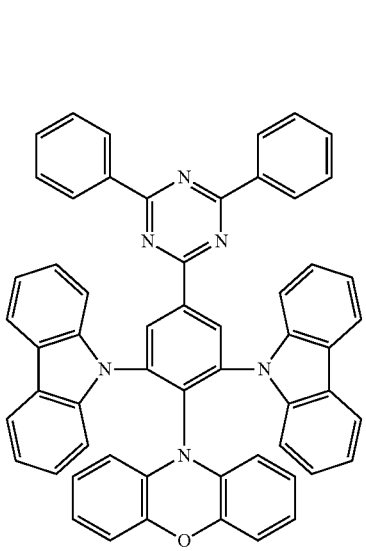

T-434 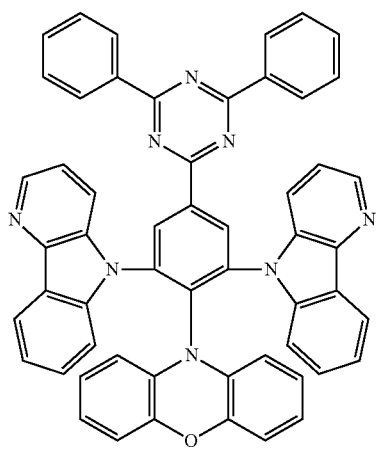
T-435 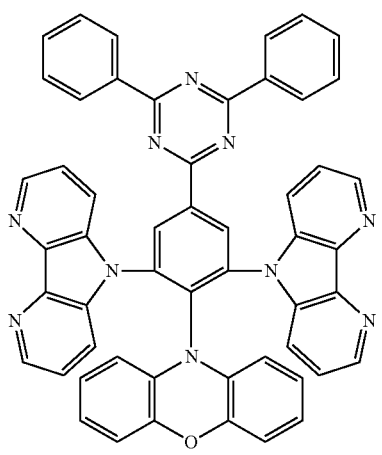
T-436 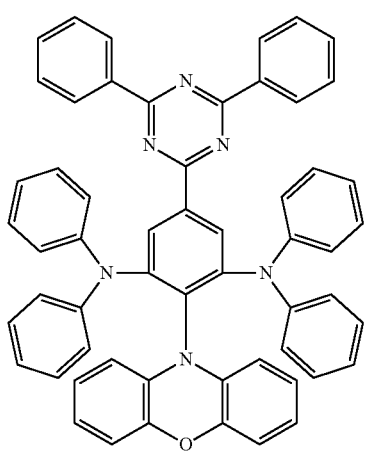
T-437 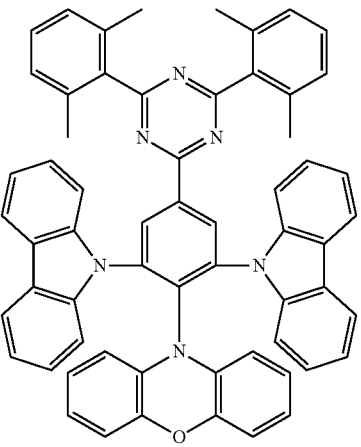
T-438 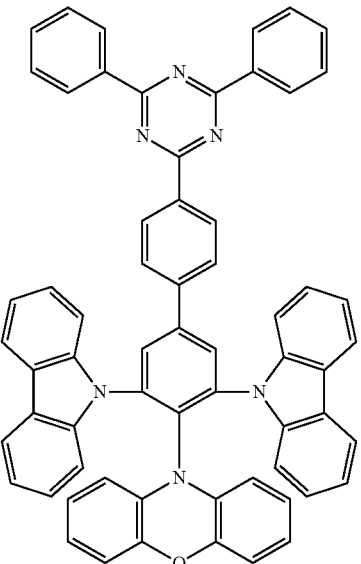
[Formula 63]
T-439 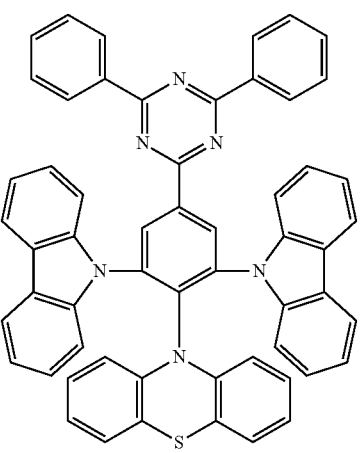

T-440
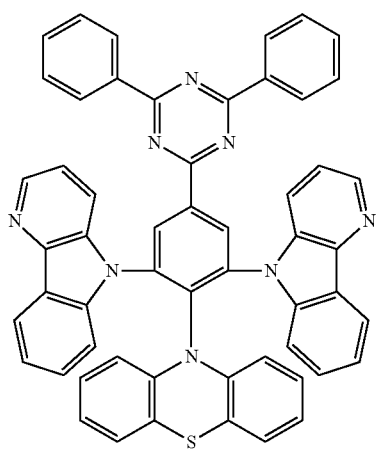
T-441
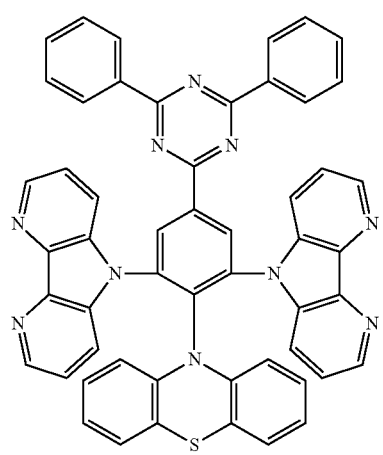
T-442
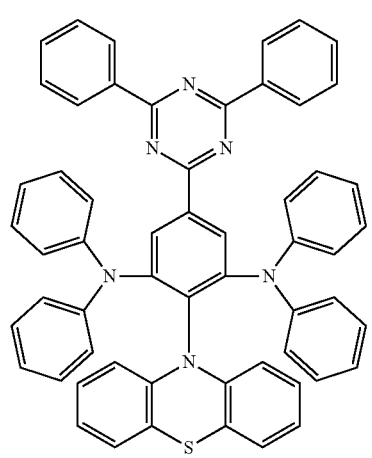
T-443
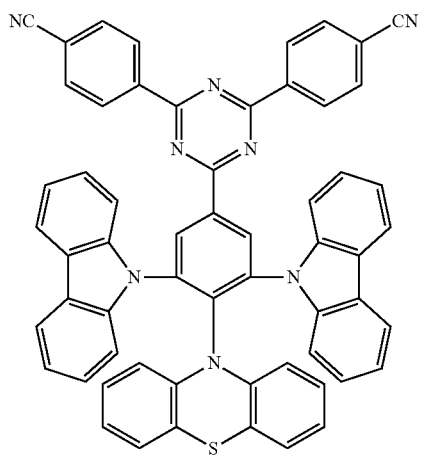
T-444
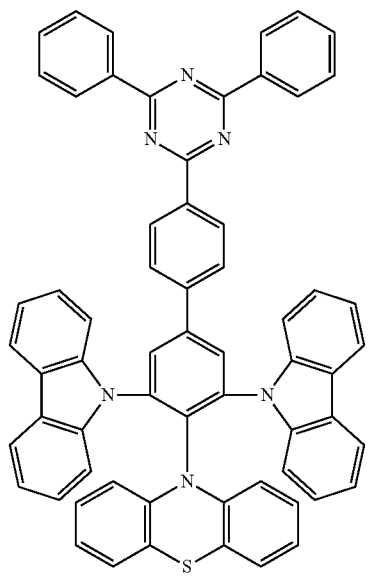
T-445
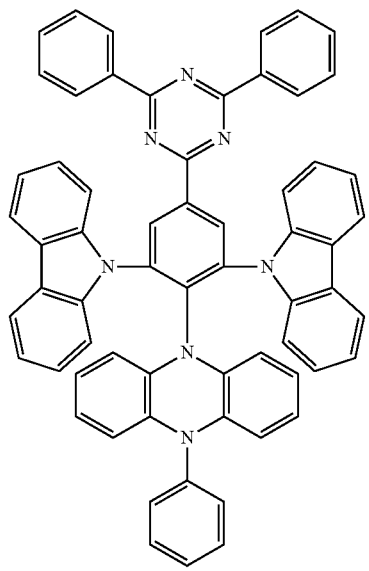

[Formula 64]
T-446
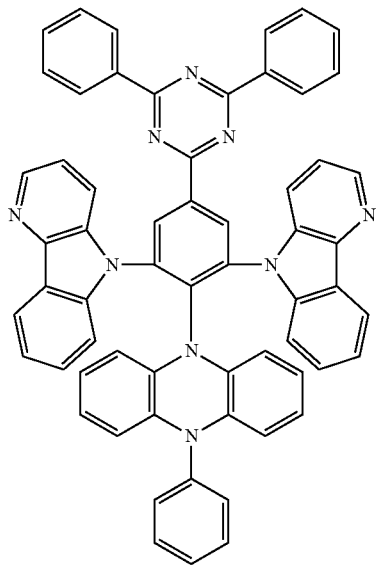
T-448
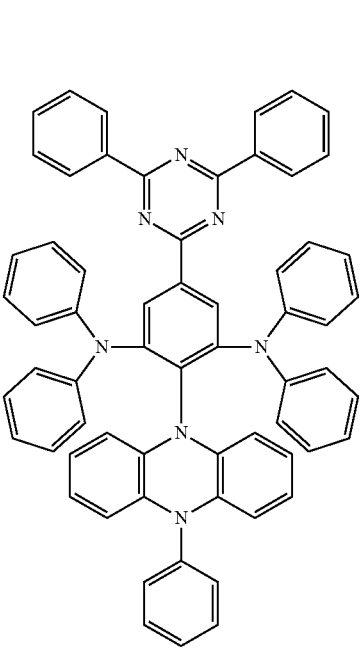
T-447
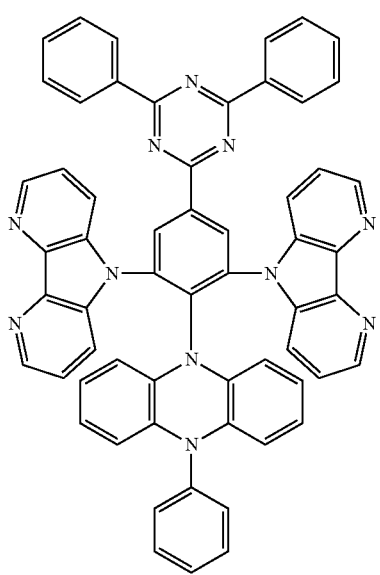
T-449
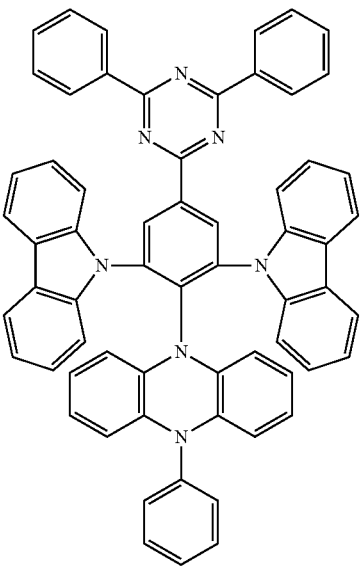

T-450
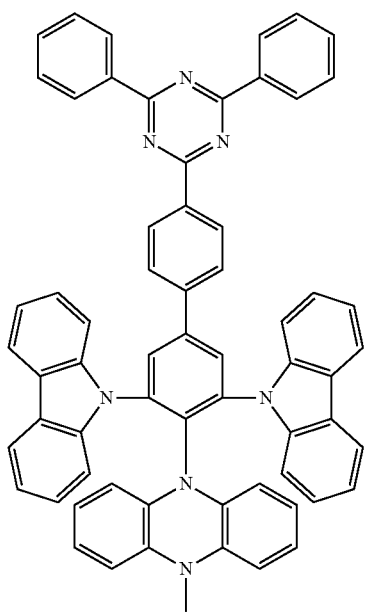
T-451
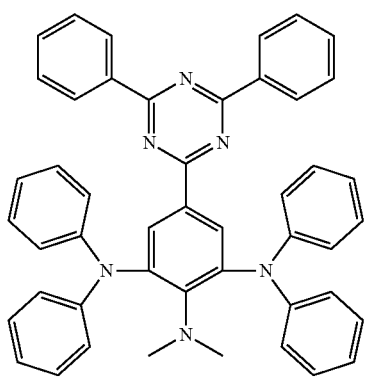
T-452
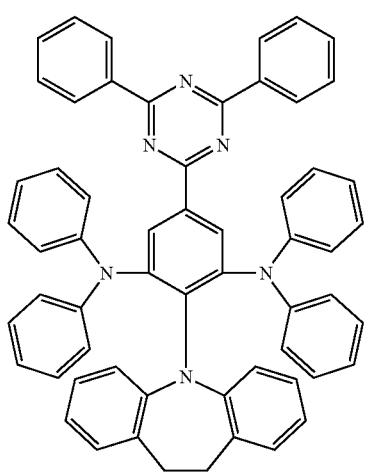
T-453
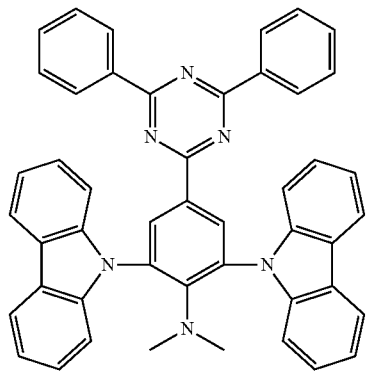
T-454
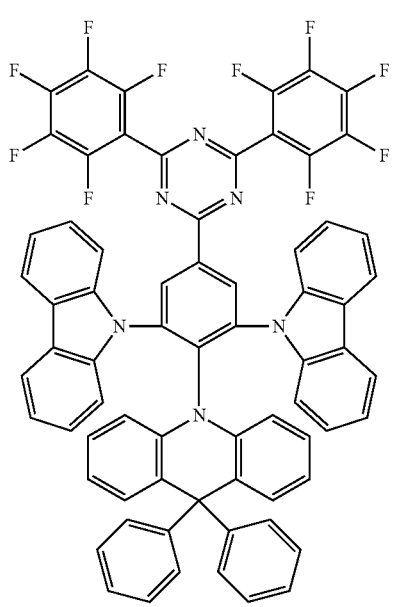
T-455
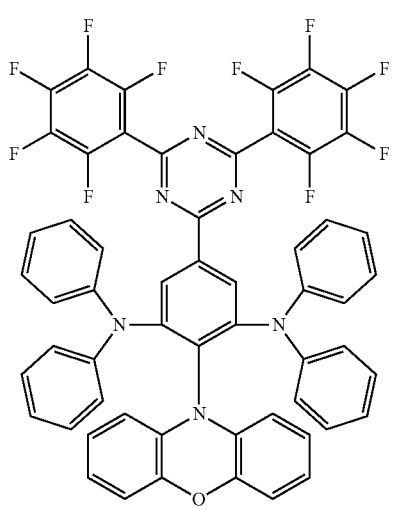

T-456
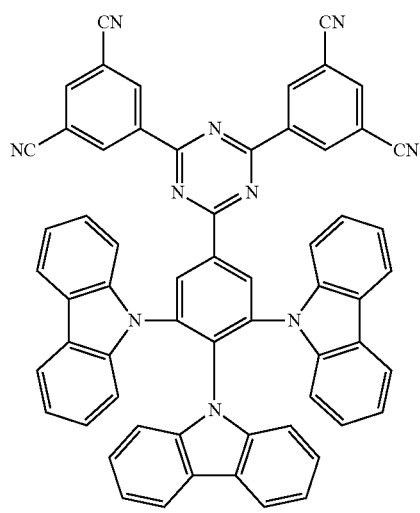
[Formula 65]
T-457
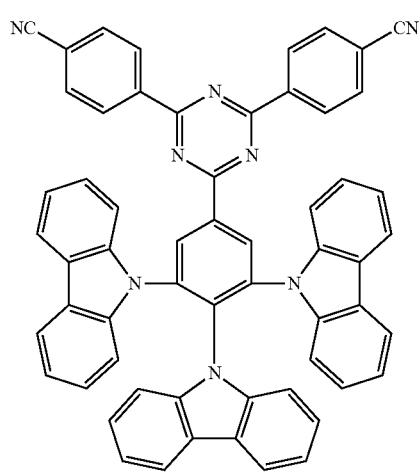
T-458
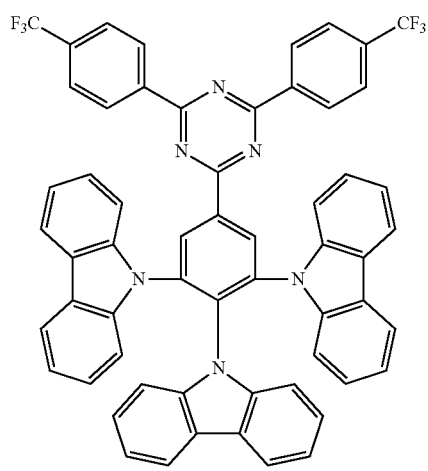
T-459
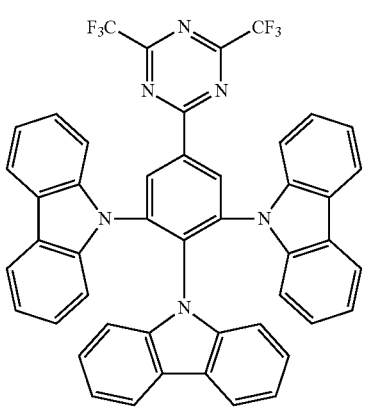
T-460
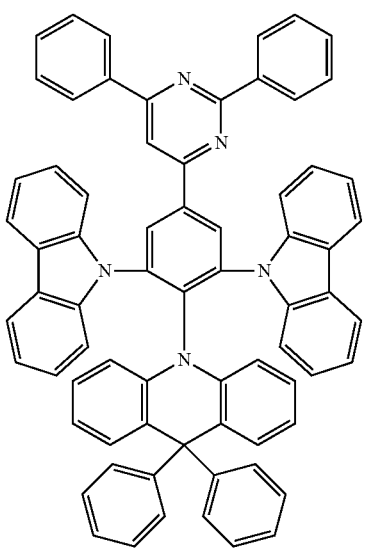
T-461
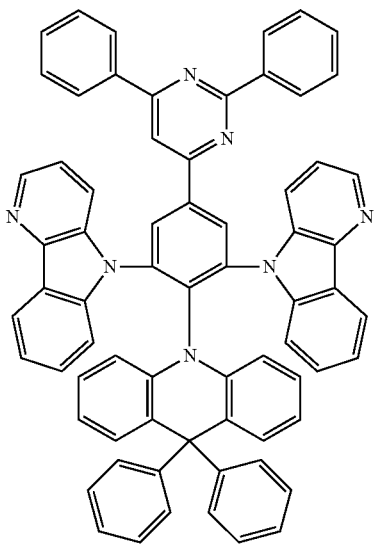

T-462
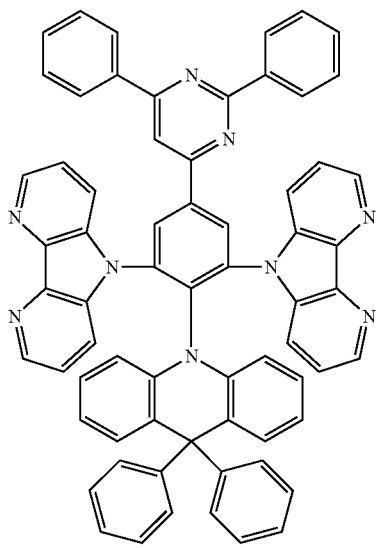
T-463
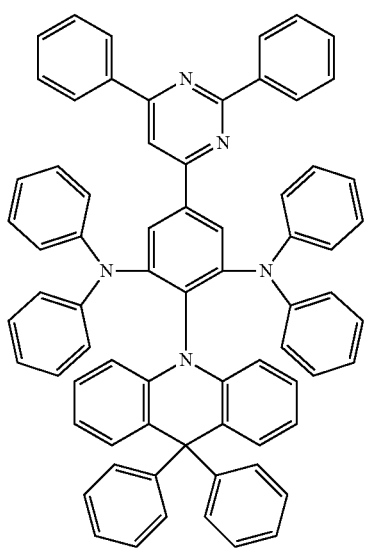
T-464
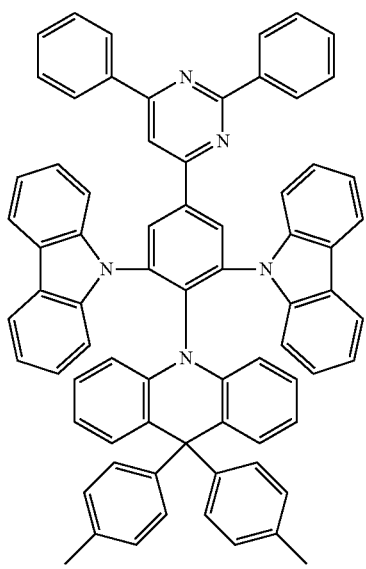
T-465
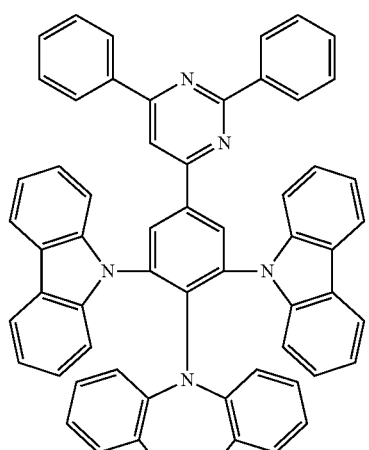
[Formula 66]
T-466
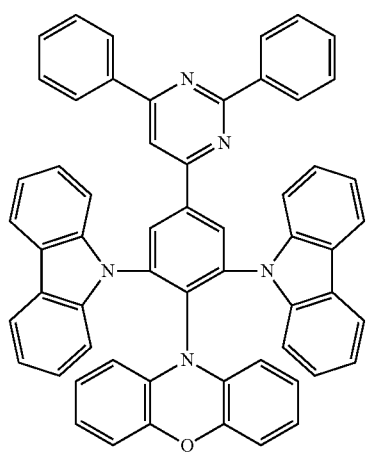
T-467
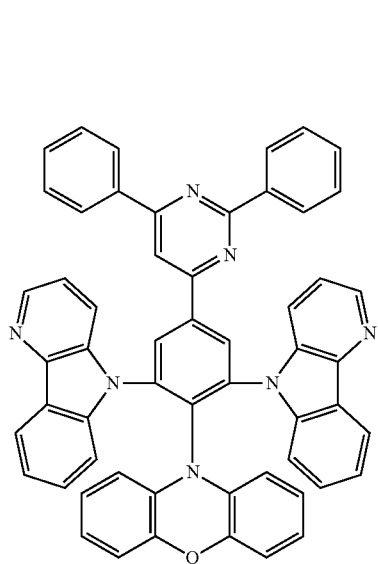

-continued
T-468
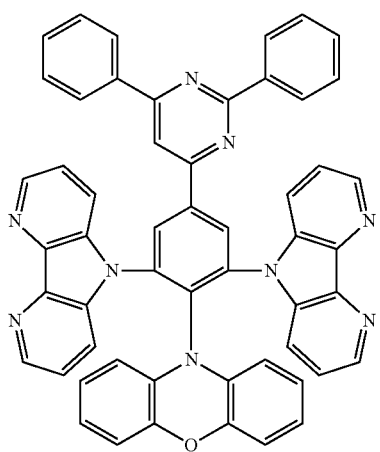
T-469
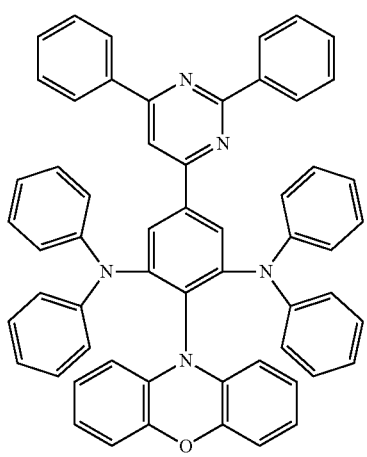
T-470
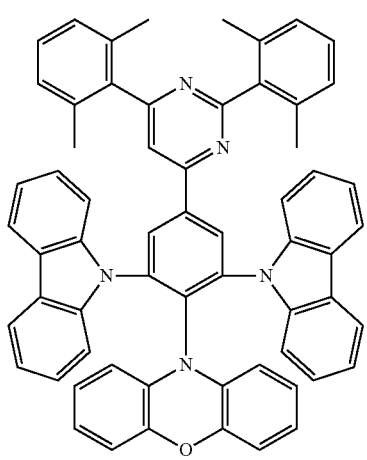
-continued
T-471
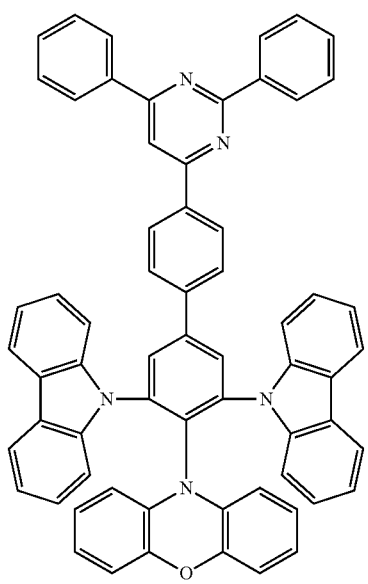
T-472
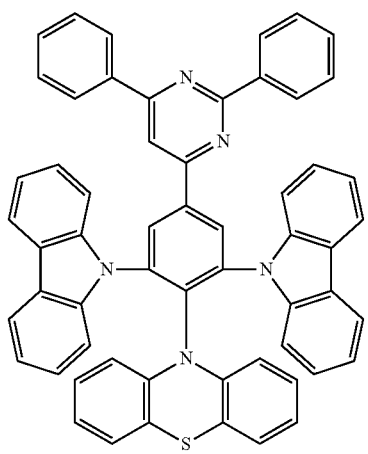
T-473
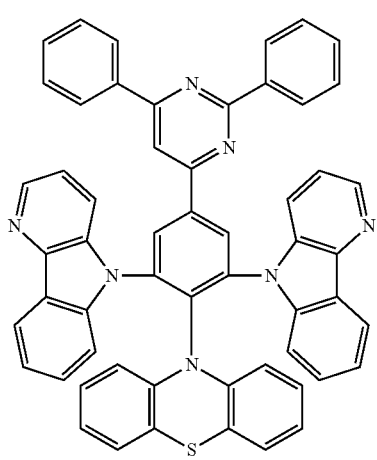

-continued
T-474
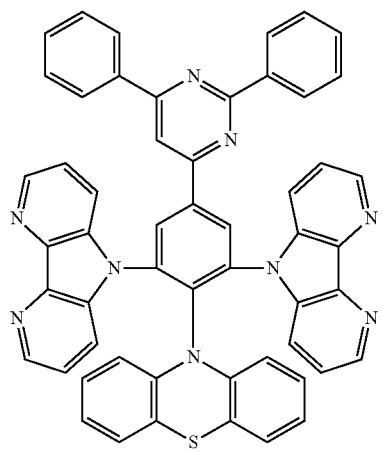
[Formula 67]
T-475
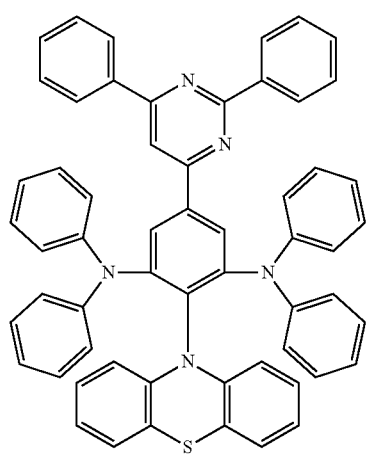
T-476
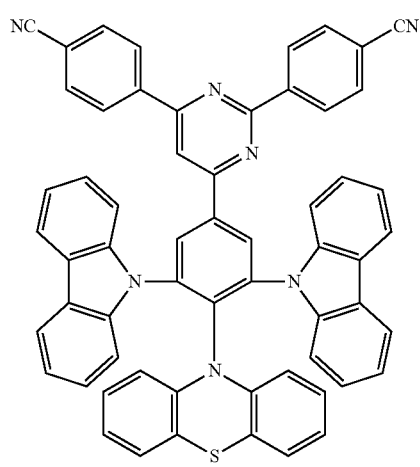
-continued
T-477
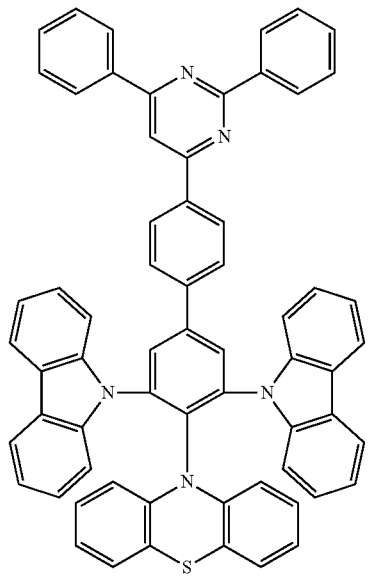
T-478
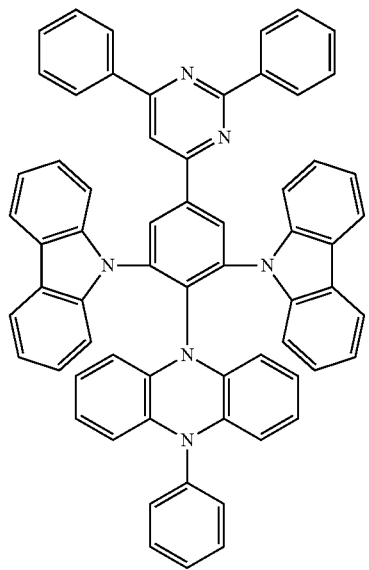

T-479
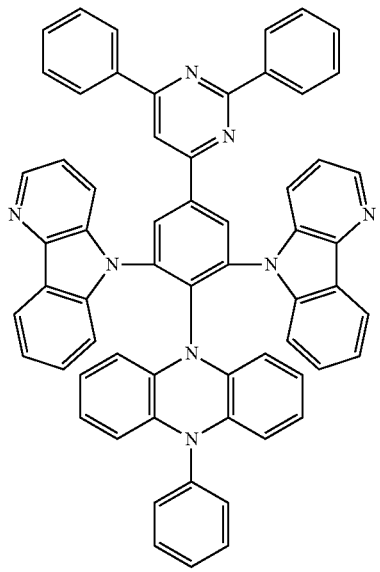
T-481
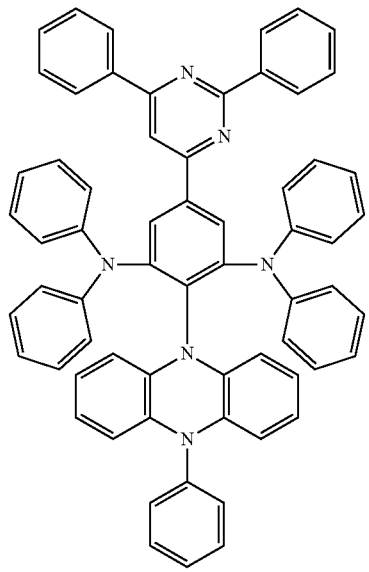
T-480
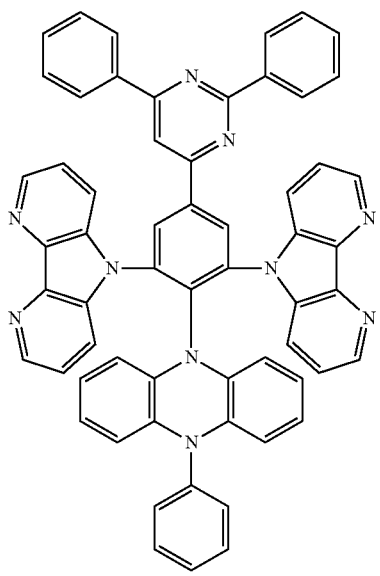
T-482
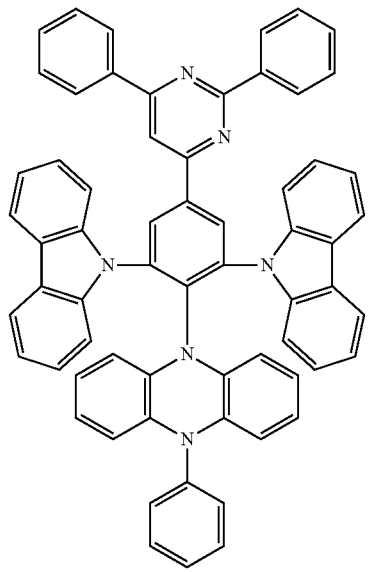

T-483
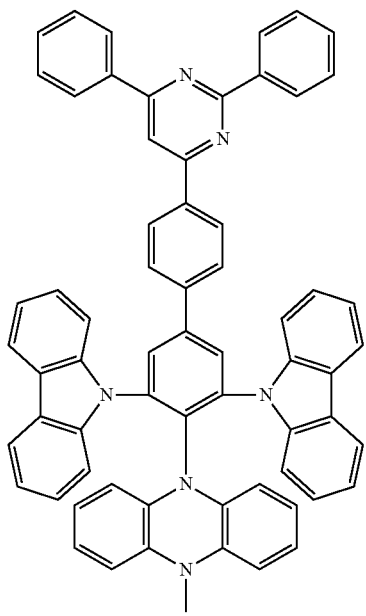
[Formula 68]
T-484
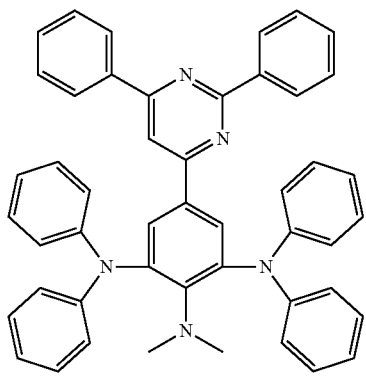
T-485
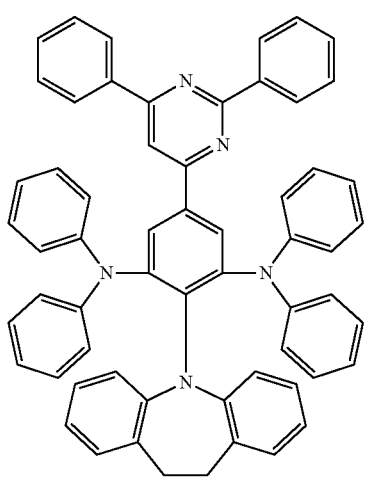
T-486
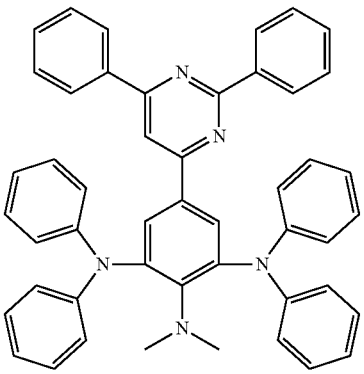
T-487
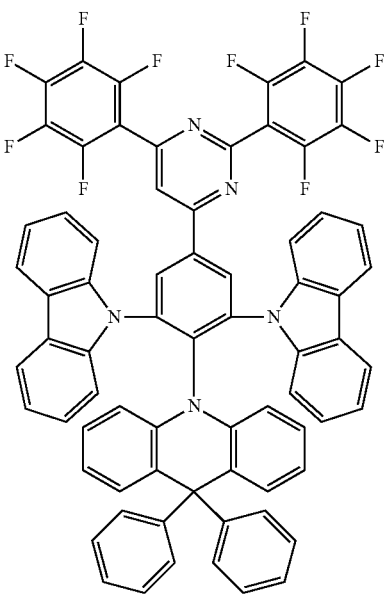
T-488
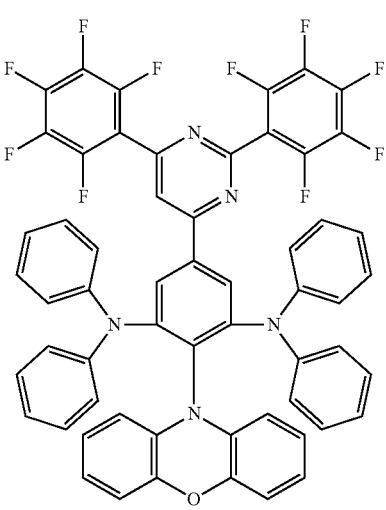

T-489
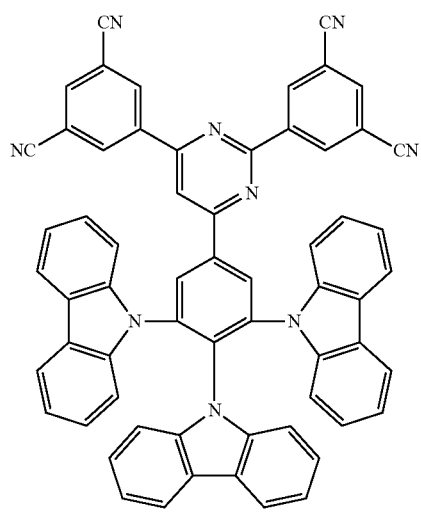
T-490
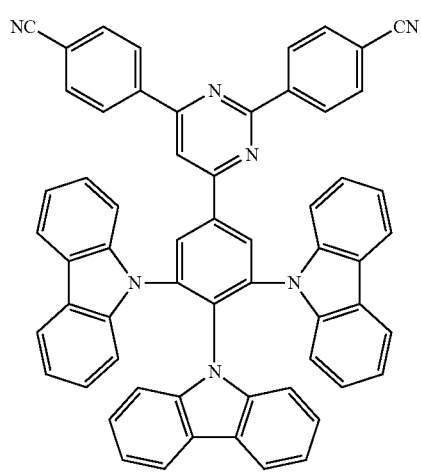
T-491
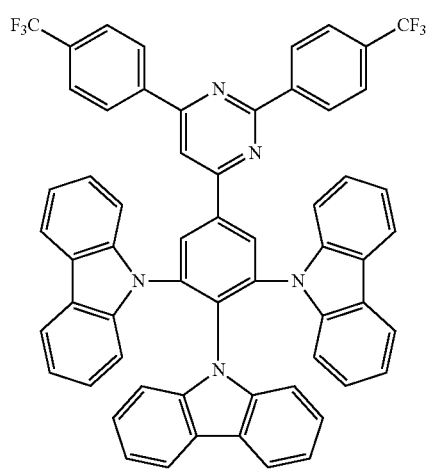
T-492
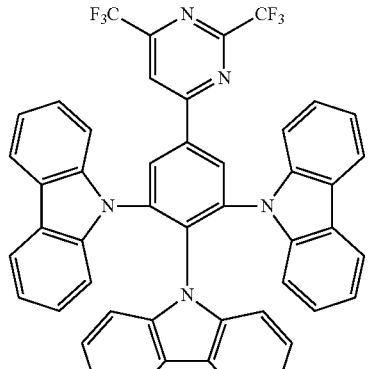
[Formula 69]
T-493
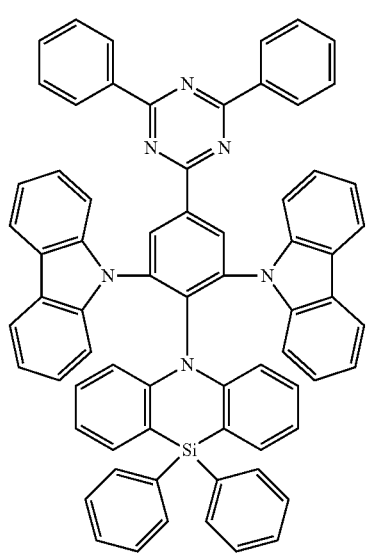
T-494
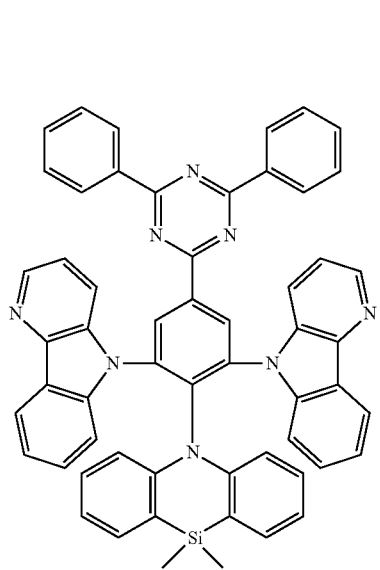

T-495
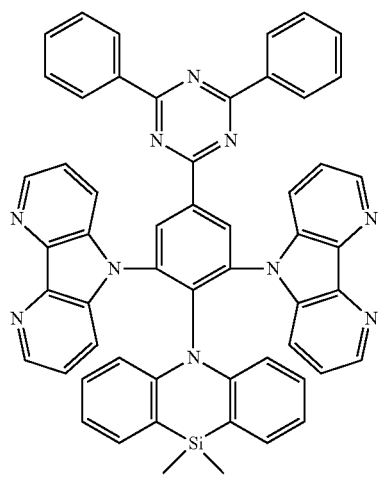
T-496
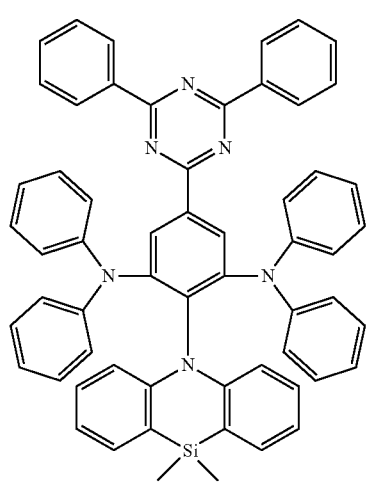
T-497
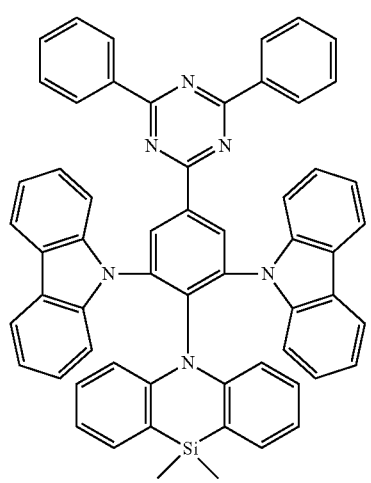
T-498
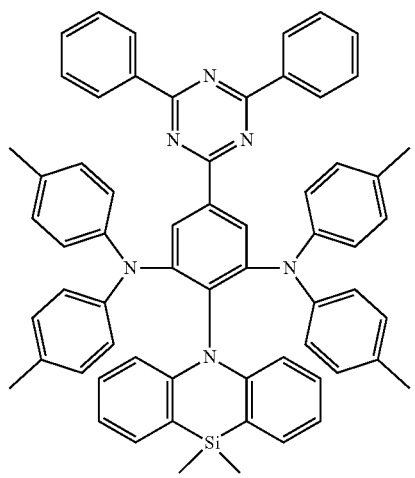
T-499
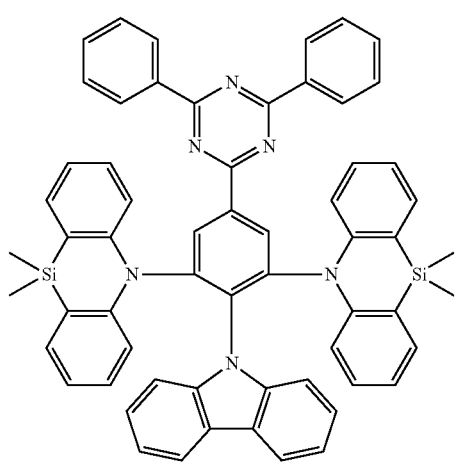
T-500
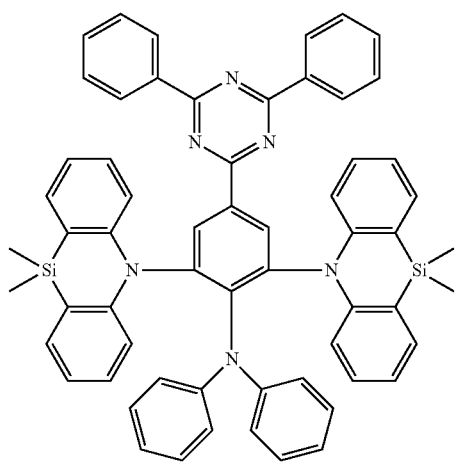

T-501
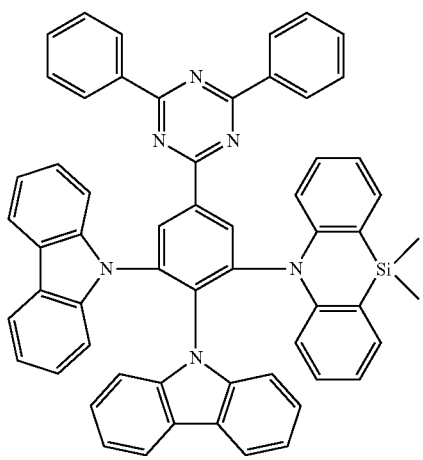
[Formula 70]
T-502
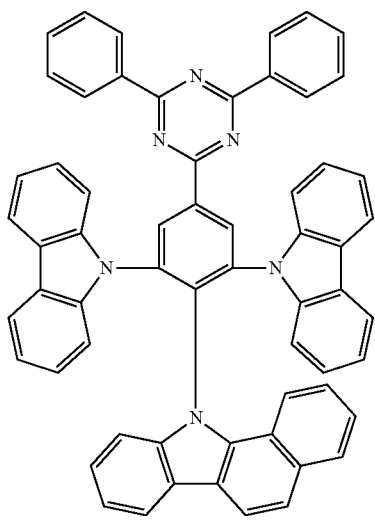
T-503
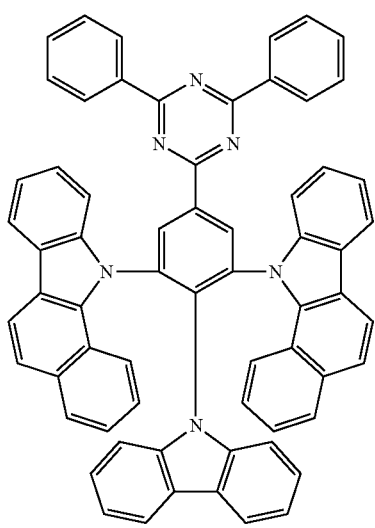
T-504
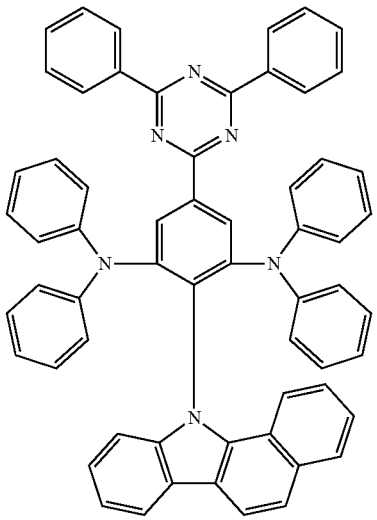
T-505
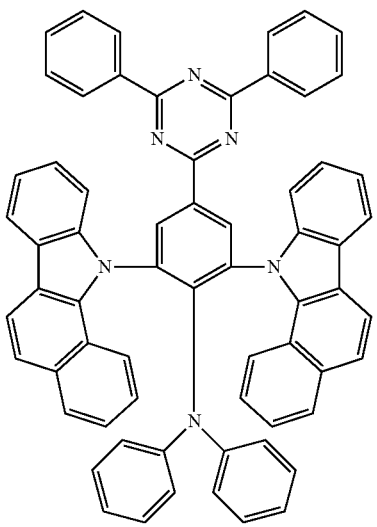
T-506
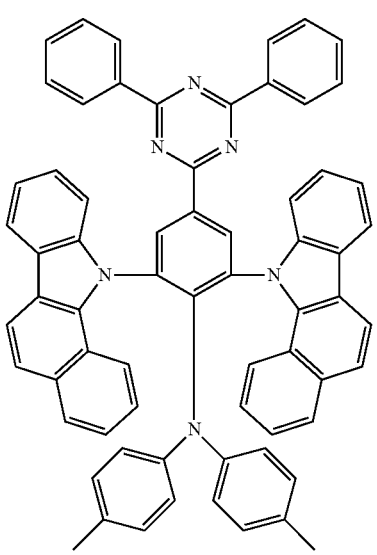

T-507
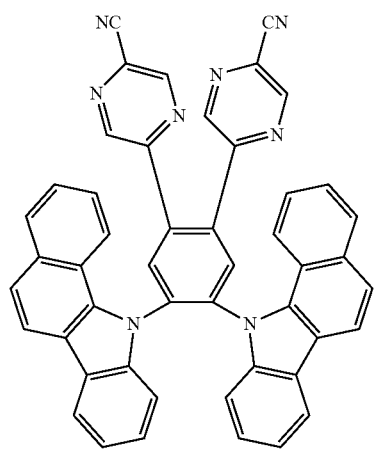
T-510
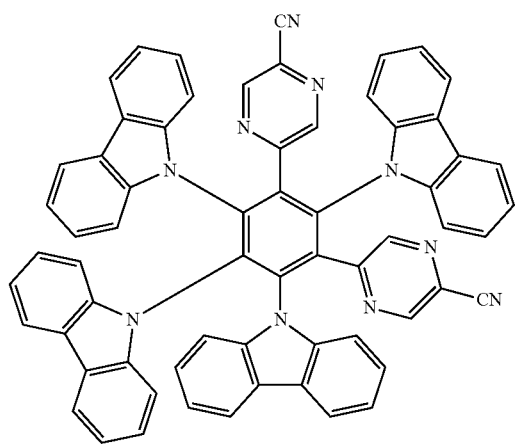
[Formula 71]
T-508
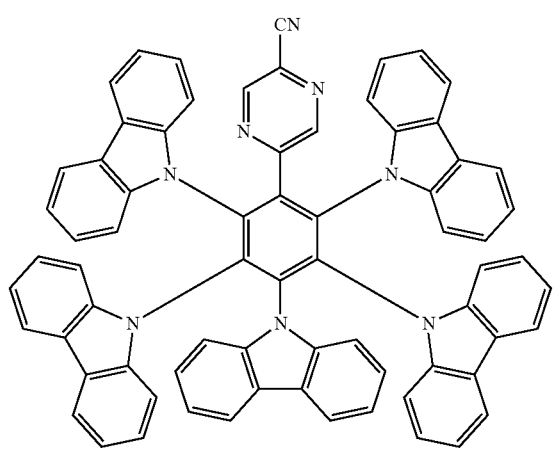
T-511
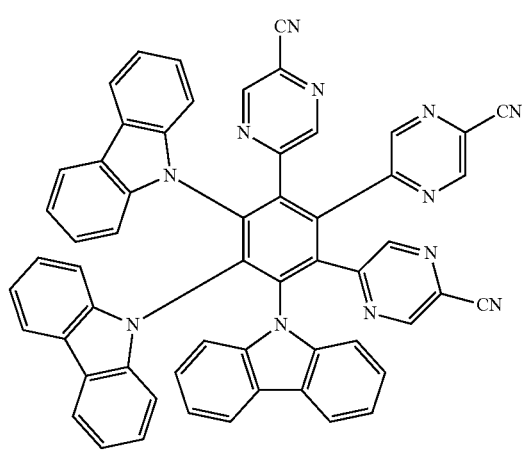
T-509
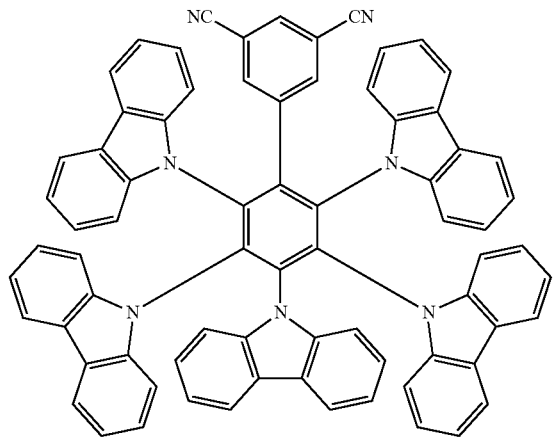
T-512
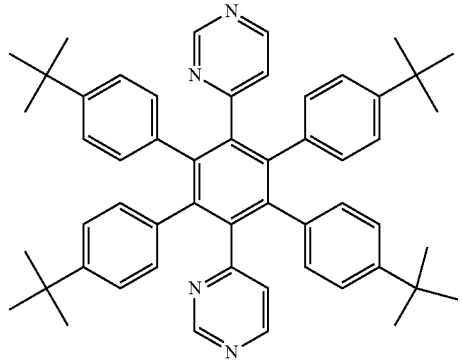

T-513
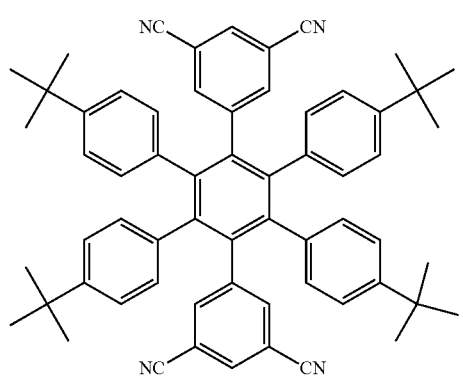
T-514
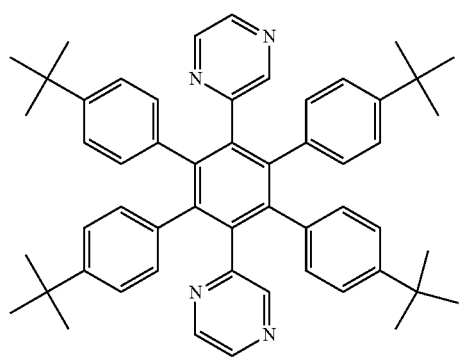
T-515
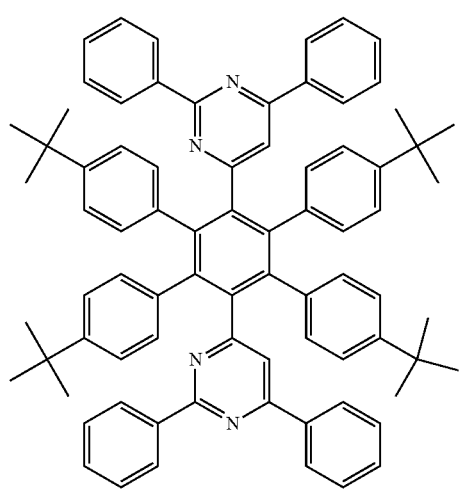
T-516
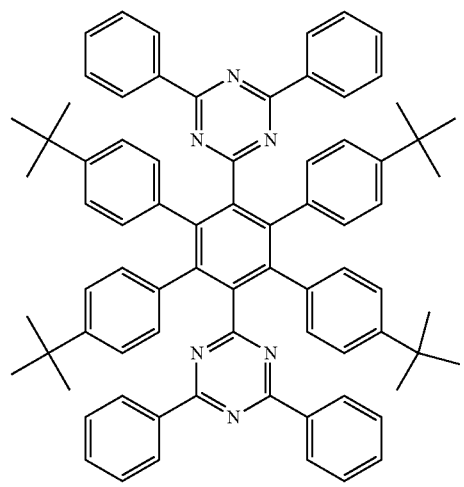
T-517
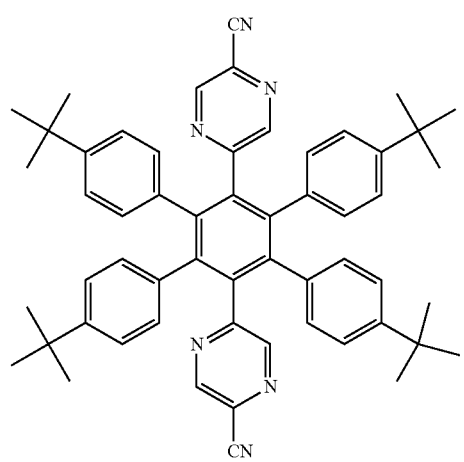
T-518
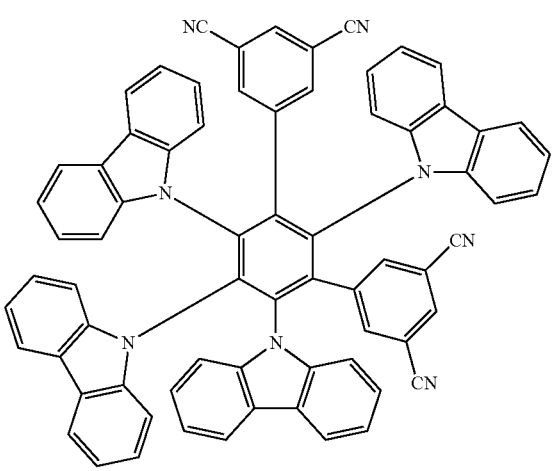

-continued
T-519
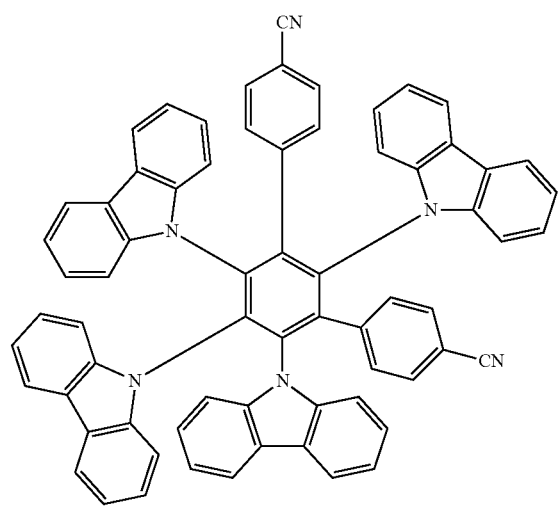
[Formula 72]
T-520
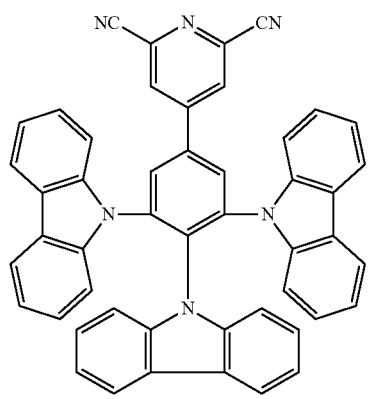
T-521
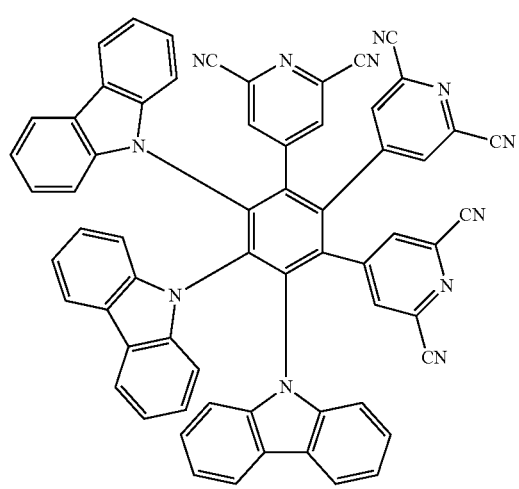
-continued
T-522
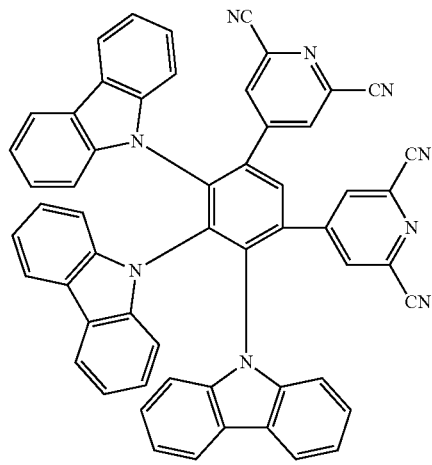
T-523
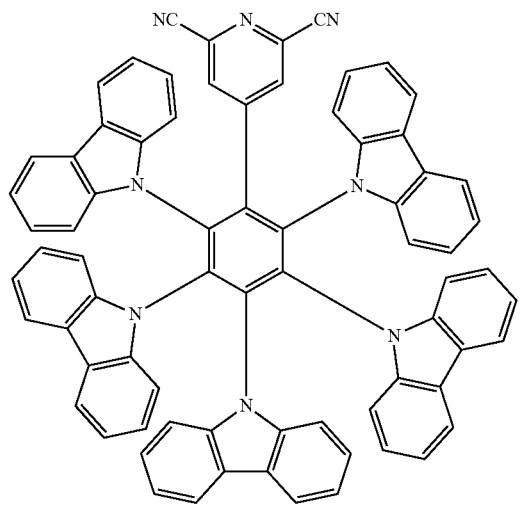
T-524
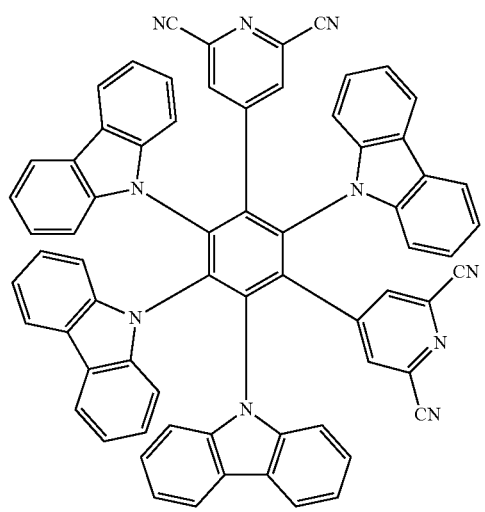

-continued
T-525
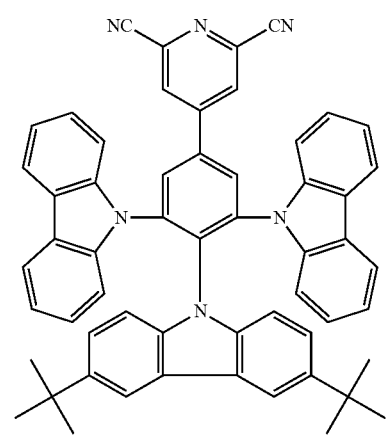
T-526
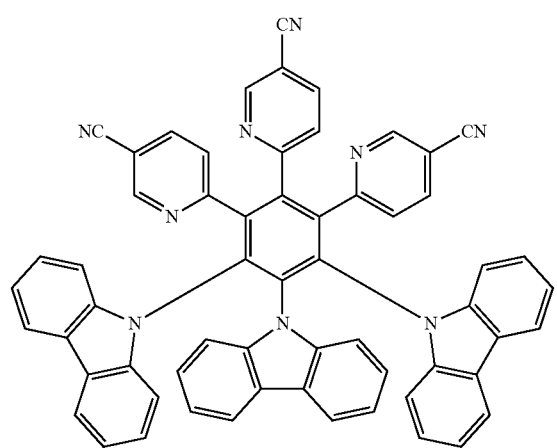
T-527
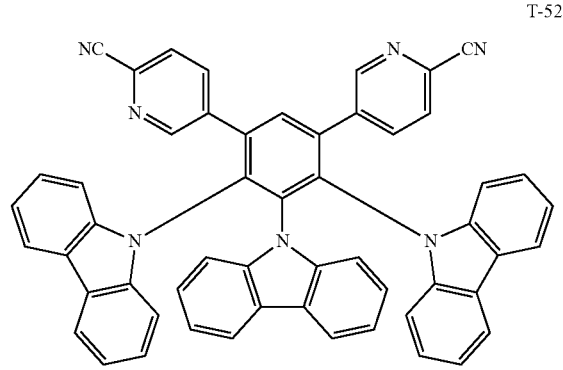
T-528
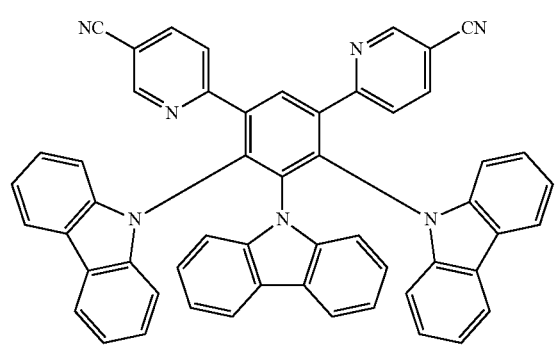
-continued
T-529
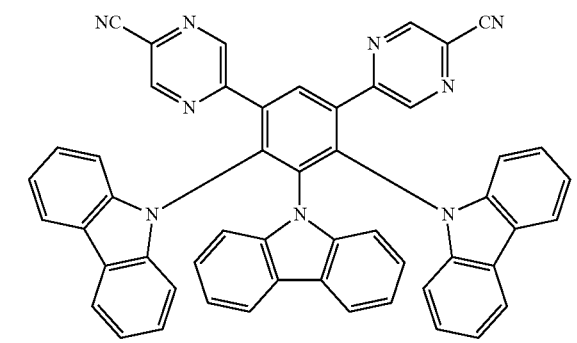
T-530
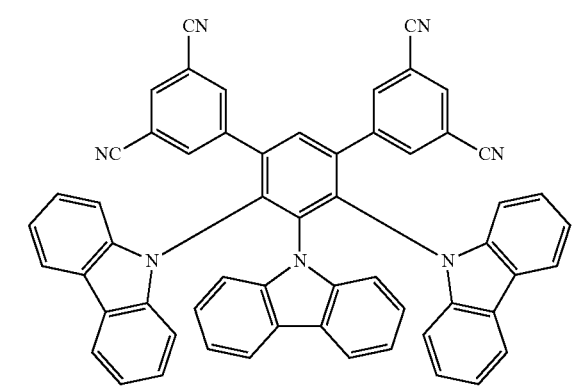
T-531
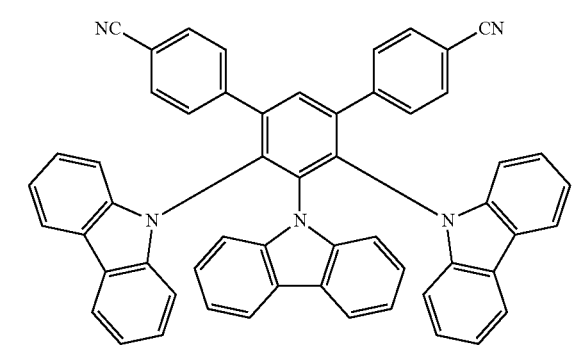
[Formula 73]
T-532
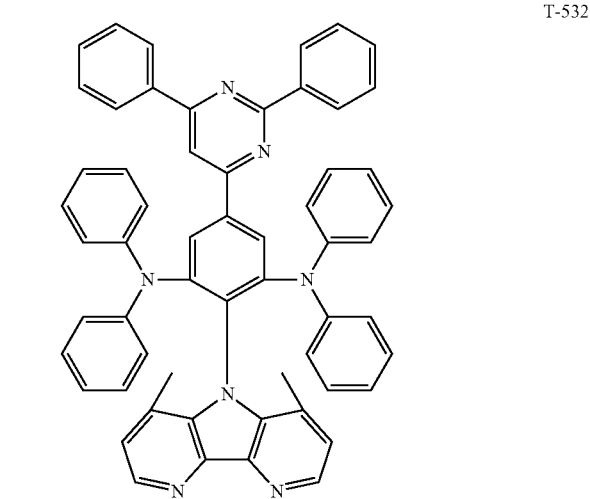

T-533
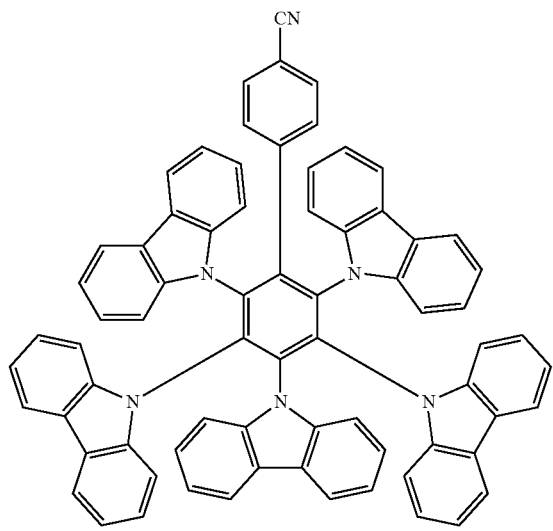
T-534
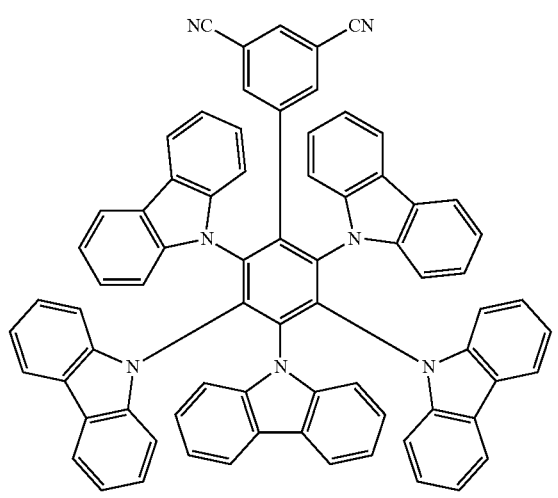
T-535
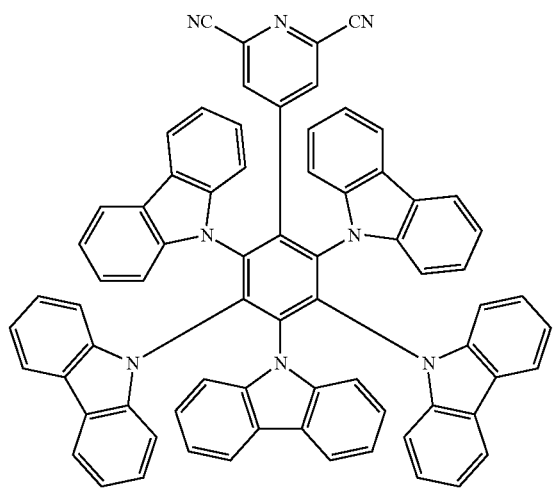
T-536
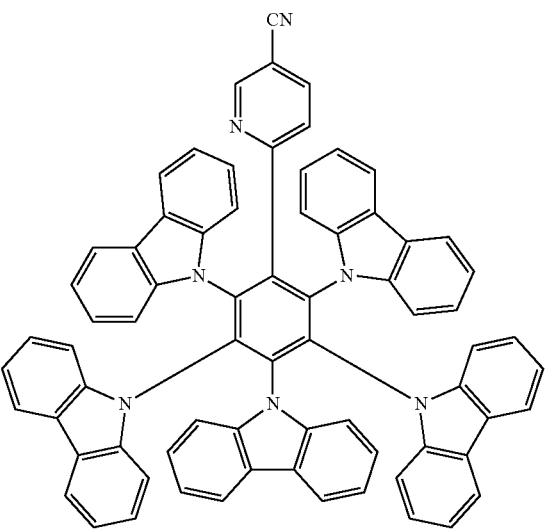
T-537
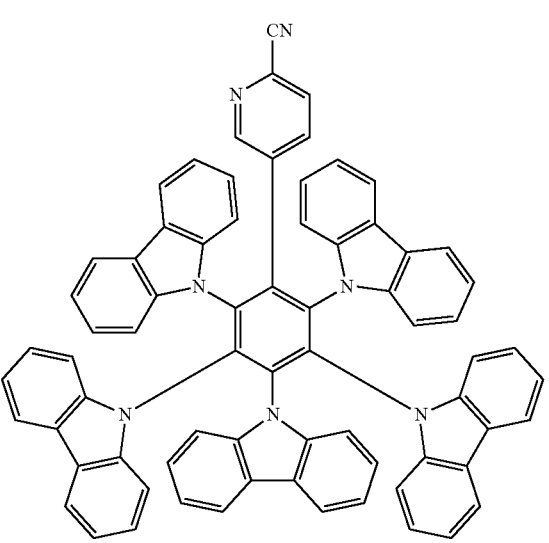
T-538
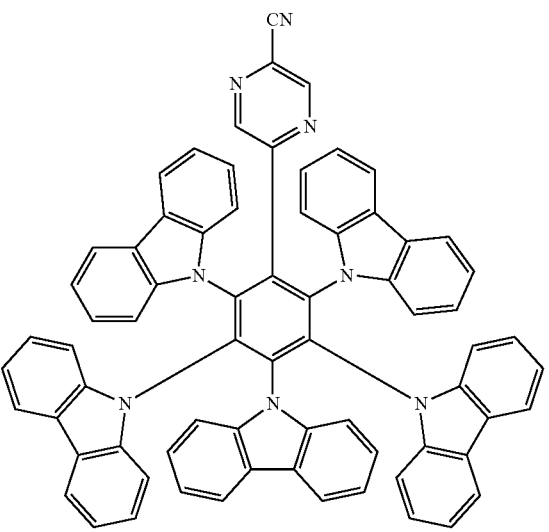

[Formula 74]
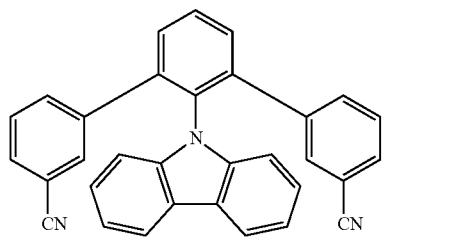 T-539
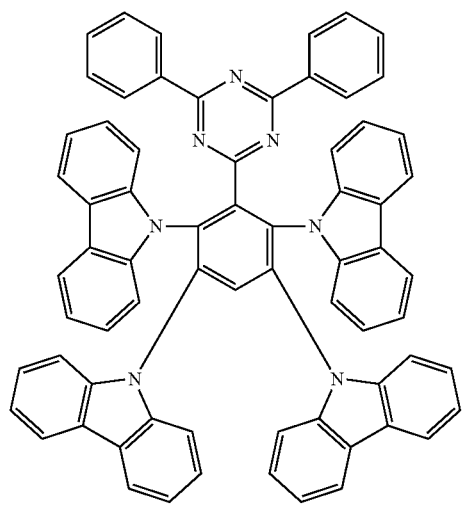 T-540
T-541
T-542
T-543
T-544

T-545
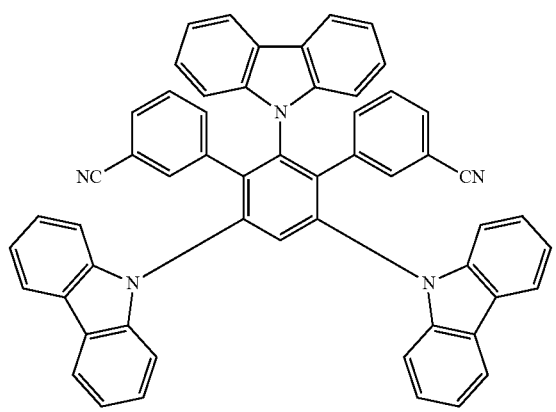
T-548
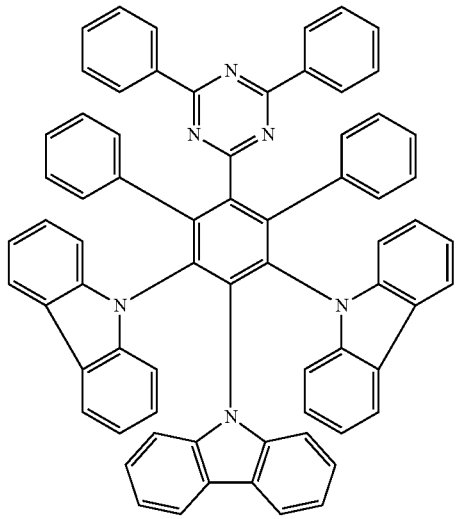
T-546
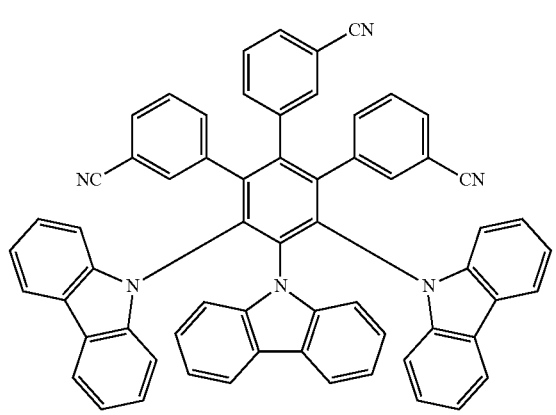
T-549
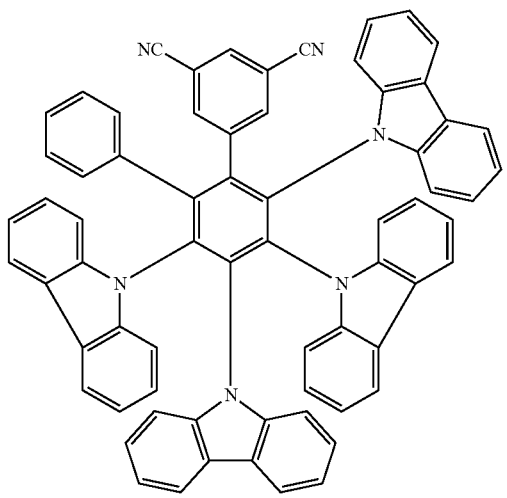
T-547
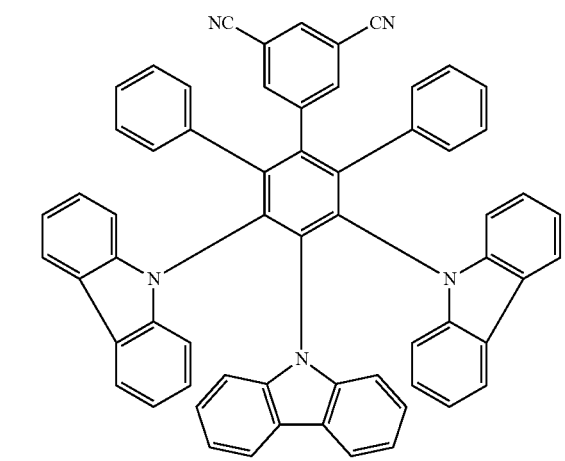
T-550
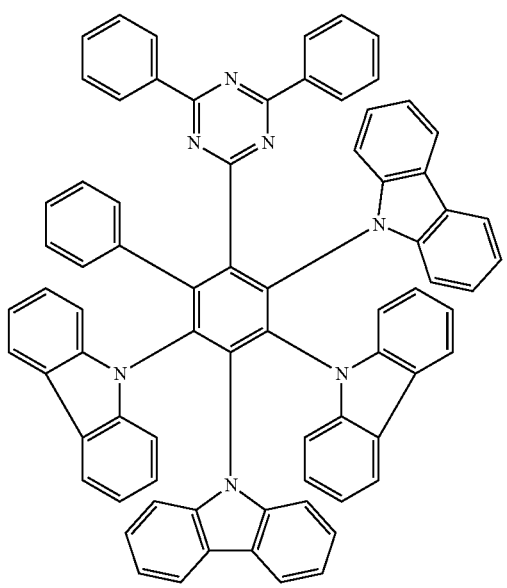

-continued
[Formula 75]
T-551
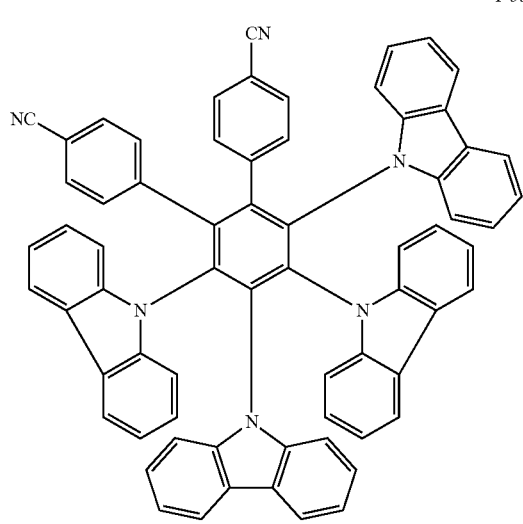
T-552
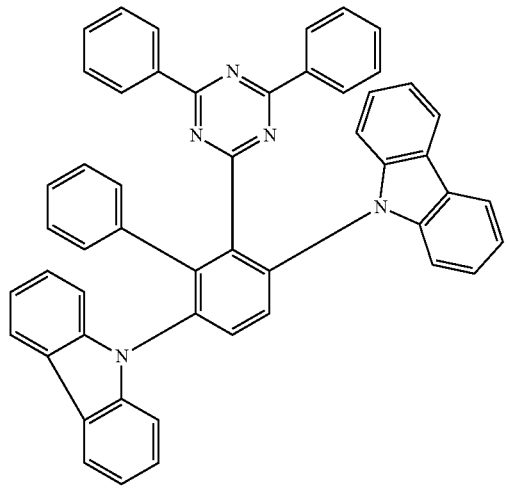
T-553
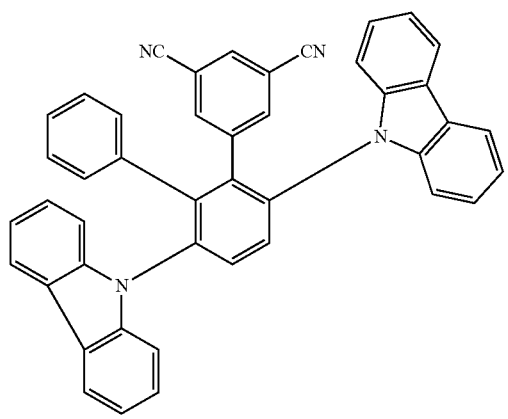
-continued
T-554
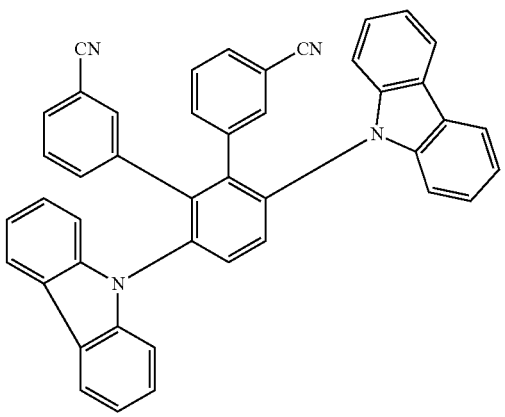
T-555
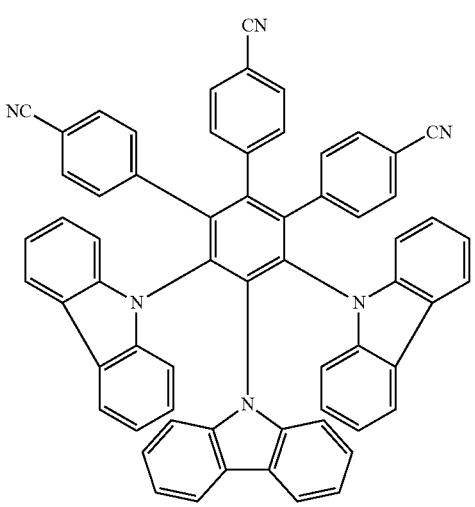
T-556
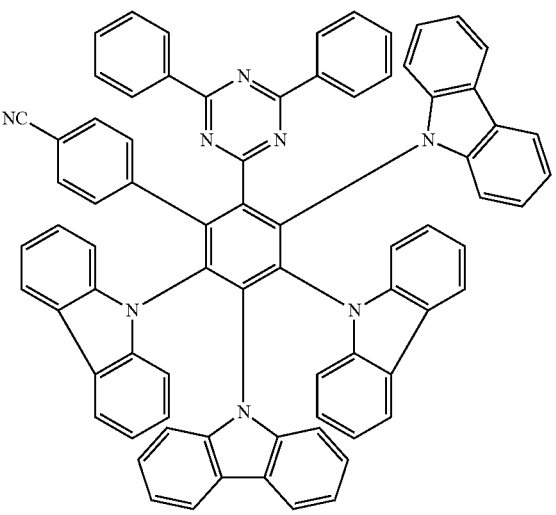

T-557
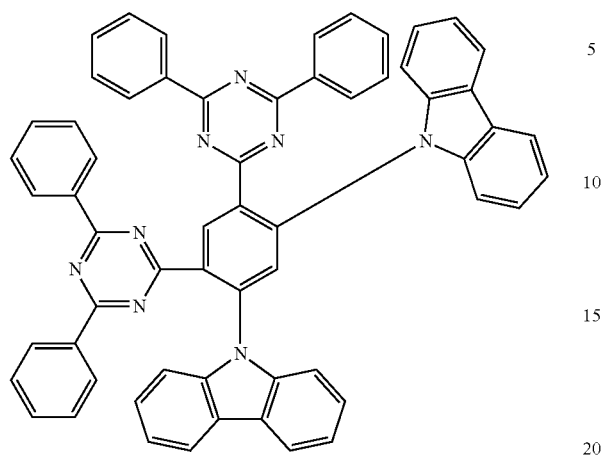
T-560
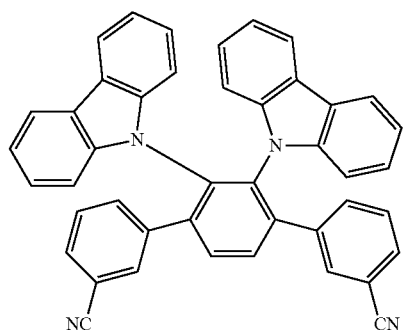
T-558
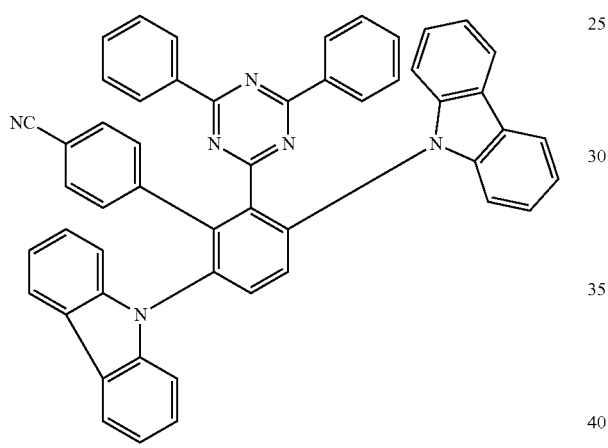
T-561
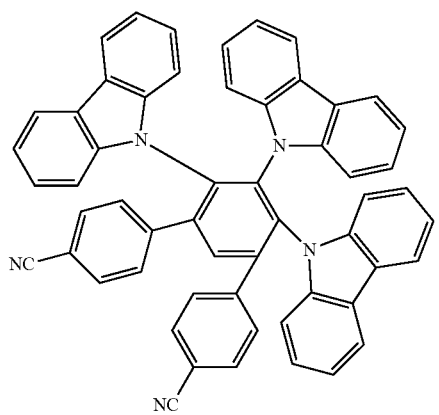
T-559
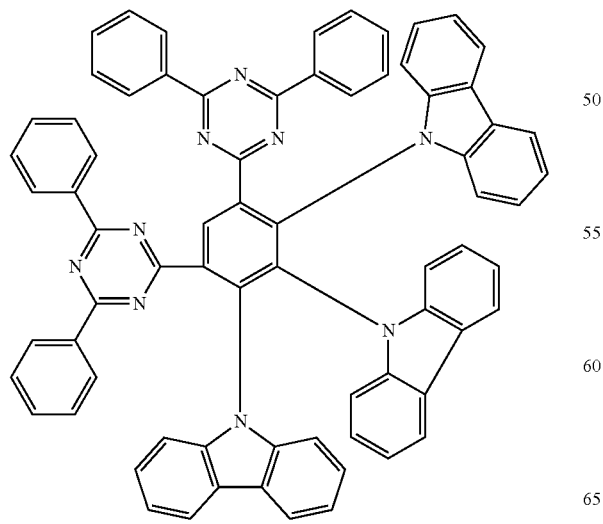
T-562
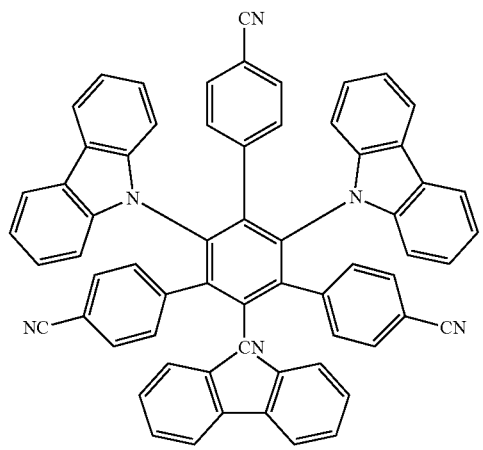

[Formula 76]
T-563
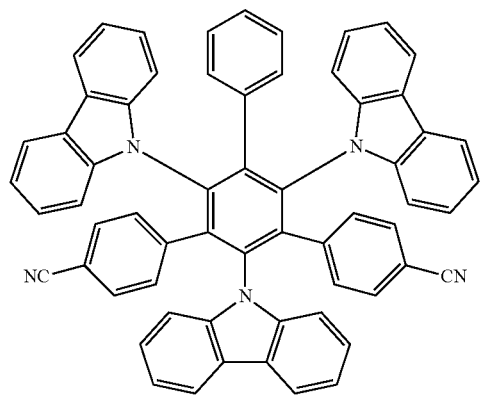
T-564
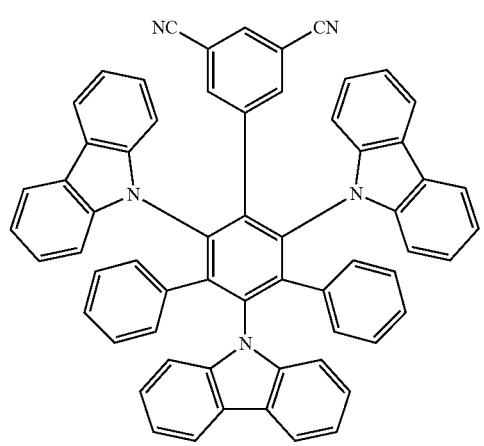
T-565
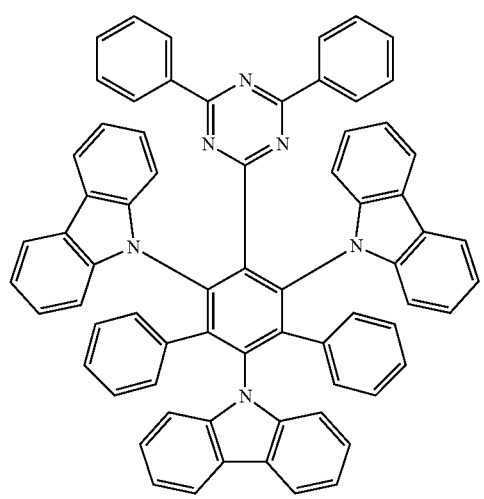
T-566
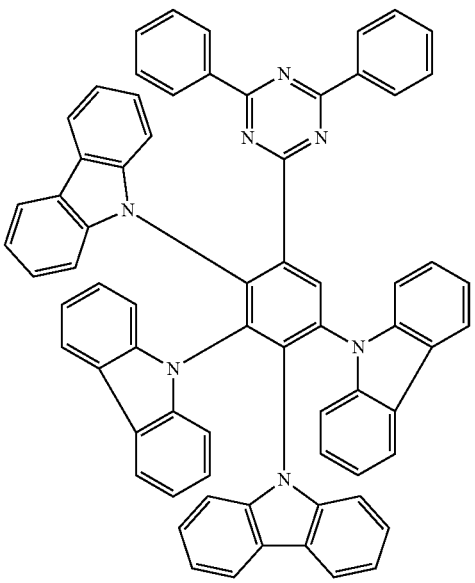
T-567
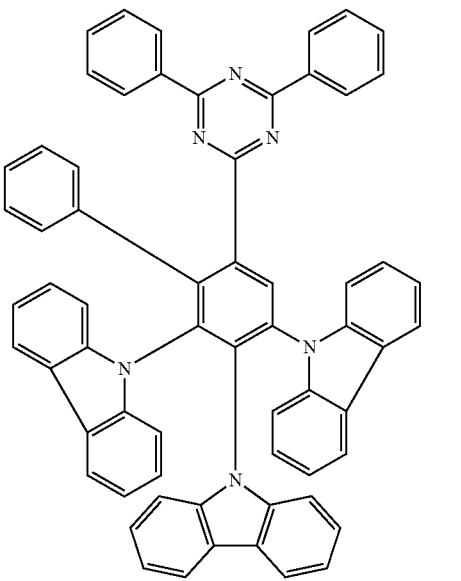

T-568
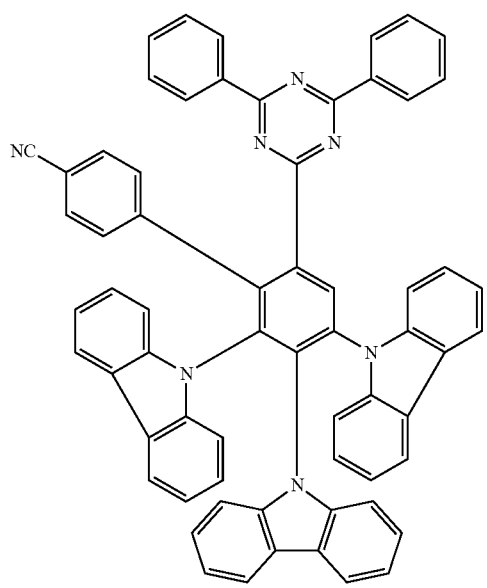
T-571
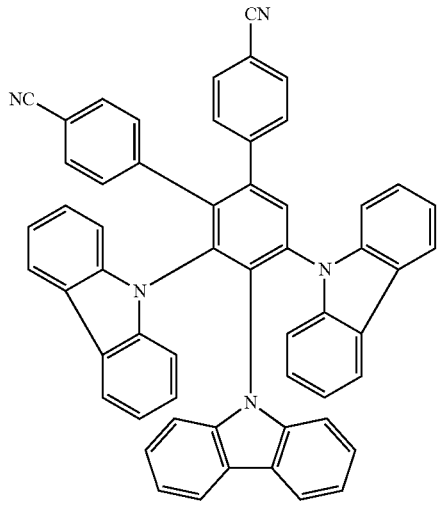
T-569
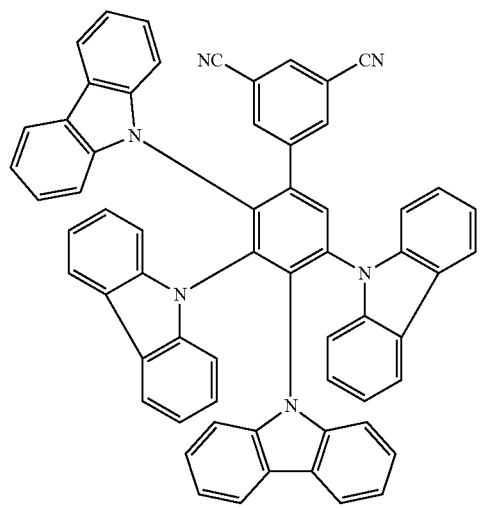
T-572
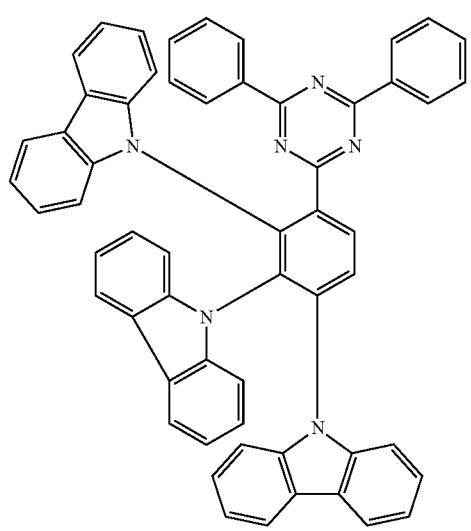
T-570
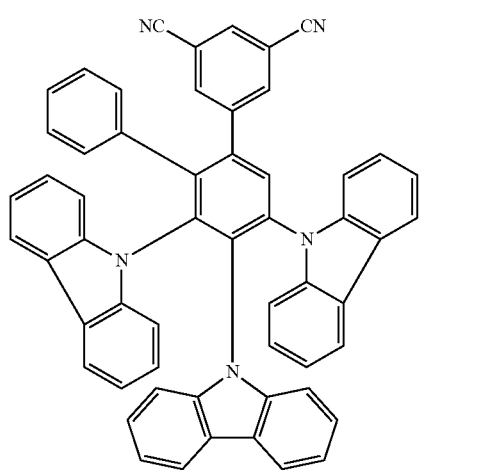
T-573
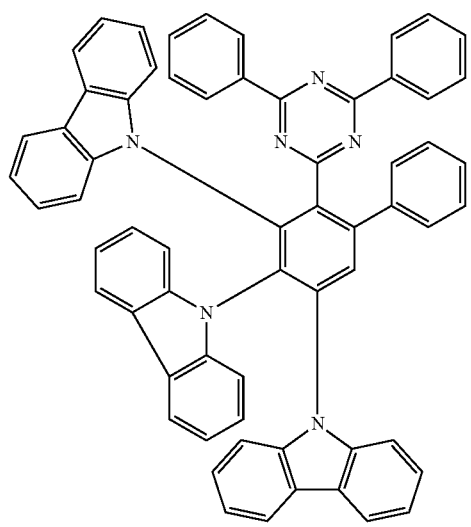

-continued

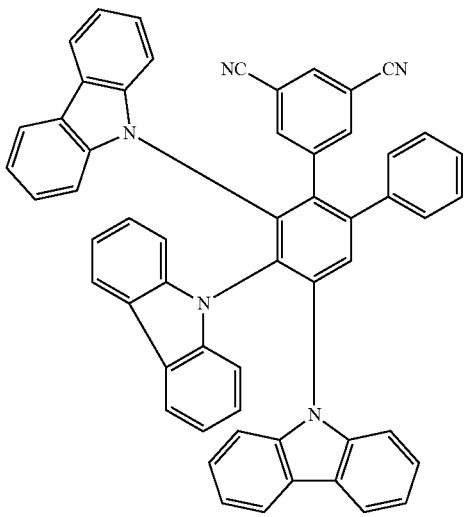

[Formula 77]

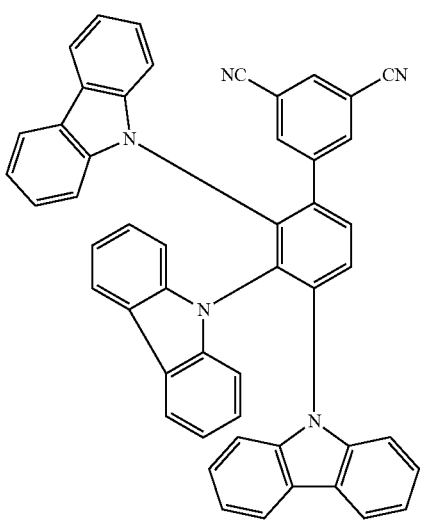

Of these compounds, materials having an absolute value of $\Delta E_{ST}$ of 0.50 eV or less may exhibit a TADF property (delayed fluorescence), that is, may emit delayed fluorescence. Exhibiting delayed fluorescence herein means that there are two or more components having different decay rates of fluorescence to be emitted when the fluorescence decay is measured. In general, slow-decay components often have a decay time of a sub-microsecond or more. However, the decay time, which depends on material, is not limited. The fluorescence decay can be generally measured as follows. A solution or thin film of a π-conjugated compound (luminescent compound) or a co-deposition film of a π-conjugated compound and a second component is irradiated with excited light under a nitrogen atmosphere to calculate the number of photons at a certain emission wavelength. At this time if there are two or more components having different decay rates of fluorescence to be emitted, the π-conjugated compound is considered to exhibit delayed fluorescence.

These compounds, which have a bipolar ability and comply with various energy levels, can be used not only as light-emitting hosts, but also used as compounds adapted for hole transport and electron transport. Thus, these compounds are not limited to use for the light-emitting layer, and may be used for the aforementioned hole injection layer, hole transport layer, electron blocking layer, hole blocking layer, electron transport layer, electron injection layer, and intermediate layer, and the like.

<Specific π-Conjugated Compound>

Of π-conjugated compounds of the present invention, an example of the specific π-conjugated compound having high emission efficiency even existing in the light-emitting layer of an organic EL element at a high concentration is a compound represented by the following general formula 201.

[Formula 78]

General formula 201

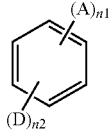

A in general formula 201, which is an electron-withdrawing group, represents an optionally substituted nitrogen-containing aromatic six-membered ring group. The nitrogen-containing aromatic six-membered ring in the "optionally substituted nitrogen-containing aromatic six-membered ring group" is a $C_{3-13}$, preferably $C_{3-5}$ electron-withdrawing nitrogen-containing aromatic six-membered ring. The nitrogen-containing aromatic six-membered ring may be a monocyclic compound or fused-ring compound. In the case where the nitrogen-containing aromatic six-membered ring is a fused-ring compound, its bonding arms protrude from the nitrogen-containing six-membered ring of the rings constituting the fused rings.

Examples of the nitrogen-containing aromatic six-membered ring include pyridine ring, pyridazine ring, pyrimidine ring, pyrazine ring, triazine ring, quinoline ring, isoquinoline ring, quinazoline ring, cinnoline ring, quinoxaline ring, phthalazine ring, pteridin ring, phenanthridine ring, and phenanthroline ring. Of these, pyridine ring, pyrimidine ring, pyrazine ring, and triazine ring are preferred. The nitrogen-containing aromatic six-membered ring may be the above two or more same or different nitrogen-containing aromatic six-membered rings connected.

Examples of the substituent that may be carried on the nitrogen-containing aromatic six-membered ring group include fluorine atom, cyano group, alkyl groups optionally substituted by a fluorine atom, optionally substituted aryl groups, and optionally substituted heteroaryl groups. The upper limit number of carbon atoms of the substituent that may be carried on the nitrogen-containing aromatic six-membered ring group may be, for example, 30, preferably 15.

The alkyl group in the "alkyl group optionally substituted by a fluorine atom" may be any of straight-chain, branched or cyclic groups, and, for example, may be a $C_{1-20}$ straight-chain or branched alkyl group or $C_{5-20}$ cyclic alkyl group. Examples of the alkyl group include methyl group, ethyl group, n-propyl group, isopropyl group, n-butyl group, s-butyl group, t-butyl group, n-pentyl group, neopentyl group, n-hexyl group, cyclohexyl group, 2-ethylhexyl group, n-heptyl group, n-octyl group, 2-hexyloctyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-icosyl group; and the alkyl group is preferably methyl group, ethyl group, isopropyl group, t-butyl group, cyclohexyl group, 2-ethylhexyl group, and 2-hexyloctyl group.

The aryl group in the "optionally substituted aryl group" is preferably a group derived from a $C_{6-24}$ aromatic hydrocarbon ring. Examples of the aromatic hydrocarbon ring include benzene ring, indene ring, naphthalene ring, azulene ring, fluorene ring, phenanthrene ring, anthracene ring, acenaphthylene ring, biphenylene ring, naphthacene ring, pyrene ring, pentalene ring, aceanthrylene ring, heptalene ring, triphenylene ring, as-indacene ring, chrysene ring, s-indacene ring, pleiadene ring, phenalene ring, fluoranthene ring, perylene ring, acephenanthrylene ring, biphenyl ring, terphenyl ring, and tetraphenyl ring. Of these, benzene ring, naphthalene ring, fluorene ring, phenanthrene ring, anthracene ring, biphenylene ring, chrysene ring, pyrene ring, triphenylene ring, chrysene ring, fluoranthene ring, perylene ring, biphenyl ring, and terphenyl ring are preferred. Examples of the substituent that may be carried on the aryl group include alkyl groups optionally substituted by a fluorine atom, alkoxy groups, cyano group, heteroaryl groups, aryloxy groups, a fluorine atom, and alkylsulfonyl groups.

The heteroaryl group in the "optionally substituted heteroaryl group" is a $C_{3-13}$, preferably $C_{3-5}$ heteroaryl group, and examples thereof include groups exemplified as the aforementioned nitrogen-containing aromatic six-membered ring groups and triazole groups. Examples of the substituent that may be carried on the heteroaryl group include alkyl groups optionally substituted by a fluorine atom, alkoxy groups, cyano group, aryl groups, aryloxy groups, and arylcarbonyl groups.

The optionally substituted nitrogen-containing aromatic six-membered ring group is preferably represented by general formula A-1 or A-2.

[Formula 79]

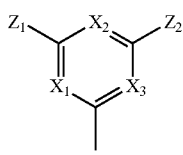

General formula A-1

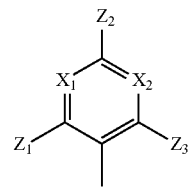

General formula A-2

$X_1$ to $X_3$ in general formula A-1 or A-2 are independently —CH or a nitrogen atom, and at least one of $X_1$ to $X_3$ represents a nitrogen atom. In the viewpoint of obtaining a satisfactory electron-withdrawing property, two or more of $X_1$ to $X_3$ are preferably nitrogen atoms.

$Z_1$ to $Z_3$ in general formula A-1 or A-2 are a hydrogen atom or have the same definition as the substituent that may be carried on the nitrogen-containing aromatic six-membered ring group of general formula 201. Of these, $Z_1$ to $Z_3$ are independently preferably a hydrogen atom, cyano group, optionally substituted aryl group, or optionally substituted heteroaryl group, more preferably an optionally substituted aryl group. $Z_1$ to $Z_3$ each may be the same or different.

n1 in general formula 201 represents an integer of 1 to 3. In the case where n1 is 2 or more, two or more A's each may be the same or different.

D in general formula 201 is an electron-donating group and represents an "optionally substituted amino group", "alkyl group" or "aryl group substituted by an electron-donating group".

Examples of the substituent in the "optionally substituted amino group" include optionally substituted aryl groups and optionally substituted heteroaryl groups. The upper limit number of carbon atoms of the substituent in the "optionally substituted amino group" may be, for example, 30, preferably 20. These substituents may be bonded to each other to form a ring or may be form no ring. From the viewpoint of easily achieving a satisfactory electron-donating property, these substituents preferably form a ring. The ring may be any of a five-membered ring, six-membered ring, and seven-membered ring, and is preferably a five-membered ring or six-membered ring. Atoms constituting the ring may further include a hetero atom other than a nitrogen atom (e.g., an oxygen atom, sulfur atom, or silicon atom).

The "alkyl group" has the same definition as the alkyl group in the "alkyl group optionally substituted by a fluorine atom" exemplified as the substituent that may be carried on the aforementioned nitrogen-containing aromatic six-membered ring group.

The aryl group in the "aryl group substituted by an electron-donating group" is similar to the aryl group in the "optionally substituted aryl group" exemplified as substituent that may be carried on the aforementioned nitrogen-containing aromatic six-membered ring group. Examples of the electron-donating group that may be carried on the aryl group include alkyl groups, alkoxy groups, and optionally substituted amino groups, and are preferably optionally substituted amino groups.

The alkyl group and optionally substituted amino group, as electron-donating groups, each have the same definition as the aforementioned alkyl group and optionally substituted amino group.

The alkoxy group as an electron-donating group may be any of straight-chain, branched or cyclic groups, and, for example, may be a $C_{1-20}$ straight-chain or branched alkoxy group or $C_{6-20}$ cyclic alkoxy group. Examples of the alkoxy group include methoxy group, ethoxy group, n-propoxy group, isopropoxy group, n-butoxy group, isobutoxy group, t-butoxy group, n-pentyloxy group, neopentyloxy group, n-hexyloxy group, cyclohexyloxy group, n-heptyloxy group, n-octyloxy group, 2-ethylhexyloxy group, nonyloxy group, decyloxy group, 3,7-dimethyloctyloxy group, n-undecyloxy group, n-dodecyloxy group, n-tridecyloxy group, n-tetradecyloxy group, 2-n-hexyl-n-octyloxy group, n-pentadecyloxy group, n-hexadecyloxy group, n-heptadecyloxy group, n-octadecyloxy group, n-nonadecyloxy group, and n-icosyloxy group, and the alkoxy group is preferably methoxy group, ethoxy group, isopropoxy group, t-butoxy group, cyclohexyloxy group, 2-ethylhexyloxy group, and 2-hexyloctyloxy group.

Of these, D in general formula 201 is preferably an optionally substituted amino group because its electron-donating property is high, and preferably a group represented by general formula D-1.

[Formula 80]

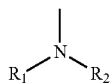

General formula D-1

$R_1$ and $R_2$ in general formula D-1 each represent an optionally substituted aryl group or optionally substituted heteroaryl group.

The optionally substituted aryl group has the same definition as the aforementioned "aryl group substituted by an electron-donating group".

The "heteroaryl group" in the optionally substituted heteroaryl group is a $C_{3-8}$ heteroaryl group, and examples thereof include benzothieno groups, benzofuryl groups, and pyridinyl groups. Examples of substituents that may be carried on the heteroaryl group include alkyl groups and optionally substituted amino groups.

$R_1$ and $R_2$ may be bonded to each other to form a ring or may be form no ring. From the viewpoint of easily achieving a satisfactory electron-donating property, these substituents preferably form a ring. The ring formed by bonding $R_1$ and $R_2$ to each other has the same definition as the ring formed by bonding the substituents to each other in the "optionally substituted amino group" represented by the aforementioned D.

Examples of the group represented by general formula D-1 include diphenylamino groups, dipyridylamino groups, an indole ring, carbazole ring, indoloindole ring, 9,10-dihydroacridine ring, phenoxazine ring, phenothiazine ring, indolocarbazole ring, benzofurylcarbazole ring, benzothienocarbazole ring, benzocarbazole ring, dibenzocarbazole ring, and azacarbazole ring, and groups derived from a diazacarbazole ring, benzofurylindole ring, or benzothienoindole ring.

n2 in general formula 201 represents 2 or 3, provided that at least two D's are each located in the ortho position. Accordingly, a plurality of electron-donating groups D's substituting the benzene ring become spatially adjacent, and the plurality of electron-donating groups can spatially resonate to stabilize the positive charge carried by the electron-donating moiety in an excited state. At least two D's each may be the same or different.

The π-conjugated compound represented by general formula 201 is preferably represented by any of the following general formulas 202 to 205.

[Formula 81]

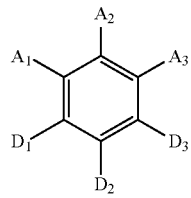

General formulas 202

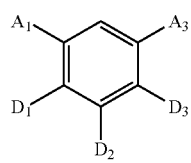

General formulas 203

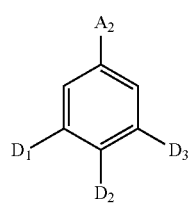

General formulas 204

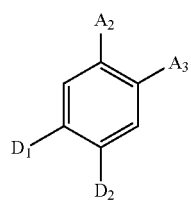

General formulas 205

$A_1$ to $A_3$ in general formulas 202 to 205 each have the same definition as A in general formula 201, and $D_1$ to $D_3$ in general formula 202 to 205 each have the same definition as D in general formula 201.

$A_1$ to $A_3$ each may be the same or different. In general formulas 202, 203, and 205, from the viewpoint of easily achieving resonance stabilization in the excited state, two or more of $A_1$ to $A_3$ is preferably the same. $D_1$ to $D_3$ each may be the same or different. From the viewpoint of easily achieving resonance stabilization in the excited state, two or more of $D_1$ to $D_3$ is preferably the same.

Of these, from the viewpoint of allowing the HOMO and LUMO to be separately localized to easily achieve the TADF property, the compound represented by general formula 204 is preferred.

The π-conjugated compound represented by general formula 201 is more preferably represented by any of the following general formulas 206 to 208.

[Formula 82]

General formula 206

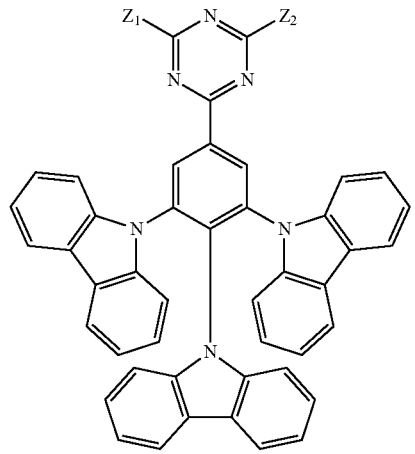

-continued

General formula 207

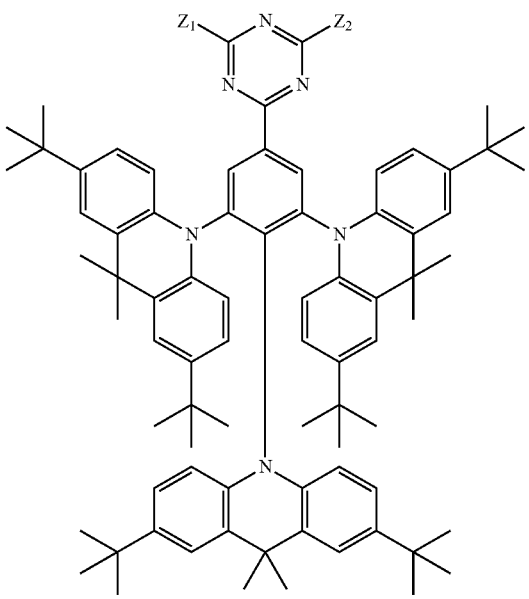

$Z_1$ and $Z_2$ in general formulas 206 and 207 each have the same definition as $Z_1$ to $Z_3$ in general formula A-1 or A-2 and are preferably an optionally substituted aryl group. Examples of combinations of $Z_1$ and $Z_2$ include the following.

| | Exemplified compound number | |
|---|---|---|
| [Formula 83] | (✳)-$Z_1$ | (✳)-$Z_2$ |
| C-1 | (✳)–C₆H₄–CH₃ (o-tolyl) | (✳)–C₆H₄–CH₃ (o-tolyl) |
| C-2 | (✳)–C₆H₃(CH₃)₂ (3,4-dimethylphenyl) | (✳)–C₆H₃(CH₃)₂ (3,4-dimethylphenyl) |
| C-3 | (✳)–2,4,6-trimethylphenyl (mesityl) | (✳)–2,4,6-trimethylphenyl (mesityl) |

-continued
| Exemplified compound number | | |
|---|---|---|
| C-4 | 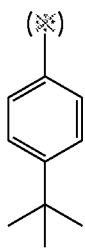 | 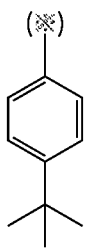 |
| C-5 | 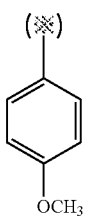 | 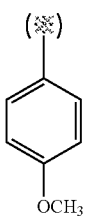 |
| C-6 | 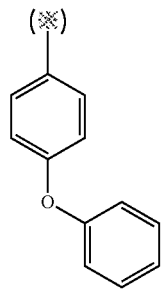 | 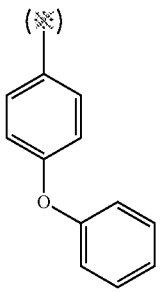 |
| C-7 | 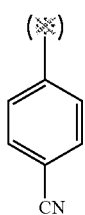 | 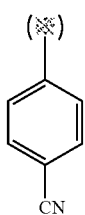 |
| C-8 | 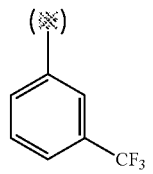 | 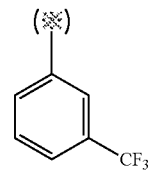 |
| C-9 | 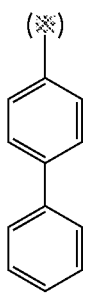 | 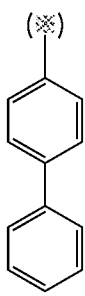 |

-continued
| Exemplified compound number | | |
|---|---|---|
| C-10 | 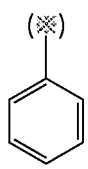 | 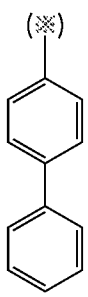 |
| C-11 | 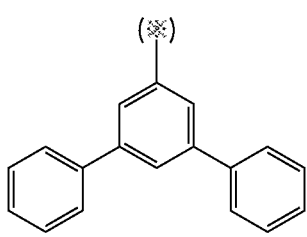 | 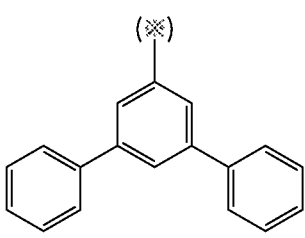 |
| C-12 | 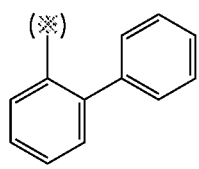 | 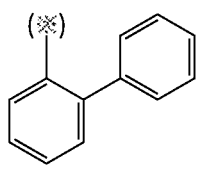 |
| C-13 | 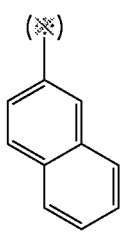 | 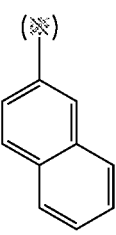 |
| C-14 | 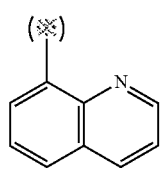 | 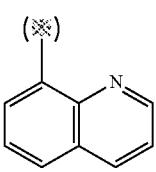 |
| C-15 | 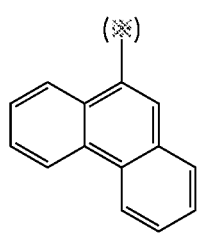 | 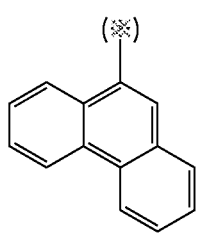 |

-continued
| Exemplified compound number |
|---|
C-16 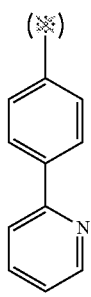 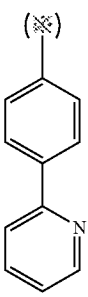
C-17 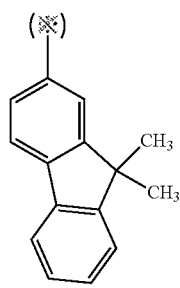 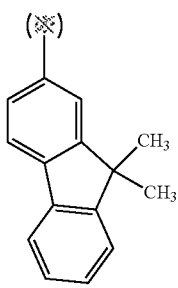
C-18 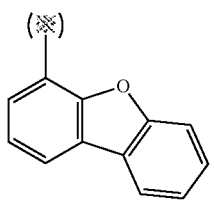 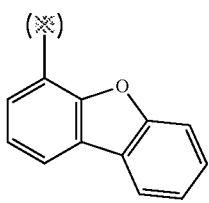
C-19 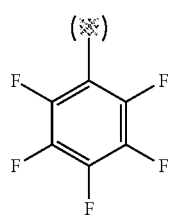 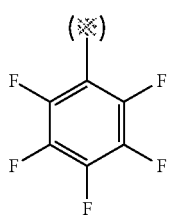
C-20 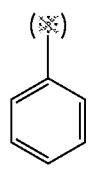 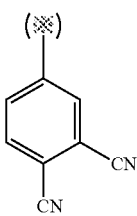
C-21 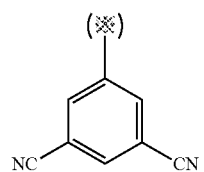 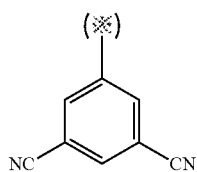

-continued
| Exemplified compound number | | |
|---|---|---|
| C-22 | 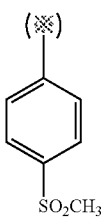 | 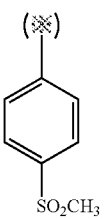 |
| C-23 | 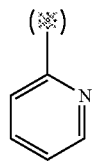 | 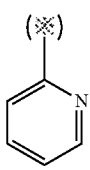 |
| C-24 | 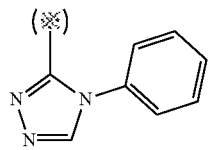 | 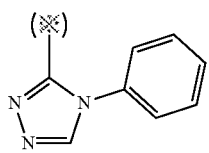 |
| C-25 | 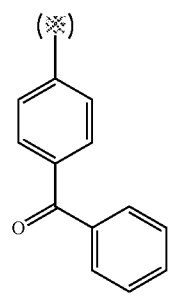 | 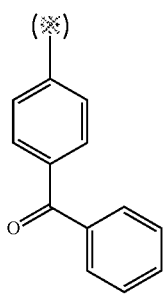 |
| C-26 | 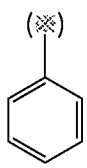 | 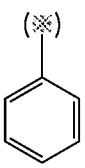 |

[Formula 88]

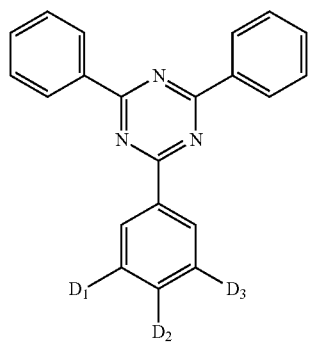

General formula 208

$D_1$ to $D_3$ in general formula 208 are preferably an optionally substituted amino group. The optionally substituted amino group has the same definition as the "optionally substituted amino group" represented by D in general formula 201. Examples of combinations of $D_1$ and $D_3$ include the following.

| Exemplified compound number | (※)—$D_1$ | (※)—$D_2$ | (※)—$D_3$ |
|---|---|---|---|

[Formula 89]

| | | | |
|---|---|---|---|
| B-1 | 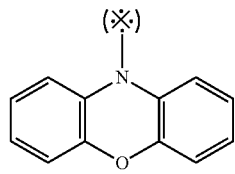 | 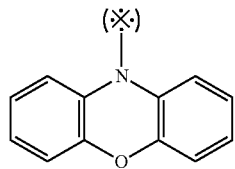 | 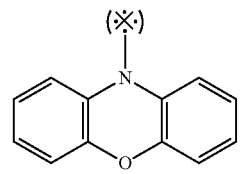 |
| B-2 | 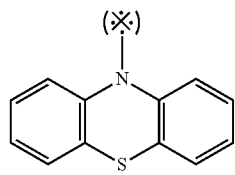 | 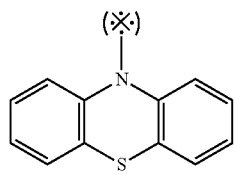 | 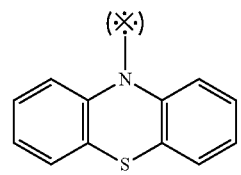 |
| B-3 | 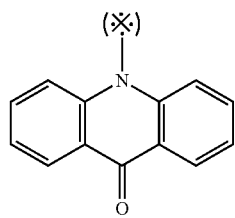 | 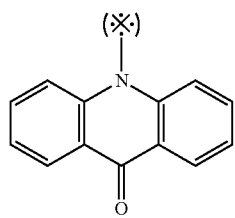 | 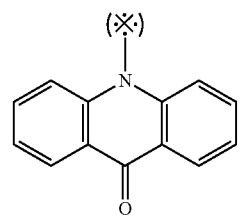 |
| B-4 | 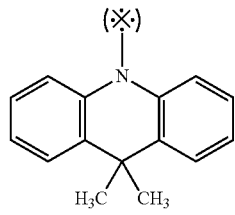 | 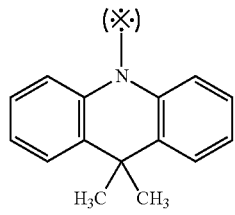 | 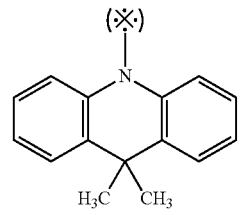 |

| Exemplified compound number | (※)—D₁ | (※)—D₂ | (※)—D₃ |
|---|---|---|---|
| B-5 | 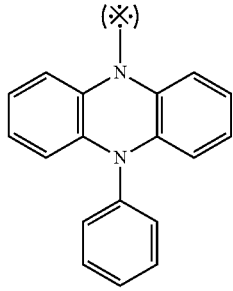 | 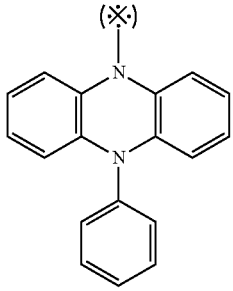 | 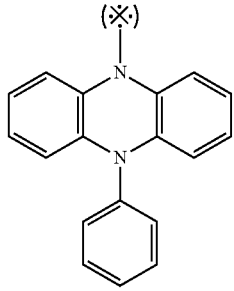 |ує
| [Formula 90] | | | |
| B-6 | 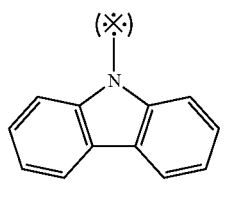 | 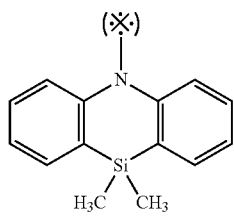 | 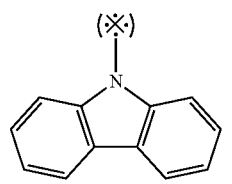 |
| B-7 | 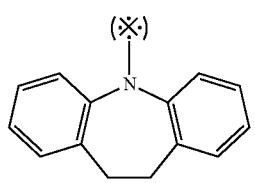 | 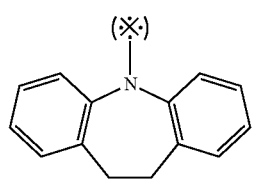 | 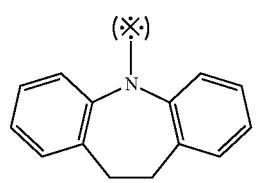 |
| B-8 | 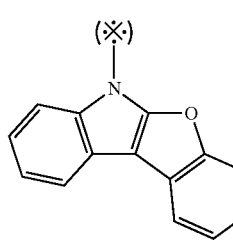 | 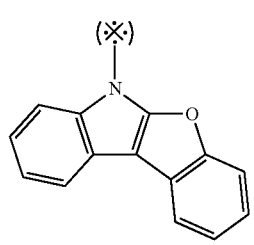 | 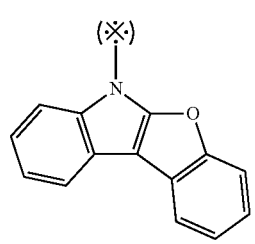 |
| B-9 | 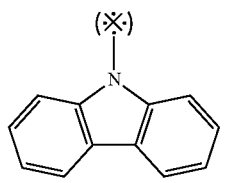 | 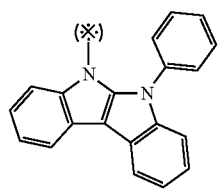 | 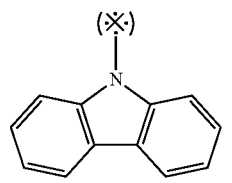 |
| B-10 | 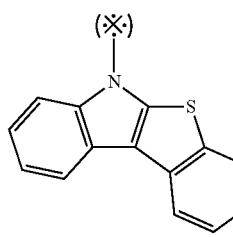 | 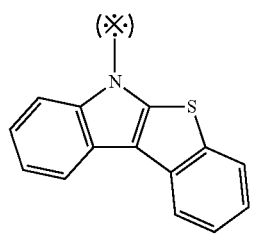 | 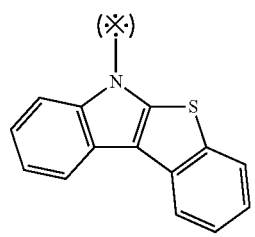 |

| Exemplified compound number | (※)—D₁ | (※)—D₂ | (※)—D₃ |
|---|---|---|---|
| [Formula 91] | | | |
| B-11 | 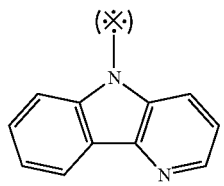 | 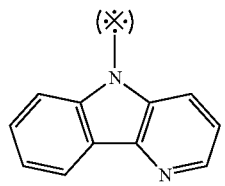 | 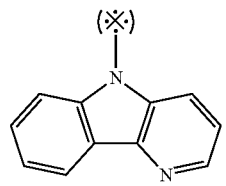 |
| B-12 | 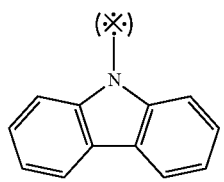 | 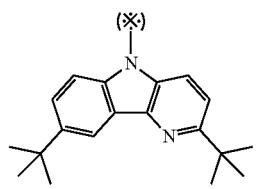 | 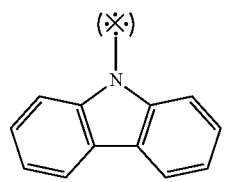 |
| B-13 | 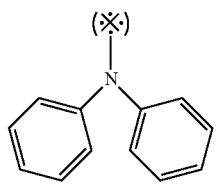 | 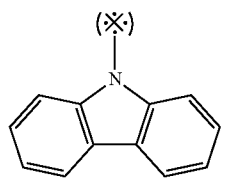 | 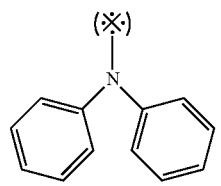 |
| B-14 | 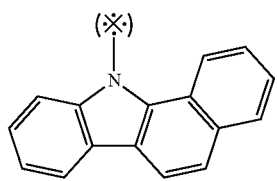 | 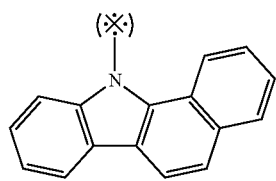 | 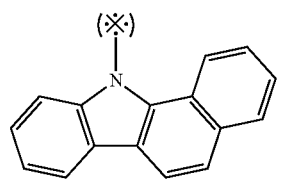 |
| B-15 | 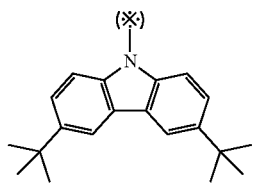 | 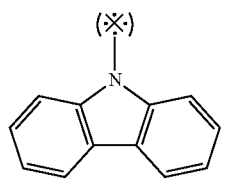 | 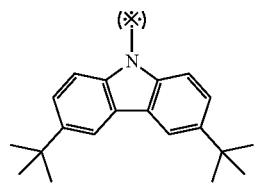 |
| [Formula 92] | | | |
| B-16 | 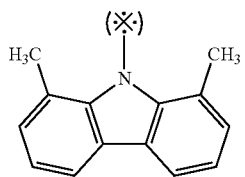 | 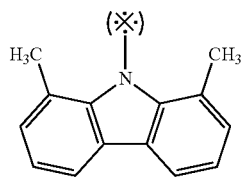 | 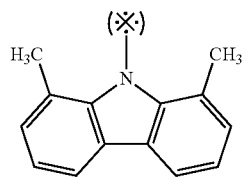 |

-continued
| Exemplified compound number | (※)—D₁ | (※)—D₂ | (※)—D₃ |
|---|---|---|---|
| B-17 | | | |
| B-18 | | | |
| B-19 | | | |
| B-20 | | | |
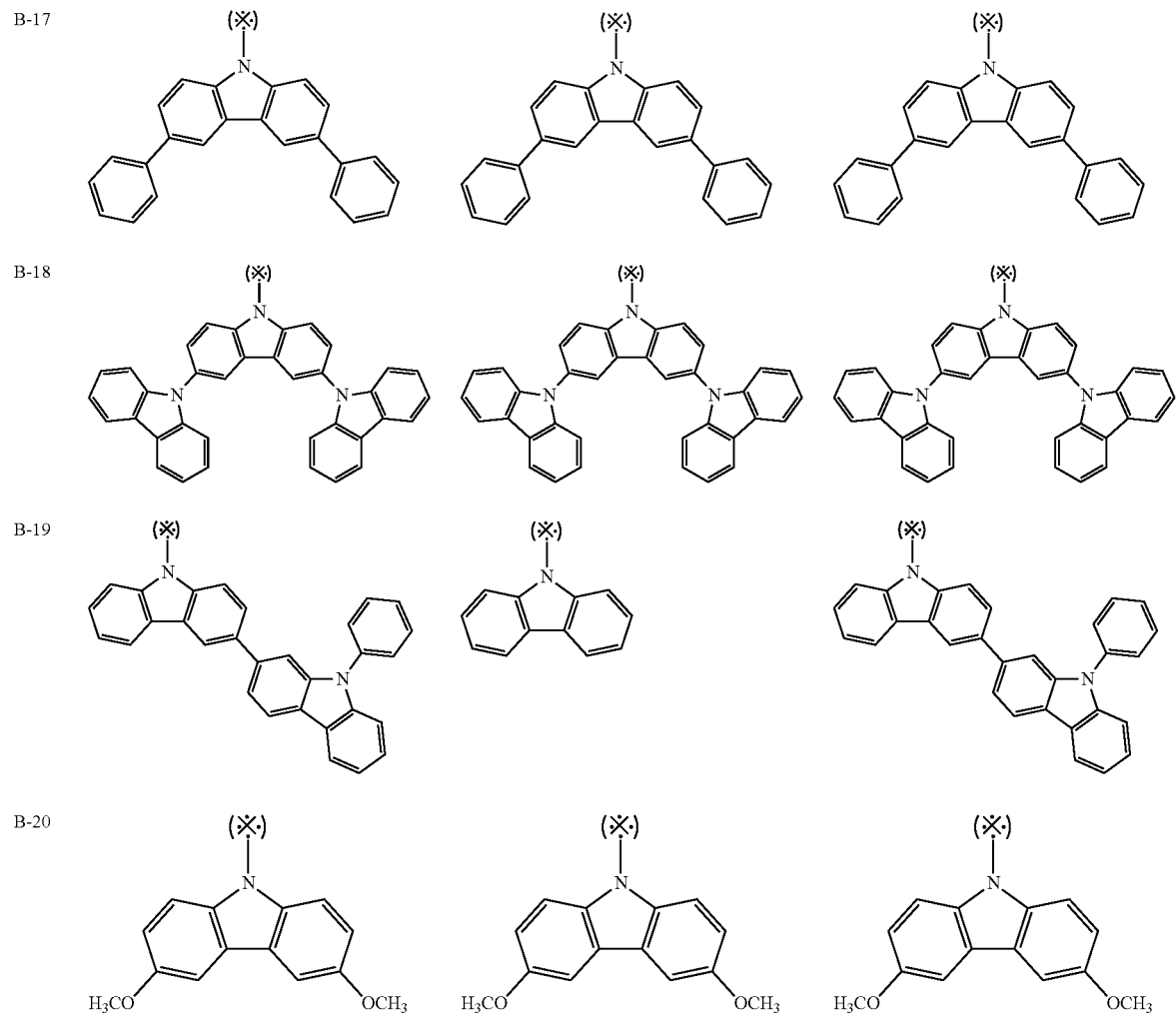
[Formula 93]
| B-21 | | | |
|---|---|---|---|
| B-22 | | | |
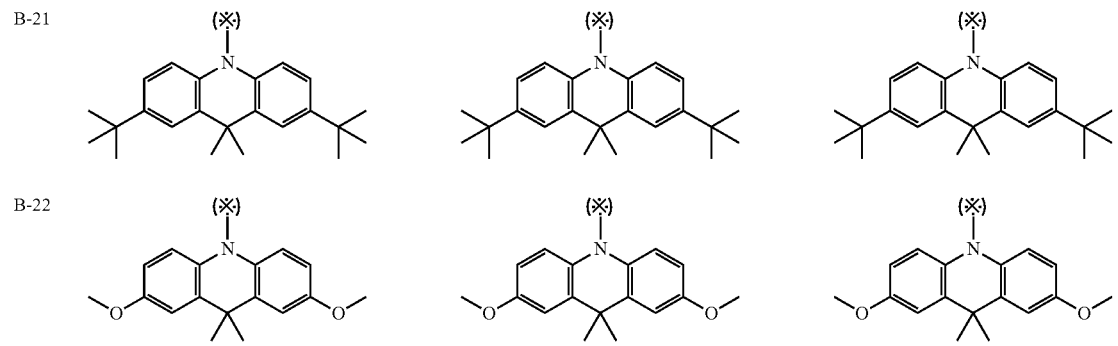

-continued
| Exemplified compound number | (※)—D₁ | (※)—D₂ | (※)—D₃ |
|---|---|---|---|
| B-23 | 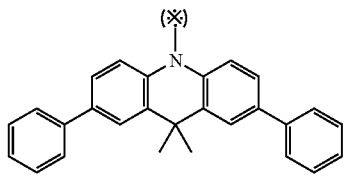 | 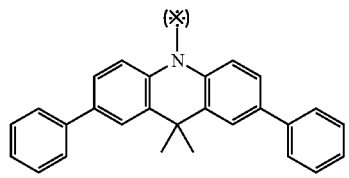 | 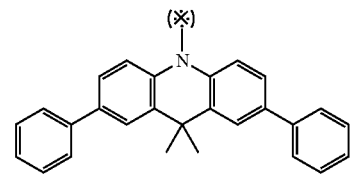 |
| B-24 | 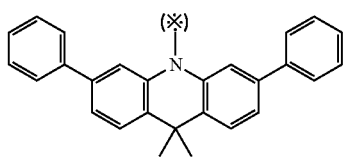 | 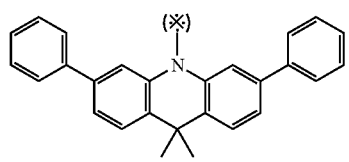 | 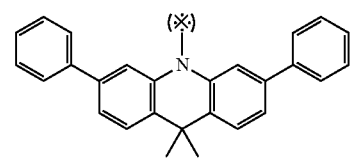 |
| B-25 | 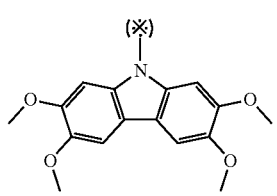 | 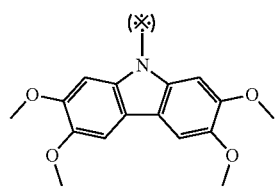 | 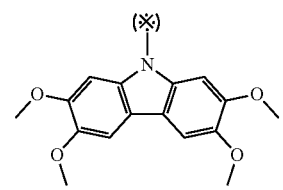 |
| B-26 | 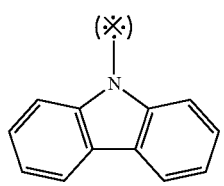 | 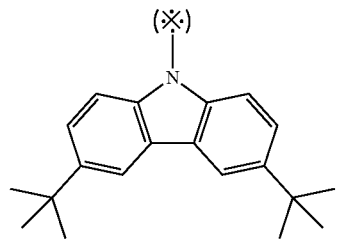 | 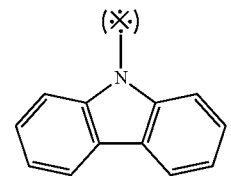 |

Example of the π-conjugated compound represented by general formula 201 include the following.
[Formula 94]
Compound 1
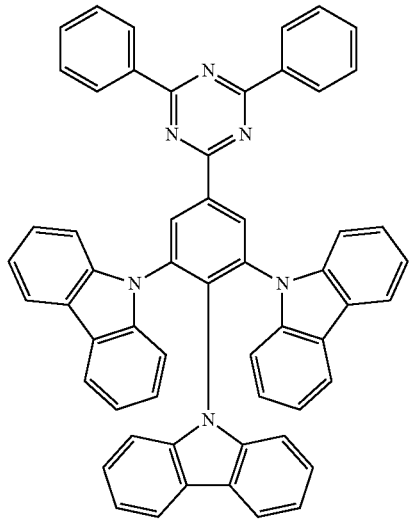
Compound 2
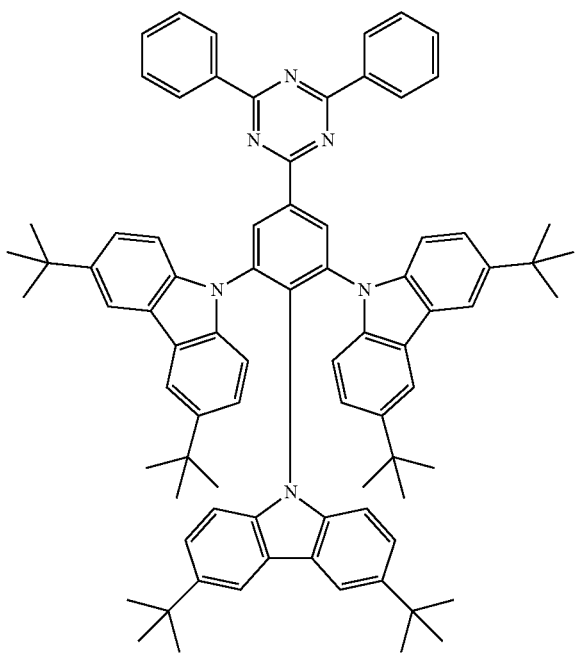
Compound 3
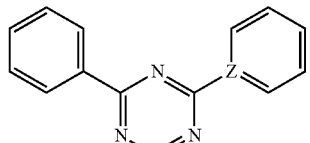
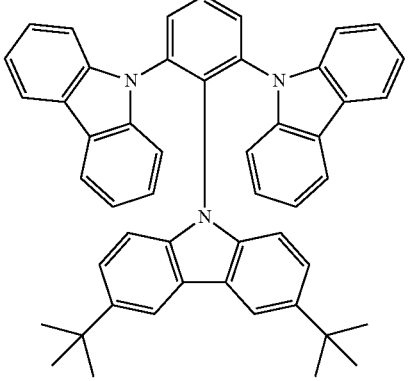
Compound 4
Compound 5
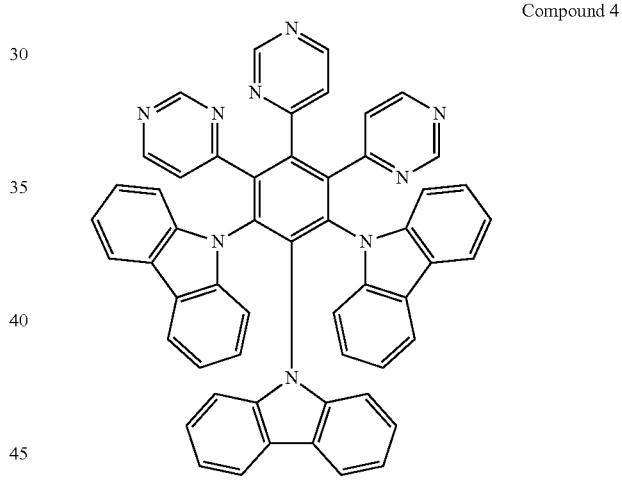

Compound 6

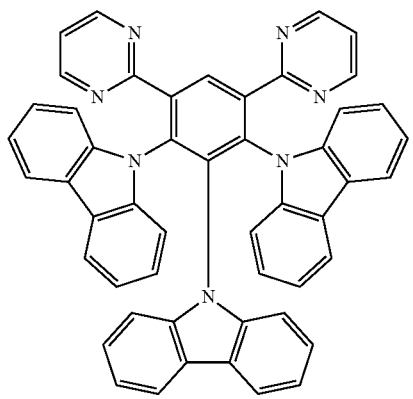

[Formula 95]

Compound 7

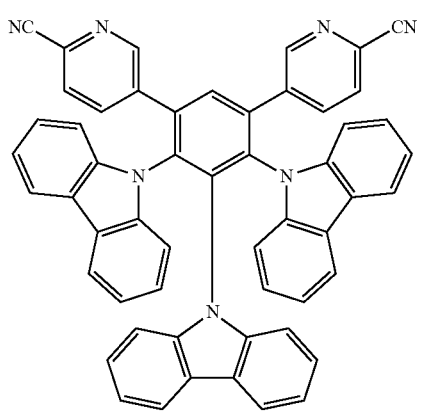

Compound 8

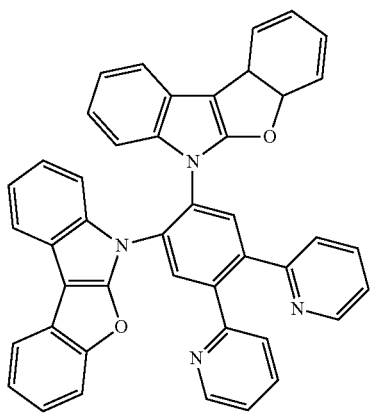

Compound 9

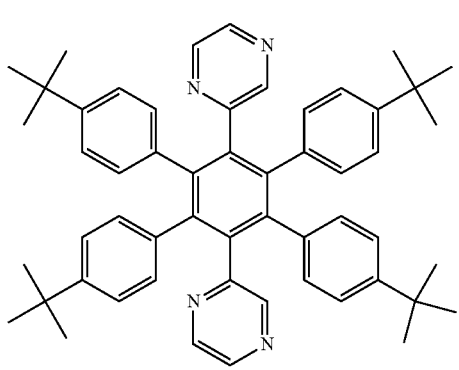

Compound 10

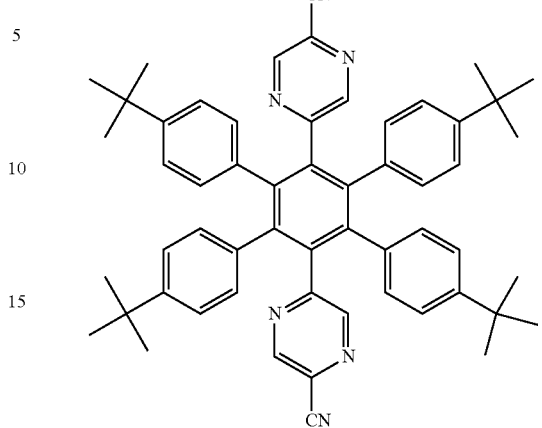

Compound 11

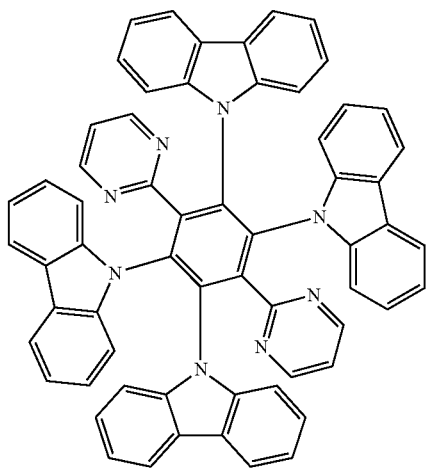

The absolute value of the energy difference between the lowest singlet excited level and the lowest triplet excited level of the π-conjugated compound represented by general formula 201 ($\Delta E_{ST}$) is preferably 0.50 eV or less. The π-conjugated compound like this may exhibit a satisfactory TADF property.

The π-conjugated compound represented by general formula 201 is preferably contained in organic electroluminescent elements, the element material or the light-emitting thin film.

The π-conjugated compound represented by general formula 201 is preferably included in the light-emitting layer of the organic electroluminescent elements. In other words, from the viewpoint of a high light-emitting property, the light-emitting layer is preferably substantially constituted by the π-conjugated compound represented by general formula 201 or substantially constituted by the π-conjugated compound represented by general formula 201 and a guest compound.

Organic electroluminescent elements containing the π-conjugated compound represented by general formula 201 also may be suitably included in lighting apparatuses and display apparatuses.

Furthermore, the π-conjugated compound represented by general formula 201, which has a bipolar ability and complies with various energy levels, can be used not only as a host compound, but also used as a compound suitable for hole transport and electron transport. Thus, the compound is not limited to use in the light-emitting layer, and may be used for the aforementioned hole injection layer, hole transport layer, electron blocking layer, hole blocking layer, electron transport layer, electron injection layer, intermediate layer or the like.

<Synthesis Method>

The π-conjugated compound represented by the above general formula 1 (including the compound represented by general formula 201) can be synthesized with reference to the methods described in, for example, WO 2010/113755, Organic Letters, 2002, 4, 1783-1785, and Angew. Chem. Int. Ed. 2010, 49, 2014-2017, or the methods described in the references described in these literatures.

Subsequently, now will be described an emission mode of organic EL and light-emitting materials, which relate to the technical concept of the present invention.

<Emission Mode of Organic EL>

Organic EL emits light based on either the following two emission modes: "phosphorescence," which occurs during transfer of excitons from the triplet excited state to the ground state, and "fluorescence," which occurs during transfer of excitons from the singlet excited state to the ground state.

In the case of electric-field excitation as in organic EL, triplet excitons are generated at a probability of 75%, and singlet excitons are generated at a probability of 25%. Thus, a phosphorescent mode exhibits emission efficiency higher than that of the fluorescent mode, and is excellent for reducing power consumption.

Meanwhile, also in the case of fluorescence, triplet excitons are generated at a probability of 75%, and their energy is usually converted into only heat due to non-radiative deactivation. By increasing the density of such triplet excitons, one singlet exciton is generated from two triplet excitons to thereby improve the emission efficiency. A mode has been found in which this mechanism, called a triplet-triplet annihilation (TTA) (also called triplet-triplet fusion and abbreviated as TTF), is employed.

Adachi, et al. have more recently found that a reduced energy gap between the singlet excited state and the triplet excited state causes reverse intersystem crossing from the triplet excited state, which has a lower energy level, to the singlet excited state depending on the Joule heat during emission and/or the ambient temperature around a light-emitting element, resulting in a phenomenon that achieves fluorescence at substantially 100% (referred to as "thermally activated delayed fluorescence (TADF)"). They have also found a fluorescent substance that achieves this phenomenon (see NPL 1 and the like).

<Phosphorescence-Emitting Compound>

Theoretically, phosphorescence has emission efficiency three times higher than that of fluorescence as described above. Unfortunately, energy deactivation from the triplet excited state to the singlet ground state (i.e., phosphorescence) is a forbidden transition and the intersystem crossing from the singlet excited state to the triplet excited state is also a forbidden transition. Hence, the rate constant of such a transition is generally small, in other words, the transition is less likely to occur. Thus, the lifetime of excitons is on the order of milliseconds to seconds, and intended emission is difficult to achieve.

In the case of emission of a complex containing a heavy metal, such as iridium or platinum, the rate constant of the aforementioned forbidden transition increases by three or more orders of magnitude by the heavy atom effect of the central metal, and a phosphorescent quantum efficiency of 100% may be achieved depending on the selection of a ligand.

Unfortunately, such ideal emission requires the use of a noble metal called "a platinum group metal", such as iridium, palladium, or platinum, which is a rare metal, and the use of large amounts of rare metals may cause industrially significant problems on the reserves and price of the metals.

<Fluorescence-Emitting Compound>

Unlike the phosphorescence-emitting compound, a common fluorescence-emitting compound is not necessarily a heavy metal complex, and may be an organic compound composed of a combination of common elements, such as carbon, oxygen, nitrogen, and hydrogen. In such a fluorescent compound, other non-metal elements, such as phosphorus, sulfur, or silicon can be used, and a complex of a typical metal, such as aluminum or zinc can be employed. A wide variety of such elements may be used without substantial limitation.

Unfortunately, with a conventional fluorescent compound, in which only 25% of excitons is used for light emission as aforementioned, highly effective emission phosphorescence cannot be anticipated.

<Delayed Fluorescent Compound>

[Excited Triplet-Triplet Annihilation (TTA) Delayed Fluorescent Compound]

An emission mode utilizing delayed fluorescence has emerged for solving the problems involved in a fluorescence-emitting compound. The TTA mode, which is based on collision between triplet excitons, is described by the general formula as follows. That is, the TTA mode is advantageous in that a portion of triplet excitons, the energy of which would otherwise be converted into only heat by non-radiative deactivation, undergo reverse intersystem crossing, to generate singlet excitons that can contribute to luminescence. In an actual organic EL element, the TTA mode can achieve an external extraction quantum efficiency twice that achieved in a conventional fluorescent element.

General formula: $T^*+T^* \rightarrow S^*+S$ wherein, T* represents a triplet exciton, S* represents a singlet exciton, and S represents a molecule in the ground state.

Unfortunately, the TTA mode fails to achieve 100% internal quantum efficiency in principle because two triplet excitons generate only one singlet exciton that contributes to luminescence, also as illustrated in the aforementioned formula.

[Thermally Activated Delayed Fluorescent (TADF) Compound]

The TADF mode, which is another highly efficient fluorescent mode, can solve problems involved in the TTA mode.

The fluorescence-emitting compound is advantageous in that the compound can be molecularly designed without limitation, as described above. In other words, of molecularly designed compounds, some compounds exhibit an extremely small difference between the energy level of a triplet excited state and the energy level of a singlet excited state.

Such a compound, although having no heavy atom in the molecule, undergoes reverse intersystem crossing from the triplet excited state to the singlet excited state, which cannot normally occur, because of small ΔEst. Furthermore, since the rate constant of deactivation from the singlet excited state to the ground state (i.e., fluorescence) is extremely large, the transfer of triplet excitons to the ground state via the singlet excited state with emission of fluorescence is kinetically more advantageous than the transfer of the triplet excitons to the ground state with thermal deactivation (non-radiative deactivation). Thus, in the TADF mode, 100% fluorescence can be theoretically achieved.

<Molecular Designing Idea Concerning $\Delta E_{ST}$>

A molecular designing idea to reduce the $\Delta Est$ will be described.

In order to reduce the value of $\Delta Est$, in principle, reducing the spatial overlaps of the highest occupied molecular orbital (HOMO) and the lowest unoccupied molecular orbital (LUMO) in the molecule is most effective.

It is known that in the electronic orbitals of the molecule, the HOMO has a distribution to an electron donating position and the LUMO has a distribution to an electron withdrawing position, in general. By introducing an electron donating skeleton and electron withdrawing skeleton in the molecule, it is possible to keep apart the positions in which the HOMO and the LUMO exist.

In "An advanced stage of organic optoelectronics with the aim of commercialization" OYO BUTURI Vol. 82, No. 6, 2013, for example, by introducing an electron withdrawing skeleton such as a cyano group, a triazine group or the like, and an electron donating skeleton such as a carbazole group, a diphenylamino group or the like, the LUMO and HOMO are respectively made localized.

In addition, it is also effective to reduce the molecular structure change between the ground state and the triplet excited state of the compound. As a method of reducing the structure change, it is effective to allow a compound to be stiff. Stiffness referred to herein means that freely movable portions in the molecule are not abundant such as by prevention of a free rotation of the bond between the rings in the molecule, or by introduction of a condensed ring having a large π-conjugate plane, for example. In particular, by making the portion participating in the light emission stiffer, it is possible to reduce the molecular structure change in the excited state.

<Common Problem Possessed by TADF Compound>

A TADF compound possesses a variety of problems arisen from the aspects of its light emission mechanism and its molecular structure. Some common problems possessed by a TADF compound will be described in the following.

In a TADF compound, it is required to keep apart the portion in which the HOMO exists and the portion in which the LUMO exist as much as possible in order to reduce $\Delta Est$. For this reason, the electronic state of the molecule becomes almost near the donor/acceptor intramolecular CT state in which the HOMO portion and the LUMO portion are separated (intramolecular charge transfer state).

When a plurality of such molecules exists, bringing the donor portion in one molecule and the acceptor portion in other molecule close to each other achieves their stabilization. Such a stabilized condition is formed not only with two molecules but also can be formed with a plurality of molecules, such as three or five molecules. As a result, there are produced a variety of stabilized conditions having a broad distribution. The shape of absorption spectrum or the emission spectrum will be broad. Further, even if a multiple molecular aggregation of more than two molecules is not formed, there may be formed a variety of existing conditions having different interaction directions, angles or the like of two molecules. Thus, basically, the shape of absorption spectrum or the emission spectrum will be broad.

When the emission spectrum becomes broad, it will generate two major problems. One is a problem of decreasing the color purity of the emission color. This is not so significant when the compound is applied to an illumination application. However, when the compound is used for an electronic display application, the color reproduction region becomes small, and the color reproduction of pure colors will become decreased. As a result, it is difficult to actually apply the compound to a commercial product.

Another problem is the shortened wavelength of the rising wavelength in the short wavelength side of the emission spectrum (referred to as a "fluorescent zero-zero band"). That is, the $S_1$ level becomes high (becoming higher energy level of the lowest excited singlet energy).

When the wavelength of the fluorescent zero-zero band becomes shortened, the wavelength of the phosphorescent zero-zero band derived from $T_1$ which has lower energy than $S_1$ will naturally become shortened (increase in the $T_1$ level). Therefore, the host compound is required to have a high $S_1$ level and a high $T_1$ level in order to prevent the reverse energy transfer from the dopant.

This is an extremely major problem. A host compound basically made of an organic compound will take plural active and unstable chemical species conditions such as a cationic radical state, an anionic radical state, and an excited state in an organic EL element. These chemical species can be made existed in a relatively stable condition by expanding a π-conjugate system in the molecule.

However, in order to impart a high $S_1$ level and a high $T_1$ level to a molecule, the π-conjugate system in the molecule has to be reduced or cut. This makes it difficult to achieve stability at the same time. As a result, the lifetime of the light emission element becomes shorten.

Further, in a TADF compound containing no heavy metal, the deactivation transition from the triplet excited state to the ground state is forbidden transition. The presence time at the triplet excited state (exciton lifetime) is extremely long such as in an order of several hundred microseconds to milliseconds. Therefore, even if the $T_1$ energy level of the host compound is higher than that of the fluorescence-emitting compound, the probability of a reverse energy transfer from the triplet excited state of the fluorescence-emitting compound to the host compound will be increased due to the long presence time. As a result, an originally intended reverse intersystem crossing from the triplet excited state to the singlet excited state of the TADF compound does not occur sufficiently. Instead, an undesirable reverse energy transfer to the host compound mainly occurs to result in failing to obtain sufficient emission efficiency.

In order to solve the above-described problem, it is required to sharpen the shape of an emission spectrum of the TADF compound and to decrease the difference between the emission maximum wavelength and the rising wavelength of the emission spectrum. This can be achieved basically by reducing the change of the molecular structure of the singlet excited state and the triplet excited state.

Further, in order to prevent the reverse energy transfer to the host compound, it is effective to shorten the presence time of the triplet excited state of the TADF compound (exciton lifetime). In order to realize this, it is possible to solve the problem by reducing the molecular structure change between the ground state and the triplet excited state; introducing a suitable substituent or element to loosen the forbidden transition and the like.

The π-conjugated compound of the present invention (the compound represented by general formula 1) includes a benzene ring, and an electron-withdrawing group A and an electron-donating group D substituting the benzene ring. Any of "an electron-donating group D and an electron-donating group D", "an electron-withdrawing group A and an electron-withdrawing group A", and "an electron-withdrawing group A and an electron-donating group D" is used as at least one combination in the ortho position substituting the benzene ring.

Two or more electron-donating groups (or two or more electron-withdrawing groups A's) substitute the benzene ring at the ortho position, that is, are "adjacent to each other in space". Then, a plurality of electron-donating groups (or electron-withdrawing groups) can spatially resonate to stabilize the positive charge carried by the electron-donating moiety (or a negative charge carried by the electron-withdrawing moiety) in an excited state. Thus, it is conceived that the excited state is stabilized and non-radiative deactivation is inhibited to thereby enable the emission efficiency to be improved.

When an electron-withdrawing group A and an electron-donating group D are located in the ortho position of the benzene ring, the electron-donating group D and the electron-withdrawing group A are "spatially adjacent to each other". Accordingly, it is conceived that the emission efficiency is improved not because a CT-type excited state is formed via bonding from the electron-donating group D to the electron-withdrawing group A but because a CT-type excited state can be formed between the electron-donating group D and the electron-withdrawing group A extremely vicinally located to thereby stabilize the CT-type excited state.

Furthermore, in any aspects, since the electron-withdrawing group A and the electron-donating group D interact with each other not via through-bond coupling but via through-space coupling, it is conceived that lengthening of wavelengths in absorption spectrum or emission spectrum can be inhibited.

In particular, in the above specific π-conjugated compound (compound represented by general formula 201) including a benzene ring, and an electron-withdrawing group A and a plurality of electron-donating groups D's substituting the benzene ring, the plurality of electron-donating groups D's are allowed to substitute the benzene ring in the ortho position. As a result, the intermolecular interaction is unlikely to occur, the non-radiative deactivation is inhibited, and the emission efficiency can be improved. In this manner, the specific π-conjugated compound has high emission efficiency even when existing singly in the light-emitting layer, and thus a host compound conventionally required is no longer required.

In the specific π-conjugated compound, as the electron-withdrawing group A substituting the benzene ring, a "nitrogen-containing aromatic six-membered ring" is employed to enable high electron transportability to be achieved.

In addition, in the specific π-conjugated compound represented by general formula 201, the plurality of electron-donating groups D's are adjacent to each other. Thus, not interaction via molecule chains, but interaction via space is likely to occur. It is conceived that this interaction also can inhibit lengthening of wavelengths in absorption spectrum or emission spectrum.

Various measuring methods in respect of the π-conjugated compound according to the present invention will be described hereinafter.

[Electron Density Distribution]

In the π-conjugated compound according to the present invention, the HOMO and the LUMO are preferably substantially separated in the molecule, from the viewpoint of reducing $\Delta E_{ST}$. The distribution of the HOMO and the LUMO can be determined from the electron density distribution when the structure is optimized obtained by molecular orbital calculation.

The structure optimization and calculation of the electron density distribution by molecular orbital calculation of the π-conjugated compound in the present invention can be carried out by using, as a calculation technique, software for molecular orbital calculation including B3LYP as a functional and 6-31G (d) as a basis function. The software is not particularly limited, and the distribution can be determined similarly by using any software.

In the present invention, Gaussian 09 available from Gaussian Inc., USA (Revision C. 01, M. J. Frisch, et al., Gaussian, Inc., 2010.) was used as the software for molecular orbital calculation.

"The HOMO and the LUMO are substantially separated" means that the center of the HOMO orbital distribution and the center of the LUMO orbital distribution calculated by the molecular calculation described above are apart from each other and more preferably that the distribution of the HOMO orbit and the distribution of the LUMO orbit do not substantially overlap.

In respect of the separation state of the HOMO and the LUMO, from the aforementioned structure optimization calculation including B3LYP as the functional and 6-31G (d) as the basis function, excited state calculation by means of the time-dependent density functional theory (Time-Dependent DFT) is further carried out to determine energy levels of $S_1$ and $T_1$, ($E(S_1)$ and $E(T_1)$, respectively), and thus, the state can be calculated as $\Delta E_{ST}=|E(S_1)-E(T_1)|$. The smaller $\Delta E_{ST}$ calculated indicates that the HOMO and LUMO are more separate from each other. In the present invention, $\Delta E_{ST}$ calculated by using the calculation technique similar to that aforementioned is preferably 0.50 eV or less, more preferably 0.30 eV or less, still more preferably 0.10 eV or less.

[Lowest Excited Singlet Energy Level $S_1$]

The lowest excited singlet energy level $S_1$ of the π-conjugated compound in the present invention is defined based on one calculated by a typical method, also in the present invention. Specifically, a target compound is deposited onto a quartz substrate to prepare a sample, and an absorption spectrum of the sample is measured at ambient temperature (300 K) (vertical axis: absorbance, horizontal axis: wavelength). A tangential line is drawn at the rising point of the absorption spectrum on the longer wavelength side, and the lowest excited singlet energy level is calculated by a specific conversion expression on the basis of the wavelength at the point of intersection of the tangential line with the horizontal axis.

When the molecule itself of the π-conjugated compound used for the present invention has relatively high cohesion, errors due to cohesion may occur in thin film measurement. In the present invention, the lowest excited singlet energy level $S_1$ is determined from, as an approximation, the peak wavelength of emission of a solution of the π-conjugated compound at room temperature (25° C.) in consideration of a relatively small Stokes shift of the π-conjugated compound and a small change in the structure of the compound between the excited state and the ground state.

A solvent that may be used herein is one less likely to affect the cohesion state of the π-conjugated compound, that is, one having a small influence of a solvent effect, for example, a non-polar solvent, such as cyclohexane, toluene or the like can be used.

[Lowest Excited Triplet Energy Level $T_1$]

The lowest excited triplet energy level $T_1$ of the π-conjugated compound used for the present invention was calculated on the basis of the photoluminescent (PL) properties of a solution or thin film. For example, in respect of a calculation method in a thin film, a thin film is prepared from a dilute dispersion of the π-conjugated compound, and the transient PL properties of the thin film are determined with a streak camera to separate a fluorescent component and a phosphorescent component. By using the absolute value of the energy difference therebetween as ΔEst, the lowest excited triplet energy level can be determined on the basis of the lowest excited singlet energy level.

In measurement and evaluation, the absolute PL quantum efficiency was determined with an absolute PL quantum efficiency measuring apparatus C9920-02 (manufactured by Hamamatsu Photonics K.K.). The emission lifetime was determined with a streak camera C4334 (manufactured by Hamamatsu Photonics K.K.) under excitation of the sample with a laser beam.

<<Constituent Layer of Organic EL Element>>

The organic EL element of the present invention is an organic electroluminescent element including at least a light-emitting layer between an anode and a cathode, wherein at least one layer of the light-emitting layer contains a π-conjugated compound having a structure represented by general formula 1 aforementioned.

Representative element configurations in the organic EL element of the present invention are, but not limited to, as follows.

(1) Anode/Light-emitting layer/Cathode (2) Anode/Light-emitting layer/Electron transport layer/Cathode (3) Anode/Hole transport layer/Light-emitting layer/Cathode (4) Anode/Hole transport layer/Light-emitting layer/Electron transport layer/Cathode (5) Anode/Hole transport layer/Light-emitting layer/Electron transport layer/Electron injection layer/Cathode (6) Anode/Hole injection layer/Hole transport layer/Light-emitting layer/Electron transport layer/Cathode (7) Anode/Hole injection layer/Hole transport layer/(Electron blocking layer/) Light-emitting layer/(Hole blocking layer/) Electron transport layer/Electron injection layer/Cathode Among the above, the configuration (7) is preferably used, but the structure is not limited thereto.

A light-emitting layer of the present invention is composed of a single layer or a plurality of layers. When the light-emitting layer is composed of a plurality of layers, a non-luminescent intermediate layer(s) may be disposed between light-emitting layers.

As required, a hole blocking layer (also referred to as a hole barrier layer) and/or an electron injection layer (also referred to as a cathode buffer layer) may be disposed between the light-emitting layer and a cathode. Further, an electron blocking layer (also referred to as an electron barrier layer) and/or a hole injection layer (also referred to as an anode buffer layer) may be disposed between the light-emitting layer and an anode.

An electron transport layer used for the present invention is a layer having a function of transporting electrons. The electron injection layer and the hole blocking layer are types of the electron transport layer in a broad sense. The electron transport layer may be composed of a plurality of layers.

A hole transport layer of the present invention is a layer having a function of transporting holes. The hole injection layer and the electron blocking layer are types of the hole transport layer in a broad sense. The electron transport layer may be composed of a plurality of layers.

(Tandem Structure)

An organic EL element of the present invention may be so-called a tandem structure element in which a plurality of light-emitting units each containing at least one light-emitting layer are layered.

A representative element configuration of the tandem structure is, for example, the following configuration.

Anode/First Light-Emitting Unit/Intermediate Layer/Second Light-Emitting Unit/Intermediate Layer/Third Light-Emitting Unit/Cathode All the first light-emitting unit, second light-emitting unit, and third light-emitting unit described above may be the same or different from each other. Alternatively, two light-emitting units may be the same with the remaining one light-emitting unit different therefrom.

The light-emitting units may be laminated directly or may be laminated through an intermediate layer, which may be referred to as an intermediate electrode, an intermediate conductive layer, a charge generating layer, an electron drawing layer, a connecting layer, or an intermediate insulating layer. Any known material configuration can be used as long as a layer has a function of supplying electrons to an adjacent layer on the anode side and holes to an adjacent layer on the cathode side.

Examples of the material used for the intermediate layer include conductive inorganic compound layers of indium tin oxide (ITO), indium zinc oxide (IZO), $ZnO_2$, TiN, ZrN, HfN, TiOx, VOx, CuI, InN, GaN, $CuAlO_2$, $CuGaO_2$, $SrCu_2O_2$, $LaB_6$, $RuO_2$, and Al, two-layer films of $Au/Bi_2O_3$, multilayer films of $SnO_2/Ag/SnO_2$, ZnO/Ag/ZnO, $Bi_2O_3/Au/Bi_2O_3$, $TiO_2/TiN/TiO_2$, and $TiO_2/ZrN/TiO_2$, conductive organic substance layers of fullerenes such as fullerene $C_{60}$ and oligothiophene, and conductive organic compound layers of metal phthalocyanines, metal-free phthalocyanines, metal porphyrins, and metal-free porphyrins. The present invention is not limited thereto.

Examples of a preferable configuration in the light-emitting unit include those formed by removing the anode and the cathode from the representative element configurations (1) to (7) listed above, but the present invention is not limited thereto.

Specific examples of the tandem structure organic EL elements include, for example, the element structure and constituent materials disclosed in the following literature: U.S. Pat. Nos. 6,337,492, 7,420,203, 7,473,923, 6,872,472, 6,107,734, 6,337,492, WO2005/009087, Japanese Patent Application Laid-Open No. 2006-228712, Japanese Patent Application Laid-Open No. 2006-24791, Japanese Patent Application Laid-Open No. 2006-49393, Japanese Patent Application Laid-Open No. 2006-49394, Japanese Patent Application Laid-Open No. 2006-49396, Japanese Patent Application Laid-Open No. 2011-96679, Japanese Patent Application Laid-Open No. 2005-340187, Japanese Patent No. 4711424, Japanese Patent No. 3496681, Japanese Patent No. 3884564, Japanese Patent No. 4213169, Japanese Patent Application Laid-Open No. 2010-192719, Japanese Patent Application Laid-Open No. 2009-076929, Japanese Patent Application Laid-Open No. 2008-078414, Japanese Patent Application Laid-Open No. 2007-059848, Japanese Patent Application Laid-Open No. 2003-272860, Japanese Patent Application Laid-Open No. 2003-045676, WO2005/094130 and the like, but the present invention is not limited thereto.

Hereinafter, the layers constituting the organic EL element of the present invention will be described.

<<Light-Emitting Layer>>

The light-emitting layer used for the present invention is a layer which provides a place of light emission via excitons produced by recombination of electrons and holes injected from the electrodes or the adjacent layers. The luminescent portion may be either in the light-emitting layer or at an interface between the light-emitting layer and the adjacent layer. The configuration of the light-emitting layer used for the present invention is not particularly limited as long as it satisfies the requirements defined by the present invention.

The total thickness of the light-emitting layer(s) is not particularly limited, but is adjusted to be in preferably the range from 2 nm to 5 μm, more preferably the range from 2 nm to 500 nm, still more preferably the range from 5 nm to 200 nm from the viewpoints of homogeneity of layers formed, prevention of application of an unnecessarily high voltage during light emission, and increase in stability of emission colors against drive current.

The thickness of each light-emitting layer used for the present invention is adjusted to be in preferably the range from 2 nm to 1 μm, more preferably the range from 2 nm to 200 nm, still more preferably the range from 3 nm to 150 nm.

The light-emitting layer used for the present invention may be a single layer or may be constituted by a plurality of layers. When the π-conjugated compound according to the present invention is used for the light-emitting layer, the compound may be singly used or may be used in mixture with a host material, a fluorescent material, a phosphorescent material and the like described below. For example, at least one layer of the light-emitting layers may be a layer that contains a luminescent dopant (also referred to as a luminescent compound, a light-emitting dopant, or simply a dopant) and further contains a host compound (also referred to as a matrix material, a luminescent host compound, or simply a host). At least one layer of the light-emitting layer preferably contains the π-conjugated compound according to the present invention and a host compound because the emission efficiency will be improved. Also, at least one layer of the light-emitting layer preferably contains the π-conjugated compound according to the present invention and at least one of fluorescence-emitting compounds and phosphorescence-emitting compounds because the emission efficiency will be improved. At least one layer of the light-emitting layer preferably contains the π-conjugated compound according to the present invention, at least one of fluorescence-emitting compounds and phosphorescence-emitting compounds, and a host compound because the emission efficiency will be improved.

(1) Luminescent Dopant

As the luminescent dopant, a fluorescence-emitting dopant (also referred to as a fluorescence-emitting compound or fluorescent dopant) and a phosphorescence-emitting dopant (also referred to as a phosphorescence-emitting compound or phosphorescent dopant) are preferably used. In the present invention, the light-emitting layer contains the π-conjugated compound according to the present invention as a fluorescence-emitting compound or assist dopant in the range of 0.1 to 50 mass % and preferably particularly in the range of 1 to 30 mass %.

In the present invention, the light-emitting layer contains the luminescent compound in the range of 0.1 to 50 mass % and particularly preferably in the range of 1 to 30 mass %.

The concentration of the luminescent compound in the light-emitting layer may be arbitrarily determined based on the specific luminescent compound employed and the requirements of the device. The concentration of the luminescent compound may be contained at a homogeneous concentration in the thickness direction of the light-emitting layer or may have any concentration distribution.

As the luminescent compound used for the present invention, a plurality of luminescent compounds may be used in combination. A combination of fluorescence-emitting compounds having different structures or a combination of a fluorescence-emitting compound and a phosphorescence-emitting compound may be used. Any emission color can be obtained thereby.

When the light-emitting layer contains the π-conjugated compound according to the present invention, in which the absolute value of the energy difference between the lowest excited singlet energy level and the lowest excited triplet energy level ($\Delta E_{ST}$) is 0.50 eV or less, a luminescent compound, and a host compound, the π-conjugated compound according to the present invention serves as an assist dopant. In contrast, when the light-emitting layer contains the π-conjugated compound according to the present invention and a luminescent compound and contains no host compound, the π-conjugated compound according to the present invention serves as a host compound. When the light-emitting layer contains only the π-conjugated compound according to the present invention, the π-conjugated compound according to the present invention serves both as a host compound and a luminescent compound.

The mechanism by which the effects of the present invention are exerted is the same in any case and is based on conversion of triplet excitons generated on the π-conjugated compound according to the present invention into single excitons through reverse intersystem crossing (RISC).

Accordingly, the overall exciton energy generated on the π-conjugated compound according to the present invention can theoretically undergo fluorescence resonance energy transfer (FRET) to a luminescent compound, resulting in high light emission efficiency.

Thus, when the light-emitting layer contains three components: the π-conjugated compound according to the present invention, a luminescent compound, and a host compound, the energy levels $S_1$ and $T_1$ of the π-conjugated compound are preferably lower than the energy levels $S_1$ and $T_1$ of the host compound and higher than the energy levels $S_1$ and $T_1$ of the luminescent compound.

Similarly, when the light-emitting layer contains two components: the π-conjugated compound according to the present invention and a luminescent compound, the energy levels $S_1$ and $T_1$ of the π-conjugated compound are preferably higher than the energy levels $S_1$ and $T_1$ of the luminescent compound.

Figure 3:
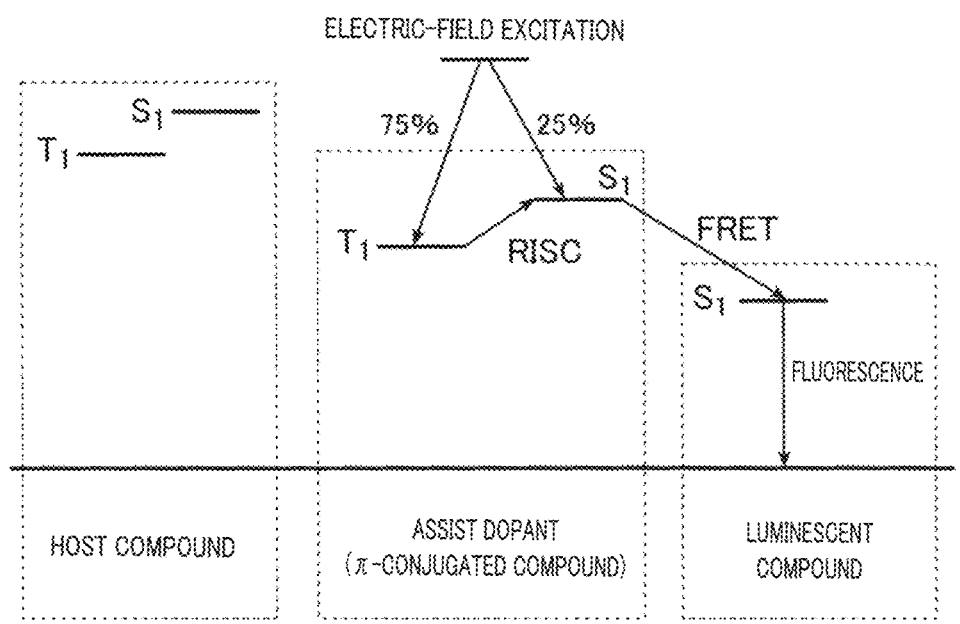
FIG. 3 is a schematic illustration of an energy diagram when the π-conjugated compound serves as an assist dopant material.
Figure 4:
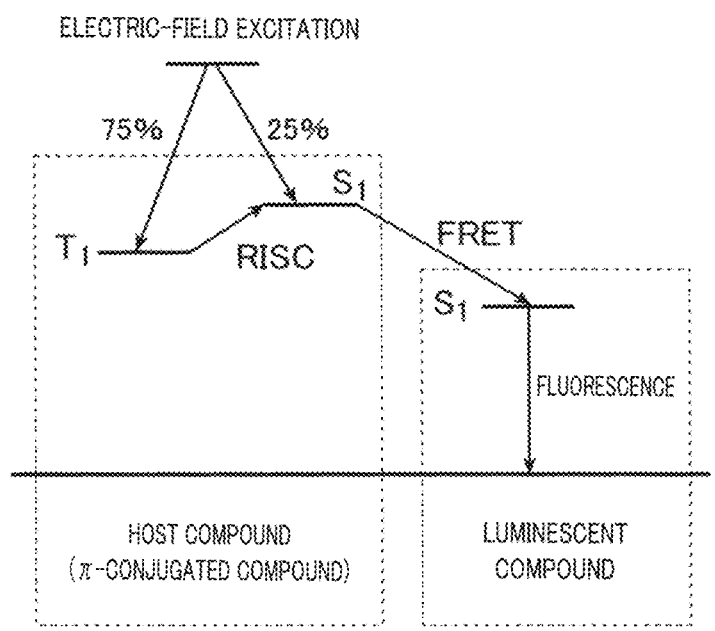
FIG. 4 is a schematic illustration of an energy diagram when the π-conjugated compound serves as a host material.

FIG. 3 schematically illustrates the case where the π-conjugated compound of the present invention serves as an assist dopant, and FIG. 4 schematically illustrates the case where the compound serves as a host compound. FIGS. 3 and 4 are exemplary. The generation process of triplet excitons generating on the π-conjugated compound according to the present invention is not only through electric-field excitation but also through energy transfer or electron transfer in the light-emitting layer or from the interface between the light-emitting layer and a layer adjacent thereto.

Although FIGS. 3 and 4 illustrate the case where the light-emitting material is a fluorescence-emitting compound, the light-emitting material is not limited thereto. A phosphorescence-emitting compound may be used or both a fluorescence-emitting compound and a phosphorescence-emitting compound may be used.

When the π-conjugated compound according to the present invention is used as an assist dopant, the light-emitting layer preferably contains a host compound in an amount of 100% or more by mass ratio relative to the π-conjugated compound, and a fluorescence-emitting compound and/or a phosphorescence-emitting compound in an amount of 0.1 to 50% by mass ratio relative to the π-conjugated compound.

When the π-conjugated compound according to the present invention is used as a host compound, the light-emitting layer preferably contains a fluorescence-emitting compound and/or a phosphorescence-emitting compound in an amount of 0.1 to 50% by mass ratio relative to the π-conjugated compound.

When the π-conjugated compound according to the present invention is used as an assist dopant or a host compound, the emission spectrum of the π-conjugated compound according to the present invention and the absorption spectrum of the luminescent compound preferably overlap each other.

Emission colors of an organic EL element of the present invention or the compound used for the present invention are determined by applying results obtained with a CS-1000 Spectroradiometer (produced by Konica Minolta Inc.) to the CIE chromaticity coordinates in FIG. 3.16 on page 108 of "Shinpen Shikisai Kagaku Handobukku (New Edition Handbook of Color Science)" (edited by The Color Science Association of Japan, University of Tokyo Press, 1985).

In the present invention, one or more light-emitting layers preferably contain luminescent dopants having different emission colors so that white light is preferably emitted.

A combination of luminescent dopants emitting white light is not particularly limited, and examples thereof include combinations of: blue and orange; and blue, green and red or the like.

The "white" in an organic EL element of the present invention preferably shows chromaticity in the region of x=0.39±0.09 and y=0.38±0.08 in the CIE 1931 Color Specification System at 1,000 cd/m$^2$, when 2-degree viewing angle front luminance is measured by the method aforementioned.

(1.1) Fluorescence-Emitting Dopant

As the fluorescence-emitting dopant (fluorescent dopant), the π-conjugated compound of the present invention may be used. Alternatively, the dopant may be appropriately selected and used from known fluorescent dopants or delayed fluorescent dopants used for light-emitting layers of organic EL elements.

Specific examples of known fluorescent dopants that can be used for the present invention include anthracene derivatives, pyrene derivatives, chrysene derivatives, fluoranthene derivatives, perylene derivatives, fluorene derivatives, arylacetylene derivatives, styrylarylene derivatives, styrylamine derivatives, arylamine derivatives, boron complexes, coumarin derivatives, pyran derivatives, cyanine derivatives, croconium derivatives, squarylium derivatives, oxobenzanthracene derivatives, fluorescein derivatives, rhodamine derivatives, pyrylium derivatives, perylene derivatives, polythiophene derivatives, and rare earth complex compounds. In recent years, luminescent dopants making use of delayed fluorescence have been developed, and these may be used. Specific examples of the luminescent dopants making use of delayed fluorescence are compounds described in, for example, WO 2011/156793, Japanese Patent Application Laid-Open Nos. 2011-213643 and 2010-93181, Japanese Patent No. 5366106 and the like, but the present invention is not limited thereto.

(1.2) Phosphorescence-Emitting Dopant

The phosphorescence-emitting dopant used for the present invention will be described.

The phosphorescence-emitting dopant used for the present invention is a compound in which the light emission from excited triplets can be observed and, specifically, a compound that emits phosphorescence at room temperature (25° C.). The compound is defined as a compound having a phosphorescence quantum efficiency of 0.01 or more at 25° C., and the phosphorescence quantum efficiency is preferably 0.1 or more.

The phosphorescence quantum efficiency described above can be measured by a method described on page 398 of Bunko II of Dai 4 Han Jikken Kagaku Koza 7 (Spectroscopy II of Lecture of Experimental Chemistry vol. 7, 4th edition) (1992, published by Maruzen Co., Ltd.). The phosphorescence quantum efficiency in a solution can be measured by using various solvents. It is only necessary for the phosphorescent dopant used for the present invention to exhibit the above phosphorescence quantum efficiency (0.01 or more) in any of the solvents.

The phosphorescent dopant can be appropriately selected and used from known phosphorescent dopants used for light-emitting layers of organic EL elements. Specific examples of the known phosphorescent dopants usable in the present invention include compounds described in the following literatures.

Nature 395,151(1998), Appl. Phys. Lett. 78,1622(2001), Adv. Mater. 19,739(2007), Chem. Mater. 17,3532(2005), Adv. Mater. 17,1059(2005), WO2009/100991, WO2008/101842, WO2003/040257, US Patent Application Laid-Open No. 2006-835469, US Patent Application Laid-Open No. 2006-0202194, US Patent Application Laid-Open No. 2007-0087321, US Patent Application Laid-Open No. 2005-0244673, Inorg. Chem. 40,1704(2001), Chem. Mater. 16,2480(2004), Adv. Mater. 16,2003(2004), Angew. Chem. Int. Ed. 2006, 45, 7800, Appl. Phys. Lett. 86,153505(2005), Chem. Lett. 34,592(2005), Chem. Commun. 2906(2005), Inorg. Chem. 42,1248(2003), WO2009/050290, WO2002/015645, WO2009/000673, US Patent Application Laid-Open No. 2002-0034656, U.S. Pat. No. 7,332,232, US Patent Application Laid-Open No. 2009-0108737, US Patent Application Laid-Open No. 2009-0039776, U.S. Pat. Nos. 6,921,915, 6,687,266, US Patent Application Laid-Open No. 2007-0190359, US Patent Application Laid-Open No. 2006-0008670, US Patent Application Laid-Open No. 2009-0165846, US Patent Application Laid-Open No. 2008-0015355, U.S. Pat. Nos. 7,250,226, 7,396,598, US Patent Application Laid-Open No. 2006-0263635, US Patent Application Laid-Open No. 2003-0138657, US Patent Application Laid-Open No. 2003-0152802, U.S. Pat. No. 7,090,928, Angew. Chem. Int. Ed. 47,1(2008), Chem. Mater. 18,5119(2006), Inorg. Chem. 46,4308(2007), Organometallics 23,3745(2004), Appl. Phys. Lett. 74,1361(1999), WO2002/002714, WO2006/009024, WO2006/056418, WO2005/019373, WO2005/123873, WO2005/123873, WO2007/004380, WO2006/082742, US Patent Application Laid-Open No. 2006-0251923, US Patent Application Laid-Open No. 2005/0260441, U.S. Pat. Nos. 7,393,599, 7,534,505, 7,445,855, US Patent Application Laid-Open No. 2007/0190359, US Patent Application Laid-Open No. 2008/0297033, U.S. Pat. No. 7,338,722, US Patent Application Laid-Open No. 2002-0134984, U.S. Pat. No. 7,279,704, US Patent Application Laid-Open No. 2006-098120, US Patent Application Laid-Open No. 2006-103874, WO2005/076380, WO2010/032663, WO2008/140115, WO2007/052431, WO2011/134013, WO2011/157339, WO2010/086089, WO2009/113646, WO2012/020327, WO2011/051404, WO2011/004639, WO2011/073149, US Patent Application Laid-Open No. 2012-228583, US Patent Application Laid-Open No. 2012-212126, Japanese Patent Application Laid-Open No. 2012-069737, Japanese Patent Application No. 2011-181303, Japanese Patent Application Laid-Open No. 2009-114086, Japanese Patent Application Laid-Open No. 2003-81988, Japanese Patent Application Laid-Open No. 2002-302671, Japanese Patent Application Laid-Open No. 2002-363552 and the like.

Of these, preferable phosphorescent dopants include an organic metal complex having Ir as central metal. More preferably, a complex containing at least one coordination mode of a metal-carbon bond, metal-nitrogen bond, metal-oxygen bond, or metal-sulfur bond.

(2) Host Compound

The host compound used for the present invention is a compound which is mainly responsible for injecting and transporting charges in the light-emitting layer. In an organic EL element, light emission from the host compound itself is not observed substantially.

The host compound in the layer preferably has a mass ratio of 20% or more relative to the compounds contained in the light-emitting layer.

The host compound may be singly used or two or more thereof may be used in combination. Use of a plurality of host compounds enables adjustment of charge transfer, thereby increasing the efficiency of an organic electroluminescent element.

A host compound preferably used for the present invention will be described hereinbelow.

As the host compound, a π-conjugated compound used for the present invention as described above may be used, and the host compound is not particularly limited. From the viewpoint of a reverse energy transfer, those having excited energy higher than the excited singlet energy of the dopant are preferred, and those having excited triplet energy higher than the excited triplet energy of the dopant are more preferred.

The host compound, in a light-emitting layer, is responsible for transporting carriers and generating excitons. Thus, preferably, the host compound can exist stably in all of the active species of a cation radical state, anion radial state, and excited state and causes no chemical reactions such as decomposition and addition. Further, the host molecule preferably will not move in the layer at an Angstrom level when an electric current is applied.

In particular, when the luminescent dopant to be used in combination exhibits TADF emission, due to the long lifetime of the triplet excited state of the TADF compound, an appropriate design of a molecular structure is required to prevent the host compound from having a lower $T_1$ level such that the host compound has a high $T_1$ energy level; that the host compounds will not form a low $T_1$ state when associated with each other; that the TADF compound and the host compound will not form an exciplex; and that the host compound will not form an electromer by applying an electric field, for example.

In order to satisfy such requirements, it is required that: the host compound itself have a high electron hopping mobility; the host compound have a high hole hopping mobility; and the host compound have small structural change when it is brought into a triplet excited state. Examples of a representative host compound satisfying these requirements preferably include compounds having a high $T_1$ energy level, such as compounds having a carbazole skeleton, azacarbazole skeleton, dibenzofuran skeleton, dibenzothiophene skeleton, or azadibenzofuran skeleton.

The host compound preferably has a high glass transition temperature (Tg) from the viewpoints of having a hole transporting ability and an electron transporting ability, preventing lengthening of an emission wavelength, and additionally stably operating an organic electroluminescent element when the element is driven at high temperature or against heat generated while the element is driven. The compound has a Tg of 90° C. or more, more preferably of 120° C. or more.

The glass transition temperature (Tg) herein is a value obtained using differential scanning colorimetry (DSC) by a method in conformity to JIS-K-7121-2012.

Also as the host compound used for the present invention, the π-conjugated compound according to the present invention may be suitably used as aforementioned. This is because the π-conjugated compound according to the present invention, which has high $T_1$, can be suitably used for light-emitting materials having a short emission wavelength (i.e., high energy levels $T_1$ and $S_1$).

When a known host compound is used for the organic EL element of the present invention, specific examples thereof include compounds described in the following literatures, but the present invention is not limited thereto.

Japanese Patent Application Laid-Open No. 2001-257076, Japanese Patent Application Laid-Open No. 2002-308855, Japanese Patent Application Laid-Open No. 2001-313179, Japanese Patent Application Laid-Open No. 2002-319491, Japanese Patent Application Laid-Open No. 2001-357977, Japanese Patent Application Laid-Open No. 2002-334786, Japanese Patent Application Laid-Open No. 2002-8860, Japanese Patent Application Laid-Open No. 2002-334787, Japanese Patent Application Laid-Open No. 2002-15871, Japanese Patent Application Laid-Open No. 2002-334788, Japanese Patent Application Laid-Open No. 2002-43056, Japanese Patent Application Laid-Open No. 2002-334789, Japanese Patent Application Laid-Open No. 2002-75645, Japanese Patent Application Laid-Open No. 2002-338579, Japanese Patent Application Laid-Open No. 2002-105445, Japanese Patent Application Laid-Open No. 2002-343568, Japanese Patent Application Laid-Open No. 2002-141173, Japanese Patent Application Laid-Open No. 2002-352957, Japanese Patent Application Laid-Open No. 2002-203683, Japanese Patent Application Laid-Open No. 2002-363227, Japanese Patent Application Laid-Open No. 2002-231453, Japanese Patent Application Laid-Open No. 2003-3165, Japanese Patent Application Laid-Open No. 2002-234888, Japanese Patent Application Laid-Open No. 2003-27048, Japanese Patent Application Laid-Open No. 2002-255934, Japanese Patent Application Laid-Open No. 2002-260861, Japanese Patent Application Laid-Open No. 2002-280183, Japanese Patent Application Laid-Open No. 2002-299060, Japanese Patent Application Laid-Open No. 2002-302516, Japanese Patent Application Laid-Open No. 2002-305083, Japanese Patent Application Laid-Open No. 2002-305084, Japanese Patent Application Laid-Open No. 2002-308837, US Patent Application Laid-Open No. 2003-0175553, US Patent Application Laid-Open No. 2006-0280965, US Patent Application Laid-Open No. 2005-0112407, US Patent Application Laid-Open No. 2009-0017330, US Patent Application Laid-Open No. 2009-0030202, US Patent Application Laid-Open No. 2005-0238919, WO2001/039234, WO2009/021126, WO2008/056746, WO2004/093207, WO2005/089025, WO2007/063796, WO2007/063754, WO2004/107822, WO2005/030900, WO2006/114966, WO2009/086028, WO2009/003898, WO2012/023947, Japanese Patent Application Laid-Open No. 2008-074939, Japanese Patent Application Laid-Open No. 2007-254297, EP Patent No. 2034538, WO2011/055933, WO2012/035853, Japanese Patent Application Laid-Open No. 2015-38941 and the like.

Examples of the host compound described in Japanese Patent Application Laid-Open No. 2015-38941 include Compounds H-1 to H-230 described in [0255] to [0293] of the description.

Specific examples of the compound are shown hereinafter, as the host compound to be used for the present invention, but the compound is not limited thereto.

[Formula 96]

H-231

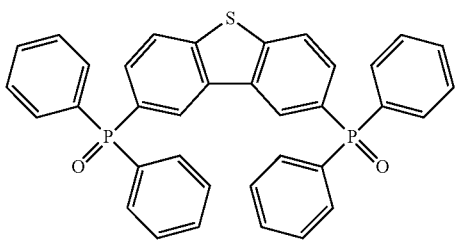

H-232

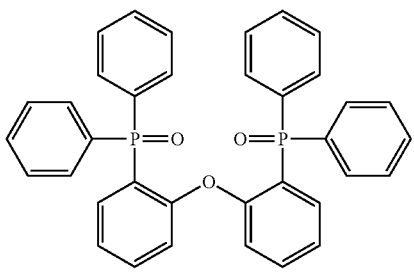

H-233

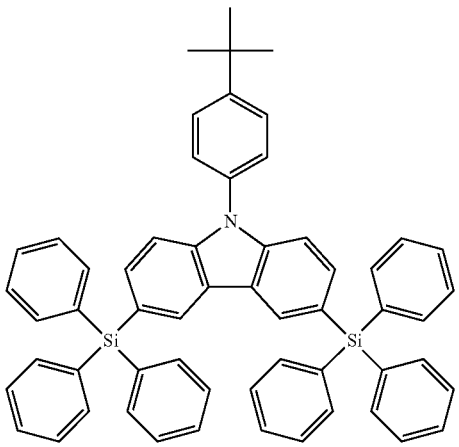

H-234

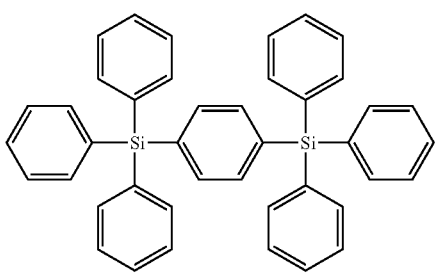

Furthermore, the host compound used for the present invention is preferably a compound represented by the following general formula I. The compound represented by the following general formula I has a bipolar ability and is very stable. Thus, when the host compound is the compound represented by the following general formula I, the organic EL element is likely to have a longer lifetime.

[Formula 97]

General formula I

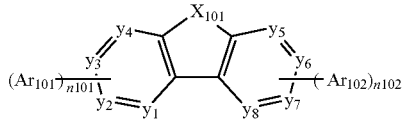

Wherein, $X_{101}$ represents $NR_{101}$, an oxygen atom, sulfur atom, sulfinyl group, sulfonyl group, $CR_{102}R_{103}$, or $SiR_{104}R_{105}$. $y_1$ to $y_8$ each independently represent $CR_{106}$ or a nitrogen atom. Herein, $R_{101}$ to $R_{106}$ each independently represent a hydrogen atom or substituent, and may be bonded with each other to form a ring. Examples of the substituent that may be $R_{101}$ to $R_{106}$ include the following groups:

straight-chain or branched alkyl groups (such as methyl group, ethyl group, propyl group, isopropyl group, t-butyl group, pentyl group, hexyl group, octyl group, dodecyl group, tridecyl group, tetradecyl group, and pentadecyl group);

alkenyl groups (such as vinyl group and aryl group);

alkynyl groups (such as ethynyl group and propargyl group);

aromatic hydrocarbon ring groups (also referred to as aromatic carbon ring groups or aryl groups, such as a group derived from a benzene ring, biphenyl, naphthalene ring, azulene ring, anthracene ring, phenanthrene ring, pyrene ring, chrysene ring, naphthacene ring, triphenylene ring, o-terphenyl ring, m-terphenyl ring, p-terphenyl ring, acenaphthene ring, coronene ring, indene ring, fluorene ring, fluoranthene ring, naphthacene ring, pentacene ring, perylene ring, pentaphene ring, picene ring, pyrene ring, pyranthrene ring, anthanthrene ring, and tetralin);

aromatic heterocyclic groups (such as a group derived from a furan ring, dibenzofuran ring, thiophene ring, dibenzothiophene ring, oxazole ring, pyrrole ring, pyridine ring, pyridazine ring, pyrimidine ring, pyrazine ring, triazine ring, benzimidazole ring, oxadiazole ring, triazole ring, imidazole ring, pyrazole ring, thiazole ring, indole ring, indazole ring, benzimidazole ring, benzothiazole ring, benzoxazole ring, quinoxaline ring, quinazoline ring, cinnoline ring, quinoline ring, isoquinoline ring, phthalazine ring, naphthyridine ring, carbazole ring, carboline ring, and diazacarbazole ring (a group derived from a ring in which one of the carbon atoms of the hydrocarbon ring constituting the carboline ring is replaced with nitrogen atoms and the like; the carboline ring and diazacarbazole ring, in combination, may be referred to as an "azacarbazole ring");

non-aromatic hydrocarbon ring groups (such as a cyclopentyl group and cyclohexyl group);

non-aromatic heterocyclic groups (such as a pyrrolidyl group, imidazolidyl group, morpholyl group, and oxazolidyl group);

alkoxy groups (such as a methoxy group, ethoxy group, propyloxy group, pentyloxy group, hexyloxy group, octyloxy group, and dodecyloxy group);

cycloalkoxy groups (such as a cyclopentyloxy group and cyclohexyloxy group);

aryloxy groups (such as a phenoxy group and naphthyloxy group);

alkylthio groups (such as a methylthio group, ethylthio group, propylthio group, pentylthio group, hexylthio group, octylthio group, and dodecylthio group);

cycloalkylthio groups (such as a cyclopentylthio group, and cyclohexylthio group);

arylthio groups (such as a phenylthio group and naphthylthio group);

alkoxycarbonyl groups (such as a methyloxycarbonyl group, ethyloxycarbonyl group, butyloxycarbonyl group, octyloxycarbonyl group and dodecyloxycarbonyl group);

aryloxycarbonyl groups (such as a phenyloxycarbonyl group and naphthyloxycarbonyl group);

sulfamoyl groups (such as an aminosulfonyl group, methylaminosulfonyl group, dimethylaminosulfonyl group, butylaminosulfonyl group, hexylaminosulfonyl group, cyclohexylaminosulfonyl group, octylaminosulfonyl group, dodecylaminosulfonyl group, phenylaminosulfonyl group, naphthylaminosulfonyl group, and 2-pyridylaminosulfonyl group);

acyl groups (such as an acetyl group, ethylcarbonyl group, propylcarbonyl group, pentylcarbonyl group, cyclohexylcarbonyl group, octylcarbonyl group, 2-ethylhexylcarbonyl group, dodecylcarbonyl group, phenylcarbonyl group, naphthylcarbonyl group, and pyridylcarbonyl group);

acyloxy groups (such as an acetyloxy group, ethylcarbonyloxy group, butylcarbonyloxy group, octylcarbonyloxy group, dodecylcarbonyloxy group, and phenylcarbonyloxy group);

amido groups (such as a methylcarbonylamino group, ethylcarbonylamino group, dimethylcarbonylamino group, propylcarbonylamino group, pentylcarbonylamino group, cyclohexylcarbonylamino group, 2-ethyhexylcarbonylamino group, octylcarbonylamino group, dodecylcarbonylamino group, phenylcarbonylamino group, and naphthylcarbonylamino group);

carbamoyl groups (such as an aminocarbonyl group, methylaminocarbonyl group, dimethylaminocarbonyl group, propylaminocarbonyl group, pentylaminocarbonyl group, cyclohexylaminocarbonyl group, octylaminocarbonyl group, 2-ethylhexylaminocarbonyl group, dodecylaminocarbonyl group, phenylaminocarbonyl group, naphthylaminocarbonyl group, and 2-pyridylaminocarbonyl group);

ureido groups (such as a methylureido group, ethylureido group, pentylureido group, cyclohexylureido group, octylureido group, dodecylureido group, phenylureido group, naphthylureido group, and 2-pyridylaminoureido group);

sulfinyl groups (such as methylsulfinyl group, ethylsufinyl group, butylsulfinyl group, cyclohexylsulfinyl group, 2-ethylhexylsulfinyl group, dodecylsulfinyl group, phenylsulfinyl group, naphthylsulfinyl group, and 2-pyridylsulfinyl group);

alkylsulfonyl groups (such as a methylsulfonyl group, ethylsulfonyl group, butylsulfinyl group, cyclohexylsulfonyl group, 2-ethylhexylsulfonyl group, and dodecylsulfonyl group);

arylsulfonyl groups or heteroarylsulfonyl groups (such as a phenylsulfonyl group, naphthylsulfonyl group, and 2-pyridylsulfonyl group);

amino groups (such as an amino group, ethylamino group, dimethylamino group, butylamino group, cyclopentylamino group, 2-ethylhexylamino group, dodecylamino group, anilino group, naphthylamino group, 2-pyridylamino group, and diphenylamino group);

halogen atoms (such as a fluorine atom, chlorine atom, and bromine atom);

fluorinated hydrocarbon groups (such as a fluoromethyl group, trifluoromethyl group, pentafluoroethyl group, and pentafluorophenyl group);

a cyano group;
a nitro group
a hydroxyl group;
thiol groups;
silyl groups (such as a trimethylsilyl group, triisopropylsilyl group, triphenylsilyl group, and phenyldiethylsilyl group); and
a deuterium atom.

Examples of preferred groups of those described above include straight-chain or branched alkyl groups, aromatic hydrocarbon ring groups, aromatic heterocyclic groups, amino groups, a fluorine atom, fluorinated hydrocarbon groups, cyano group, and silyl groups.

$Ar_{101}$ and $Ar_{102}$ each independently represent an optionally substituted aryl group or an optionally substituted heteroaryl group. The aryl group in the "optionally substituted aryl group" is preferably a group derived from a $C_{6-24}$ aromatic hydrocarbon ring. Examples of the aromatic hydrocarbon ring include benzene ring, indene ring, naphthalene ring, azulene ring, fluorene ring, phenanthrene ring, anthracene ring, acenaphthylene ring, biphenylene ring, naphthacene ring, pyrene ring, pentalene ring, aceanthrylene ring, heptalene ring, triphenylene ring, as-indacene ring, chrysene ring, s-indacene ring, pleiadene ring, phenalene ring, fluoranthene ring, perylene ring, acephenanthrylene ring, biphenyl ring, terphenyl ring, and tetraphenyl ring. The aromatic hydrocarbon ring is preferably a benzene ring, biphenyl ring, or terphenyl ring.

The heteroaryl group in the "optionally substituted heteroaryl group" is preferably a group derived from various aromatic heterocycles. Examples of such aromatic heterocycles include pyrrole ring, indole ring, carbazole ring, indoloindole ring, 9,10-dihydroacridine ring, 5,10-dihydrophenazine ring, phenoxazine ring, phenothiazine ring, dibenzothiophene ring, benzofurylindole ring, benzothienoindole ring, indolocarbazole ring, benzofurylcarbazole ring, benzothienocarbazole ring, benzothienobenzothiophene ring, benzocarbazole ring, dibenzocarbazole ring, azacarbazole ring, azadibenzofuran ring, diazacarbazole ring, diazadibenzofuran ring, dibenzothiopheneoxide ring, dibenzothiophenedioxide ring, pyridine ring, pyridazine ring, pyrimidine ring, pyrazine ring, triazine ring, quinoline ring, isoquinoline ring, quinazoline ring, cinnoline ring, quinoxaline ring, phthalazine ring, pteridin ring, phenanthridine ring, phenanthroline ring, dibenzofuran ring, dibenzosilole ring, dibenzoborole ring, and dibenzophospholeoxide ring. The aromatic heterocycle is preferably a carbazole ring, benzocarbazole ring, azacarbazole ring, azadibenzofuran ring, diazacarbazole ring, diazadibenzofuran ring, pyridine ring, pyrimidine ring, or triazine ring.

Examples of the substituent that may be carried on the aryl group or heteroaryl group include aryl groups optionally substituted by an alkyl group, fluorine atom, cyano group, alkyl groups optionally substituted by fluorine, optionally substituted carbonyl groups, optionally substituted sulfonyl groups, optionally substituted phosphine oxide groups, optionally substituted boryl groups, optionally substituted heterocyclic groups, optionally substituted amino groups, and optionally substituted silyl groups.

The "alkyl group" described above may be any of straight-chain, branched or cyclic groups, and, for example, may be a $C_{1-20}$ straight-chain or branched alkyl group or $C_{5-20}$ cyclic alkyl group. Examples of the alkyl group include methyl group, ethyl group, n-propyl group, isopropyl group, n-butyl group, s-butyl group, t-butyl group, n-pentyl group, neopentyl group, n-hexyl group, cyclohexyl group, 2-ethylhexyl group, n-heptyl group, n-octyl group, 2-hexyloctyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-icosyl group. The "aryl group" and "heterocyclic group" may be similar to the aryl group and heteroaryl group represented by $Ar_{101}$ and $Ar_{102}$.

In the above general formula I, n101 and n102 each represent an integer of 0 to 4. When $R_{101}$ is a hydrogen atom, n101 represents an integer of 1 to 4.

The host compound having a structure represented by the above general formula I more preferably has a structure represented by the following general formula II.

[Formula 98]

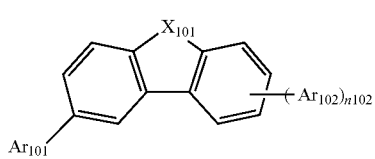

General formula II

In general formula II, $X_{101}$ represents $NR_{101}$, an oxygen atom, sulfur atom, sulfinyl group, sulfonyl group, $CR_{102}R_{103}$, or $SiR_{104}R_{105}$. $R_{101}$ to $R_{105}$ each independently represent a hydrogen atom or substituent, and may be bonded with each other to form a ring. $R_{101}$ to $R_{105}$ have the same definition as $R_{101}$ to $R_{105}$ in general formula I.

$Ar_{101}$ and $Ar_{102}$ each independently represent an optionally substituted aryl group or optionally substituted heteroaryl group, and $Ar_{101}$ and $Ar_{102}$ have the same definition as $Ar_{101}$ and $Ar_{102}$ in general formula I.

n102 represents an integer of 0 to 4.

Furthermore, the compound represented by general formula II is preferably a compound represented by the following general formulas III-1, III-2, or III-3.

[Formula 99]

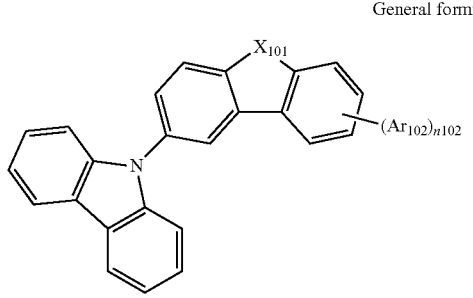

General formula III-1

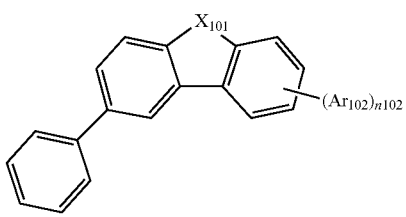

General formula III-2

General formula III-3

In general formulas III-1 to III-3, $X_{101}$, $Ar_{102}$, and n102 have the same definition as $X_{101}$, $Ar_{102}$, and n102 in general formula II aforementioned. In general formula 111-2, $R_{104}$ has the same definition as $R_{104}$ in general formula I aforementioned.

In general formulas III-1 to III-3, a fused ring, carbazole ring and benzene ring formed by containing $X_{101}$ may further have a substituent as long as the function of the host compound is not inhibited.

Preferred specific example of the host compound represented by the above general formula I, II, or III-1 to III-3 will be listed. In some cases, these compounds may further have a substituent, or structural isomers or the like may exist, and thus, the compound is not limited to this description.

[Formula 100]

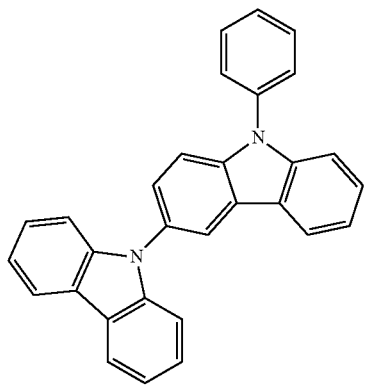

J-1

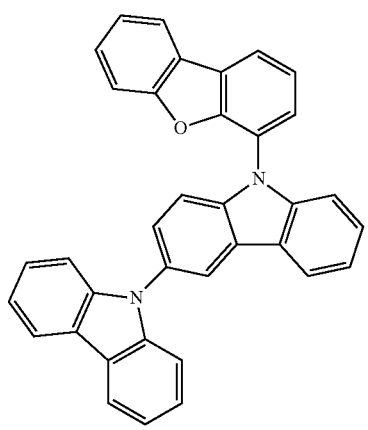

J-2

-continued
J-3
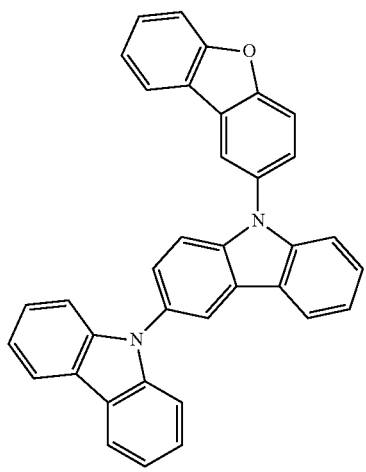
J-4
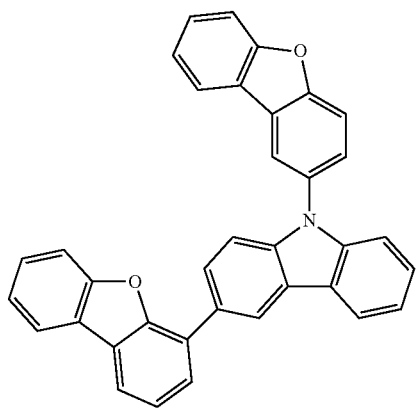
J-5
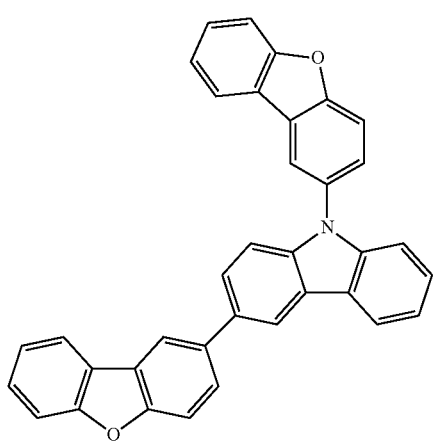
J-6
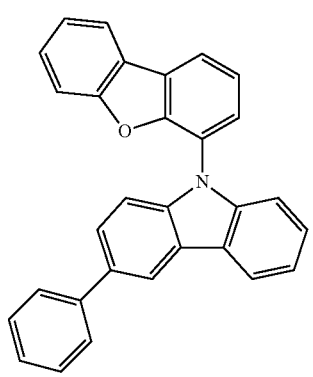
J-7
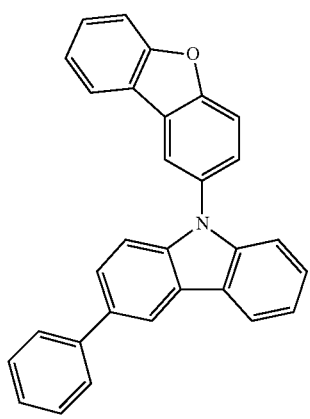
J-8
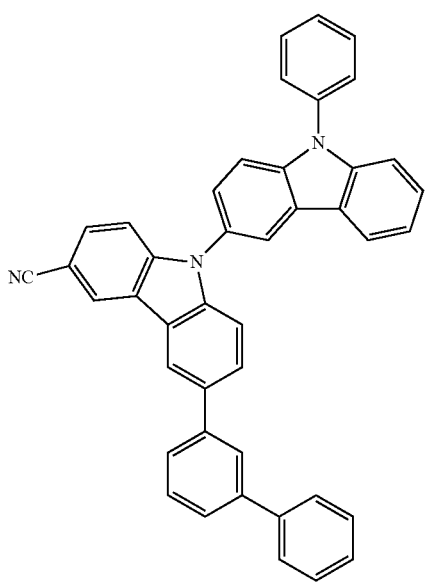

-continued
J-9
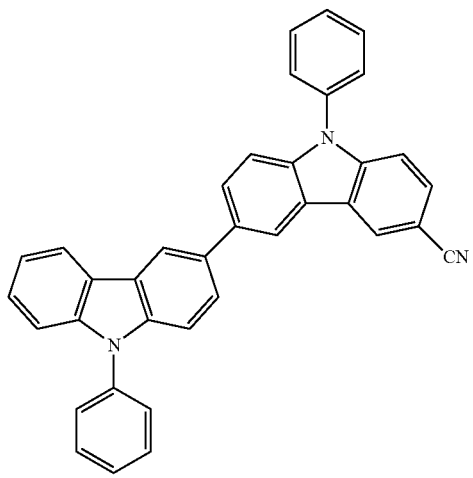
J-10
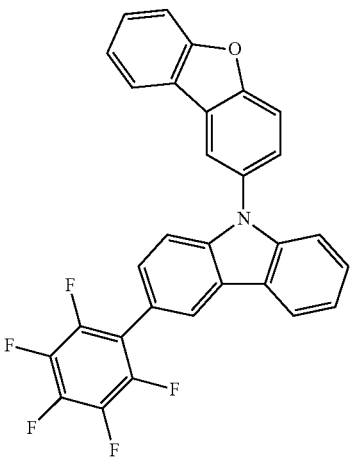
J-11
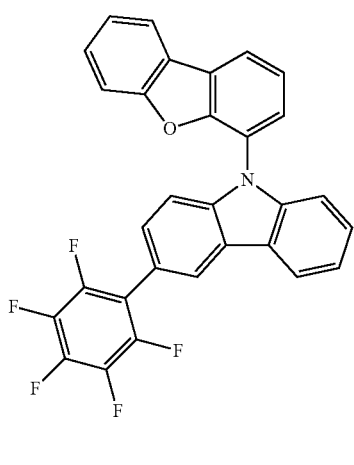
J-12
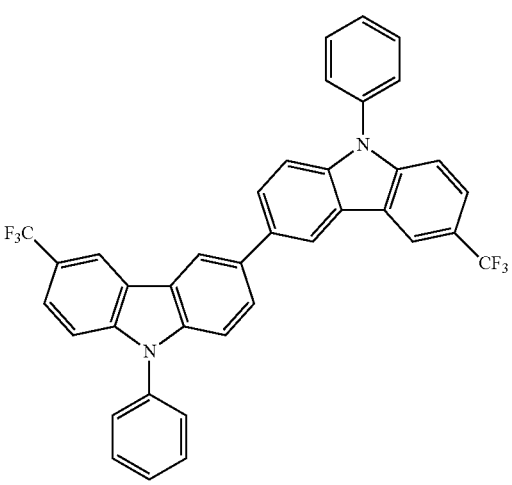
[Formula 101]
J-13
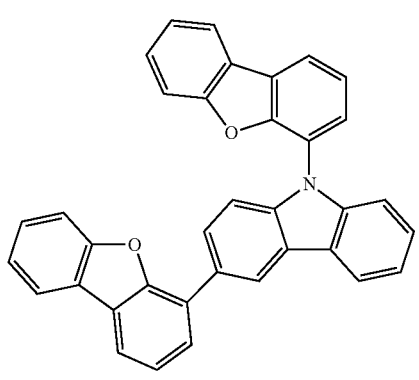
J-14
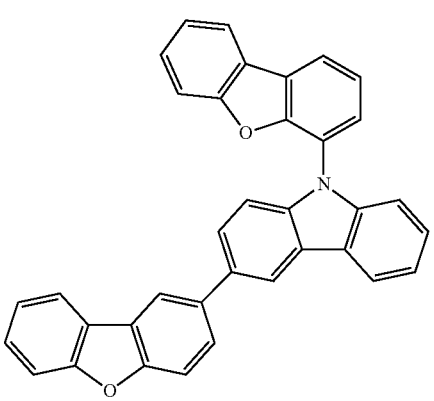

-continued
J-15
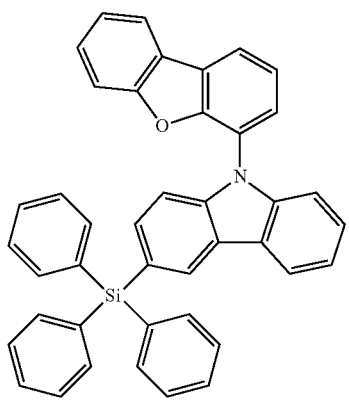
J-16
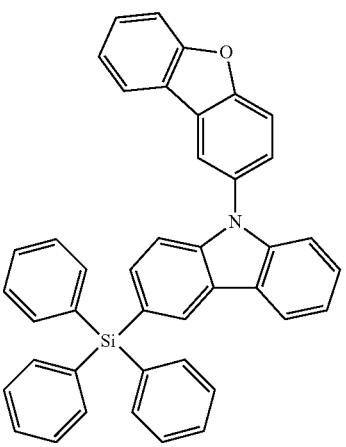
J-17
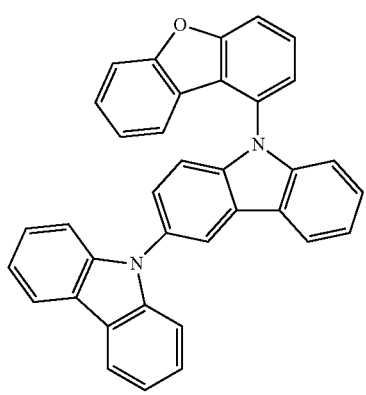
J-18
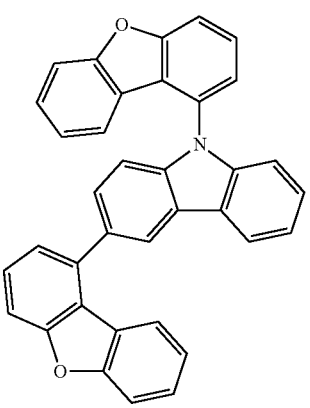
J-19
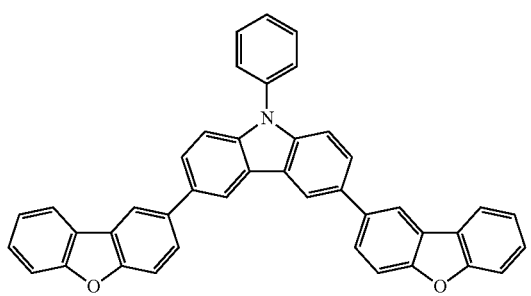
J-20
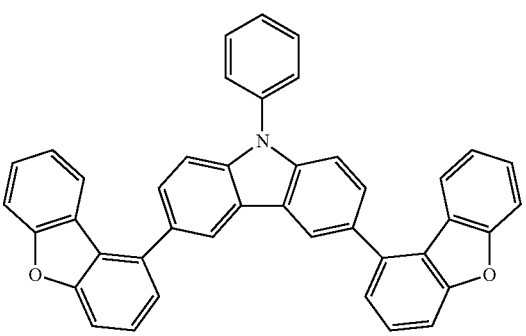
J-21
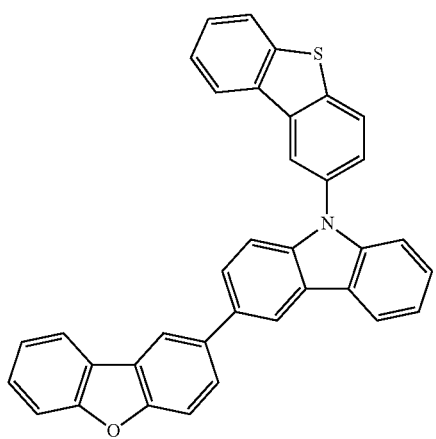
J-22
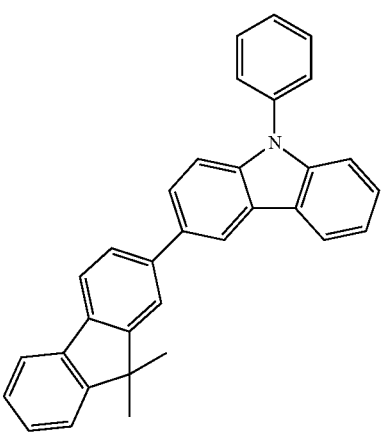

-continued
J-23
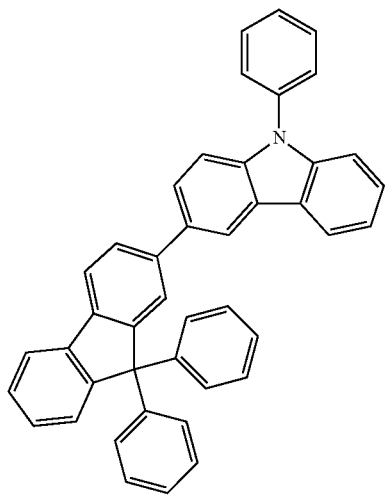
[Formula 102]
J-24
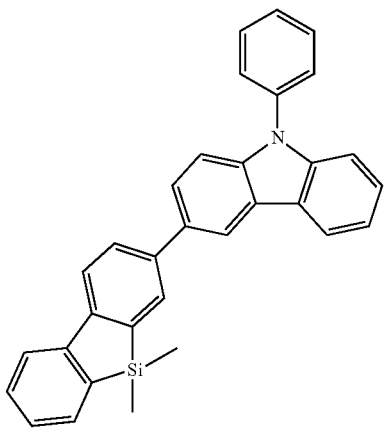
J-25
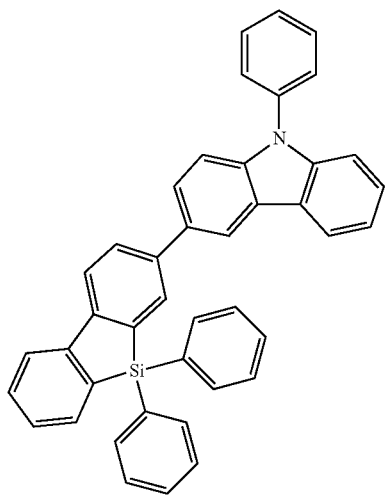
J-26
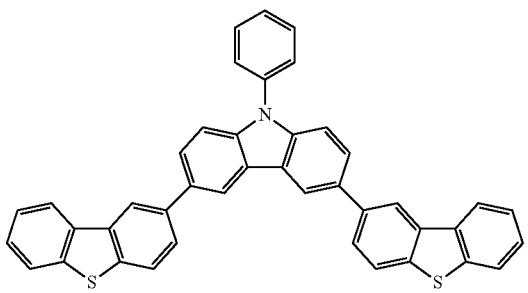
J-27
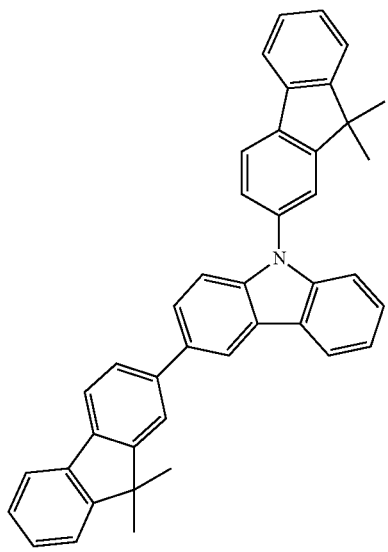
J-28
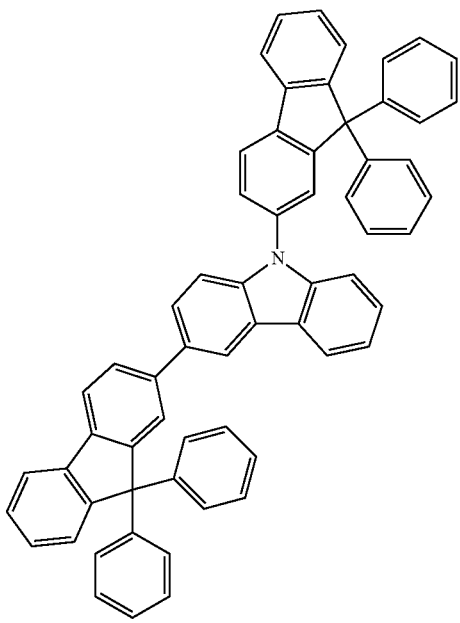

-continued
J-29
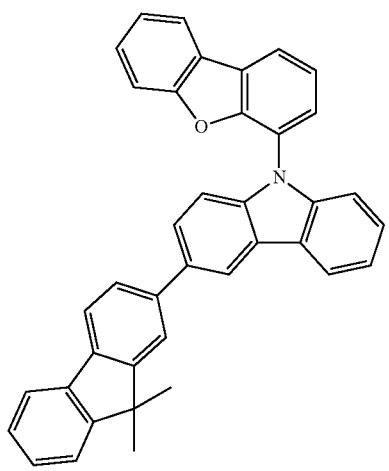
J-30
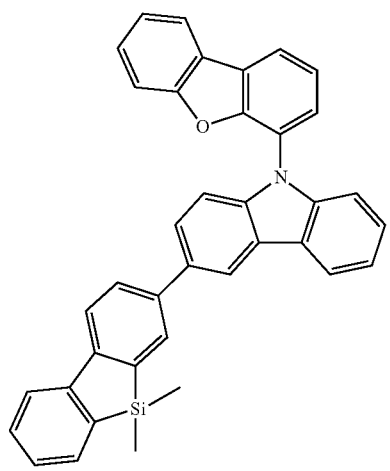
J-31
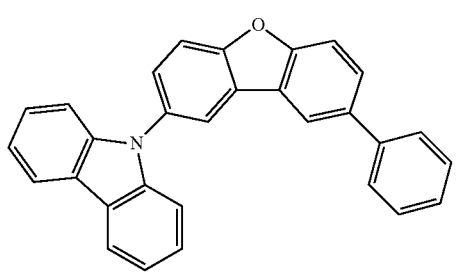
J-32
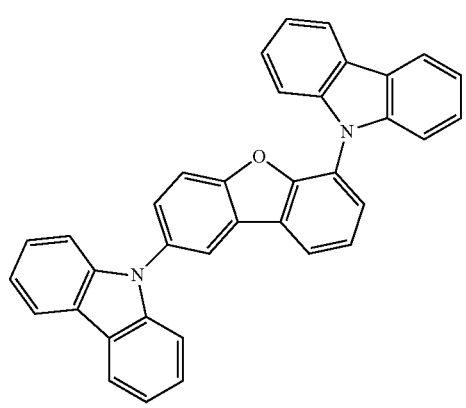
J-33
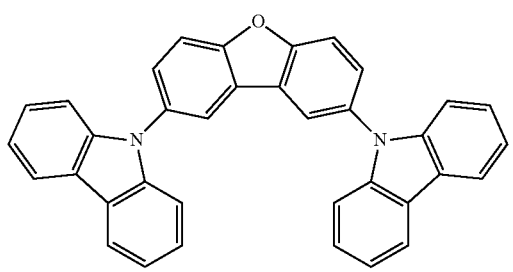
J-34
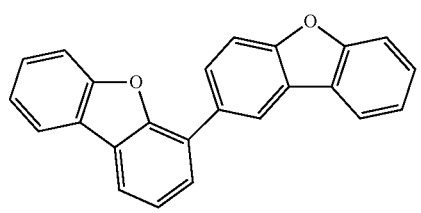
J-35
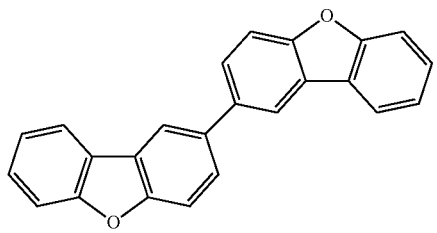
J-36
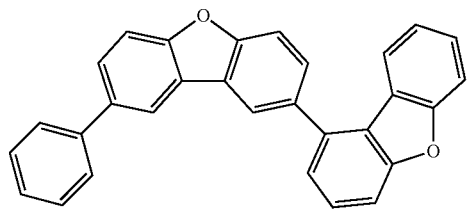

[Formula 103]
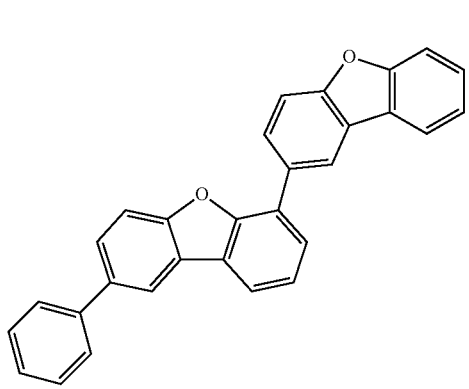
J-37
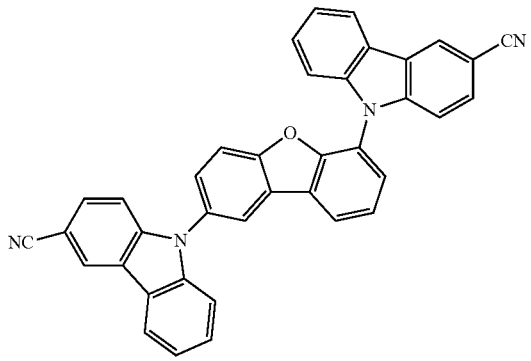
J-38
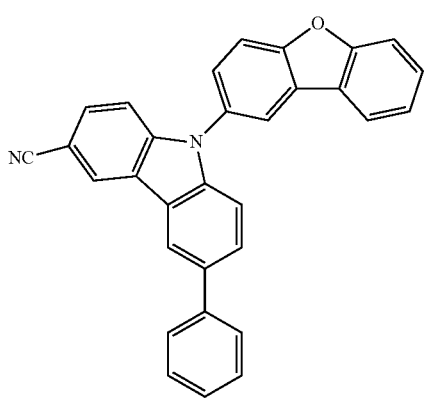
J-39
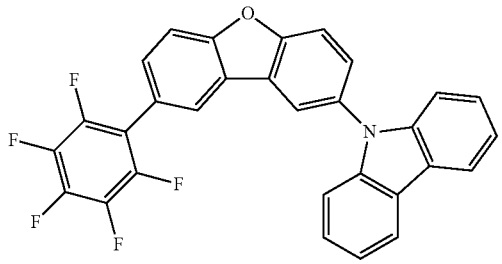
J-40
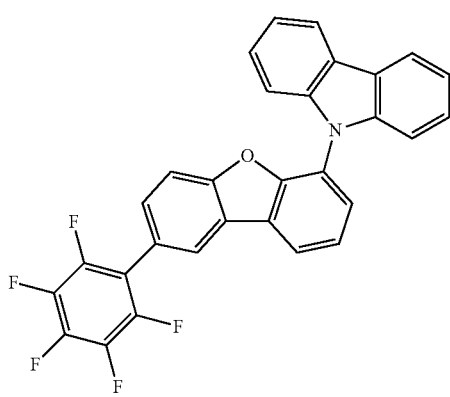
J-41
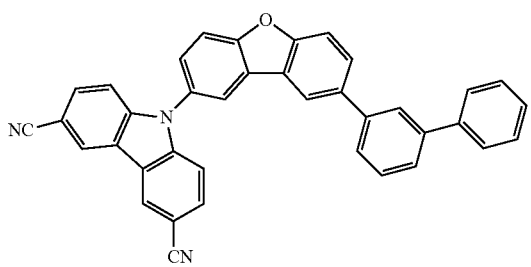
J-42

-continued
J-43
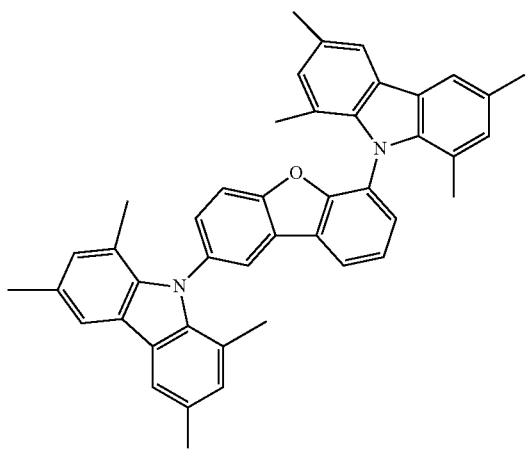
J-44
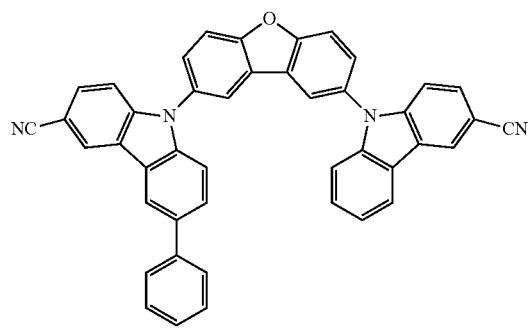
J-45
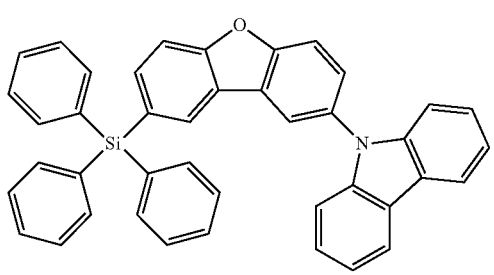
J-46
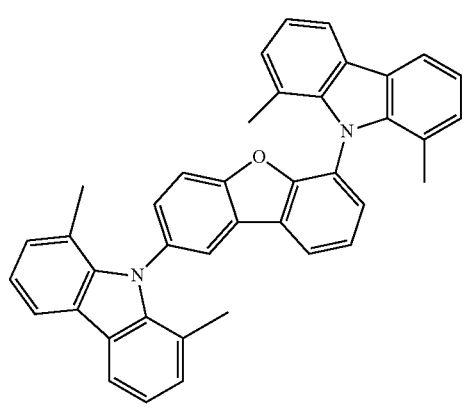
J-47
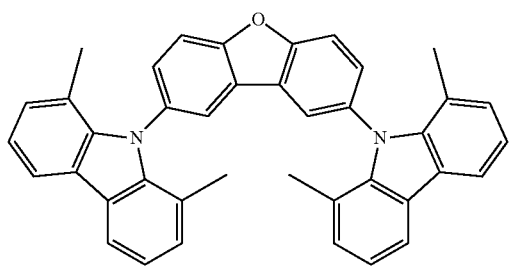
J-48
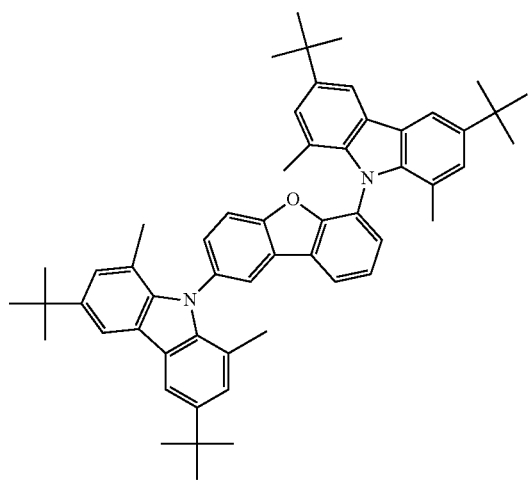
[Formula 104]
J-49
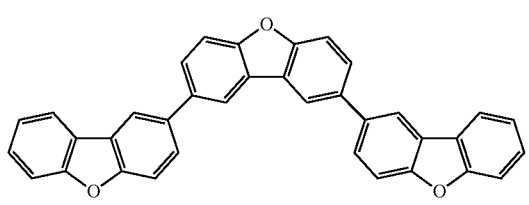
J-50
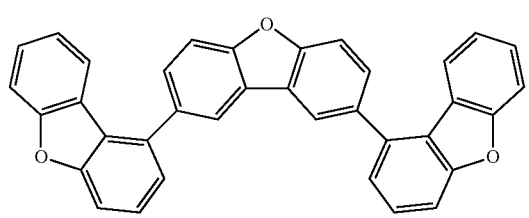

-continued
J-51
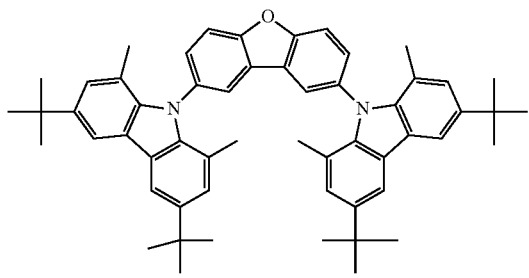
J-52
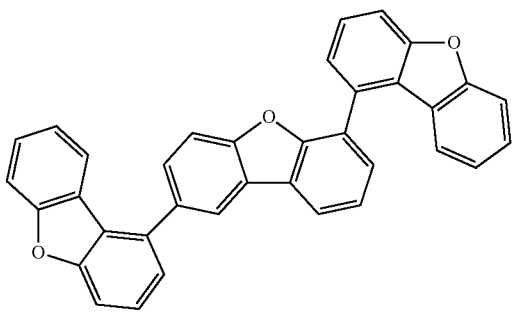
J-53
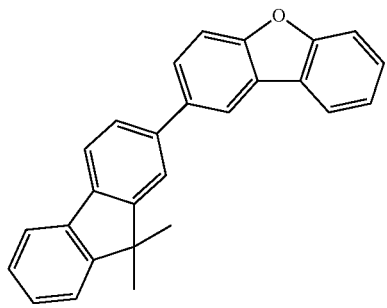
J-54
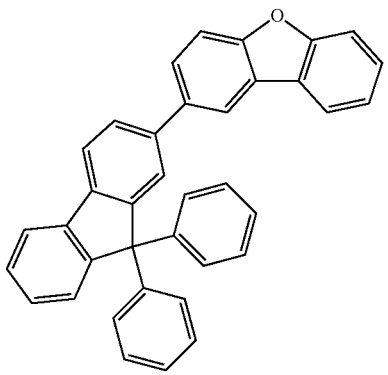
J-55
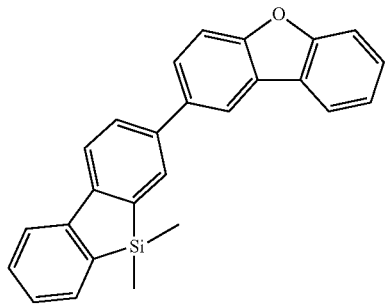
J-56
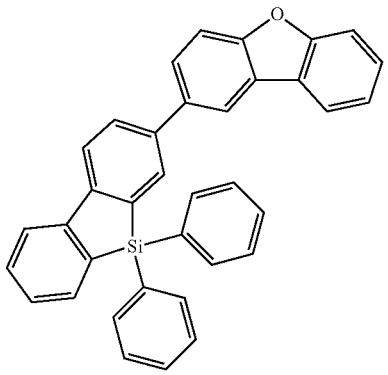
J-57
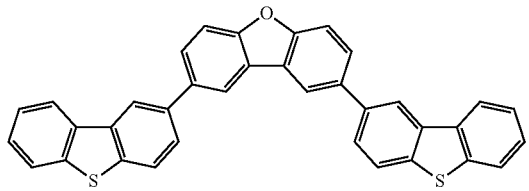
J-58
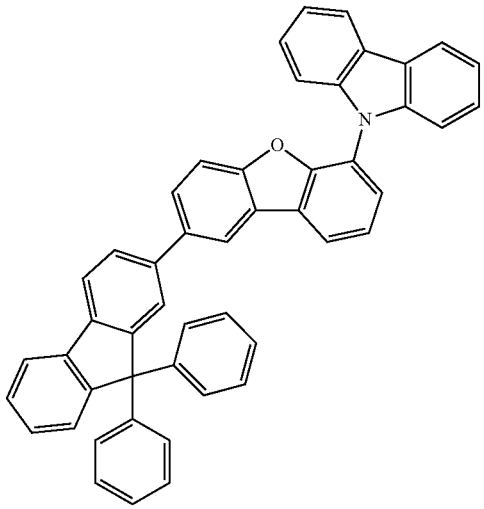

-continued
J-59
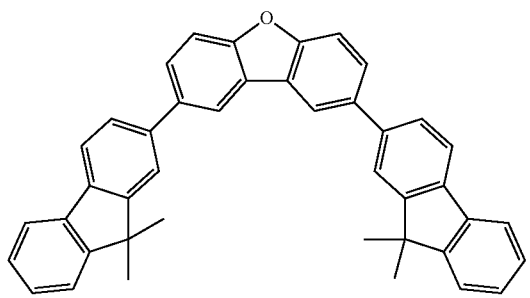
J-60
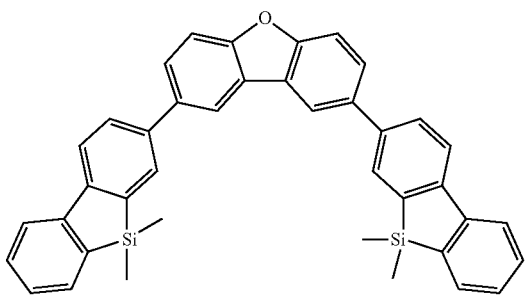
[Formula 105]
J-61
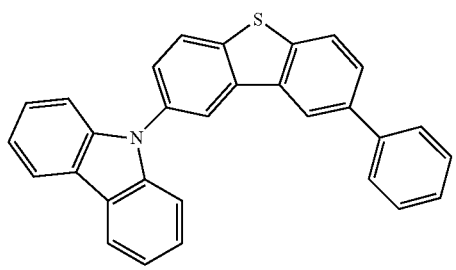
J-62
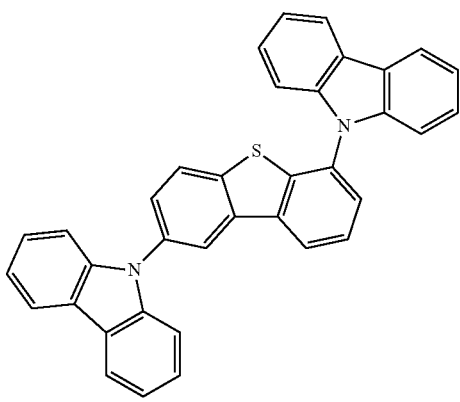
J-63
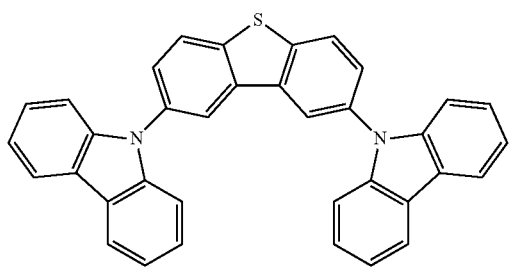
J-64
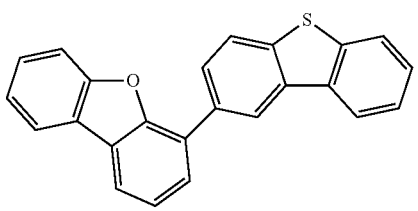
J-65
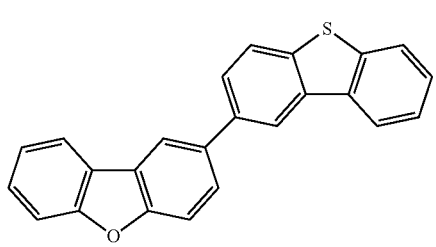
J-66
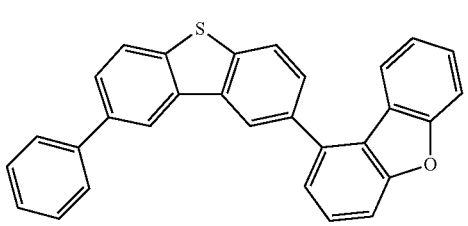

-continued
J-67
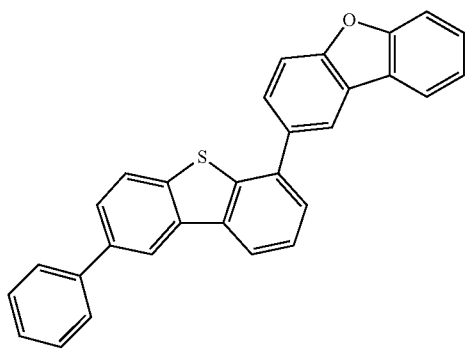
J-68
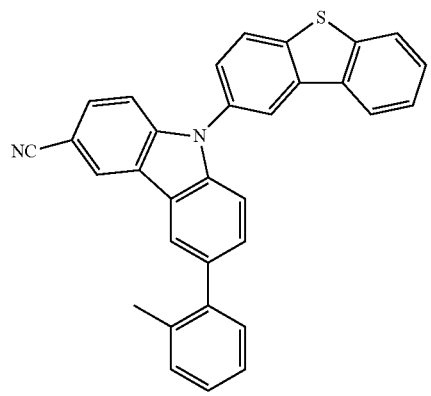
J-69
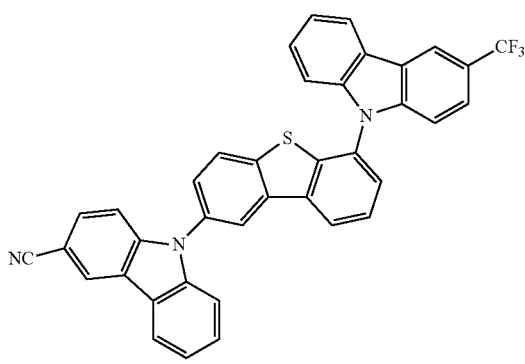
J-70
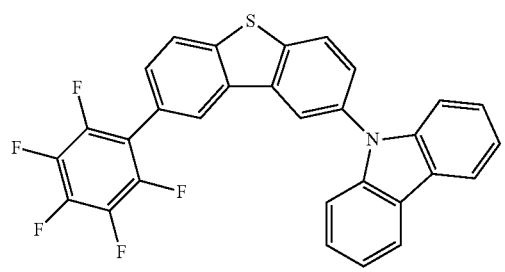
J-71
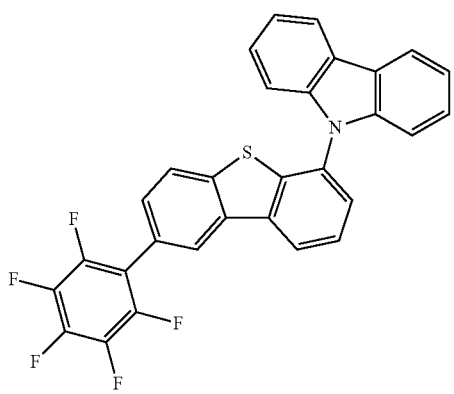
J-72
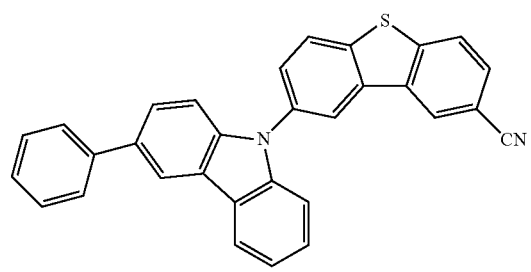
[Formula 106]
J-73
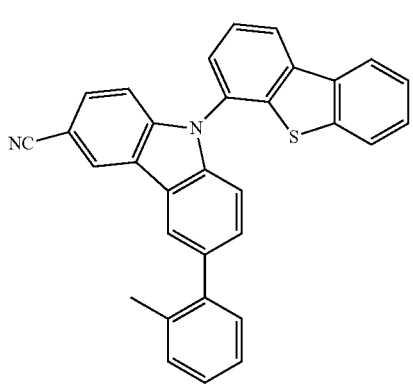
J-74
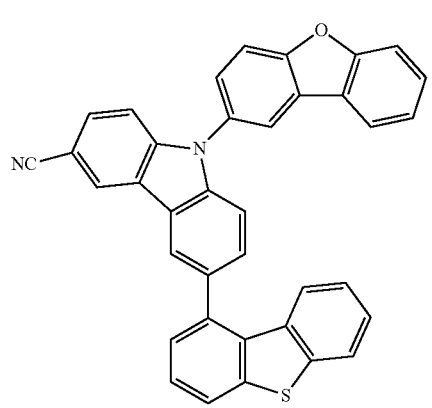

-continued
J-75
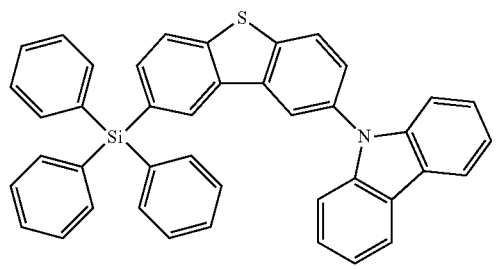
J-76
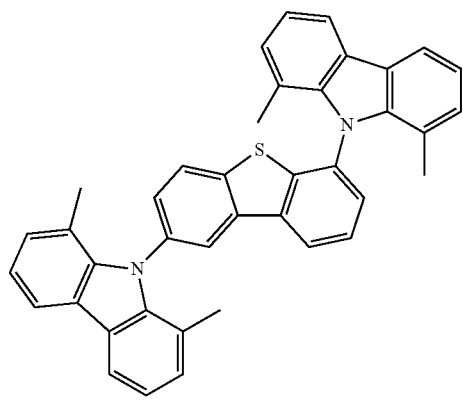
J-77
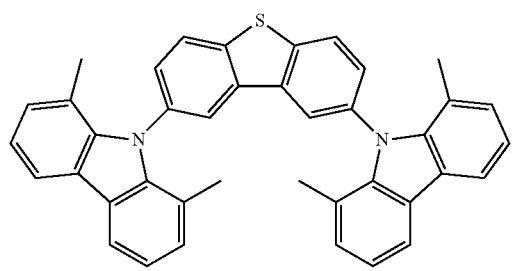
J-78
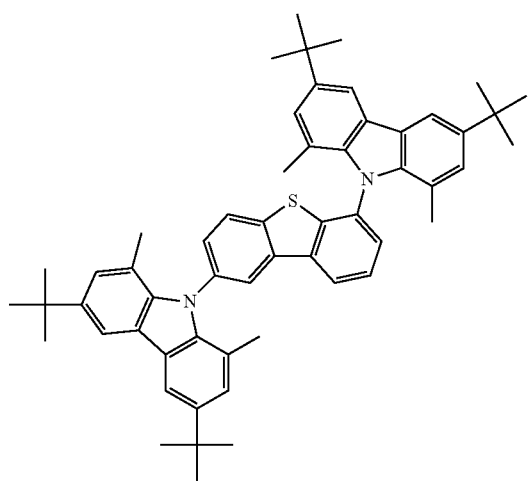
J-79
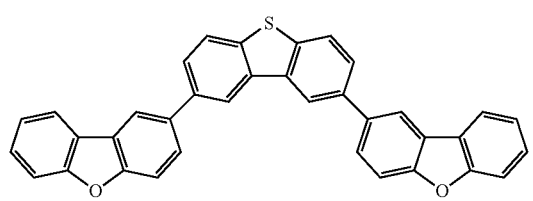
J-80
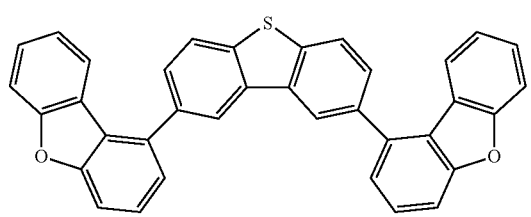
J-81
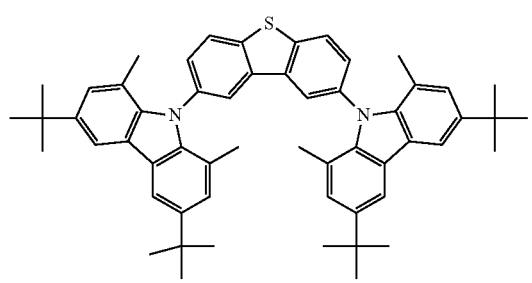
J-82
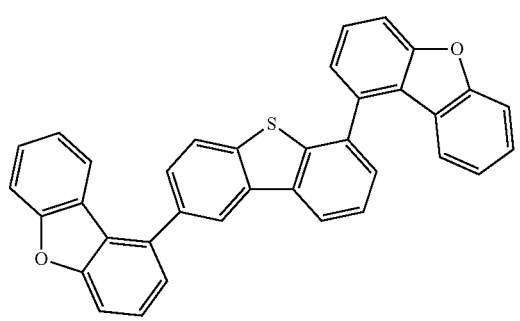

J-83
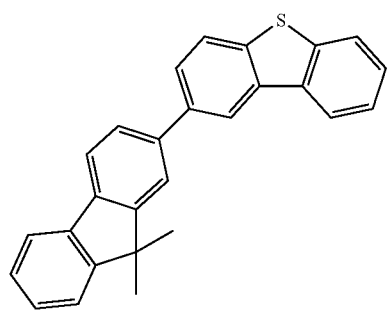
J-84
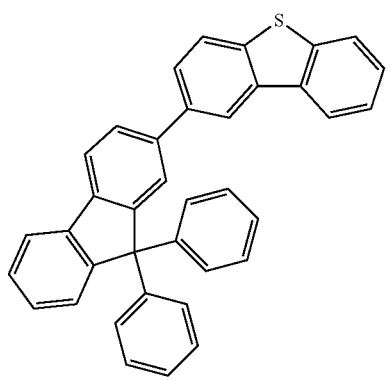
[Formula 107]
J-85
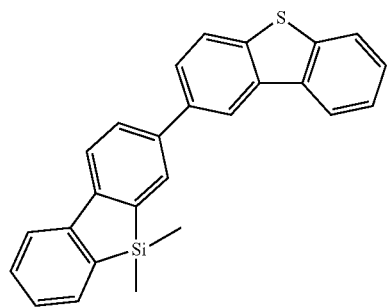
J-86
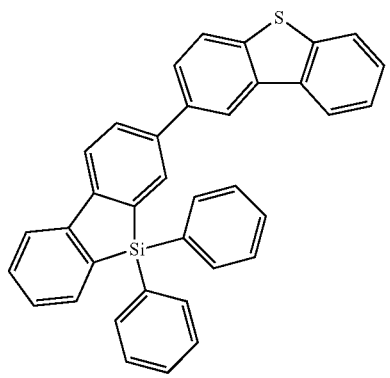
J-87
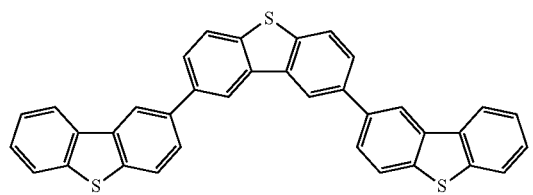
J-88
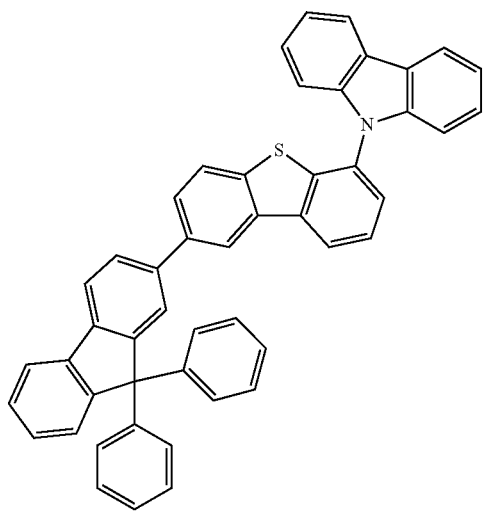
J-89
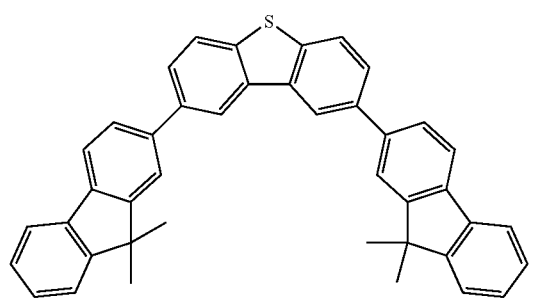
J-90
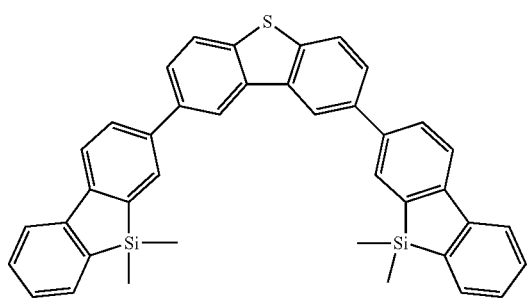

-continued
J-91
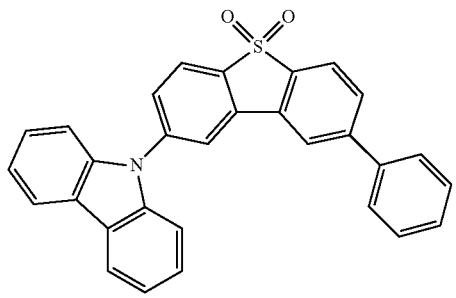
J-92
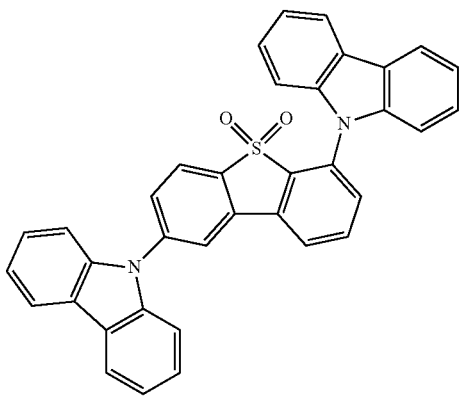
J-93
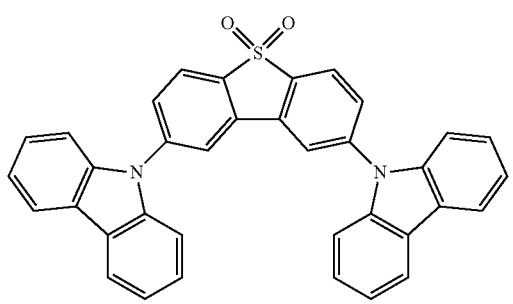
J-94
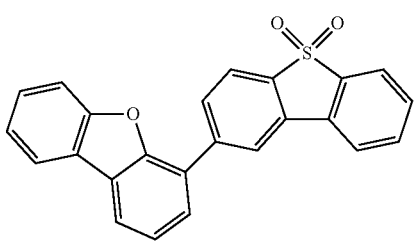
J-95
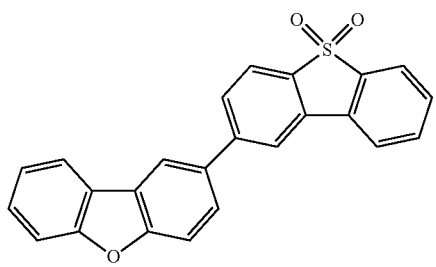
J-96
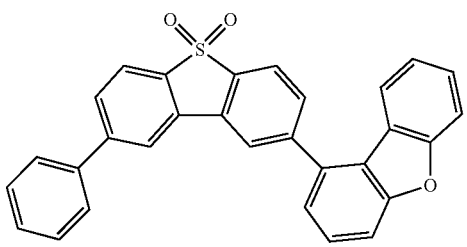
[Formula 108]
J-97
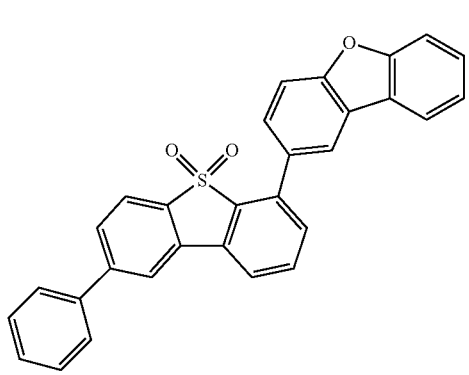
J-98
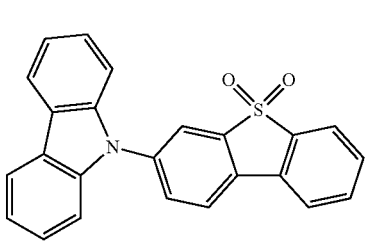
J-99
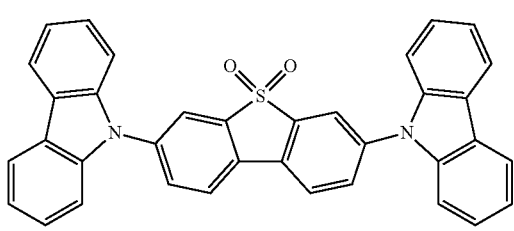
J-100
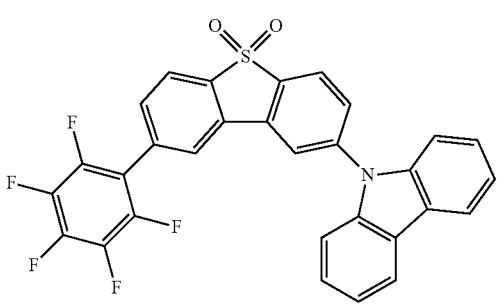

-continued
| J-101 | J-102 |
|---|---|
| 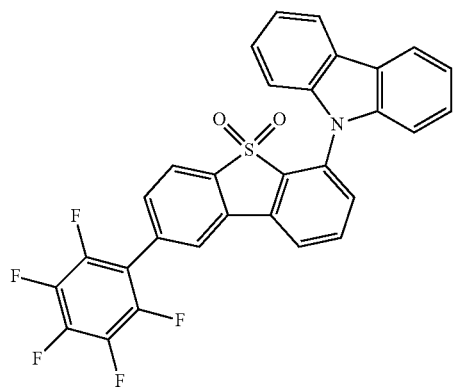 | 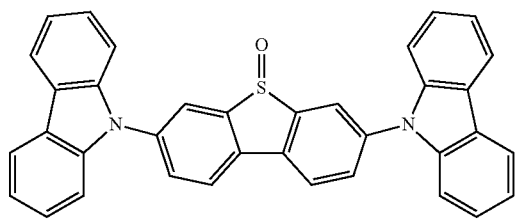 |
| J-103 | J-104 |
| 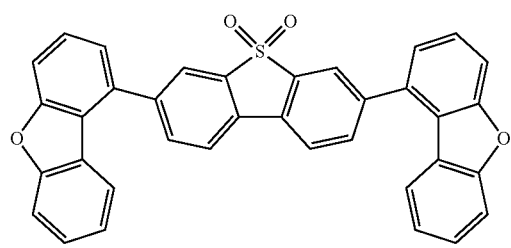 | 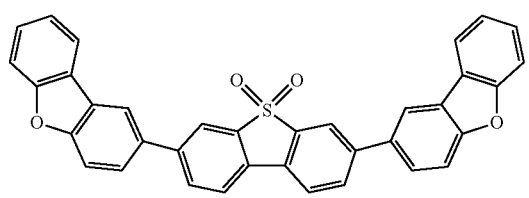 |
| J-105 | J-106 |
| 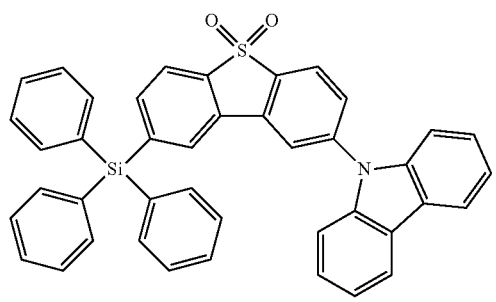 | 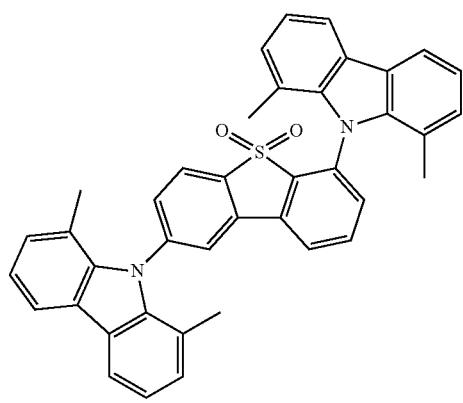 |
| J-107 | J-108 |
| 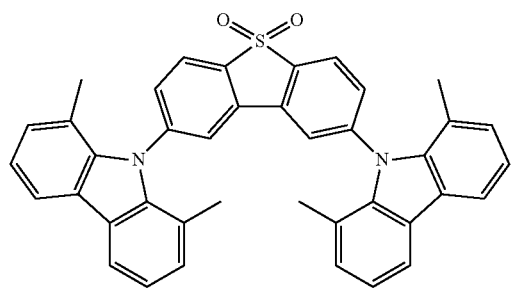 | 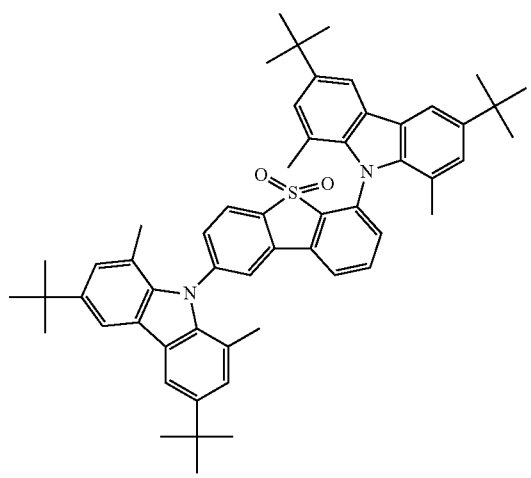 |

-continued
[Formula 109]
J-109
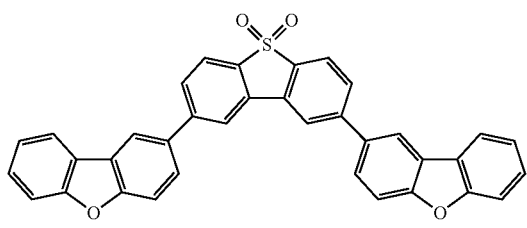
J-110
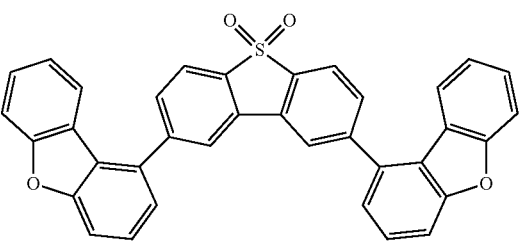
J-111
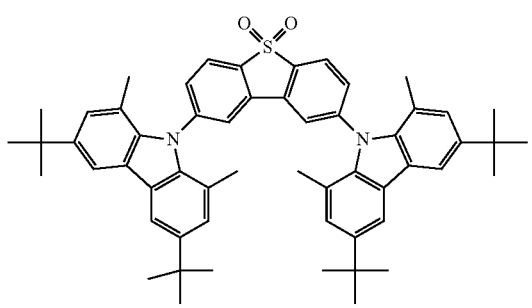
J-112
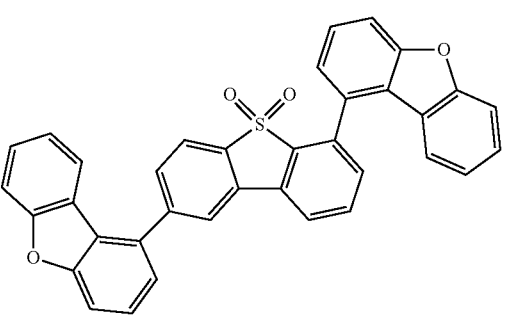
J-113
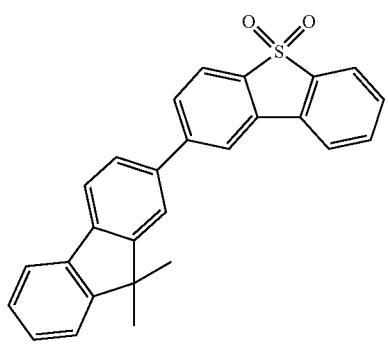
J-114
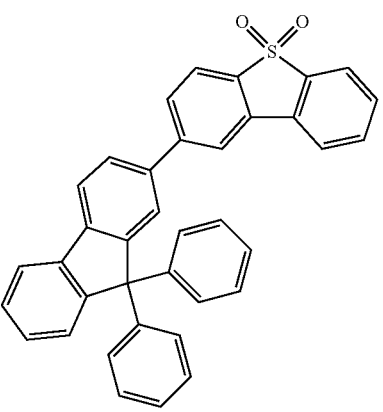
J-115
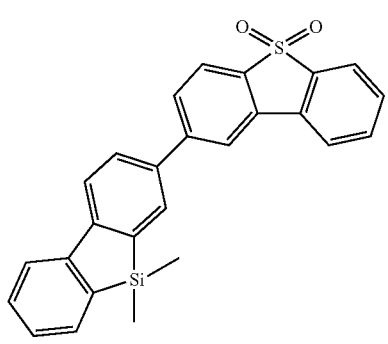
J-116
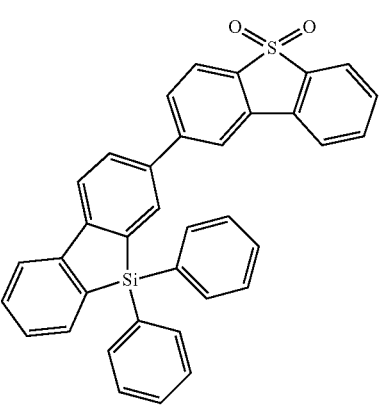

-continued
J-117
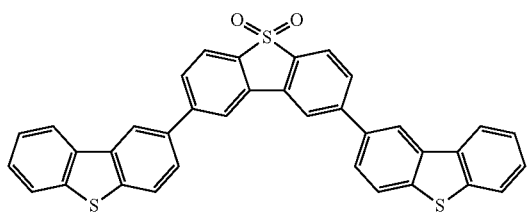
J-118
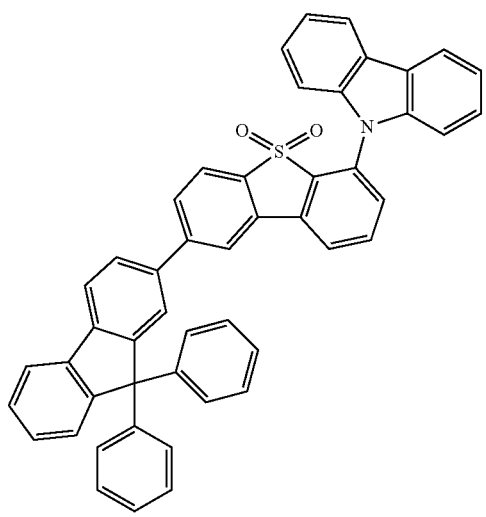
J-119
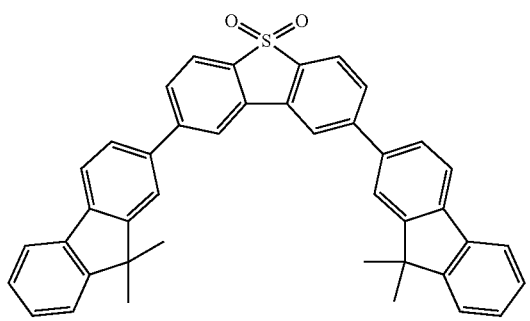
J-120
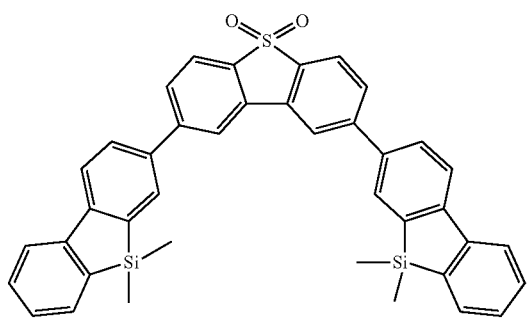
[Formula 110]
J-121
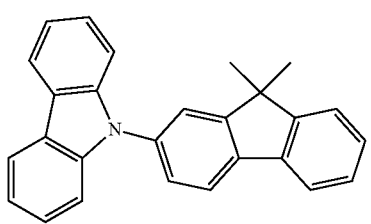
J-122
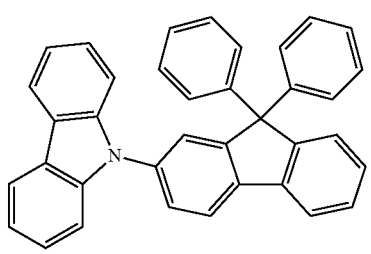
J-123
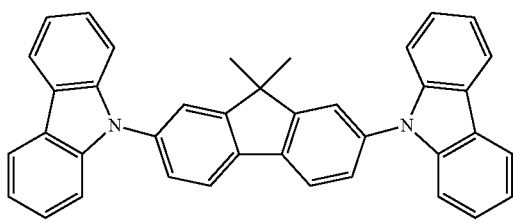
J-124
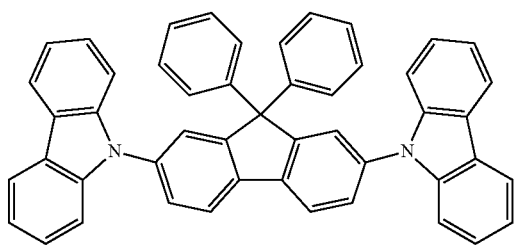

-continued
J-125
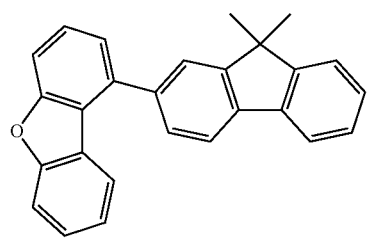
J-126
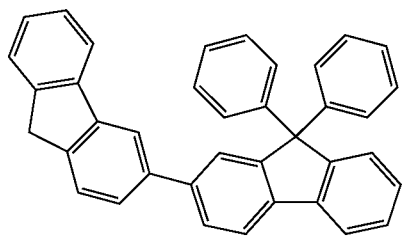
J-127
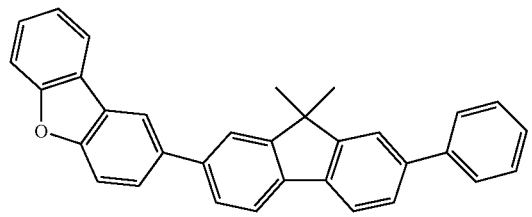
J-128
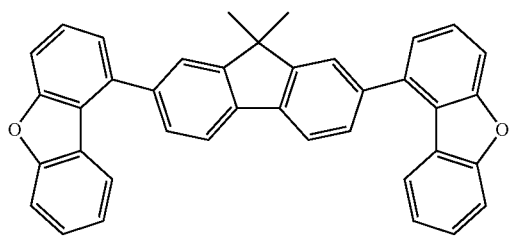
J-129
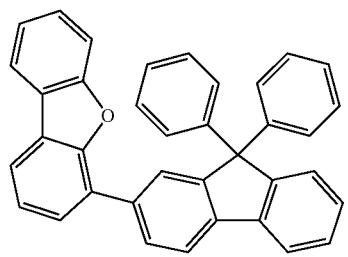
J-130
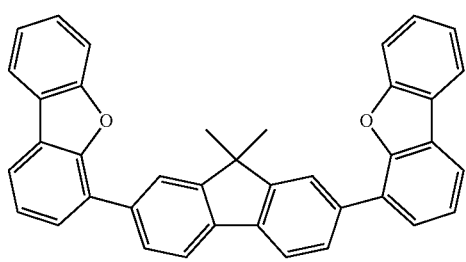
J-131
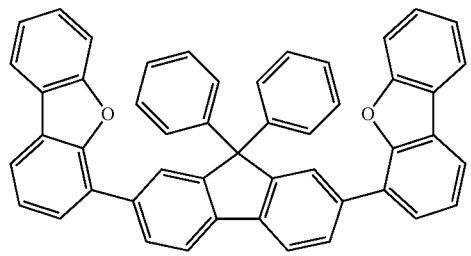
J-132
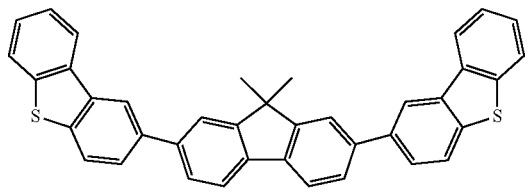
[Formula 111]
J-133
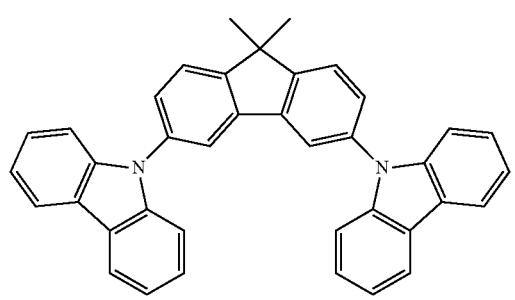
J-134
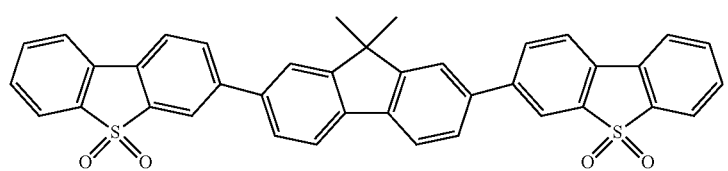

-continued
J-135
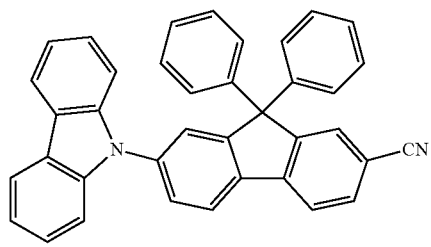
J-136
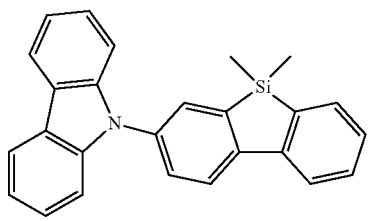
J-137
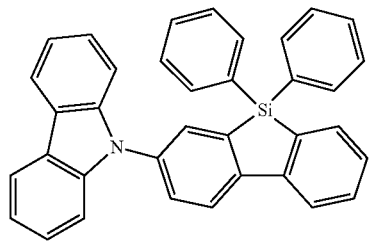
J-138
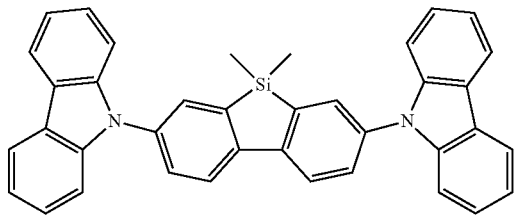
J-139
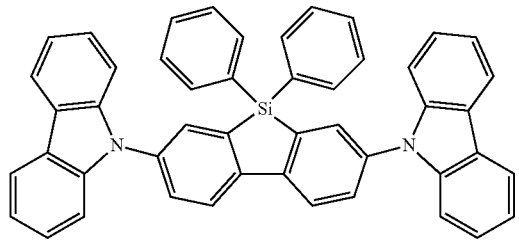
J-140
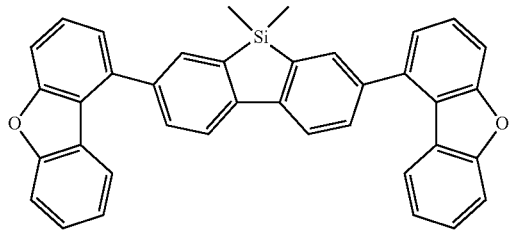
J-141
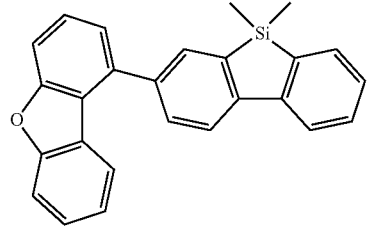
J-142
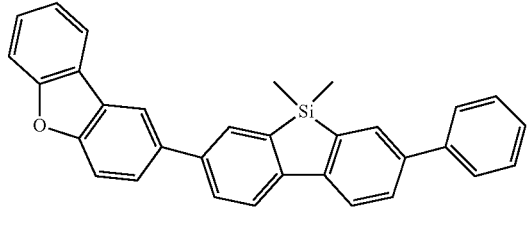
J-143
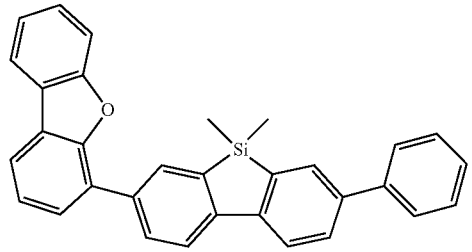
J-144
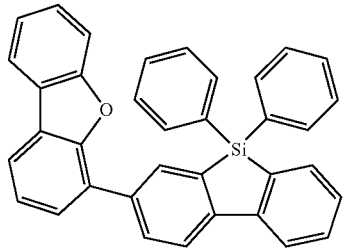
[Formula 112]
J-145
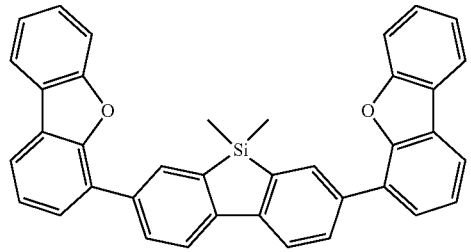
J-146
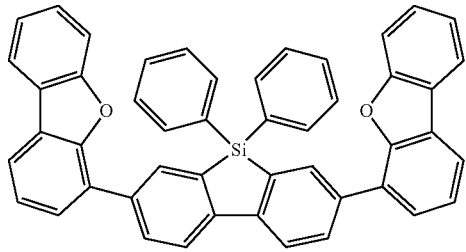

-continued
J-147
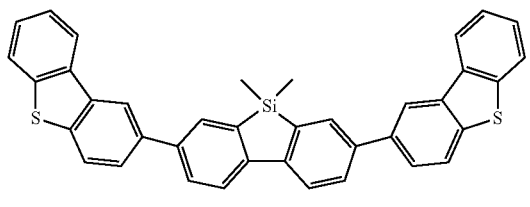
J-148
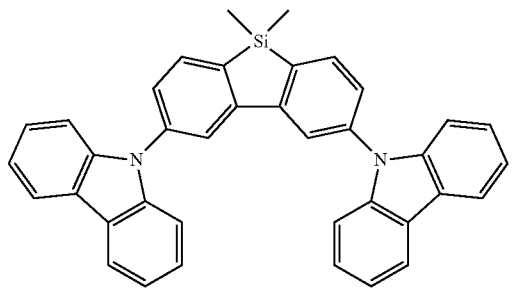
J-149
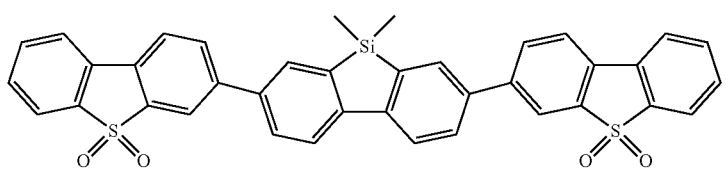
J-150
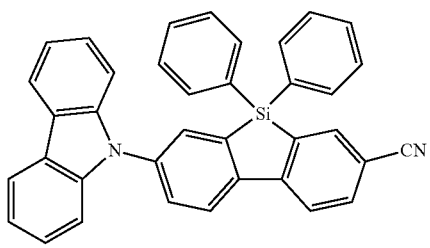
J-151
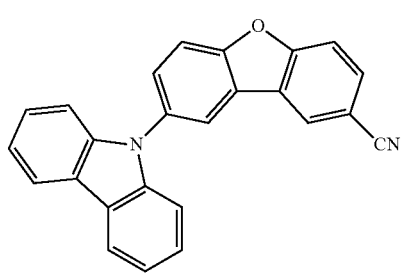
J-152
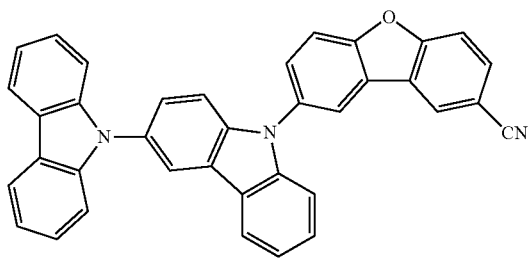
J-153
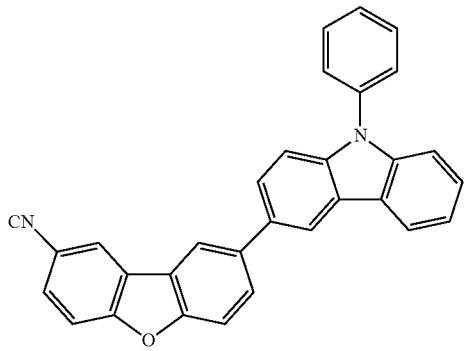
J-154
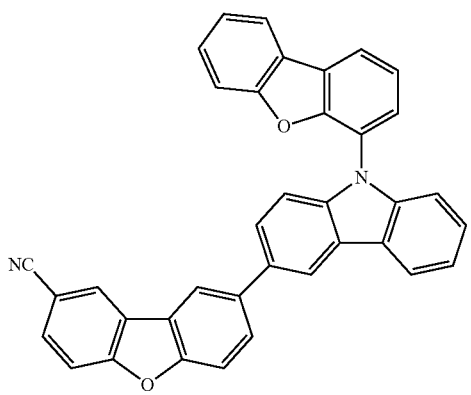
J-155
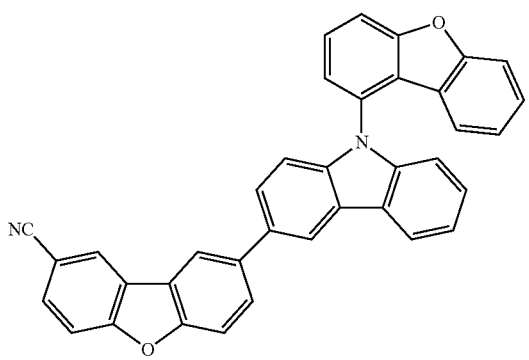

-continued
J-156
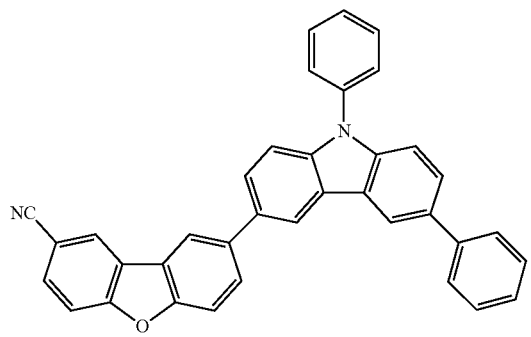
[Formula 113]
J-157
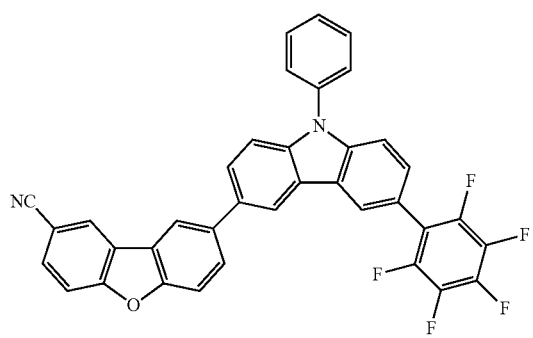
J-158
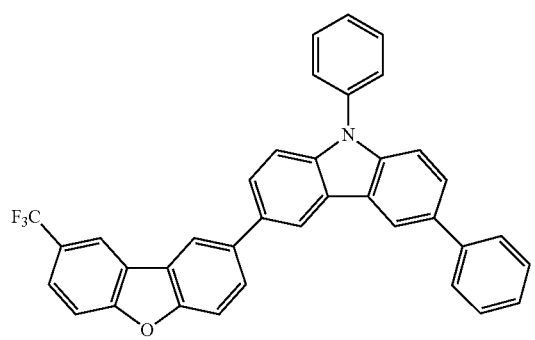
J-159
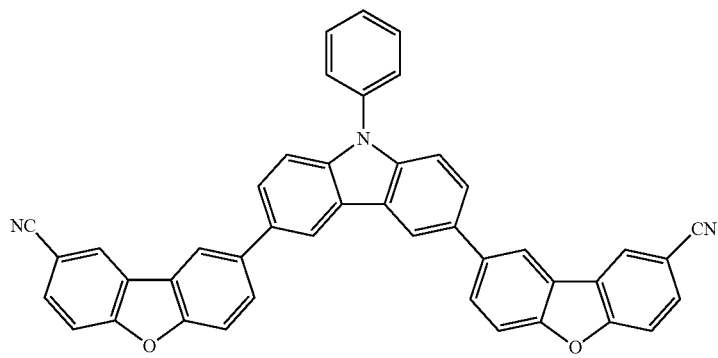
J-160
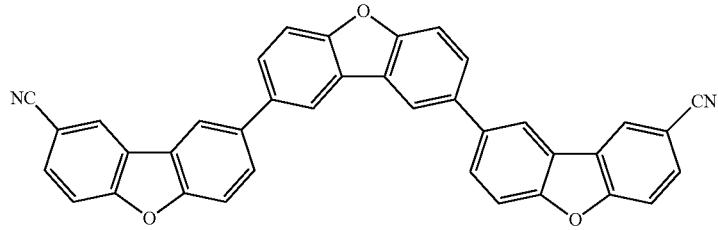
J-161
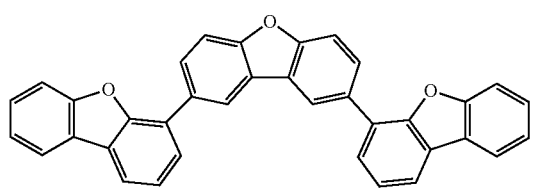
J-162
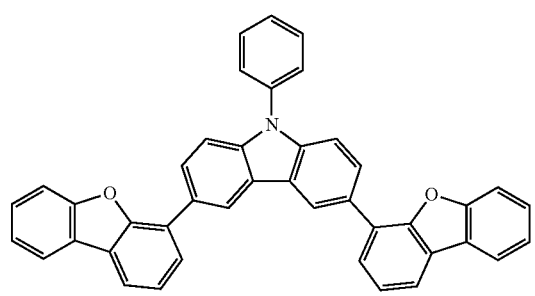

-continued
J-163
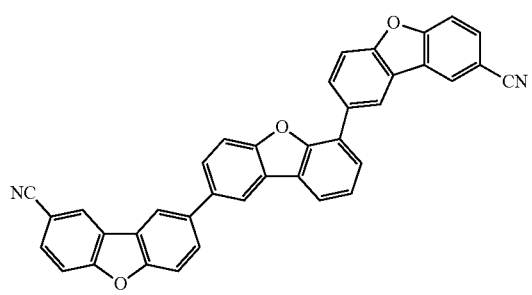
J-164
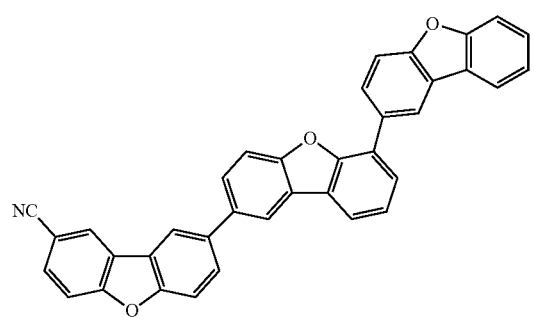
J-165
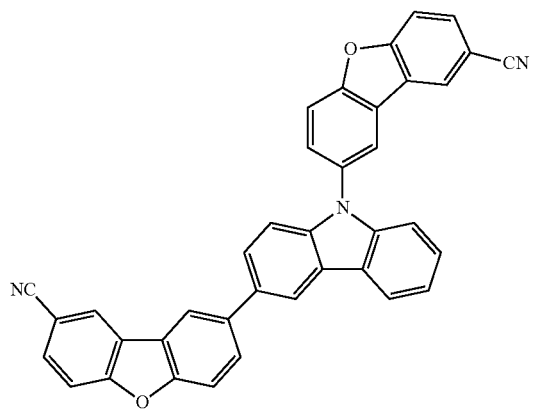
J-166
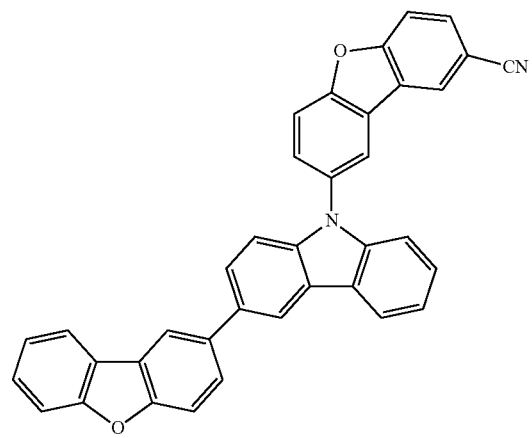
J-167
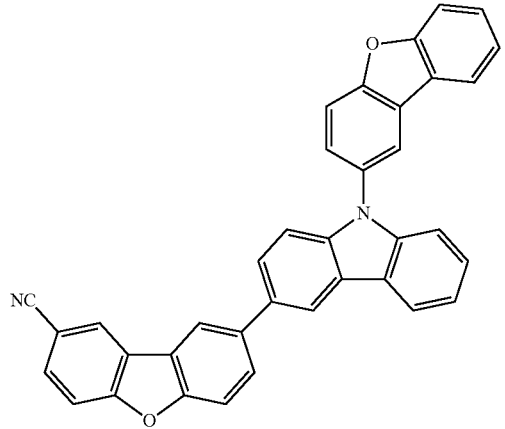
J-168
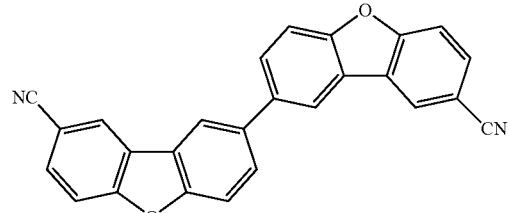

[Formula 114]
J-169 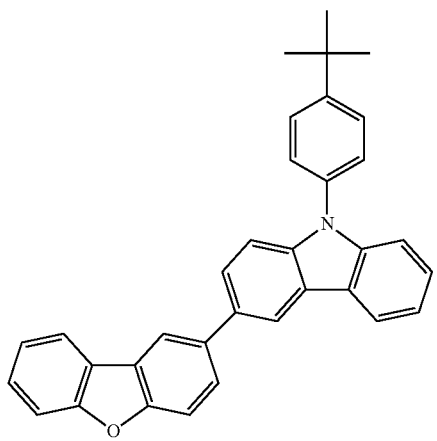
J-170 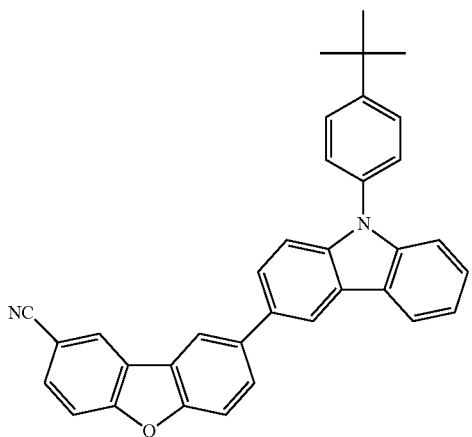
J-171 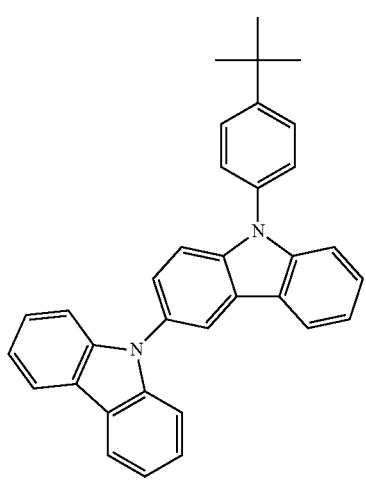
J-172 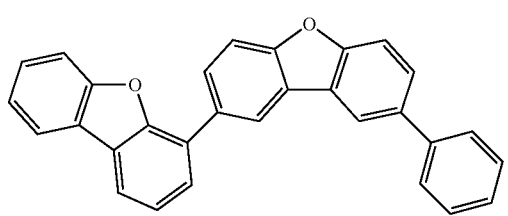
J-173 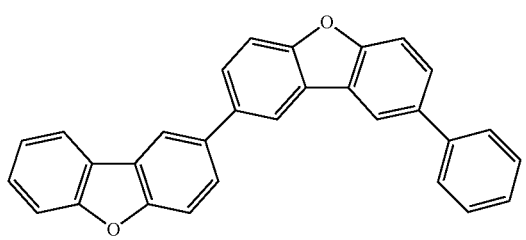
J-174 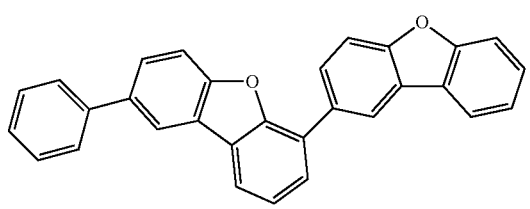
J-175 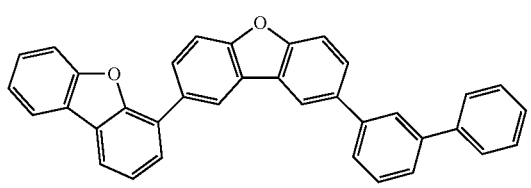
J-176 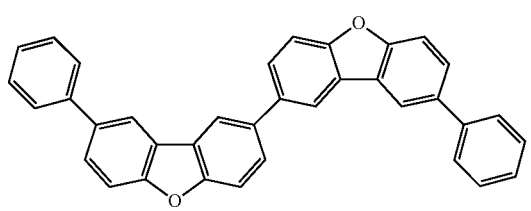
J-177 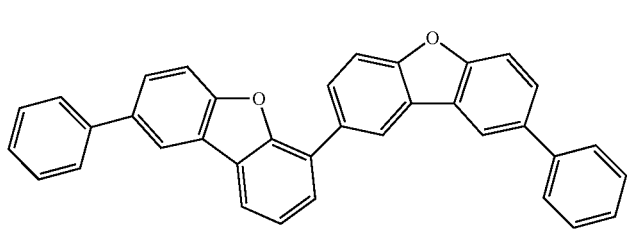

[Formula 115]
J-178
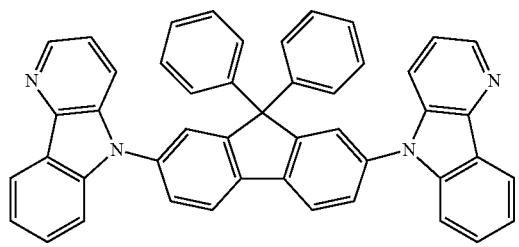
J-179
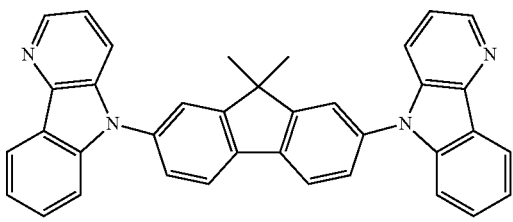
J-180
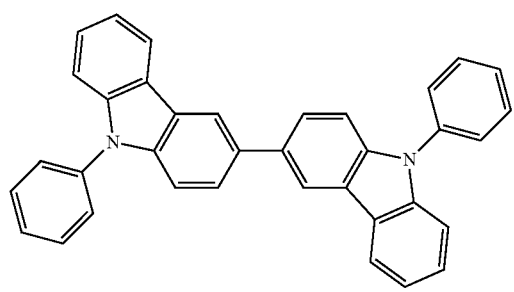
J-181
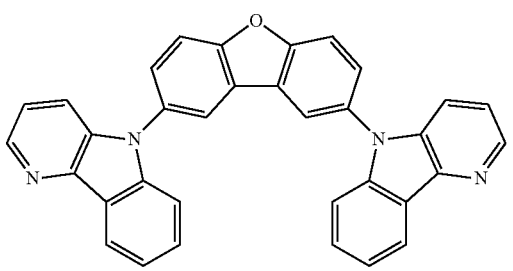
J-182
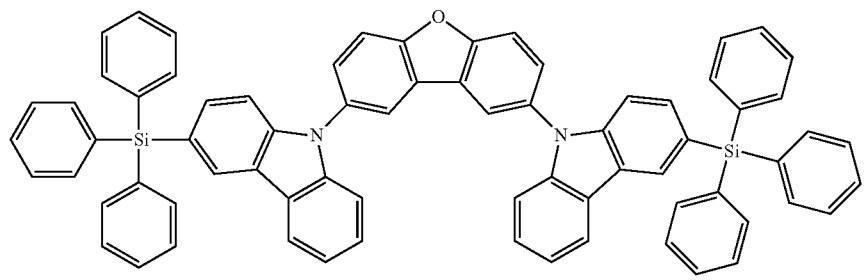
J-183
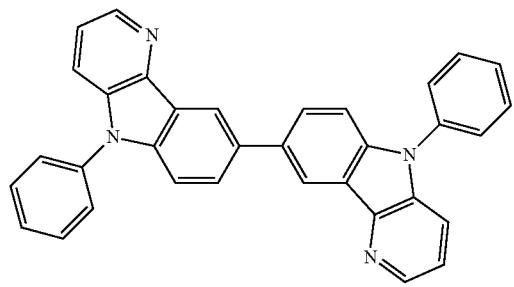
J-184
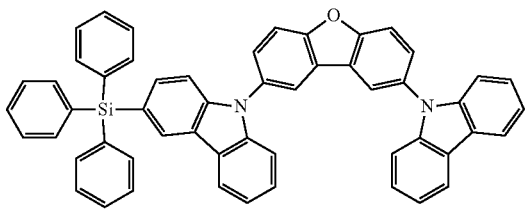

-continued
J-185
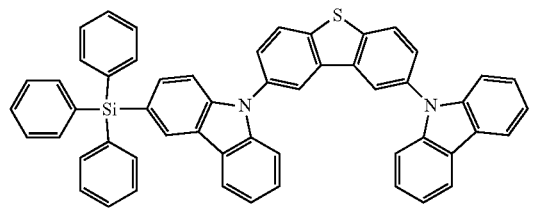
J-186
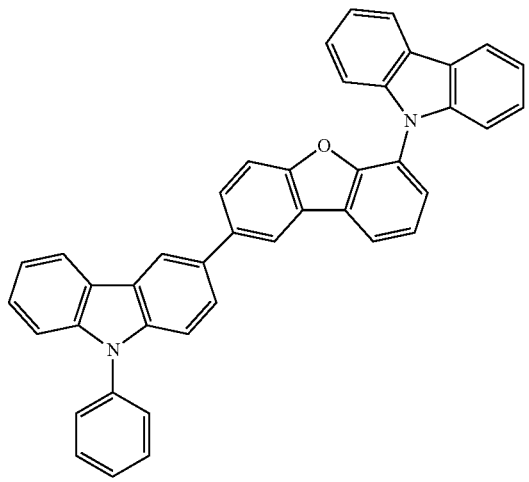
J-187
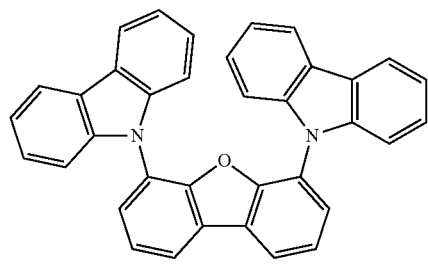
J-188
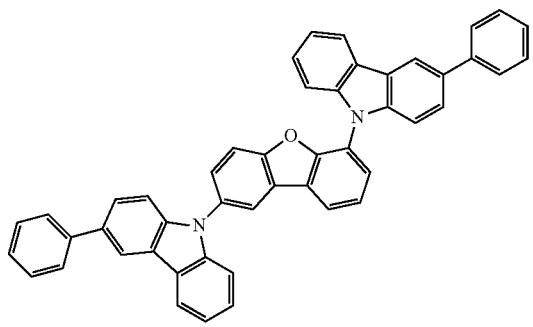
J-189
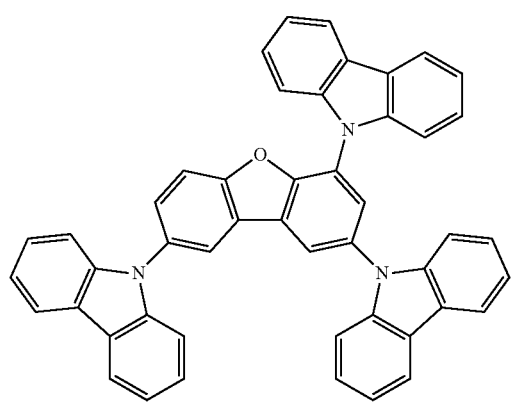

[Formula 116]
J-190
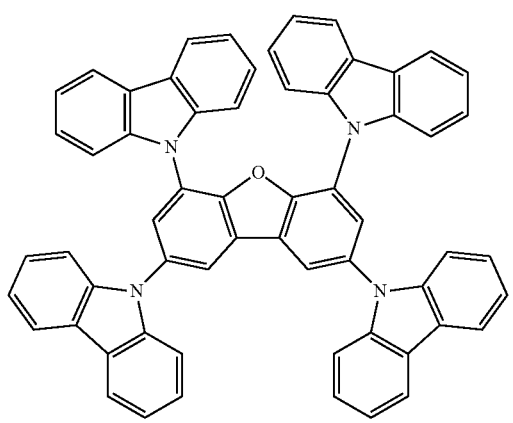
J-191
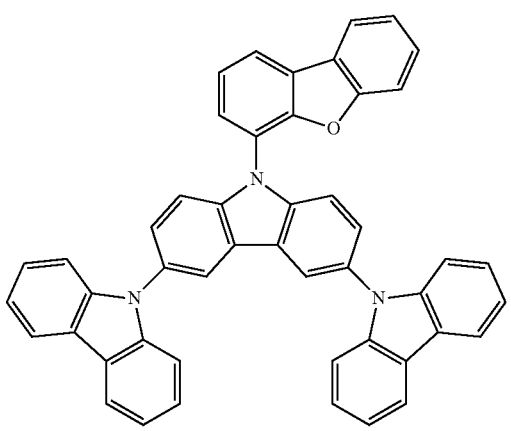
J-192
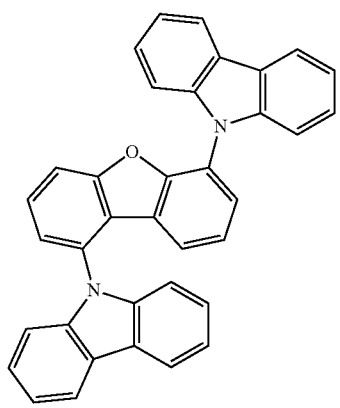
J-193
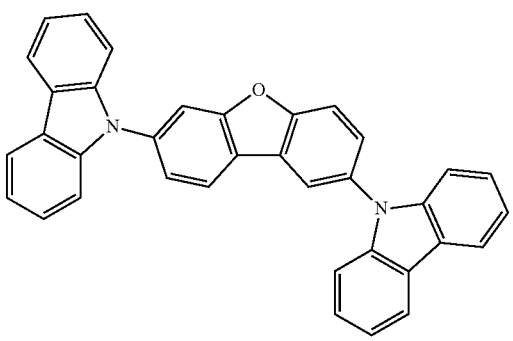
J-194
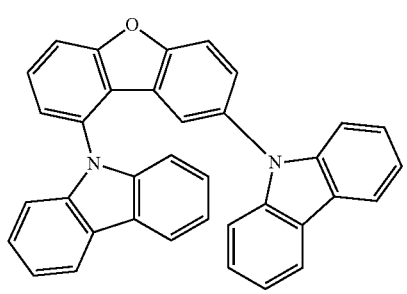
J-195
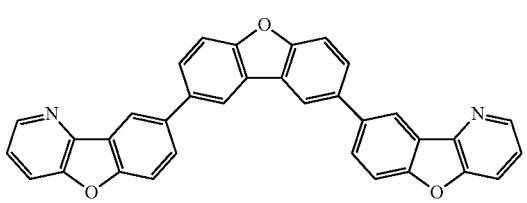
J-196
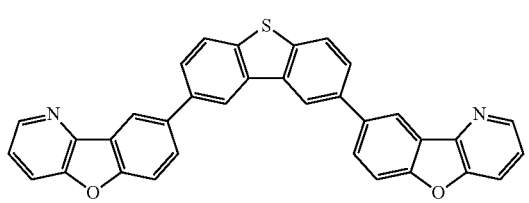
J-197
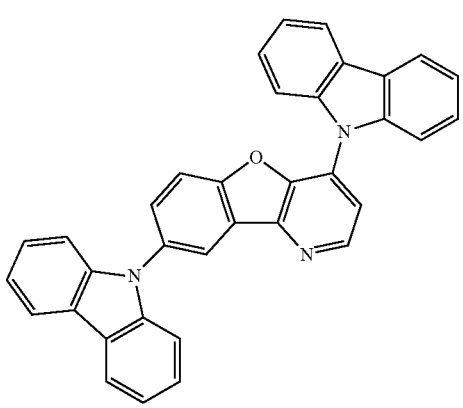

-continued
J-198
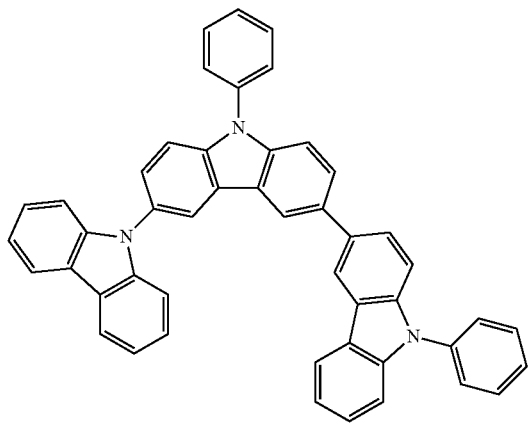
J-199
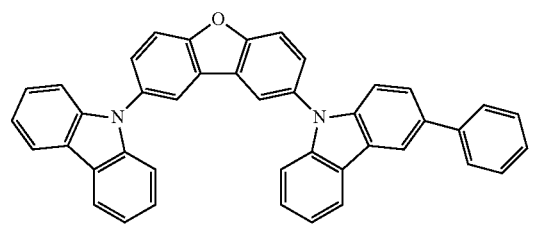
J-200
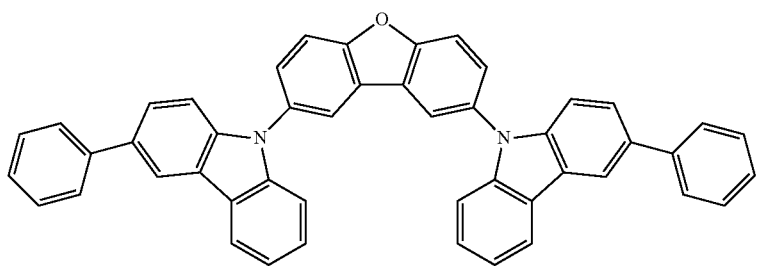
J-201
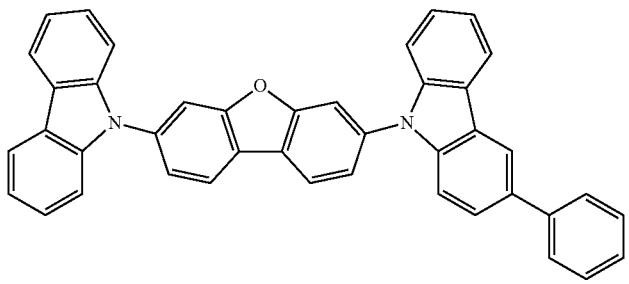
[Formula 117]
J-202
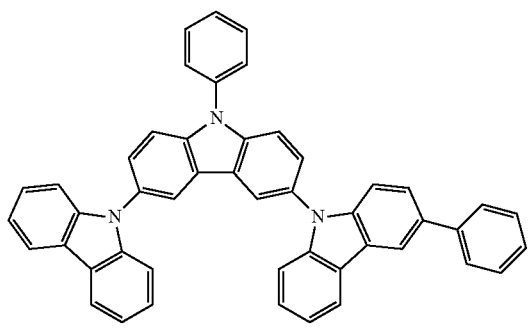
J-203
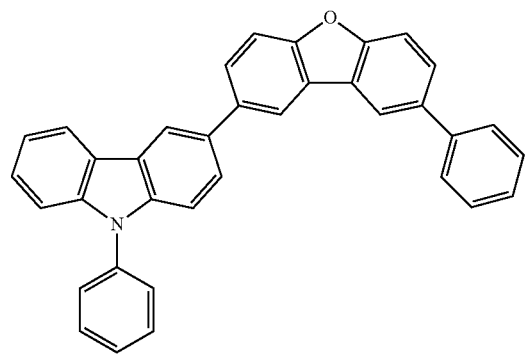

J-204
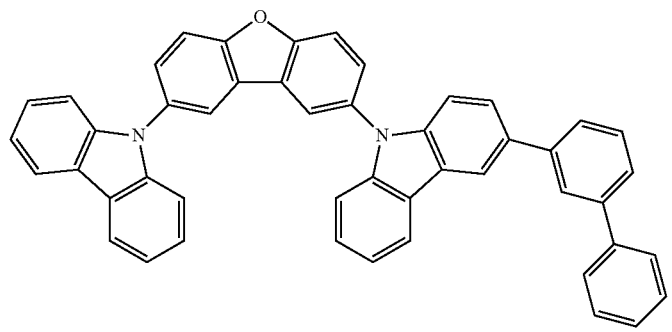
J-205
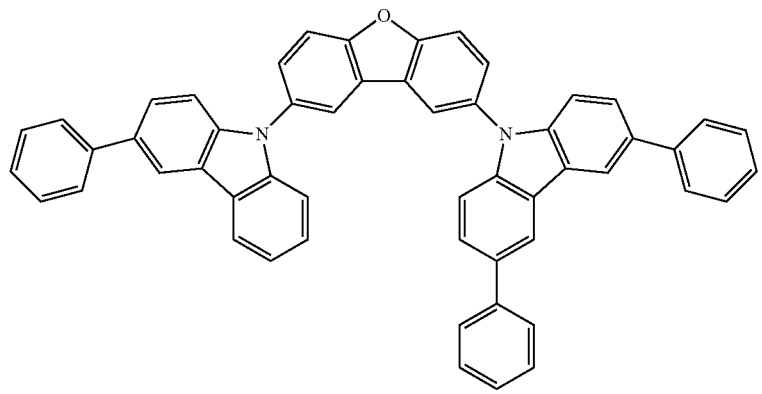
J-206
J-207
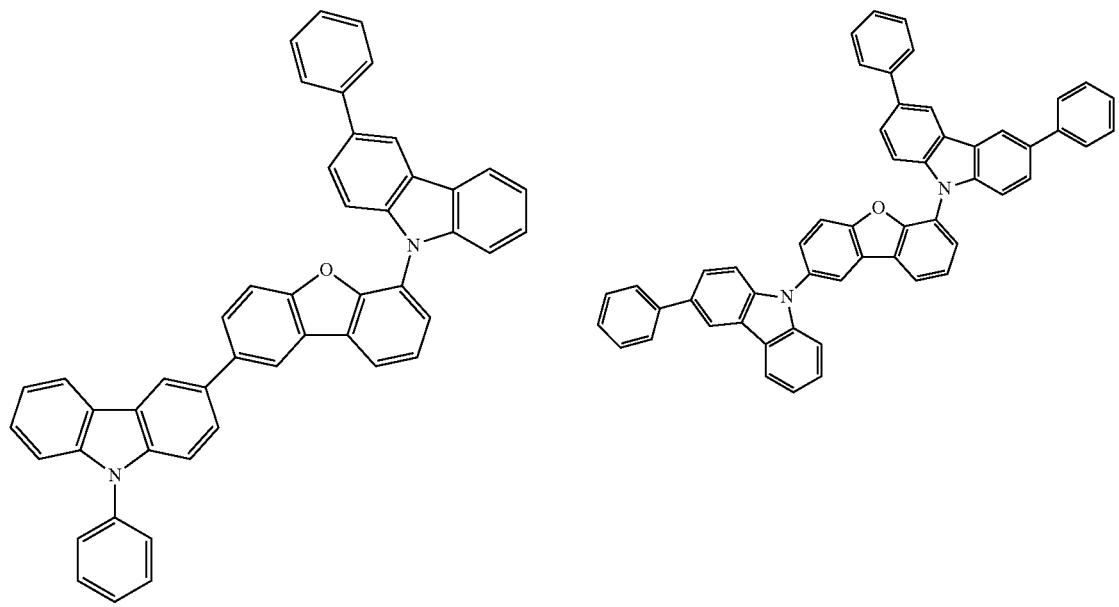

-continued
J-208
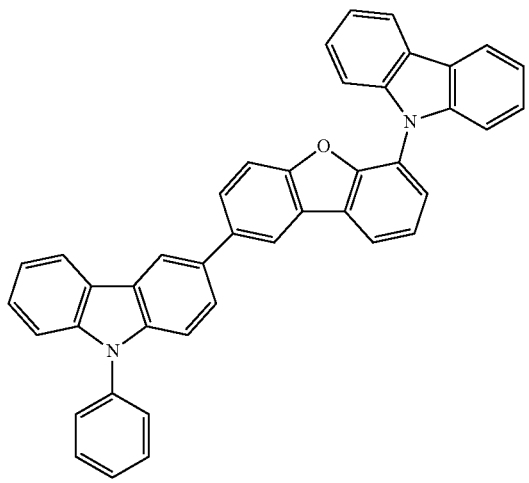
J-209
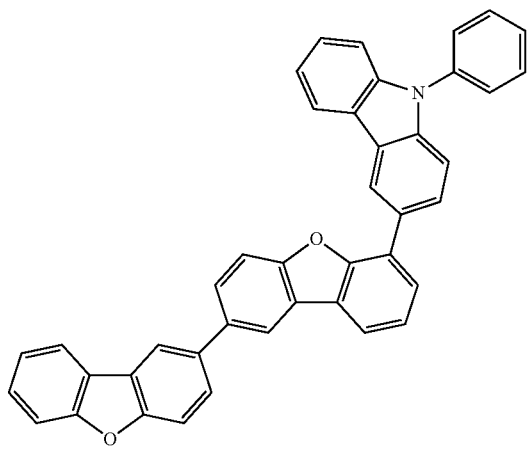
J-210
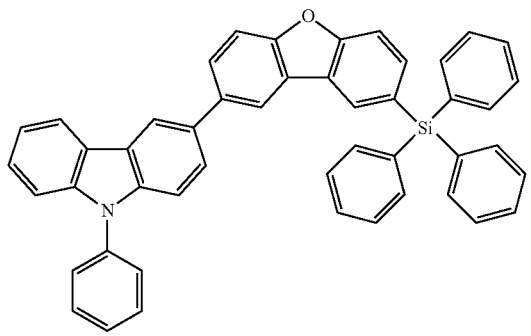
J-211
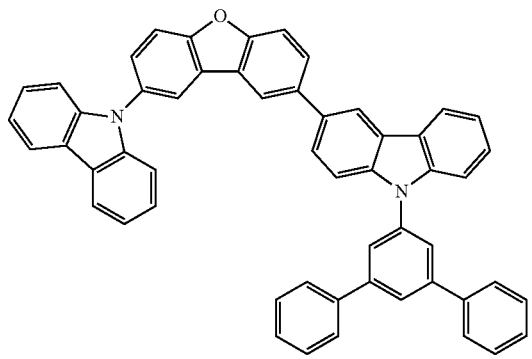
J-212
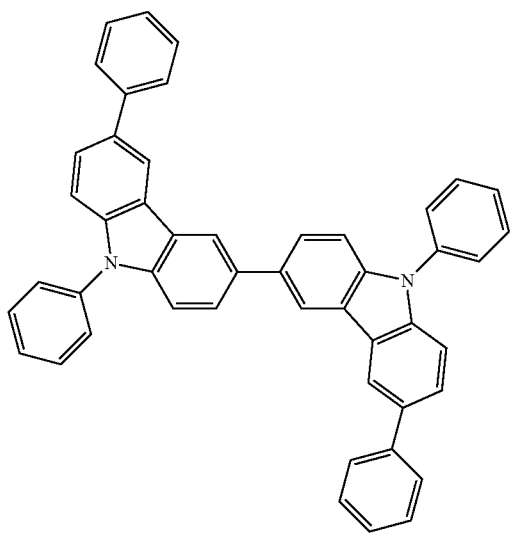
J-213
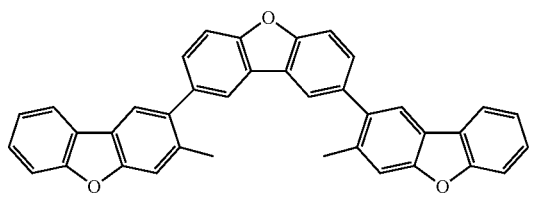

-continued
J-214
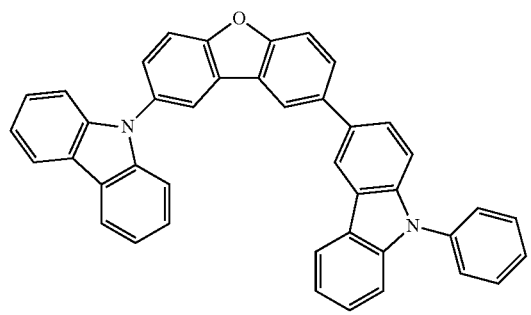
J-215
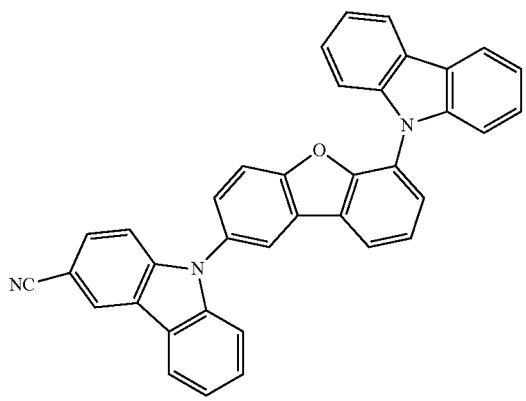
J-216
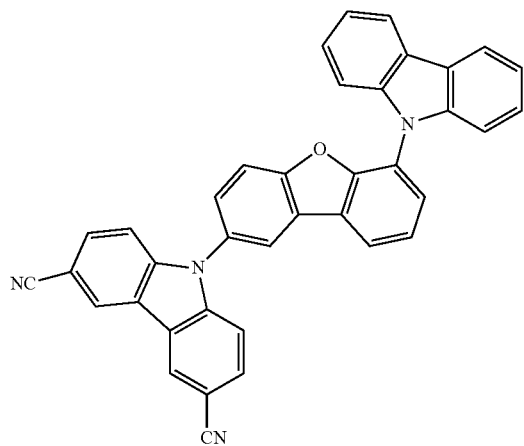
J-217
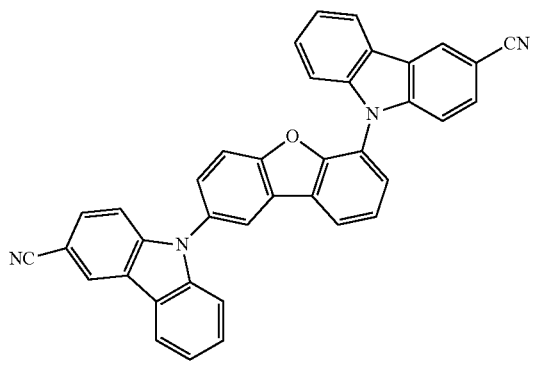
J-218
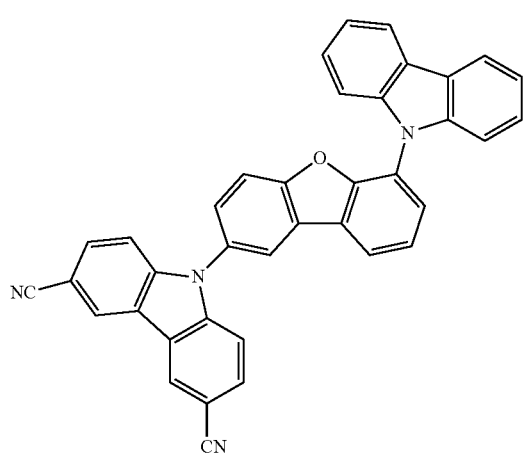

<<Electron Transport Layer>>

An electron transport layer in the present invention is only required to be composed of a material having a function of transporting an electron and have a function of transferring an injected electron from a cathode to a light-emitting layer.

A total layer thickness of the electron transport layer according to the present invention is not particularly limited. The total thickness is usually in the range of 2 nm to 5 μm, preferably in the range of 2 to 500 nm, more preferably in the range of 5 to 200 nm.

In an organic EL element, it is known that, at the moment of extracting light produced in the light-emitting layer from the electrode, there occurs interference between light directly extracted from the light-emitting layer and light extracted after reflected at the electrode located at the opposite side of the electrode from which the light is extracted. When light is reflected at the cathode, it is possible to use effectively this interference effect by suitably adjusting the total thickness of the electron transport layer in the range of several nm to several μm.

On the other hand, the voltage will be increased when the layer thickness of the electron transport layer is made thick. Therefore, especially when the layer thickness is large, the electron mobility in the electron transport layer is preferably $10^{-5}$ cm$^2$/Vs or more.

As a material used for an electron transport layer (hereinafter, referred to as an electron transport material), it is only required to have either a property of injecting or transporting electrons or a barrier property against holes. Any of the conventionally known compounds can be selected and used.

Examples of the material include nitrogen-containing aromatic heterocycle derivatives (carbazole derivatives, azacarbazole derivatives (formed such that one or more carbon atoms of a carbazole ring are substituted by a nitrogen atom(s)), pyridine derivatives, pyrimidine derivatives, pyrazine derivatives, pyridazine derivatives, triazine derivatives, quinoline derivatives, quinoxaline derivatives, phenanthroline derivatives, azatriphenylene derivatives, oxazole derivatives, thiazole derivatives, oxadiazole derivatives, thiadiazole derivatives, triazole derivatives, benzimidazole derivatives, benzoxazole derivatives, and benzothiazole derivatives), dibenzofuran derivatives, dibenzothiophene derivatives, silole derivatives, and aromatic hydrocarbon ring derivatives (naphthalene derivatives, anthracene derivatives, and triphenylene derivatives).

Further, metal complexes each having a ligand of a quinolinol skeleton or dibnenzoquinolinol skeleton such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum, bis(8-quinolinol)zinc (Znq) and the like; and metal complexes each formed such that central metal of each of the above metal complexes is substituted by In, Mg, Cu, Ca, Sn, Ga, or Pb can also be used as an electron transport material.

Further, metal-free or metal phthalocyanine, or a phthalocyanine derivative whose terminal is substituted by an alkyl group, sulfonic acid group or the like can be preferably utilized as an electron transport material. In addition, a distyrylpyradine derivative which was cited as a light emitting material can be used as an electron transport material. Similarly to the case of a hole injection layer and to the case of a hole transfer layer, an inorganic semiconductor such as an n-type-Si and n-type-SiC can be also utilized as an electron transport material.

Polymer materials, in which these materials are introduced in a polymer chain or these materials form the main chain of a polymer, can be also utilized.

In the electron transport layer according to the present invention, the electron transport layer may be doped with a doping material as a guest material so as to form an (electron-rich) electron transport layer having a high n property. Examples of the doping material include n-type dopants, for example, metal compounds such as a metal complex and a metal halide. Specific examples of the electron transport layer having such a configuration include those described in literatures such as Japanese Patent Application Laid-Open No. Nos. 4-297076, 10-270172, 2000-196140, and 2001-102175; and J. Appl. Phys., 95, 5773 (2004).

Specific examples of the known electron transport materials preferably used for an organic EL element of the present invention include compounds described in the following literatures, but the present invention is not limited thereto.

U.S. Pat. Nos. 6,528,187, 7,230,107, US Patent Application Laid-Open No. 2005-0025993, US Patent Application Laid-Open No. 2004-0036077, US Patent Application Laid-Open No. 2009-0115316, US Patent Application Laid-Open No. 2009-0101870, US Patent Application Laid-Open No. 2009-0179554, WO2003/060956, WO2008/132085, Appl. Phys. Lett. 75,4(1999), Appl. Phys. Lett. 79,449(2001), Appl. Phys. Lett. 81,162(2002), Appl. Phys. Lett. 81,162 (2002), Appl. Phys. Lett. 79,156(2001), U.S. Pat. No. 7,964, 293, US Patent Application Laid-Open No. 2009-030202, WO2004/080975, WO2004/063159, WO2005/085387, WO2006/067931, WO2007/086552, WO2008/114690, WO2009/069442, WO2009/066779, WO2009/054253, WO2011/086935, WO2010/150593, WO2010/047707, EP Patent No. 2311826, Japanese Patent Application Laid-Open No. 2010-251675, Japanese Patent Application Laid-Open No. 2009-209133, Japanese Patent Application Laid-Open No. 2009-124114, Japanese Patent Application Laid-Open No. 2008-277810, Japanese Patent Application Laid-Open No. 2006-156445, Japanese Patent Application Laid-Open No. 2005-340122, Japanese Patent Application Laid-Open No. 2003-45662, Japanese Patent Application Laid-Open No. 2003-31367, Japanese Patent Application Laid-Open No. 2003-282270, WO2012/115034 and the like.

Examples of a more preferably known electron transport material in the present invention include aromatic heterocyclic compounds containing at least one nitrogen atom and compounds containing a phosphorous atom, such as pyridine derivatives, pyrimidine derivatives, pyrazine derivatives, triazine derivatives, dibenzofuran derivatives, dibenzothiophene derivatives, azadibenzofuran derivatives, azadibenzothiophene derivatives, carbazole derivatives, azacarbazole derivatives, benzimidazole derivatives, and arylphosphine oxide derivatives.

The electron transport material may be singly used or two or more thereof may be used in combination.

<<Hole Blocking Layer>>

The hole blocking layer is a layer having a function of the electron transport layer in a broad sense. The hole blocking layer is preferably composed of a material having a function of transporting electrons with a small ability of transporting holes and can increase the recombination probability of electrons and holes by blocking holes while transporting electrons.

The configuration of the electron transport layer described above can be used for the hole blocking layer of the present invention as required.

The hole blocking layer disposed in an organic EL element of the present invention is preferably disposed adjacent to the light-emitting layer on the cathode side.

The thickness of the hole blocking layer according to the present invention is preferably in the range of 3 nm to 100 nm, more preferably in the range of 5 nm to 30 nm.

As the material used for the hole blocking layer, the materials used for the electron transport layer aforementioned are preferably used, and the materials used as the host compound aforementioned are also preferably used for the hole blocking layer.

<<Electron Injection Layer>>

The electron injection layer (also referred to as a "cathode buffer layer") of the present invention is a layer disposed between the cathode and the light-emitting layer for reduction in drive voltage and increase in emission luminance, which is detailed in Part 2, Chapter 2 "Denkyoku Zairyo (Electrode Material)" (pp. 123-166) of "Yuki EL Soshi To Sono Kogyoka Saizensen (Organic EL Element and Front of Industrialization thereof) (Nov. 30, 1998, published by N.T.S Co., Ltd.)".

In the present invention, the electron injection layer may be provided as required and, as described above, may be present between the cathode and the light-emitting layer or between the cathode and the electron transport layer.

The electron injection layer is preferably a very thin film. The thickness thereof is preferably in the range of 0.1 nm to 5 nm depending on the material thereof. The layer may be an inhomogeneous layer (film) in which the constituent material intermittently exists.

The electron injection layer is also detailed in Japanese Patent Application Laid-Open Nos. 6-325871, 9-17574, 10-74586 and the like, and specific examples of a material preferably used for the electron injection layer include metals represented by strontium and aluminum, alkali metal compounds represented by lithium fluoride, sodium fluoride, and potassium fluoride, alkali earth metal compounds represented by magnesium fluoride and calcium fluoride, metal oxides represented by aluminum oxide, and metal complexes represented by lithium 8-hydroxyquinolinate (Liq). The electron transport materials aforementioned may also be used therefor.

The materials used for the electron injection layer described above may be singly used or two or more thereof may be used in combination.

<<Hole Transport Layer>>

The hole transport layer in the present invention is composed of a material having a function of transporting holes and is only required to have a function of transmitting holes injected from the anode to the light-emitting layer.

The total thickness of the hole transport layer according to the present invention is not particularly limited and usually in the range of 5 nm to 5 μm, more preferably in the range 2 nm to 500 nm, still more preferably in the range of 5 nm to 200 nm.

The material used for the hole transport layer (hereinafter, referred to as the hole transport material) is only required to have either a property of injecting or transporting holes or a barrier property against electrons. Any of conventionally known compounds can be selected and used.

Examples thereof include porphyrin derivatives, phthalocyanine derivatives, oxazole derivatives, oxadiazole derivatives, triazole derivatives, imidazole derivatives, pyrazoline derivatives, pyrazolone derivatives, phenylenediamine derivatives, hydrazone derivatives, stilbene derivatives, polyarylalkane derivatives, triarylalkane derivatives, carbazole derivatives, indolocarbazole derivatives, isoindole derivatives, acene-based derivatives such as anthracene and naphthalene, fluorene derivatives, fluorenone derivatives, polyvinyl carbazole, polymers or oligomers in which aromatic amine is introduced to a main chain or a side chain, polysilane, and conductive polymers or oligomers (such as PEDOT/PSS, aniline-based copolymers, polyaniline, and polythiophene).

Examples of the triarylamine derivative include benzidine types represented by α-NPD (4,4'-bis[N-(1-naphthyl)-N-phenylamino]biphenyl), star-burst types represented by MTDATA, compounds having fluorenone or anthracene at a triarylamine linking core portion.

Hexaazatriphenylene derivatives described in Japanese Unexamined Patent Application Publication (Translation of PCT Application) No. 2003-519432, Japanese Patent Application Laid-Open No. 2006-135145 and the like can also be used as the hole transport material.

The hole transport layer doped with impurities, thereby having a high p property can also be used. Examples thereof include those described in Japanese Patent Application Laid-Open Nos. 4-297076, 2000-196140, and 2001-102175, and J. Appl. Phys., 95, 5773 (2004) and the like.

It is also possible to use so-called p-type hole transport materials described in literatures such as Japanese Patent Application Laid-Open No. 11-251067 and Appl. Phys. Lett. 80 (2002), p. 139 by J. Huang et al., and inorganic compounds such as a p-type-Si and a p-type-SiC. Further, an ortho-metalated organic metal complex having Ir or Pt as central metal, represented by Ir(ppy)3, is also preferably used.

The materials described above can be used as the hole transport material, and preferably used are triarylamine derivatives, carbazole derivatives, indolocarbazole derivatives, azatriphenylene derivatives, organic metal complexes, polymer materials or oligomers in which aromatic amine is introduced to a main chain or a side chain and the like.

Specific examples of the known hole transport materials preferably used in an organic EL element of the present invention also include compounds described in the following literatures in addition to the above literatures, but the present invention is not limited thereto.

For example, Appl. Phys. Lett. 69,2160(1996), J. Lumin 72-74,985(1997), Appl. Phys. Lett. 78,673(2001), Appl. Phys. Lett. 90,183503(2007), Appl. Phys. Lett. 90,183503 (2007), Appl. Phys. Lett. 51,913(1987), Synth. Met. 87,171 (1997), Synth. Met. 91,209(1997), Synth. Met. 111,421 (2000), SID Symposium Digest,37,923(2006), J. Mater. Chem. 3,319(1993), Adv. Mater. 6,677(1994), Chem. Mater. 15,3148(2003), US Patent Application Laid-Open No. 2003-0162053, US Patent Application Laid-Open No. 2002-0158242, US Patent Application Laid-Open No. 2006-0240279, US Patent Application Laid-Open No. 2008-0220265, U.S. Pat. No. 5,061,569, WO2007/002683, WO2009/018009, EP650955, US Patent Application Laid-Open No. 2008-0124572, US Patent Application Laid-Open No. 2007-0278938, US Patent Application Laid-Open No. 2008-0106190, US Patent Application Laid-Open No. 2008-0018221, WO2012/115034, Japanese Unexamined Patent Application Publication (Translation of PCT Application) No. 2003-519432, Japanese Patent Application Laid-Open No. 2006-135145, Japanese Patent Application No. 13-585981 and the like.

The hole transport materials may be singly used or two or more thereof may be used in combination.

<<Electron Blocking Layer>>

The electron blocking layer is a layer having a function of the hole transport layer in a broad sense. The electron blocking layer is preferably composed of a material having a function of transporting holes with a small ability of transporting electrons and can increase the recombination probability of electrons and holes by blocking electrons while transporting holes.

The configuration of the hole transport layer described above can be used for the electron blocking layer of the present invention as required.

The electron blocking layer disposed in an organic EL element of the present invention is preferably disposed adjacent to the light-emitting layer on the anode side.

The thickness of the electron blocking layer according to the present invention is preferably in the range of 3 nm to 100 nm, more preferably in the range of 5 nm to 30 nm.

As the material used for the electron blocking layer, the materials used for the hole transport layer aforementioned are preferably used, and the host compound aforementioned is also preferably used for the electron blocking layer.

<<Hole Injection Layer>>

The hole injection layer (also referred to as the "anode buffer layer") according to the present invention is a layer disposed between the anode and the light-emitting layer for reduction in drive voltage and increase in emission luminance, which is detailed in Part 2, Chapter 2 "Denkyoku Zairyo (Electrode Material)" (pp. 123-166) of "Yuki EL Soshi To Sono Kogyoka Saizensen (Organic EL Element and Front of Industrialization thereof) (Nov. 30, 1998, published by N.T.S Co., Ltd.)".

In the present invention, the hole injection layer may be provided as required and, as described above, may be present between the anode and the light-emitting layer or between the anode and the hole transport layer.

The hole injection layer is also detailed in documents such as Japanese Patent Application Laid-Open Nos. 9-45479, 9-260062, and 8-288069, and examples of a material used for the hole injection layer include the materials used for the hole transport layer aforementioned.

Of these, preferable are phthalocyanine derivatives represented by copper phthalocyanine, hexaazatriphenylene derivatives described in Japanese Unexamined Patent Application Publication (Translation of PCT Application) No. 2003-519432 and Japanese Patent Application Laid-Open No. 2006-135145 and the like, metal oxides represented by vanadium oxide, amorphous carbon, conductive polymers such as polyaniline (emeraldine) and polythiophene, ortho-metalated complexes represented by a tris(2-phenylpyridine) iridium complex, triarylamine derivatives and the like.

The materials used for the hole injection layer aforementioned may be singly used or two or more thereof may be used in combination.

<<Additives>>

The layers aforementioned each may further include other additives.

Examples of the additives include halogen elements such as bromine, iodine, and chlorine, halogenated compounds, and compounds, complexes, and salts of alkali metals, alkali earth metals, and transition metals such as Pd, Ca, and Na.

The content of the additives can be optionally determined, and is preferably 1,000 ppm or less, more preferably 500 ppm or less, still more preferably 50 ppm or less based on the total mass % of the layer in which the additives are included.

Depending on the purpose of improving the property of transporting electrons or holes or the purpose of facilitating energy transfer of excitons, other ranges may be used.

<<Method for Forming Each Layer>>

A method for forming each layer aforementioned (a hole injection layer, hole transport layer, light-emitting layer, hole blocking layer, electron transport layer, electron injection layer, intermediate layer and the like) will be described.

The method for forming each layer aforementioned is not specifically limited. There can be employed conventionally known forming methods such as a vacuum vapor deposition method, wet method (also referred to as a wet process) and the like.

Examples of the wet method include a spin coating method, cast method, ink jetting method, printing method, die coating method, blade coating method, roll coating method, spray coating method, curtain coating method, and LB method (Langmuir Blodgett method). Preferred are processes highly suitable for a roll-to-roll system, such as a die coating method, roll coating method, ink jetting method, spray coating method and the like, from the viewpoint of easy formation of a homogeneous thin film and high productivity.

Examples of the liquid medium that can be used for dissolving or dispersing of the organic EL materials used for the present invention include ketones such as methyl ethyl ketone and cyclohexanone, fatty acid esters such as ethyl acetate, halogenated hydrocarbons such as dichlorobenzene, aromatic hydrocarbons such as toluene, xylene, mesitylene, and cyclohexylbenzene, aliphatic hydrocarbons such as cyclohexane, decalin, and dodecane, and organic solvents such as DMF and DMSO.

Examples of the usable dispersion technique include ultrasonic dispersion, high shearing force dispersion, and medium dispersion.

Further, different layers may be formed through different processes. If a layer is formed by a deposition process, appropriate deposition conditions, which may vary depending on the type of a compound used, are preferably selected as appropriate from generally the following ranges: a boat heating temperature of 50 to 450° C., a vacuum of $10^{-6}$ to $10^{-2}$ Pa, a deposition rate of 0.01 to 50 nm/second, a substrate temperature of −50 to 300° C., and a layer thickness of 0.1 nm to 5 μm, preferably 5 to 200 nm.

Formation of each layer aforementioned is preferably continuously carried out from a hole injection layer to a cathode with one time vacuuming. The layers may be taken out on the way, and a different layer forming method may be employed. In this case, the operation is preferably done under a dry inert gas atmosphere.

<<Anode>>

The anode of the organic EL element is preferably formed of, as an electrode material, metal, alloy or conductive compound each having a large work function (4 eV or more, preferably 4.5 eV or more), or a mixture thereof. Specific examples of such an electrode material include metals such as Au, and transparent electroconductive materials such as CuI, indium tin oxide (ITO), $SnO_2$, and ZnO. A material that is amorphous and capable of forming a transparent conductive layer such as IDIXO ($In_2O_3$—ZnO) or the like may be used.

The anode may be formed in such a manner that the electrode material is formed into a thin film by a method as vapor deposition or sputtering, and the film is patterned into a desired pattern by a photolithography method. Alternatively, in the case where the pattern may not require high accuracy (for example, approximately 100 μm or more), the pattern may be formed with a mask having a desired shape on vapor deposition or sputtering of the electrode material.

In the case of using a material capable of being applied as a coating, such as an organic electroconductive compound, a wet film forming method, such as a printing method and coating method, may be used. In the case where emitted light is to be taken out through the anode, the anode preferably has a transmittance of more than 10%, and preferably has a sheet resistance of several hundred Ohms per square or less.

The thickness thereof may be generally selected from the range of 10 nm to 1 μm, preferably of 10 to 200 nm, while depending on the material used.

<<Cathode>>

The cathode is preferably formed of, as an electrode material, a metal (referred to as an electron injection metal), an alloy or a conductive compound each having a small work function (4 eV or less), or a mixture thereof. Specific examples of the electrode material include sodium, sodium-potassium alloys, magnesium, lithium, magnesium-copper mixtures, magnesium-silver mixtures, magnesium-aluminum mixtures, magnesium-indium mixtures, aluminum/aluminum oxide ($Al_2O_3$) mixtures, indium, lithium/aluminum mixtures, aluminum, and rare earth metals. Of these, mixtures of an electron injection metal and a second metal that is a stable metal having a larger work function than the electron injection metal, for example, magnesium/silver mixtures, magnesium/aluminum mixtures, magnesium/indium mixtures, aluminum/aluminum oxide ($Al_2O_3$) mixtures, lithium/aluminum mixtures, aluminum and the like are preferred in respect of the electron injection property and the durability against oxidation and the like.

The cathode can be produced by forming the electrode material into a thin film by a method such as vapor deposition or sputtering. The cathode preferably has a sheet resistance of several hundred Ohms per square or less, and the thickness thereof may be usually selected from the range of from 10 nm to 5 μm, preferably of 50 to 200 nm.

For transmitting the emitted light, any one of the anode and the cathode of the organic EL element is preferably transparent or translucent, thereby enhancing the emission luminance After the metal described above has been formed into a film having a thickness of from 1 nm to 20 nm as a cathode, the conductive transparent material mentioned in the description of the anode is formed into a film on the cathode, thereby being able to produce a transparent or translucent cathode. Through the application of this method, an element in which both the anode and cathode have transparency can be produced.

<<Organic EL Element Containing Specific π-conjugated Compound>>

Of π-conjugated compounds of the present invention, a specific π-conjugated compound represented by general formula 201 aforementioned has high emission efficiency even when existing singly in the light-emitting layer, eliminating the host compound conventionally required. Thus, the specific π-conjugated compound can simplify the configuration of organic EL elements without compromising their emission efficiency and durability. Hereinafter, an organic EL element containing the specific π-conjugated compound will be described.

The organic EL element including the specific π-conjugated compound includes an anode, a cathode, and an organic layer disposed between the anode and the cathode. The organic layer substantially contains no host compound other than the π-conjugated compound represented by general formula 201. In other words, the organic layer is preferably composed substantially of the π-conjugated compound represented by general formula 201 (first aspect) or composed substantially of the π-conjugated compound represented by general formula 201 and a guest compound (second aspect). In the first organic EL element, the π-conjugated compound represented by general formula 201 may function as both a host compound and a luminescent compound. In the second organic EL element, the π-conjugated compound represented by general formula 201 may function as a host compound.

"The organic layer is composed substantially of the π-conjugated compound represented by general formula 201" means that the organic layer may contain impurities to an extent so as not to affect its light-emitting performance and durability, and specifically means that the content of the π-conjugated compound represented by general formula 201 in the organic layer is 95 vol % or more, preferably 99 vol % or more, particularly preferably 100 vol %. Likewise, "composed substantially of the π-conjugated compound represented by general formula 201 and a guest compound" means that the total content of the π-conjugated compound represented by general formula 201 and a guest compound in the organic layer is 95 vol % or more, preferably 99 vol % or more, particularly preferably 100 vol %.

The organic layer is preferably a light-emitting layer. The light-emitting layer may be composed of a single layer or may be composed of a plurality of layers. Such a light-emitting layer may emit light at high efficiency even if containing no conventional host compound. Thus, the configuration of organic EL elements can be simplified to thereby increase their productivity and reliability. Hereinafter, each aspect will be described.

(Organic EL Element of First Aspect)

Figure 5A:
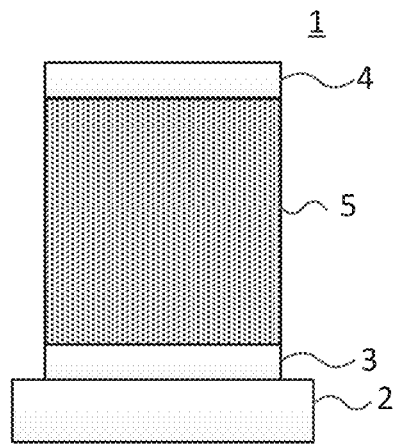
FIG. 5A is a diagram illustrating an exemplary configuration of an organic EL element of a first aspect including a specific π-conjugated compound.
Figure 5B:
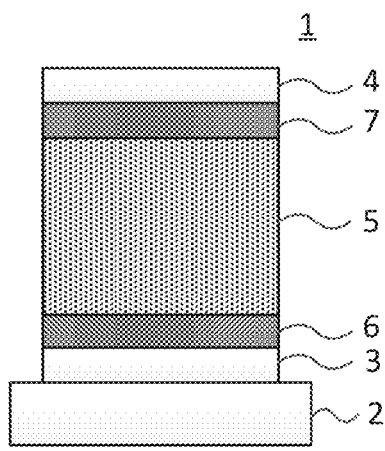
FIG. 5B is a diagram illustrating an exemplary configuration of the organic EL element of the first aspect including the specific π-conjugated compound.
Figure 5C:
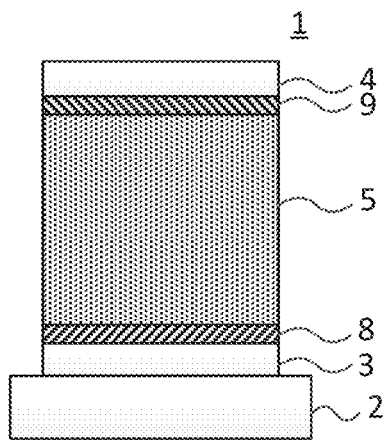
FIG. 5C is a diagram illustrating an exemplary configuration of the organic EL element of the first aspect including the specific π-conjugated compound.

FIGS. 5A to 5C are diagrams illustrating an exemplary configuration of the organic EL element of the first aspect including the specific π-conjugated compound. As shown in FIGS. 5A to 5C, organic EL element 1 of the first aspect includes anode 3 and cathode 4 placed on supporting substrate 2, and light-emitting layer 5 disposed between anode 3 and cathode 4.

Light-emitting layer 5 is substantially constituted by the π-conjugated compound represented by general formula 201. Light-emitting layer 5, as the aforementioned organic EL element, is a layer which provides a place of light emission via excitons produced by recombination of electrons and holes injected from the electrodes (the adjacent layers when the organic EL element includes other layers). The luminescent portion may be either in the light-emitting layer or may be an interface between the light-emitting layer and the adjacent layer when the organic EL element include other layers.

Light-emitting layer 5 may be composed of a single layer or may be composed of a plurality of layers. The total thickness of light-emitting layer 5 or the thickness of one layer of light-emitting layer 5 may be same as in the aforementioned organic EL element.

Here, the π-conjugated compound represented by general formula 201 contained in light-emitting layer 5 preferably has a TADF property. Since 75% $T_1$ energy generated by electric-field excitation undergoes intersystem crossing to $S_1$ to thereby cause fluorescence, excited energy generated can be used without any loss, and a high external quantum efficiency is easily achieved. When the organic EL element include other layers, a compound contained in the adjacent layer and the π-conjugated compound represented by general formula 201 contained in light-emitting layer 5 may form an excited complex to emit light.

Organic EL element 1 of the first aspect may further include at least one of hole transport layer 6 disposed between light-emitting layer 5 and anode 3 and electron transport layer 7 disposed between light-emitting layer 5 and cathode 4 as required (see FIG. 5B). Hole transport layer 6, which functions as a layer to adjust the mobility of holes, and electron transport layer 7, which functions as a layer to adjust the mobility of electrons, may increase the recombination probability to thereby improve the emission efficiency or reduce the drive voltage.

Organic EL element 1 of the first aspect may further include at least one of hole injection layer 8 disposed between light-emitting layer 5 and anode 3 and electron injection layer 9 disposed between light-emitting layer 5 and cathode 4 (see FIG. 5C). Hole injection layer 8 and electron injection layer 9 can improve the bondability between light-emitting layer 5 and anode 3 or cathode 4, constituted by inorganic materials, to thereby easily inject electrons or holes into the organic layer.

Organic EL element 1 of the first aspect may further include at least one of a hole blocking layer (not shown) disposed between light-emitting layer 5 and cathode 4 and an electron blocking layer (not shown) disposed between light-emitting layer 5 and anode 3 as required.

Of these, from the viewpoint of reducing the number of layers constituting the organic EL element and easily increasing the productivity and reliability, the organic EL element of the first aspect preferably includes no layer between light-emitting layer 5 and anode 3 and between light-emitting layer 5 and cathode 4 as required (see 5A). In other words, preferably, one surface of light-emitting layer 5 is in contact with anode 3 and the other surface of light-emitting layer 5 is in contact with cathode 4.

A representative element configuration in the organic EL element of the first aspect may be the same as that in organic EL element aforementioned, but the configuration described above is not limited thereto. The electron transport layer, hole blocking layer, electron injection layer, hole transport layer, electron blocking layer, and hole injection layer included in the organic EL element, additives contained in these layers, and a method for forming each layer may be the same as in the case of the organic EL element aforementioned.

(Organic EL Element of Second Aspect)

Figure 6:
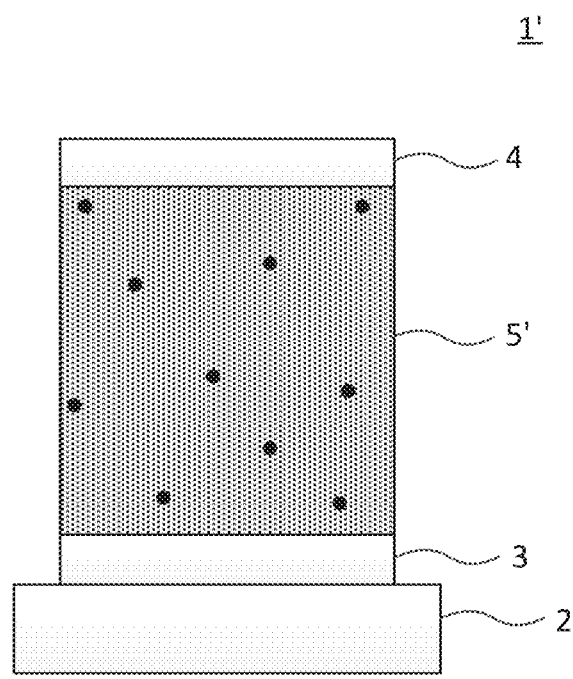
FIG. 6 is a diagram illustrating an exemplary configuration of an organic EL element of a second aspect including a specific π-conjugated compound.

FIG. 6 is a diagram illustrating an exemplary configuration of an organic EL element of a second aspect including a specific π-conjugated compound. As shown in FIG. 6, organic EL element 1' of the second aspect includes anode 3 and cathode 4 placed on supporting substrate 2, and light-emitting layer 5' of which one surface is in contact with anode 3 and of which the other surface is in contact with cathode 4.

Light-emitting layer 5' is substantially constituted by the π-conjugated compound represented by general formula 201 and a guest compound. Light-emitting layer 5' may be composed of a single layer or may be composed of a plurality of layers, in the same manner as in light-emitting layer 5 of the organic EL element of the first aspect. Total thickness of light-emitting layer 5' and the thickness of one layer thereof may be same as the total thickness of light-emitting layer 5 of the organic EL element of the first aspect and the thickness of one layer thereof.

The guest compound contained in light-emitting layer 5' may be a fluorescent-emitting compound other than the π-conjugated compound represented by general formula 201 (referred to as a fluorescence-emitting dopant or a fluorescent dopant) or a phosphorescence-emitting compound (referred to as a phosphorescence-emitting dopant or a phosphorescent dopant). A plurality of guest compounds may be used in combination. A combination of fluorescence-emitting compounds having different structures or a combination of a fluorescence-emitting compound and a phosphorescence-emitting compound may be used. Any emission color can be obtained thereby.

The content of the guest compound in light-emitting layer 5' is preferably 0.1 to 20 vol %, more preferably 0.1 to 5 vol %, still more preferably 0.1 to 1 vol % based on light-emitting layer 5'. This is because, when the content of the guest compound exceeds 20 vol %, electrons and holes in the light-emitting layer 5' are likely to recombine on the guest compound, and the energy $T_1$, which is generated with a probability of 75% after recombination on the guest compound, is deactivated without emitting light to be a factor for reducing the external quantum efficiency. The guest compound may be contained at a homogeneous concentration in the layer thickness direction of light-emitting layer 5' or may have any concentration distribution.

The π-conjugated compound represented by general formula 201 contained in light-emitting layer 5' preferably has a TADF property. When the π-conjugated compound represented by general formula 201 has a TADF property, the $T_1$ energy generated on the π-conjugated compound undergoes reverse intersystem crossing to $S_1$. Subsequently, the $T_1$ energy further undergoes energy transfer (fluorescent resonance energy transfer (FRET)) onto the guest compound. Then the guest compound emits light, and thus a high quantum efficiency can be achieved. Accordingly, in light-emitting layer 5' constituted by two components: the π-conjugated compound represented by general formula 201 and the guest compound, the $S_1$ and $T_1$ energy levels of the π-conjugated compound are preferably higher than the $S_1$ and $T_1$ energy levels of the guest compound.

FIG. 4 schematically illustrates the case where the π-conjugated compound represented by general formula 201 serves as a host compound. FIG. 4 is exemplary. The generation process of triplet excitons generating on the π-conjugated compound represented by general formula 201 is not only through electric-field excitation but also through energy transfer or electron transfer in the light-emitting layer or from the interface between the light-emitting layer and a layer adjacent thereto. Although FIG. 4 illustrates the case where the light-emitting material is a fluorescence-emitting compound as a guest compound (luminescent compound), the light-emitting material is not limited thereto and may be a phosphorescence-emitting compound or may be both a fluorescence-emitting compound and a phosphorescence-emitting compound.

When the π-conjugated compound represented by general formula 201 functions as a host compound, the emission spectrum of the π-conjugated compound represented by general formula 201 and the absorption spectrum of the guest compound preferably overlap each other.

In light-emitting layer 5', the π-conjugated compound represented by general formula 201 and the guest compound may form a complex (form an exciplex) in the excited state to emit light.

Emission colors of an organic EL element of the present invention and the compound used for the present invention may be the same as in the case of the aforementioned organic EL element.

Light-emitting dopants and phosphorescence-emitting dopants that can be used for the light-emitting layer of the second aspect may be the same as in the case of fluorescence-emitting dopants and phosphorescent dopants that can be used for the aforementioned organic EL element. As a fluorescence-emitting dopant, a delayed fluorescent dopant may be selected and used. A delayed fluorescent dopant is a compound having $\Delta E_{ST}$ of 0.5 eV or less other than the π-conjugated compound represented by general formula 201. Light-emitting layer 5' may be formed in the same manner as the method for forming each layer of the aforementioned organic EL element.

[Supporting Substrate]

The supporting substrate (also referred to as a substrate or a base material hereinafter) that can be used for the organic EL element of the present invention may be composed of glass or plastic, which may be of any type and may be transparent or opaque. For extraction of light from the supporting substrate side, the supporting substrate is preferably transparent. Examples of the transparent supporting substrate preferably used include glass, quartz, and transparent resin films. A particularly preferred supporting substrate is a resin film capable of imparting flexibility to the organic EL element.

Examples of the resin film include films of polyesters such as polyethylene terephthalate (PET) and polyethylene naphthalate (PEN), polyethylene, polypropylene, cellophane, cellulose esters and their derivatives such as cellulose diacetate, cellulose triacetate (TAC), cellulose acetate butyrate, cellulose acetate propionate (CAP), cellulose acetate phthalate, and cellulose nitrate, polyvinylidene chloride, polyvinyl alcohol, poly(ethylene-vinyl alcohol), syndiotactic polystyrene, polycarbonate, norbornene resin, polymethylpentene, polyether ketone, polyimide, polyether sulfone (PES), polyphenylene sulfide, polysulfones, polyether imide, polyether ketone imide, polyamide, fluorine resin, Nylon, poly(methyl methacrylate), acrylic and polyarylates and cycloolefin resins such as ARTON (trade name, manufactured by JSR Corp.), and APEL (trade name, manufactured by Mitsui Chemicals Inc.).

On the surface of the resin film, an inorganic or organic coating film or hybrid coating film composed of the both may be formed. The coating film is preferably a barrier film having a water vapor transmittance (permeability) of 0.01 $g/m^2 \cdot 24$ h or less (at 25±0.5° C. and 90±2% relative humidity (RH)) measured by a method in accordance with JIS K 7129-1992, and more preferably a high barrier film having an oxygen transmittance of $1 \times 10^{-3}$ $mL/m^2 \cdot 24$ h·atm·or less measured by a method in accordance with JIS K 7126-1987 and a water vapor transmittance of $1 \times 10^{-5}$ $g/m^2 \cdot 24$ h or less.

As for the material for forming the barrier film, any material that can block infiltration of substances such as moisture and oxygen causing degradation of the element can be used, and examples of the material that can be used include silicon oxide, silicon dioxide, and silicon nitride. In order to improve the fragility of the film, a barrier film is more preferably allowed to have a laminate structure composed of the inorganic layer and organic material layer. The inorganic layer and the organic material layer may be laminated in any order, and the both layers are preferably alternately laminated multiple times.

The method for forming the barrier film is not particularly limited, and examples thereof include vacuum deposition, sputtering, reactive sputtering, molecular beam epitaxy, cluster ion-beam deposition, ion plating, plasma polymerization, atmospheric pressure plasma polymerization, plasma CVD, laser CVD, thermal CVD, and coating methods. A particularly preferred method is atmospheric pressure plasma polymerization as described in Japanese Patent Application Laid-Open No. 2004-68143A.

Examples of the opaque supporting substrate include sheets and films of metal such as aluminum and stainless steel, opaque resin substrates, and substrates of ceramic.

The external extraction quantum efficiency of emission of the organic EL element of the present invention at room temperature (25° C.) is preferably 1% or more, more preferably 5% or more.

Herein, the external extraction quantum efficiency (%)= (number of photons emitted from the organic EL element to the exterior)/(number of electrons supplied to the organic EL element)×100.

A hue improving filter such as a color filter or a color conversion filter that converts the color of light emitted by the organic EL element to many colors using a fluorescent compound may be used in combination.

[Sealing]

Examples of the sealing means used in the organic EL element of the present invention include a method in which a sealing member, electrodes, and a supporting substrate are bonded with an adhesive. It is only required to dispose the sealing member so as to cover a displaying area of the organic EL element, and the sealing member may be in the form of a recess or flat plate. Further, the sealing member may have any transparency and electrical insulation.

Examples of the sealing member include glass plates, polymer plates and films, and metal plates and films. Examples of the glass plate include soda-lime glass, barium.strontium-containing glass, lead glass, aluminosilicate glass, borosilicate glass, barium borosilicate glass, and quartz plates. Examples of the polymer plate include polycarbonate, acryl, polyethylene terephthalate, polyether sulfide, and polysulfone plates. The metal plate may be composed of at one or more metals or alloys selected from the group consisting of stainless steel, iron, copper, aluminum, magnesium, nickel, zinc, chromium, titanium, molybdenum, silicon, germanium, and tantalum.

In the present invention, a polymer film or metal film is preferably used, from the viewpoint of reduction in the film thickness of the organic EL element. The polymer film preferably has an oxygen transmittance of $1 \times 10^{-3}$ $mL/m^2 \cdot 24$ h·atm or less measured by a method in compliance with JIS K 7126-1987 and a water vapor transmittance of $1 \times 10^{-3}$ $mL/m^2 \cdot 24$ h·atm or less (at 25±0.5° C. and 90±2% relative humidity) measured by a method in compliance with JIS K 7129-1992.

The sealing member is formed into a recessed form by, for example, sand blasting or chemical etching.

Specific examples of the adhesive include photo-curable or thermo-curable adhesives having reactive vinyl groups, such as acrylic acid oligomers and methacrylic acid oligomers and moisture curable adhesives such as 2-cyanoacrylate. Examples thereof also include thermally or chemically curable (two-liquid mixing type) adhesives, such as epoxy adhesives. Examples thereof also include hot-melt polyamide, polyester, and polyolefin adhesives. Examples thereof also include UV curable epoxy resin adhesives of cation curing type.

Since the organic EL element may be degraded by heat treatment, the adhesive can be cured preferably at a temperature from room temperature up to 80° C. A drying agent may be dispersed in the adhesive. The adhesive may be applied to the sealing portion with a commercially available dispenser or by printing such as screen printing.

A sealing film can be preferably prepared as a layer of an inorganic or organic compound. The sealing film is formed on outer side of the electrode opposed to the supporting substrate via a constituent layer of the organic EL element (for example, the light-emitting layer) so as to cover the electrode and the above constituent layer and to be in contact with the supporting substrate. In this case, the sealing film may be formed of any material that can block infiltration of substances such as water and oxygen that causes degradation of the element, and examples of the material that can be used include silicon oxide, silicon dioxide, and silicon nitride.

In order to further improve the fragility of the film, a sealing film is preferably allowed to have a laminate structure composed of the inorganic layer and organic material. The method for forming these films is not particularly limited, and examples thereof include vacuum deposition, sputtering, reactive sputtering, molecular beam epitaxy, cluster ion-beam deposition, ion plating, plasma polymerization, atmospheric pressure plasma polymerization, plasma CVD, laser CVD, thermal CVD, and coating methods.

The gap between the sealing member and the displaying portion of the organic EL element is preferably filled with, in the case of the form of a gas or liquid phase, an inert gas such as nitrogen or argon or an inactive liquid such as fluorinated hydrocarbon or silicone oil. The gap can be in a vacuum state. Alternatively, the gap may be filled with a hygroscopic compound.

Examples of the hygroscopic compound include metal oxides (such as sodium oxide, potassium oxide, calcium oxide, barium oxide, magnesium oxide, and aluminum oxide), sulfates (such as sodium sulfate, calcium sulfate, magnesium sulfate, and cobalt sulfate), metal halides (such as calcium chloride, magnesium chloride, cesium fluoride, tantalum fluoride, cerium bromide, magnesium bromide, barium iodide, and magnesium iodide), and perchlorates (such as barium perchlorate and magnesium perchlorate). The sulfates, metal halides, and perchlorates are suitably used in the form of anhydride.

[Protective Film, Protective Plate]

In order to enhance the mechanical strength of the element, a protective film or plate may be provided on the outer side of the sealing layer or film opposed to the supporting substrate via the constituent layer of the organic EL element. Particularly when sealing is achieved by the sealing film, the mechanical strength of the sealing film is not sufficiently high. Thus, such a protective film or plate is preferably provided. Examples of the material used for the protective film or plate include glass plates, polymer plates and films, and metal plates and films similar to those used for sealing. From the viewpoint of reduction in the weight and the film thickness, polymer films are preferably used.

[Technique for Improving Light Extraction]

It is generally said that an organic EL element generates light in a layer having a refractive index higher than air (within the refractive index range of about 1.6 to 2.1) and only about 15% to 20% of the light generated in the light-emitting layer can be extracted. This is because incident light on the interface (interface between a transparent substrate and the air) at an angle θ larger than a critical angle is totally reflected and cannot be extracted from the element, or because light is totally reflected at the interface between the transparent electrode or light-emitting layer and the transparent substrate and is guided to the transparent electrode or the light-emitting layer to escape the light to the side surface of the element.

Examples of techniques for improving the light extraction efficiency include a process of forming irregularities on a surface of a transparent substrate to prevent total reflection at the interface between the transparent substrate and the air (e.g., U.S. Pat. No. 4,774,435); a process of providing light-condensing properties to a substrate to improve the efficiency (e.g., Japanese Patent Application Laid-Open No. 63-314795 A); a process of forming a reflection surfaces on the side surfaces of an element (e.g., Japanese Patent Application Laid-Open No. 1-220394 A); a process of introducing a flat layer between a substrate and a luminescent material to form an anti-reflection layer, wherein the flat layer has a refractive index between the substrate and the luminescent material (e.g., Japanese Patent Application Laid-Open No. 62-172691 A); a process of introducing a flat layer between a substrate and a luminescent material, wherein the flat layer has a refractive index lower than that of the substrate (e.g., Japanese Patent Application Laid-Open No. 2001-202827 A); and a process of forming a diffraction grating between any layers of a substrate, transparent electrode layer, and light-emitting layer (including on the substrate surface facing the exterior) (e.g., Japanese Patent Application Laid-Open No. 11-283751 A).

In the present invention, these processes can be used in combination with the organic EL element of the present invention. The process of introducing a flat layer between a substrate and a luminescent material, wherein the flat layer has a refractive index lower than that of the substrate or the luminescent material or the process of forming a diffraction grating between any layers of a substrate, transparent electrode layer, and light-emitting layer (including on the substrate surface facing the exterior) can be suitably employed.

The present invention can provide an element exhibiting higher luminance or more excellent durability by combining those means.

When a low refractive index medium is allowed to have a thickness greater than light wavelength between a transparent electrode and a transparent substrate, the extraction efficiency of light from the transparent electrode to the exterior increases with decrease in the refractive index of the medium.

Examples of materials for the low refractive index layer include aero gel, porous silica, magnesium fluoride, and fluorinated polymer. The refractive index of a transparent substrate usually ranges about 1.5 to 1.7, and thus the refractive index of the low refractive index layer is preferably about 1.5 or less, more preferably 1.35 or less.

The low refractive index medium desirably has a thickness twice or more the wavelength of the light in the medium. This is because when the low refractive index medium has a thickness similar to the wavelength of the light, the electromagnetic waves exuding as evanescent waves penetrate into the substrate, resulting in a reduction in the effect of the low refractive index layer.

The process of introducing a diffraction grating onto the interface at which total reflection occurs or into any media is characterized by being highly effective of improving the light extraction efficiency. In this method, a diffraction grating is introduced between any two layers or in any medium (in the transparent substrate or the transparent electrode) to extract the light generated in the light-emitting layer that cannot exit due to total reflection between the layers and the like, by the use of the property of the diffraction gratings that can change the direction of light to a specific direction different from that of refraction by Bragg diffraction such as primary diffraction or secondary diffraction.

The diffraction grating to be introduced desirably has two-dimensional periodic refractive indices. Because light generated in a light-emitting layer is emitted randomly in all the directions, a general one-dimensional diffraction grating having a periodic refractive index distribution only in the specific direction can diffract only the light traveling in a specific direction and cannot greatly increase the light extraction efficiency.

When the refractive index distribution is allowed to be two-dimensional, light traveling in all directions are diffracted to thereby result in an increase in light extraction efficiency.

The diffraction grating may be introduced between any two layers or in any medium (in the transparent substrate or the transparent electrode), but is desirably introduced near the organic light-emitting layer, which is a site generating light. The period of the diffraction grating is preferably about a half to three times the wavelength of light in the medium. The array of the diffraction grating is preferably two-dimensionally repeated such as a square lattice shape, triangular lattice shape, or honeycomb lattice shape.

[Light-Condensing Sheet]

The organic EL element of the present invention can enhance the luminance in a specific direction by condensing light in this specific direction, for example, in the front direction with respect to the light emitting plane of the element by providing, for example, a micro-lens array structure on the light extraction side of the supporting substrate (substrate) of the element or combining with a so-called light-condensing sheet.

In an example of a micro-lens array, quadrangular pyramids having a side of 30 μm and having a vertex angle of 90 degrees are two-dimensionally arranged on the light extraction side of the substrate. The quadrangular pyramid preferably has a side in the range of 10 μm to 100 μm. A side shorter than this range causes coloration due to the effect of diffraction, while a side longer than this range makes the thickness unfavorably large.

A light-condensing sheet that can be used is one practically used for an LED backlight of a liquid crystal display apparatus, for example. A typical example of the sheet is a brightness enhancing film (BEF) manufactured by SUMITOMO 3M Limited. A prism sheet may have, for example, a shape having triangular stripes with a vertex angle of 90 degrees and a pitch of 50 μm, a shape having a round apex, a shape having randomly changed pitches, or other shapes, formed on a base material.

In order to control the emission angle of light from the organic EL element, a light diffusion plate or film may be used in combination with the light-condensing sheet. For example, a diffusion film (Light-Up) manufactured by KIMOTO Co., Ltd. can be used.

[Applications]

The organic EL element of the present invention can be used as an electronic apparatus, such as a display apparatus, a display, or various light-emitting apparatuses.

Examples of the light-emitting apparatus include, but not limited to, lighting apparatuses (lamps for household use and car room lamps), backlights for watches and liquid crystals, light sources for board advertisements, traffic lights, and optical memory media, light sources for electrophotographic copiers, light sources for optical communication instruments, and light sources for optical sensors. In particular, the organic EL element can be effectively used as a backlight for a liquid crystal display apparatus or a lighting source.

In the organic EL element of the present invention, films may be patterned with a metal mask, by ink-jet printing or the like during film deposition. The patterning may be performed on only the electrodes, on the electrodes and the light-emitting layer, or on all layers of the element. In the production of the element, conventionally known methods can be employed.

<Display Apparatus>

The display apparatus including the organic EL element of the present invention may be monochromatic or multichromatic. Herein, a multichromatic display apparatus will now be described.

In the case of a multichromatic display apparatus, a shadow mask is provided only during formation of the light-emitting layer. The film can be formed on one side by a vacuum deposition method, casting method, spin coating method, ink jetting method, printing method or the like.

In the case of patterning only the light-emitting layer, the patterning may be performed by any method. The method is preferably a vacuum deposition method, ink jetting method, spin coating method, or printing method.

The configuration of the organic EL element included in the display apparatus is selected from the exemplary configurations of the organic EL element mentioned above as required.

The method of producing the organic EL element is as shown in one embodiment of the production of the organic EL element of the present invention which has been described above.

When a direct current voltage is applied to the multichromatic display apparatus thus obtained, light emission can be observed by allowing the anode to have a positive (+) polarity and the cathode to have a negative (−) polarity and applying an voltage of about 2 V to 40 V. Application of a voltage of the reverse polarity causes no current to flow and generates no light emission. Alternatively, when an alternating current voltage is applied, light is emitted only in the state of the anode being positive (+) and cathode being negative (−). Meanwhile, the alternating current to be applied may have any wave shape.

The multichromatic display apparatus can be used as a display device, display, or various light emission sources. In a display device or display, full color display can be achieved with three types of organic EL elements that emit blue, red, and green light.

Examples of the display device or display include television sets, personal computers, mobile equipment, AV equipment, teletext displays, and information displays in automobiles. In particular, the display apparatus may be used for displaying still images or moving images. The driving system in the case of using the display apparatus used for playback of moving images may be either a simple matrix (passive matrix) system or an active matrix system.

Examples of the light-emitting apparatus include lamps for household use, car room lamps, backlights for watches and liquid crystals, light sources for board advertisements, traffic lights, and optical memory media, light sources for electrophotographic copiers, light sources for optical communication instruments, and light sources for optical sensors, and the present invention is not limited thereto.

Hereinbelow, an example of the display device having the organic EL element of the present invention will be described with reference to accompanying drawings.

Figure 7:
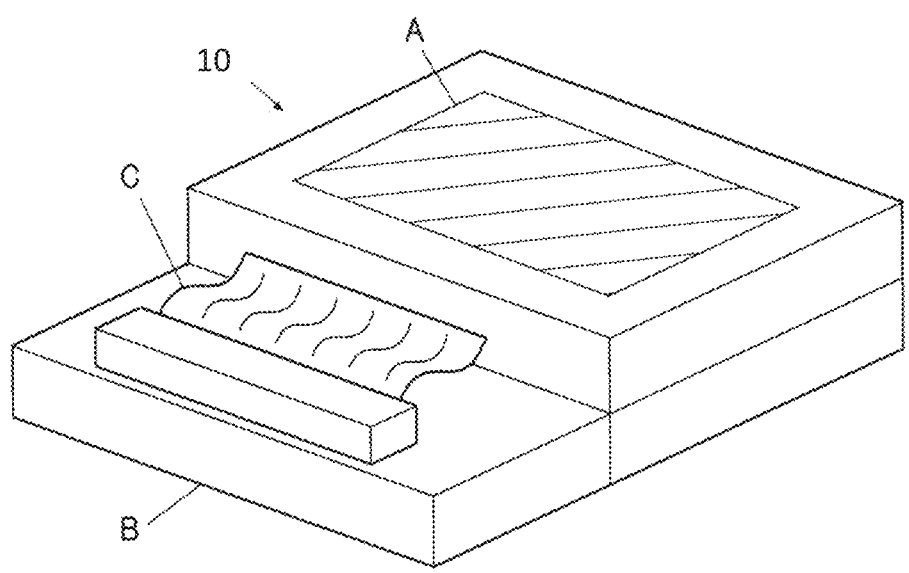
FIG. 7 is a schematic illustration of one exemplary display apparatus constituted by the organic EL element.

FIG. 7 is a schematic illustration of one exemplary display apparatus constituted by the organic EL element. FIG. 7 is a schematic illustration illustrating a display for, for example, a mobile phone to display image information through light emission of the organic EL element.

Display 10 has display part A having a plurality of pixels, control part B to perform image scanning of display part A based on image information, wiring portion C electrically connecting display part A and control part B and the like.

Control part B is electrically connected to display part A via wiring portion C and sends scanning signals and image data signals to each of pixels based on external image information. The pixels of each scanning line sequentially emit light by the scanning signals and in response to the image data signal to perform image scanning, displaying the image information on display part A.

Figure 8:
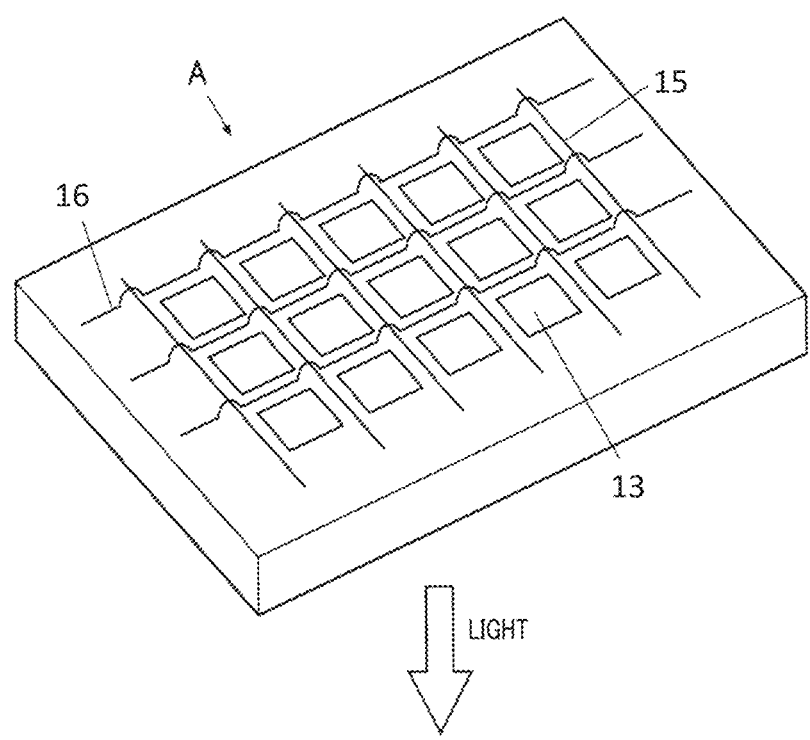
FIG. 8 is a schematic illustration of an active matrix display apparatus.

FIG. 8 is a schematic illustration of an active matrix display apparatus.

Display part A includes wiring portion C including a plurality of scanning lines 15 and data lines 16, and a plurality of pixels 13 on a substrate. The main members of display part A will be described hereinafter.

FIG. 8 illustrates a case in which light emitted from pixels 3 is extracted to the direction shown by the white arrow (downward direction).

Scanning lines 15 and plural data lines 16 in the wiring portion are each made of an electrically conductive material. Scanning lines 15 and data lines 16 intersect at right angles in a grid pattern and are connected to pixels 13 at the intersections (details are not shown).

When a scanning signal is applied from scanning line 15, pixels 13 receive an image data signal from data line 16 and emit light in response to the image data received.

Full color display can be achieved by appropriately disposing pixels that emit light in a red region, pixels that emit light in a green region, and pixels that emit light in a blue region in parallel on the same substrate.

Figure 9:
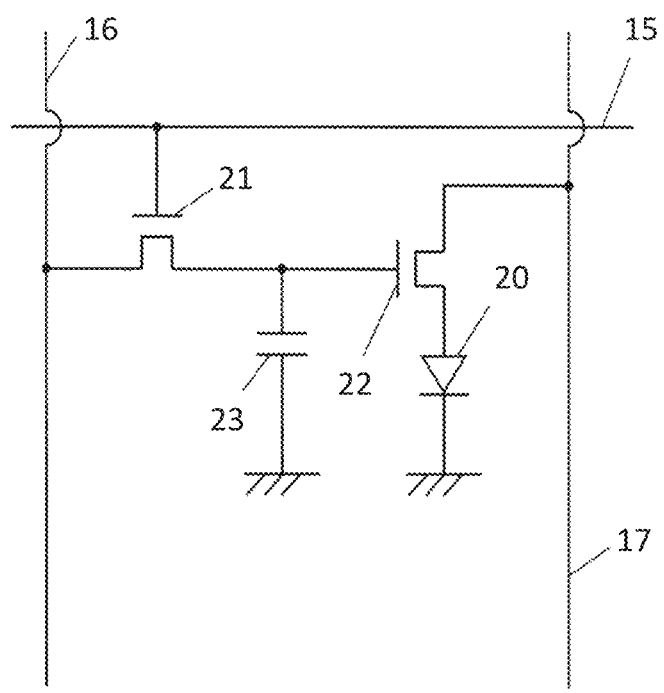
FIG. 9 is a schematic view of a pixel circuit.

Next, the light-emitting process by a pixel will now be described. FIG. 9 is a schematic illustration of a pixel circuit.

The pixel includes organic EL element 20, switching transistor 21, driving transistor 22, condenser 23 and the like. Full color display can be performed by using, as organic EL element 20 for plural pixels, organic EL elements emitting red light, green light, and blue light and disposing the elements in parallel on the same substrate.

In FIG. 9, an image data signal from control part B is applied to the drain of switching transistor 21 via data line 16. A scanning signal from control part B is then applied to the gate of switching transistor 21 via scanning line 15 to turn on driving of switching transistor 21, and the image data signal applied to the drain is transmitted to condenser 23 and gate of driving transistor 22.

Condenser 23 is charged through the transmission of the image data signal depending on the potential of the image data signal, and driving of driving transistor 22 is turned on. In driving transistor 22, the drain is connected to power source line 17 and a source is connected to the electrode of organic EL element 20 to supply a current to organic EL element 20 from power source line 17 depending on the potential of the image data signal applied to the gate.

The scanning signal is transmitted to next scanning line 15 by sequential scanning by control part B to turn off driving of switching transistor 21. However, condenser 23 maintains the charged potential of the image data signal even after the turning-off of driving of switching transistor 21, and thereby the driving state of driving transistor 22 is maintained to continue the light emission by organic EL element 20 until the next scanning signal is applied. Driving transistor 22 is driven in response to the potential of the subsequent image data signal in synchronization with the subsequent scanning signal applied by sequential scanning, resulting in light emission by organic EL element 20.

That is, light emission by organic EL element 20 is performed by providing switching transistor 21 and driving transistor 22 serving as active elements to organic EL element 20 of each of the plurality of pixels and allowing each of organic EL elements 20 of plural pixels 3 to emit light. Such a light emitting process is called an active matrix system.

Light emission from organic EL element 20 herein may have multiple gradations according to multi-valued image data signals having different gradation potentials, or a predetermined intensity of on-off light according to a binary image data signal. The electric potential of condenser 23 may be maintained until the subsequent scanning signal is applied, or may be discharged immediately before the subsequent scanning signal is applied.

In the present invention, the light emitting process is not limited to the active matrix system described above, and may be a passive matrix system, in which light is emitted from the organic EL element in response to the data signal only during scanning of the scanning signals.

Figure 10:
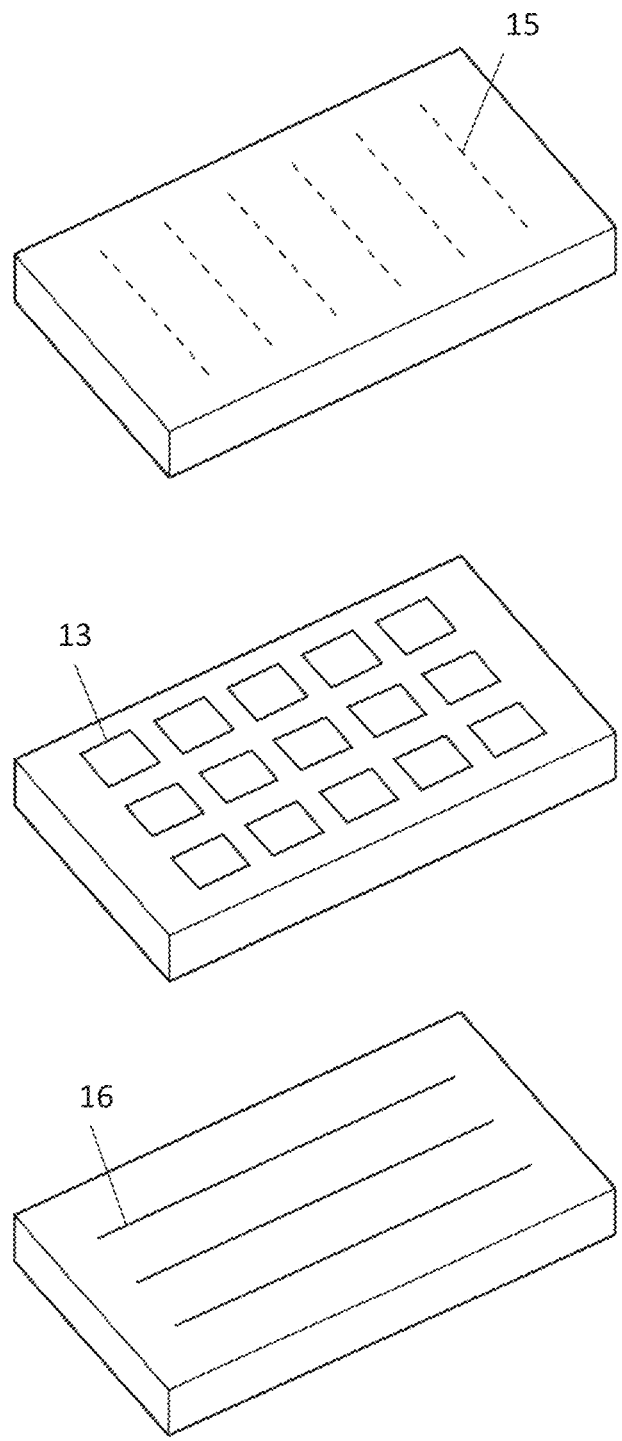
FIG. 10 is a schematic illustration of a passive matrix display apparatus.

FIG. 10 is a schematic illustration of a passive matrix display apparatus. In FIG. 10, a plurality of scanning lines 15 and a plurality of image data lines 16 are provided opposingly via pixels 13 in a grid pattern.

When a scanning signal is applied to scanning line 15 by sequential scanning, pixel 13 connected to applied scanning line 15 emits light in response to the image data signal.

The passive matrix system does not have any active element in pixels 13, resulting in a reduction in manufacturing cost.

Use of the organic EL element of the present invention can provide a display apparatus having improved emission efficiency.

<Lighting Apparatus>

The organic EL element of the present invention can be used also for a lighting apparatus.

The organic EL element of the present invention may be used also as an organic EL element having a resonator configuration. The organic EL element having such a resonator configuration may be intended to be used for, but not limited to, a light source for an optical memory medium, light source for an electrophotographic copier, light source for an optical communication instrument, light source for an optical sensor or the like. Alternatively, the organic EL element may be used for the above-mentioned purposes by laser oscillation.

The organic EL element of the present invention may be used as a lamp such as a lighting source or an exposure light source or may be used as a projector for projecting images or a display apparatus (display) for direct view of still or moving images.

The driving system of the display apparatus used for playback of moving images may be either a passive matrix system or an active matrix system. Furthermore, a full-color display apparatus can be produced by employing two or more organic EL elements of the present invention that emit light of different colors.

The π-conjugated compound used for the present invention can be applied to a lighting apparatus including an organic EL element that emits substantially white light. For example, when a plurality of light-emitting materials are used, a plurality of emitted light colors are emitted simultaneously. Mixing the colors can provide white light emission. The combination of the emitted light colors may be a combination containing three maximum light emission wavelengths of three primary colors of blue, green, and red or a combination containing two maximum light emission wavelengths utilizing a relationship of complementary colors such as blue and yellow or bluish green and orange.

In the method of forming the organic EL element of the present invention, a mask is disposed only during formation of a light-emitting layer, hole transport layer, electron transport layer or the like. It is only required that the mask be simply disposed for separate coating by use of the mask, for example. Patterning with the mask or the like is not necessary because the other layers are common. A film, such as an electrode film, can be formed on the entire surface by a vapor deposition method, casting method, spin coating method, ink jetting method, printing method or the like. The productivity is thereby enhanced.

According to this method, the organic EL element itself emits white light, unlike a white light-emitting organic EL apparatus including an array of multiple light-emitting elements disposed in parallel.

One Embodiment of Lighting Apparatus of Present Invention

One embodiment of the lighting device including the organic EL element of the present invention will now be described.

The non-light emitting surface of the organic EL element of the present invention is covered with a glass case, and a glass substrate having a thickness of 300 μm is used as a sealing substrate. As a sealing material, an epoxy photocurable adhesive (LUXTRACK LC0629B manufactured by Toagosei Co., Ltd.) is applied to the periphery, and the product is placed onto the cathode and is attached to the transparent supporting substrate, followed by curing the adhesive by irradiation with UV light through the glass substrate for sealing. Accordingly, a lighting apparatus shown in FIGS. 11 and 12 can be formed.

Figure 11:
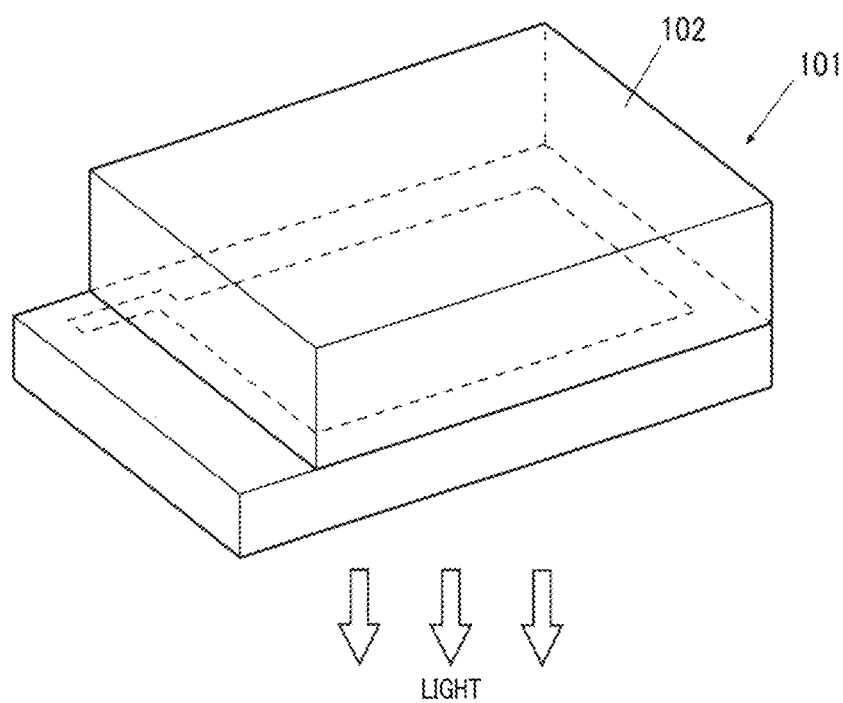
FIG. 11 is a schematic view of a lighting apparatus.

FIG. 11 is a schematic view of the lighting apparatus. The organic EL element of the present invention (organic EL element 101 in the lighting apparatus) is covered with glass cover 102 (sealing with the glass cover was performed in a glove box under a nitrogen atmosphere (an atmosphere of high purity nitrogen gas having a purity of at least 99.999%) to avoid contact of organic EL element 101 in the lighting apparatus with air).

Figure 12:
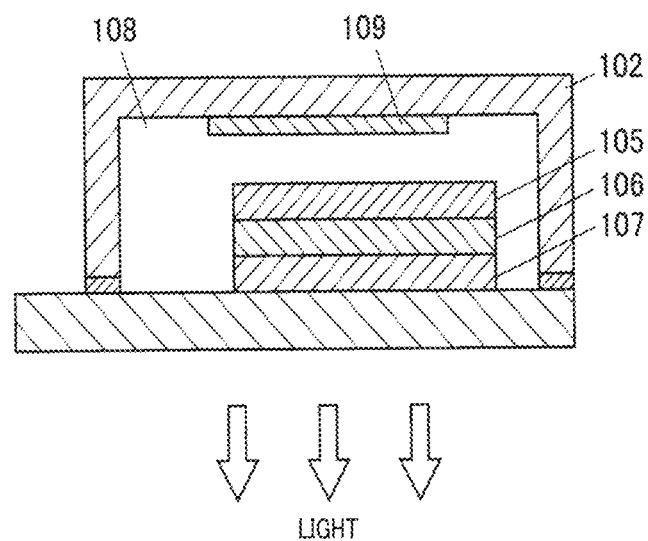
FIG. 12 is a schematic illustration of the lighting apparatus.
Figure 13:
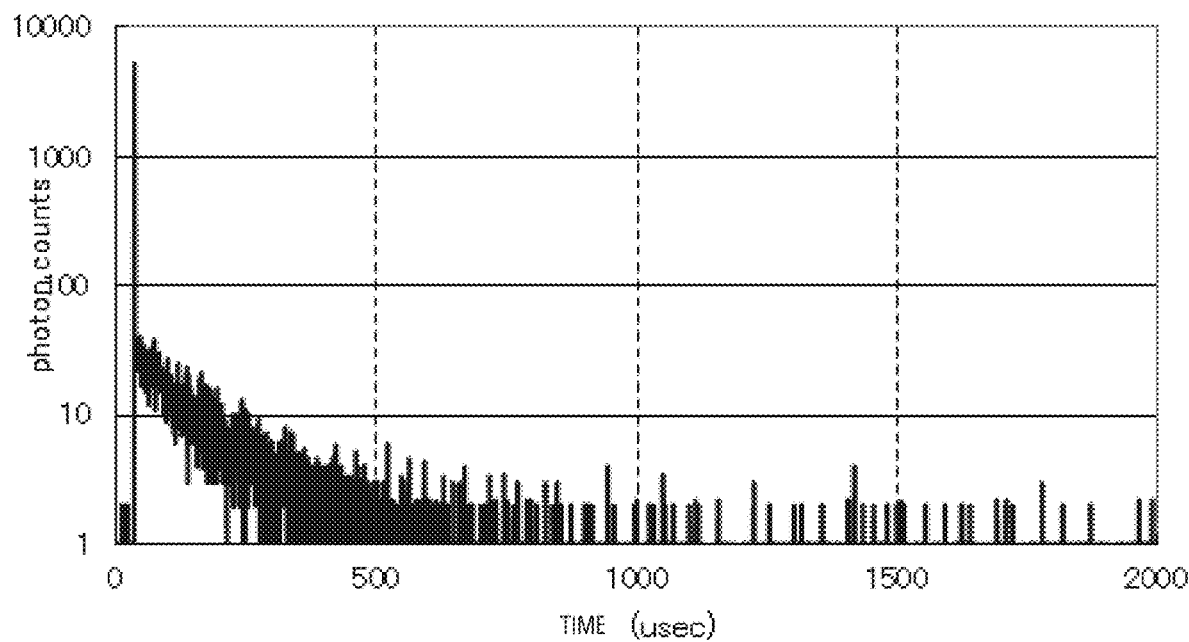
FIG. 13 is a graph illustrating the relation between the time after excitation light irradiation and the number of photons when the co-deposition film 6-1 containing a π-conjugated compound of the present invention produced in Example was subjected to fluorescence decay measurement.
Figure 14:
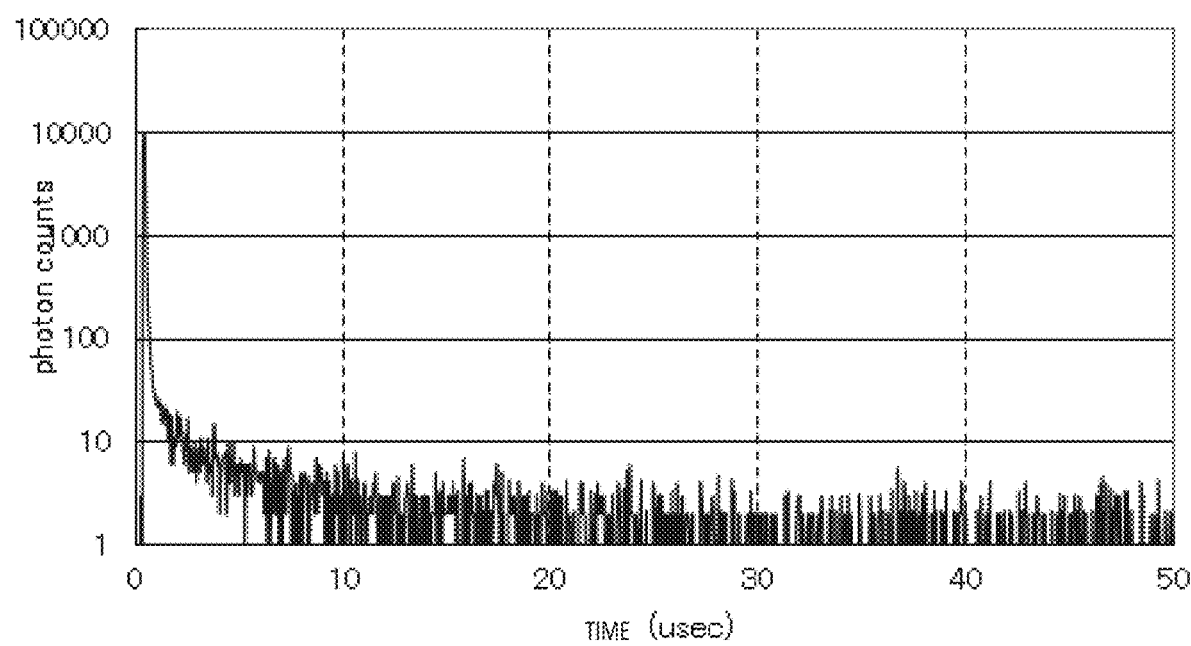
FIG. 14 is a graph illustrating the relation between the time after excitation light irradiation and the number of photons when the co-deposition film 6-2 containing a π-conjugated compound of the present invention produced in Example was subjected to fluorescence decay measurement.
Figure 15:
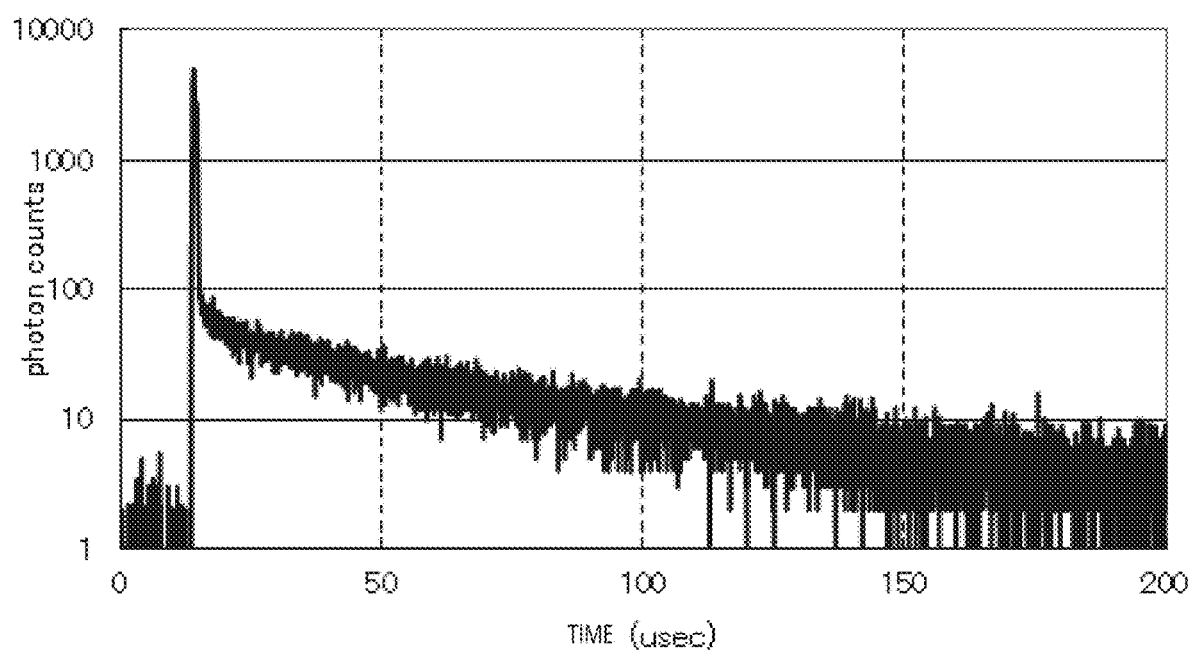
FIG. 15 is a graph illustrating the relation between the time after excitation light irradiation and the number of photons when the co-deposition film 6-3 containing a π-conjugated compound of the present invention produced in Example was subjected to fluorescence decay measurement.
Figure 16:
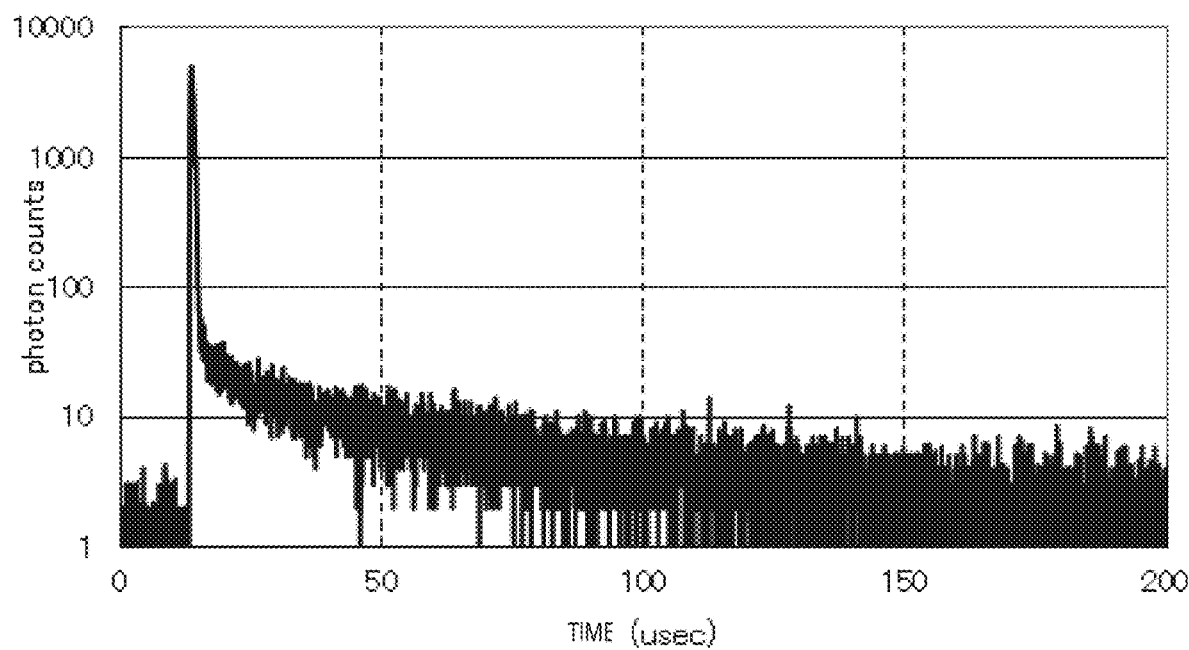
FIG. 16 is a graph illustrating the relation between the time after excitation light irradiation and the number of photons when the co-deposition film 6-4 containing a π-conjugated compound of the present invention produced in Example was subjected to fluorescence decay measurement.

FIG. 12 is a cross-sectional view of the lighting apparatus, wherein 105 indicates a cathode, 106 indicates a constituent layer of the organic EL element (for example, the light-emitting layer), and 107 indicates a glass substrate provided with a transparent electrode. Meanwhile, the inside of glass cover 102 is filled with nitrogen gas 108 and is provided with water absorbent 109.

Use of the organic EL element of the present invention can provide a lighting apparatus having improved emission efficiency.

<Light-Emitting Material>

The π-conjugated compound of the present invention can emit fluorescence by means of electric-field excitation and the like. The compound thus can be used as various light-emitting materials. The light-emitting material may contain other components as required in addition to the π-conjugated compound. The light-emitting material may be used also in the form of powder or may be processed into a desired shape before use. The light-emitting material can be applied to, for example, a material for forming a light-emitting thin film described below, fluorescent paint, and bioimaging fluorescent dye.

In the case where the absolute value of $\Delta E_{ST}$ of the π-conjugated compound is 0.50 eV or less, the π-conjugated compound may emit delayed fluorescence. Such a compound can be applied to bioimaging fluorescent dye. Delayed fluorescence, which is known to be quenched by means of an enzyme, also can be applied to oxygen-sensing materials.

<Light-Emitting Thin Film>

A light-emitting thin film according to the present invention, which is characteristic of containing the aforementioned π-conjugated compound according to the present invention, can be produced in the same manner as in the method for forming each layer constituting the organic EL element.

The light-emitting thin film according to the present invention can be produced in the same manner as in the method for forming each layer constituting the organic EL element.

The method for forming the light-emitting thin film of the present invention is not particularly limited. There can be employed conventionally known forming methods such as a vacuum vapor deposition method, wet method (also referred to as a wet process) and the like.

Examples of the wet method include a spin coating method, cast method, ink jetting method, printing method, die coating method, blade coating method, roll coating method, spray coating method, curtain coating method, and LB method (Langmuir Blodgett method). Preferred are processes highly suitable for a roll-to-roll system, such as a die coating method, roll coating method, ink jetting method, spray coating method, from the viewpoint of easy formation of a homogeneous thin film and high productivity.

Examples of the liquid medium that can be used for dissolving or dispersing of the light-emitting material used for the present invention include ketones such as methyl ethyl ketone and cyclohexanone, fatty acid esters such as ethyl acetate, halogenated hydrocarbons such as dichlorobenzene, aromatic hydrocarbons such as toluene, xylene, mesitylene, and cyclohexylbenzene, aliphatic hydrocarbons such as cyclohexane, decalin, and dodecane, and organic solvents such as DMF and DMSO.

Examples of the method for dispersing the light-emitting material include ultrasonic dispersion, high shearing force dispersion, and medium dispersion.

Further, different layers may be formed through different film deposition processes. When a vapor deposition process is used for film deposition, appropriate vapor deposition conditions, which may vary depending on the type of a compound used, are preferably selected as appropriate from generally the following ranges: a boat heating temperature of 50 to 450° C., a vacuum of $10^{-6}$ to $10^{-2}$ Pa, a deposition rate of 0.01 to 50 nm/second, a substrate temperature of −50 to 300° C., and a layer thickness of 0.1 nm to 5 μm, preferably 5 to 200 nm.

In the case where a spin coating method is employed for film deposition, a spin coater is operated in the range of 100 to 1,000 rpm for the range of 10 to 120 seconds under a dry inert gas atmosphere.

EXAMPLES

The present invention will now be described specifically by way of examples, but the present invention is not limited thereto. The sign "%" used in the examples refer to "mass %" unless otherwise specified.

Compounds used in examples and comparative examples are shown below.

[Formula 118]
T-2
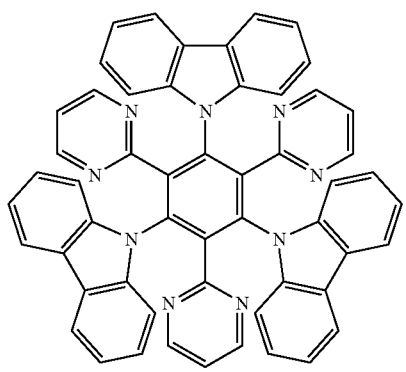
T-3
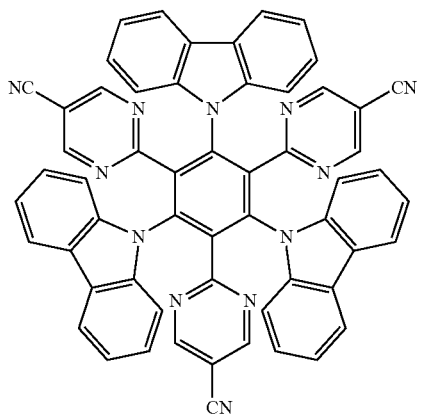
T-13
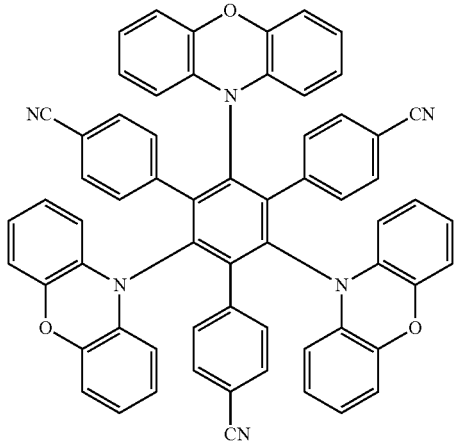
T-27
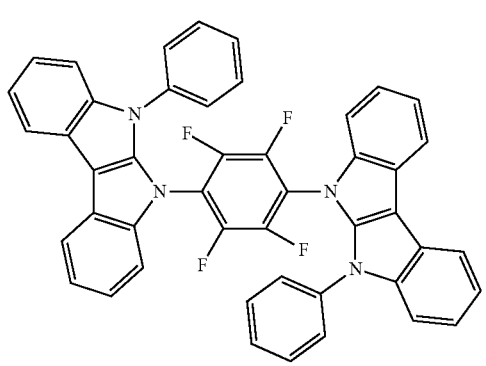
T-33
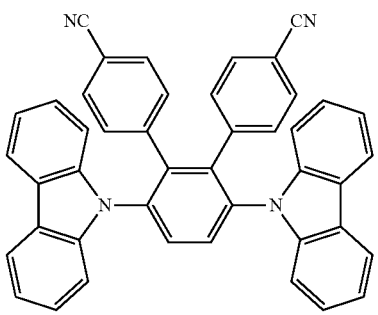
T-59
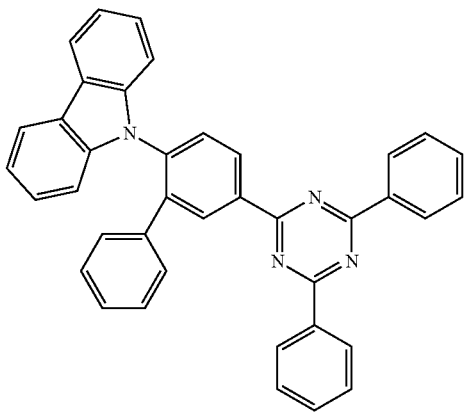
T-66
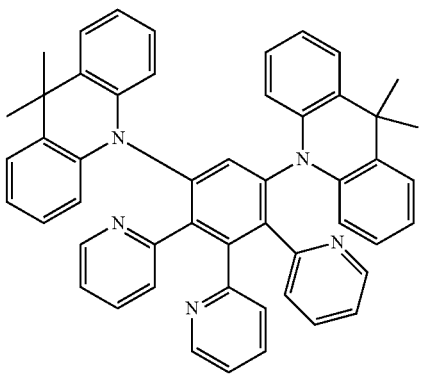
T-74
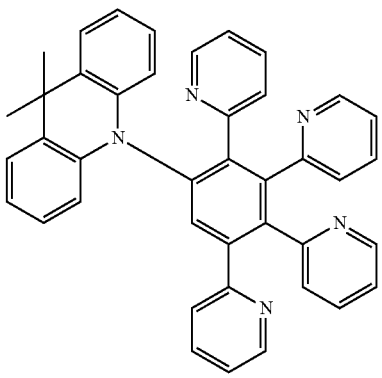

-continued
T-78
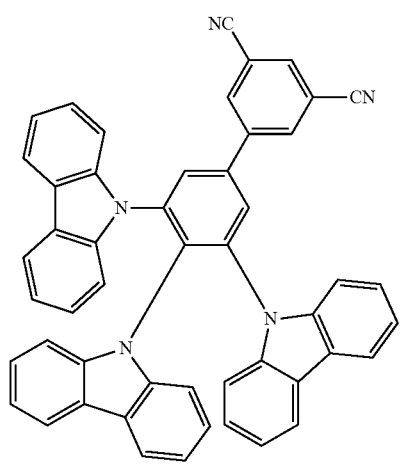
T-79
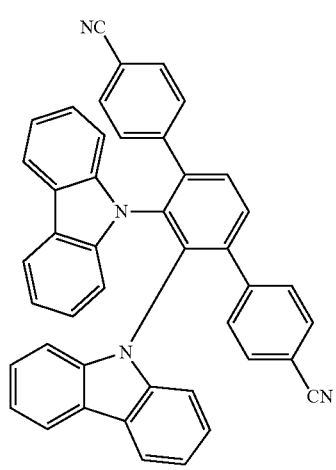
T-82
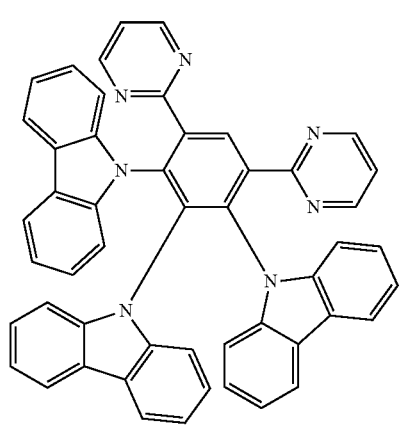
-continued
T-83
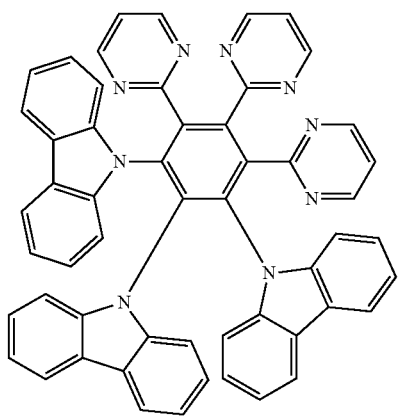
T-84
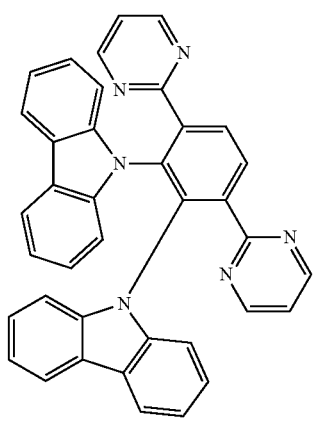
T-85
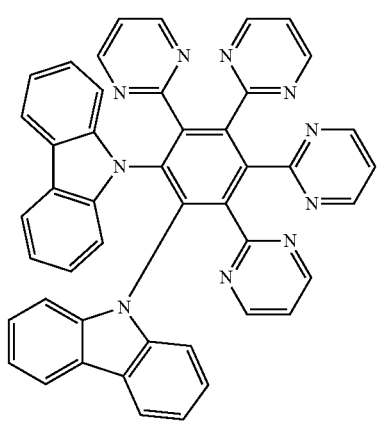

T-96
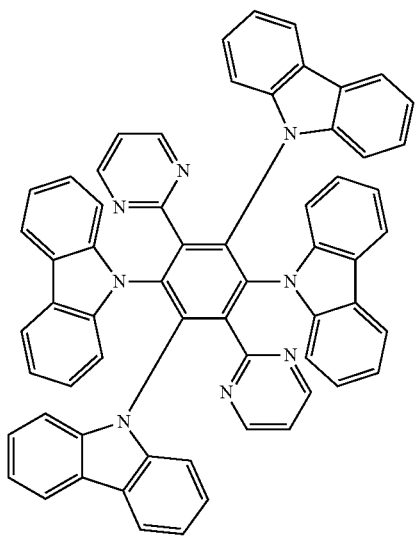
T-124
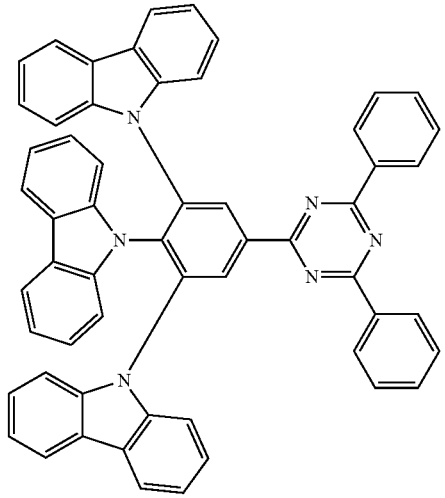
[Formula 119]
T-101
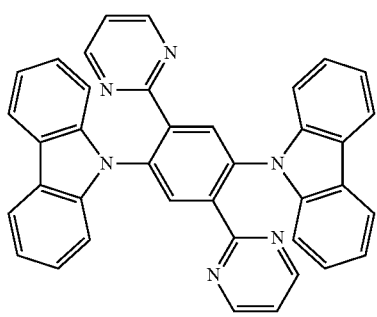
T-125
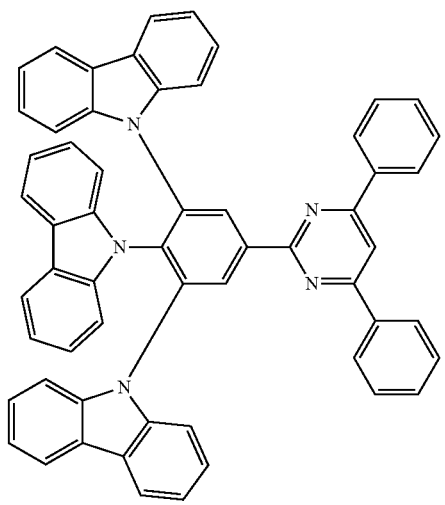
T-117
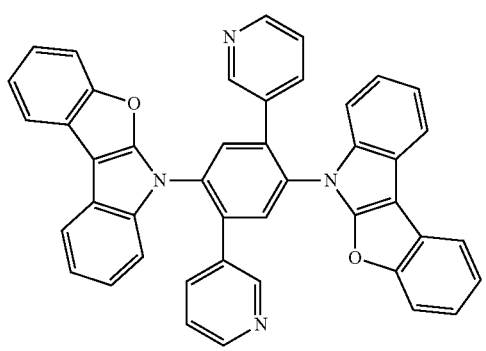
T-131
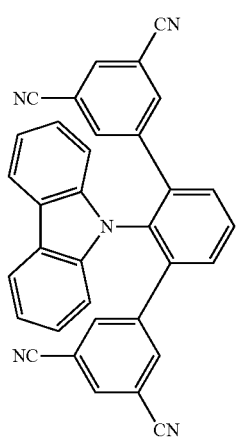

T-132
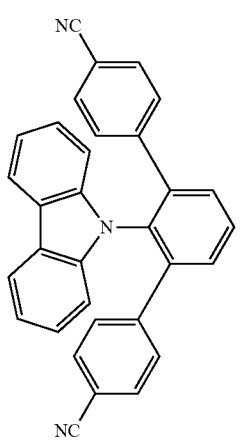
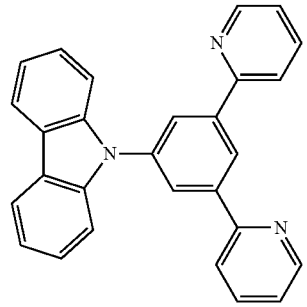
Comparative compound 3
T-133
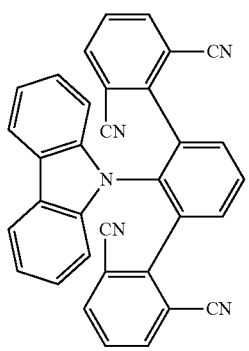
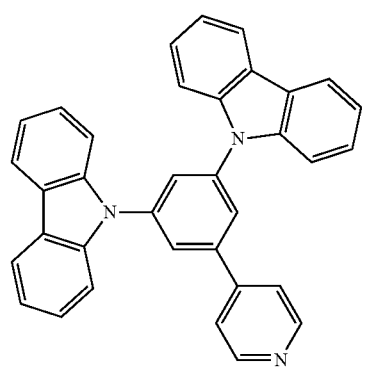
Comparative compound 4
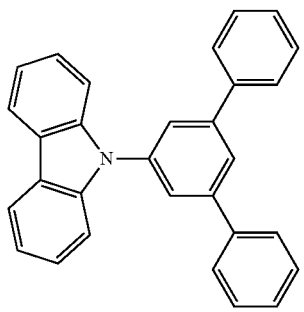
Comparative compound 1
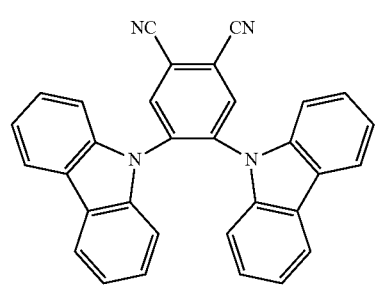
Comparative compound 5
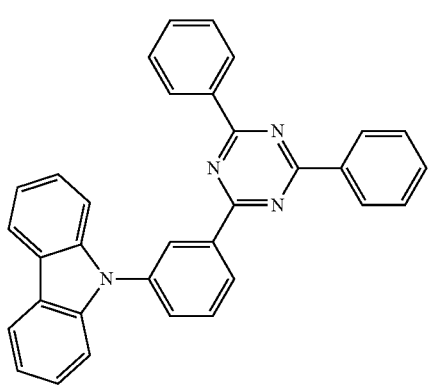
Comparative compound 2
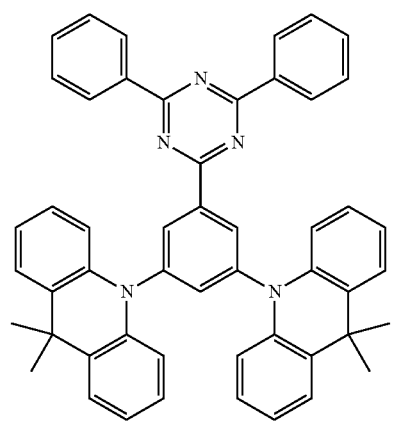
Comparative compound 6

355
-continued
Comparative compound 7
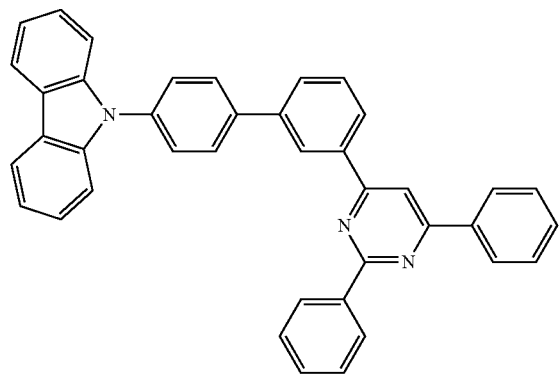
Comparative compound 8
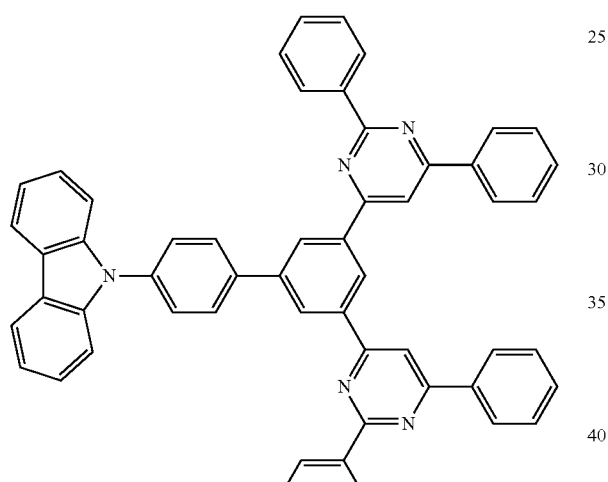
Comparative compound 9
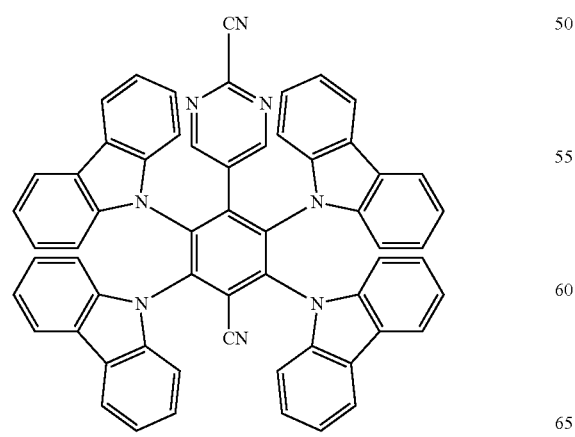
356
-continued
[Formula 120]
T-176
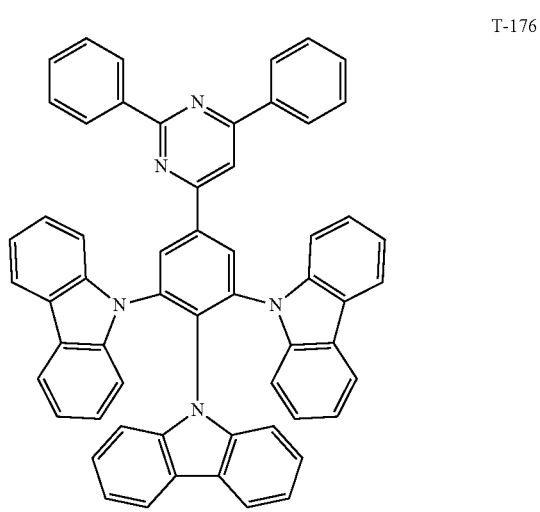
T-180
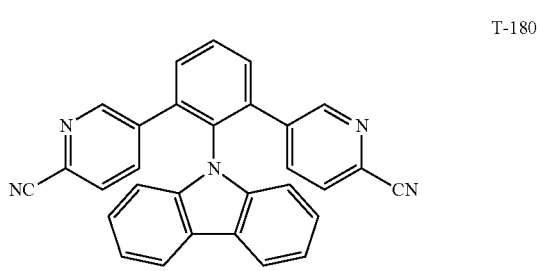
T-182
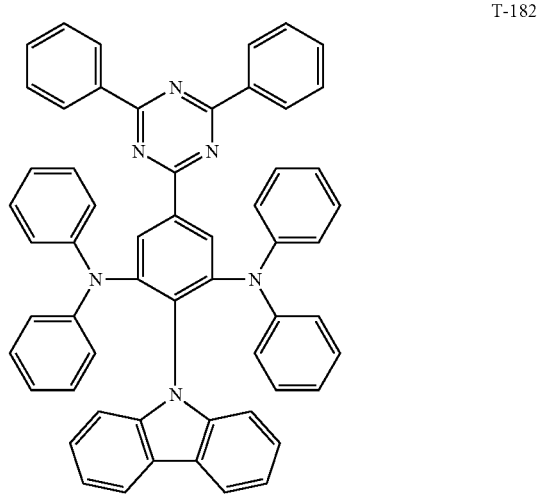

T-183
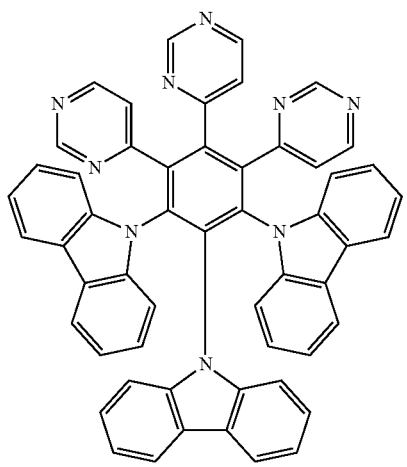
T-184
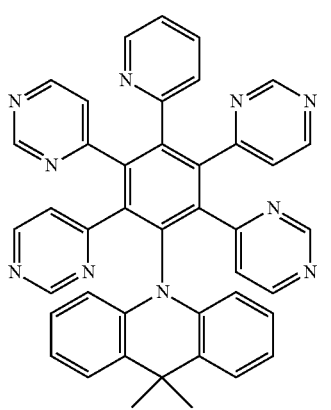
T-185
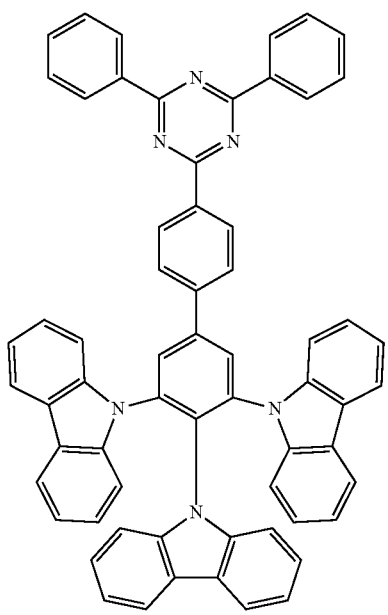
T-186
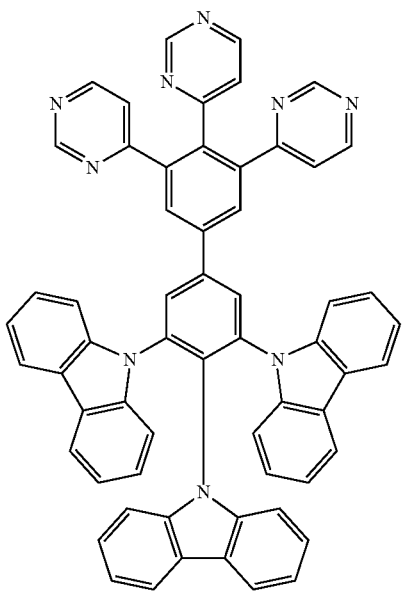
T-187
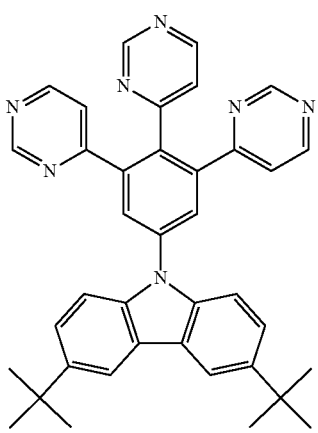
T-188
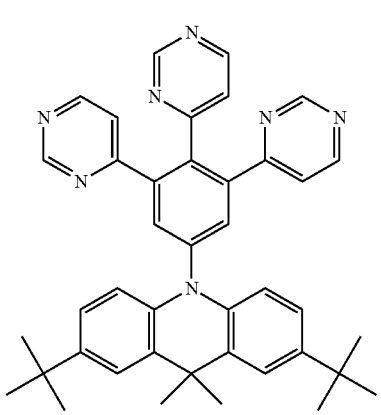

T-189
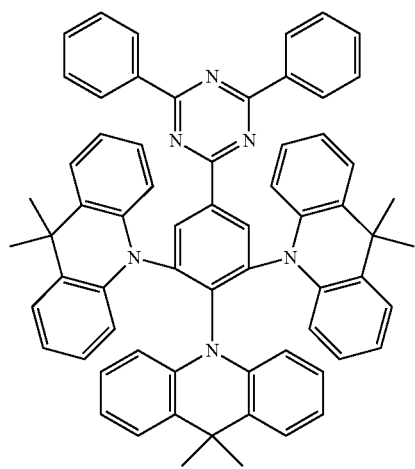
T-190
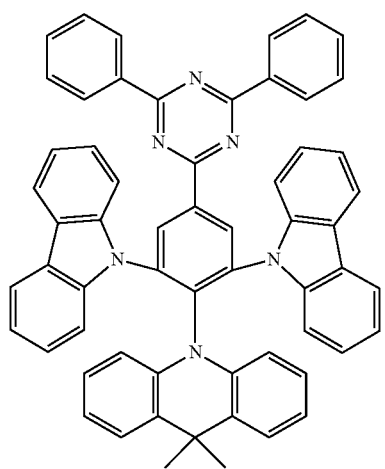
[Formula 121]
T-191
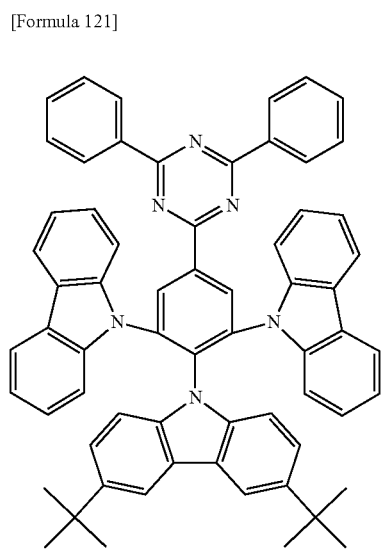
T-192
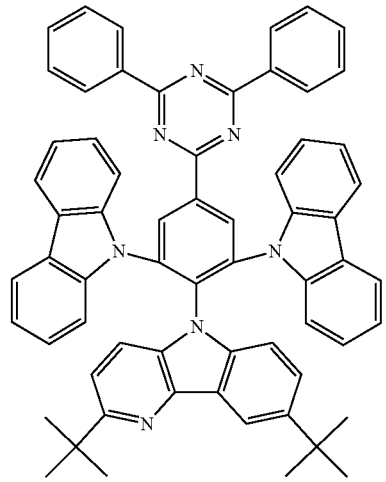
T-193
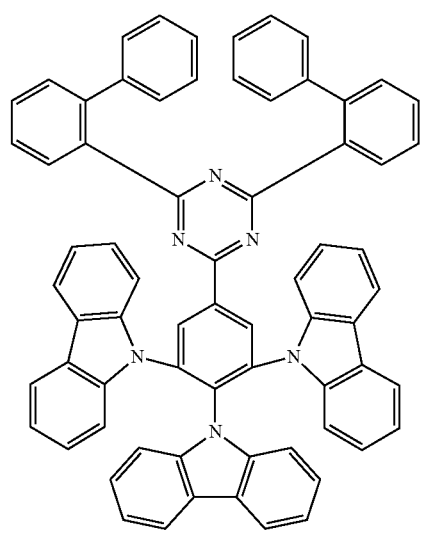
T-194
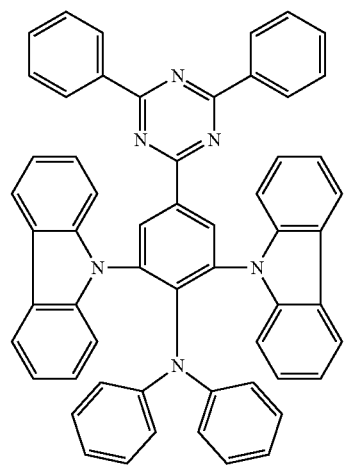

T-195
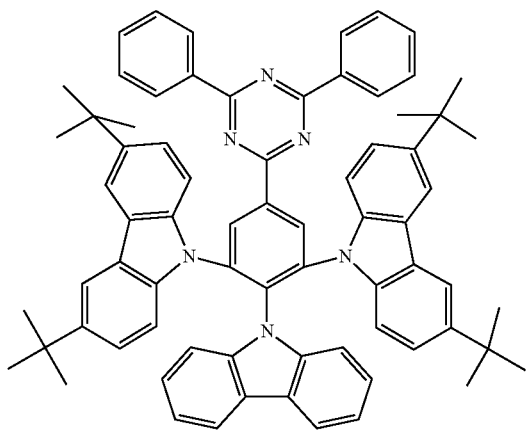
T-198
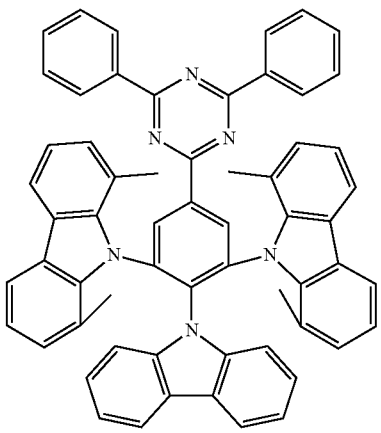
T-196
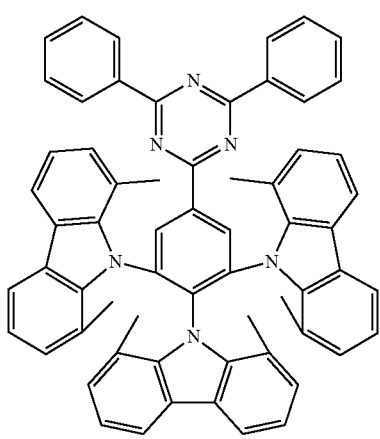
T-199
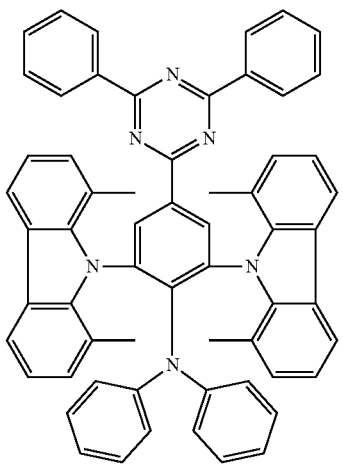
T-197
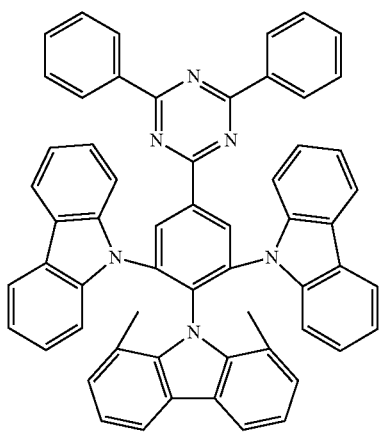
T-200
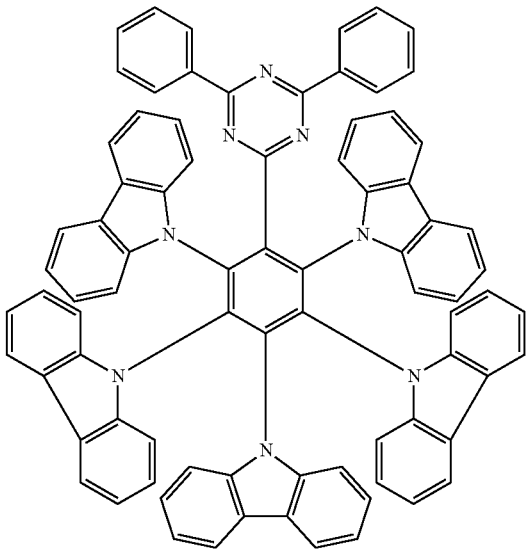

T-201
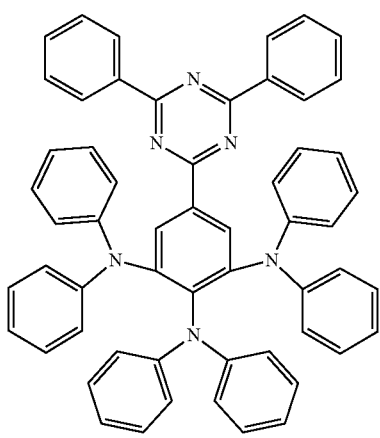
T-202
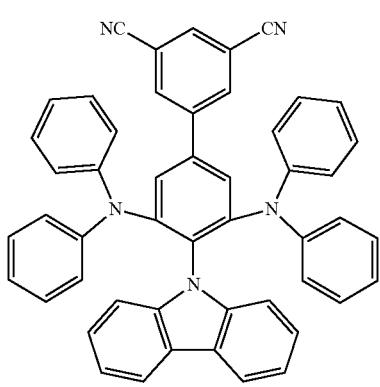
[Formula 122]
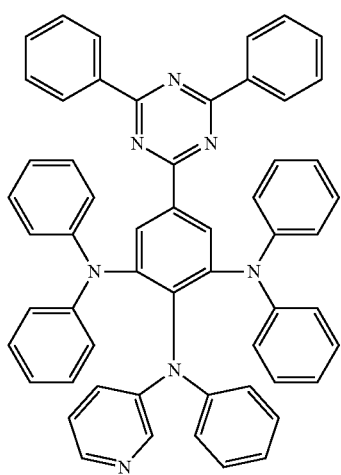
T-204
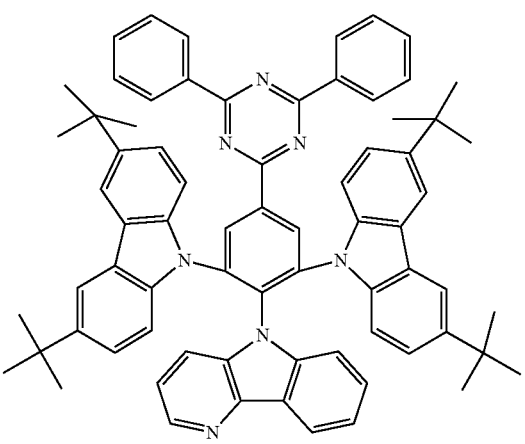
T-205
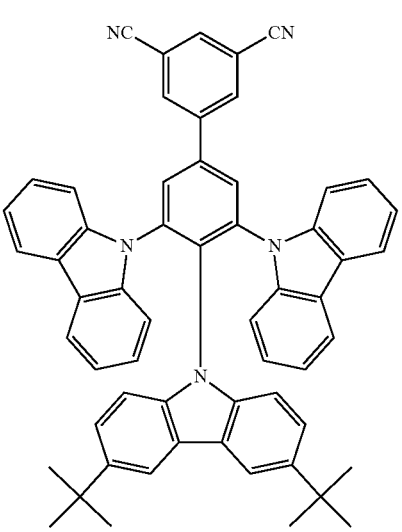
T-203
T-206
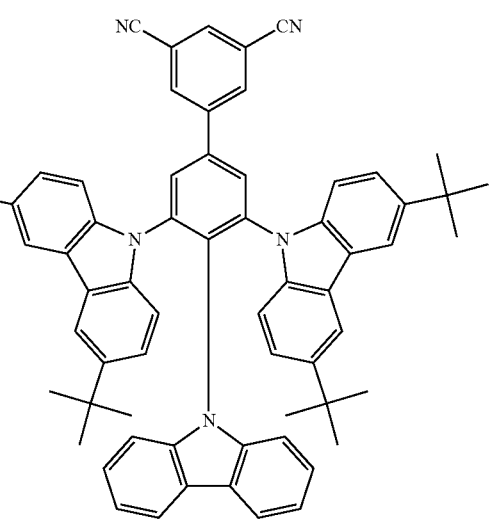

T-207
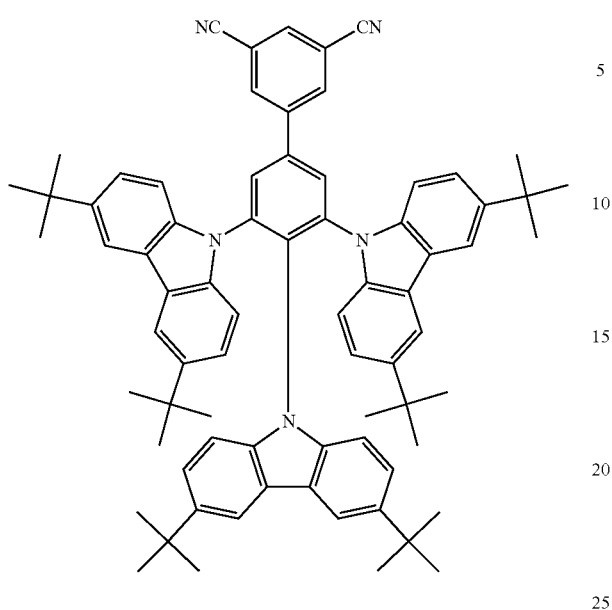
T-211 [Formula 123]
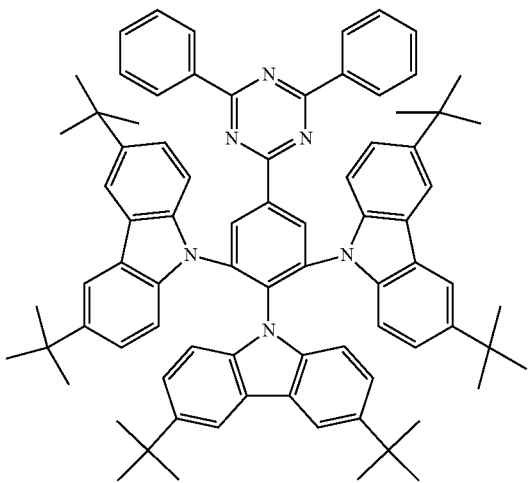
T-208
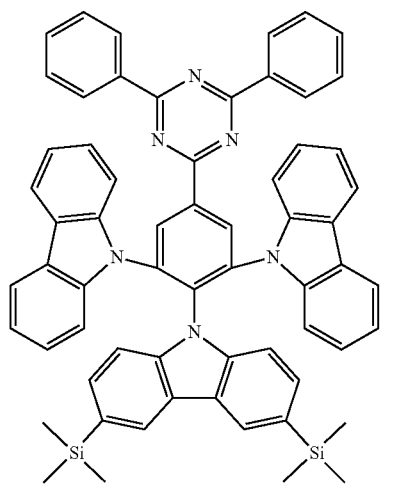
T-212
T-210
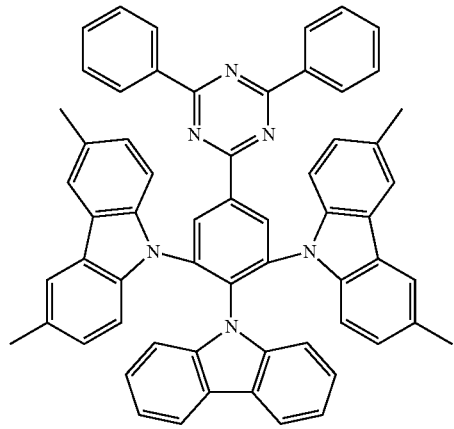
T-214
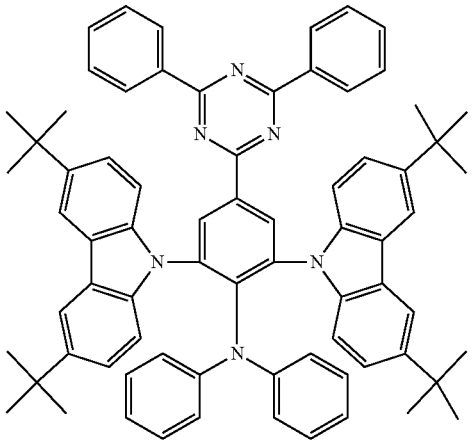

-continued
T-216
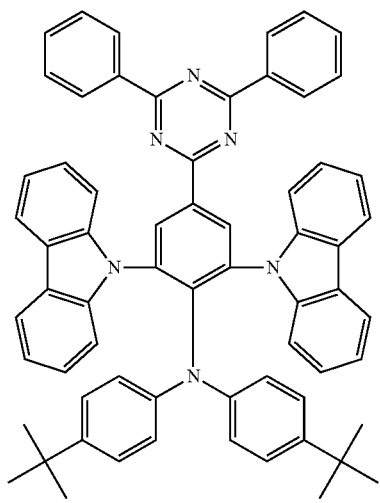
T-221
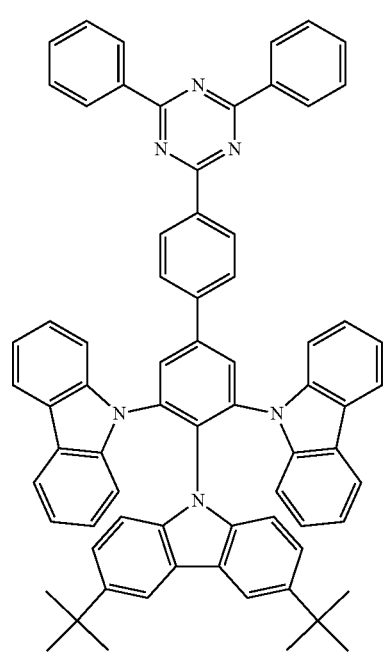
T-227
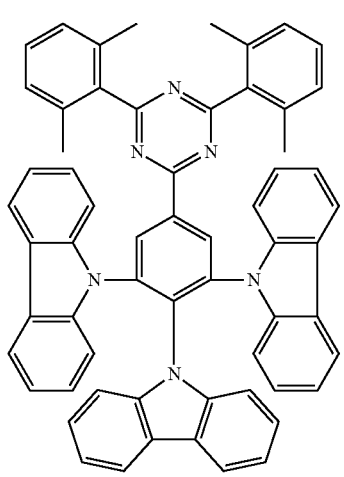
-continued
T-240
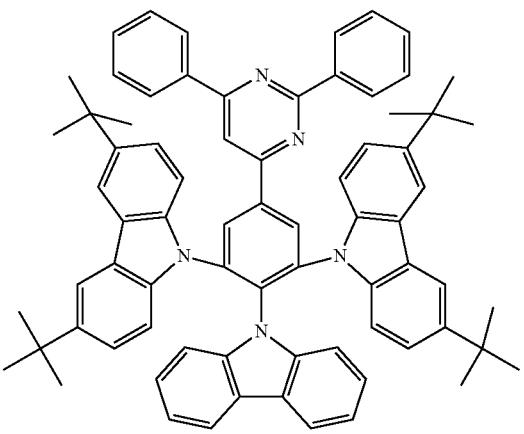
T-249
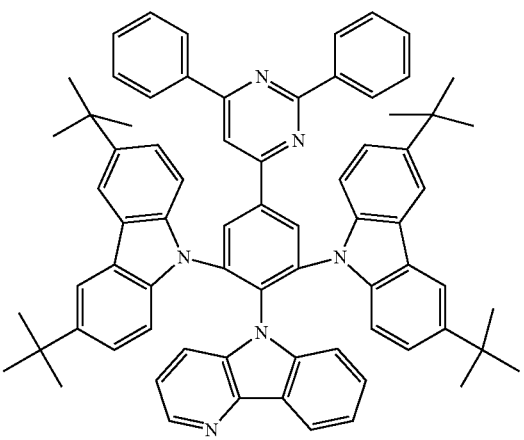
T-252
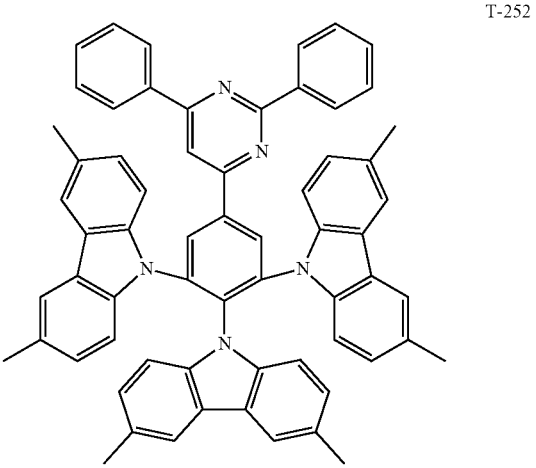

T-254
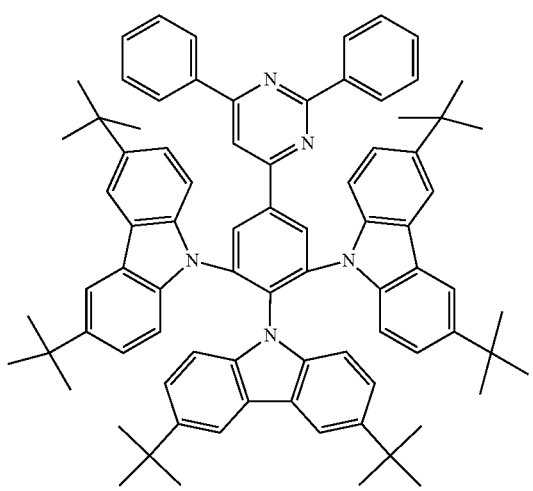
T-275
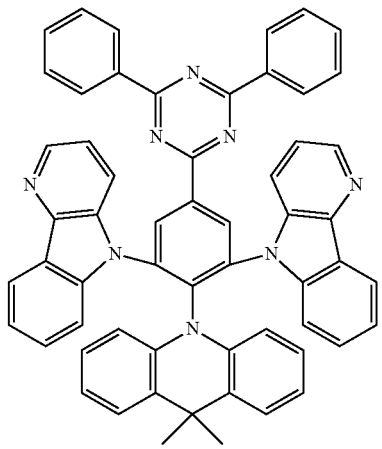
T-257
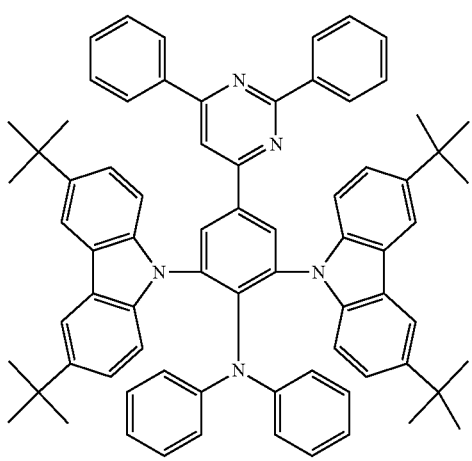
T-282
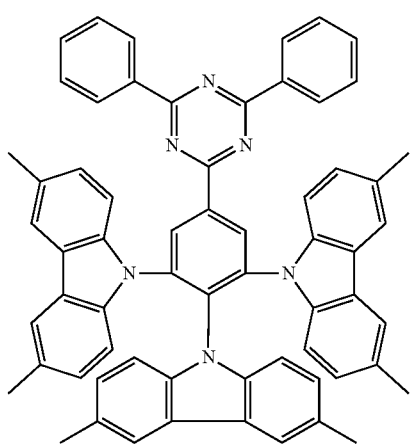
[Formula 124]
T-265
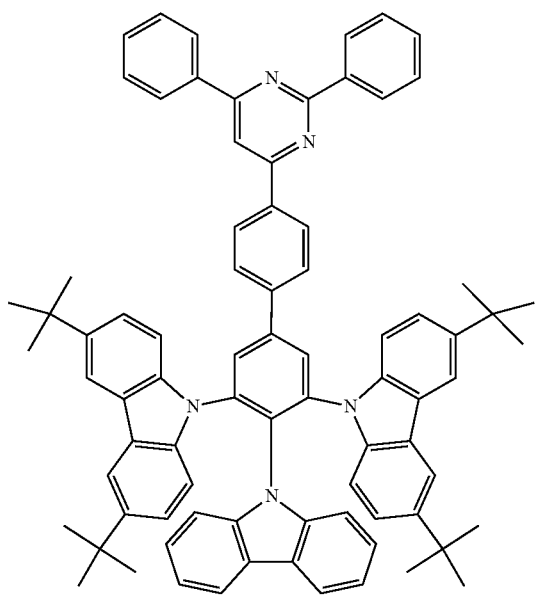
T-298
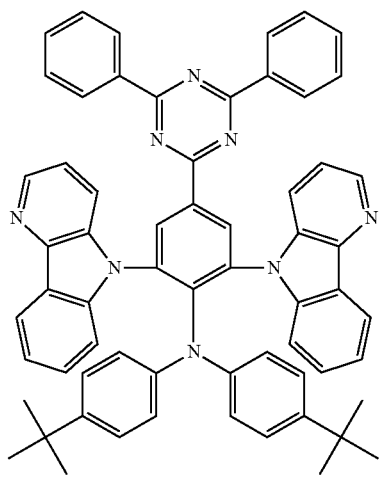

T-306 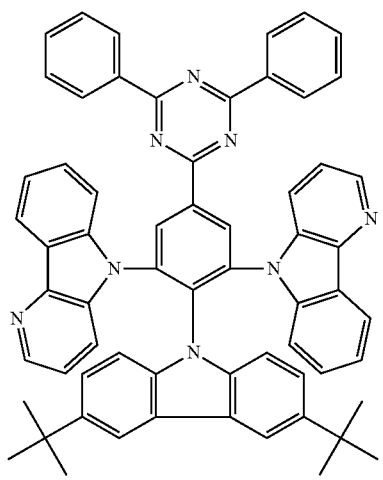
T-354 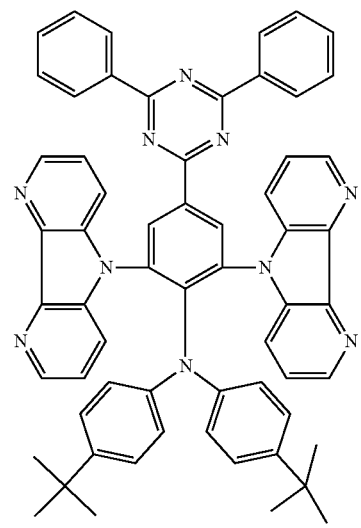
T-328 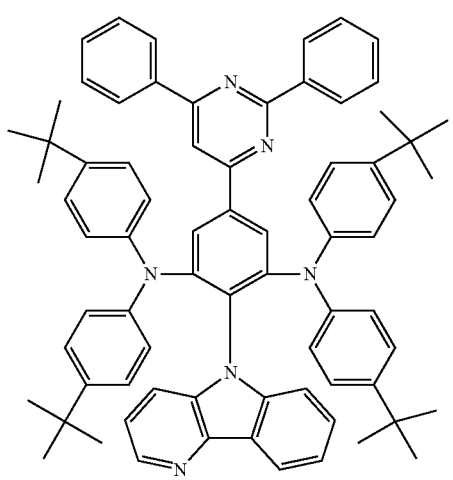
T-365 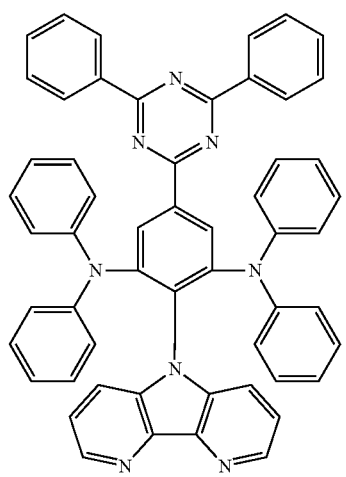
T-353 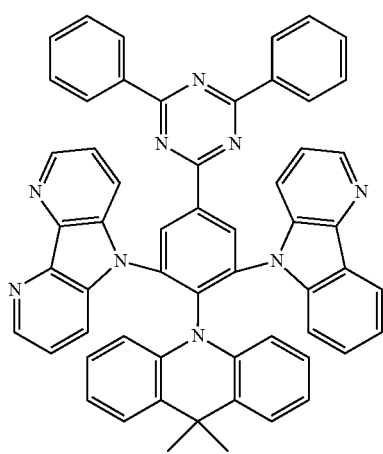
T-366 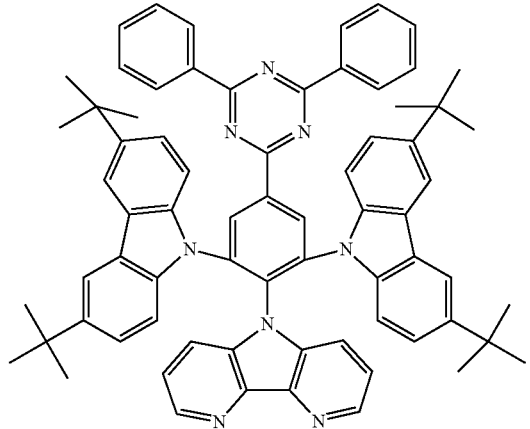

T-399
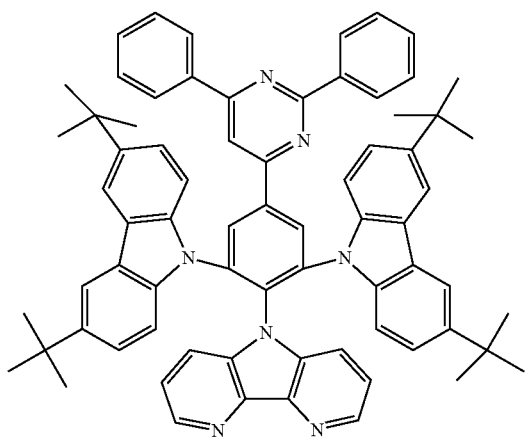
[Formula 125]
T-429
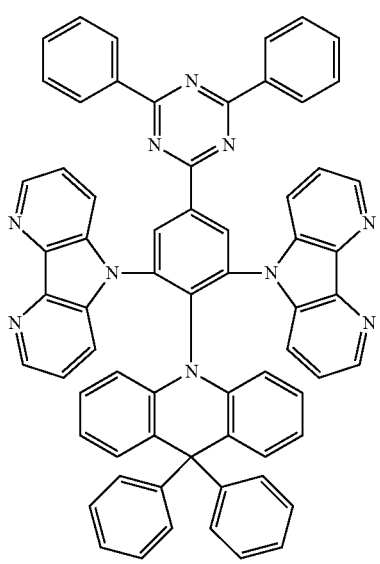
T-432
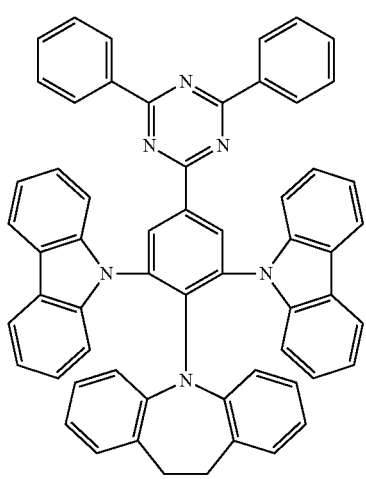
T-434
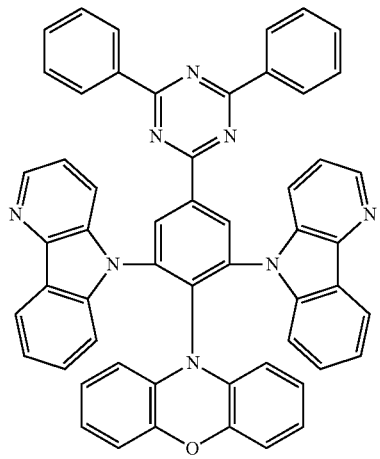
T-442
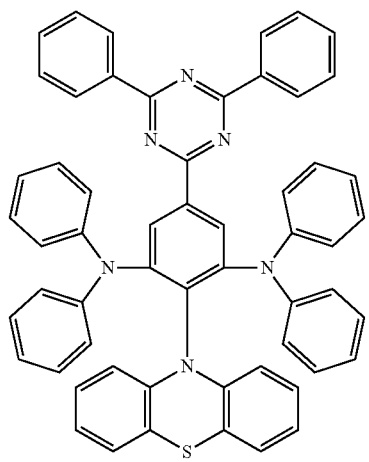
T-447
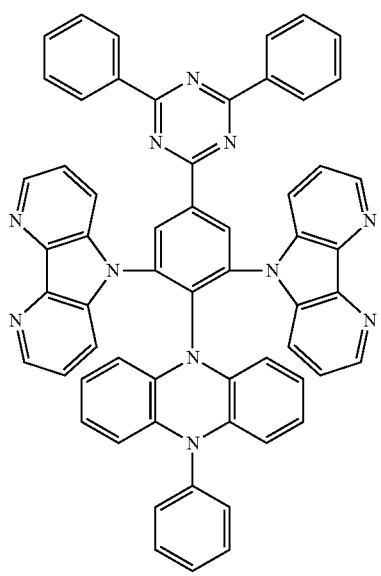

-continued
T-453
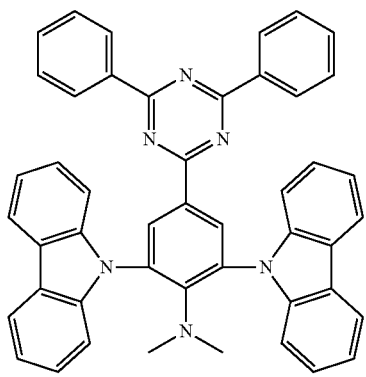
T-456
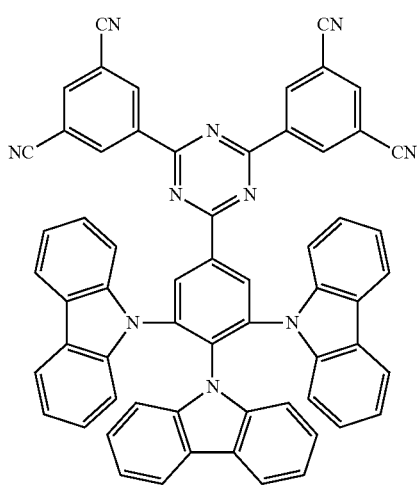
T-457
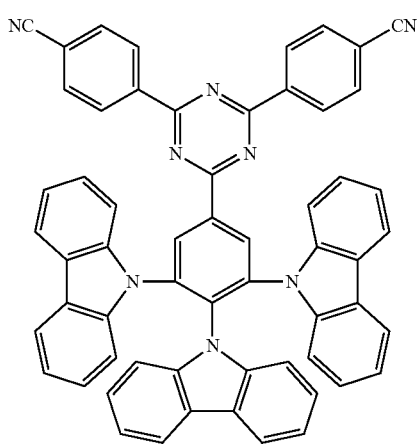
-continued
T-458
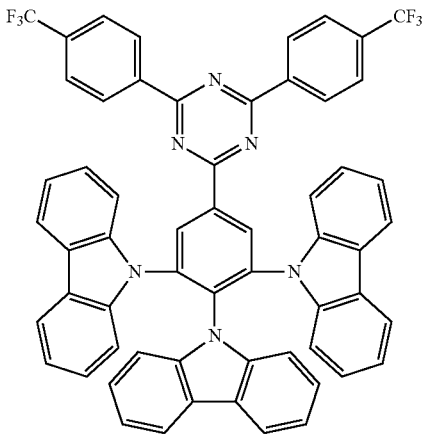
T-459
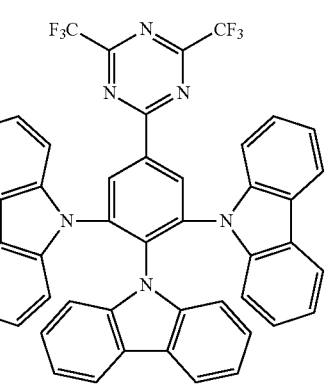
T-497
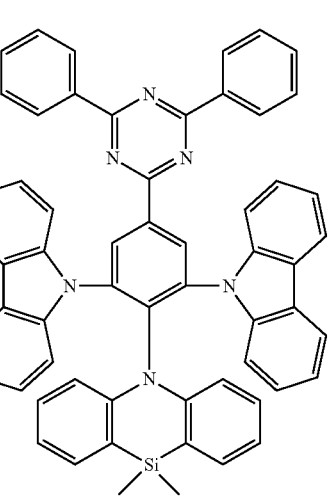

T-504
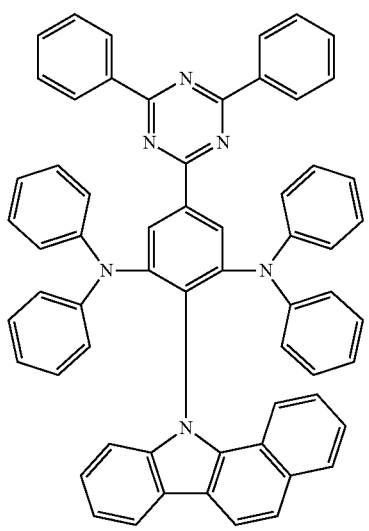
[Formula 126]
T-511
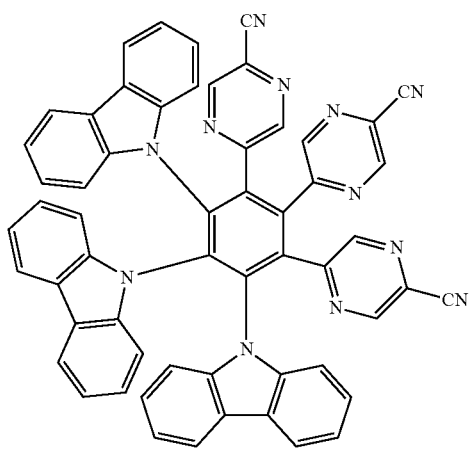
T-512
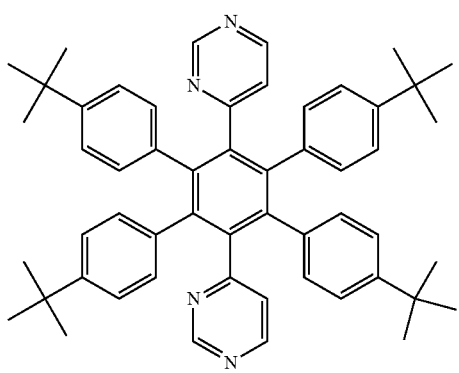
T-513
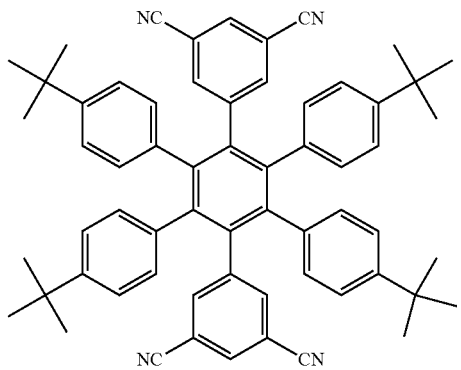
T-514
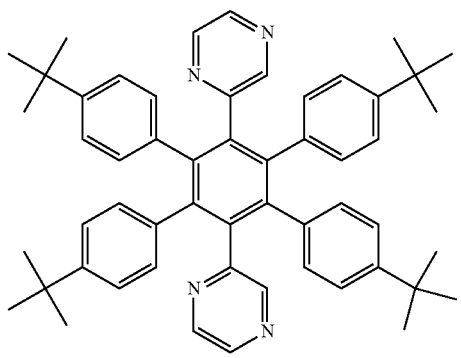
T-515
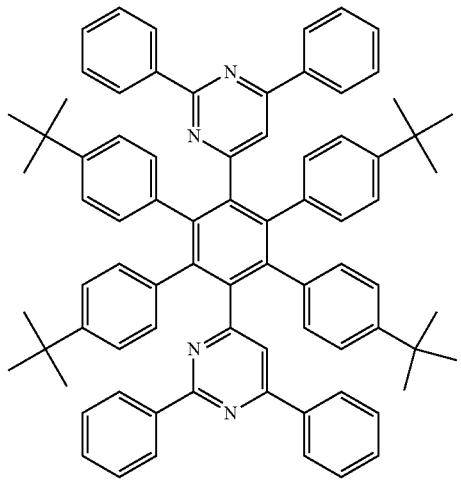

-continued
T-516
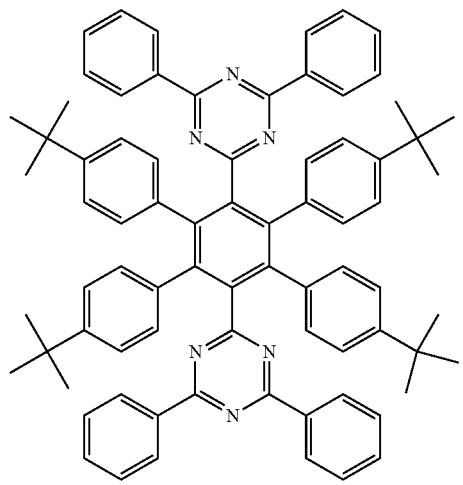
T-517
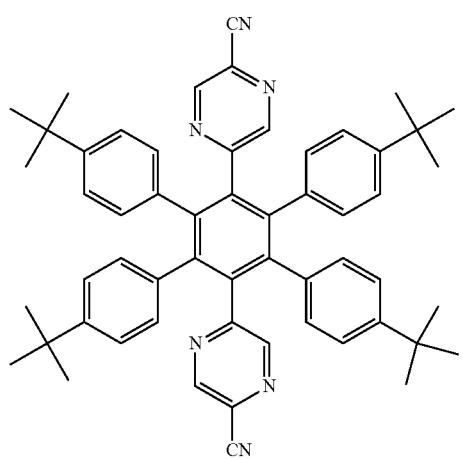
T-518
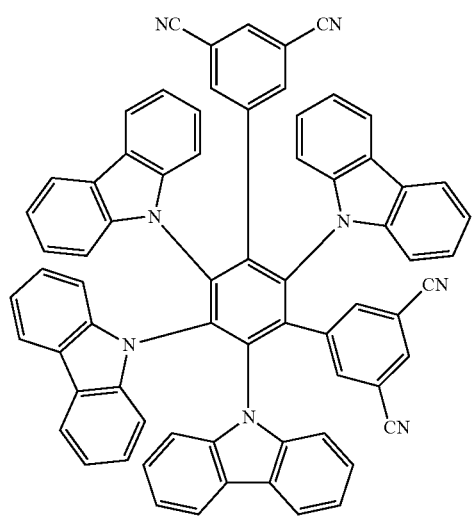
-continued
T-519
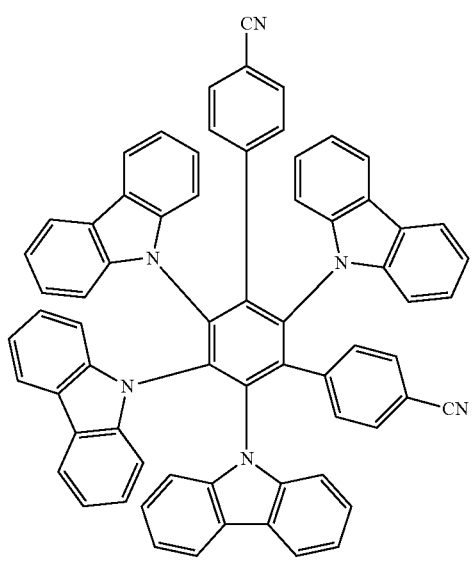
T-520
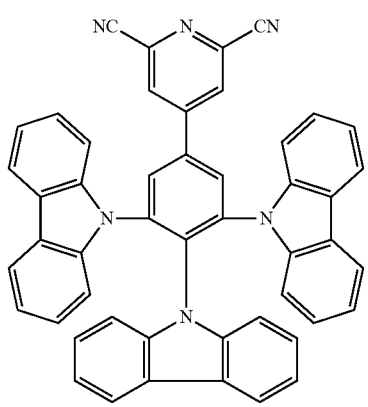
T-522
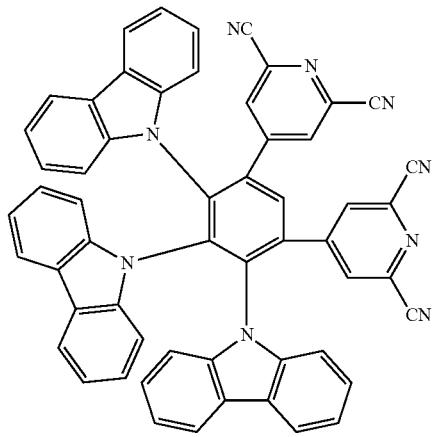

-continued
T-525
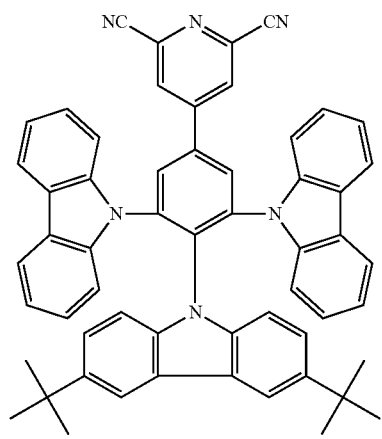
[Formula 127]
T-526
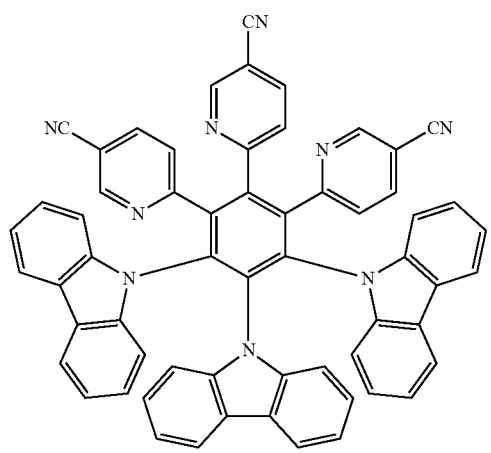
T-527
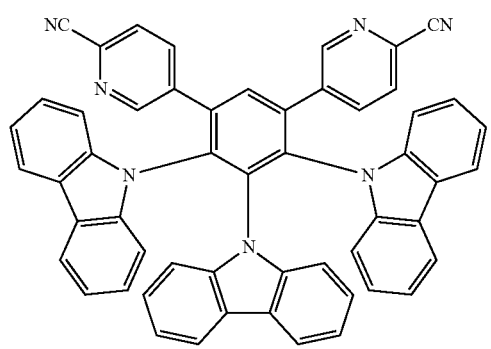
-continued
T-530
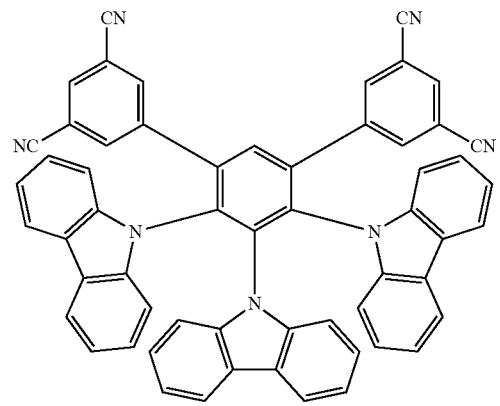
T-531
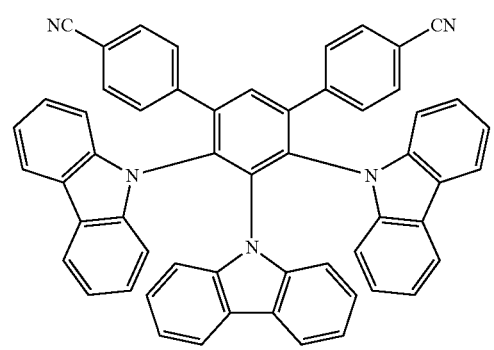
T-540
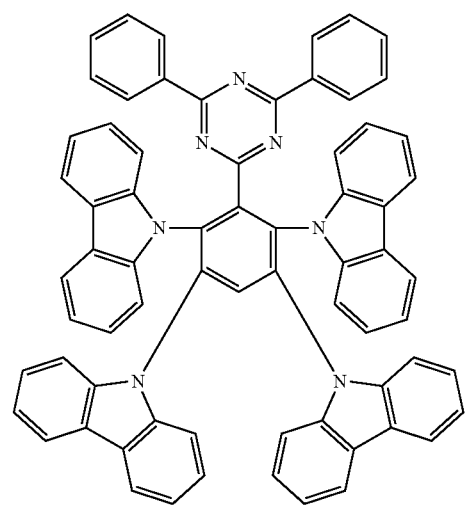

T-541
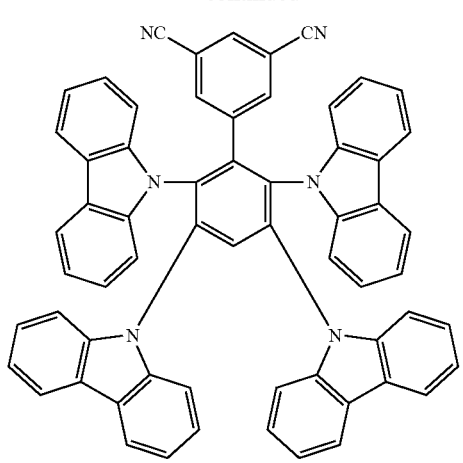
[Formula 128]
T-542
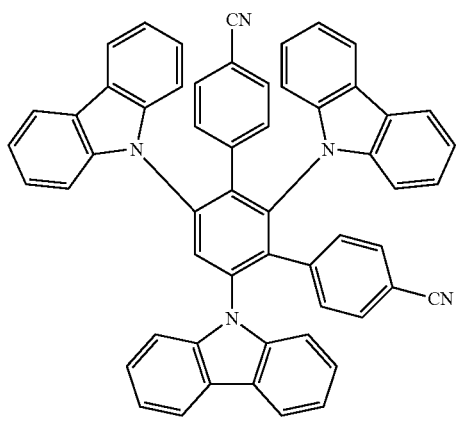
T-543
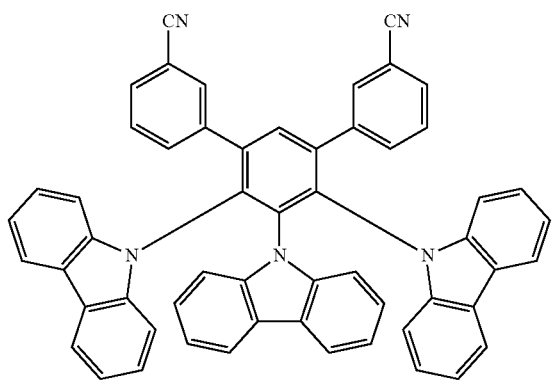
T-544
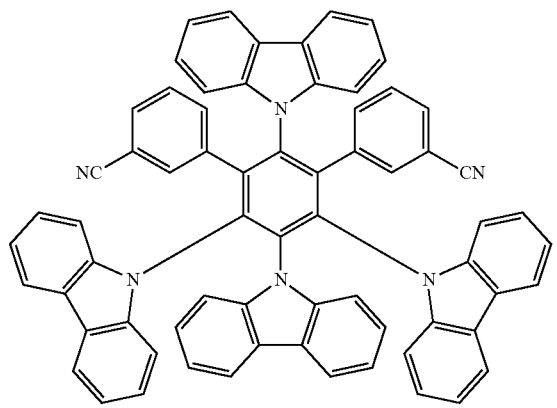
T-545
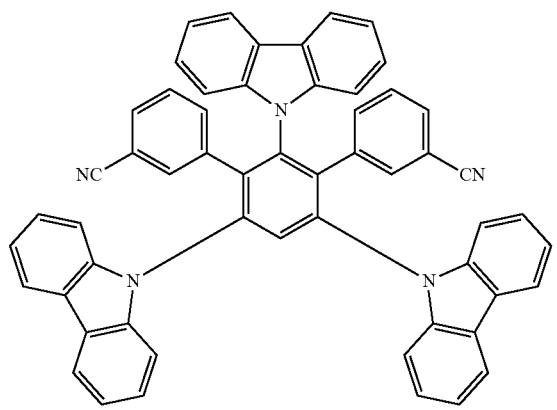
T-546
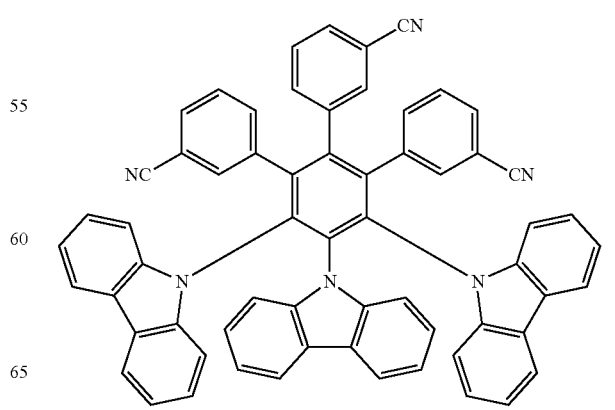

-continued
T-547
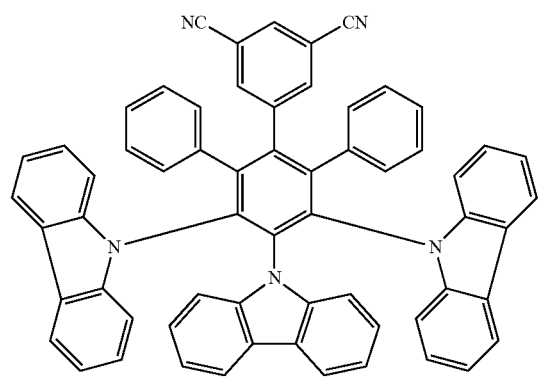
T-548
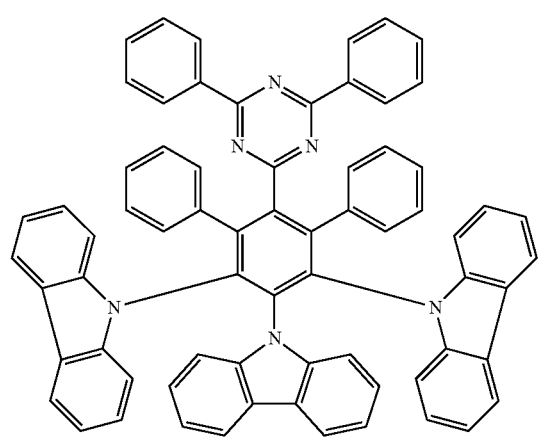
T-549
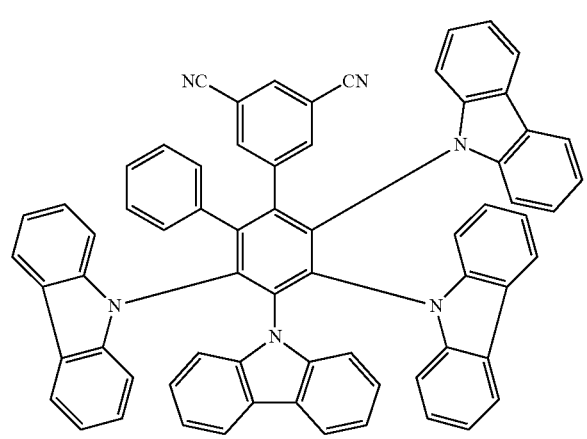
-continued
T-550
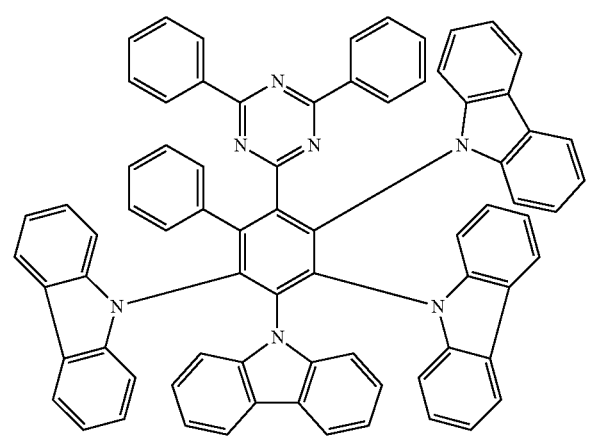
[Formula 129]
T-551
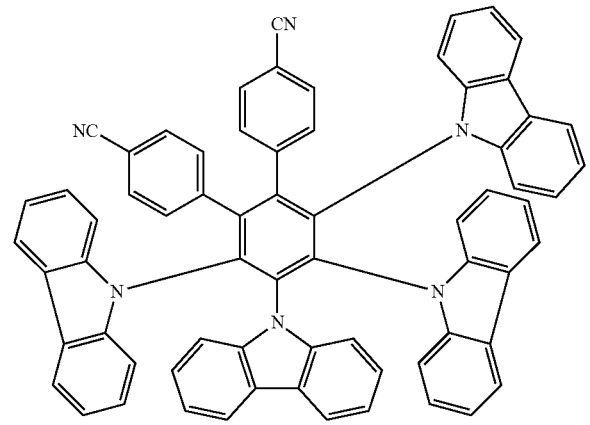
T-552
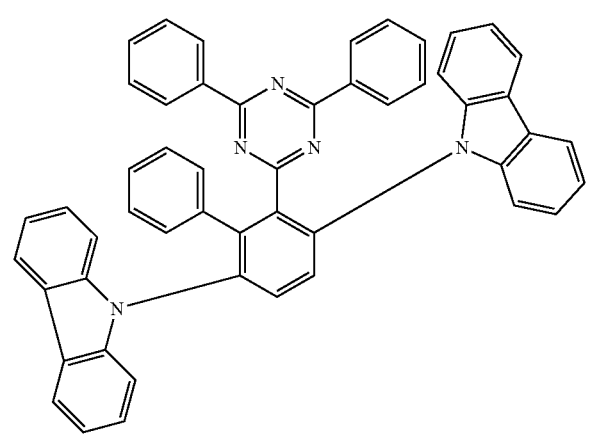

-continued
T-553
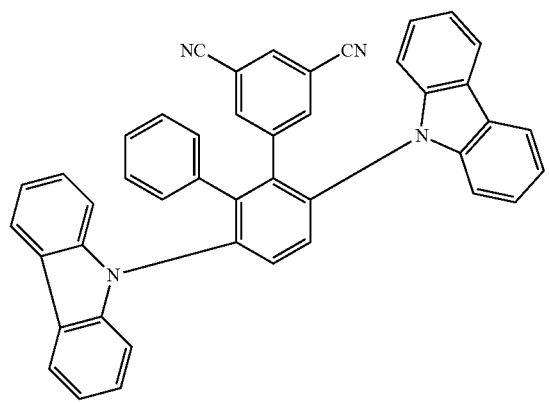
T-558
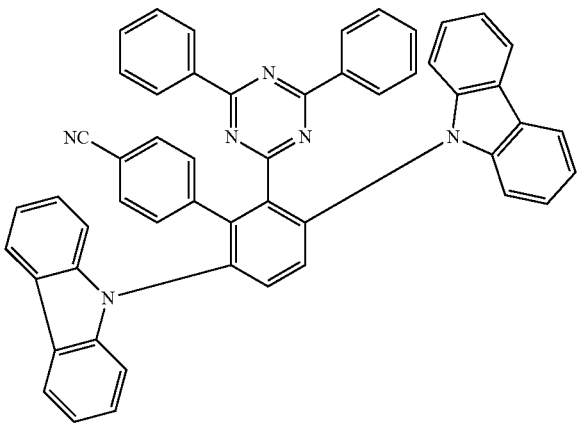
T-555
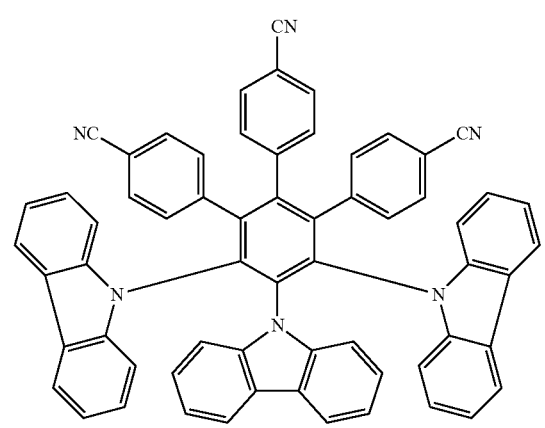
T-561
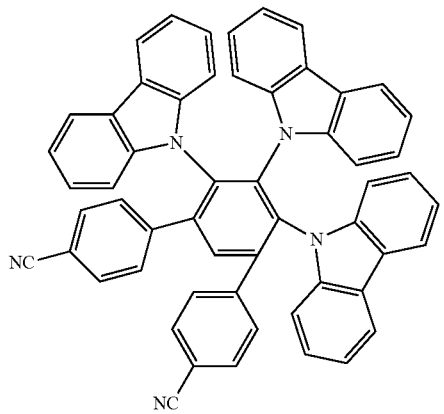
T-556
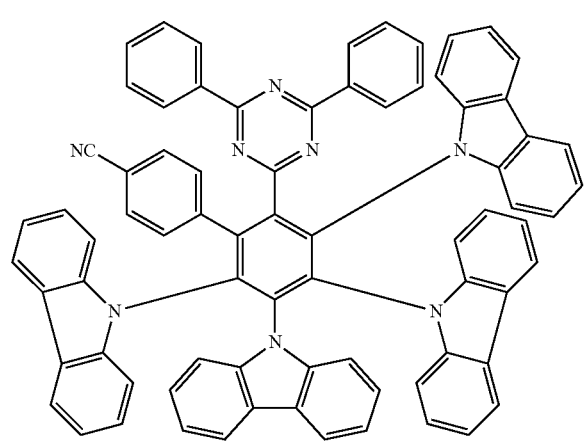
T-562
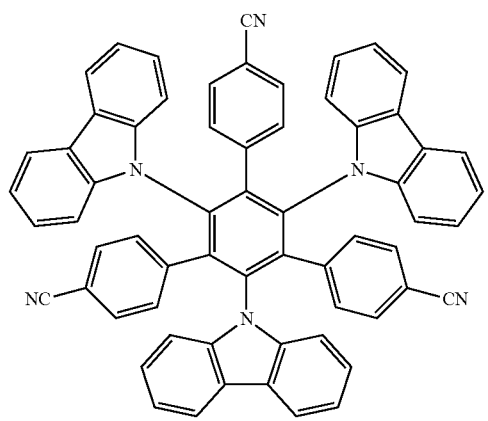

-continued
[Formula 130]
T-563
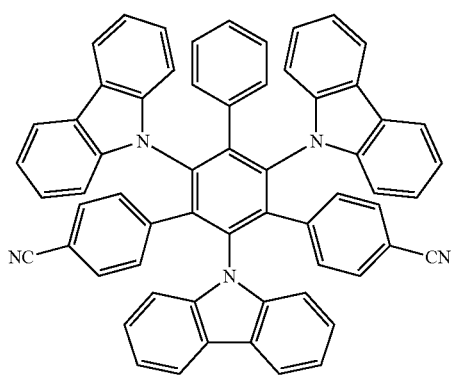
T-564
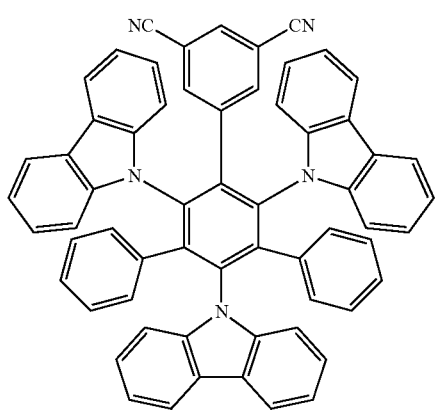
T-565
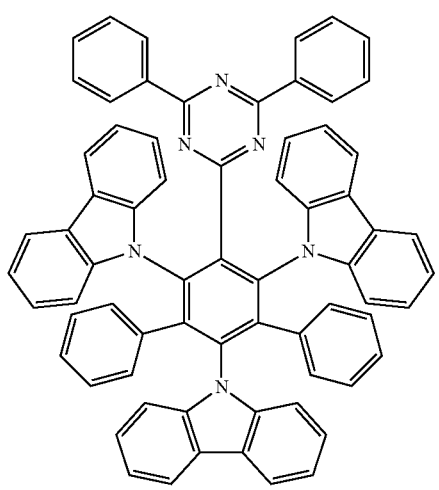
-continued
T-566
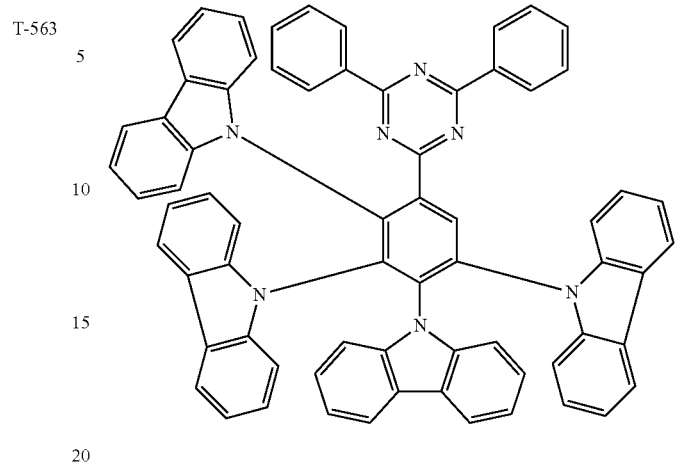
T-567
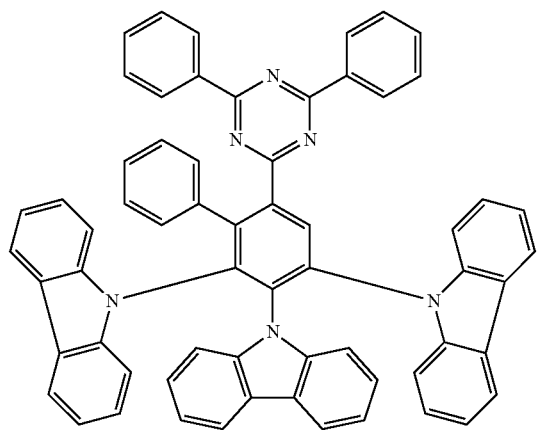
T-568
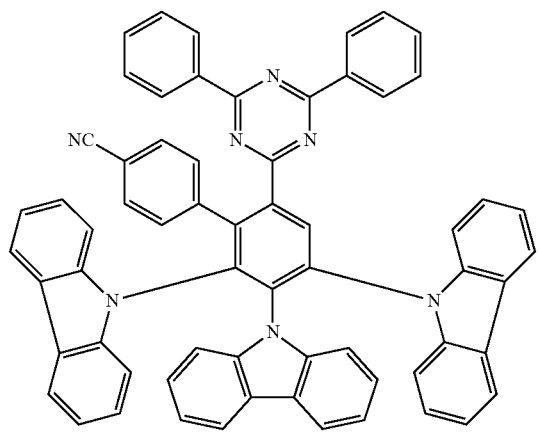

T-569
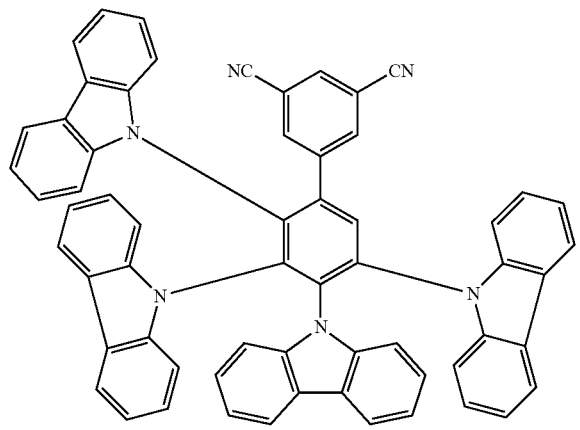
T-570
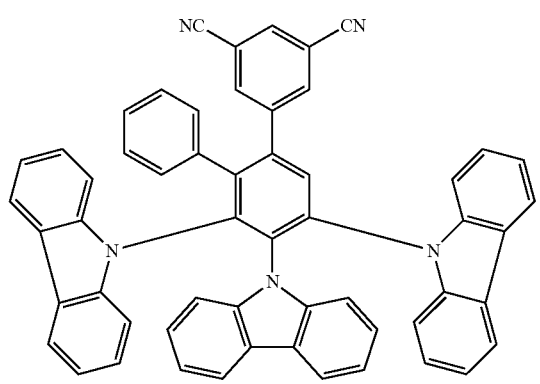
T-571
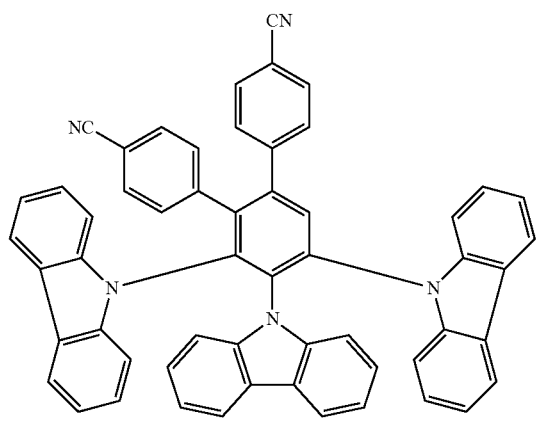
T-572
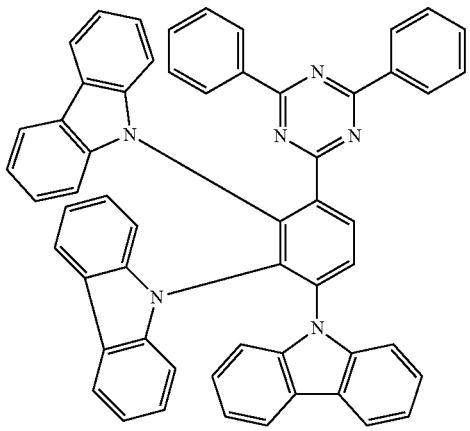
T-573
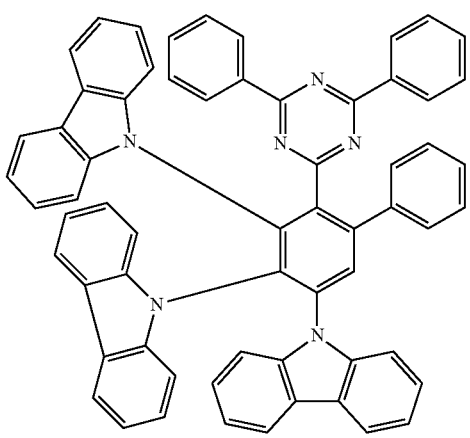
T-574
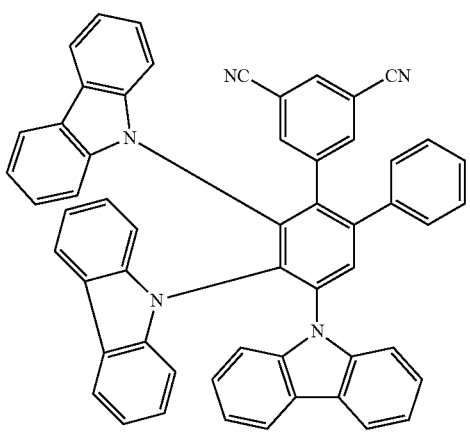

-continued
[Formula 131] T-576
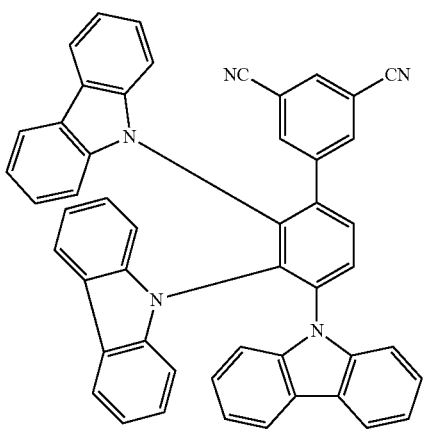
[Formula 132] HAT-CN
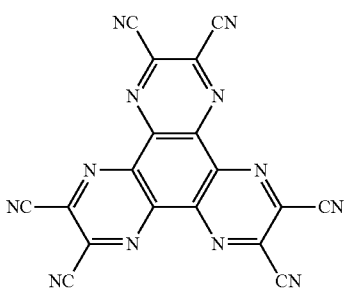
GD-1
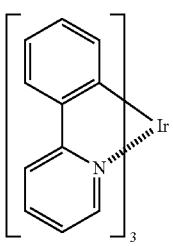
HB-1
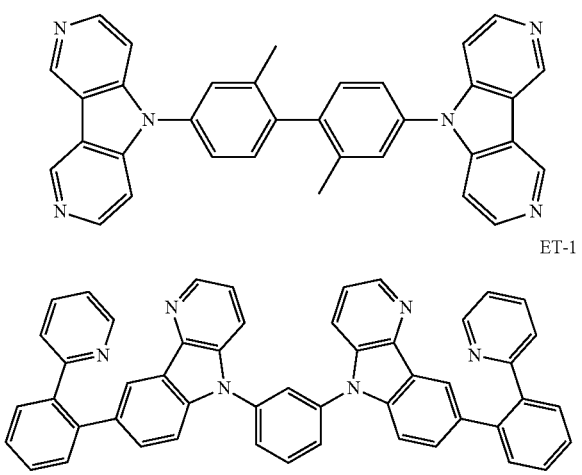
ET-1
-continued
H-232
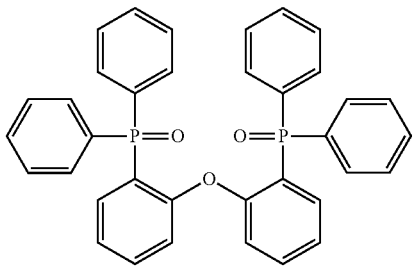
H-234
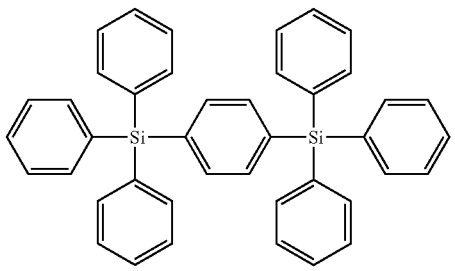
J-1
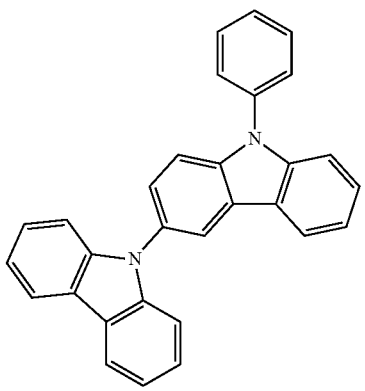
J-5
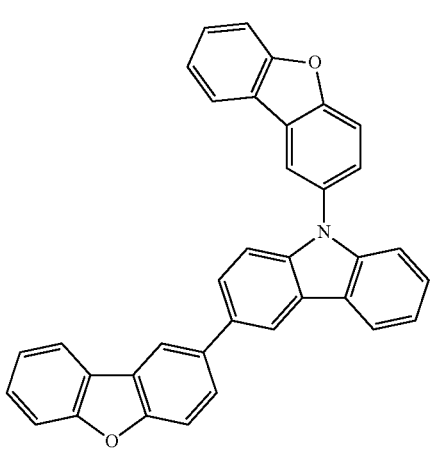

J-16
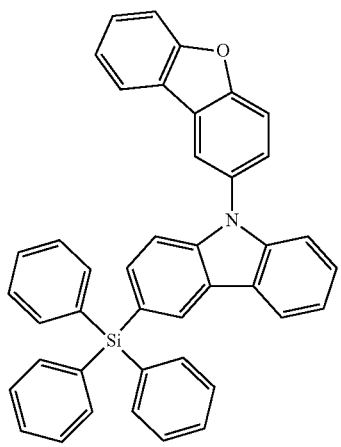
J-17
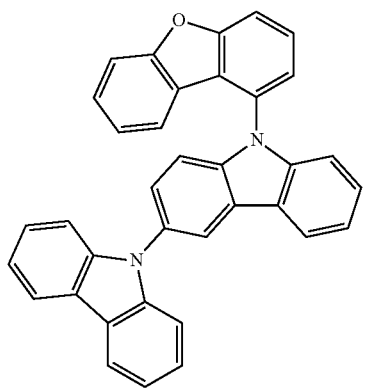
[Formula 133]
J-32
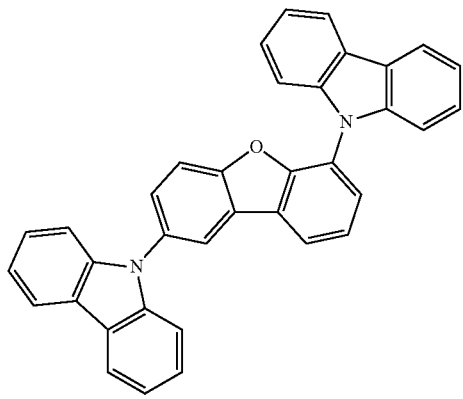
J-33
J-38
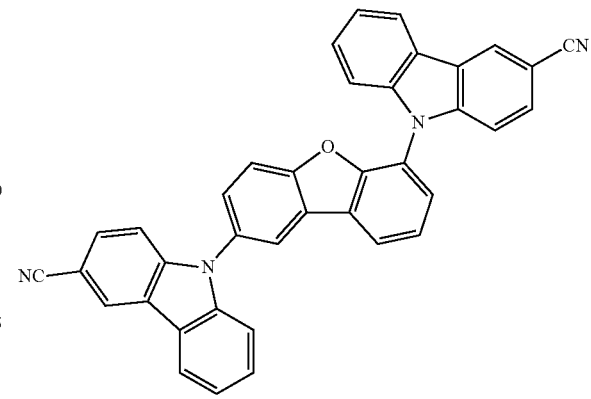
J-43
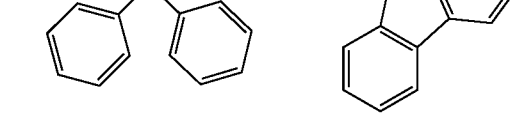
J-45
J-46
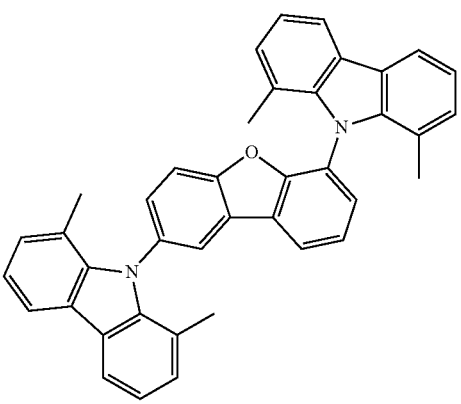

-continued
J-48
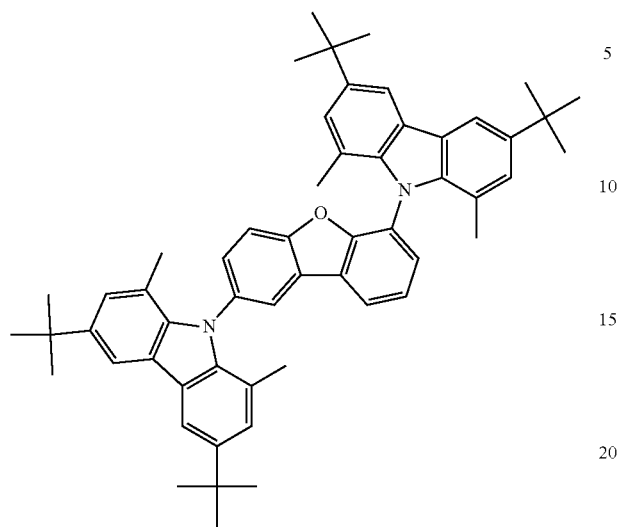
J-52
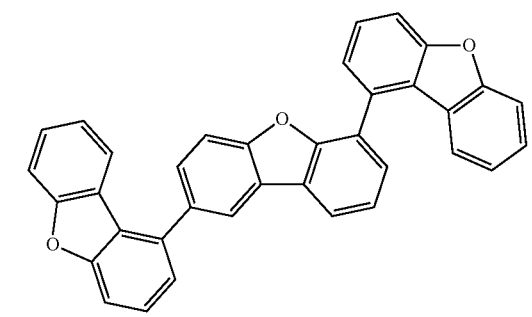
J-54
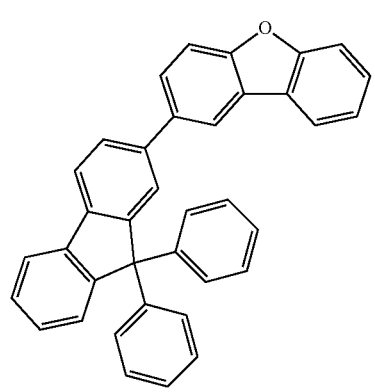
J-66
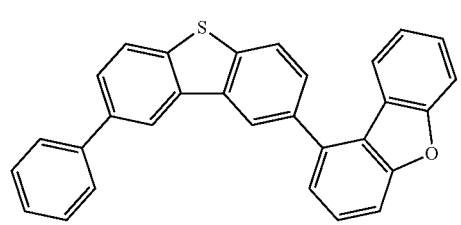
-continued
J-155
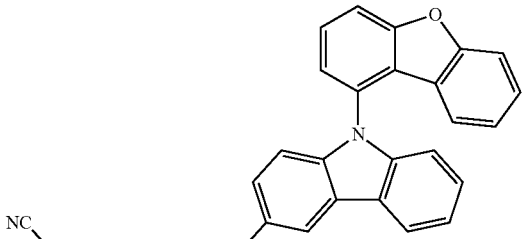
J-168
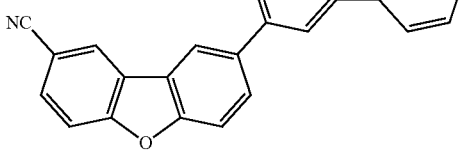
J-183
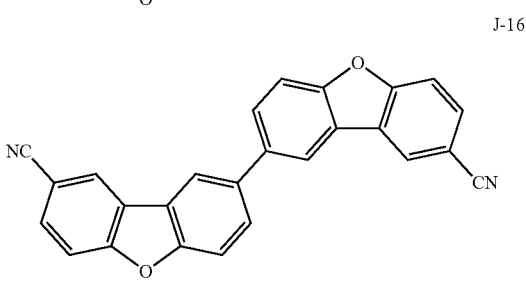
J-192
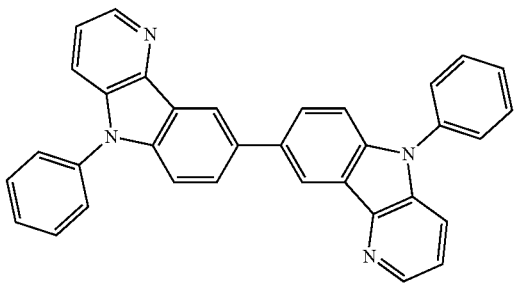
J-194
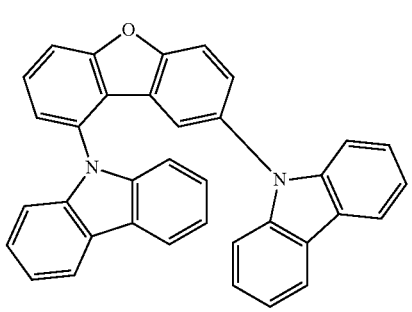

J-213
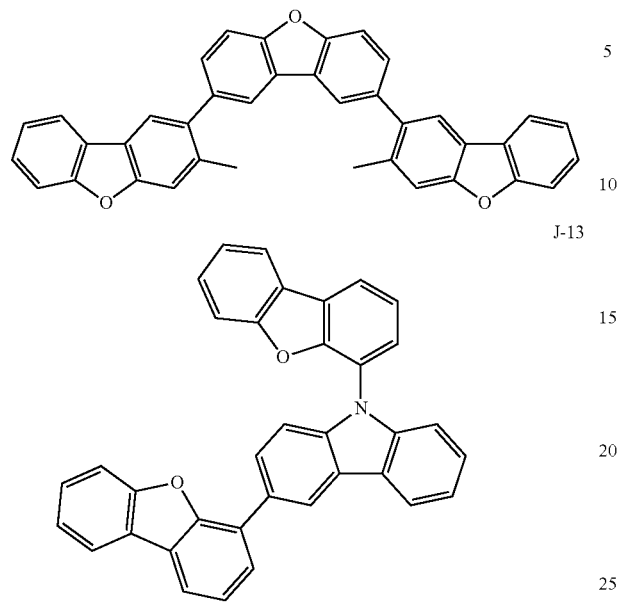
J-13
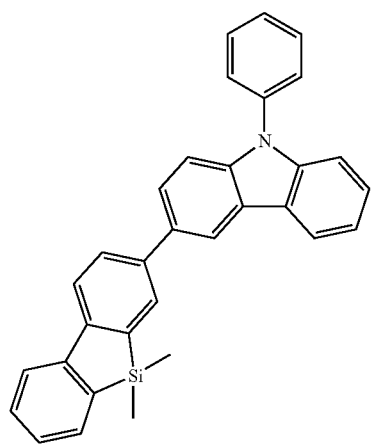
[Formula 134]
J-24
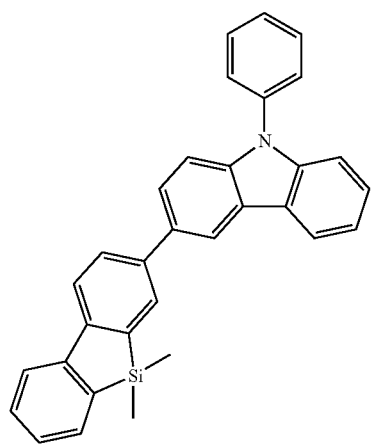
J-164
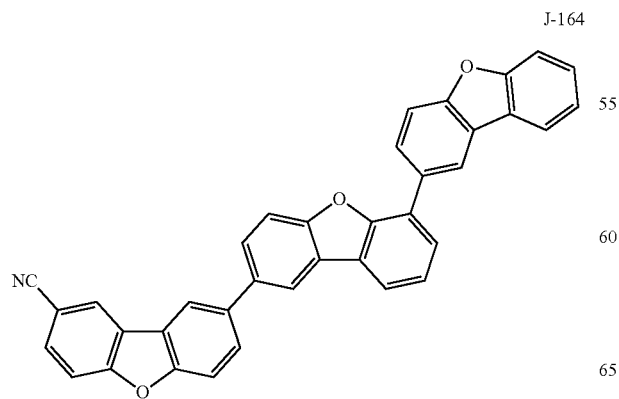
J-170
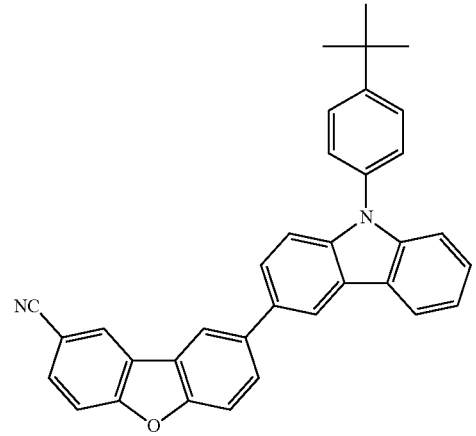
J-197
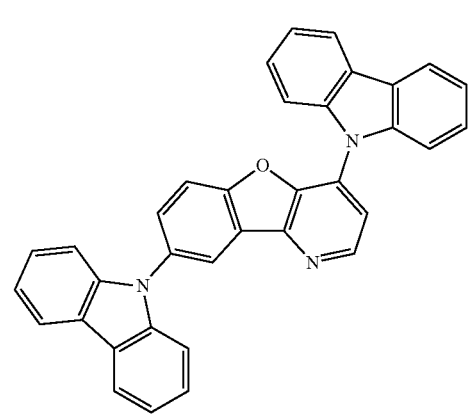
J-41
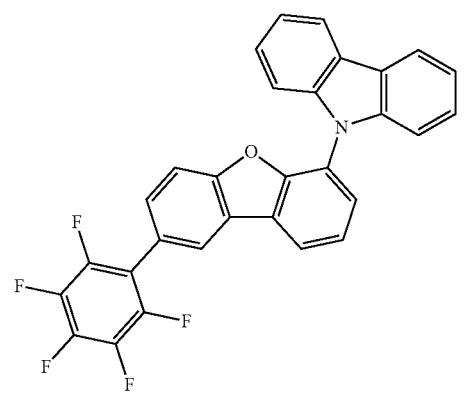
J-11
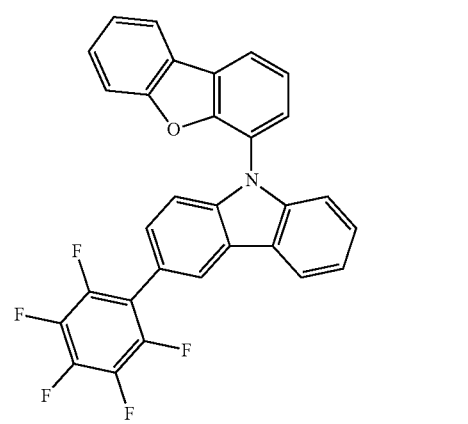

J-25
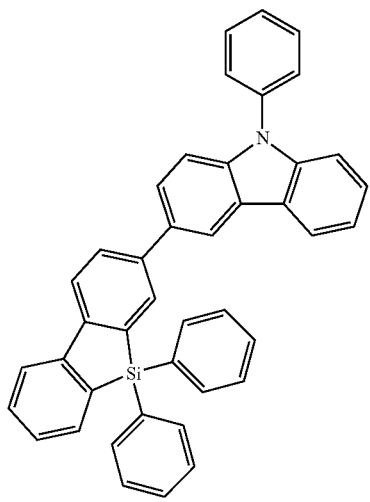
J-36
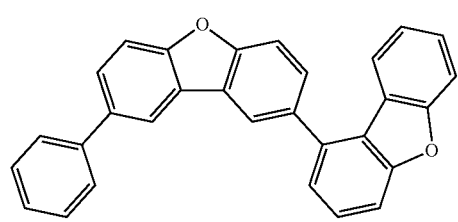
J-42
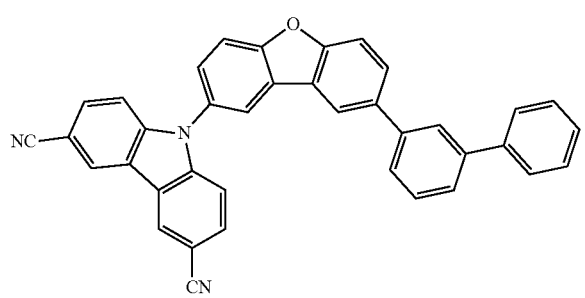
J-56
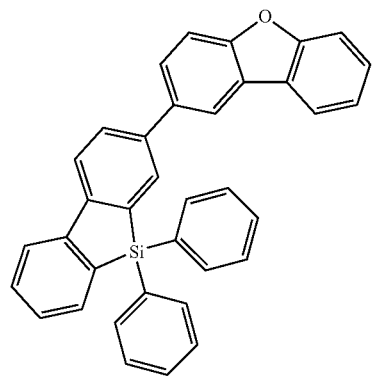
J-68
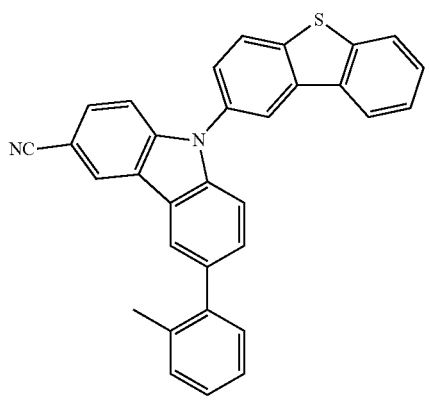
J-83
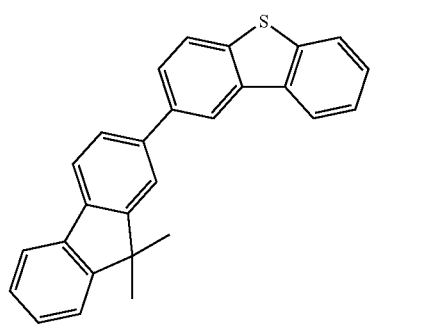
J-91
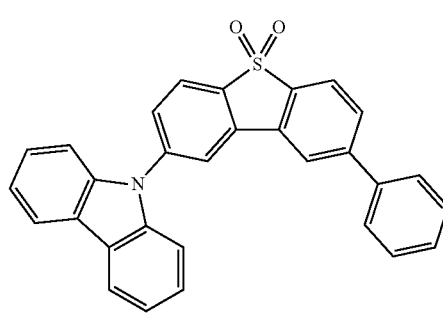
J-102
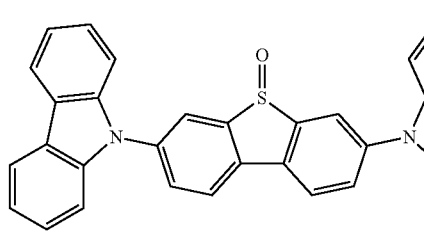
J-113
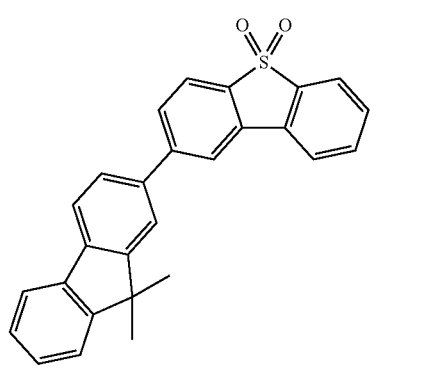

-continued
J-128
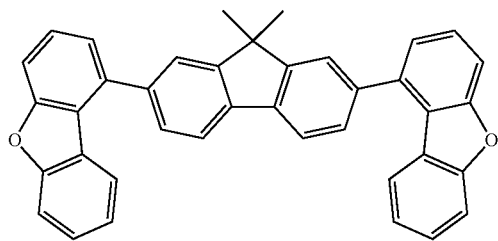
J-129
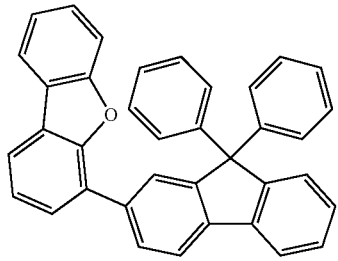
[Formula 135]
J-137
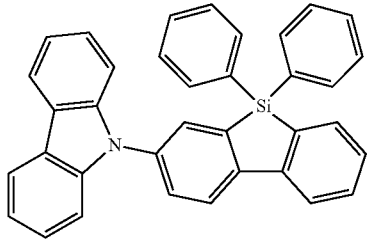
J-148
J-153
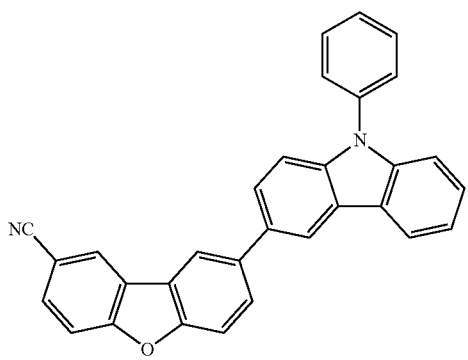
-continued
J-161
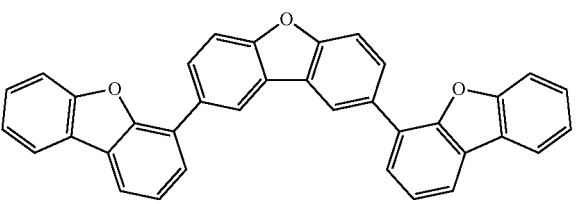
J-171
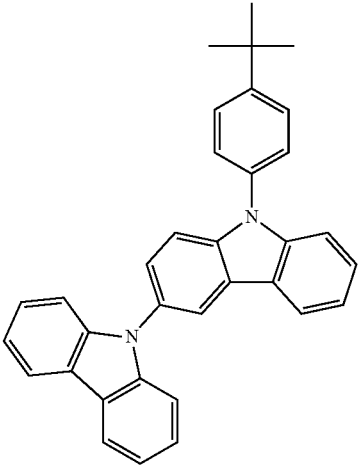
J-172
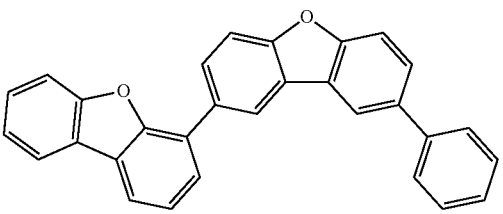
J-187
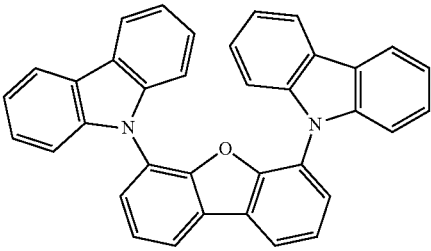
J-204
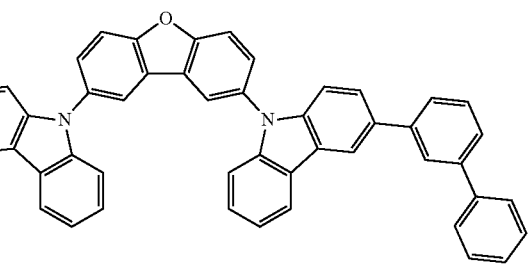

-continued

J-151
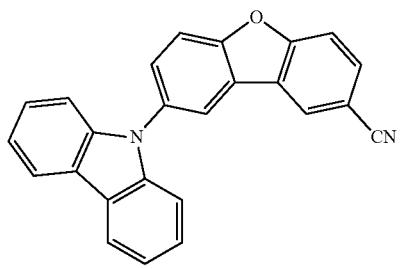

J-168
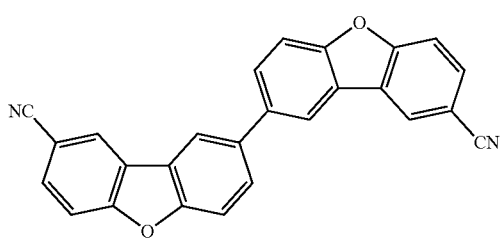

J-197
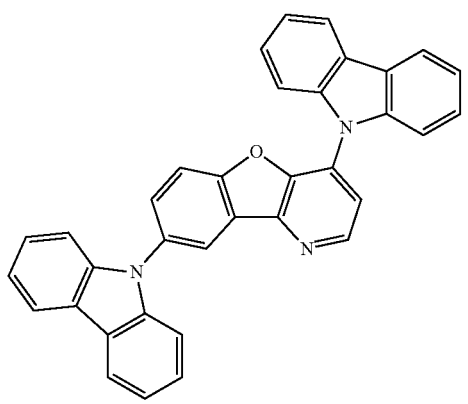

J-210
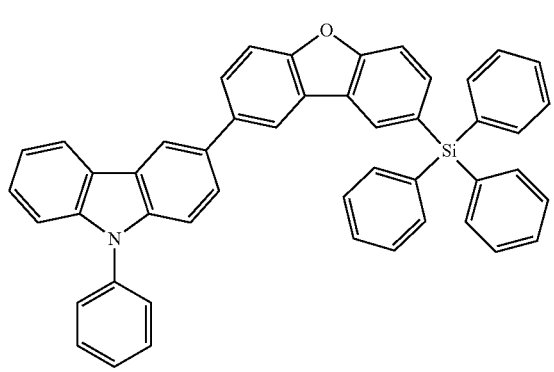

J-213
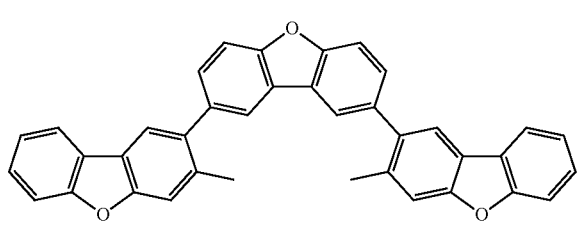

(Synthesis of Compound T-83)

The methods described in WO2010/113755, Organic Letters, 2002, 4, 1783-1785, and Angew. Chem. Int. Ed. 2010, 49, 2014-2017 were used to synthesize Compound T-83. Specifically, 1-bromo-3,4,5-trifluorobenzene and a pyrimidine derivative were subjected to cross-coupling reaction to obtain a 1-pyrimidyl-3,4,5-trifluorobenzene intermediate. The 1-pyrimidyl-3,4,5-trifluorobenzene intermediate was reacted with bromopyrimidine in the presence of a ruthenium catalyst to obtain a 1,2,3-terpyrimidyl-4,5,6-trifluorobenzene intermediate. Under basic conditions, carbazole was reacted with the 1,2,3-terpyrimidyl-4,5,6-trifluorobenzene intermediate to obtain a crude purified product of Compound T-83. Then, the crude purified product was subjected to column chromatography, recrystallization, and purification by sublimation to obtain a high purified product of Compound T-83.

(Synthesis of Other Compounds)

In the same manner described above, the following compounds were synthesized: T-2, T-3, T-13, T-27, T-33, T-59, T-66, T-74, T-78, T-79, T-82, T-83, T-84, T-85, T-96, T-101, T-117, T-124, T-125, T-131 to T-133, T-176, T-180, T-182 to T-208, T-210 to T-212, T-214, T-216, T-221, T-227, T-240, T-249, T-252, T-254, T-257, T-265, T-275, T-282, T-298, T-306, T-328, T-353, T-354, T-365, T-366, T-399, T-429, T-432, T-434, T-442, T-447, T-453, T-456 to T-459, T-497, T-504, T-511 to T-520, T-522, T-525 to T-527, T-530, T-531, T-540 to T-553, T-555, T-556, T-558, T-561 to T-574, and T-576.

$\Delta E_{ST}$ was determined for the compound obtained and comparative compounds 1 and 2 by calculation in accordance with the following method.

(Calculation of $\Delta E_{ST}$)

The structure optimization and calculation of the electron density distribution by molecular orbital calculation of the compound was calculated by using, as a calculation technique, software for molecular orbital calculation including B3LYP as a functional and 6-31G (d) as a basis function. Gaussian 09 available from Gaussian Inc., USA (Revision C. 01, M. J. Frisch, et al., Gaussian, Inc., 2010.) was used as the software for molecular orbital calculation.

From the structure optimization calculation including B3LYP as the functional and 6-31G (d) as the basis function, excited state calculation by means of the time-dependent density functional theory (Time-Dependent DFT) was further carried out to determine energy levels of $S_1$ and $T_1$, ($E(S_1)$ and $E(T_1)$, respectively), which were used for calculation in $\Delta E_{ST}=|E(S_1)-E(T_1)|$.

Example 1

(Production of Organic EL Element 1-1)

Onto a glass substrate having a size of 50 mm×50 mm and a thickness of 0.7 mm, indium tin oxide (ITO) was deposited into a thickness of 150 nm as an anode, which was subjected to patterning. Subsequently, the transparent substrate provided with the ITO transparent electrode was ultrasonic cleaned in isopropyl alcohol, was dried with dry nitrogen gas, and was cleaned with UV ozone for 5 minutes. This transparent substrate was fixed to a substrate holder of a commercially available vacuum evaporation apparatus.

Materials for individual layers, in optimum amounts for producing an element, were placed into individual vapor deposition crucibles in the vacuum evaporation apparatus. The vapor deposition crucibles used were composed of a material for resistance heating, such as molybdenum or tungsten.

After the apparatus was evacuated to a degree of vacuum of $1\times10^{-4}$ Pa, the vapor deposition crucible containing 1,4,5,8,9,12-hexaazatriphenylene hexacarbonitrile (HAT-CN) was energized and heated to deposit HAT-CN onto the ITO transparent electrode at a deposition rate of 0.1 nm/s, thereby forming a hole injection/transport layer having a thickness of 10 nm.

Subsequently, 4,4'-bis[N-(1-naphthyl)-N-phenylamino] biphenyl (α-NPD) was deposited onto the hole injection layer at a deposition rate of 0.1 nm/s, thereby forming a hole transport layer having a thickness of 40 nm. Host compound H-232 and comparative compound 1 were co-deposited at a deposition rate of 0.1 nm/s so as to achieve 94 vol % and 6 vol % each, thereby forming a light-emitting layer having a thickness of 30 nm.

Subsequently, 2,9-dimethyl-4,7-diphenyl-1,10-phenanthroline (BCP) was deposited at a deposition rate of 0.1 nm/s, thereby forming an electron transport layer having a thickness of 30 nm.

Additionally, lithium fluoride was deposited into a thickness of 0.5 nm, and then aluminum was deposited to 100 nm thereon, thereby forming a cathode.

The non-light emitting surface side of the element described above was covered with a can-shaped glass case under an atmosphere of high purity nitrogen gas having a purity of at least 99.999% and electrode extraction wiring was installed thereto, thereby producing the organic EL element 1-1.

(Production of Organic EL Elements 1-2 to 1-141)

Organic EL elements 1-2 to 1-141 were produced in the same manner as organic EL element 1-1 except that the luminescent compound was changed from comparative compound 1 to those shown in Tables 1 to 4.

TABLE 1

| Organic EL element | Luminescent compound | $\Delta E_{ST}$ (eV) | Relative emission efficiency (%) | Remarks |
|---|---|---|---|---|
| 1-1 | Comparative compound 1 | 0.55 | 100 | Comparative Example |
| 1-2 | Comparative compound 2 | 0.16 | 110 | Comparative Example |
| 1-3 | Comparative compound 3 | 0.26 | 107 | Comparative Example |
| 1-4 | Comparative compound 4 | 0.31 | 105 | Comparative Example |
| 1-5 | T-2 | 0.05 | 145 | Present invention |
| 1-6 | T-3 | 0.03 | 155 | Present invention |
| 1-7 | T-13 | 0.04 | 160 | Present invention |
| 1-8 | T-27 | 0.22 | 120 | Present invention |
| 1-9 | T-59 | 0.19 | 122 | Present invention |
| 1-10 | T-66 | 0.04 | 150 | Present invention |
| 1-11 | T-74 | 0.04 | 143 | Present invention |
| 1-12 | T-82 | 0.10 | 140 | Present invention |
| 1-13 | T-83 | 0.14 | 137 | Present invention |
| 1-14 | T-84 | 0.06 | 143 | Present invention |
| 1-15 | T-85 | 0.08 | 141 | Present invention |
| 1-16 | T-96 | 0.13 | 136 | Present invention |
| 1-17 | T-101 | 0.11 | 137 | Present invention |
| 1-18 | T-117 | 0.16 | 127 | Present invention |
| 1-19 | T-124 | 0.18 | 125 | Present invention |
| 1-20 | T-125 | 0.28 | 119 | Present invention |
| 1-21 | T-131 | 0.04 | 162 | Present invention |
| 1-22 | T-133 | 0.05 | 159 | Present invention |
| 1-23 | Comparative compound 5 | 0.34 | 112 | Comparative Example |
| 1-24 | Comparative compound 6 | 0.01 | 113 | Comparative Example |
| 1-25 | Comparative compound 9 | 0.08 | 111 | Comparative Example |
| 1-26 | T-78 | 0.22 | 147 | Present invention |
| 1-27 | T-176 | 0.22 | 142 | Present invention |
| 1-28 | T-182 | 0.24 | 163 | Present invention |
| 1-29 | T-183 | 0.09 | 182 | Present invention |
| 1-30 | T-184 | 0.03 | 172 | Present invention |
| 1-31 | T-185 | 0.23 | 123 | Present invention |
| 1-32 | T-186 | 0.23 | 155 | Present invention |
| 1-33 | T-187 | 0.18 | 119 | Present invention |
| 1-34 | T-188 | 0.02 | 132 | Present invention |
| 1-35 | T-189 | 0.04 | 161 | Present invention |
| 1-36 | T-190 | 0.14 | 154 | Present invention |
| 1-37 | T-191 | 0.19 | 146 | Present invention |
| 1-38 | T-192 | 0.18 | 121 | Present invention |
| 1-39 | T-193 | 0.20 | 122 | Present invention |
| 1-40 | T-194 | 0.45 | 151 | Present invention |
| 1-41 | T-195 | 0.01 | 182 | Present invention |
| 1-42 | T-196 | 0.01 | 151 | Present invention |
| 1-43 | T-197 | 0.15 | 150 | Present invention |

TABLE 2

| Organic EL element | Luminescent compound | $\Delta E_{ST}$ (eV) | Relative emission efficiency (%) | Remarks |
|---|---|---|---|---|
| 1-44 | T-198 | 0.02 | 149 | Present invention |
| 1-45 | T-199 | 0.30 | 154 | Present invention |
| 1-46 | T-200 | 0.15 | 160 | Present invention |
| 1-47 | T-201 | 0.35 | 133 | Present invention |
| 1-48 | T-202 | 0.10 | 155 | Present invention |
| 1-49 | T-203 | 0.24 | 125 | Present invention |
| 1-50 | T-204 | 0.10 | 138 | Present invention |
| 1-51 | T-205 | 0.19 | 151 | Present invention |
| 1-52 | T-206 | 0.11 | 155 | Present invention |
| 1-53 | T-207 | 0.17 | 161 | Present invention |
| 1-54 | T-208 | 0.18 | 134 | Present invention |
| 1-55 | T-210 | 0.10 | 150 | Present invention |
| 1-56 | T-211 | 0.16 | 174 | Present invention |
| 1-57 | T-212 | 0.23 | 124 | Present invention |
| 1-58 | T-214 | 0.36 | 129 | Present invention |

TABLE 2-continued

| Organic EL element | Luminescent compound | ΔEST (eV) | Relative emission efficiency (%) | Remarks |
|---|---|---|---|---|
| 1-59 | T-216 | 0.47 | 118 | Present invention |
| 1-60 | T-221 | 0.18 | 120 | Present invention |
| 1-61 | T-227 | 0.19 | 138 | Present invention |
| 1-62 | T-240 | 0.12 | 140 | Present invention |
| 1-63 | T-249 | 0.11 | 131 | Present invention |
| 1-64 | T-252 | 0.18 | 135 | Present invention |
| 1-65 | T-254 | 0.18 | 140 | Present invention |
| 1-66 | T-257 | 0.39 | 121 | Present invention |
| 1-67 | T-265 | 0.21 | 133 | Present invention |
| 1-68 | T-275 | 0.14 | 150 | Present invention |
| 1-69 | T-282 | 0.10 | 123 | Present invention |
| 1-70 | T-298 | 0.19 | 125 | Present invention |
| 1-71 | T-306 | 0.19 | 119 | Present invention |
| 1-72 | T-328 | 0.21 | 120 | Present invention |
| 1-73 | T-353 | 0.14 | 125 | Present invention |
| 1-74 | T-354 | 0.47 | 124 | Present invention |
| 1-75 | T-365 | 0.24 | 149 | Present invention |
| 1-76 | T-366 | 0.10 | 145 | Present invention |
| 1-77 | T-399 | 0.11 | 128 | Present invention |
| 1-78 | T-429 | 0.11 | 131 | Present invention |
| 1-79 | T-432 | 0.25 | 121 | Present invention |
| 1-80 | T-434 | 0.15 | 141 | Present invention |
| 1-81 | T-442 | 0.06 | 157 | Present invention |
| 1-82 | T-447 | 0.14 | 123 | Present invention |
| 1-83 | T-453 | 0.54 | 117 | Present invention |
| 1-84 | T-456 | 0.07 | 167 | Present invention |
| 1-85 | T-457 | 0.11 | 161 | Present invention |

TABLE 3

| Organic EL element | Luminescent compound | $\Delta E_{ST}$ (eV) | Relative emission efficiency (%) | Remarks |
|---|---|---|---|---|
| 1-86 | T-458 | 0.14 | 141 | Present invention |
| 1-87 | T-459 | 0.11 | 131 | Present invention |
| 1-88 | T-180 | 0.08 | 116 | Present invention |
| 1-89 | T-497 | 0.13 | 155 | Present invention |
| 1-90 | T-504 | 0.26 | 141 | Present invention |
| 1-91 | T-511 | 0.04 | 168 | Present invention |
| 1-92 | T-517 | 0.29 | 128 | Present invention |
| 1-93 | T-518 | 0.07 | 167 | Present invention |
| 1-94 | T-519 | 0.09 | 157 | Present invention |
| 1-95 | T-520 | 0.14 | 132 | Present invention |
| 1-96 | T-522 | 0.05 | 164 | Present invention |
| 1-97 | T-525 | 0.16 | 134 | Present invention |
| 1-98 | T-526 | 0.04 | 169 | Present invention |
| 1-99 | T-527 | 0.05 | 171 | Present invention |
| 1-100 | T-530 | 0.05 | 173 | Present invention |
| 1-101 | T-531 | 0.07 | 169 | Present invention |
| 1-102 | T-512 | 0.73 | 115 | Present invention |
| 1-103 | T-513 | 0.62 | 115 | Present invention |
| 1-104 | T-514 | 0.36 | 116 | Present invention |
| 1-105 | T-515 | 0.54 | 116 | Present invention |
| 1-106 | T-516 | 0.43 | 116 | Present invention |

TABLE 4

| Organic EL element | Luminescent compound | $\Delta E_{ST}$ (eV) | Relative emission efficiency (%) | Remarks |
|---|---|---|---|---|
| 1-107 | T-132 | 0.22 | 145 | Present invention |
| 1-108 | T-540 | 0.10 | 157 | Present invention |
| 1-109 | T-541 | 0.18 | 150 | Present invention |
| 1-110 | T-542 | 0.09 | 160 | Present invention |
| 1-111 | T-543 | 0.11 | 158 | Present invention |
| 1-112 | T-544 | 0.17 | 153 | Present invention |
| 1-113 | T-545 | 0.14 | 155 | Present invention |
| 1-114 | T-546 | 0.11 | 157 | Present invention |
| 1-115 | T-547 | 0.27 | 142 | Present invention |
| 1-116 | T-548 | 0.01 | 173 | Present invention |
| 1-117 | T-549 | 0.15 | 153 | Present invention |
| 1-118 | T-550 | 0.07 | 168 | Present invention |
| 1-119 | T-551 | 0.17 | 152 | Present invention |
| 1-120 | T-552 | 0.05 | 172 | Present invention |
| 1-121 | T-553 | 0.05 | 173 | Present invention |
| 1-122 | T-33 | 0.10 | 155 | Present invention |
| 1-123 | T-555 | 0.09 | 156 | Present invention |
| 1-124 | T-556 | 0.09 | 157 | Present invention |
| 1-125 | T-558 | 0.05 | 167 | Present invention |
| 1-126 | T-79 | 0.05 | 168 | Present invention |
| 1-127 | T-561 | 0.06 | 161 | Present invention |
| 1-128 | T-562 | 0.08 | 160 | Present invention |
| 1-129 | T-563 | 0.06 | 162 | Present invention |
| 1-130 | T-564 | 0.03 | 170 | Present invention |
| 1-131 | T-565 | 0.04 | 169 | Present invention |
| 1-132 | T-566 | 0.09 | 155 | Present invention |
| 1-133 | T-567 | 0.13 | 150 | Present invention |
| 1-134 | T-568 | 0.14 | 147 | Present invention |
| 1-135 | T-569 | 0.15 | 145 | Present invention |
| 1-136 | T-570 | 0.12 | 152 | Present invention |
| 1-137 | T-571 | 0.18 | 149 | Present invention |
| 1-138 | T-572 | 0.07 | 160 | Present invention |
| 1-139 | T-573 | 0.04 | 169 | Present invention |
| 1-140 | T-574 | 0.08 | 158 | Present invention |
| 1-141 | T-576 | 0.09 | 156 | Present invention |

Example 2

(Production of Organic EL Element 2-1)

As an anode, a substrate obtained by depositing indium tin oxide (ITO) into a thickness of 100 nm onto a glass substrate of 100 mm×100 mm×1.1 mm (NA45 manufactured by NH Techno Glass Co., Ltd.) was subjected to patterning. Subsequently, the transparent supporting substrate provided with the ITO transparent electrode was ultrasonic cleaned in isopropyl alcohol, was dried with dry nitrogen gas, and was cleaned with UV ozone for 5 minutes.

On this transparent supporting substrate, a thin film was formed by the spin coating method by using a solution of poly(3,4-ethylenedioxythiophene)-polystyrenesulfonate (PEDOT/PSS, manufactured by Bayer AG, Baytron PA14083) diluted with pure water to 70% under conditions of 3,000 rpm for 30 seconds. The thin film was dried at 200° C. for an hour, providing a hole injection layer having a thickness of 20 nm. This transparent supporting substrate was fixed to a substrate holder of a commercially available vacuum evaporation apparatus. Materials for individual layers, in optimum amounts for producing an element, were placed into individual vapor deposition crucibles in the vacuum evaporation apparatus. The vapor deposition crucibles used were composed of a material for resistance heating, such as molybdenum or tungsten.

After the apparatus was evacuated to a degree of vacuum of 1×10⁻⁴ Pa, α-NPD was deposited onto the hole injection layer at a deposition rate of 0.1 nm/s, thereby forming a hole transport layer having a thickness of 40 nm. H-234 and 2,5,8,11-tetra-t-butylperylene were co-deposited at a deposition rate of 0.1 nm/s so as to achieve 97 vol % and 3 vol % each, thereby forming a light-emitting layer having a thickness of 30 nm.

Subsequently, 1,3,5-tris(N-phenylbenzimidazol-2-yl) (TPBi) was deposited at a deposition rate of 0.1 nm/s, thereby forming an electron transport layer having a thickness of 30 nm.

Additionally, sodium fluoride was deposited into a thickness of 1 nm, and then aluminum was deposited to 100 nm thereon, thereby forming a cathode.

The non-light emitting surface side of the element described above was covered with a can-shaped glass case under an atmosphere of high purity nitrogen gas having a purity of at least 99.999% and electrode extraction wiring was installed thereto, thereby producing the organic EL element 2-1.

(Production of Organic EL Element 2-2)

Organic EL element 2-2 was produced in the same manner as organic EL element 2-1 except that the light-emitting layer was formed such that 82 vol % of H-234 as the host compound, 3 vol % of 2,5,8,11-tetra-t-butylperylene as the luminescent compound, and 15 vol % of comparative compound 1 as the third component were achieved.

(Production of Organic EL Elements 2-3 to 2-40)

Organic EL elements 2-3 to 2-40 were produced in the same manner as organic EL element 2-2 except that the third component was changed as shown in Tables 5 and 6.

TABLE 5

| Organic EL element | Third component | $\Delta E_{ST}$ (eV) | Relative emission efficiency (%) | Remarks |
|---|---|---|---|---|
| 2-1 | Absent | — | 100 | Comparative Example |
| 2-2 | Comparative compound 1 | 0.55 | 87 | Comparative Example |
| 2-3 | Comparative compound 2 | 0.16 | 113 | Comparative Example |
| 2-4 | Comparative compound 3 | 0.26 | 108 | Comparative Example |
| 2-5 | Comparative compound 4 | 0.31 | 103 | Comparative Example |
| 2-6 | T-2 | 0.05 | 148 | Present invention |
| 2-7 | T-27 | 0.22 | 128 | Present invention |
| 2-8 | T-74 | 0.04 | 150 | Present invention |
| 2-9 | T-83 | 0.14 | 134 | Present invention |
| 2-10 | T-85 | 0.08 | 142 | Present invention |
| 2-11 | T-96 | 0.13 | 138 | Present invention |
| 2-12 | T-101 | 0.11 | 140 | Present invention |
| 2-13 | Comparative compound 5 | 0.34 | 113 | Comparative Example |
| 2-14 | Comparative compound 6 | 0.01 | 116 | Comparative Example |
| 2-15 | Comparative compound 7 | 0.35 | 106 | Comparative Example |
| 2-16 | Comparative compound 8 | 0.31 | 104 | Comparative Example |
| 2-17 | Comparative compound 9 | 0.08 | 103 | Comparative Example |
| 2-18 | T-78 | 0.22 | 160 | Present invention |
| 2-19 | T-124 | 0.18 | 175 | Present invention |
| 2-20 | T-191 | 0.19 | 177 | Present invention |
| 2-21 | T-195 | 0.01 | 181 | Present invention |
| 2-22 | T-197 | 0.15 | 141 | Present invention |
| 2-23 | T-204 | 0.10 | 144 | Present invention |
| 2-24 | T-207 | 0.17 | 171 | Present invention |
| 2-25 | T-211 | 0.16 | 178 | Present invention |
| 2-26 | T-249 | 0.11 | 143 | Present invention |
| 2-27 | T-282 | 0.10 | 141 | Present invention |
| 2-28 | T-306 | 0.19 | 135 | Present invention |
| 2-29 | T-366 | 0.10 | 146 | Present invention |
| 2-30 | T-399 | 0.11 | 125 | Present invention |
| 2-31 | T-457 | 0.11 | 167 | Present invention |
| 2-32 | T-497 | 0.13 | 155 | Present invention |
| 2-33 | T-530 | 0.05 | 169 | Present invention |

TABLE 6

| Organic EL element | Third component | $\Delta E_{ST}$ (eV) | Relative emission efficiency (%) | Remarks |
|---|---|---|---|---|
| 2-34 | T-79 | 0.10 | 140 | Present invention |
| 2-35 | T-544 | 0.17 | 135 | Present invention |
| 2-36 | T-551 | 0.17 | 136 | Present invention |
| 2-37 | T-555 | 0.09 | 143 | Present invention |
| 2-38 | T-562 | 0.08 | 146 | Present invention |
| 2-39 | T-563 | 0.06 | 150 | Present invention |
| 2-40 | T-564 | 0.03 | 152 | Present invention |

Example 3

(Production of Organic EL Element 3-1)

Onto a glass substrate having a size of 50 mm×50 mm and a thickness of 0.7 mm, indium tin oxide (ITO) was deposited into a thickness of 150 nm as an anode, which was subjected to patterning. Subsequently, the transparent substrate provided with the ITO transparent electrode was ultrasonic cleaned in isopropyl alcohol, was dried with dry nitrogen gas, and was cleaned with UV ozone for 5 minutes. This transparent substrate was fixed to a substrate holder of a commercially available vacuum evaporation apparatus.

Materials for individual layers, in optimum amounts for producing an element, were placed into individual resistive-heating boats in the vacuum evaporation apparatus. The resistive-heating boats used were composed of molybdenum or tungsten.

After the apparatus was evacuated to a degree of vacuum of $1\times10^{-4}$ Pa, a resistive-heating boat containing HAT-CN was energized and heated to deposit HAT-CN onto the ITO transparent electrode at a deposition rate of 0.1 nm/s, thereby forming a hole injection layer having a thickness of 15 nm.

Subsequently, 4,4'-bis[N-(1-naphthyl)-N-phenylamino]biphenyl (α-NPD) was deposited thereon at a deposition rate of 0.1 nm/s, thereby forming a hole transport layer having a thickness of 30 nm.

Then, resistive-heating boats each containing comparative compound 1, which was a comparative host compound, and GD-1 were energized and heated to co-deposit comparative compound 1 at a deposition rate of 0.1 nm/s and GD-1 at 0.010 nm/s onto the hole transport layer, thereby forming a light-emitting layer having a thickness of 40 nm.

Subsequently, HB-1 was deposited thereon at a deposition rate of 0.1 nm/s, thereby forming a first electron transport layer having a thickness of 5 nm.

Furthermore, ET-1 was deposited thereon at a deposition rate of 0.1 nm/s, thereby forming a second electron transport layer having a thickness of 45 nm.

Thereafter, lithium fluoride was deposited into a thickness of 0.5 nm, and then aluminum was deposited to 100 nm thereon to form a cathode, thereby producing organic EL element 3-1.

(Production of Organic EL Elements 3-2 to 3-43)

Organic EL elements 3-2 to 3-43 were produced in the same manner as organic EL element 3-1 except that the host compound was changed from comparative compound 1 to those shown in Tables 7 and 8.

TABLE 7

| Organic EL element | Host compound | $\Delta E_{ST}$ (eV) | Relative emission efficiency (%) | Remarks |
|---|---|---|---|---|
| 3-1 | Comparative compound 1 | 0.55 | 100 | Comparative Example |
| 3-2 | Comparative compound 2 | 0.16 | 109 | Comparative Example |
| 3-3 | Comparative compound 3 | 0.26 | 105 | Comparative Example |
| 3-4 | Comparative compound 4 | 0.31 | 101 | Comparative Example |
| 3-5 | T-2 | 0.05 | 145 | Present invention |
| 3-6 | T-27 | 0.22 | 118 | Present invention |
| 3-7 | T-66 | 0.04 | 148 | Present invention |
| 3-8 | T-74 | 0.04 | 149 | Present invention |
| 3-9 | T-83 | 0.14 | 138 | Present invention |
| 3-10 | T-96 | 0.13 | 135 | Present invention |
| 3-11 | T-131 | 0.04 | 152 | Present invention |
| 3-12 | T-133 | 0.05 | 143 | Present invention |
| 3-13 | Comparative compound 5 | 0.34 | 95 | Comparative Example |
| 3-14 | Comparative compound 6 | 0.01 | 90 | Comparative Example |
| 3-15 | Comparative compound 7 | 0.35 | 108 | Comparative Example |
| 3-16 | Comparative compound 8 | 0.31 | 104 | Comparative Example |
| 3-17 | Comparative compound 9 | 0.08 | 87 | Comparative Example |
| 3-18 | T-78 | 0.22 | 161 | Present invention |
| 3-19 | T-124 | 0.18 | 155 | Present invention |
| 3-20 | T-191 | 0.19 | 143 | Present invention |
| 3-21 | T-193 | 0.20 | 141 | Present invention |
| 3-22 | T-205 | 0.19 | 165 | Present invention |
| 3-23 | T-206 | 0.11 | 166 | Present invention |
| 3-24 | T-211 | 0.16 | 141 | Present invention |
| 3-25 | T-227 | 0.19 | 124 | Present invention |
| 3-26 | T-240 | 0.12 | 121 | Present invention |
| 3-27 | T-252 | 0.18 | 123 | Present invention |
| 3-28 | T-282 | 0.10 | 118 | Present invention |
| 3-29 | T-306 | 0.19 | 121 | Present invention |
| 3-30 | T-366 | 0.10 | 134 | Present invention |
| 3-31 | T-399 | 0.11 | 132 | Present invention |
| 3-32 | T-456 | 0.07 | 140 | Present invention |
| 3-33 | T-457 | 0.11 | 141 | Present invention |
| 3-34 | T-458 | 0.14 | 138 | Present invention |
| 3-35 | T-527 | 0.05 | 135 | Present invention |
| 3-36 | T-531 | 0.07 | 165 | Present invention |

TABLE 8

| Organic EL element | Host compound | $\Delta E_{ST}$ (eV) | Relative emission efficiency (%) | Remarks |
|---|---|---|---|---|
| 3-37 | T-540 | 0.10 | 165 | Present invention |
| 3-38 | T-541 | 0.18 | 160 | Present invention |
| 3-39 | T-552 | 0.05 | 170 | Present invention |
| 3-40 | T-33 | 0.10 | 164 | Present invention |
| 3-41 | T-563 | 0.06 | 167 | Present invention |
| 3-42 | T-566 | 0.09 | 166 | Present invention |
| 3-43 | T-567 | 0.13 | 162 | Present invention |

(Emission Efficiency Measurement)

The emission efficiency of each sample during operation of the organic EL element was evaluated by conducting the following measurement.

(Relative Emission Efficiency Measurement)

Each organic EL element produced as described above was allowed to emit light with a constant electric current of 2.5 mA/cm² at room temperature (about 25° C.). The emission luminance immediately after the light emission started was measured by using a spectroradiometer CS-2000 (manufactured by Konica Minolta, Inc.).

The relative values of the emission luminance obtained (the relative value to the emission luminance of organic EL element 1-1 in Example 1, the relative value to the emission luminance of organic EL element 2-1 in Example 2, and the relative value to the emission luminance of organic EL element 3-1 in Example 3) are shown in Tables 1 to 8.

In any case of elements 1 to 8, the compound of the present invention exhibited emission efficiency higher than that of comparative example.

Example 4

(Production of Organic EL Element 4-1)

Onto a glass substrate having a size of 50 mm×50 mm and a thickness of 0.7 mm, indium tin oxide (ITO) was deposited into a thickness of 150 nm as an anode, which was subjected to patterning. Subsequently, the transparent substrate provided with the ITO transparent electrode was ultrasonic cleaned in isopropyl alcohol, was dried with dry nitrogen gas, and was cleaned with UV ozone for 5 minutes. This transparent substrate was fixed to a substrate holder of a commercially available vacuum evaporation apparatus.

Materials for individual layers, in optimum amounts for producing an element, were placed into individual resistive-heating boats in the vacuum evaporation apparatus. The resistive-heating boats used were composed of molybdenum or tungsten.

After the apparatus was evacuated to a degree of vacuum of $1 \times 10^{-4}$ Pa, a resistive-heating boat containing 4,4'-bis[N-(1-naphthyl)-N-phenylamino]biphenyl (α-NPD) was energized and heated to deposit α-NPD at a deposition rate of 0.1 nm/s onto the ITO transparent electrode, thereby forming a hole injection layer having a thickness of 30 nm.

Subsequently, tris(4-carbazoyl-9-ylphenyl)amine (TCTA) was deposited at a deposition rate of 0.1 nm/s thereon, thereby forming a first hole transport layer having a thickness of 20 nm.

Furthermore, H-233 was deposited thereon at a deposition rate of 0.1 nm/s, thereby forming a second hole transport layer having a thickness of 10 nm.

Then, resistive-heating boats each containing comparative compound 1, which was a comparative host compound, and 2,5,8,11-tetra-tert-butylperylene (TBPe) were energized and heated to co-deposit comparative compound 1 at a deposition rate of 0.1 nm/s and TBPe at 0.010 nm/s onto the hole transport layer, thereby forming a light-emitting layer having a thickness of 20 nm.

Subsequently, H-232 was deposited thereon at a deposition rate of 0.1 nm/s, thereby forming a first electron transport layer having a thickness of 10 nm.

Furthermore, 1,3,5-tris(1-phenyl-1H-benzimidazol-2-yl)benzene (TBPI) was deposited at a deposition rate of 0.1 nm/s thereon, thereby forming a second electron transport layer having a thickness of 30 nm.

Thereafter, lithium fluoride was deposited into a thickness of 0.5 nm, and then aluminum was deposited to 100 nm thereon to form a cathode, thereby producing organic EL element 4-1.

(Production of Organic EL Elements 4-2 to 4-49)

Organic EL elements 4-2 to 4-49 were produced in the same manner as organic EL element 4-1 except that the host compound was changed from comparative compound 1 to those shown in Tables 9 and 10.

(Relative Emission Efficiency Measurement)

Each organic EL element produced as described above was allowed to emit light with a constant electric current of 2.5 mA/cm$^2$ at room temperature (about 25° C.). The emission luminance immediately after the light emission started was measured by using a spectroradiometer CS-2000 (manufactured by Konica Minolta, Inc.).

The relative values of the emission luminance obtained (the relative value to the emission luminance of organic EL element 4-1 in Example 4) are shown in Table 6.

TABLE 9

| Organic EL element | Host compound | $\Delta E_{ST}$ (eV) | Relative emission efficiency (%) | Remarks |
|---|---|---|---|---|
| 4-1 | Comparative compound 1 | 0.55 | 100 | Comparative Example |
| 4-2 | Comparative compound 2 | 0.16 | 110 | Comparative Example |
| 4-3 | Comparative compound 3 | 0.26 | 85 | Comparative Example |
| 4-4 | Comparative compound 4 | 0.31 | 90 | Comparative Example |
| 4-5 | Comparative compound 5 | 0.34 | 96 | Comparative Example |
| 4-6 | Comparative compound 6 | 0.01 | 89 | Comparative Example |
| 4-7 | Comparative compound 7 | 0.35 | 101 | Comparative Example |
| 4-8 | Comparative compound 8 | 0.31 | 88 | Comparative Example |
| 4-9 | Comparative compound 9 | 0.08 | 85 | Comparative Example |
| 4-10 | T-78 | 0.22 | 165 | Present invention |
| 4-11 | T-124 | 0.18 | 170 | Present invention |
| 4-12 | T-183 | 0.09 | 145 | Present invention |
| 4-13 | T-191 | 0.19 | 174 | Present invention |
| 4-14 | T-192 | 0.18 | 141 | Present invention |
| 4-15 | T-193 | 0.20 | 135 | Present invention |
| 4-16 | T-195 | 0.01 | 176 | Present invention |
| 4-17 | T-197 | 0.15 | 169 | Present invention |
| 4-18 | T-204 | 0.10 | 138 | Present invention |
| 4-19 | T-205 | 0.19 | 171 | Present invention |
| 4-20 | T-206 | 0.11 | 175 | Present invention |
| 4-21 | T-207 | 0.17 | 176 | Present invention |
| 4-22 | T-208 | 0.18 | 147 | Present invention |
| 4-23 | T-210 | 0.10 | 179 | Present invention |
| 4-24 | T-211 | 0.16 | 180 | Present invention |
| 4-25 | T-221 | 0.18 | 153 | Present invention |
| 4-26 | T-227 | 0.19 | 147 | Present invention |
| 4-27 | T-240 | 0.12 | 129 | Present invention |
| 4-28 | T-249 | 0.11 | 134 | Present invention |
| 4-29 | T-252 | 0.18 | 136 | Present invention |
| 4-30 | T-254 | 0.18 | 135 | Present invention |
| 4-31 | T-265 | 0.21 | 128 | Present invention |
| 4-32 | T-282 | 0.10 | 125 | Present invention |
| 4-33 | T-298 | 0.19 | 134 | Present invention |
| 4-34 | T-306 | 0.19 | 142 | Present invention |
| 4-35 | T-366 | 0.10 | 133 | Present invention |
| 4-36 | T-399 | 0.10 | 123 | Present invention |
| 4-37 | T-459 | 0.11 | 120 | Present invention |
| 4-38 | T-527 | 0.05 | 161 | Present invention |
| 4-39 | T-531 | 0.07 | 167 | Present invention |
| 4-40 | T-27 | 0.22 | 115 | Present invention |
| 4-41 | T-101 | 0.11 | 118 | Present invention |
| 4-42 | T-117 | 0.16 | 117 | Present invention |
| 4-43 | T-131 | 0.04 | 119 | Present invention |

TABLE 10

| Organic EL element | Host compound | $\Delta E_{ST}$ (eV) | Relative emission efficiency (%) | Remarks |
|---|---|---|---|---|
| 4-44 | T-542 | 0.09 | 164 | Present invention |
| 4-45 | T-549 | 0.15 | 154 | Present invention |
| 4-46 | T-553 | 0.05 | 169 | Present invention |
| 4-47 | T-565 | 0.04 | 170 | Present invention |
| 4-48 | T-572 | 0.07 | 167 | Present invention |
| 4-49 | T-576 | 0.09 | 163 | Present invention |

In any case of organic EL element 4, the compound of the present invention exhibited emission efficiency higher than that of comparative example.

Example 5

The elements 1-19 of Example 5 were measured for their luminance half-time when allowed to emit light at an initial luminance of 300 cd/m$^2$.

(Production of Organic EL Elements 5-1 to 5-47)

Organic EL elements 5-1 to 5-47 were produced from elements 1-19 of Example 1 in the same manner as organic EL elements 1-19 except that the host compound and luminescent compound were changed as shown in Tables 11 and 12.

TABLE 11

| Organic EL element | Luminescent compound | Host compound | Relative luminance half-time (Ratio) | Remarks |
|---|---|---|---|---|
| 1-19 | T-124 | H-232 | 50 | Present invention |
| 5-1 | T-124 | J-1 | 4200 | Present invention |
| 5-2 | T-124 | J-32 | 8000 | Present invention |
| 5-3 | T-124 | J-46 | 7500 | Present invention |
| 5-4 | T-124 | J-183 | 5000 | Present invention |
| 1-26 | T-78 | H-232 | 42 | Present invention |
| 5-5 | T-78 | J-52 | 5000 | Present invention |
| 5-6 | T-78 | J-192 | 6000 | Present invention |
| 5-7 | T-78 | J-155 | 4900 | Present invention |
| 1-28 | T-182 | H-232 | 45 | Present invention |
| 5-8 | T-182 | J-41 | 4300 | Present invention |
| 5-9 | T-182 | J-168 | 5000 | Present invention |
| 5-10 | T-182 | J-194 | 7500 | Present invention |
| 1-37 | T-191 | H-232 | 38 | Present invention |
| 5-11 | T-191 | J-33 | 5000 | Present invention |
| 5-12 | T-191 | J-38 | 3500 | Present invention |
| 5-13 | T-191 | J-43 | 4600 | Present invention |
| 1-50 | T-204 | H-232 | 31 | Present invention |
| 5-14 | T-204 | J-16 | 1300 | Present invention |
| 5-15 | T-204 | J-48 | 1500 | Present invention |
| 5-16 | T-204 | J-213 | 2500 | Present invention |
| 1-56 | T-211 | H-232 | 33 | Present invention |
| 5-17 | T-211 | J-5 | 4300 | Present invention |
| 5-18 | T-211 | J-45 | 3200 | Present invention |
| 5-19 | T-211 | J-54 | 2100 | Present invention |
| 5-20 | T-211 | J-66 | 1000 | Present invention |
| 1-62 | T-240 | H-232 | 36 | Present invention |
| 5-21 | T-240 | J-17 | 4800 | Present invention |

TABLE 12

| Organic EL element | Luminescent compound | Host compound | Relative luminance half-time (Ratio) | Remarks |
|---|---|---|---|---|
| 5-22 | T-240 | J-42 | 3400 | Present invention |
| 5-23 | T-240 | J-56 | 1600 | Present invention |

TABLE 12-continued

| Organic EL element | Luminescent compound | Host compound | Relative luminance half-time (Ratio) | Remarks |
|---|---|---|---|---|
| 1-68 | T-275 | H-232 | 27 | Present invention |
| 5-24 | T-275 | J-11 | 1500 | Present invention |
| 5-25 | T-275 | J-68 | 900 | Present invention |
| 5-26 | T-275 | J-91 | 750 | Present invention |
| 5-27 | T-275 | J-129 | 2500 | Present invention |
| 1-73 | T-353 | H-232 | 25 | Present invention |
| 5-28 | T-353 | J-171 | 700 | Present invention |
| 5-29 | T-353 | J-137 | 1000 | Present invention |
| 5-30 | T-353 | J-161 | 2500 | Present invention |
| 1-76 | T-366 | H-232 | 29 | Present invention |
| 5-31 | T-366 | J-187 | 3000 | Present invention |
| 5-32 | T-366 | J-153 | 2100 | Present invention |
| 5-33 | T-366 | J-204 | 5400 | Present invention |
| 5-34 | T-366 | J-210 | 1000 | Present invention |
| 1-85 | T-457 | H-232 | 47 | Present invention |
| 5-35 | T-457 | J-128 | 5000 | Present invention |
| 5-36 | T-457 | J-148 | 3700 | Present invention |
| 5-37 | T-457 | J-172 | 6500 | Present invention |
| 1-99 | T-530 | H-232 | 40 | Present invention |
| 5-38 | T-530 | J-25 | 4200 | Present invention |
| 5-39 | T-530 | J-36 | 5500 | Present invention |
| 5-40 | T-530 | J-83 | 3100 | Present invention |
| 5-41 | T-530 | J-102 | 2200 | Present invention |
| 5-42 | T-530 | J-113 | 250 | Present invention |
| 1-8 | T-27 | H-232 | 1 | Present invention |
| 5-43 | T-27 | J-13 | 45 | Present invention |
| 1-11 | T-74 | H-232 | 26 | Present invention |
| 5-44 | T-74 | J-24 | 350 | Present invention |
| 1-14 | T-84 | H-232 | 8 | Present invention |
| 5-45 | T-84 | J-164 | 50 | Present invention |
| 1-18 | T-117 | H-232 | 3 | Present invention |
| 5-46 | T-117 | J-170 | 18 | Present invention |
| 1-88 | T-180 | H-232 | 5 | Present invention |
| 5-47 | T-180 | J-197 | 30 | Present invention |

Organic EL element 5 had a particularly long relative luminance half-time when the host compound was a compound presented by the aforementioned general formula I. Additionally, the luminescent compound had a long relative luminance half-time when three or more electron-donating groups or electron-withdrawing groups were sequentially located in the ortho position.

Example 6

(Production of Co-Deposition Film 6-1)

A quartz substrate having a size of 50 mm×50 mm and a thickness of 0.7 mm was ultrasonic cleaned in isopropyl alcohol, was dried with dry nitrogen gas, and was cleaned with UV ozone for 5 minutes. This transparent substrate was fixed to a substrate holder of a commercially available vacuum evaporation apparatus.

Into individual vapor deposition crucibles in the vacuum evaporation apparatus, 1,3-bis(N-carbazolyl)benzene (mCP) and luminescent compound T-124 were placed. The vapor deposition crucibles used were composed of a material for resistance heating, such as molybdenum or tungsten.

After the apparatus was evacuated to a degree of vacuum of 1×10$^{-4}$ Pa, 1,3-bis(N-carbazolyl)benzene (mCP) and luminescent compound T-124 were co-deposited at a deposition rate of 0.1 nm/s so as to achieve 94 vol % and 6 vol % each, thereby forming a co-deposition film having a thickness of 40 nm.

(Production of Co-Deposition Films 6-2 to 4)

Co-deposition films 6-2 to 6-4 were produced in the same manner as co-deposition film 6-1 except that the luminescent compound was changed from T-124 to those shown in Table 13.

TABLE 13

| Co-deposition film | Light-emitting material |
|---|---|
| 6-1 | T-124 |
| 6-2 | T-180 |
| 6-3 | T-211 |
| 6-4 | T-527 |

(Delayed Fluorescence Measurement of Co-Deposition Films 6-1 to 4)

The co-deposition films 6-1 to 4 were irradiated with excited light at 355 nm under a nitrogen atmosphere to conduct fluorescence decay measurement at each of their maximum light emission wavelength. Graphs illustrating the relation between the time and the number of photons of co-deposition films 6-1 to 6-4 are each shown in FIGS. 13 to 16. As shown in FIGS. 13 to 16, it was confirmed that all the π-conjugated compounds of the present invention (T-124, T-180, T-211, and T-527) have two or more components having different decay rates of fluorescence and emit delayed fluorescence.

Hereinafter, examples and comparative examples including a specific π-conjugated compound will be presented. Compounds used in the following examples and comparative examples are shown below.

<π-Conjugated Compounds Represented by General Formula 201>

[Formula 136]

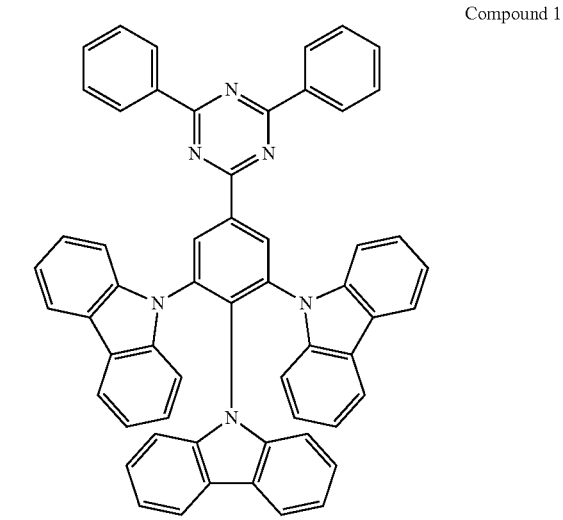

Compound 1

Compound 2
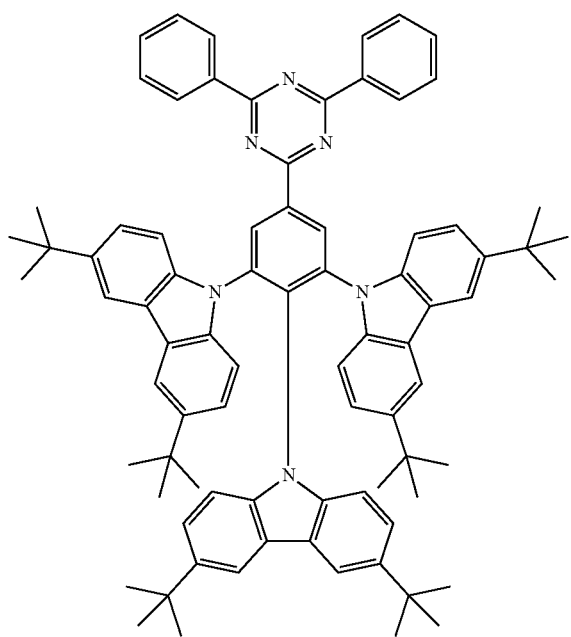
Compound 3
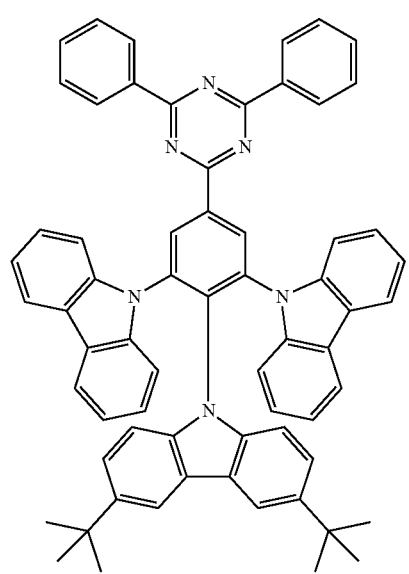
Compound 4
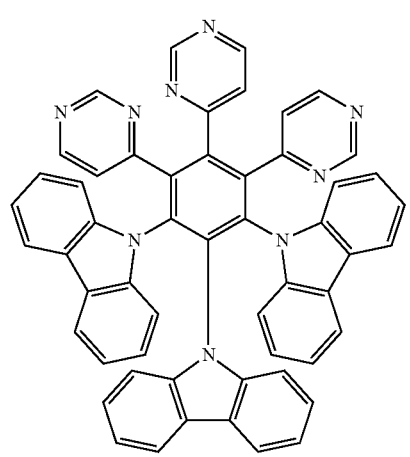
Compound 5
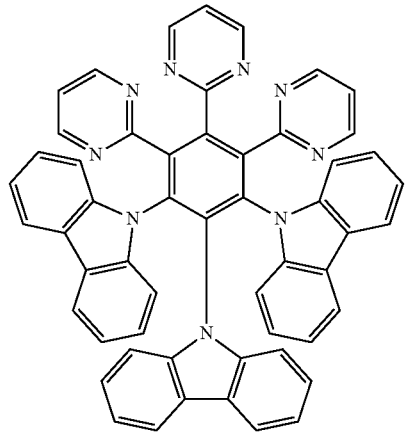
Compound 6
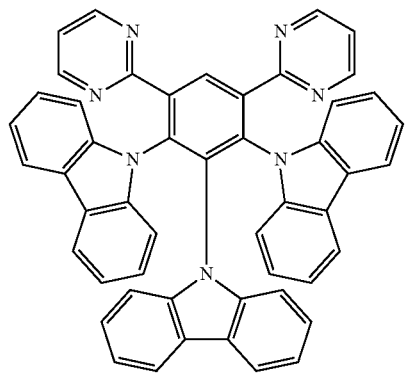
Compound 7
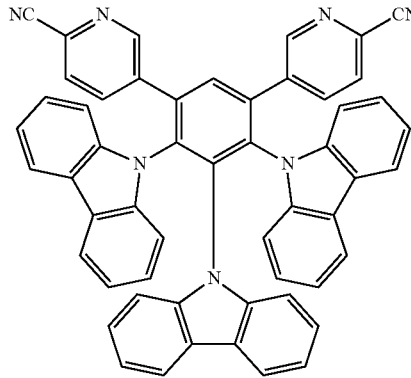
Compound 8
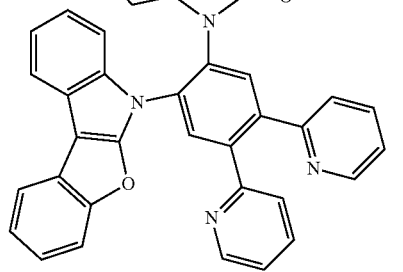

-continued
Compound 9
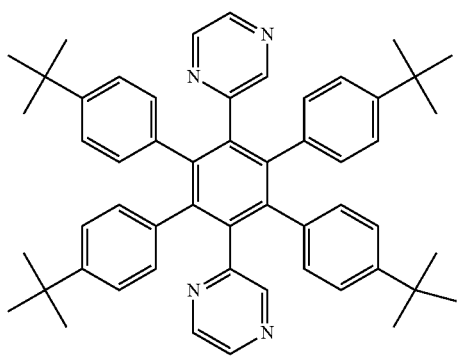
[Formula 137]
Compound 10
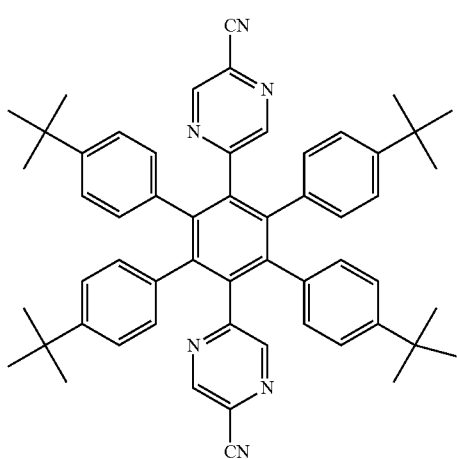
Compound 11
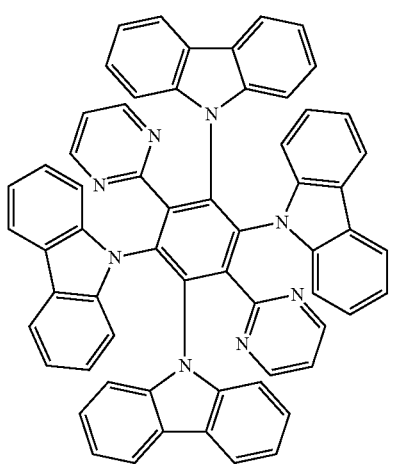
<Comparative Compounds>
[Formula 138]
Comparative compound 1
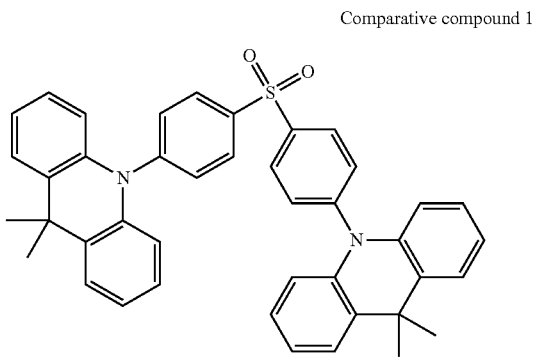
DMAC-DPS
Comparative compound 2
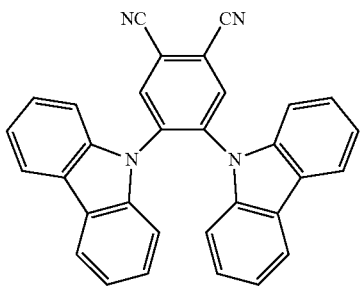
2CzPN
Comparative compound 3
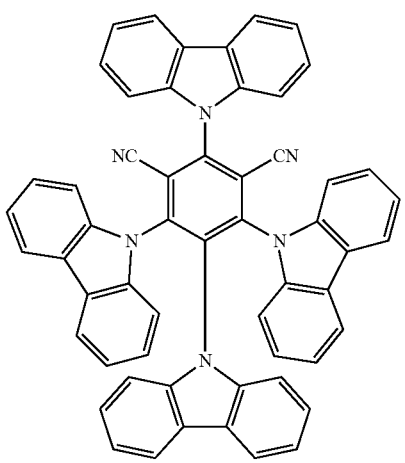
4CzIPN <Other Compounds>

[Formula 139]

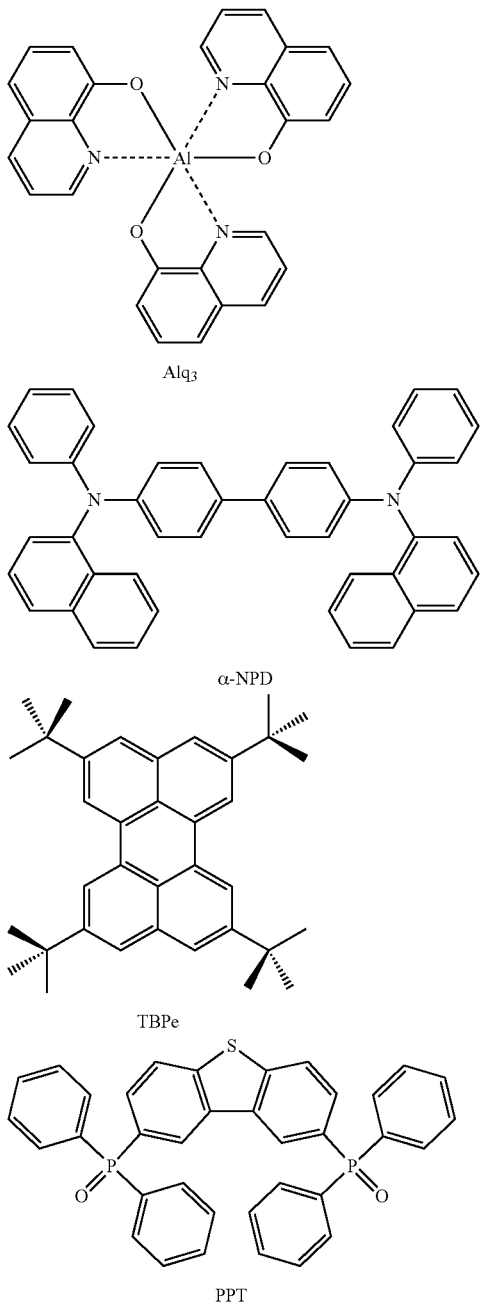

$\Delta E_{ST}$ was determined for the above compounds 1 to 11 and comparative compounds 1 and 3 by calculation in accordance with the following method. The results are shown in Table 14.

(Calculation of $\Delta E_{ST}$)

The structure optimization and calculation of the electron density distribution by molecular orbital calculation of the compound was calculated by using, as a calculation technique, software for molecular orbital calculation including B3LYP as a functional and 6-31G (d) as a basis function. Gaussian 09 available from Gaussian Inc., USA (Revision C. 01, M. J. Frisch, et al., Gaussian, Inc., 2010.) was used as the software for molecular orbital calculation.

From the structure optimization calculation including B3LYP as the functional and 6-31G (d) as the basis function, excited state calculation by means of the time-dependent density functional theory (Time-Dependent DFT) was further carried out to determine energy levels of $S_1$ and $T_1$, ($E(S_1)$ and $E(T_1)$, respectively), which were used for calculation in $\Delta E_{ST}=|E(S_1)-E(T_1)|$.

TABLE 14

|  | ΔEst (eV) |
| --- | --- |
| Compound 1 | 0.18 |
| Compound 2 | 0.16 |
| Compound 3 | 0.19 |
| Compound 4 | 0.09 |
| Compound 5 | 0.14 |
| Compound 7 | 0.05 |
| Compound 6 | 0.10 |
| Compound 8 | 0.16 |
| Compound 9 | 0.36 |
| Compound 10 | 0.29 |
| Compound 11 | 0.13 |
| Comparative compound 1 | 0.01 |
| Comparative compound 2 | 0.34 |
| Comparative compound 3 | 0.12 |

It was confirmed that ΔEst's of compounds 1 to 11, which are the π-conjugated compounds represented by general formula 201, were sufficiently lower than ΔEst's of comparative compound 1 (DMAC-DPS), comparative compound 2(2CzPN), and comparative compound 3 (4CzIPN) and were values small enough to exhibit a TADF property.

Example 7

(Production of Organic EL Element 7-1)

Onto a glass substrate having a size of 50 mm×50 mm and a thickness of 0.7 mm, indium tin oxide (ITO) was deposited into a thickness of 150 nm as an anode, which was subjected to patterning. The transparent substrate provided with the ITO transparent electrode was ultrasonic cleaned in isopropyl alcohol, was dried with dry nitrogen gas, and was cleaned with UV ozone for 5 minutes.

On this transparent supporting substrate, a thin film was formed by the spin coating method by using a solution of poly(3,4-ethylenedioxythiophene)-polystyrenesulfonate (PEDOT/PSS, manufactured by Bayer AG, Baytron P Al 4083) diluted with pure water to 70% under conditions of 3,000 rpm for 30 seconds. The thin film was dried at 200° C. for an hour, providing a hole injection layer having a thickness of 20 nm.

This transparent substrate was fixed to a substrate holder of a commercially available vacuum evaporation apparatus. Materials for individual layers, in optimum amounts for producing an element, were placed into individual vapor deposition crucibles in the vacuum evaporation apparatus. The vapor deposition crucibles used were composed of a material for resistance heating, such as molybdenum or tungsten.

After the apparatus was evacuated to a degree of vacuum of $1\times10^{-4}$ Pa, the vapor deposition crucible containing α-NPD was energized and heated to deposit α-NPD onto the ITO transparent electrode at a deposition rate of 0.1 nm/s, thereby forming a hole transport layer having a thickness of 30 nm.

Subsequently, DMAC-DPS (comparative compound 1) as the luminescent compound was deposited at a deposition rate of 0.1 nm/s, thereby forming a light-emitting layer having a thickness of 30 nm.

Thereafter, PPT was deposited at a deposition rate of 0.1 nm/s, thereby forming a hole blocking layer having a thickness of 10 nm. Furthermore, compound $Alq_3$ was deposited thereon at a deposition rate of 0.1 nm/s, thereby forming an electron transport layer having a thickness of 30 nm.

Additionally, lithium fluoride was deposited to a thickness of 0.5 nm to form an electron injection layer, and then aluminum was deposited to 100 nm thereon, thereby forming a cathode.

The non-light emitting surface side of the element described above was covered with a can-shaped glass case under an atmosphere of high purity nitrogen gas having a purity of at least 99.999% and electrode extraction wiring was installed thereto, thereby producing the organic EL element 7-1.

(Production of Organic EL Elements 7-2 to 7-9)

Organic EL elements 7-2 to 7-9 were produced in the same manner as organic EL element 7-1 except that the luminescent compound was changed to compounds shown in Table 2.

The organic EL elements produced as described above were measured for the external quantum efficiency (EQE) and half-life (continuous drive stability) in accordance with the following methods. The evaluation results are shown in Table 2.

(Evaluation of External Quantum Efficiency (EQE))

Each organic EL element produced as described above was allowed to emit light with a constant electric current of 2.5 $mA/cm^2$ at room temperature (about 25° C.). The emission luminance immediately after the light emission started was measured by using a spectroradiometer CS-2000 (manufactured by Konica Minolta, Inc.). The relative luminance value of each organic EL element was determined based on the luminance of organic EL element 1-1 as 100.

(Evaluation of Half-Life (Continuous Drive Stability))

Each sample was measured for its luminance by using a spectroradiometer CS-2000 described above while continuously driven at an initial luminance of 1,000 $cd/m^2$ to determine the time during which the luminance measured was reduced by half (LT50). The relative value of LT 50 of each organic EL element was determined based on LT50 of organic EL element 7-1 as 100. This value was used as a measure of the continuous drive stability.

The evaluation results are shown in Table 15. Table 15 shows that the larger the numerical value of EQE, the higher the external quantum efficiency and that the larger the numerical value of the half-life, the more excellent the continuous drive stability (the longer the life-time).

TABLE 15

| Organic EL element | Luminescent compound in light-emitting layer | EQE (relative value) | Half-life (relative value) | Remarks |
|---|---|---|---|---|
| 7-1 | Comparative compound 1 | 100 | 100 | Comparative |
| 7-2 | Comparative compound 2 | 20.5 | 12.5 | Comparative |
| 7-3 | Comparative compound 3 | 35.5 | 25 | Comparative |

TABLE 15-continued

| Organic EL element | Luminescent compound in light-emitting layer | EQE (relative value) | Half-life (relative value) | Remarks |
|---|---|---|---|---|
| 7-4 | Compound 1 | 110 | 212500 | Present invention |
| 7-5 | Compound 3 | 95 | 150000 | Present invention |
| 7-6 | Compound 7 | 75 | 162500 | Present invention |
| 7-7 | Compound 8 | 65 | 118750 | Present invention |
| 7-8 | Compound 9 | 56 | 108750 | Present invention |
| 7-9 | Compound 11 | 60 | 111250 | Present invention |

As shown in Table 15, it is indicated that organic EL elements 7-4 to 7-9 containing the π-conjugated compound represented by general formula 201 have a greatly improved half-life while having EQE comparable to that of organic EL element 7-1 including comparative compound 1. It is also indicated that organic EL elements 7-4 to 7-9 containing the π-conjugated compound represented by general formula 201 have EQE and a half-life (particularly a half-life) greatly improved relative to those of organic EL elements 7-2 and 7-3 including comparative compound 2 and 3.

Example 8

(Production of Organic EL Element 8-1)

Onto a glass substrate having a size of 50 mm×50 mm and a thickness of 0.7 mm, indium tin oxide (ITO) was deposited into a thickness of 150 nm as an anode, which was subjected to patterning. The transparent substrate provided with the ITO transparent electrode was ultrasonic cleaned in isopropyl alcohol, was dried with dry nitrogen gas, and was cleaned with UV ozone for 5 minutes.

This transparent substrate was fixed to a substrate holder of a commercially available vacuum evaporation apparatus. Materials for individual layers, in optimum amounts for producing an element, were placed into individual vapor deposition crucibles in the vacuum evaporation apparatus. The vapor deposition crucibles used were composed of a material for resistance heating, such as molybdenum or tungsten.

After the apparatus was evacuated to a degree of vacuum of $1 \times 10^{-4}$ Pa, the vapor deposition crucible containing DMAC-DPS (comparative compound 1) as the luminescent compound was energized and heated to deposit DMAC-DPS onto the ITO transparent electrode at a deposition rate of 0.1 nm/s, thereby forming a light-emitting layer having a thickness of 120 nm.

Aluminum was deposited to 100 nm onto the light-emitting layer obtained, thereby forming a cathode.

The non-light emitting surface side of the element described above was covered with a can-shaped glass case under an atmosphere of high purity nitrogen gas having a purity of at least 99.999% and electrode extraction wiring was installed thereto, thereby producing the organic EL element 8-1.

(Production of Organic EL Elements 8-2 to 8-9)

Organic EL elements 8-2 to 8-9 were produced in the same manner as organic EL element 8-1 except that the luminescent compound was changed to compounds shown in Table 16.

The organic EL elements produced as described above were measured for the external quantum efficiency (EQE)

and half-life (continuous drive stability) in accordance with the methods as aforementioned. Then, the relative values of each organic EL element were determined when the EQE and half-life of organic EL element 8-1 were taken as 100. The evaluation results are shown in Table 16.

TABLE 16

| Organic EL element | Luminescent compound in light-emitting layer | EQE (relative value) | Half-life (relative value) | Remarks |
|---|---|---|---|---|
| 8-1 | Comparative compound 1 | 100 | 100 | Comparative |
| 8-2 | Comparative compound 2 | 5 | 30 | Comparative |
| 8-3 | Comparative compound 3 | 10 | 65 | Comparative |
| 8-4 | Compound 1 | 3000 | 50000 | Present invention |
| 8-5 | Compound 2 | 3000 | 45000 | Present invention |
| 8-6 | Compound 5 | 1750 | 20000 | Present invention |
| 8-7 | Compound 6 | 1250 | 25000 | Present invention |
| 8-8 | Compound 10 | 1100 | 17500 | Present invention |
| 8-9 | Compound 11 | 1200 | 19000 | Present invention |

As shown in Table 16, it is indicated that organic EL elements 8-4 to 8-9 containing the π-conjugated compound represented by general formula 201 have EQE and a half-life, particularly a half-life, greatly improved relative to those of organic EL element 8-1 to 8-3 each including a comparative compound.

Example 9

(Production of Organic EL Element 9-1)

Onto a glass substrate having a size of 50 mm×50 mm and a thickness of 0.7 mm, indium tin oxide (ITO) was deposited into a thickness of 150 nm as an anode, which was subjected to patterning. This transparent substrate provided with the ITO transparent electrode was ultrasonic cleaned in isopropyl alcohol, was dried with dry nitrogen gas, and was cleaned with UV ozone for 5 minutes.

This transparent substrate was fixed to a substrate holder of a commercially available vacuum evaporation apparatus. Materials for individual layers, in optimum amounts for producing an element, were placed into individual vapor deposition crucibles in the vacuum evaporation apparatus. The vapor deposition crucibles used were composed of a material for resistance heating, such as molybdenum or tungsten.

After the apparatus was evacuated to a degree of vacuum of 1×10$^{-4}$ Pa, the vapor deposition crucible containing a compound to be deposited was energized and heated to co-deposit the host compound and the guest compound of the light-emitting layer at a deposition rate of 0.1 nm/s so as to achieve the proportion described in Table 4, thereby forming a light-emitting layer having a thickness of 120 nm.

Aluminum was deposited to 100 nm onto the light-emitting layer obtained, thereby forming a cathode.

The non-light emitting surface side of the element described above was covered with a can-shaped glass case under an atmosphere of high purity nitrogen gas having a purity of at least 99.999% and electrode extraction wiring was installed thereto, thereby producing the organic EL element 9-1.

(Production of Organic EL Element 9-2)

Organic EL element 9-2 was produced in the same manner as organic EL element 9-1 except that the luminescent compound was changed to compounds shown in Table 17.

Each organic EL element produced as described above was measured for the half-life (continuous drive stability) in accordance with the methods as aforementioned. Then, the relative values of the half-life of organic EL element 9-2 was determined based on the half-life of organic EL element 9-1 as 100. The evaluation results are shown in Table 4.

TABLE 17

| | | Light-emitting layer | | | |
|---|---|---|---|---|---|
| Organic EL element | Host compound | Guest compound (luminescent compound) | Doping concentration (vol %) | Half-life (relative value) | Remarks |
| 9-1 | Compound 1 | — | 0 | 100 | Present invention |
| 9-2 | Compound 1 | TBPe | 1 | 12000 | Present invention |

As shown in Table 17, it is indicated that organic EL element 9-2 including a combination of the π-conjugated compound represented by general formula 201 and a guest compound has a half-life further improved relative to that of organic EL element 9-1 not combined with a guest compound.

(Production of Organic EL Element 9-3)

Onto a glass substrate having a size of 50 mm×50 mm and a thickness of 0.7 mm, indium tin oxide (ITO) was deposited into a thickness of 150 nm as an anode, which was subjected to patterning. This transparent substrate provided with the ITO transparent electrode was ultrasonic cleaned in isopropyl alcohol, was dried with dry nitrogen gas, and was cleaned with UV ozone for 5 minutes.

This transparent substrate was fixed to a substrate holder of a commercially available vacuum evaporation apparatus. Materials for individual layers, in optimum amounts for producing an element, were placed into individual vapor deposition crucibles in the vacuum evaporation apparatus. The vapor deposition crucibles used were composed of a material for resistance heating, such as molybdenum or tungsten.

After the apparatus was evacuated to a degree of vacuum of 1×10$^{-4}$ Pa, the vapor deposition crucible containing a compound to be deposited was energized and heated to co-deposit the host compound and the guest compound of the light-emitting layer at a deposition rate of 0.1 nm/s so as to achieve the proportion described in Table 18, thereby forming a light-emitting layer having a thickness of 110 nm.

Aluminum was deposited to 100 nm onto the light-emitting layer obtained, thereby forming a cathode.

The non-light emitting surface side of the element described above was covered with a can-shaped glass case under an atmosphere of high purity nitrogen gas having a purity of at least 99.999% and electrode extraction wiring was installed thereto, thereby producing the organic EL element 9-3.

(Production of Organic EL Elements 9-4 to 9-5)

Organic EL elements 9-4 to 9-5 were produced in the same manner as organic EL element 9-3 except that the luminescent compound was changed to compounds shown in Table 5.

The organic EL elements produced as described above were measured for the external quantum efficiency (EQE) in accordance with the methods as aforementioned. Then, the relative values of the EQE of organic EL elements 9-4 and 9-5 were determined based on the EQE value of organic EL element 3-3 as 100. The evaluation results are shown in Table 18.

TABLE 18

| Organic EL element | Compound | Guest compound (luminescent compound) | Doping concentration (vol %) | EQE (relative value) | Remarks |
|---|---|---|---|---|---|
| 9-3 | Compound 1 | TBPe | 21 | 100 | Present invention |
| 9-4 | Compound 1 | TBPe | 6 | 197 | Present invention |
| 9-5 | Compound 1 | TBPe | 0.8 | 330 | Present invention |

As shown in Table 18, it is indicated that organic EL elements 9-4 to 9-5, of which doping concentration of the guest compound in the light-emitting layer is less than 20 vol %, have EQE improved relative to the that of organic EL element 9-3, of which doping concentration of the guest compound in the light-emitting layer exceeds 20 vol %.

The present application claims the benefit of Japanese Patent Application No. 2015-095804 filed on May 8, 2015, Japanese Patent Application No. 2015-203876 filed on Oct. 15, 2015, and Japanese Patent Application No. 2015-203878 filed on Oct. 15, 2015, the disclosure of which including the specification and drawings is incorporated herein by reference in its entirety.

INDUSTRIAL APPLICABILITY

According to the present invention, a novel π-conjugated compound that may improve the emission efficiency of organic electroluminescent elements, for example, can be provided. Additionally, an organic electroluminescent element material, a light-emitting thin film, a light-emitting material, and an organic electroluminescent element containing the π-conjugated compound and a display apparatus and a lighting apparatus including the organic electroluminescent element can be provided.

REFERENCE SIGNS LIST

10 Display
13 Pixel
15 Scanning line
16 Data lines
17 Power source line
20 Organic EL element
21 Switching transistor
22 Driving transistor
23 Condenser
101 Organic EL element in lighting apparatus
102 Glass cover
105 Cathode
106 Constituent layer of organic EL element
107 Glass substrate provided with transparent electrode
108 Nitrogen gas
109 Water absorbent
A Display part
B Control part
C Wiring portion

The invention claimed is:

1. A π-conjugated compound comprising a structure represented by the following general formula (30):

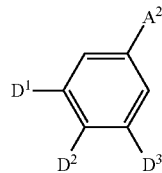

(30)

wherein $D^1$ to $D^3$ each independently comprise a group selected from a phenyl group substituted by an electron-donating group, an optionally substituted 9,10-dihydroacridyl group, an optionally substituted phenoxazyl group, an optionally substituted phenothiazyl group, an optionally substituted 5,10-dihydrophenazyl group, an optionally substituted diphenylamino group, and an optionally substituted dialkylamino group, and $A^2$ comprises a group selected from an aryl group substituted by a cyano group, an unsubstituted nitrogen-containing aromatic six-membered ring group, a nitrogen-containing aromatic six-membered ring group substituted by a fluorine atom, a nitrogen-containing aromatic six-membered ring group substituted by a cyano group, a nitrogen-containing aromatic six-membered ring group substituted by a fluorine-substituted alkyl group, and a nitrogen-containing aromatic six-membered ring group substituted by an optionally substituted aryl group.

2. The π-conjugated compound according to claim 1, wherein $D^1=D^2=D^3$ in general formulas (30) are satisfied.

3. The π-conjugated compound according to claim 1, wherein the absolute value of the energy difference between the lowest singlet excited level and the lowest triplet excited level $\Delta E_{ST}$, is 0.50 eV or less.

4. An organic electroluminescent element material comprising the π-conjugated compound according to claim 1.

5. A light-emitting material comprising the π-conjugated compound according to claim 1, wherein the π-conjugated compound emits fluorescence.

6. An organic electroluminescent element comprising an anode, a cathode, and an organic layer disposed between the anode and the cathode, wherein the organic layer substantially comprises a π-conjugated compound represented by general formula 206 or 207:

General formula 206

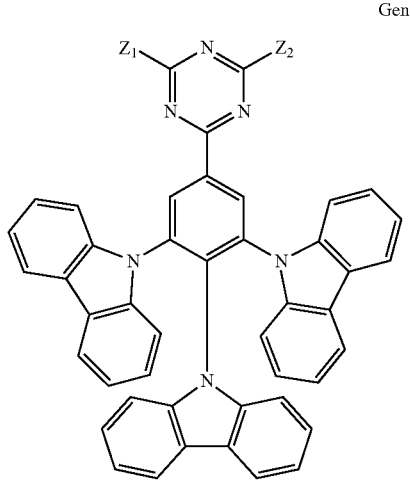

General formula 207

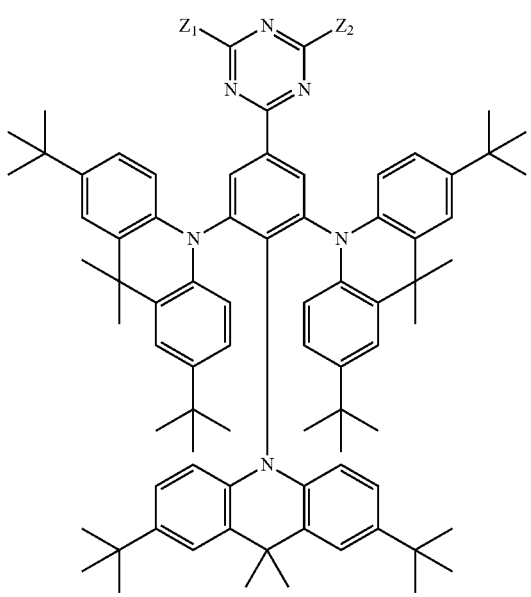

wherein
$Z^1$ and $Z^2$ are each an optionally substituted aryl group.

7. An organic electroluminescent element comprising an anode, a cathode, and an organic layer disposed between the anode and the cathode,
wherein the organic layer substantially comprises a π-conjugated compound represented general formula 208:

General formula 208

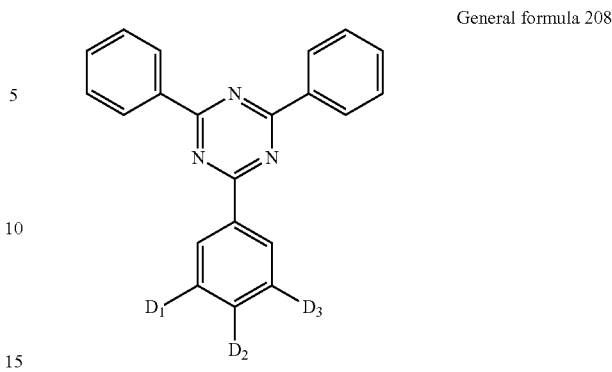

wherein
$D^1$ to $D^3$ are each an optionally substituted amino group.

8. The π-conjugated compound according to claim 1, comprising a structure represented by the following general formula 207:

General formula 207

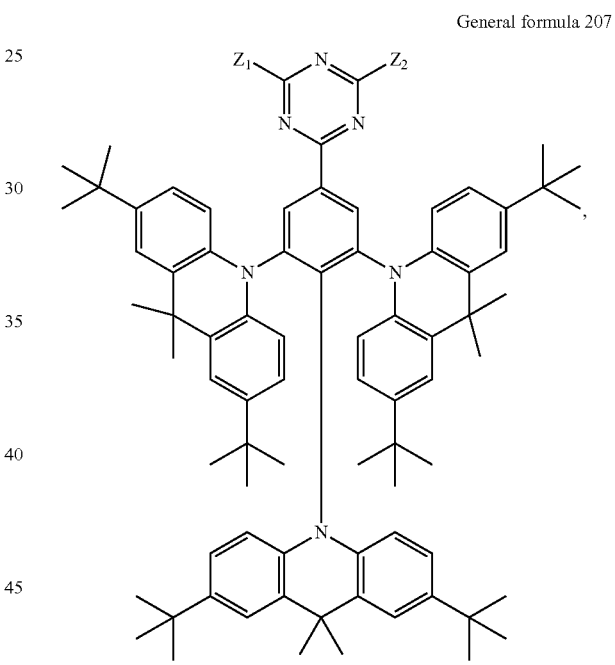

wherein $Z^1$ and $Z^2$ are each an optionally substituted aryl group.

* * * * *